US009580416B2

(12) United States Patent
Chen et al.

(10) Patent No.: US 9,580,416 B2
(45) Date of Patent: Feb. 28, 2017

(54) INHIBITORS OF BRUTON'S TYROSINE KINASE

(71) Applicant: PHARMACYCLICS LLC, Sunnyvale, CA (US)

(72) Inventors: Wei Chen, Fremont, CA (US); Longcheng Wang, Palo Alto, CA (US); Shunqi Yan, Irvine, CA (US); David J. Loury, Incline Village, NV (US); Zhaozhong J. Jia, San Mateo, CA (US); Leah Lynn Frye, Portland, OR (US); Jeremy Robert Greenwood, Brooklyn, NY (US); Mee Yoo Shelley, Tigard, OR (US); Gordana Babic Atallah, Fremont, CA (US); Riccardo Zanaletti, Verona (IT); Maria Pia Catalani, Verona (IT); Luca Francesco Raveglia, Milan (IT)

(73) Assignee: PHARMACYCLICS LLC, Sunnyvale, CA (US)

( * ) Notice: Subject to any disclaimer, the term of this patent is extended or adjusted under 35 U.S.C. 154(b) by 0 days.

(21) Appl. No.: 14/790,978

(22) Filed: Jul. 2, 2015

(65) Prior Publication Data
US 2016/0002225 A1    Jan. 7, 2016

Related U.S. Application Data

(60) Provisional application No. 62/019,961, filed on Jul. 2, 2014.

(51) Int. Cl.
A61K 31/437    (2006.01)
C07D 471/04    (2006.01)
C07D 487/04    (2006.01)
C07D 519/00    (2006.01)
C07D 471/06    (2006.01)

(52) U.S. Cl.
CPC ......... C07D 471/04 (2013.01); C07D 471/06 (2013.01); C07D 487/04 (2013.01); C07D 519/00 (2013.01)

(58) Field of Classification Search
CPC .................................................. C07D 471/04
See application file for complete search history.

(56) References Cited

U.S. PATENT DOCUMENTS

| 5,981,533 | A | 11/1999 | Traxler et al. |
| 6,251,911 | B1 | 6/2001 | Bold et al. |
| 7,504,509 | B2 | 3/2009 | Ibrahim et al. |
| 8,163,732 | B2 | 4/2012 | Bennani et al. |
| 2003/0207910 | A1 | 11/2003 | Wang et al. |
| 2004/0110785 | A1 | 6/2004 | Wang et al. |
| 2004/0167030 | A1 | 8/2004 | Bernotas et al. |
| 2005/0288290 | A1 | 12/2005 | Borzilleri et al. |
| 2006/0004006 | A1 | 1/2006 | Borzilleri et al. |
| 2006/0211695 | A1 | 9/2006 | Borzilleri et al. |
| 2007/0032519 | A1 | 2/2007 | Zhang et al. |
| 2007/0066641 | A1 | 3/2007 | Ibrahim et al. |
| 2007/0191289 | A1 | 8/2007 | Fushimi et al. |
| 2008/0139595 | A1 | 6/2008 | Schirok et al. |
| 2008/0293664 | A1 | 11/2008 | Billedeau et al. |
| 2008/0317739 | A1 | 12/2008 | Eswarakumar et al. |
| 2010/0144739 | A1 | 6/2010 | Aronov et al. |
| 2010/0184790 | A1 | 7/2010 | Meijer et al. |
| 2010/0204197 | A1 | 8/2010 | Diels et al. |
| 2010/0256356 | A1 | 10/2010 | Blake et al. |
| 2011/0130406 | A1 | 6/2011 | DeMeese et al. |
| 2011/0183983 | A1 | 7/2011 | Kim et al. |
| 2013/0274259 | A1 | 10/2013 | Zhang et al. |
| 2014/0037617 | A1 | 2/2014 | Bollag et al. |
| 2014/0155594 | A1 | 6/2014 | Pav et al. |
| 2014/0171453 | A1 | 6/2014 | Honigberg et al. |
| 2014/0256704 | A1 | 9/2014 | Vankayalapati et al. |

FOREIGN PATENT DOCUMENTS

| GB | 2515785 A | 7/2015 |
| KR | 1505783 B1 | 3/2015 |
| WO | 02062423 A1 | 8/2002 |

(Continued)

OTHER PUBLICATIONS

M. Mackay et al., Gas-Phase Synthesis of Pyrazolo[3,4-b]pyridin-4-ones—Synthesis (2015), 47(2), 242-248.
J. Shin et al., NPS-1034, a novel MET inhibitor, inhibits the activated MET receptor and its constitutively active mutants—Investigational New Drugs (2014), 32(3), 389-399.
M. Morshed, Identification of Aurora-A Inhibitors by Ligand and Structure-Based Virtual Screening—Molecular Informatics (2014), 33(5), 369-381.
J. Rho et al., MET and AXL Inhibitor NPS-1034 Exerts Efficacy against Lung Cancer Cells Resistant to EGFR Kinase Inhibitors Because of MET or AXL Activation—Cancer Research (2014), 74(1), 253-262.
J. Lee et al., Multicomponent System of NPS-1034, an Orally Administered Lung Cancer Drug Candidate, with Sulfonic Acids and Solid State Characterization—Crystal Growth and Design (2013), 13(9), 3958-3968.

(Continued)

Primary Examiner — Brian McDowell
(74) Attorney, Agent, or Firm — Foley Hoag LLP

(57) ABSTRACT

Disclosed herein are compounds that inhibit Bruton's tyrosine kinase (Btk) having the structure of Formula (B):

Formula (B)

Also disclosed are pharmaceutical compositions that include the compounds. Methods of using the Btk inhibitors are disclosed, alone or in combination with other therapeutic agents, for the treatment of autoimmune diseases or conditions, heteroimmune diseases or conditions, cancer, including lymphoma, and inflammatory diseases or conditions.

18 Claims, No Drawings

(56) References Cited

FOREIGN PATENT DOCUMENTS

| | | |
|---|---|---|
| WO | 03045949 A1 | 6/2003 |
| WO | 2005062795 A2 | 7/2005 |
| WO | 2007002433 A1 | 1/2007 |
| WO | 2007076423 A3 | 7/2007 |
| WO | 2007103308 A3 | 9/2007 |
| WO | 2008064265 A2 | 5/2008 |
| WO | 2008079521 A2 | 7/2008 |
| WO | 2009033084 A1 | 3/2009 |
| WO | 2009073300 A1 | 6/2009 |
| WO | 2009089352 A1 | 7/2009 |
| WO | 2009140320 A1 | 11/2009 |
| WO | 2010003133 A2 | 1/2010 |
| WO | 2011022439 A1 | 2/2011 |
| WO | 2011057022 A1 | 5/2011 |
| WO | 2011063159 A1 | 5/2011 |
| WO | 2012148540 A1 | 11/2012 |
| WO | 2012158957 A3 | 11/2012 |
| WO | 2012170752 A1 | 12/2012 |
| WO | 2013032797 A2 | 3/2013 |
| WO | 2013043715 A1 | 3/2013 |
| WO | 2013062945 A1 | 5/2013 |
| WO | 2013071264 A1 | 5/2013 |
| WO | 2013111150 A1 | 8/2013 |
| WO | 2013128465 A1 | 9/2013 |
| WO | 2013142427 A1 | 9/2013 |
| WO | 2014052699 A1 | 4/2014 |
| WO | 2014093383 A1 | 6/2014 |
| WO | 2014151147 A1 | 9/2014 |

OTHER PUBLICATIONS

M. Silva-Santisteban et al., Fragment-Based Screening Maps Inhibitor Interactions in the ATP-Binding Site of Checkpoint Kinase 2—PLOS One (2013), 8(6), e65689.
D. Diaz et al., Pharmacokinetic drivers of toxicity for basic molecules: Strategy to lower pKa results in decreased tissue exposure and toxicity for a small molecule Met inhibitor—Toxicology and Applied Pharmacology (2013), 266(1), 86-94.
B. Liederer et al., Preclinical stereoselective disposition and toxicokinetics of two novel MET inhibitors—Xenobiotica (2012), 42(5), 456-465.
K. Kumaran et al., Synthesis, Spectral Characterization and Antimicrobial Studies of New 3- and 4-substituted in 7-Aza Indole Derivatives—International Journal of PharmTech Research (2012), 4(1), 169-175.
X. Liang et al., Evaluation of dried blood spot sampling following cassette dosing in drug discovery—Bioanalysis (2011), 3(20), 2291-2302.
J. Caballero et al., Docking and quantitative structure-activity relationship studies for 3-fluoro-4- . . . —Journal of Computer-Aided Molecular Design (2011), 25(4), 349-369.
B. Liederer et al., Preclinical absorption, distribution, metabolism, excretion, and pharmacokinetic-pharmacodynamic . . . —Xenobiotica (2011), 41(4), 327-339.
J. Quiroga et al., A hydrogen-bonded dimer in 6-(4-bromophenyl) . . . —Acta Crystallographica, Section C: Crystal Structure Communications (2010), 66(4), 0163-0167.
T. Wang et al., Janus Kinase 2 Inhibitors. Synthesis and Characterization of a Novel Polycyclic Azaindole—Journal of Medicinal Chemistry (2009), 52(24), 7938-7941.
Z. Cai et al., Discovery of orally active pyrrolopyridine . . . —Bioorganic & Medicinal Chemistry Letters (2008), 18(11), 3224-3229.
E. Bisagni et al., Synthesis of 3-aryl-r-acetyl- . . . —Heterocycles (1989), 29(9), 1815-24.
Nguyen, et al., "Evaluation of dried blood," Bioanalysis, 3(20): 2291-2302 (2011).

INHIBITORS OF BRUTON'S TYROSINE KINASE

CROSS-REFERENCE TO RELATED APPLICATION

This application claims the benefit of U.S. Provisional Application No. 62/019,961, filed Jul. 2, 2014, which is incorporated herein by reference in its entirety.

FIELD OF THE INVENTION

Described herein are compounds, methods of making such compounds, pharmaceutical compositions and medicaments containing such compounds, and methods of using such compounds and compositions to inhibit the activity of tyrosine kinases.

BACKGROUND OF THE INVENTION

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival (Kurosaki, *Curr Op Imm*, 2000, 276-281; Schaeffer and Schwartzberg, *Curr Op Imm* 2000, 282-288). In addition, Btk plays a role in a number of other hematopoetic cell signaling pathways, e.g., Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. See, e.g., C. A. Jeffries, et al., (2003), *Journal of Biological Chemistry* 278:26258-26264; N. J. Horwood, et al., (2003), *The Journal of Experimental Medicine* 197: 1603-1611; Iwaki et al. (2005), *Journal of Biological Chemistry* 280(48):40261-40270; Vassilev et al. (1999), *Journal of Biological Chemistry* 274(3):1646-1656, and Quek et al. (1998), *Current Biology* 8(20):1137-1140.

SUMMARY OF THE INVENTION

Described herein are inhibitors of Bruton's tyrosine kinase (Btk). Also described herein are irreversible inhibitors of Btk. Also described herein are reversible inhibitors of Btk. Further described are irreversible inhibitors of Btk that form a covalent bond with a cysteine residue on Btk. Further described herein are irreversible inhibitors of other tyrosine kinases, wherein the other tyrosine kinases share homology with Btk by having a cysteine residue (including a Cys 481 residue) that can form a covalent bond with the irreversible inhibitor (such tyrosine kinases, are referred herein as "Btk tyrosine kinase cysteine homologs").

Further described are irreversible inhibitors of Btk that form a covalent bond with a serine residue on C481S mutated Btk. Specifically described are irreversible inhibitors of Btk that form a covalent bond with a serine481 residue on C481S mutated Btk (Woyach, et al. Resistance mechanisms for the Bruton's tyrosine kinase inhibitor ibrutinib, *N Engl J Med*. 2014, 12; 370(24):2286-94). Further described herein are irreversible inhibitors of other tyrosine kinases, wherein the other tyrosine kinases share homology with C481S mutated Btk by having a serine residue (including a homologous resisdue to BTK C481S residue) that can form a covalent bond with the inhibitor.

Further described herein are reversible inhibitors of C481S mutated Btk.

Further described herein are reversible inhibitors of other tyrosine kinases, wherein the other tyrosine kinases share homology with Btk.

Also described herein are methods for synthesizing such reversible or irreversible inhibitors, methods for using such reversible or irreversible inhibitors in the treatment of diseases (including diseases wherein irreversible inhibition of Btk provides therapeutic benefit to a patient having the disease). Further described are pharmaceutical formulations that include a reversible or irreversible inhibitor of Btk.

Thus, in one specific aspect, the present invention provides methods for preventing, treating or ameliorating in a mammal a disease or condition that is causally related to the activity of a tyrosine kinase in vivo, which comprises administering to the mammal an effective disease-treating or condition-treating amount of a compound according to Formula (IA) having the structure:

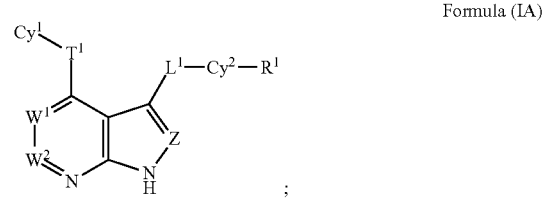

Formula (IA)

or a solvate, pharmaceutically acceptable salt, or prodrug thereof; or a stereoisomer or an isotopic variant thereof; wherein:
one of $W^1$ and $W^2$ is $=C(R^9)-$, or $=N-$; and the other is $=C(R^9)-$;
Z is $=C(R^9)-$, or $=N-$;
$L^1$ is $C_1$-$C_3$ alkyl, $-N(R^5)-$, $-O-$, or $-S-$;
$T^1$ is a single bond, $C_1$-$C_3$ alkylene, $-N(R^5)-$, $-O-$, or $-S-$;
$Cy^1$ is substituted aryl or substituted heteroaryl;
$Cy^2$ is substituted or unsubstituted cycloalkyl, substituted or unsubstituted heterocycloalkyl, substituted or unsubstituted aryl, or substituted or unsubstituted heteroaryl;
$R^1$ is H, halo, alkyl, alkoxyalkyl, hydroxyalkyl, haloalkyl, cyano, $-C(O)-R^{1a}$, $-C(S)-R^{1a}$, $-C(O)-O-R^{1b}$, $-C(O)-N(R^{1c})R^{1d}$, $-S(O)_p-R^{1a}$, or $-S(O)_p-N(R^{1c})R^{1d}$; p is 1 or 2;
each of $R^{1a}$, $R^{1b}$, $R^{1c}$, and $R^{1d}$ is independently H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;
each of $R^5$ is independently H, $C_1$-$C_6$ alkyl, or $C_1$-$C_6$ heteroalkyl; or when each of $L^1$ and $T^1$ is independently $-N(R^5)-$, then the two R's may join together to form a substituted or unsubstituted heterocycle;
each $R^9$ is independently H, halogen, $-CN$, $-OH$, $-NH_2$, $-SH$, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$cycloalkyl.

In one embodiment, the tyrosine kinase receptor is a Btk receptor.

In one embodiment, the disease or condition is an autoimmune disease, a heteroimmune disease, a cancer, mastocytosis, osteoporosis or bone resorption disorder, or an inflammatory disease.

In one embodiment, with respect to the methods, the compound is according to Formula (IA), and $Cy^2$ is substituted or unsubstituted cycloalkyl, substituted or unsubstituted heterocycloalkyl, or substituted or unsubstituted aryl.

In one embodiment, with respect to the methods, the compound is according to Formula (IA), and $Cy^2$ is other than substituted or unsubstituted heteroaryl.

In one embodiment, with respect to the methods, the compound is according to Formula (IA), and $Cy^2$ is substituted or unsubstituted heteroaryl.

In another aspect, the present invention provides a compound according to Formula (A) having the structure:

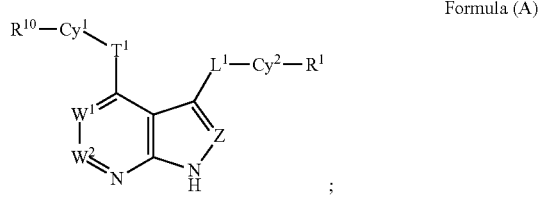

Formula (A)

or a solvate, pharmaceutically acceptable salt, or prodrug thereof; or a stereoisomer or an isotopic variant thereof; wherein:

one of $W^1$ and $W^2$ is $=C(R^9)-$, or $=N-$; and the other is $=C(R^9)-$;

Z is $=C(R^9)-$, or $=N-$;

$L^1$ is a single bond, $-CH_2-$, $-NH-CH_2-$, $-N(R^5)-$, $-O-$, or $-S-$;

$T^1$ is a single bond, $C_1$-$C_3$ alkylene, $-N(R^5)-$, $-O-$, or $-S-$;

$Cy^1$ is substituted or unsubstituted cycloalkyl, substituted or unsubstituted aryl or substituted or unsubstituted heteroaryl;

$Cy^2$ is substituted or unsubstituted cycloalkyl, substituted or unsubstituted heterocycloalkyl, substituted or unsubstituted aryl, or substituted or unsubstituted heteroaryl;

$R^1$ is H, halo, alkyl, OH, alkoxyalkyl, hydroxyalkyl, haloalkyl, cyano, $-O-R^{1a}$, $-C(O)-R^{1a}$, $-C(S)-R^{1a}$, $-C(O)-O-R^{1b}$, $-C(O)-C(O)-N(R^{1c})R^{1d}$, $-N(R^{1c})-C(O)R^{1d}$, $-C(O)-N(R^{1c})R^{1d}$, $-S(O)_p-R^{1a}$, or $-S(O)_p-N(R^{1c})R^{1d}$;

$R^{10}$ is halo, nitro, oxo, thioxo, $-R^{10b}-R^{10c}$, alkoxyalkyl, hydroxyalkyl, haloalkyl, cyano, $-R^{10b}-OR^{10a}$, $-R^{10b}-OC(O)R^{10a}$, $-R^{10b}-SR^{10a}$, $-R^{10b}-C(O)R^{10a}$, $-R^{10b}-C(S)R^{10a}$, $-R^{10b}-C(O)OR^{10a}$, $-R^{10b}-C(O)N(R^{10a})R^{10a}$, $-R^{10b}-O-R^{10e}-C(O)N(R^{10a})_2$, $-R^{10b}-OCH_2R^{10a}$, $-R^{10b}-SCH_2R^{10a}$, $-R^{10b}-N(R^{10d})C(O)R^{10c}$, $-R^{10b}-N(R^{10d})C(O)OR^{10c}$, $-R^{10b}-N(R^{10d})C(O)N(R^{10a})R^{10a}$, $-R^{10b}-N(R^{10a})R^{10a}$, $-R^{10b}-N(R^{10d})S(O)_pR^{10a}$, $-S(O)_pR^{10a}$, $-R^{10b}-S(O)_pOR^{10a}$, or $-R^{10b}-S(O)_pN(R^{10a})R^{1a}$;

p is 1 or 2;

each of $R^{1a}$, $R^{1b}$, $R^{1c}$, $R^{1d}$, and $R^{10a}$ is independently H, cyano, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

$R^{10b}$ is a single bond or a straight or branched alkylene or alkenylene chain;

$R^{10c}$ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

$R^{10d}$ is H, substituted or unsubstituted $C_1$-$C_6$alkyl, or substituted or unsubstituted $C_3$-$C_8$cycloalkyl;

$R^{10e}$ is a straight or branched alkylene or alkenylene chain;

each of $R^5$ is independently H, $-C(O)-R^{5a}$, $C_1$-$C_6$ alkyl, or $C_1$-$C_6$ heteroalkyl; or when each of $L^1$ and $T^1$ is independently $-N(R^5)-$, then the two R's may join together to form a substituted or unsubstituted heterocycle;

$R^{5a}$ is substituted or unsubstituted $C_1$-$C_4$alkyl, substituted or unsubstituted $C_2$-$C_4$alkenyl, or substituted or unsubstituted $C_2$-$C_4$alkynyl; and each $R^9$ is independently H, halogen, $-CN$, $-OH$, $-NH_2$, $-SH$, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$cycloalkyl;

provided that (1) when $L^1$ is a single bond, then $Cy^2$ is substituted or unsubstituted fully saturated heterocycloalkyl, $R^1$ is $-C(O)-R^{1a}$ or $-N(R^{1c})-C(O)R^{1d}$, and $T^1$ is $C_1$-$C_3$ alkylene, $-N(R^5)-$, $-O-$, or $-S-$; and (2) when $L^1$ is $-NH-CH_2-$, then $Cy^2$ is substituted or unsubstituted fully saturated heterocycloalkyl, and $R^1$ is $-C(O)-R^{1a}$, $-C(S)-R^{1a}$, $-C(O)-O-R^{1b}$, $-C(O)-N(R^{1c})R^{1d}$, $-S(O)_p-R^{1a}$, or $-S(O)_p-N(R^{1c})R^{1d}$;

(3) when $L^1$ is $-CH_2-$, then $R^1$ is other than H;

(4) when $T^1$ is a single bond, then $R^{10}$ is $-R^{10b}-C(O)N(R^{10a})R^{10a}$, $-R^{10b}-O-R^{10e}-C(O)N(R^{10a})_2$, $-R^{10b}-N(R^{10d})C(O)R^{10c}$, $-R^{10b}-N(R^{10d})C(O)OR^{10c}$, $-R^{10b}-N(R^{10d})C(O)N(R^{10a})R^{10a}$, $-R^{10b}-N(R^{10d})S(O)_pR^{10a}$, $-S(O)_pR^{10a}$, $-R^{10b}-S(O)_pOR^{10a}$, or $-R^{10b}-S(O)_pN(R^{10a})R^{10a}$;

(5) when $T^1$ is a $-CH_2-CH_2-$, and $L^1$ and O, then $Cy^2$ is other than tetrahydropyran substituted with three or more substituents independently selected from OH, $CH_2OH$, OC(O)-t-Bu and $CH_2OC(O)$-t-Bu;

(6) when $W^1$ is $=N-$, $L^1$ and $T^1$ are both $-N(R^5)-$, $Cy^1$ and $Cy^2$ are both phenyl, and $R^1$ is H, halo, alkyl, OH, alkoxyalkyl, hydroxyalkyl, haloalkyl or cyano, then $R^{10}$ is $-R^{10b}-R^{10c}$, $-R^{10b}-OR^{10a}$, $-R^{10b}-OC(O)R^{10a}$, $-R^{10b}-SR^{10a}$, $-R^{10b}-C(O)R^{10a}$, $-R^{10b}-C(S)R^{10a}$, $-R^{10b}-C(O)OR^{10a}$, $-R^{10b}-C(O)N(R^{10a})R^{10a}$, $-R^{10b}-O-R^{10e}-C(O)N(R^{10a})_2$, $-R^{10b}-OCH_2R^{10a}$, $-R^{10b}-SCH_2R^{10a}$, $-R^{10b}-N(R^{10d})C(O)R^{10c}$, $-R^{10b}-N(R^{10d})C(O)OR^{10c}$, $-R^{10b}-N(R^{10d})C(O)N(R^{10a})R^{10a}$, $-R^{10b}-N(R^{10a})R^{10a}$, $-R^{10b}-N(R^{10d})S(O)_pR^{10a}$, $-S(O)_pR^{10a}$, $-R^{10b}-S(O)_pOR^{10a}$, or $-R^{10b}-S(O)_pN(R^{10a})R^{1a}$, and wherein at least one of $R^{10a}$ and $R^{10c}$ is substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

(7) when $W^1$ is $=N-$, then -$Cy^1$-$R^{10}$ together is other than unsubstituted 3-Cl-phenyl;

(8) -$Cy^1$-$R^{10}$ together is other than substituted or unsubstituted 2-F-phenyl; and (9) when $Cy^1$ is substituted or unsubstituted cycloalkyl, then $T^1$ is $C_1$-$C_3$ alkylene, $-N(R^5)-$, $-O-$, or $-S-$, and $R^{10}$ is $-C(O)R^{10a}$ or $-C(O)NHR^{10a}$.

In another aspect, the present invention provides a compound according to Formula (IA) having the structure:

Formula (IA)

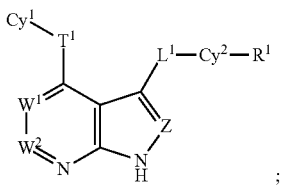

or a solvate, pharmaceutically acceptable salt, or prodrug thereof; or a stereoisomer or an isotopic variant thereof; and wherein $Cy^1$, $Cy^2$, $L^1$, $T^1$, $W^1$, $W^2$, Z, and $R^1$ are as described herein.

In one embodiment, the compound is other than benzoic acid, 4-[[4-[(3-chlorophenyl)amino]-1H-pyrazolo[3,4-d]pyrimidin-3-yl]amino]-, 1,1-dimethylethyl ester.

In one embodiment, when $R^2$ is Cl, $Cy^2$ is phenyl, and $R^1$ is —C(O)—O—$R^{1b}$; then $R^{1b}$ is other than t-Bu.

In a particular embodiment, $R^1$ is —C(O)—$R^{1a}$, —C(S)—$R^{1a}$, —C(O)—O—$R^{1b}$, —C(O)—N($R^{1c}$)$R^{1d}$, —S(O)$_p$—$R^{1a}$, or —S(O)$_p$—N($R^{1c}$)$R^{1d}$; p is 1 or 2; $R^{1a}$, $R^{1b}$, $R^{1c}$, and $R^{1d}$ are as described herein.

In some embodiments, when $T^1$ is a single bond, then $Cy^2$ is substituted or unsubstituted fully saturated heterocycloalkyl. In some embodiments, when $L^1$ is —$CH_2$—, then $R^1$ is —C(O)—$R^{1a}$, —C(S)—$R^{1a}$, —C(O)—N($R^{1c}$)$R^{1d}$, —S(O)$_p$—$R^{1a}$, or —S(O)$_p$—N($R^{1c}$)$R^{1d}$.

In some embodiments, -$Cy^2$-$R^1$ is other than tetrahydropyran substituted with three or more substituents independently selected from OH, $CH_2OH$, OC(O)-t-Bu or $CH_2OC$(O)-t-Bu. In some embodiments, $Cy^2$ is other than substituted or unsubstituted tetrahydropyran.

In some embodiments, -$Cy^1$-$R^{10}$ together is other than substituted or unsubstituted 2-F-phenyl. In some embodiments, -$Cy^1$-$R^{10}$ together is other than unsubstituted 3-Cl-phenyl. In some embodiments, $R^{10}$ is other than —$R^{10b}$—N($R^{10d}$)C(O)O-t-Bu and —$R^{10b}$—C(O)O-t-Bu. In some embodiments, when $W^1$ is =C($R^9$)—, $W^2$ is N, and $Cy^1$ is phenyl, then $R^{10}$ is other than halo, alkyl or substituted alkyl. In some embodiments, when $R^1$ is H, halo, alkyl, OH, alkoxyalkyl, hydroxyalkyl, haloalkyl or cyano, then $R^{10}$ is —$R^{10b}$—$R^{10c}$, —$R^{10b}$—O$R^{10a}$, —$R^{10b}$—OC(O)$R^{10a}$, —$R^{10b}$—S$R^{10a}$, —$R^{10b}$—C(O)$R^{10a}$, —$R^{10b}$—C(S)$R^{10a}$, —$R^{10b}$—C(O)O$R^{10a}$, —$R^{10b}$—C(O)N($R^{10a}$)$R^{10a}$, —$R^{10b}$—O—$R^{10e}$—C(O)N($R^{10a}$)$_2$, —$R^{10b}$—OCH$_2$$R^{10a}$, —$R^{10b}$—SCH$_2$$R^{10a}$, —$R^{10b}$—N($R^{10d}$)C(O)$R^{10c}$, —$R^{10b}$—N($R^{10d}$)C(O)O$R^{10c}$, —$R^{10b}$—N($R^{10d}$)C(O)N($R^{10a}$)$R^{10a}$, —$R^{10b}$—N($R^{10a}$)$R^{10a}$, —$R^{10b}$—N($R^{10d}$)S(O)$_p$$R^{10a}$, —S(O)$_p$$R^{10a}$, —$R^{10b}$—S(O)$_p$O$R^{10a}$, or —$R^{10b}$—S(O)$_p$N($R^{10a}$)$R^{10a}$; and wherein at least one of $R^{10a}$ and $R^{10c}$ is substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl.

In some embodiments, when $L^1$ is a single bond, then $Cy^2$ is substituted or unsubstituted fully saturated heterocycloalkyl, $R^1$ is —C(O)—$R^{1a}$ or —N($R^{1c}$)—C(O)$R^{1d}$, and $T^1$ is $C_1$-$C_3$ alkylene, —O—, or —S—.

In some embodiments, when $T^1$ is a single bond, then $Cy^2$ is substituted or unsubstituted fully saturated heterocycloalkyl.

In some embodiments, when $W^1$ is N, and $W^2$ is =C($R^9$)—, then $Cy^2$ is heterocycloalkyl and $R^1$ is —C(O)—$R^{1a}$, —C(S)—$R^{1a}$, —C(O)—O—$R^{1b}$, —C(O)—C(O)—N($R^{1c}$)$R^{1d}$, —N($R^{1c}$)—C(O)$R^{1d}$, —C(O)—N($R^{1c}$)$R^{1d}$, —S(O)$_p$—$R^{1a}$, or —S(O)$_p$—N($R^{1c}$)$R^{1d}$.

In another aspect, the present invention provides pharmaceutical compositions comprising a therapeutically effective amount of a compound of Formula (A) or (IA) and a pharmaceutically acceptable excipient. In one embodiment, the pharmaceutical composition comprising the compound of Formula (A) or (IA) is formulated for a route of administration selected from oral administration, parenteral administration, buccal administration, nasal administration, topical administration, or rectal administration. In another aspect, a method for treating an autoimmune disease or condition is provided comprising administering to a patient in need a therapeutically effective amount of a compound of Formula (A) or (IA). In one embodiment the autoimmune disease is selected from rheumatoid arthritis or lupus. In a further aspect, a method for treating a heteroimmune disease or condition is provided comprising administering to a patient in need a therapeutically effective amount of a compound of Formula (A) or (IA). In yet another embodiment, a method for treating a cancer is provided comprising administering to a patient in need a therapeutically effective amount of a compound of Formula (A) or (IA). In one embodiment the cancer is a B-cell proliferative disorder.

In another embodiment the B-cell proliferative disorder is diffuse large B cell lymphoma, follicular lymphoma or chronic lymphocytic leukemia.

In yet a further aspect, a method for treating mastocytosis is provided comprising administering to a patient in need a therapeutically effective amount of a compound of Formula (IA).

In another aspect, a method for treating osteoporosis or bone resorption disorders is provided comprising administering to a patient in need a therapeutically effective amount of a compound of Formula (A) or (IA).

In a further aspect, a method for treating an inflammatory disease or condition is provided comprising administering to a patient in need a therapeutically effective amount of a compound of Formula (A) or (IA).

Any combination of the groups described above for the various variables is contemplated herein.

It is understood that substituents and substitution patterns on the compounds provided herein can be selected by one of ordinary skill in the art to provide compounds that are chemically stable and that can be synthesized by techniques known in the art, as well as those set forth herein.

In a further aspect are provided pharmaceutical compositions, which include a therapeutically effective amount of at least one of any of the compounds herein, or a pharmaceutically acceptable salt, pharmaceutically active metabolite, prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

In certain embodiments, provided herein is a pharmaceutical composition containing: i) a physiologically acceptable carrier, diluent, and/or excipient; and ii) one or more compounds provided herein.

In one aspect, provided herein are methods for treating a patient by administering a compound provided herein. In some embodiments, provided herein is a method of inhibiting the activity of tyrsoine kinase(s), such as Btk, or of treating a disease, disorder, or condition, which would benefit from inhibition of tyrosine kinase(s), such as Btk, in a patient, which includes administering to the patient a therapeutically effective amount of at least one of any of the compounds herein, or a pharmaceutically acceptable salt, pharmaceutically active metabolite, prodrug, or pharmaceutically acceptable solvate.

In another aspect, provided herein is the use of a compound disclosed herein for inhibiting Bruton's tyrosine kinase (Btk) activity or for the treatment of a disease, disorder, or condition, which would benefit from inhibition of Bruton's tyrosine kinase (Btk) activity.

In some embodiments, compounds provided herein are administered to a human.

In some embodiments, compounds provided herein are orally administered.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (Btk) activity.

Articles of manufacture including packaging material, a compound or composition or pharmaceutically acceptable derivative thereof provided herein, which is effective for inhibiting the activity of tyrosine kinase(s), such as Btk, within the packaging material, and a label that indicates that the compound or composition, or pharmaceutically acceptable salt, pharmaceutically active metabolite, prodrug, or pharmaceutically acceptable solvate thereof, is used for inhibiting the activity of tyrosine kinase(s), such as Btk, are provided.

In another aspect, provided are inhibited tyrosine kinases comprising a Bruton's tyrosine kinase, a Bruton's tyrosine kinase homolog, or a Btk tyrosine kinase cysteine homolog thereof covalently bound to an inhibitor having the structure:

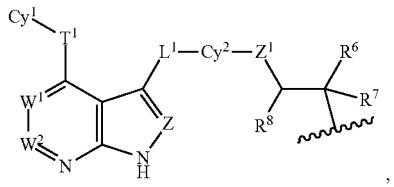

wherein $Cy^1$, $Cy^2$, $L^1$, $T^1$, $W^1$, $W^2$, $Z$, $R^1$, $R^6$, $R^7$ and $R^8$ are as described herein, $Z^1$ is —O—, —C(O)—, —C(S)—, —C(O)—O—, —C(O)—C(O)—N($R^{1c}$)—, —N($R^{1c}$)—C(O)—, —C(O)—N($R^{1c}$)—, —S(O)$_p$—, or —S(O)$_p$—N($R^{1c}$)—, wherein $R^{1c}$ and p are as defined herein, and ⁓⁓⁓ indicates the point of attachment between the inhibitor and the tyrosine kinase. In a further embodiment, the inhibitor is covalently bound to a cysteine residue on the tyrosine kinase.

In a further aspect, provided herein is a method for inhibiting Bruton's tyrosine kinase in a subject in need thereof by administering to the subject thereof a composition containing a therapeutically effective amount of at least one compound having the structure of Formula (I). In some embodiments, the subject in need is suffering from an autoimmune disease, e.g., inflammatory bowel disease, arthritis, lupus, rheumatoid arthritis, psoriatic arthritis, osteoarthritis, Still's disease, juvenile arthritis, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In other embodiments, the subject in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In certain embodiments, the subject in need is suffering from an inflammatory disease, e.g., asthma, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In further embodiments, the subject in need is suffering from a cancer. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the abovementioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In further embodiments, the subject in need is suffering from a thromboembolic disorder, e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of at least one compound described herein. In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In a further aspect, provided herein is a method for treating a heteroimmune condition or disease by administering to a subject in need thereof a composition containing a therapeutically effective amount of at least one compound having the structure of Formula described herein. In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId). In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId). In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId). In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In a further aspect, provided herein is a method for treating an autoimmune disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating a heteroimmune condition or disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In a further aspect, provided herein is a method for treating an inflammatory disease by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase. In yet another aspect, provided herein is a method for treating a cancer by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In another aspect, provided herein is a method for treating a thromboembolic disorder by administering to a subject in need thereof a composition containing a therapeutically effective amount of a compound that forms a covalent bond with Bruton's tyrosine kinase. In one embodiment, the compound forms a covalent bound with the activated form of Bruton's tyrosine kinase. In further or alternative embodiments, the compound irreversibly inhibits the Bruton's tyrosine kinase to which it is covalently bound. In a further or alternative embodiment, the compound forms a covalent bond with a cysteine residue on Bruton's tyrosine kinase.

In another aspect are methods for modulating, including irreversibly inhibiting the activity of Btk or other tyrosine kinases, wherein the other tyrosine kinases share homology with Btk by having a cysteine residue (including a Cys 481 residue) that can form a covalent bond with at least one irreversible inhibitor described herein, in a mammal comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId). In another aspect are methods for modulating, including reversibly or irreversibly inhibiting, the activity of Btk in a mammal comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId). In another aspect are methods for treating Btk-dependent or Btk mediated conditions or diseases, comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId).

In another aspect are methods for treating inflammation comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId).

A further aspect are methods for the treatment of cancer comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId). The type of cancer may include, but is not limited to, pancreatic cancer and other solid or hematological tumors.

In another aspect are methods for treating respiratory diseases comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId). In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, and seasonal asthma.

In another aspect are methods for preventing rheumatoid arthritis and osteoarthritis comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId).

In another aspect are methods for treating inflammatory responses of the skin comprising administering to the mammal at least once an effective amount of at least one compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a first compound having the structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId).

In another aspect is the use of a compound of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) in the manufacture of a medicament for treating an inflammatory disease or condition in an animal in which the activity of Btk or other tyrosine kinases, wherein the other tyrosine kinases share homology with Btk by having a cysteine residue (including a Cys 481 residue) that can form a covalent bond with at least one irreversible inhibitor described herein, contributes to the pathology and/or symptoms of the disease or condition. In one embodiment of this aspect, the tyrosine kinase protein is Btk. In another or further embodiment of this aspect, the inflammatory disease or conditions are respiratory, cardiovascular, or proliferative diseases.

In any of the aforementioned aspects are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (i) the effective amount of the compound is administered rectally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; and at the end of the drug holiday, dosing of the compound is resumed. The length of the drug holiday can vary from 2 days to 1 year.

In any of the aforementioned aspects involving the treatment of proliferative disorders, including cancer, are further embodiments comprising administering at least one additional agent selected from the group consisting of alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, or dronabinol.

In any of the aforementioned aspects involving the prevention or treatment of Btk-dependent or tyrosine kinase mediated diseases or conditions are further embodiments comprising identifying patients by screening for a tyrosine kinase gene haplotype. In further or alternative embodiments the tyrosine kinase gene haplotype is a tyrosine kinase pathway gene, while in still further or alternative embodiments, the tyrosine kinase gene haplotype is a Btk haplotype.

In a further or alternative embodiment, the compounds of formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are reversible inhibitors of Bruton's tyrosine kinase (Btk), while in still further or alternative embodiments, such reversible inhibitors are selective for Btk. In even further or alternative embodiments, such inhibitors have an $IC_{50}$ below 10 microM in enzyme assay. In one embodiment, a Btk irreversible inhibitor has an $IC_{50}$ of less than 1 microM, and in another embodiment, less than 0.25 microM.

In a further or alternative embodiment, the compounds of formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are selective reversible inhibitors for Btk over Itk. In further or alternative embodiment, the compounds of formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) are selective reversible inhibitors for Btk over Lck. In a further or alternative embodiment, the compounds of formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are selective reversible inhibitors for Btk over ABL. In a further or alternative embodiment, the compounds of (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are selective reversible inhibitors for Btk over CMET. In a further or alternative embodiment, the compounds of formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) are selective reversible inhibitors for Btk over EGFR. In a further or alternative embodiment, the compounds of formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) are selective reversible inhibitors for Btk over Lyn.

In further or alternative embodiments, the reversible Btk inhibitors are also inhibitors of EGFR.

In a further or alternative embodiment, the compounds of Formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are irreversible inhibitors of Bruton's tyrosine kinase (Btk), while in still further or alternative embodiments, such irreversible inhibitors are selective for Btk. In even further or alternative embodiments, such inhibitors have an $IC_{50}$ below 10 microM in an enzyme assay. In one embodiment, a Btk irreversible inhibitor has an $IC_{50}$ of less than 1 microM, and in another embodiment, less than 0.25 microM.

In a further or alternative embodiment, the compounds of Formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-

(XIIId), (XIVa)-(XIVd), (XVa)-(XVd), (XVIa)-(XVId) or (XVIIa)-(XVIId) are selective irreversible inhibitors for Btk over Itk. In a further or alternative embodiment, the compounds of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) are selective irreversible inhibitors for Btk over Lck. In a further or alternative embodiment, the compounds of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) are selective irreversible inhibitors for Btk over ABL. In further or alternative embodiment, the compound of (A)-(C), (IA), (I), (IIa)-(IIb), (IIIa)-(IIId), (IVa)-(IVh), (Va)-(Vh), (Va)-(VIb), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) are selective irreversible inhibitors for Btk over CMET. In a further or alternative embodiment, the compounds of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) are selective irreversible inhibitors for Btk over EGFR. In a further or alternative embodiment, the compounds of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are selective irreversible inhibitors for Btk over Lyn.

In further or alternative embodiments, the irreversible Btk inhibitors are also inhibitors of EGFR.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

DETAILED DESCRIPTION OF THE INVENTION

Certain Terminology

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl (n-pr), 1-methylethyl (iso-propyl or i-Pr), n-butyl (n-Bu), n-pentyl, 1,1-dimethylethyl (t-butyl, or t-Bu), 3-methylhexyl, 2-methylhexyl, and the like. Unless stated otherwise specifically in the specification, an alkyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

The alkyl group could also be a "lower alkyl" having 1 to 6 carbon atoms.

As used herein, C$_1$-C$_x$ includes C$_1$-C$_2$, C$_1$-C$_3$ . . . C$_1$-C$_x$.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_p$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, from one to six carbon atoms, or from one to four carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, from one to six carbon atoms, or from one to four carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted by one or more of the following substituents: halo, cyano, nitro, aryl, cycloalkyl, heterocyclyl, heteroaryl, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2) and —S(O)$_t$N(R$^a$)$_2$ (where t is 1 or 2) where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, from six to ten carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl (Ph), fluorenyl, and naphthyl. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms or three to eight carbon atoms. In other embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N(R^a)_2$, —$R^b$—C(O)$R^a$, —$R^b$—C(O)$OR^a$, —$R^b$—C(O)N(R^a)_2$, —$R^b$—O—$R^c$—C(O)N(R^a)_2$, —$R^b$—N(R^a)C(O)$OR^a$, —$R^b$—N(R^a)C(O)$R^a$, —$R^b$—N(R^a)S(O)$_t$R^a$ (where t is 1 or 2), —$R^b$—S(O)$_t$OR^a$ (where t is 1 or 2) and —$R^b$—S(O)$_t$N(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Halo" or "halogen" refers to bromo (Br), chloro (Cl), fluoro (F) or iodo (I) substituents.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three to 14 ring atoms, such as three, four, five, six, seven, eight, nine, or more than nine atoms. $C_x$heterocycloalkyl refers to a heterocycloalkyl having x number of ring carbon atoms wherein the remaining ring atom(s) are heteroatom(s). Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

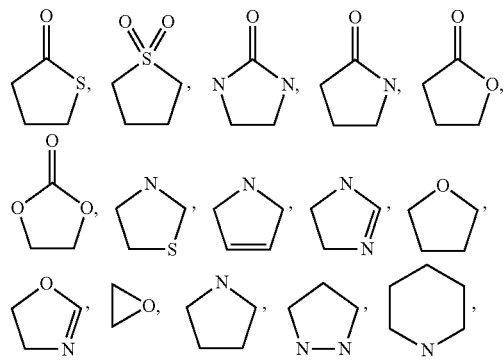

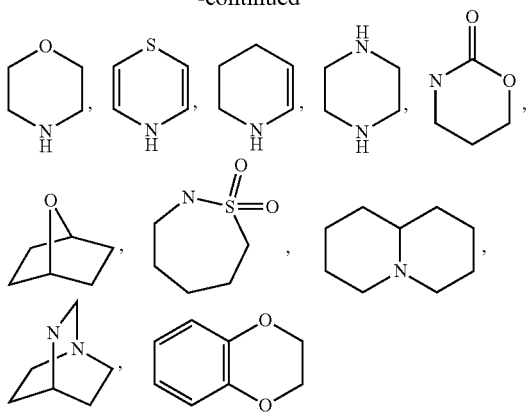

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In some embodiments, heteroaryl rings have five, six, seven, eight, nine, or more than nine ring atoms. $C_x$heteroaryl refers to a heteroaryl having x number of ring carbon atoms wherein the remaining ring atom(s) are heteroatom(s). The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,1-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$SR^a$, —$R^b$—OC(O)—$R^a$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Sulfanyl" refers to the —S— radical.
"Sulfinyl" refers to the —S(=O)— radical.
"Sulfonyl" refers to the —S(=O)$_2$— radical.
"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Imino" refers to the =NH radical.
"Thioxo" refers to the =S radical.
An "alkoxy" group refers to a (alkyl)O— group, where alkyl is as defined herein.
An "aryloxy" group refers to an (aryl)O— group, where aryl is as defined herein.

"Carbocyclylalkyl" means an alkyl radical, as defined herein, substituted with a carbocyclyl group. "Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

As used herein, the terms "heteroalkyl", "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond," "direct bond" or "single bond" refers to a chemical bond between two atoms, or two moieties when the atoms joined by the bond are considered to be part of larger substructure.

An "isocyanato" group refers to a —NCO group.

An "isothiocyanato" group refers to a —NCS group.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "alkylthioalkyl" group refers to an alkyl group substituted with a —S-alkyl group.

As used herein, the term "acyloxy" refers to a group of formula RC(=O)O—.

"Carboxy" means a —C(O)OH radical.

As used herein, the term "acetyl" refers to a group of formula —C(=O)$CH_3$.

"Acyl" refers to the group —C(O)R.

As used herein, the term "trihalomethanesulfonyl" refers to a group of formula $X_3$CS(=O)$_2$— where X is a halogen.

"Cyanoalkyl" means an alkyl radical, as defined herein, substituted with at least one cyano group.

As used herein, the term "N-sulfonamido" or "sulfonylamino" refers to a group of formula RS(=O)$_2$NH—.

As used herein, the term "O-carbamyl" refers to a group of formula —OC(=O)NR$_2$.

As used herein, the term "N-carbamyl" refers to a group of formula ROC(=O)NH—.

As used herein, the term "O-thiocarbamyl" refers to a group of formula —OC(=S)NR$_2$.

As used herein, "N-thiocarbamyl" refers to a group of formula ROC(=S)NH—.

As used herein, the term "C-amido" refers to a group of formula —C(=O)NR$_2$.

"Aminocarbonyl" refers to a —CONH$_2$ radical.

As used herein, the term "N-amido" refers to a group of formula RC(=O)NH—.

As used herein, the substituent "R" appearing by itself and without a number designation refers to a substituent selected from among from alkyl, cycloalkyl, aryl, heteroaryl (bonded through a ring carbon) and non-aromatic heterocycle (bonded through a ring carbon).

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to an (alkenyl)O— group, where alkenyl is as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, N.Y., 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O) O—, -(substituted or unsubstituted $C_1$-$C_6$ alkyl), or -(substituted or unsubstituted $C_2$-$C_6$ alkenyl); and each $R_s$ is independently selected from H, (substituted or unsubstituted $C_1$-$C_4$alkyl), (substituted or unsubstituted $C_3$-$C_6$cycloalkyl), aryl, heteroaryl, or heteroalkyl. The protecting groups that may form the protective derivatives of the above substituents are known to those of skill in the art and may be found in references such as Greene and Wuts, above.

The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile. Non-limiting examples of Michael acceptor moieties include substituted or unsubstituted alkenyl and substituted or unsubstituted alkynyl connected to an electronic withdrawing group such as —C(O)—, —SO$_2$—, CN or NO$_2$, etc.

The term "nucleophile" or "nucleophilic" refers to an electron rich compound, or moiety thereof. An example of a nucleophile includes, but in no way is limited to, a cysteine residue of a molecule, such as, for example Cys 481 of Btk.

The term "electrophile", or "electrophilic" refers to an electron poor or electron deficient molecule, or moiety thereof. Examples of electrophiles include, but in no way are limited to, Michael acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which compounds disclosed herein, such as, compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are absorbed into the general circulation when the pharmaceutical composition is taken orally as compared to intravenous injection.

"Blood plasma concentration" refers to the concentration of compounds disclosed herein, such as, compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) in the plasma component of blood of a subject. It is understood that the plasma concentration of compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) may vary significantly between subjects, due to variability with respect to metabolism and/or possible interactions with other therapeutic agents. In accordance with one embodiment disclosed herein, the blood plasma concentration of the compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) may vary from subject to subject. Likewise, values such as maximum plasma concentration (Cm) or time to reach maximum plasma concentration ($T_{max}$), or total area under the plasma concentration time curve (AUC$_{(0-\infty)}$) may vary from subject to subject. Due to this variability, the amount necessary to constitute "a therapeutically effective amount" of a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) may vary from subject to subject.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Acession No. AAB47246), dog (GenBank Acession No. XP_549139.), rat (GenBank Acession No. NP_001007799), chicken (GenBank Acession No. NP_989564), or zebra fish (GenBank Acession No. XP_698117), and fusion proteins of any of the foregoing that exhibit kinase activity towards one or more substrates of Bruton's tyrosine kinase (e.g. a peptide substrate having the amino acid sequence "AVLESEEELYS-SARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein, refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages are presented to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor. In contrast, a reversible inhibitor compound upon contact with a target protein does not cause the formation of a new covalent bond with or within the protein and therefore can associate and dissociate from the target protein.

The term "irreversible Btk inhibitor," as used herein, refers to an inhibitor of Btk that can form a covalent bond with an amino acid residue of Btk. In one embodiment, the irreversible inhibitor of Btk can form a covalent bond with a Cys residue of Btk; in particular embodiments, the irreversible inhibitor can form a covalent bond with a Cys 481 residue (or a homolog thereof) of Btk or a cysteine residue in the homologous corresponding position of another tyrosine kinase.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which they are associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient which will relieve to some extent, one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

The methods described herein include administering to a subject in need a composition containing a therapeutically effective amount of one or more reversible or irreversible Btk inhibitor compounds described herein. Without being bound by theory, the diverse roles played by Btk signaling in various hematopoietic cell functions, e.g., B-cell receptor activation, suggests that small molecule Btk inhibitors are useful for reducing the risk of or treating a variety of diseases affected by or affecting many cell types of the hematopoetic lineage including, e.g., autoimmune diseases, heteroimmune conditions or diseases, inflammatory diseases, cancer (e.g., B-cell proliferative disorders), and thromboembolic disorders. Further, the irreversible Btk inhibitor compounds described herein can be used to inhibit a small subset of other tyrosine kinases that share homology with Btk by having a cysteine residue (including a Cys 481 residue) that can form a covalent bond with the irreversible inhibitor. Thus, a subset of tyrosine kinases other than Btk is also expected to be useful as therapeutic targets in a number of health conditions.

In some embodiments, the methods described herein can be used to treat an autoimmune disease, which includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

In some embodiments, the methods described herein can be used to treat heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In further embodiments, the methods described herein can be used to treat an inflammatory disease, which includes, but is not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In yet other embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In further embodiments, the methods described herein can be used to treat thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Symptoms, diagnostic tests, and prognostic tests for each of the above-mentioned conditions are known in the art. See, e.g., *Harrison's Principles of Internal Medicine©,"* 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of reversible or irreversible Btk inhibitor compounds for treating any of the foregoing diseases.

For example, dosing of reversible or irreversible Btk inhibitor compounds for treating an autoimmune disease can be assessed in a mouse model of rheumatoid arthitis. In this model, arthritis is induced in Balb/c mice by administering anti-collagen antibodies and lipopolysaccharide. See Nandakumar et al. (2003), *Am. J. Pathol* 163:1827-1837.

In another example, dosing of reversible or irreversible Btk inhibitors for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866.

Animal models for treatment of thromboembolic disorders are also known.

The therapeutic efficacy of the compound for one of the foregoing diseases can be optimized during a course of treatment. For example, a subject being treated can undergo a diagnostic evaluation to correlate the relief of disease symptoms or pathologies to inhibition of in vivo Btk activity achieved by administering a given dose of an irreversible Btk inhibitor. Cellular assays known in the art can be used to determine in vivo activity of Btk in the presence or absence of an irreversible Btk inhibitor. For example, since activated Btk is phosphorylated at tyrosine 223 (Y223) and tyrosine 551 (Y551), phospho-specific immunocytochemical staining of P-Y223 or P-Y551-positive cells can be used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor compound that is administered to a subject can be increased or decreased as needed so as to maintain a level of Btk inhibition optimal for treating the subject's disease state.

Compounds

In the following description of reversible or irreversible Btk compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. In addition, nucleic acid and amino acid sequences for Btk (e.g., human Btk) are known in the art as disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

The Btk inhibitor compounds described herein are selective for Btk and kinases having a cysteine residue in an amino acid sequence position of the tyrosine kinase that is homologous to the amino acid sequence position of cysteine 481 in Btk. Inhibitor compounds described herein include a Michael acceptor moiety.

Further described are irreversible inhibitors of Btk that form a covalent bond with a serine residue on C481S mutated Btk. Specifically described are irreversible inhibitors of Btk that form a covalent bond with a serine481 residue on C481S mutated Btk (Woyach, et al. Resistance mechanisms for the Bruton's tyrosine kinase inhibitor ibrutinib, *N Engl J Med.* 2014, 12; 370(24):2286-94). Further described herein are irreversible inhibitors of other tyrosine kinases, wherein the other tyrosine kinases share homology with C481S mutated Btk by having a serine residue (including a homologous resisdue to BTK C481S residue) that can form a covalent bond with the inhibitor.

Further described herein are reversible inhibitors of C481S mutated Btk.

Further described herein are reversible inhibitors of other tyrosine kinases, wherein the other tyrosine kinases share homology with Btk.

Also described herein are reversible inhibitors of Btk.

Generally, a reversible or irreversible inhibitor compound of Btk used in the methods described herein is identified or characterized in an in vitro assay, e.g., an acellular biochemical assay or a cellular functional assay. Such assays are useful to determine an in vitro $IC_{50}$ for a reversible or irreversible Btk inhibitor compound.

For example, an acellular kinase assay can be used to determine Btk activity after incubation of the kinase in the absence or presence of a range of concentrations of a candidate irreversible Btk inhibitor compound. If the candidate compound is in fact an irreversible Btk inhibitor, Btk kinase activity will not be recovered by repeat washing with inhibitor-free medium. See, e.g., J. B. Smaill, et al. (1999), *J. Med. Chem.* 42(10):1803-1815. Further, covalent complex formation between Btk and a candidate irreversible Btk inhibitor is a useful indicator of irreversible inhibition of Btk that can be readily determined by a number of methods known in the art (e.g., mass spectrometry). For example, some irreversible Btk-inhibitor compounds can form a covalent bond with Cys 481 of Btk (e.g., via a Michael reaction).

Cellular functional assays for Btk inhibition include measuring one or more cellular endpoints in response to stimulating a Btk-mediated pathway in a cell line (e.g., BCR activation in Ramos cells) in the absence or presence of a range of concentrations of a candidate irreversible Btk inhibitor compound. Useful endpoints for determining a response to BCR activation include, e.g., autophosphorylation of Btk, phosphorylation of a Btk target protein (e.g., PLC-γ), and cytoplasmic calcium flux.

High throughput assays for many acellular biochemical assays (e.g., kinase assays) and cellular functional assays (e.g., calcium flux) are well known to those of ordinary skill in the art. In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of reversible or irreversible Btk compounds without undue effort.

Reversible or irreversible Btk inhibitor compounds can used for the manufacture of a medicament for treating any of the foregoing conditions (e.g., autoimmune diseases, inflammatory diseases, allergy disorders, B-cell proliferative disorders, or thromboembolic disorders).

In some embodiments, the reversible or irreversible Btk inhibitor compound used for the methods described herein inhibits Btk or a Btk homolog kinase activity with an in vitro $IC_{50}$ of less than about 10 µM. (e.g., less than about 1 µM, less than about 0.5 µM, less than about 0.4 µM, less than about 0.3 µM, less than about 0.1 µM, less than about 0.08 µM, less than about 0.06 µM, less than about 0.05 µM, less than about 0.04 µM, less than about 0.03 µM, less than about 0.02 µM, less than about 0.01 µM, less than about 0.008 µM, less than about 0.006 µM, less than about 0.005 µM, less than about 0.004 µM, less than about 0.003 µM, less than about 0.002 µM, less than about 0.001 µM, less than about 0.00099 µM, less than about 0.00098 µM, less than about 0.00097 µM, less than about 0.00096 µM, less than about 0.00095 µM, less than about 0.00094 µM, less than about 0.00093 µM, less than about 0.00092 µM, or less than about 0.00090 µM).

In one embodiment, the irreversible Btk inhibitor compound selectively and irreversibly inhibits an activated form of its target tyrosine kinase (e.g., a phosphorylated form of the tyrosine kinase). For example, activated Btk is transphosphorylated at tyrosine 551. Thus, in these embodiments the irreversible Btk inhibitor inhibits the target kinase in cells only once the target kinase is activated by the signaling events.

Described herein are compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId). Also described herein are pharmaceutically acceptable salts, pharmaceutically acceptable solvates, pharmaceutically active metabolites, and prodrugs of such compounds. Pharmaceutical compositions that include at least one such compound or a pharmaceutically acceptable salt, pharmaceutically acceptable solvate, pharmaceutically active metabolite or prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of Formula (A)-(C), (IA), (I), (IIa)-(IIb), (IIIa)-(IIId), (IVa)-(IVh), (Va)-(Vh), (Va)-(VIh), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are also provided.

In another aspect, the present invention provides a compound according to Formula (A) having the structure:

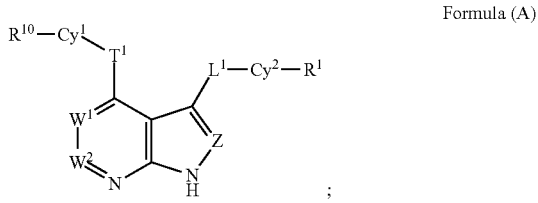

Formula (A)

or a solvate, pharmaceutically acceptable salt, or prodrug thereof; or a stereoisomer or an isotopic variant thereof; wherein:

one of $W^1$ and $W^2$ is $=C(R^9)-$, or $=N-$; and the other is $=C(R^9)-$;

Z is $=C(R^9)-$, or $=N-$;

$L^1$ is a single bond, $-CH_2-$, $-NH-CH_2-$, $-N(R^5)-$, $-O-$, or $-S-$;

$T^1$ is a single bond, $C_1$-$C_3$ alkylene, $-N(R^5)-$, $-O-$, or $-S-$;

$Cy^1$ is substituted or unsubstituted cycloalkyl, substituted or unsubstituted heterocycloalkyl, substituted or unsubstituted aryl or substituted or unsubstituted heteroaryl;

$Cy^2$ is substituted or unsubstituted cycloalkyl, substituted or unsubstituted heterocycloalkyl, substituted or unsubstituted aryl, or substituted or unsubstituted heteroaryl;

$R^1$ is H, halo, alkyl, OH, alkoxyalkyl, hydroxyalkyl, haloalkyl, cyano, $-O-R^{1a}$, $-C(O)-R^{1a}$, $-C(S)-R^{1a}$, $-C(O)-O-R^{1b}$, $-C(O)-C(O)-N(R^{1c})R^{1d}$, $-N(R^{1c})-C(O)R^{1d}$, $-C(O)-N(R^{1c})R^{1d}$, $-S(O)_p-R^{1a}$, or $-S(O)_p-N(R^{1c})R^{1d}$;

$R^{10}$ is halo, nitro, oxo, thioxo, $-R^{10b}-R^{10c}$, alkoxyalkyl, hydroxyalkyl, haloalkyl, cyano, $-R^{10b}-OR^{10a}$, $-R^{10b}-OC(O)R^{10a}$, $-R^{10b}-SR^{10a}$, $-R^{10b}-C(O)R^{10a}$, $-R^{10b}-C(S)R^{10a}$, $-R^{10b}-C(O)OR^{10a}$, $-R^{10b}-C(O)N(R^{10a})R^{10a}$, $-R^{10b}-O-R^{10e}-C(O)N(R^{10a})_2$, $-R^{10b}-OCH_2R^{10a}$, $-R^{10b}-SCH_2R^{10a}$, $-R^{10b}-N(R^{10d})C(O)R^{10c}$, $-R^{10b}-N(R^{10d})C(O)OR^{10c}$, $-R^{10b}-N(R^{10d})C(O)N(R^{10a})R^{10a}$, $-R^{10b}-N(R^{10a})R^{10a}$, $-R^{10b}-N(R^{10d})S(O)_pR^{10a}$, $-S(O)_pR^{10a}$, $-R^{10b}-S(O)_pOR^{10a}$, or $-R^{10b}-S(O)_pN(R^{10a})R^{10a}$;

p is 1 or 2;

each of $R^{1a}$, $R^{1b}$, $R^{1c}$, $R^{1d}$, and $R^{10a}$ is independently H, cyano, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

$R^{10b}$ is a single bond or a straight or branched alkylene or alkenylene chain;

$R^{10c}$ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

$R^{10d}$ is H, substituted or unsubstituted $C_1$-$C_6$alkyl, or substituted or unsubstituted $C_3$-$C_8$cycloalkyl;

$R^{10e}$ is a straight or branched alkylene or alkenylene chain;

each of $R^5$ is independently H, $-C(O)-R^{5a}$, $C_1$-$C_6$ alkyl, or $C_1$-$C_6$ heteroalkyl; or when each of $L^1$ and $T^1$ is independently $-N(R^5)-$, then the two R's may join together to form a substituted or unsubstituted heterocycle;

$R^{5a}$ is substituted or unsubstituted $C_1$-$C_4$alkyl, substituted or unsubstituted $C_2$-$C_4$alkenyl, or substituted or unsubstituted $C_2$-$C_4$alkynyl;

each $R^9$ is independently H, halogen, $-CN$, $-OH$, $-NH_2$, $-SH$, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$cycloalkyl;

provided that (1) when $L^1$ is a single bond, then $Cy^2$ is substituted or unsubstituted fully saturated heterocycloalkyl, $R^1$ is cyano, $-C(O)-R^{1a}$ or $-N(R^{1c})-C(O)R^{1d}$, and $T^1$ is $C_1$-$C_3$ alkylene, $-N(R^5)-$, $-O-$, or $-S-$; and (2) when $L^1$ is $-NH-CH_2-$, then $Cy^2$ is substituted or unsubstituted fully saturated heterocycloalkyl; and (3) when $Cy^1$ is substituted or unsubstituted cycloalkyl or substituted or unsubstituted heterocycloalkyl, then $T^1$ is $C_1$-$C_3$ alkylene, $-N(R^5)-$, $-O-$, or $-S-$, and $R^{10}$ is cyano, $-C(O)R^{10a}$ or $-C(O)NHR^{10a}$.

In another aspect, the present invention provides a compound according to Formula (B) having the structure:

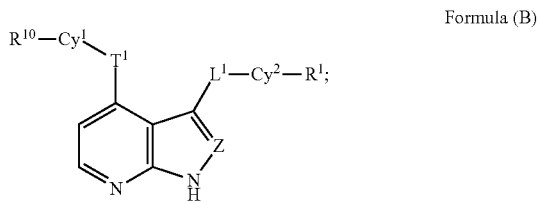

Formula (B)

or a solvate, pharmaceutically acceptable salt, or prodrug thereof; or a stereoisomer or an isotopic variant thereof; wherein:

Z is $=C(R^9)-$, or $=N-$;

$L^1$ is a single bond, $-CH_2-$, $-NH-CH_2-$, $-N(R^5)-$, $-O-$, or $-S-$;

$T^1$ is a single bond, $C_1$-$C_3$ alkylene, $-N(R^5)-$, $-O-$, or $-S-$;

$Cy^1$ is substituted or unsubstituted cycloalkyl, substituted or unsubstituted heterocycloalkyl, substituted or unsubstituted aryl or substituted or unsubstituted heteroaryl;

$Cy^2$ is substituted or unsubstituted cycloalkyl, substituted or unsubstituted heterocycloalkyl, substituted or unsubstituted aryl, or substituted or unsubstituted heteroaryl;

$R^1$ is H, halo, alkyl, OH, alkoxyalkyl, hydroxyalkyl, haloalkyl, cyano, $-O-R^{1a}$, $-C(O)-R^{1a}$, $-C(S)-R^{1a}$, $-C(O)-O-R^{1b}$, $-C(O)-C(O)-N(R^{1c})R^{1d}$, $-N(R^{1c})-C(O)R^{1d}$, $-C(O)-N(R^{1c})R^{1d}$, $-S(O)_p-R^{1a}$, or $-S(O)_p-N(R^{1c})R^{1d}$;

$R^{10}$ is halo, nitro, oxo, thioxo, $-R^{10b}-R^{10c}$, alkoxyalkyl, hydroxyalkyl, haloalkyl, cyano, $-R^{10b}-OR^{10a}$, $-R^{10b}-OC(O)R^{10a}$, $-R^{10b}-SR^{10a}$, $-R^{10b}-C(O)R^{10a}$, $-R^{10b}-$ C(S)R$^{10a}$, —R$^{10b}$—C(O)OR$^{10a}$, —R$^{10b}$—C(O)N(R$^{10a}$)R$^{10a}$, —R$^{10b}$—O—R$^{10e}$—C(O)N(R$^{1a}$)$_2$, —R$^{10b}$—OCH$_2$R$^{10a}$, —R$^{10b}$—SCH$_2$R$^{10a}$, —R$^{10b}$—N(R$^{10d}$)C(O)R$^{10c}$, —R$^{10b}$—N(R$^{10d}$)C(O)OR$^{10c}$, —R$^{10b}$—N(R$^{10d}$)C(O)N(R$^{10a}$)R$^{10a}$, —R$^{10b}$—N(R$^{10a}$)R$^{10a}$, —R$^{10b}$—N(R$^{10d}$)S(O)$_p$R$^{10a}$, —S(O)$_p$R$^{10a}$, —R$^{10b}$—S(O)$_p$OR$^{10a}$, or —R$^{10b}$—S(O)$_p$N(R$^{10a}$)R$^{10a}$;

p is 1 or 2;

each of R$^{1a}$, R$^{1b}$, R$^{1c}$, R$^{1d}$, and R$^{10a}$ is independently H, cyano, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

R$^{10b}$ is a single bond or a straight or branched alkylene or alkenylene chain;

R$^{10c}$ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

R$^{10d}$ is H, substituted or unsubstituted C$_1$-C$_6$alkyl, or substituted or unsubstituted C$_3$-C$_8$cycloalkyl;

R$^{10e}$ is a straight or branched alkylene or alkenylene chain;

each of R$^5$ is independently H, —C(O)—R$^{5a}$, C$_1$-C$_6$ alkyl, or C$_1$-C$_6$ heteroalkyl; or when each of L$^1$ and T$^1$ is independently —N(R$^5$)—, then the two R's may join together to form a substituted or unsubstituted heterocycle;

R$^{5a}$ is substituted or unsubstituted C$_1$-C$_4$alkyl, substituted or unsubstituted C$_2$-C$_4$alkenyl, or substituted or unsubstituted C$_2$-C$_4$alkynyl;

each R$^9$ is independently H, halogen, —CN, —OH, —NH$_2$, —SH, substituted or unsubstituted C$_1$-C$_6$alkyl, substituted or unsubstituted C$_1$-C$_4$alkoxy, substituted or unsubstituted C$_1$-C$_6$heteroalkyl, substituted or unsubstituted phenyl, substituted or unsubstituted heteroaryl, or substituted or unsubstituted C$_3$-C$_8$cycloalkyl;

provided that (1) Cy$^1$-R$^{10}$ together is other than substituted or unsubstituted 2-F-phenyl;

(2) when L$^1$ is a single bond, T$^1$ is —N(R$^5$)—; then Cy$^2$-R$^1$ is other than 2-amino-4-pyrimidinyl or 3-phenoxyphenyl;

(3) when L$^1$ is a single bond, T$^1$ is —N(R$^5$)—; then Cy$^2$-R$^1$ is other than 4-morpholinylcarbonylphenyl; and (4) when T$^1$ is a single bond, then Cy$^2$ is substituted or unsubstituted fully saturated heterocycloalkyl.

In one embodiment, when L$^1$ is a single bond, then Cy$^2$ is substituted or unsubstituted fully saturated heterocycloalkyl, R$^1$ is cyano, —C(O)—R$^{1a}$ or —N(R$^{1c}$)—C(O)R$^{1d}$, and T$^1$ is C$_1$-C$_3$ alkylene, —O—, or —S—.

In another aspect, the present invention provides a compound according to Formula (C) having the structure:

Formula (C)

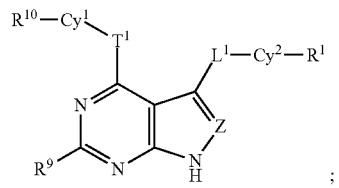

or a solvate, pharmaceutically acceptable salt, or prodrug thereof; or a stereoisomer or an isotopic variant thereof;

wherein:

Z is =C(R$^9$)—, or =N—;

L$^1$ is a single bond, —CH$_2$—, —NH—CH$_2$—, —N(R$^5$)—, —O—, or —S—;

T$^1$ is a single bond, C$_1$-C$_3$ alkylene, —N(R$^5$)—, —O—, or —S—;

Cy$^1$ is substituted or unsubstituted cycloalkyl, substituted or unsubstituted heterocycloalkyl, substituted or unsubstituted aryl or substituted or unsubstituted heteroaryl;

Cy$^2$ is heterocycloalkyl;

R$^1$ is cyano, —C(O)—R$^{1a}$, —C(S)—R$^{1a}$, —C(O)—O—R$^{1b}$, —C(O)—C(O)—N(R$^{1c}$)R$^{1d}$, —N(R$^{1c}$)—C(O)R$^{1d}$, —C(O)—N(R$^{1c}$)R$^{1d}$, —S(O)$_p$R$^{1a}$, or —S(O)$_p$—N(R$^{1c}$)R$^{1d}$;

R$^{10}$ is halo, nitro, oxo, thioxo, —R$^{10b}$—R$^{10c}$, alkoxyalkyl, hydroxyalkyl, haloalkyl, cyano, —R$^{10b}$—OR$^{10a}$, —R$^{10b}$—OC(O)R$^{10a}$, —R$^{10b}$—SR$^{10a}$, —R$^{10b}$—C(O)R$^{10a}$, —R$^{10b}$—C(S)R$^{10a}$, —R$^{10b}$—C(O)OR$^{10a}$, —R$^{10b}$—C(O)N(R$^{10a}$)R$^{10a}$, —R$^{10b}$—O—R$^{10e}$—C(O)N(R$^{10a}$)$_2$, —R$^{10b}$—OCH$_2$R$^{10a}$, —R$^{10b}$—SCH$_2$R$^{10a}$, —R$^{10b}$—N(R$^{10d}$)C(O)R$^{10c}$, —R$^{10b}$—N(R$^{10d}$)C(O)OR$^{10e}$, —R$^{10b}$—N(R$^{10d}$)C(O)N(R$^{10a}$)R$^{10a}$, —R$^{10b}$—N(R$^{10a}$)R$^{10a}$, —R$^{10b}$—N(R$^{10d}$)S(O)$_p$R$^{10a}$, —S(O)$_p$R$^{10a}$, —R$^{10b}$—S(O)$_p$OR$^{10a}$, or —R$^{10b}$—S(O)$_p$N(R$^{10a}$)R$^{1a}$;

p is 1 or 2;

each of R$^{1a}$, R$^{1b}$, R$^{1c}$, R$^{1d}$, and R$^{10a}$ is independently H, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

R$^{10b}$ is a single bond or a straight or branched alkylene or alkenylene chain;

R$^{10}$ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

R$^{10d}$ is H, substituted or unsubstituted C$_1$-C$_6$alkyl, or substituted or unsubstituted C$_3$-C$_8$cycloalkyl;

R$^{10e}$ is a straight or branched alkylene or alkenylene chain;

each of R$^5$ is independently H, —C(O)—R$^{5a}$, C$_1$-C$_6$ alkyl, or C$_1$-C$_6$ heteroalkyl; or when each of L$^1$ and T$^1$ is independently —N(R$^5$)—, then the two R's may join together to form a substituted or unsubstituted heterocycle;

R$^{5a}$ is substituted or unsubstituted C$_1$-C$_4$alkyl, substituted or unsubstituted C$_2$-C$_4$alkenyl, or substituted or unsubstituted C$_2$-C$_4$alkynyl;

each R$^9$ is independently H, halogen, —CN, —OH, —NH$_2$, —SH, substituted or unsubstituted C$_1$-C$_6$alkyl, substituted or unsubstituted C$_1$-C$_4$alkoxy, substituted or unsubstituted C$_1$-C$_6$heteroalkyl, substituted or unsubstituted phenyl, substituted or unsubstituted heteroaryl, or substituted or unsubstituted C$_3$-C$_8$cycloalkyl.

In one embodiment, Z is =N—, T$^1$ is NH, L$^1$ is a single bond, Cy$^2$ is piperazinyl, R$^1$ is —C(O)—R$^{1a}$; and Cy$^1$-R$^{10}$ is other than unsubstituted 3-chlorophenyl.

In one embodiment, when Z is =N—, T$^1$ is NH, L$^1$ is a single bond, Cy$^2$ is piperazinyl, and R$^1$ is —C(O)—R$^{1a}$; then Cy$^1$-R$^{10}$ is other than unsubstituted 3-chlorophenyl.

In one embodiment, Cy$^1$ is substituted or unsubstituted cycloalkyl. In another embodiment, Cy$^1$ is substituted or unsubstituted heterocycloalkyl. In another embodiment, Cy$^1$ is substituted or unsubstituted aryl. In another embodiment, Cy$^1$ is substituted or unsubstituted heteroaryl.

In some embodiments, Cy$^2$ is substituted or unsubstituted cycloalkyl. In some embodiments, Cy$^2$ is substituted or unsubstituted heterocycloalkyl. In another embodiment, Cy$^2$ is substituted or unsubstituted aryl. In some embodiments, Cy² is substituted or unsubstituted heteroaryl.

In some embodiments, $L^1$ is —CH$_2$—, —NH—CH$_2$—, —N(R$^5$)—, —O—, or —S—; and $T^1$ is C$_1$-C$_3$ alkylene, —N(R$^5$)—, —O—, or —S—.

In some embodiments, $L^1$ is a single bond. In some embodiments, $L^1$ is C$_1$-C$_3$ alkylene. In another embodiment, $L^1$ is —N(R$^5$)—CH$_2$—. In some embodiments, $L^1$ is —N(R$^5$)—. In another embodiment, $L^1$ is —O—. In another embodiment, $L^1$ is —S—.

In some embodiments, $T^1$ is a single bond. In some embodiments, $T^1$ is C$_1$-C$_3$ alkylene. In some embodiments, $T^1$ is —N(R$^5$)—CH$_2$—. In some embodiments, $T^1$ is —N(R$^5$)—. some embodiments, $T^1$ is —O—. In some embodiments, $T^1$ is —S—.

some embodiments, R$^1$ is halo, alkyl, OH, alkoxyalkyl, hydroxyalkyl, haloalkyl, cyano, —O—R$^{1a}$, —C(O)—R$^{1a}$, —C(S)—R$^{1a}$, —C(O)—O—R$^{1b}$, —C(O)—C(O)—N(R$^{1c}$)R$^d$, —N(R$^{1c}$)—C(O)R$^{1d}$, —C(O)—N(R$^{1c}$)R$^{1d}$, —S(O)$_p$—R$^{1a}$, or —S(O)$_p$—N(R$^{1c}$)R$^{1d}$, wherein R$^{1a}$, R$^{1b}$, R$^{1c}$, and R$^{1d}$ are as defined herein.

In some embodiments, R$^{10}$ is halo, cyano, —R$^{10b}$—R$^{10c}$, alkoxyalkyl, hydroxyalkyl, haloalkyl, —R$^{10b}$—OR$^{10a}$, —R$^{10b}$—OC(O)R$^{10a}$, —R$^{10b}$—C(O)R$^{10a}$, —R$^{10b}$—C(O) OR$^{10a}$, —R$^{10b}$—C(O)N(R$^{10a}$)R$^{10a}$, —R$^{10b}$—O—R$^{10e}$—C (O)N(R$^{10a}$)$_2$, —R$^{10b}$—OCH$_2$R$^{10a}$, —R$^{10b}$—N(R$^{10d}$)C(O) R$^{10a}$, —R$^{10b}$—N(R$^{10d}$)C(O)OR$^{10c}$, —R$^{10b}$—N(R$^{10d}$)C(O) N(R$^{10a}$)R$^{10a}$, —R$^{10b}$—N(R$^{10a}$)R$^{10a}$, —R$^{10b}$—N(R$^{10d}$) S(O)$_p$R$^{10a}$, —S(O)$_p$R$^{10a}$, or —R$^{10b}$—S(O)$_p$N(R$^{10a}$)R$^{10a}$.

In some embodiments, R$^{1a}$ is C$_1$-C$_6$ alkyl substituted with one, two or three substituents independently selected from CN, halo, hydroxyl, C$_1$-C$_6$ alkoxy, substituted or unsubstituted amino (e.g., alkylamino or dialkylamino wherein the alkyl is optionally substituted), phosphinic acid ester, phosphonic acid ester, phosphinamidate, phosphonamidate, a boronic acid or —B(OH)$_2$ group. In some embodiments, R$^{1a}$ is phenyl substituted with one, two, three, four or five substituents independently selected from boronic acid or —B(OH)$_2$.

In some embodiments, each R$^{1a}$, R$^{1b}$, R$^{1d}$, and R$^{10a}$ is independently selected from substituted or unsubstituted cycloalkyl, substituted or unsubstituted heterocycloalkyl, substituted or unsubstituted aryl, or substituted or unsubstituted heteroaryl.

In some embodiments, each R$^{1a}$, R$^{1b}$, R$^{1d}$, and R$^{10a}$ is independently H, substituted or unsubstituted alkyl, substituted or unsubstituted alkenyl or substituted or unsubstituted alkynyl. In some embodiments, each R$^{1a}$, R$^{1b}$, R$^{1d}$, and R$^{10a}$ is independently selected from CN,

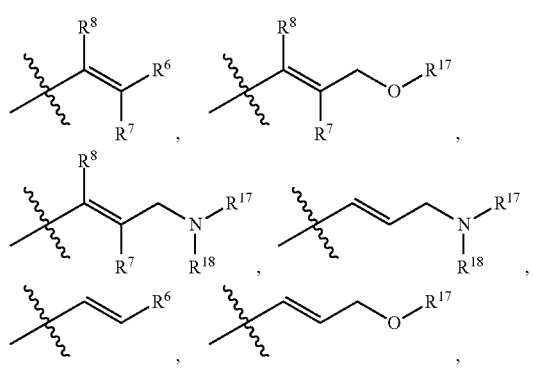

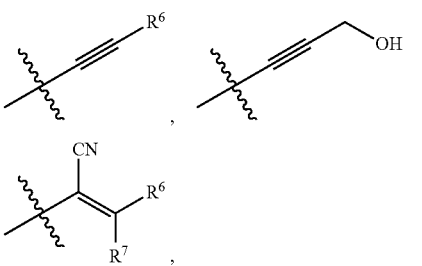

wherein R$^6$, R$^7$ and R$^8$ are each independently H, CN, halo, substituted or unsubstituted C$_1$-C$_4$alkyl, substituted or unsubstituted C$_3$-C$_8$cycloalkyl, substituted or unsubstituted 3- to 8-membered heterocycloalkyl, substituted or unsubstituted C$_6$-C$_{12}$aryl, or substituted or unsubstituted 5- to 8-membered heteroaryl; or R$^7$ and R$^8$ together form a bond; and R$^{17}$ and R$^{18}$ are independently H, substituted or unsubstituted C$_1$-C$_3$alkyl, substituted or unsubstituted C$_3$-C$_6$cycloalkyl, substituted or unsubstituted 3- to 8-membered heterocycloalkyl, substituted or unsubstituted C$_6$-C$_{12}$aryl, or substituted or unsubstituted 3- to 8-membered heteroaryl. In some embodiments, R$^6$ is H, CN, halo, substituted or unsubstituted C$_1$-C$_4$alkyl, substituted or unsubstituted C$_3$-C$_8$cycloalkyl, substituted or unsubstituted 3- to 8-membered heterocycloalkyl, substituted or unsubstituted C$_6$-C$_{12}$aryl, or substituted or unsubstituted 5- to 8-membered heteroaryl, and R$^7$ and R$^8$ are each independently H, CN, or halo; or R$^7$ and R$^8$ together form a bond. In some embodiments, R$^8$ is H, CN, F or Cl.

In some embodiments, each R$^{1a}$, R$^{1b}$, R$^{1d}$, and R$^{10a}$ is independently selected from

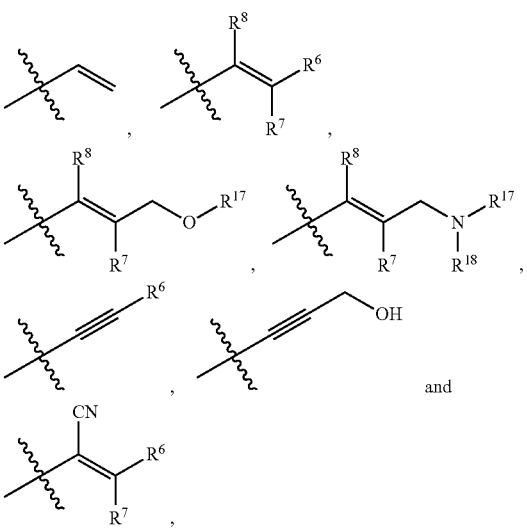

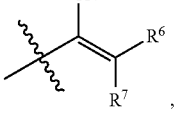

wherein R$^6$, R$^7$, R$^8$, R$^{17}$, and R$^{18}$ are as defined herein.

In some embodiments, R$^{1c}$ is H or C$_1$-C$_3$ alkyl. In some embodiments, R$^{10c}$ is H or C$_1$-C$_3$ alkyl.

In some embodiments, R$^{10b}$ is a single bond. In some embodiments, R$^{10b}$ is —CH$_2$—.

In a further embodiment provided herein are compounds having the structure of Formula (IA):

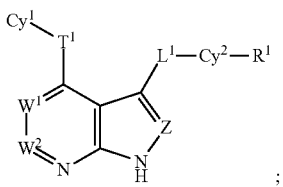

Formula (IA)

wherein:
one of $W^1$ and $W^2$ is $=C(R^9)—$, or $=N—$; and the other is $=C(R^9)—$;
Z is $=C(R^9)—$, or $=N—$;
$L^1$ is $C_1$-$C_3$ alkyl, $—N(R^5)—$, $—O—$, or $—S—$;
$T^1$ is a single bond, $C_1$-$C_3$ alkylene, $—N(R^5)—$, $—O—$, or $—S—$;
$Cy^1$ is substituted aryl or substituted heteroaryl;
$Cy^2$ is substituted or unsubstituted cycloalkyl, substituted or unsubstituted heterocycloalkyl, substituted or unsubstituted aryl, or substituted or unsubstituted heteroaryl;
$R^1$ is H, halo, alkyl, alkoxyalkyl, hydroxyalkyl, haloalkyl, cyano, $—C(O)—R^{1a}$, $—C(S)—R^{1a}$, $—C(O)—O—R^{1b}$, $—C(O)—N(R^{1c})R^{1d}$, $—S(O)_pR^{1a}$, or $—S(O)_p—N(R^{1c})R^{1d}$; p is 1 or 2;
each of $R^{1a}$, $R^{1b}$, $R^{1c}$, and $R^{1d}$ is independently H, cyano, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;
each of $R^5$ is independently H, $C_1$-$C_6$ alkyl, or $C_1$-$C_6$ heteroalkyl; or when each of $L^1$ and $T^1$ is independently $—N(R^5)—$, then the two R's may join together to form a substituted or unsubstituted heterocycle;
each $R^9$ is independently H, halogen, $—CN$, $—OH$, $—NH_2$, $—SH$, substituted or unsubstituted $C_1$-$C_6$alkyl, substituted or unsubstituted $C_1$-$C_4$alkoxy, substituted or unsubstituted $C_1$-$C_6$heteroalkyl, substituted or unsubstituted phenyl, substituted or unsubstituted heteroaryl, or substituted or unsubstituted $C_3$-$C_8$ cycloalkyl;
or a solvate, pharmaceutically acceptable salt, or prodrug thereof; or a stereoisomer or an isotopic variant thereof.

In one embodiment, $W^2$ is $C(R^9)$. In another embodiment, $W^2$ is $C(R^9)$; and $R^9$ is H, halogen, $—CN$, $—OH$, $—NH_2$, $—SH$, or substituted or unsubstituted $C_1$-$C_6$alkyl.

In another embodiment, $W^2$ is C(H).

In one embodiment, $T^1$ is $—CH_2—$, $—N(R^5)—$, $—O—$, or $—S—$.

In one embodiment, $Cy^1$ is substituted or unsubstituted phenyl. In another embodiment, $Cy^1$ is substituted or unsubstituted heteroaryl. In another embodiment, $Cy^1$ is substituted or unsubstituted pyridyl or pyrimidinyl.

In one embodiment, $Cy^1$ is substituted or unsubstituted heterocycle. In another embodiment, $Cy^1$ is substituted or unsubstituted pyridone.

In one particular embodiment, $Cy^1$ is substituted phenyl. In one embodiment, the substitution on phenyl is other than $—NH—C(O)$-heteroaryl.

In another particular embodiment, $Cy^1$ is substituted with at least one $R^2$; and $R^2$ is $-L^2$-$Cy^3$; $L^2$ is a single bond, $—CH_2—$, $—CH(OH)—$, $—C(O)—$, $—CH_2O—$, $—OCH_2—$, $—SCH_2—$, $—CH_2S—$, $—C(O)N(R^{21})—$, $—N(R^{21})C(O)—$, $—N(R^{21})—$, $—O—$, $—S—$, $—S(O)—$, $—S(O)_2—$, $—N(R^{21})S(O)_2—$, $—N(R^{21})S(O)—$, or $—S(O)_2N(R^{21})—$; and $Cy^3$ is a substituted or unsubstituted cycloalkyl, unsubstituted heterocycloalkyl, substituted or unsubstituted aryl, or a substituted or unsubstituted heteroaryl.

In one particular embodiment, $Cy^2$ is cycloalkyl, and $R^1$ is other than hydroxyl or trifluoroacyloxy.

In one particular embodiment, $Cy^2$ is heterocycloalkyl, and $R^1$ is other than alkyl, hydroxyalkyl, alkoxyalkyl, or fluoroalkyl.

In one particular embodiment, $Cy^2$ is cycloalkyl or heterocycloalkyl, $R^1$ is $—C(O)—R^{1a}$, $—C(S)—R^{1a}$, $—C(O)—O—R^{1b}$, $—C(O)—N(R^{1c})R^{1d}$, $—S(O)_p—R^{1a}$, or $—S(O)_p—N(R^{1c})R^{1d}$; p is 1 or 2; $R^{1a}$, $R^{1b}$, $R^{1c}$, and $R^{1d}$ are as described herein.

In another particular embodiment, $R^1$ is CN, $—C(O)—R^{1a}$, $—C(S)—R^{1a}$, $—C(O)—O—R^{1b}$, $—C(O)—N(R^{1c})R^{1d}$, $—S(O)_p—R^{1a}$, or $—S(O)_p—N(R^{1c})R^{1d}$; p is 1 or 2; $R^{1a}$, $R^{1b}$, $R^{1c}$, and $R^{1d}$ are as described herein.

In some embodiments, when $R^{10}$ is chloro, $Cy^1$ and $Cy^2$ are phenyl, then $R^1$ is other than $—C(O)—O—C(CH_3)_3$.

In some embodiments, when $L^1$ is $—NH—CH_2—$, then $Cy^2$ is substituted or unsubstituted fully saturated heterocycloalkyl and $R^1$ is $—C(O)—R^{1a}$, $—C(S)—R^{1a}$, $—C(O)—O—R^{1b}$, $—C(O)—N(R^{1c})R^{1d}$, $—S(O)_p—R^{1a}$, or $—S(O)_p—N(R^{1c})R^{1d}$.

In some embodiments, when $L^1$ is $—CH_2—$, then $R^1$ is other than H.

In some embodiments, when $T^1$ is a single bond, then $R^{10}$ is $—R^{10b}—C(O)N(R^{10a})R^{10a}$, $—R^{10b}—O—R^{10e}—C(O)N(R^{10a})_2$, $—R^{10b}—N(R^{10d})C(O)R^{10a}$, $—R^{10b}—N(R^{10d})C(O)OR^{10c}$, $—R^{10b}—N(R^{10d})C(O)N(R^{10a})R^{10a}$, $—R^{10b}—N(R^{10d})S(O)_pR^{1a}$, $—S(O)_pR^{10a}$, $—R^{10b}—S(O)_pOR^{10a}$, or $—R^{10b}—S(O)_pN(R^{10a})R^{10a}$.

In some embodiments, when $T^1$ is a $—CH_2—CH_2—$, and $L^1$ and O, then $Cy^2$ is other than tetrahydropyran substituted with three or more substituents independently selected from OH, $CH_2OH$, OC(O)-t-Bu and $CH_2OC(O)$-t-Bu.

In some embodiments, when $W^1$ is $=N—$, L and $T^1$ are both $—N(R^5)—$, $Cy^1$ and $Cy^2$ are both phenyl, and $R^1$ is H, halo, alkyl, OH, alkoxyalkyl, hydroxyalkyl, haloalkyl or cyano, then $R^{10}$ is $—R^{10b}—R^{10c}$, $—R^{10b}—OR^{10a}$, $—R^{10b}—OC(O)R^{10a}$, $—R^{10b}—SR^{10a}$, $—R^{10b}—C(O)R^{10a}$, $—R^{10b}—C(S)R^{10a}$, $—R^{10b}—C(O)OR^{10a}$, $—R^{10b}—C(O)N(R^{10a})R^{10a}$, $—R^{10b}—O—R^{10e}—C(O)N(R^{10a})_2$, $—R^{10b}—OCH_2R^{10a}$, $—R^{10b}—SCH_2R^{10a}$, $—R^{10b}—N(R^{10d})C(O)R^{10c}$, $—R^{10b}—N(R^{10d})C(O)OR^{10c}$, $—R^{10b}—N(R^{10d})C(O)N(R^{10a})R^{10a}$, $—R^{10b}—N(R^{10a})R^{10a}$, $—R^{10b}—N(R^{10d})S(O)_pR^{10a}$, $—S(O)_pR^{10a}$, $—R^{10b}—S(O)_pOR^{10a}$, or $—R^{10b}—S(O)_pN(R^{10a})R^{10a}$, and wherein at least one of $R^{10a}$ and $R^{10c}$ is substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl.

In some embodiments, when $W^1$ is $=N—$, then-$Cy^1$-$R^{10}$ together is other than unsubstituted 3-Cl-phenyl.

In some embodiments, -$Cy^1$-$R^{10}$ together is other than substituted or unsubstituted 2-F-phenyl.

In some embodiments, when $Cy^1$ is substituted or unsubstituted cycloalkyl, then $T^1$ is $C_1$-$C_3$ alkylene, $—N(R^5)—$, $—O—$, or $—S—$, and $R^{10}$ is $—C(O)R^{10a}$ or $—C(O)NHR^{10a}$.

In another embodiment, the compound is according to Formula (I) having the structure:

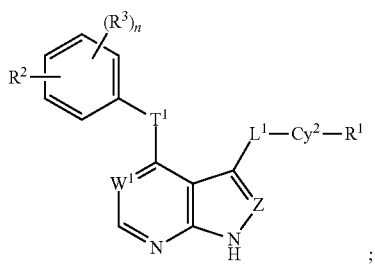

Formula (I)

wherein:
W$^1$ is =C(H)—, or =N—;
Z is =C(R$^9$)—, or =N—;
L$^1$ is C$_1$-C$_3$ alkyl, —N(R$^5$)—, —O—, or —S—;
T$^1$ is —CH$_2$—, —N(R$^5$)—, —O—, or —S—;
Cy$^2$ is substituted or unsubstituted cycloalkyl, substituted or unsubstituted heterocycloalkyl, substituted or unsubstituted aryl, or substituted or unsubstituted heteroaryl;
R$^1$ is cyano, —C(O)—R$^{1a}$, —C(S)—R$^{1a}$, —C(O)—O—R$^{1b}$, —C(O)—N(R$^{1c}$)R$^{1d}$, —S(O)$_p$—R$^{1a}$, or —S(O)$_p$—N(R$^{1c}$)R$^{1d}$; p is 1 or 2;
each of R$^{1a}$, R$^{1b}$, R$^{1c}$, and R$^{1d}$ is independently H, cyano, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;
R$^2$ is halogen, —CN, —NO$_2$, —OH, —OR$^{20}$, —OCF$_3$, —OCH$_2$F, —OCF$_2$H, —CF$_3$, —SR$^{21}$, —N(R$^{21}$)C(=O)R$^{23}$, —N(R$^{21}$)S(=O)$_2$R$^{23}$, —S(=O)$_2$N(R$^{21}$)(R$^{22}$), —S(=O)R$^{23}$, —S(=O)$_2$R$^{23}$, —C(=O)R$^{23}$, —OC(=O)R$^{23}$, —CO$_2$R$^{21}$, —N(R$^{21}$)(R$^{22}$), substituted or unsubstituted alkyl, substituted or unsubstituted heteroalkyl, substituted or unsubstituted heterocycloalkyl, substituted or unsubstituted cycloalkyl, or -L$^2$-Cy$^3$;
L$^2$ is a single bond, —CH$_2$—, —CH(OH)—, —C(O)—, —CH$_2$O—, —OCH$_2$—, —SCH$_2$—, —CH$_2$S—, —C(O)N(R$^{21}$)—, —N(R$^{21}$)C(O)—, —N(R$^{21}$)—, —O—, —S—, —S(O)—, —S(O)$_2$—, —N(R$^{21}$)S(O)$_2$—, —N(R$^{21}$)S(O)—, or —S(O)$_2$N(R$^{21}$)—;
Cy$^3$ is a substituted or unsubstituted cycloalkyl, unsubstituted heterocycloalkyl, substituted or unsubstituted aryl, or a substituted or unsubstituted heteroaryl;
each R$^3$ is each independently halogen, —CN, —NO$_2$, —OH, —OCF$_3$, —OCH$_2$F, —OCF$_2$H, —CF$_3$, —SR$^{21}$, —N(R$^{21}$)S(=O)$_2$R$^{23}$, —S(=O)$_2$N(R$^{21}$)(R$^{22}$), —S(=O)R$^{23}$, —S(=O)$_2$R$^{23}$, —C(=O)R$^{23}$, —OC(=O)R$^{23}$, —CO$_2$R$^{21}$, —N(R$^{21}$)(R$^{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;
each of R$^5$ is independently H, C$_1$-C$_6$ alkyl, or C$_1$-C$_6$ heteroalkyl; or when each of L$^1$ and T$^1$ is independently —N(R$^5$)—, then the two R's may join together to form a substituted or unsubstituted heterocycle;
R$^9$ is H, halogen, —CN, —OH, —NH$_2$, —SH, substituted or unsubstituted C$_1$-C$_6$alkyl, substituted or unsubstituted C$_1$-C$_4$alkoxy, substituted or unsubstituted C$_1$-C$_6$heteroalkyl, substituted or unsubstituted phenyl, substituted or unsubstituted heteroaryl, or substituted or unsubstituted C$_3$-C$_8$ cycloalkyl;
R$^{20}$ is substituted or unsubstituted C$_1$-C$_6$alkyl, substituted or unsubstituted C$_1$-C$_8$heteroalkyl, substituted or unsubstituted heteroaryl, or substituted or unsubstituted aryl;
each R$^{21}$ and R$^{22}$ are each independently H, substituted or unsubstituted C$_1$-C$_6$alkyl, or substituted or unsubstituted C$_3$-C$_8$cycloalkyl;
R$^{23}$ is each independently substituted or unsubstituted C$_1$-C$_6$alkyl, or substituted or unsubstituted C$_3$-C$_8$cycloalkyl;
n is 0-4; or
a solvate, pharmaceutically acceptable salt, or prodrug thereof.

In one embodiment, the compound is other than benzoic acid, 4-[[4-[(3-chlorophenyl)amino]-1H-pyrazolo[3,4-d]pyrimidin-3-yl]amino]-, 1,1-dimethylethyl ester.

In another embodiment, when R$^2$ is Cl, Cy$^2$ is phenyl, and R$^1$ is —C(O)—O—R$^{1b}$; then R$^{1b}$ is other than t-Bu.

In another embodiment, when Cy$^2$ is piperidin-4-yl, R$^{1b}$ is Me, CH$_2$OH, or CH$_2$NH$_2$, R$^2$ is L$^2$-Cy$^3$, L$^2$ is —NH—CO—, and n is 1; then R$^3$ is other than 2-F.

In one embodiment, each of R$^{1a}$, R$^{1b}$, R$^{1c}$, and R$^{1d}$ is independently substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl. In another embodiment, each of R$^{1a}$, R$^{1b}$, R$^{1c}$, and R$^{1d}$ is independently H.

In one embodiment, when R$^2$ is Cl, Cy$^2$ is phenyl, and R$^1$ is —C(O)—O—R$^{1b}$; then R$^{1b}$ is other than t-Bu.

In one embodiment, L$^1$ is —N(R$^5$)—CH$_2$—, —N(R$^5$)—, —O—, or —S—.

In one embodiment, T$^1$ is C$_1$-C$_3$ alkylene, —N(R$^5$)—, —O—, or —S—.

In one embodiment, L$^1$ is —N(R$^5$)—, —O—, or —S—, and T$^1$ is C$_1$-C$_3$ alkylene, —N(R$^5$)—, —O—, or —S—.

In one embodiment, L$^1$ is —O—. In another embodiment, L$^1$ is —S—. In yet another particular embodiment, L$^1$ is —N(R$^5$)—.

In one particular embodiment, L$^1$ is —N(R$^5$)—; and R$^5$ is H or C$_1$-C$_6$ alkyl.

In another particular embodiment, L$^1$ is —N(R$^5$)—; and R$^5$ is H, Me, Et, n-Pr, i-Pr, n-Bu, i-Bu, sec-Bu, or t-Bu.

In a more particular embodiment, L$^1$ is —N(R$^5$)—; and R$^5$ is H.

In another embodiment, each of L$^1$ and T$^1$ is independently —N(R$^5$)—; and the two R$^5$s are joined together to form a substituted or unsubstituted heterocycle. In one embodiment, the heterocycle is substituted with an oxo.

In one embodiment, each R$^9$ is independently H, halogen, —CN, —OH, —NH$_2$, substituted or unsubstituted C$_1$-C$_3$alkyl, substituted or unsubstituted C$_1$-C$_4$alkoxy, or substituted or unsubstituted C$_3$-C$_6$ cycloalkyl. In one embodiment, each R$^9$ is H.

In another embodiment, L$^1$ is a single bond; and Cy$^2$ and R$^1$ are as described herein.

In another embodiment, L$^1$ is —NH—; and Cy$^2$ and R$^1$ are as described herein. In one embodiment, Cy$^2$ is cycloalkyl; and R$^1$ is as described herein. In one embodiment, Cy$^2$ is heterocycloalkyl; and R$^1$ is as described herein. In one embodiment, Cy$^2$ is phenyl or pyridyl; and R$^1$ is as described herein. In one embodiment, R$^1$ is —C(O)—R$^{1a}$; and R$^{1a}$ is as described herein. In another embodiment, R$^1$ is CN, —CH=C(CN)—C(O)—NHMe, —CH=C(F)—C(O)—NHMe, —N(Me)-C(O)R$^{1a}$, or N(H)—C(O)R$^{1a}$; and $R^{1a}$ is as described herein. In a particular embodiment, $R^1$ is —C(O)—$R^{1a}$; and $R^{1a}$ is substituted or unsubstituted alkenyl.

In another embodiment, $L^1$ is —NH—CH$_2$—; and Cy$^2$ and $R^1$ are as described herein.

In a particular embodiment, $L^1$ is —NH—CH$_2$—; Cy$^2$ is heterocycloalkyl; and $R^1$ is as described herein. In one embodiment, $R^1$ is —C(O)—$R^{1a}$; and $R^{1a}$ is as described herein. In a particular embodiment, $R^1$ is —C(O)—$R^{1a}$; and $R^{1a}$ is substituted or unsubstituted alkenyl.

In another embodiment, the compound is according to Formula (IIa) or (IIb):

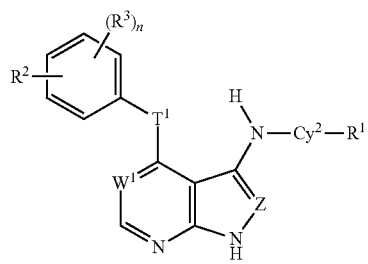
(IIa)

or

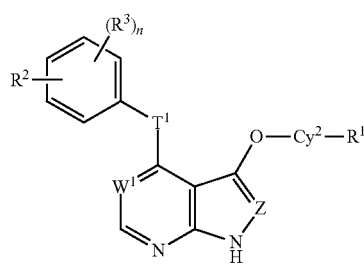
(IIb)

and wherein W$^1$, Z, Cy$^2$, T$^1$, R$^1$, R$^2$, R$^3$ and n are as described for formula (A)-(C), (I) or (IA).

In one embodiment, when the compound is according to formula IIa or IIb, Cy$^2$ is Ph or pyridyl; then $R^1$ is alkyl, alkoxyalkyl, hydroxyalkyl, haloalkyl, cyano, —C(O)—$R^{1a}$, —C(S)—$R^{1a}$, —C(O)—O—$R^{1b}$, —C(O)—N(R$^{1c}$)R$^{1d}$, —S(O)$_p$—$R^{1a}$, or —S(O)$_p$—N(R$^{1c}$)R$^{1d}$; and p is 1 or 2. In another embodiment, when the compound is according to formula IIa or IIb, Cy$^2$ is cycloalkyl, or heterocycloalkyl, $R^1$ is H, alkyl, substituted alkyl, halo, hydroxyl, or —C(O)—$R^{1a}$, and $R^{1a}$ is Me, CH$_2$OH, aminomethyl, or methylaminoethyl; then $R^3$ is other than 2-F.

In one embodiment, W$^1$ is =C(H)—. In another embodiment, W$^1$ is =N—.

In one embodiment, Z is =C(R$^9$)—. In another embodiment, Z is =C(R$^9$)—; and R$^9$ is H or C$_1$-C$_6$ alkyl. In yet another embodiment, Z is =C(R$^9$)—; and R$^9$ is H, Me, Et, n-Pr, i-Pr, n-Bu, i-Bu, sec-Bu, or t-Bu. In a further embodiment, Z is =C(R$^9$)—; and R$^9$ is F or CF$_3$.

In one particular embodiment, Z is =C(R$^9$)—; and R$^9$ is H.

In another particular embodiment, Z is =N—.

In another embodiment, the compound is according to Formula (IIIa), (IIIb), (IIIc) or (IIId):

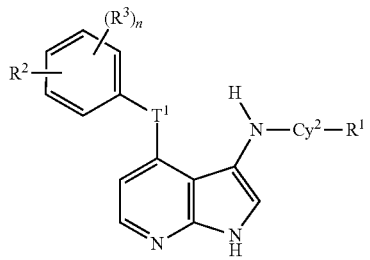
IIIa

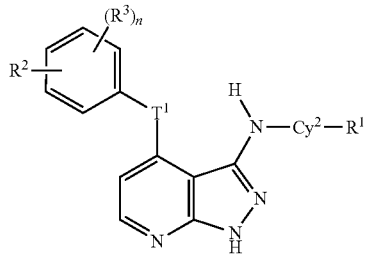
IIIb

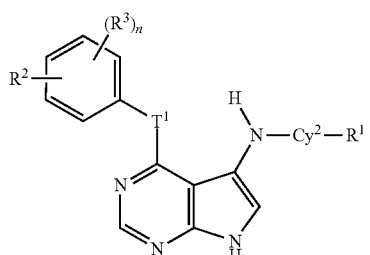
IIIc or

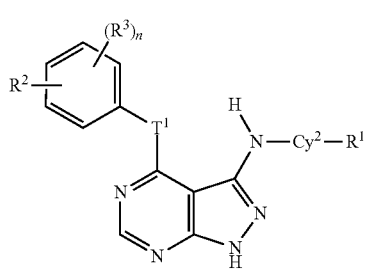
IIId and wherein Cy$^2$, T$^1$, R$^1$, R$^2$, R$^3$ and n are as described for formula (A)-(C), (I) or (IA).

In one embodiment, when the compound is according to formula IIIc or IIId, Cy$^2$ is Ph or pyridyl; then $R^1$ is alkyl, alkoxyalkyl, hydroxyalkyl, haloalkyl, cyano, —C(O)—$R^{1a}$, —C(S)—$R^{1a}$, —C(O)—O—$R^{1b}$, —C(O)—N(R$^{1c}$)R$^{1d}$, —S(O)$_p$—$R^{1a}$, or —S(O)$_p$—N(R$^{1c}$)R$^{1d}$; p is 1 or 2. In another embodiment, when the compound is according to formula IIIb, Cy$^2$ is cycloalkyl, or heterocycloalkyl, $R^1$ is H, alkyl, substituted alkyl, halo, hydroxyl, or —C(O)—$R^{1a}$, and $R^{1a}$ is Me, CH$_2$OH, aminomethyl, or methylaminoethyl; then $R^3$ is other than 2-F.

In one embodiment, Cy$^2$ is substituted or unsubstituted cycloalkyl.

In another embodiment, Cy$^2$ is cyclopropyl, cyclobutyl, cyclopentyl, cyclohexyl, or cycloheptyl.

In another embodiment, Cy$^2$ is substituted or unsubstituted aryl.

In another embodiment, Cy$^2$ is substituted or unsubstituted phenyl.

In another embodiment, Cy$^2$ is substituted or unsubstituted heteroaryl.

In another embodiment, Cy² is substituted or unsubstituted pyridyl, or pyrimidyl.

In another embodiment, Cy² is substituted or unsubstituted heterocycloalkyl.

In one particular embodiment, Cy² is substituted or unsubstituted pyrrolidinyl, piperidinyl, morpholinyl, or piperizinyl.

In a more particular embodiment, Cy² is substituted or unsubstituted pyrrolidinyl, or piperidinyl.

In one embodiment, T¹ is C₁-C₃ alkylene, —N(R⁵)—, —O—, or —S—;

In some embodiments, when T¹ is a single bond, then Cy² is substituted or unsubstituted fully saturated heterocycloalkyl.

In some embodiments, Cy² is other than substituted or unsubstituted tetrahydropyran.

In some embodiments, Cy¹-R¹⁰ together is other than substituted or unsubstituted 2-F-phenyl.

In some embodiments, when L¹ is a single bond, then Cy² is substituted or unsubstituted fully saturated heterocycloalkyl, R¹ is cyano, —C(O)—R¹ᵃ or —N(R¹ᶜ)—C(O)R¹ᵈ, and T¹ is C₁-C₃ alkylene, —O—, or —S—.

In some embodiments, when T¹ is a single bond, then Cy² is substituted or unsubstituted fully saturated heterocycloalkyl.

In some embodiments, when W¹ is N, and W² is =C(R⁹)—; then Cy² is heterocycloalkyl and R¹ is cyano, —C(O)—R¹ᵃ, —C(S)—R¹ᵃ, —C(O)—O—R¹ᵇ, —C(O)—C(O)—N(R¹ᶜ)R¹ᵈ, —N(R¹ᶜ)—C(O)R¹ᵈ, —C(O)—N(R¹)R¹ᵈ, —S(O)—R¹ᵃ, or —S(O)ₚ—N(R¹ᶜ)R¹ᵈ.

In another embodiment, the compound is according to Formula (IVa), (IVb), (IVc) or (IVd):

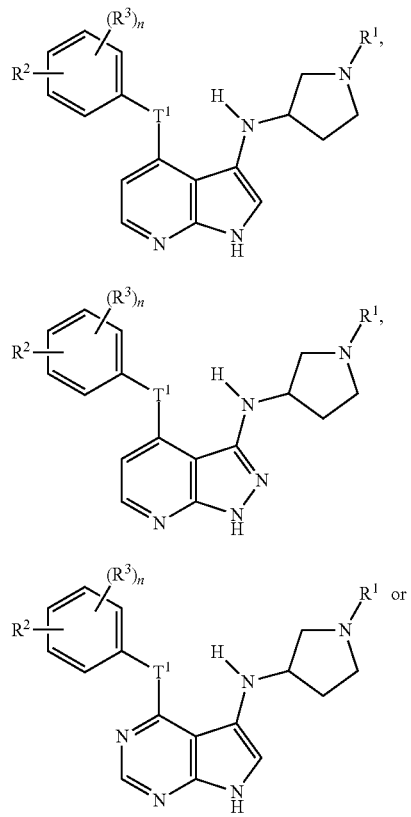

and wherein T¹, R¹, R², R³ and n are as described for formula (A)-(C), (I) or (IA).

In another embodiment, the compound is according to Formula (IVe), (IVf), (IVg) or (IVh):

and wherein T¹, R¹, R², R³ and n are as described for formula (A)-(C), (I) or (IA).

In another embodiment, the compound is according to Formula (Va), (Vb), (Vc) or (Vd):

Va

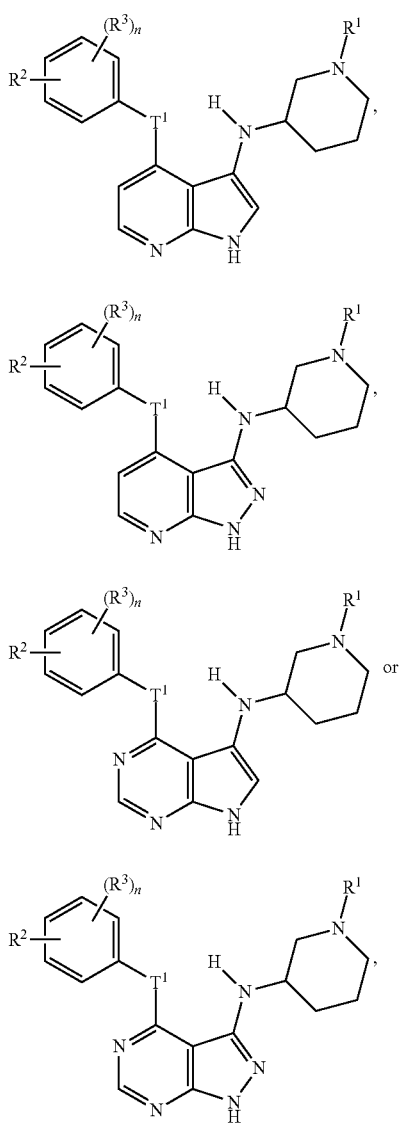

Vb

Vc

Vd and wherein $T^1$, $R^1$, $R^2$, $R^3$ and n are as described for formula (A)-(C), (I) or (IA).

In another embodiment, the compound is according to Formula (Ve), (Vf), (Vg) or (Vh):

Ve

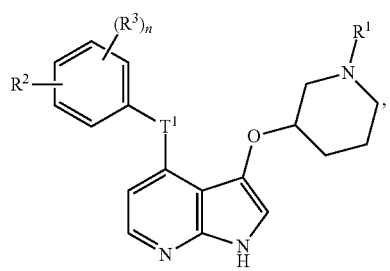

Vf

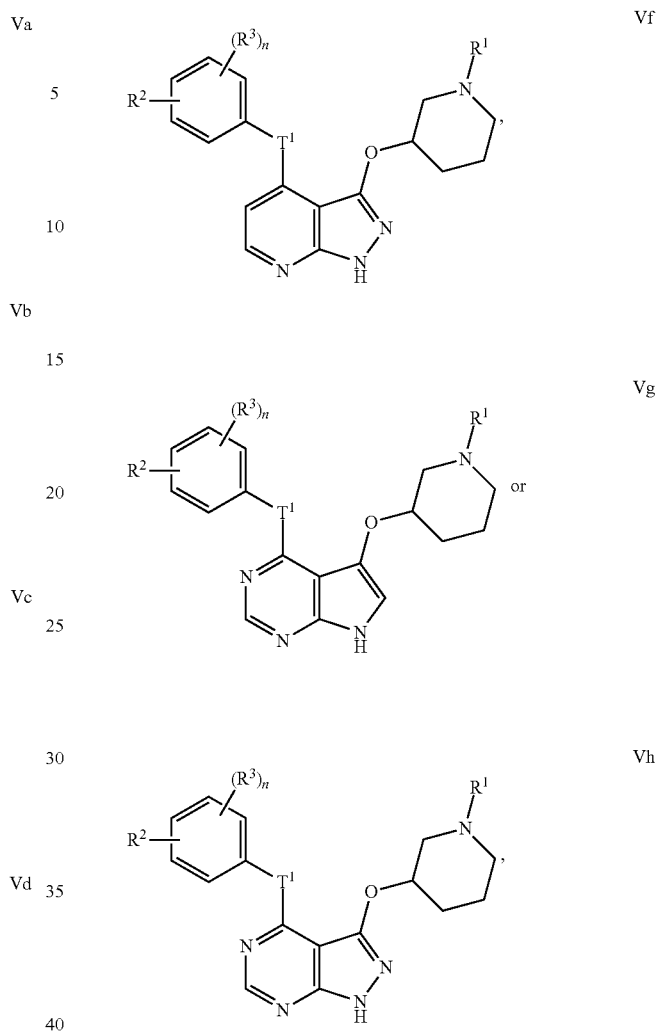

Vg

Vh and wherein $T^1$, $R^1$, $R^2$, $R^3$ and n are as described for formula (A)-(C), (I) or (IA); provided that when the compound is according to formula Vf, $T^1$ is O, n is 1, $R^3$ is 2-F; then $R^1$ is other than Me.

In one embodiment, $T^1$ is —CH$_2$—.

In another embodiment, $T^1$ is —O—, or —S—.

In one particular embodiment, $T^1$ is —N(R$^5$)—.

In a more particular embodiment, $T^1$ is —O—.

In another embodiment, the compound is according to Formula (VIa), or (VIb):

VIa

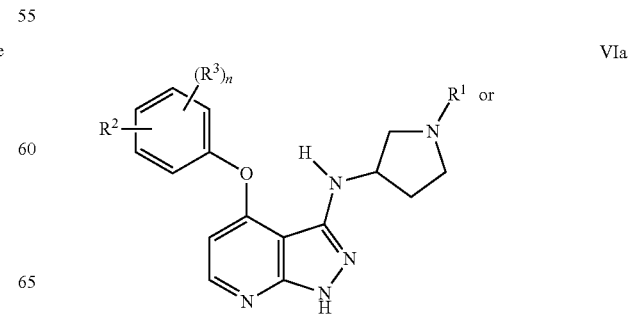

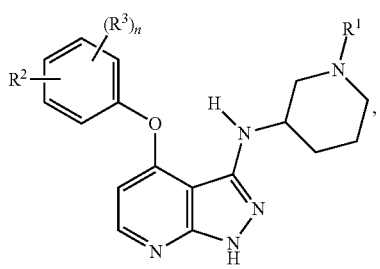
VIb and wherein $R^1$, $R^2$, $R^3$ and n are as described for formula (A), (B), (I) or (IA).

In another embodiment, the compound is according to Formula (VIc), or (VId):

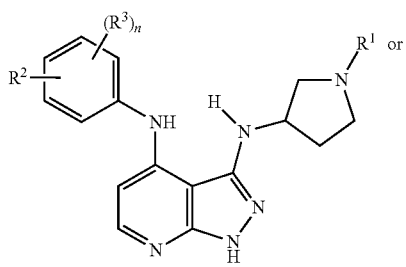
VIc

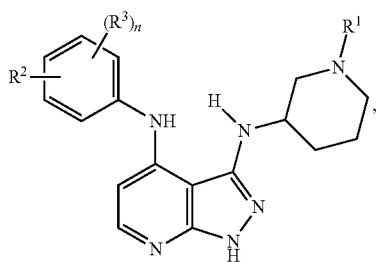
VId and wherein $R^1$, $R^2$, $R^3$ and n are as described for formula (A), (B), (I) or (IA).

In another embodiment, the compound is according to Formula (VIe), or (VIf):

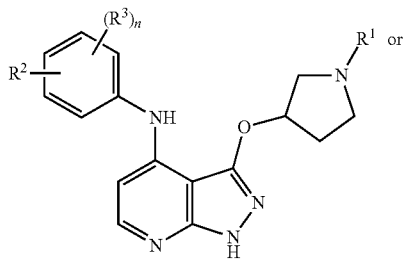
VIc

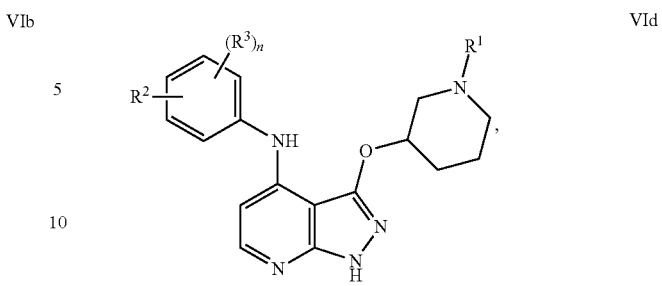
VId and wherein $R^1$, $R^2$, $R^3$ and n are as described for formula (A), (B), (I) or (IA).

In one embodiment, n is 1, 2, or 3.

In one embodiment, $R^3$ is halo, haloalkyl, CN, alkyl, hydroxyl, or alkoxy.

In one particular embodiment, n is 0.

In one embodiment, $R^2$ is halogen, —CN, —NO$_2$, —OH, —OR$^{20}$, —OCF$_3$, —OCH$_2$F, —OCF$_2$H, —CF$_3$, —SR$^{21}$, —N(R$^{21}$)S(═O)$_2$R$^{23}$, —S(═O)$_2$N(R$^{21}$)(R$^{22}$), —S(═O)R$^{23}$, —S(═O)$_2$R$^{23}$, —C(═O)R$^{23}$, —OC(═O)R$^{23}$, —CO$_2$R$^{21}$, —N(R$^{21}$)(R$^{22}$), substituted or unsubstituted alkyl, substituted or unsubstituted heteroalkyl, substituted or unsubstituted heterocycloalkyl, substituted or unsubstituted cycloalkyl.

In another embodiment, $R^2$ is -L$^2$-Cy$^3$.

In one embodiment, L$^2$ is a bond, —O— or —C(O)—NH—. In another embodiment, L$^2$ is —O— or —C(O)—NH—.

In another embodiment, the compound is according to Formula (VIIa), (VIIb), (VIIc) or (VIId):

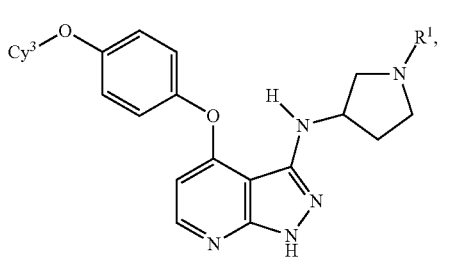
VIIa

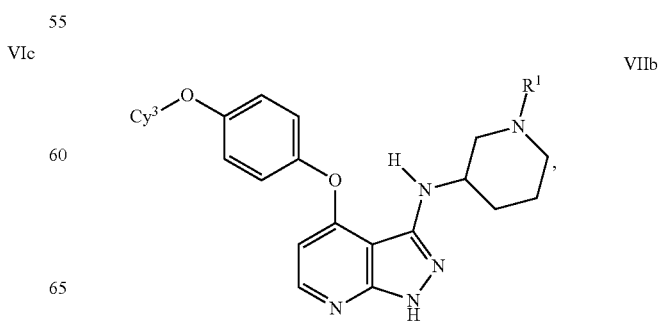
VIIb

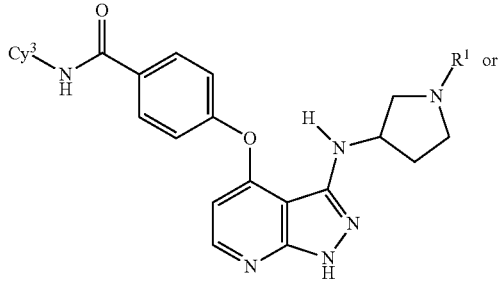

VIIc

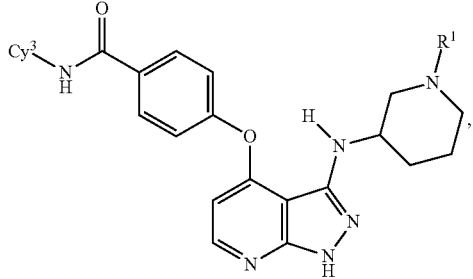

VIId and wherein Cy³ and R¹ are as described for formula (A), (B), (I) or (IA).

In another embodiment, the compound is according to Formula (VIIe), (VIIf), (VIIg) or (VIIh):

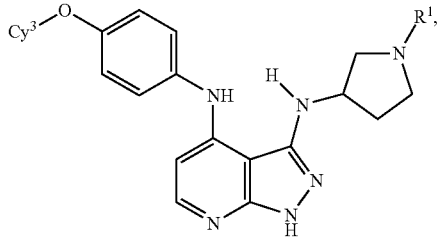

VIIe

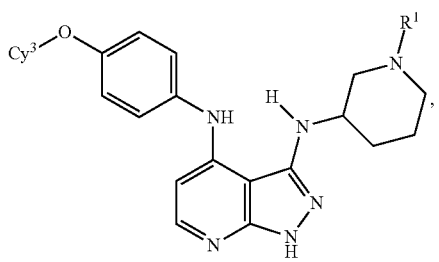

VIIf

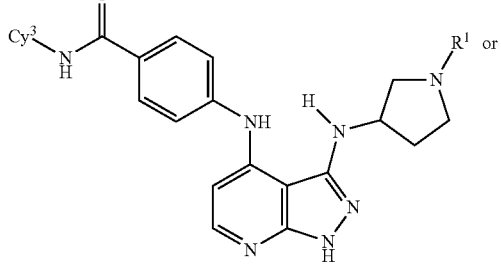

VIIg

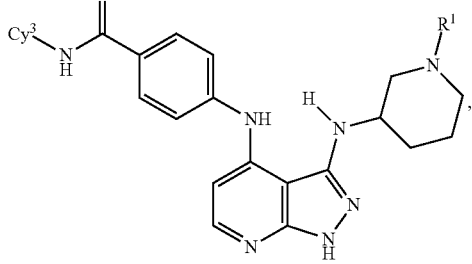

VIIh and wherein Cy³ and R¹ are as described for formula (A), (B), (I) or (IA).

In another embodiment, the compound is according to Formula (VIIi), (VIIj), (VIIk) or (VIII):

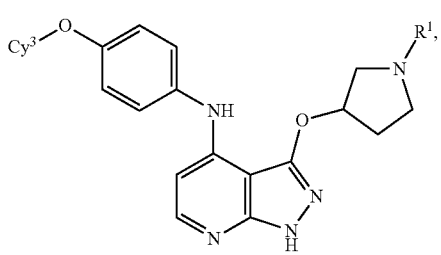

VIIi

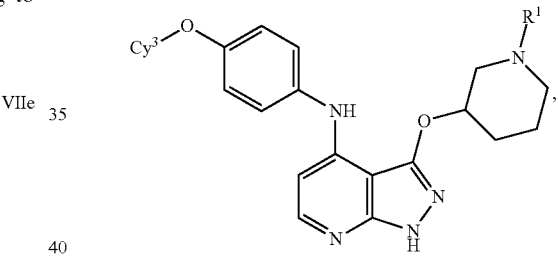

VIIj

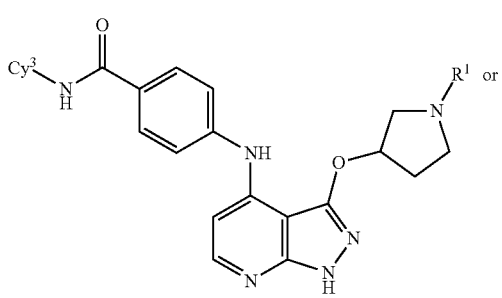

VIIk

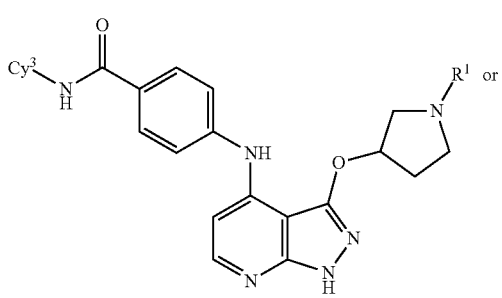

VIII and wherein Cy³ and R¹ are as described for formula (A), (B), (I) or (IA).

In one embodiment, Cy³ is substituted or unsubstituted cycloalkyl, or a substituted or unsubstituted heterocycloalkyl.

In one particular embodiment, Cy³ is substituted or unsubstituted phenyl.

In another particular embodiment, Cy³ is phenyl substituted with halo, CN, alkyl, haloalkyl, cycloalkyl, hydroxyl, or alkoxy. In another embodiment, when all of the substituent(s) of the phenyl are alkyl or when Cy³ is 4-isopropyl-3-methylphenyl, then each of $R^{1a}$, $R^{1b}$, and $R^{1d}$ is independently substituted or unsubstituted alkenyl, or substituted or unsubstituted alkynyl.

In another particular embodiment, Cy³ is substituted or unsubstituted or unsubstituted heteroaryl.

In another particular embodiment, Cy³ is substituted or unsubstituted pyrrolyl, thienyl, pyrazolyl, imidazolyl, oxazolyl, thiazolyl, traiazolyl, thiadiazolyl, pyridyl, pyrimidinyl, benzimidazolyl, benzoxazolyl, benzothiazolyl, oxazolopyridyl, or thiazolopyridyl. In a more particular embodiment, Cy³ is substituted or unsubstituted thiazolyl or pyridyl.

In another particular embodiment, Cy³ is pyridyl substituted with halo, CN, alkyl, haloalkyl, cycloalkyl, hydroxyl, or alkoxy.

In another particular embodiment, Cy³ is thiazolyl substituted with halo, CN, alkyl or haloalkyl.

In another embodiment, the compound is according to Formula (VIIIa), (VIIIb), (VIIIc) or (VIIId):

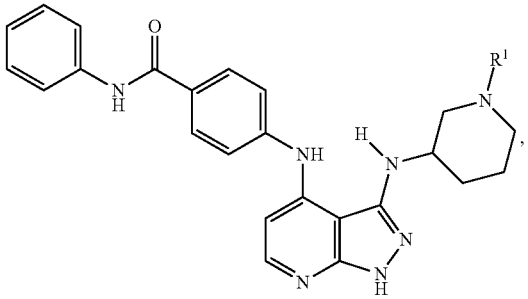

VIIIa

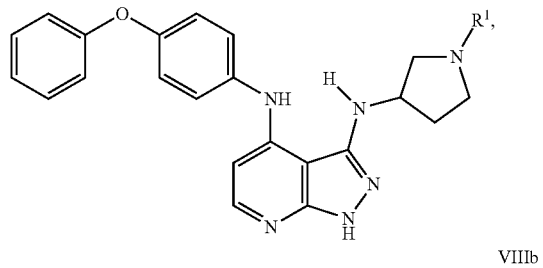

VIIIb

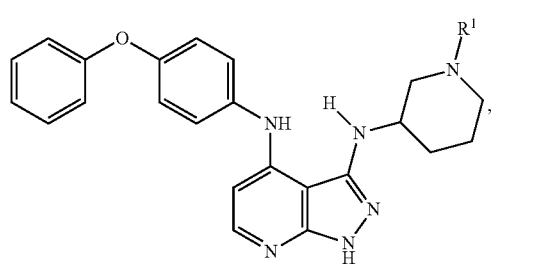

VIIIc

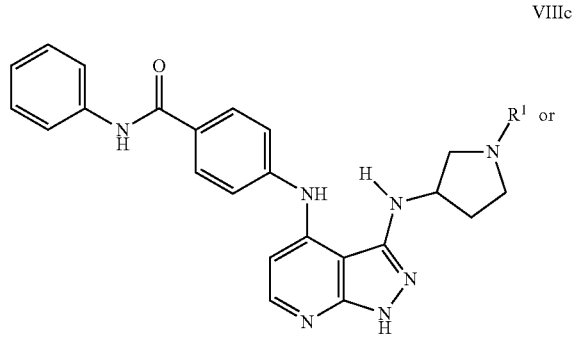

VIIId

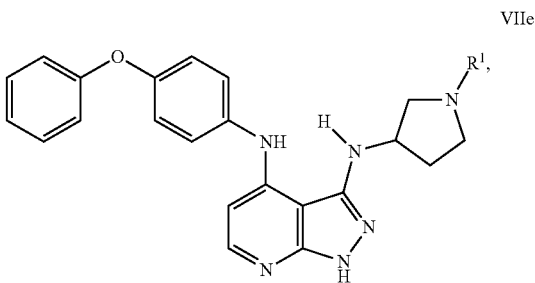

and wherein R¹ are as described for formula (A), (B) or (IA).

In another embodiment, the compound is according to Formula (VIIIe), (VIIIf), (VIIIg) or (VIIIh):

VIIe

VIIIf

VIIIg

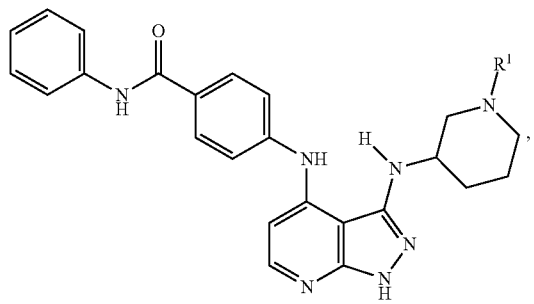
VIIIh
and wherein $R^1$ are as described for formula (A), (B) or (IA).
In another embodiment, the compound is according to Formula (VIIIi), (VIIIj), (VIIIk) or (VIIIl):
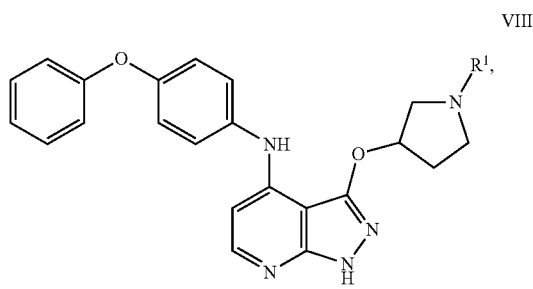
VIIIi
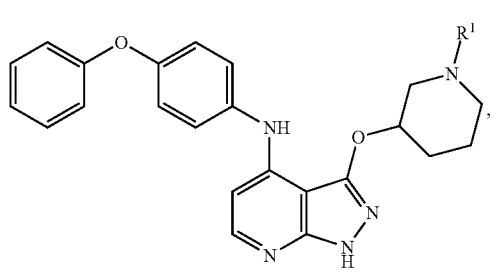
VIIIj
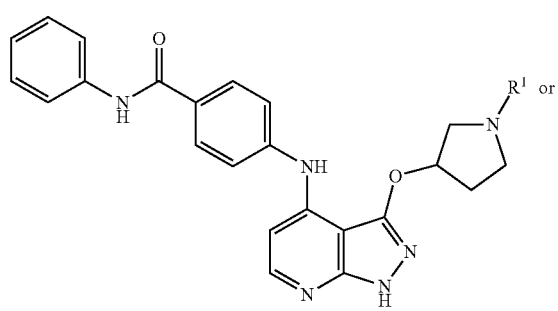
VIIIk
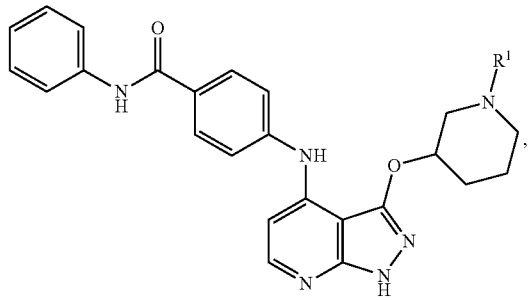
VIIIl
and wherein $R^1$ are as described for formula (A), (B) or (IA).
In another embodiment, the compound is according to Formula (IXa), (IXb), (IXc) or (IXd):
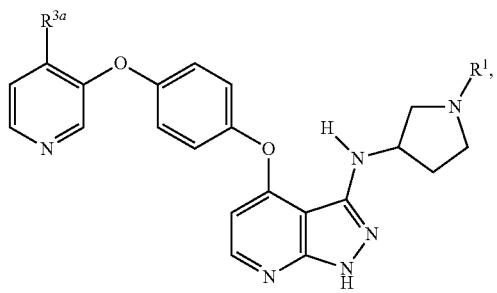
IXa
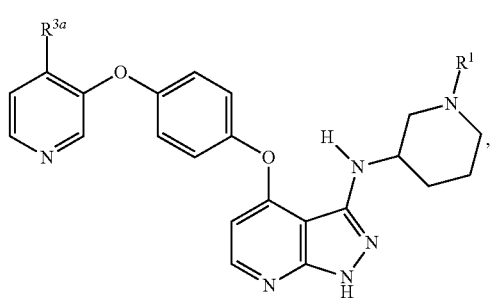
IXb
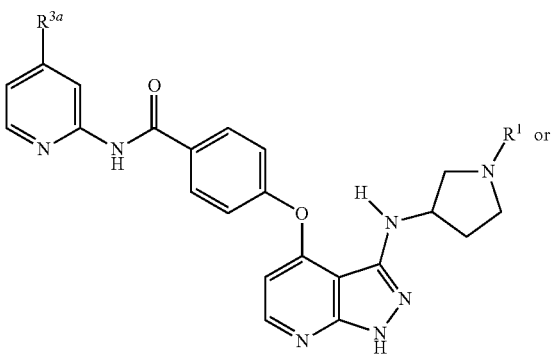
IXc IXd

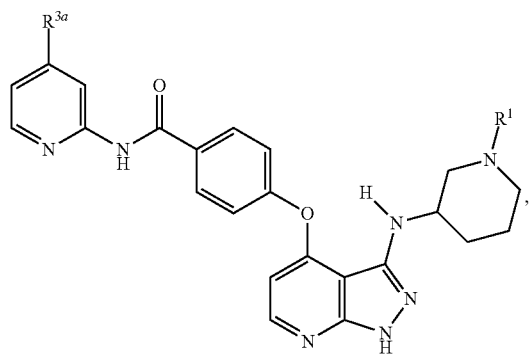

and wherein $R^1$ are as described for formula (A), (B) or (IA); and $R^{3a}$ is alkyl, haloalkyl, cycloalkyl, CN, or OH.

In another embodiment, the compound is according to Formula (IXe), (IXf), (IXg) or (IXh):

IXe

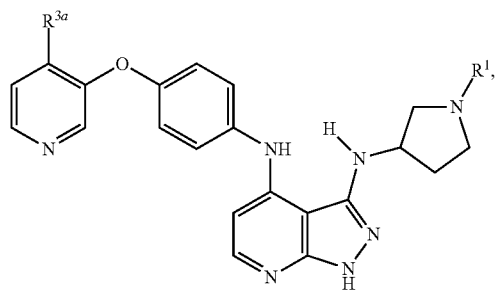

IXf

IXg

IXh

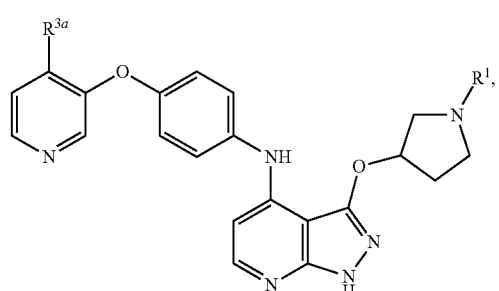

and wherein $R^1$ are as described for formula (A), (B) or (IA); and $R^{3a}$ is alkyl, haloalkyl, cycloalkyl, CN, or OH.

In another embodiment, the compound is according to Formula (IXi), (IXj), (IXk) or (IXl):

IXi

IXj

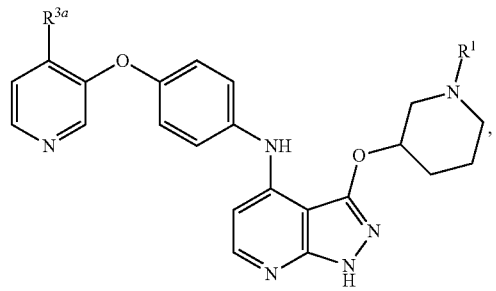

IXk

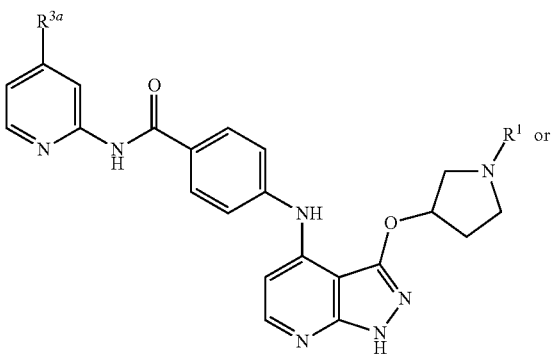

IXl

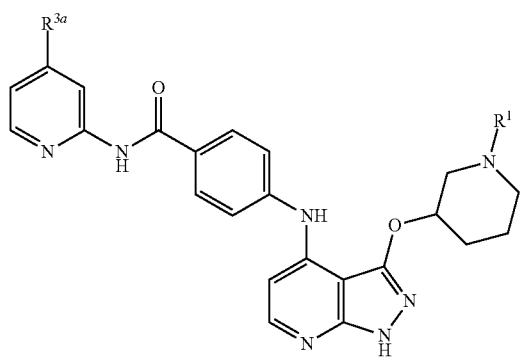

and wherein R¹ are as described for formula (A), (B) or (IA); and R³ᵃ is alkyl, haloalkyl, cycloalkyl, CN, or OH.

In one embodiment, R¹ is cyano, —C(O)—R¹ᵃ, —C(S)—R¹ᵃ, —C(O)—O—R¹ᵇ, —C(O)—N(R¹ᶜ)R¹ᵈ, —S(O)ₚ—R¹ᵃ, or —S(O)ₚ—N(R¹ᶜ)R¹ᵈ. In another embodiment, R¹ is —C(O)—R¹ᵃ; and R¹ᵃ is substituted or unsubstituted alkenyl. In another embodiment, R¹ is —C(O)—R¹ᵃ; and R¹ᵃ is substituted or unsubstituted ethenyl. In yet another embodiment, R¹ is —C(O)—R¹ᵃ; and R¹ᵃ is alkenyl, substituted with CN, C₁-C₆ alkyl, halo C₁-C₆ alkyl, substituted or unsubstituted cycloalkyl, substituted or unsubstituted aryl, substituted or unsubstituted heteroaryl, hydroxyl, hydroxyalkyl, substituted or unsubstituted aminoalkyl, or alkoxyalkyl. In yet another embodiment, and R¹ is —C(O)—R¹ᵃ; and R¹ᵃ is ethenyl substituted with substituted or unsubstituted aminoalkyl. In yet another embodiment, R¹ is —C(O)—R¹ᵃ; and R¹ᵃ is ethenyl substituted with alkylaminoalkyl, cycloalkylaminoalkyl, or diaklylaminoalkyl. In another particular embodiment, R¹ is —C(O)—R¹ᵃ; and R¹ᵃ is substituted or unsubstituted alkynyl. In another particular embodiment, R¹ is —C(O)—R¹ᵃ; and R¹ᵃ is ethynyl or propynyl. In a more particular embodiment, R¹ is —C(O)—R¹ᵃ; and R¹ᵃ is ethynyl or propynyl.

In a further particular embodiment, R¹ is —C(O)—R¹ᵃ; and R¹ᵃ is —C(R⁸)=C(R⁶)R⁷; and R⁶ is H or alkyl, R⁷ is H or substituted or unsubstituted alkyl, R⁸ is H, CN, alkyl, or cycloalkyl; or R⁷ and R⁸ are joined to form a bond.

In another embodiment, the compound is according to Formula (Xa), (Xb), (Xc) or (Xd):

Xa

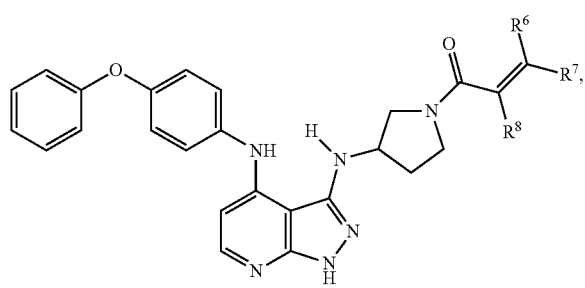

Xb

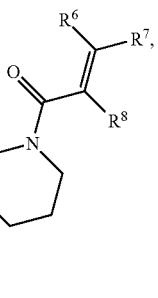

Xc

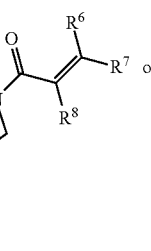

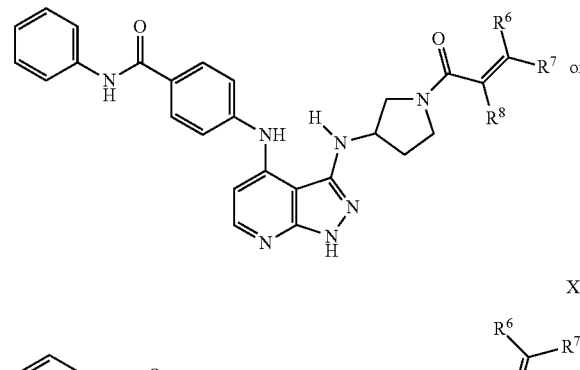

Xd

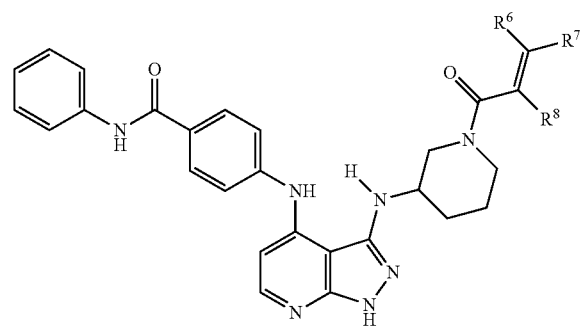

and wherein R¹ are as described for formula (A)-(C) or (IA); R⁶ is H or alkyl, R⁷ is H or substituted or unsubstituted alkyl, R⁸ is H, CN, alkyl, or cycloalkyl; or R⁷ and R⁸ are joined to form a bond.

In another embodiment, the compound is according to Formula (XIa), (XIb), (XIc) or (XId):

XIa

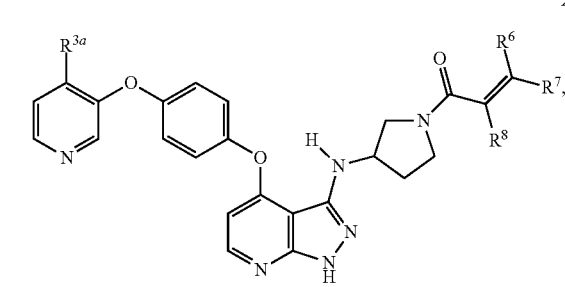

-continued

XIb
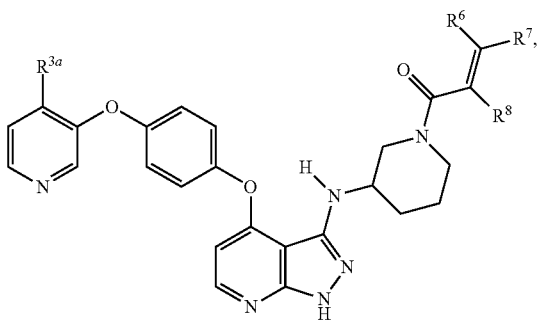

XIc
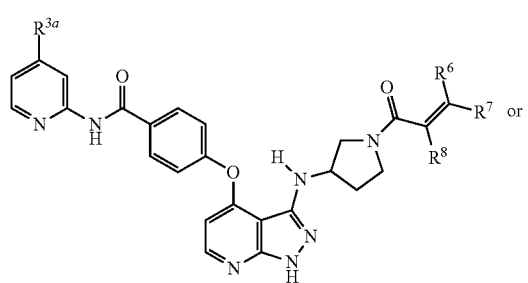
or

XId
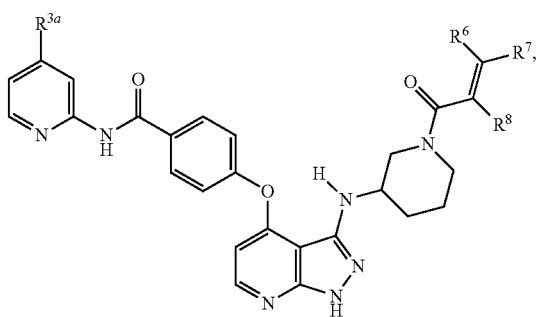

and wherein R¹ are as described for formula (A), (B) or (IA); and R$^{3a}$ is alkyl, haloalkyl, haloalkyl, cycloalkyl, CN, or OH; R$^6$ is H or alkyl, R$^7$ is H or substituted or unsubstituted alkyl, R$^8$ is H, CN, alkyl, or cycloalkyl; or R$^7$ and R$^8$ are joined to form a bond.

In another embodiment, the —N(H)— of any of Formula (Va-d), (VIa-d), (VIIa-d), (VIIIa-d), (IXa-d), (Xa-d), and (XIa-d)

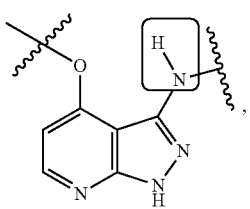 [SMILES: *Nc1n[nH]c2nccc(O*)c12]

is replaced with —O—.

In one embodiment, R$^8$ is H, CN, alkyl, or cycloalkyl. In another embodiment, R$^8$ is H, CN, Me, or cyclopropyl.

In one particular embodiment, each of R$^6$, R$^7$, and R$^8$ is H.

In another embodiment, R$^7$ and R$^8$ are joined to form a bond.

In another particular embodiment, each of R$^6$ and R$^8$ is H; and R$^7$ is alkyl or substituted alkyl.

In one embodiment, R$^7$ is alkyl substituted with alkoxy, substituted or unsubstituted amino.

In another embodiment, R$^7$ is —(CH$_2$)$_m$—OR$^{7a}$; or —(CH$_2$)$_m$—NR$^{7a}$R$^{7b}$; m is 1, 2, 3, or 4; each R$^{7a}$ and R$^{7b}$ is independently H, alkyl, haloalkyl, alkoxyalkyl, cycloalkyl, heterocycloalkyl, aryl, or heteroaryl. In yet another embodiment, R$^7$ is —(CH$_2$)$_m$—NR$^{7a}$R$^{7b}$; m is 1, 2, 3, or 4; each R$^{7a}$ and R$^{7b}$ is independently H, cyclopropyl, cyclobutyl, Me, Et, or methoxyethyl. In another embodiment, one of R$^{7a}$ and R$^{7b}$ is H, Me or Et, and the other is cyclopropyl, or cyclobutyl. In yet another embodiment, R$^7$ is —(CH$_2$)$_m$—OR$^{7a}$; m is 1, 2, 3, or 4; and R$^{7a}$ is H, cyclopropyl, Me, Et, or methoxyethyl. In yet another embodiment, R$^7$ is aryl or heteroaryl. In yet another embodiment, R$^7$ is imidazolyl, pyridyl, or pyrimidinyl. In yet another embodiment, R$^7$ is cycloalkyl. In yet another embodiment, R$^7$ is cyclopropyl, cyclobutyl, cyclopentyl, or cyclohexyl. In yet another embodiment, R$^7$ is phenyl. In a particular embodiment, m is 1. In another particular embodiment, one of R$^{7a}$ and R$^{7b}$ is Me, and the other is cyclopropyl.

In another embodiment, the compound is according to Formula (XIIa), (XIIb), (XIIc) or (XIId):

XIIa
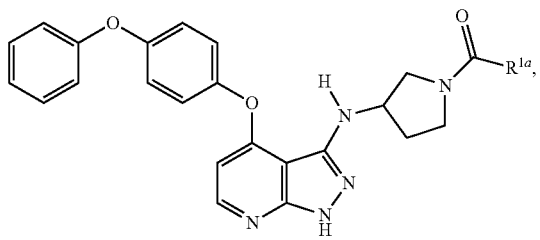

XIIb
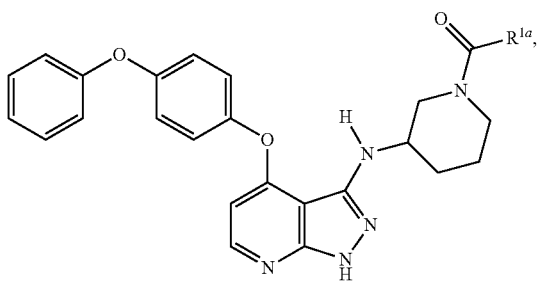

XIIc
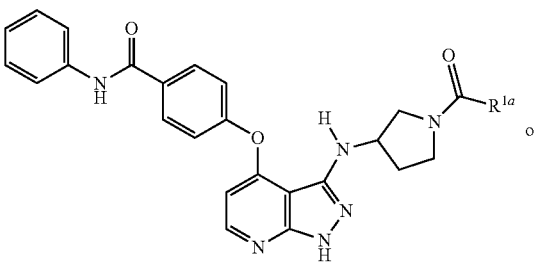
or

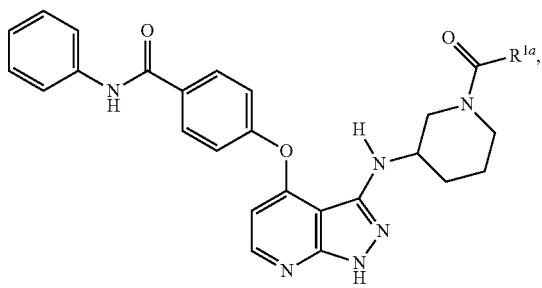

XIId and wherein $R^{1a}$ is as described for formula (A), (B) or (IA).

In another embodiment, the compound is according to Formula (XIIIa), (XIIIb), (XIIIc) or (XIIId):

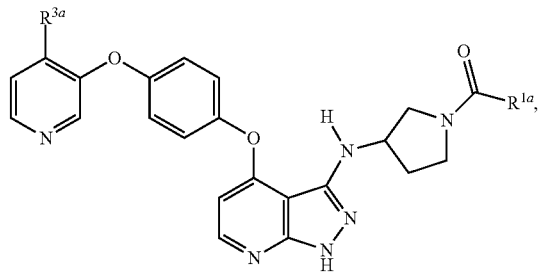

XIIIa

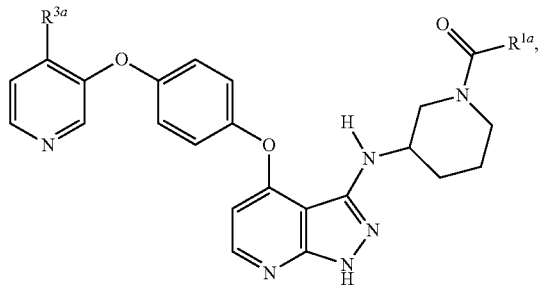

XIIIb

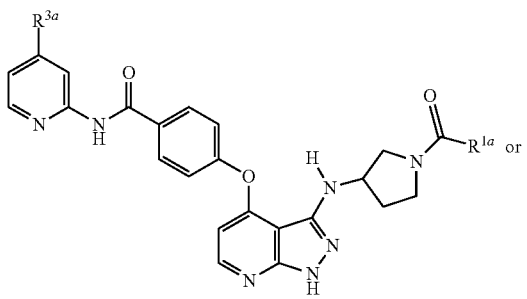

XIIIc

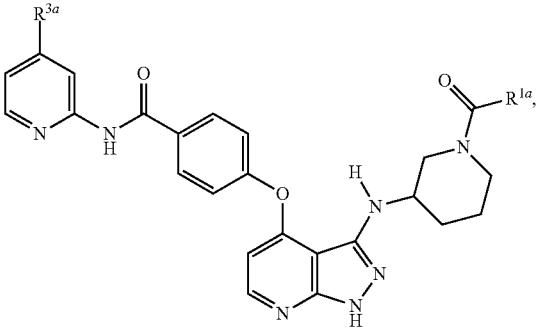

XIIId and wherein $R^{1a}$ is as described for formula (A), (B) or (IA); and $R^{3a}$ is alkyl, haloalkyl, haloalkyl, cycloalkyl, CN, or OH.

In one embodiment, $R^{1a}$ is substituted or unsubstituted $C_1$-$C_6$ alkyl. In another embodiment, $R^{1a}$ is Me, Et, n-Pr, i-Pr, n-Bu, i-Bu, sec-Bu, t-Bu. In yet another embodiment, $R^{1a}$ is $C_1$-$C_6$ alkyl substituted with CN, halo, hydroxyl, $C_1$-$C_6$ alkoxy, or substituted or unsubstituted amino. In one embodiment, $R^{3a}$ is CN, alkyl or trihaloalkyl, such as trifluoroalkyl or trichloroalkyl, $R^{1a}$ is $C_1$-$C_6$ alkyl or $C_2$-$C_6$ alkenyl optionally substituted with $NR^{17}R^{18}$, wherein $R^{17}$ and $R^{18}$ are independently H, substituted or unsubstituted $C_1$-$C_3$alkyl, substituted or unsubstituted $C_3$-$C_6$cycloalkyl, substituted or unsubstituted 3- to 8-membered heterocycloalkyl, substituted or unsubstituted $C_6$-$C_{12}$aryl, or substituted or unsubstituted 5- to 8-membered heteroaryl.

In a particular embodiment, $R^{3a}$ is CN. In another particular embodiment, $R^{3a}$ is Me. In a further particular embodiment, $R^{3a}$ is haloalkyl. In a further particular embodiment, $R^{3a}$ is $CF_3$. In a further particular embodiment, $R^{3a}$ is $CF_2CF_3$. In a further particular embodiment, $R^{3a}$ is $CHF_2$.

In yet another embodiment, $R^{1a}$ is $C_1$-$C_6$ alkyl substituted with phosphinic acid ester. In yet another embodiment, $R^{1a}$ is $C_1$-$C_6$ alkyl substituted with phosphinic acid ester; the phosphinic acid ester is —P(O)($R^{1e}$)—(O$R^{1e}$); and $R^{1e}$ is $C_1$-$C_6$ alkyl or aryl.

In yet another embodiment, $R^{1a}$ is $C_1$-$C_6$ alkyl substituted with phosphonic acid ester. In yet another embodiment, $R^{1a}$ is $C_1$-$C_6$ alkyl substituted with phosphonic acid ester; the phosphonic acid ester is —P(O)—(O$R^{1e}$)$_2$; and each $R^{1e}$ is $C_1$-$C_6$ alkyl or aryl.

In yet another embodiment, $R^{1a}$ is $C_1$-$C_6$ alkyl substituted with phosphinamidate. In yet another embodiment, $R^{1a}$ is $C_1$-$C_6$ alkyl substituted with phosphinamidate; the phosphinamidate is —P(O)($R^{1e}$)—N($R^{1f}$)$_2$ or —P(O)($R^{1e}$)—NH($R^{1f}$); and each $R^{1e}$ and $R^{1f}$ is independently H, substituted or unsubstituted $C_1$-$C_6$ alkyl or aryl. In one particular embodiment, $R^{1f}$ is H or $C_1$-$C_6$ alkyl substituted with —C(O)$R^{1g}$, and $R^{1g}$ is OH, alkyl, alkoxy, substituted or unsubstituted amino, or a heterocycle.

In yet another embodiment, $R^{1a}$ is $C_1$-$C_6$ alkyl substituted with phosphonamidate. In yet another embodiment, $R^{1a}$ is $C_1$-$C_6$ alkyl substituted with phosphonamidate; the phosphonamidate is —P(O)(O$R^{1e}$)—N($R^{1f}$)$_2$ or —P(O)(O$R^{1e}$)—NH($R^{1f}$); and each $R^{1e}$ and $R^{1f}$ is independently H, substituted or unsubstituted $C_1$-$C_6$ alkyl or aryl. In one particular embodiment, $R^{1f}$ is H or $C_1$-$C_6$ alkyl substituted with —C(O)$R^{1g}$, and $R^{1g}$ is OH, alkyl, alkoxy, substituted or unsubstituted amino, or a heterocycle.

In yet another embodiment, $R^{1a}$ is substituted or unsubstituted phenyl.

In yet another embodiment, $R^{1a}$ is phenyl substituted with a boronic acid or —B(OH)$_2$ group.

In yet another embodiment, $R^{1a}$ is $C_1$-$C_6$ alkyl substituted with a boronic acid or —B(OH)$_2$ group.

In yet another embodiment, $R^{1a}$ is $C_1$-$C_6$ alkyl substituted with alkylamino or dialkylamino. In yet another embodiment, $R^{1a}$ is $C_1$-$C_6$ alkyl substituted with CN, —OH, —OMe, —NHMe, or —NMe$_2$.

In yet another embodiment, $R^{1a}$ is $C_1$-$C_6$ alkyl substituted with one or more F.

In yet another embodiment, $R^{1a}$ is substituted or unsubstituted heterocycloalkyl. In yet another embodiment, $R^{1a}$ is substituted or unsubstituted pyrrolidinyl, piperidinyl, morpholinyl, or piperizinyl.

In yet another embodiment, $R^{1a}$ is substituted or unsubstituted oxetanyl, furanyl, or pyranyl.

In yet another embodiment, $R^{1a}$ is oxetanyl, furanyl, or pyranyl, which may be substituted with CN, $C_1$-$C_6$ alkyl, hydroxyl, hydroxyalkyl, or alkoxyalkyl.

In yet another embodiment, $R^{1a}$ is substituted or unsubstituted cycloalkyl.

In yet another embodiment, $R^{1a}$ is substituted or unsubstituted cyclopropyl, cyclobutyl, cyclopentyl, cyclohexyl, or cycloheptyl.

In yet another embodiment, $R^{1a}$ is cyclopropyl, cyclobutyl, cyclopentyl, cyclohexyl, or cycloheptyl; each of which may be substituted with CN, $C_1$-$C_6$ alkyl, hydroxyl, hydroxyalkyl, or alkoxyalkyl.

In one embodiment, $R^{1a}$ is —CH$_2$—P(O)(OMe)$_2$, —CH$_2$—P(O)(OEt)$_2$, or —CH$_2$—P(O)(Oi-Pr)$_2$.

In another embodiment, $R^{1a}$ is —CH$_2$—P(O)(Me)(OMe), —CH$_2$—P(O)(Me)(OEt), or —CH$_2$—P(O)(Me)(Oi-Pr).

In a particular embodiment, $R^{1a}$ is —CH$_2$—P(O)(OEt)(NH—CH$_2$—CO$_2$Et), —CH$_2$—P(O)(OEt)(NH—CH$_2$—CONH$_2$), or —CH$_2$—P(O)(OEt)(NH—CH$_2$—CONMe$_2$).

In another embodiment, the compound is according to Formula (XIVa), (XIVb), (XIVc) or (XIVd):

XIVa
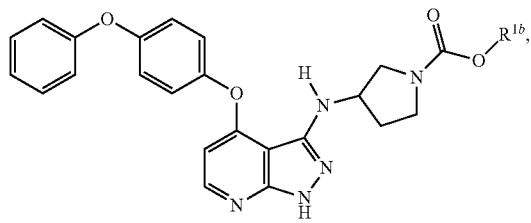

XIVb
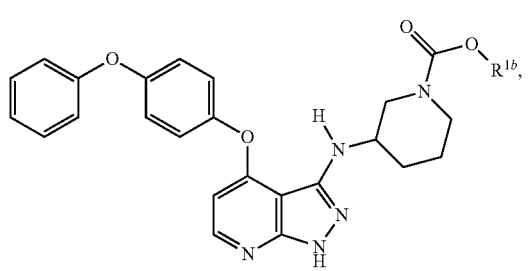

XIVc
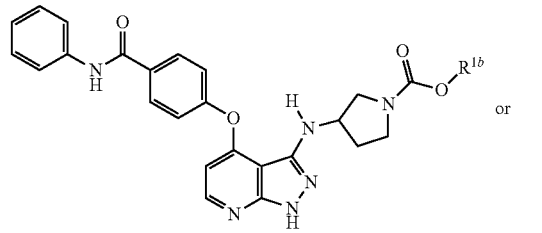

XIVd
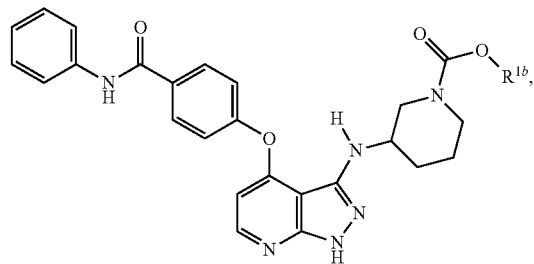

and wherein $R^{1b}$ is as described for formula (A), (B) or (IA).

In another embodiment, the compound is according to Formula (XVa), (XVb), (XVc) or (XVd):

VXa
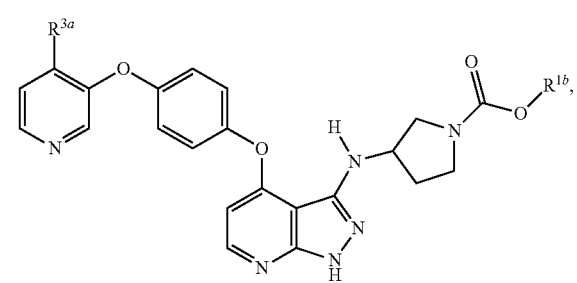

XVb
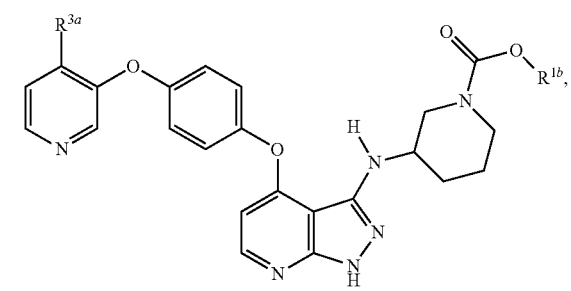

XVc
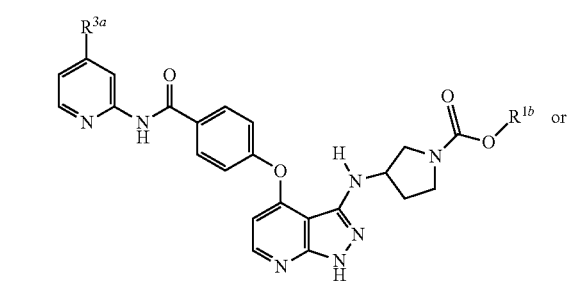

-continued

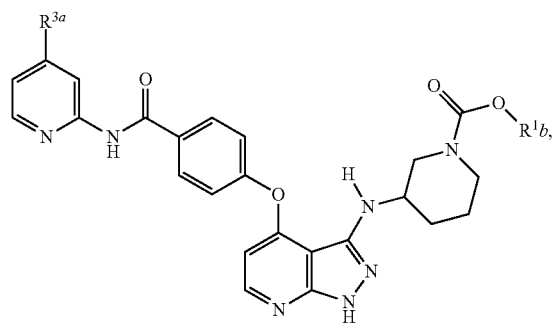

XVd and wherein $R^{1b}$ is as described for formula (A), (B) or (IA); and $R^{3a}$ is alkyl, haloalkyl, haloalkyl, cycloalkyl, CN, or OH.

In one particular embodiment, $R^{1b}$ is $C_1$-$C_6$ alkyl. In another particular embodiment, $R^{1b}$ is Me, Et, n-Pr, i-Pr, n-Bu, i-Bu, sec-Bu, t-Bu, or Ph.

In one embodiment, $R^{3a}$ is CN, alkyl or trihaloalkyl, such as trifluoroalkyl or trichloroalkyl, and $R^{1b}$ is $C_1$-$C_6$ alkyl substituted with $NR^{17}R^{18}$, wherein $R^{17}$ and $R^{18}$ are independently H, substituted or unsubstituted $C_1$-$C_3$alkyl, substituted or unsubstituted $C_3$-$C_6$cycloalkyl, substituted or unsubstituted 3- to 8-membered heterocycloalkyl, substituted or unsubstituted $C_6$-$C_{12}$aryl, or substituted or unsubstituted 5- to 8-membered heteroaryl.

In another embodiment, the compound is according to Formula (XVIa), (XVIb), (XVIc) or (XVId):

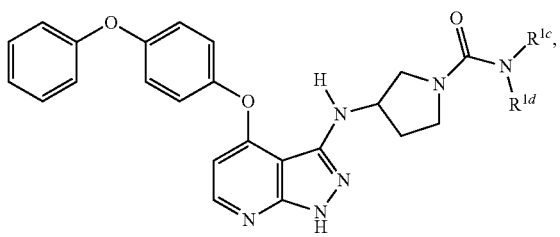

XVIa

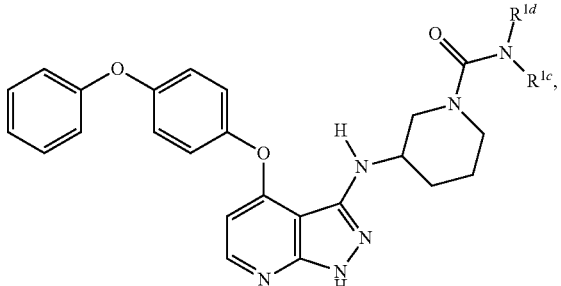

XVIb

XVIc

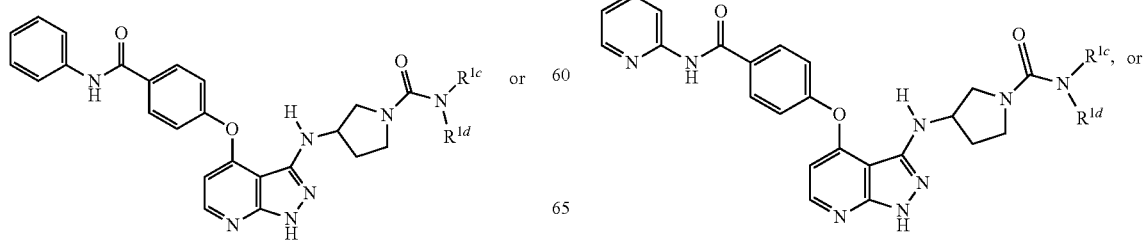

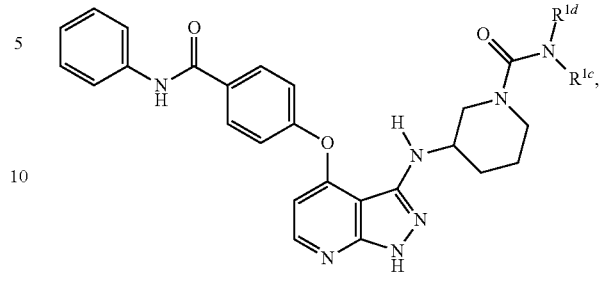

XVId and wherein $R^{1c}$ and $R^{1d}$ are as described for formula (A), (B) or (IA).

In another embodiment, the compound is according to Formula (XVIIa), (XVIIb), (XVIIc) or (XVIId):

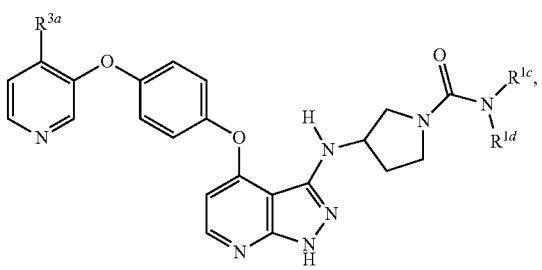

XVIIa

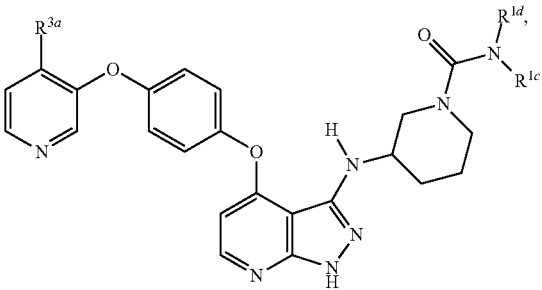

XVIIb

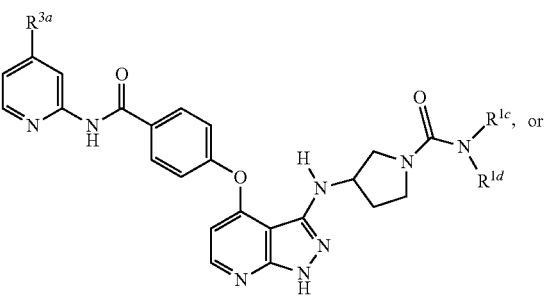

XVIIc

-continued

XVIId

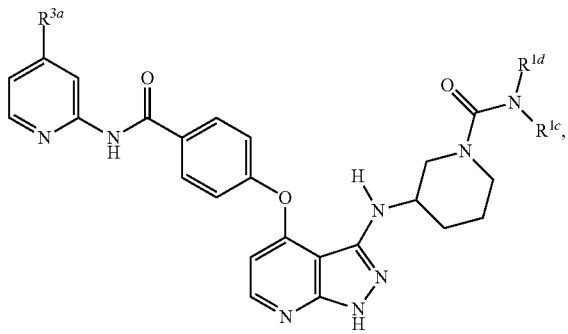

and wherein $R^{1c}$ and $R^{1d}$ are as described for formula (A), (B) or (IA); and $R^{3a}$ is alkyl, haloalkyl, cycloalkyl, CN, or OH.

In another embodiment, the —N(H)— of any of Formula (XIIa)-(XVIId)

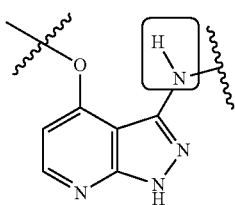 [SMILES: *Nc1n[nH]c2nccc(O*)c12]

is replaced with —O—.

In another embodiment, the —O— of any of Formula (XIIa)-(XVIId)

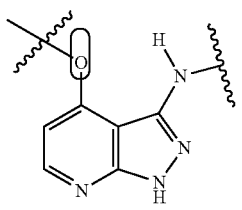 [SMILES: *Nc1n[nH]c2nccc(O*)c12]

is replaced with —N(H)—.

In one embodiment, each of $R^{1c}$ and $R^{1d}$ is independently H or $C_1$-$C_6$ alkyl. In one particular embodiment, each of $R^{1c}$ and $R^{1d}$ is independently H or Me, Et, n-Pr, i-Pr, n-Bu, i-Bu, sec-Bu, or t-Bu.

In one embodiment, $R^{3a}$ is CN, alkyl or trihaloalkyl, such as trifluoroalkyl or trichloroalkyl, $R^{1c}$ is H and $R^{1d}$ is $C_1$-$C_6$ alkyl substituted with $NR^{17}R^{18}$, wherein $R^{17}$ and $R^{18}$ are independently H, substituted or unsubstituted $C_1$-$C_3$alkyl, substituted or unsubstituted $C_3$-$C_6$cycloalkyl, substituted or unsubstituted 3- to 8-membered heterocycloalkyl, substituted or unsubstituted $C_6$-$C_{12}$aryl, or substituted or unsubstituted 5- to 8-membered heteroaryl.

In another particular embodiment, the compound is any one of the compounds selected from the compounds listed in Tables 1 and 2.

In another particular embodiment, the compound is selected from:
1-[(3R)-3-{[4-(4-chlorophenoxy)-1H-pyrazolo[3,4-b]pyridin-3-yl]amino}pyrrolidin-1-yl]prop-2-en-1-one;
1-[(3R)-3-{[4-(4-chlorophenoxy)-1H-pyrazolo[3,4-b]pyridin-3-yl](methyl)amino}pyrrolidin-1-yl]prop-2-en-1-one;
(2E)-1-[(3R)-3-{[4-(4-chlorophenoxy)-1H-pyrazolo[3,4-b]pyridin-3-yl]amino}pyrrolidin-1-yl]-4-(dimethylamino)but-2-en-1-one;
1-[(3R)-3-{[4-(4-phenoxyphenoxy)-1H-pyrazolo[3,4-b]pyridin-3-yl]amino}pyrrolidin-1-yl]prop-2-en-1-one;
(2E)-4-(dimethylamino)-1-[(3R)-3-{[4-(4-phenoxyphenoxy)-1H-pyrazolo[3,4-b]pyridin-3-yl]amino}pyrrolidin-1-yl]but-2-en-1-one;
1-[(3R)-3-{[4-(4-phenoxyphenoxy)-1H-pyrazolo[3,4-b]pyridin-3-yl]amino}piperidin-1-yl]prop-2-en-1-one;
1-[(3R)-3-{[4-(4-chlorophenoxy)-1H-pyrrolo[2,3-b]pyridin-3-yl]amino}pyrrolidin-1-yl]prop-2-en-1-one;
(2E)-4-[cyclopropyl(methyl)amino]-1-[(3R)-3-{[4-(4-phenoxyphenoxy)-1H-pyrazolo[3,4-b]pyridin-3-yl]amino}piperidin-1-yl]but-2-en-1-one;
(2E)-4-[(2-methoxyethyl)(methyl)amino]-1-[(3R)-3-{[4-(4-phenoxyphenoxy)-1H-pyrazolo[3,4-b]pyridin-3-yl]amino}pyrrolidin-1-yl]but-2-en-1-one;
(2E)-4-[cyclopropyl(methyl)amino]-1-[(3R)-3-{[4-(4-phenoxyphenoxy)-1H-pyrazolo[3,4-b]pyridin-3-yl]amino}pyrrolidin-1-yl]but-2-en-1-one;
(2E)-4-[cyclopropyl(methyl)amino]-1-[(3R)-3-{[4-(3-phenoxyphenoxy)-1H-pyrazolo[3,4-b]pyridin-3-yl]amino}pyrrolidin-1-yl]but-2-en-1-one;
(2E)-4-(dimethylamino)-1-[(3R)-3-{[4-(3-phenoxyphenoxy)-1H-pyrazolo[3,4-b]pyridin-3-yl]amino}pyrrolidin-1-yl]but-2-en-1-one;
(2E)-4-(dimethylamino)-1-[(3R)-3-{[4-(3-phenoxyphenoxy)-1H-pyrazolo[3,4-b]pyridin-3-yl]amino}piperidin-1-yl]but-2-en-1-one;
(2E)-4-(dimethylamino)-1-[(3R)-3-({4-[(4-phenoxyphenyl)amino]-1H-pyrazolo[3,4-b]pyridin-3-yl}oxy)pyrrolidin-1-yl]but-2-en-1-one;
1-benzyl-4-[(3-{[(3R)-1-[(2E)-4-(dimethylamino)but-2-enoyl]pyrrolidin-3-yl]amino}-1H-pyrazolo[3,4-b]pyridin-4-yl)oxy]-1,2-dihydropyridin-2-one;
(2E)-1-[(3R)-3-({4-[3-chloro-4-(1,3-oxazol-2-yl)phenoxy]-1H-pyrazolo[3,4-b]pyridin-3-yl}amino)pyrrolidin-1-yl]-4-(dimethylamino)but-2-en-1-one;
(2E)-4-(dimethylamino)-1-[(3R)-3-({4-[(3-phenoxyphenyl)amino]-1H-pyrazolo[3,4-b]pyridin-3-yl}oxy)pyrrolidin-1-yl]but-2-en-1-one;
(2E)-3-cyclopropyl-2-[(E)-(3R)-3-{[4-(4-phenoxyphenoxy)-1H-pyrazolo[3,4-b]pyridin-3-yl]amino}pyrrolidine-1-carbonyl]prop-2-enenitrile;
(2E)-2-[(E)-(3R)-3-{[4-(4-phenoxyphenoxy)-1H-pyrazolo[3,4-b]pyridin-3-yl]amino}pyrrolidine-1-carbonyl]-3-phenylprop-2-enenitrile;
(2E)-4-(dimethylamino)-1-[(3R)-3-[(4-{3-[(pyrimidin-4-yl)amino]phenoxy}-1H-pyrazolo[3,4-b]pyridin-3-yl)amino]pyrrolidin-1-yl]but-2-en-1-one;
(2E)-4-(dimethylamino)-N-methyl-N-[(1s,4s)-4-{[4-(3-phenoxyphenoxy)-1H-pyrazolo[3,4-b]pyridin-3-yl]amino}cyclohexyl]but-2-enamide;
(2E)-4-[cyclopropyl(methyl)amino]-1-[(3R)-3-{[4-(4-phenoxyphenoxy)-1H-pyrazolo[3,4-b]pyridin-3-yl]oxy}pyrrolidin-1-yl]but-2-en-1-one;
(2E)-4-[cyclopropyl(methyl)amino]-1-[(3R)-3-({4-[(4-phenoxyphenyl)amino]-1H-pyrazolo[3,4-b]pyridin-3-yl}amino)pyrrolidin-1-yl]but-2-en-1-one;
(2E)-4-(dimethylamino)-1-[(3R)-3-[(4-{[(3S)-1-phenylpyrrolidin-3-yl]oxy}-1H-pyrazolo[3,4-b]pyridin-3-yl)amino]pyrrolidin-1-yl]but-2-en-1-one;

2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzene-1-sulfonamide;

(2E)-2-[(E)-(3R)-3-{[4-(4-phenoxyphenoxy)-1H-pyrazolo[3,4-b]pyridin-3-yl]amino}pyrrolidine-1-carbonyl]-3-(pyridin-2-yl)prop-2-enenitrile;

(2E)-3-cyclobutyl-2-[(E)-(3R)-3-{[4-(4-phenoxyphenoxy)-1H-pyrazolo[3,4-b]pyridin-3-yl]amino}pyrrolidine-1-carbonyl]prop-2-enenitrile;

(2E)-3-(1H-imidazol-2-yl)-2-[(E)-(3R)-3-{[4-(4-phenoxyphenoxy)-1H-pyrazolo[3,4-b]pyridin-3-yl]amino}pyrrolidine-1-carbonyl]prop-2-enenitrile;

(2Z)-2-cyano-N-methyl-3-(3-{[4-(4-phenoxyphenoxy)-1H-pyrazolo[3,4-b]pyridin-3-yl]amino}phenyl)prop-2-enamide;

4-{[4-(4-phenoxyphenoxy)-1H-pyrazolo[3,4-b]pyridin-3-yl]amino}pyridine-2-carbonitrile;

(2Z)-2-fluoro-N-methyl-3-(3-{[4-(4-phenoxyphenoxy)-1H-pyrazolo[3,4-b]pyridin-3-yl]amino}phenyl)prop-2-enamide;

(2E)-4-(dimethylamino)-1-{3-[4-(4-phenoxyphenoxy)-1H-pyrazolo[3,4-b]pyridin-3-yl]piperidin-1-yl}but-2-en-1-one;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(trifluoromethyl)pyridin-2-yl]benzamide;

2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzonitrile;

2-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-5-phenoxybenzonitrile;

(2E)-4-[cyclopropyl(methyl)amino]-1-[(2S)-2-({[4-(4-phenoxyphenoxy)-1H-pyrazolo[3,4-b]pyridin-3-yl]amino}methyl)pyrrolidin-1-yl]but-2-en-1-one;

(2E)-4-[cyclopropyl(methyl)amino]-1-[(2S)-2-({[4-(4-phenoxyphenoxy)-1H-pyrazolo[3,4-b]pyridin-3-yl]amino}methyl)piperidin-1-yl]but-2-en-1-one;

(2E)-4-[cyclopropyl(methyl)amino]-N-methyl-N-(3-{[4-(4-phenoxyphenoxy)-1H-pyrazolo[3,4-b]pyridin-3-yl]amino}phenyl)but-2-enamide;

(2E)-4-(dimethylamino)-1-[(3R)-3-{[4-(4-phenoxyphenoxy)-1H-pyrazolo[3,4-d]pyrimidin-3-yl]amino}pyrrolidin-1-yl]but-2-en-1-one;

(2E)-4-[cyclopropyl(methyl)amino]-1-[(3R)-3-({4-[4-(1H-1,2,3-triazol-5-ylmethoxy)phenoxy]-1H-pyrazolo[3,4-b]pyridin-3-yl}amino)pyrrolidin-1-yl]but-2-en-1-one;

2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzamide;

3-oxo-3-[(3R)-3-{[4-(4-phenoxyphenoxy)-1H-pyrazolo[3,4-b]pyridin-3-yl]amino}pyrrolidin-1-yl]propanenitrile;

(3R)-1-methyl-N-[4-(4-phenoxyphenoxy)-1H-pyrazolo[3,4-b]pyridin-3-yl]pyrrolidin-3-amine;

1-[(3R)-3-{[4-(4-phenoxyphenoxy)-1H-pyrazolo[3,4-b]pyridin-3-yl]amino}pyrrolidin-1-yl]ethan-1-one;

N-(oxan-4-yl)-4-(4-phenoxyphenoxy)-1H-pyrazolo[3,4-b]pyridin-3-amine;

(2E)-4-[cyclopropyl(methyl)amino]-1-[(3R)-3-{[4-(4-phenoxyphenoxy)-1H-pyrazolo[3,4-d]pyrimidin-3-yl]amino}pyrrolidin-1-yl]but-2-en-1-one;

(2E)-4-[cyclopropyl(methyl)amino]-N-[(3R)-1-[(2E)-4-[cyclopropyl(methyl)amino]but-2-enoyl]pyrrolidin-3-yl]-N-[4-(4-phenoxyphenoxy)-1H-pyrazolo[3,4-d]pyrimidin-3-yl]but-2-enamide;

(3R)—N-[4-(4-phenoxyphenoxy)-1H-pyrazolo[3,4-d]pyrimidin-3-yl]piperidin-3-amine;

1-[(3R)-3-{[4-(4-phenoxyphenoxy)-1H-pyrazolo[3,4-d]pyrimidin-3-yl]amino}piperidin-1-yl]propan-1-one;

N-[4-(4-phenoxyphenoxy)-1H-pyrazolo[3,4-d]pyrimidin-3-yl]-N-[(3R)-1-propanoylpiperidin-3-yl]propanamide;

(2E)-4-(dimethylamino)-1-[(3R)-3-{[4-(4-phenoxyphenoxy)-1H-pyrazolo[3,4-d]pyrimidin-3-yl]amino}piperidin-1-yl]but-2-en-1-one;

(2E)-4-(dimethylamino)-1-[(3R)-3-{[4-(2-hydroxy-3-phenoxypropoxy)-1H-pyrazolo[3,4-b]pyridin-3-yl]amino}pyrrolidin-1-yl]but-2-en-1-one;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyridin-2-yl)benzamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-propylpyridin-2-yl)benzamide;

(2E)-4-[cyclopropyl(methyl)amino]-N-(2-{[4-(4-phenoxyphenoxy)-1H-pyrazolo[3,4-b]pyridin-3-yl]amino}phenyl)but-2-enamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-methoxypyridin-2-yl)benzamide;

4-{[4-(4-phenoxyphenoxy)-1H-pyrazolo[3,4-b]pyridin-3-yl]amino}pyridine-2-carboxamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-cyclopropylpyridin-2-yl)benzamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(propan-2-yl)pyridin-2-yl]benzamide;

N-(4-cyanopyridin-2-yl)-4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]benzamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyrimidin-2-yl)benzamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyrimidin-4-yl)benzamide;

N-(cyanomethyl)-4-{[4-(4-phenoxyphenoxy)-1H-pyrazolo[3,4-b]pyridin-3-yl]amino}pyridine-2-carboxamide;

4-[(3-{[(3R)-1-propanoylpyrrolidin-3-yl]amino}-1H-pyrazolo[3,4-b]pyridin-4-yl)oxy]-N-[4-(trifluoromethyl)pyridin-2-yl]benzamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(1H-imidazol-2-yl)benzamide;

4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(dimethylamino)pyridin-2-yl]benzamide;

N-(1H-1,3-benzodiazol-2-yl)-4-[(3-{[(3R)-1-propanoylpyrrolidin-3-yl]amino}-1H-pyrazolo[3,4-b]pyridin-4-yl)oxy]benzamide;

4-[(3-{[(3R)-1-propanoylpyrrolidin-3-yl]amino}-1H-pyrazolo[3,4-b]pyridin-4-yl)amino]-N-[4-(trifluoromethyl)pyridin-2-yl]benzamide;

4-[(3-{[(3R)-1-propanoylpyrrolidin-3-yl]oxy}-1H-pyrazolo[3,4-b]pyridin-4-yl)amino]-N-[4-(trifluoromethyl)pyridin-2-yl]benzamide;

N-(5-methyl-1,3-thiazol-2-yl)-4-[(3-{[(3R)-1-propanoylpyrrolidin-3-yl]amino}-1H-pyrazolo[3,4-b]pyridin-4-yl)oxy]benzamide; N-(1-methyl-1H-imidazol-2- yl)-4-[(3-{[(3R)-1-propanoylpyrrolidin-3-yl]amino}-1H-pyrazolo[3,4-b]pyridin-4-yl)oxy]benzamide;

N-(6-oxo-1,6-dihydropyrimidin-2-yl)-4-[(3-{[(3R)-1-propanoylpyrrolidin-3-yl]amino}-1H-pyrazolo[3,4-b]pyridin-4-yl)oxy]benzamide;

N-(5-methyl-4H-1,2,4-triazol-3-yl)-4-[(3-{[(3R)-1-propanoylpyrrolidin-3-yl]amino}-1H-pyrazolo[3,4-b]pyridin-4-yl)oxy]benzamide;

N-(4-cyanopyridin-2-yl)-4-({3-[(oxan-4-yl)amino]-1H-pyrazolo[3,4-b]pyridin-4-yl}oxy)benzamide;

ethyl (3R)-3-[(4-{4-[(4-cyanopyridin-2-yl)carbamoyl]phenoxy}-1H-pyrazolo[3,4-b]pyridin-3-yl)amino]piperidine-1-carboxylate;

(3R)-3-[(4-{4-[(4-cyanopyridin-2-yl)carbamoyl]phenoxy}-1H-pyrazolo[3,4-b]pyridin-3-yl)amino]-N-ethylpiperidine-1-carboxamide;

N-(4-cyanopyridin-2-yl)-4-[(3-{[(3R)-1-(3-methoxypropanoyl)piperidin-3-yl]amino}-1H-pyrazolo[3,4-b]pyridin-4-yl)oxy]benzamide;

N-(4-cyanopyridin-2-yl)-4-[(3-{[(3R)-1-cyclopropanecarbonylpiperidin-3-yl]amino}-1H-pyrazolo[3,4-b]pyridin-4-yl)oxy]benzamide;

N-(4-cyanopyridin-2-yl)-4-[(3-{[(1r,4r)-4-hydroxycyclohexyl]amino}-1H-pyrazolo[3,4-b]pyridin-4-yl)oxy]benzamide;

N-(4-cyanopyridin-2-yl)-4-[(3-{[(3R)-1-(3-methyloxetane-3-carbonyl)piperidin-3-yl]amino}-1H-pyrazolo[3,4-b]pyridin-4-yl)oxy]benzamide;

4-[(3-{[(3R)-1-(3-methyloxetane-3-carbonyl)piperidin-3-yl]amino}-1H-pyrazolo[3,4-b]pyridin-4-yl)oxy]-N-[4-(trifluoromethyl)pyridin-2-yl]benzamide;

N-(4-cyanopyridin-2-yl)-4-[(3-{[(1s,4s)-4-methoxycyclohexyl]amino}-1H-pyrazolo[3,4-b]pyridin-4-yl)oxy]benzamide;

4-[(3-{[(3R)-1-(3-methyloxetane-3-carbonyl)piperidin-3-yl]amino}-1H-pyrazolo[3,4-b]pyridin-4-yl)oxy]-N-(4-methylpyridin-2-yl)benzamide;

4-[(3-{[(3R)-1-(4-methyloxane-4-carbonyl)piperidin-3-yl]amino}-1H-pyrazolo[3,4-b]pyridin-4-yl)oxy]-N-(4-methylpyridin-2-yl)benzamide;

4-[(3-{[(3R)-1-(1-methylcyclobutanecarbonyl)piperidin-3-yl]amino}-1H-pyrazolo[3,4-b]pyridin-4-yl)oxy]-N-(4-methylpyridin-2-yl)benzamide;

4-[(3-{[(3R)-1-(3-methyloxolane-3-carbonyl)piperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(oxetane-3-carbonyl)piperidin-3-yl]amino}-1H-pyrazolo[3,4-b]pyridin-4-yl)oxy]benzamide;

N-(4-methylpyridin-2-yl)-4-[(3-{[(3R)-1-(morpholine-4-carbonyl)piperidin-3-yl]amino}-1H-pyrazolo[3,4-b]pyridin-4-yl)oxy]benzamide;

(R,E)-N-(4-cyclopropoxypyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide;

4-[(3-{[(3R)-1-(1-methylpiperidine-4-carbonyl)piperidin-3-yl]amino}-1H-pyrazolo[3,4-b]pyridin-4-yl)oxy]-N-(4-methylpyridin-2-yl)benzamide;

phenyl (3R)-3-[(4-{4-[(4-methylpyridin-2-yl)carbamoyl]phenoxy}-1H-pyrazolo[3,4-b]pyridin-3-yl)amino]piperidine-1-carboxylate;

N-(4-methylpyridin-2-yl)-4-[(3-{[(3R)-1-[(2S)-oxolane-2-carbonyl]piperidin-3-yl]amino}-1H-pyrazolo[3,4-b]pyridin-4-yl)oxy]benzamide;

4-[(3-{[(3R)-1-[5-(dimethylamino)pentanoyl]piperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(piperidine-4-carbonyl)piperidin-3-yl]amino}-1H-pyrazolo[3,4-b]pyridin-4-yl)oxy]benzamide;

4-[(3-{[(3R)-1-[(methylcarbamoyl)carbonyl]piperidin-3-yl]amino}-1H-pyrazolo[3,4-b]pyridin-4-yl)oxy]-N-(4-methylpyridin-2-yl)benzamide;

4-[(3-{[(3R)-1-[(dimethylcarbamoyl)carbonyl]piperidin-3-yl]amino}-1H-pyrazolo[3,4-b]pyridin-4-yl)oxy]-N-(4-methylpyridin-2-yl)benzamide;

4-[(3-{[(3R)-1-[1-(methoxymethyl)cyclobutanecarbonyl]piperidin-3-yl]amino}-1H-pyrazolo[3,4-b]pyridin-4-yl)oxy]-N-(4-methylpyridin-2-yl)benzamide;

4-[(3-{[(3R)-1-cyclopropanecarbonylpiperidin-3-yl]amino}-1H-pyrazolo[3,4-b]pyridin-4-yl)oxy]-N-(4-methylpyridin-2-yl)benzamide;

4-[(3-{[(3R)-1-(1-cyanocyclopropanecarbonyl)piperidin-3-yl]amino}-1H-pyrazolo[3,4-b]pyridin-4-yl)oxy]-N-(4-methylpyridin-2-yl)benzamide;

4-[(3-{[(3R)-1-(2-cyano-2,2-dimethylacetyl)piperidin-3-yl]amino}-1H-pyrazolo[3,4-b]pyridin-4-yl)oxy]-N-(4-methylpyridin-2-yl)benzamide;

tert-butyl 4-methyl-4-[(3R)-3-[(4-{4-[(4-methylpyridin-2-yl)carbamoyl]phenoxy}-1H-pyrazolo[3,4-b]pyridin-3-yl)amino]piperidine-1-carbonyl]piperidine-1-carboxylate;

4-[(3-{[(3R)-1-(4-methylpiperidine-4-carbonyl)piperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(oxane-4-carbonyl)piperidin-3-yl]amino}-1H-pyrazolo[3,4-b]pyridin-4-yl)oxy]benzamide;

(3R)—N,N-dimethyl-3-[(4-{4-[(4-methylpyridin-2-yl)carbamoyl]phenoxy}-1H-pyrazolo[3,4-b]pyridin-3-yl)amino]piperidine-1-carboxamide;

4-[(3-{[(3R)-1-cyclopentanecarbonylpiperidin-3-yl]amino}-1H-pyrazolo[3,4-b]pyridin-4-yl)oxy]-N-(4-methylpyridin-2-yl)benzamide;

ethyl (3R)-3-[(4-{4-[(4-methylpyridin-2-yl)carbamoyl]phenoxy}-1H-pyrazolo[3,4-b]pyridin-3-yl)amino]piperidine-1-carboxylate;

4-[(3-{[(3R)-1-benzoylpiperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(pyridine-2-carbonyl)piperidin-3-yl]amino}-1H-pyrazolo[3,4-b]pyridin-4-yl)oxy]benzamide;

4-[(3-{[(3R)-1-(3-methyloxetane-3-carbonyl)piperidin-3-yl]amino}-1H-pyrazolo[3,4-b]pyridin-4-yl)oxy]-N-(pyridin-2-yl)benzamide;

4-[(3-{[(3R)-1-(4-methyloxane-4-carbonyl)piperidin-3-yl]amino}-1H-pyrazolo[3,4-b]pyridin-4-yl)oxy]-N-(pyridin-2-yl)benzamide;

4-[(3-{[(3R)-1-(3-methyloxetane-3-carbonyl)piperidin-3-yl]amino}-1H-pyrazolo[3,4-b]pyridin-4-yl)oxy]-N-(6-methylpyridin-2-yl)benzamide;

4-[(3-{[(3R)-1-(4-methyloxane-4-carbonyl)piperidin-3-yl]amino}-1H-pyrazolo[3,4-b]pyridin-4-yl)oxy]-N-(6-methylpyridin-2-yl)benzamide;

N-(4-methylpyridin-2-yl)-4-[(3-{[(3R)-1-[(3R)-oxolane-3-carbonyl]piperidin-3-yl]amino}-1H-pyrazolo[3,4-b]pyridin-4-yl)oxy]benzamide;

N-(4-methylpyridin-2-yl)-4-[(3-{[(3R)-1-[(3S)-oxolane-3-carbonyl]piperidin-3-yl]amino}-1H-pyrazolo[3,4-b]pyridin-4-yl)oxy]benzamide;

N-(4-methylpyridin-2-yl)-4-[(3-{[(3R)-1-[(2S)-oxolane-2-carbonyl]piperidin-3-yl]amino}-1H-pyrazolo[3,4-b]pyridin-4-yl)oxy]benzamide;

4-[(3-{[(3R)-1-[3-(dimethylamino)propanoyl]piperidin-3-yl]amino}-1H-pyrazolo[3,4-b]pyridin-4-yl)oxy]-N-(4-methylpyridin-2-yl)benzamide;

4-[(3-{[(3R)-1-(3-methoxypropanoyl)piperidin-3-yl]amino}-1H-pyrazolo[3,4-b]pyridin-4-yl)oxy]-N-(4-methylpyridin-2-yl)benzamide; and 4-[(3-{[(3R)-1-(1-methylcyclopropanecarbonyl)piperidin-3-yl]amino}-1H-pyrazolo[3,4-b]pyridin-4-yl)oxy]-N-(4-methylpyridin-2-yl)benzamide.

In another aspect, the present invention provides, a pharmaceutical composition comprising a pharmaceutically acceptable carrier and a pharmaceutically effective amount of a compound according to any one of the formulas described herein. In one embodiment, the compound is according to any one of formulas: (A)-(C), (IA), (I), (IIa)-(IIb), (IIIa)-(IIId), (IVa)-(IVh), (Va)-(Vh), (VIa)-(VIf), (VIIa)-(VIIi), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId).

In one embodiment, the pharmaceutical composition is formulated for a route of administration selected from oral administration, parenteral administration, buccal administration, nasal administration, topical administration, or rectal administration.

In one embodiment, the carrier is a parenteral carrier.

In another embodiment, the carrier is an oral carrier.

In another embodiment, the carrier is a topical carrier.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further embodiments of compounds of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) include, but are not limited to, compounds described in the Examples and/or selected from the group consisting of:

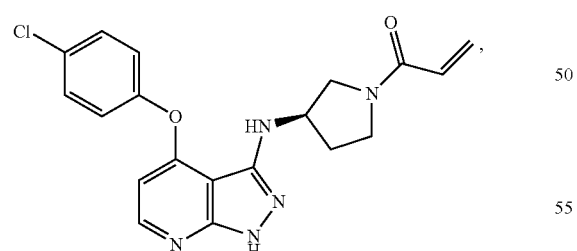

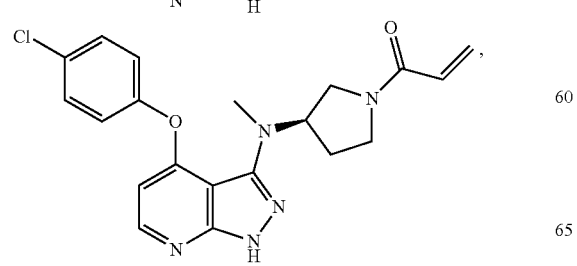

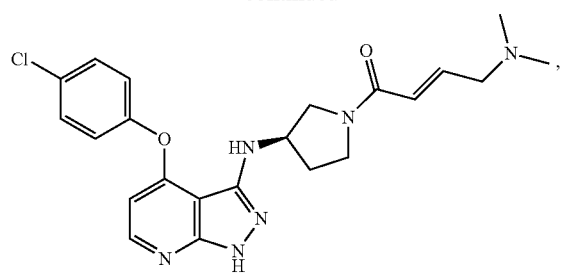

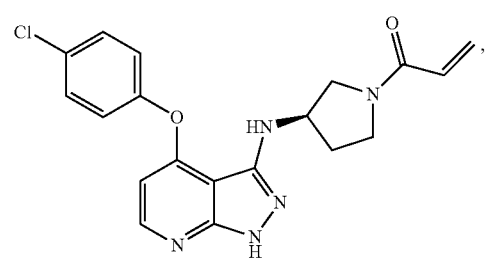

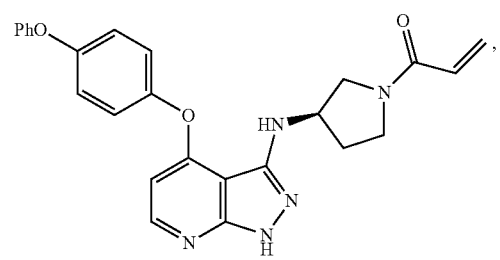

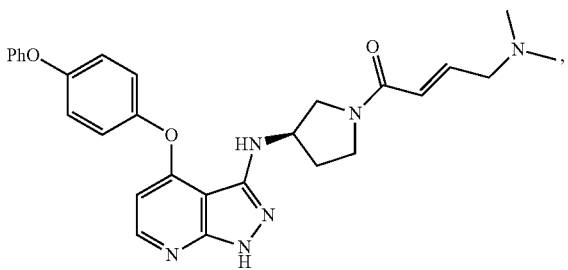

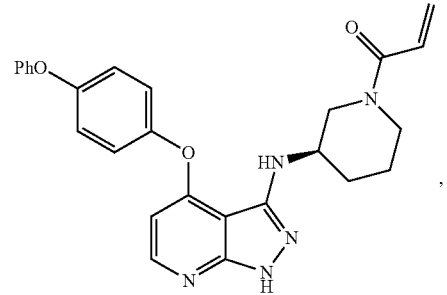

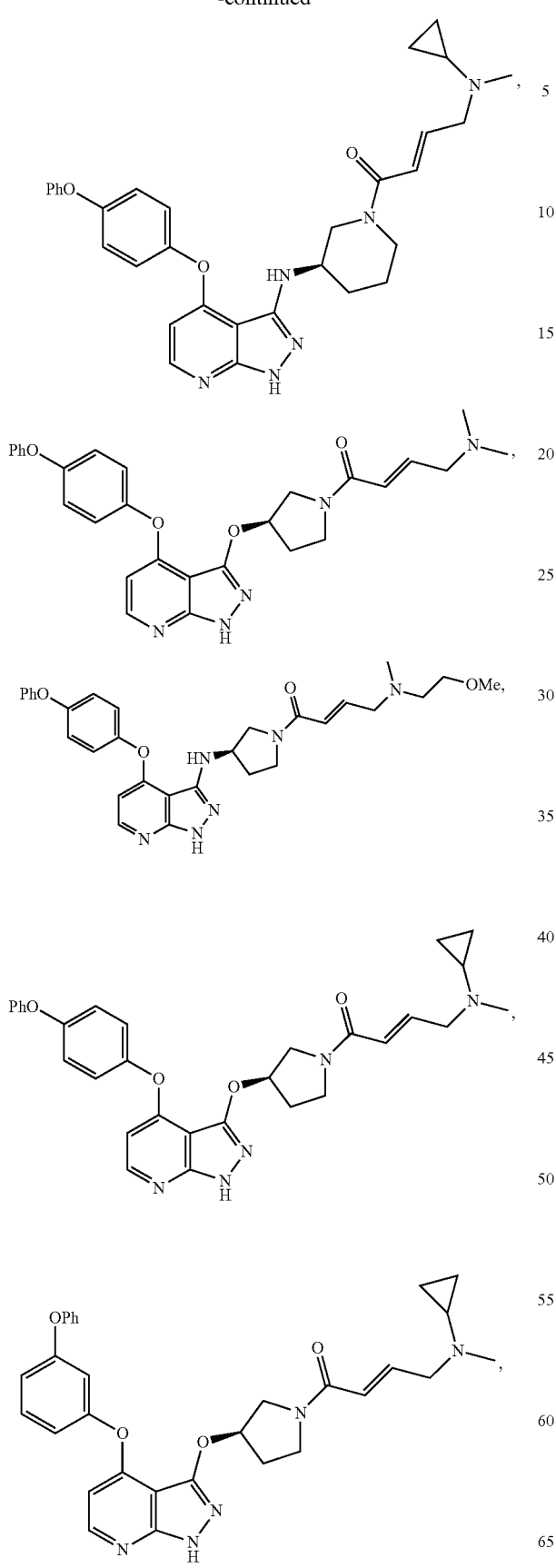
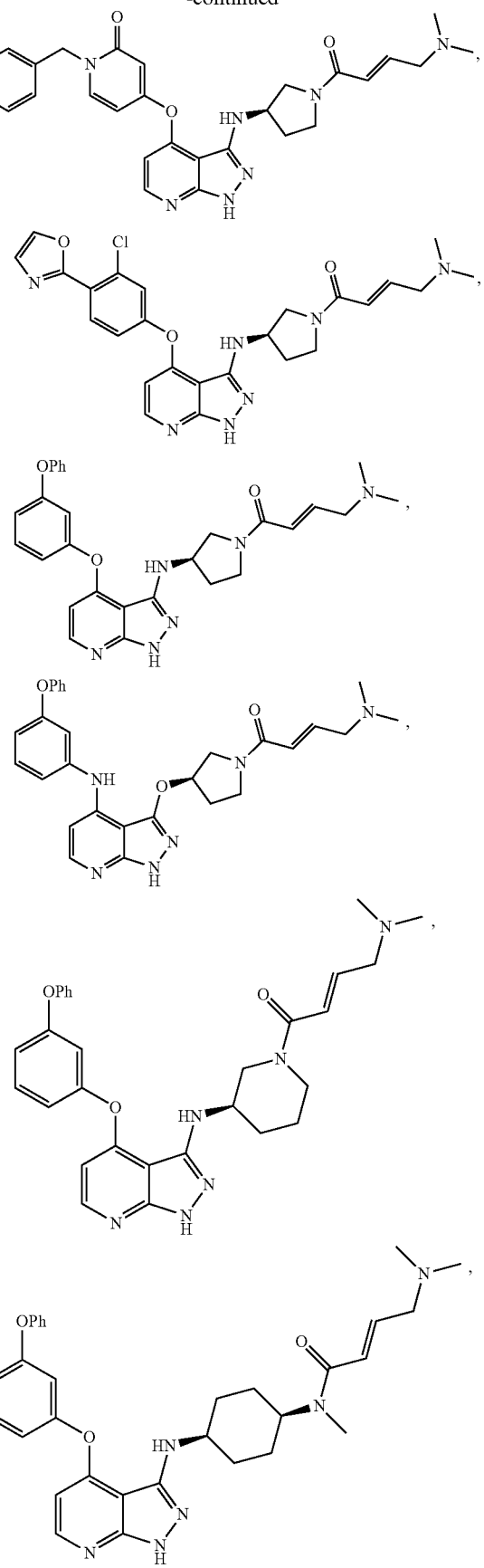

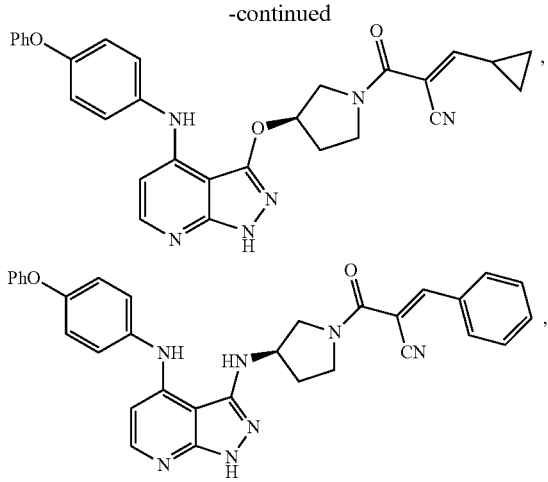

Throughout the specification, groups and substituents thereof can be chosen by one skilled in the field to provide stable moieties and compounds.

In some embodiments, the compounds of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) reversibly inhibit Btk and in other embodiments are used to treat patients suffering from Bruton's tyrosine kinase-dependent or Bruton's tyrosine kinase mediated conditions or diseases, including, but not limited to, cancer, autoimmune and other inflammatory diseases.

In some embodiments, the compounds of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) irreversibly inhibit Btk and in other embodiments are used to treat patients suffering from Bruton's tyrosine kinase-dependent or Bruton's tyrosine kinase mediated conditions or diseases, including, but not limited to, cancer, autoimmune and other inflammatory diseases.

Preparation of Compounds

Compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) may be synthesized using standard synthetic reactions known to those of skill in the art or using methods known in the art. The reactions can be employed in a linear sequence to provide the compounds or they may be used to synthesize fragments which are subsequently joined by the methods known in the art.

Described herein are compounds that inhibit the activity of tyrosine kinase(s), such as Btk, and processes for their preparation. Also described herein are pharmaceutically acceptable salts, pharmaceutically acceptable solvates, pharmaceutically active metabolites and prodrugs of such compounds. Pharmaceutical compositions that include at least one such compound or a pharmaceutically acceptable salt, pharmaceutically acceptable solvate, pharmaceutically active metabolite or prodrug of such compound, are provided.

The starting material used for the synthesis of the compounds described herein may be synthesized or can be obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography and the like. Such materials may be characterized using conventional means, including physical constants and spectral data.

Compounds described herein may be prepared as a single isomer or a mixture of isomers.

In some embodiments, the compounds of Formula (A) may be prepared according to Scheme A, wherein Cy$^1$, Cy$^2$, L$^1$, T$^1$, W$^1$, W$^2$, Z, R$^1$ and R$^{10}$ are as described herein, LG$^1$ and LG$^2$ are independently a leaving group, such as halo, tosylate or triflate, and PG is an amino protecting group such as p-methoxybenzyl (PMB). In Scheme A, Compound A-1 reacts with Compound A-2 under conditions, such as in the presence of a base (e.g., Na$_2$CO$_3$, K$_2$CO$_3$, Cs$_2$CO$_3$, etc.) and a solvent (such as DMF, DCM, etc.), to form Compound A-3. Compound A-3 reacts with Compound A-4 under conditions, such as in the presence of a base (e.g., Na$_2$CO$_3$, K$_2$CO$_3$, CsCO$_3$, etc.) and a solvent (such as DMF, DCM, etc.), and optionally a catalyst such as CuI to formula Compound A-5, which is deprotected to remove the protecting group PG to provide for the compound of Formula A. Many suitable protecting groups and respective methods of deprotection are also known in the art.

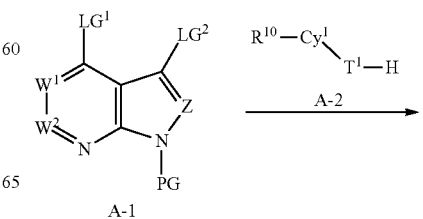

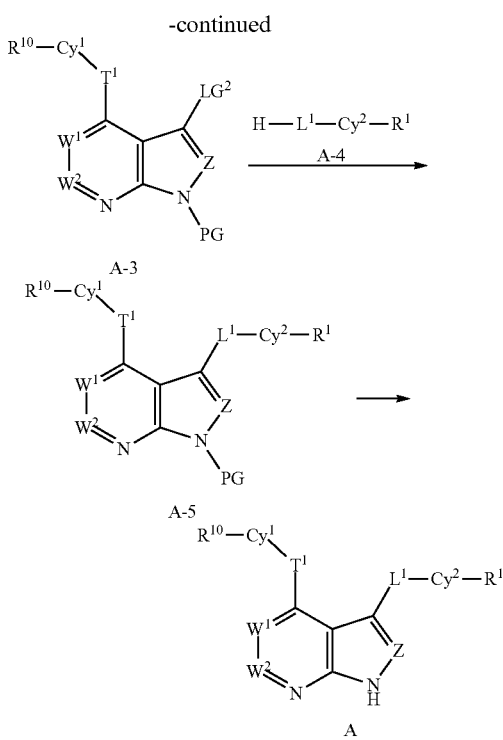

Further Forms of Compounds

Compounds disclosed herein have a structure of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXI), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId). It is understood that when reference is made to compounds described herein, it is meant to include compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXI), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) as well as to all of the specific compounds that fall within the scope of these generic formulae, unless otherwise indicated.

The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXI), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) in unoxidized form can be prepared from N-oxides of compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXI), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, Bioreversible Carriers in Drug Design, American Pharmaceutical Association and Pergamon Press, 1987, all incorporated herein in their entirety.

Sites on the aromatic ring portion of compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2$H, $^3$H, $^{13}$C, $^{14}$C, $^{15}$N, $^{18}$O, $^{17}$O, $^{35}$S, $^{18}$F, $^{36}$Cl, respectively. Certain isotopically-labeled compounds described herein, for example those into which radioactive isotopes such as $^3$H and $^{14}$C are incorporated, are useful in drug and/or substrate tissue distribution assays. Further, substitution with isotopes such as deuterium, i.e., $^2$H, can afford certain therapeutic advantages resulting from greater metabolic stability, for example increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Pharmaceutical Composition/Formulation

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), herein incorporated by reference in their entirety.

A pharmaceutical composition, as used herein, refers to a mixture of a compound described herein, such as, for example, compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitators with one or more diffusion facilitators can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel®PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, g, or ng of therapeutic agent per ml, dl, or 1 of blood serum, absorbed into the bloodstream after administration. As used herein, measurable plasma concentrations are typically measured in ng/ml or g/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) with one or more pharmaceutical excipients to form a bulk blend composition. When referring to these bulk blend compositions as homogeneous, it is meant that the particles of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId). In one embodiment, some or all of the particles of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are coated. In another embodiment, some or all of the particles of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are microencapsulated. In still another embodiment, the particles of the compound of any of Formula (IA), (I), (IIa)-(IIb), (IIIa)-(IIId), (IVa)-(IVh), (Va)-(Vh), (Va)-(VIb), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) which sufficiently isolate the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) from other non-compatible excipients. Materials compatible with compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are those that delay the release of the compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are microencapsulated prior to being formulated into one of the above forms. In still another embodiment, some or most of the particles are coated prior to being further formulated by using standard coating procedures, such as those described in *Remington's Pharmaceutical Sciences,* 20th Edition (2000).

In other embodiments, the solid dosage formulations of the compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound of Formula (A)-(C), are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated herein by reference.

The pharmaceutical solid oral dosage forms including formulations described herein, which include a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) can be further formulated to provide a controlled release of the compound of Formula (A). Controlled release refers to the release of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles<1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include a compound of Formula (A)-(C), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form including at least two groups of particles, (i.e. multiparticulate) each containing the formulation described herein. The first group of particles provides a substantially immediate dose of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId).

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms,* 2 Ed., Vol. 1, pp. 209-214 (1990); Singh et al., *Encyclopedia of Pharmaceutical Technology,* $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compounds of any of Formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology*, 2$^{nd}$ Ed., pp. 754-757 (2002). In addition to the particles of compound of Formula (A)-(C), the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®), which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon®S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated herein by reference. Formulations that include a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations.

Buccal formulations that include compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) may be administered using a variety of formulations known in the art. For example, such formulations include, but are not limited to, U.S. Pat. Nos. 4,229,447, 4,596,795, 4,755,386, and 5,739,136, each of which is specifically incorporated herein by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of any of Formula (I); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations.

Formulations that include a compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The compounds described herein can be used in the preparation of medicaments for the inhibition of Btk or a homolog thereof, or for the treatment of diseases or conditions that would benefit, at least in part, from inhibition of Btk or a homolog thereof. In addition, a method for treating any of the diseases or conditions described herein in a subject in need of such treatment, involves administration of pharmaceutical compositions containing at least one compound of any of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) described herein, or a pharmaceutically acceptable salt, pharmaceutically acceptable N-oxide, pharmaceutically active metabolite, prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary.

Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The reversible or irreversible Btk inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one reversible or irreversible Btk inhibitor compound described herein in combination with another therapeutic agent. By way of example only, if one of the side effects experienced by a patient upon receiving one of the reversible or irreversible Btk inhibitor compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) described herein, may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Exemplary Therapeutic Agents for Use in Combination with a Reversible or Irreversible Btk Inhibitor Compound Where the subject is suffering from or at risk of suffering from an autoimmune disease, an inflammatory disease, or an allergy disease, a reversible or irreversible Btk inhibitor compound can be used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Where the subject is suffering from or at risk of suffering from a B-cell proliferative disorder (e.g., plasma cell myeloma), the subjected can be treated with a reversible or irreversible Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a reversible or irreversible Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents that can be employed in combination with a reversible or irreversible Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents that can be employed in combination with a reversible or irreversible Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a reversible or irreversible Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a reversible or irreversible Btk inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination a reversible or irreversible Btk inhibitor compound include, but are not limited to, nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a reversible or irreversible Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which can be used in combination with a reversible or irreversible Btk inhibitor compound include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, lnanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Where the subject is suffering from or at risk of suffering from a thromboembolic disorder (e.g., stroke), the subject can be treated with a reversible or irreversible Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by inhibition of Btk, or in which Btk is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

C481S Mutation

The B cell lymphoma is characterized by a plurality of cells having a mutant BTK polypeptide. The mutant BTK polypeptides contain one or more amino acid substitutions that confers resistance to inhibition by a covalent and/or irreversible BTK inhibitor. The modification can be a substitution or a deletion of the amino acid at amino acid position 481 compared to a wild type BTK. Specifically, the modification can be a substitution of cysteine to serine at amino acid position 481 of the BTK polypeptide ("C481S") as described by Woyach, et al. (Resistance mechanisms for the Bruton's tyrosine kinase inhibitor ibrutinib, *N Engl J Med.* 2014, 12; 370(24):2286-94).

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet. Reference thereto evidences the availability and public dissemination of such information.

The examples below as well as throughout the application, the following abbreviations have the following meanings. If not defined, the terms have their generally accepted meanings.

aq=aqueous
[(t-Bu)$_3$PH]BF$_4$=tri-tert-butylphosphonium tetrafluoroborate
t-BuOH=tertiary butanol
DCE=1,2-dichloroethane
DCM=dichloromethane
DIEA or DIPEA=N,N-diisopropylethylamine
DMAP=dimethylaminopyridine
DMF=dimethylformamide
DMSO=dimethylsulfoxide
ESI=electron spray ionization
EtOAc or EA=ethyl acetate
Ex. X=Example X
g=gram
HCl=hydrogen chloride
HPLC=high performance liquid chromatography
hr=hour
$^1$H NMR=proton nuclear magnetic resonance
IPA=isopropyl alcohol
LC-MS=liquid chromatography mass spectroscopy
M=molar
MeCN=acetonitrile
MeOH=methanol
mg=milligram
min=minute
mL=milliliter
mM=millimolar
mmol=millimole
m.p.=melting point
MS=mass spectrometry
m/z=mass-to-charge ratio
N=normal
nM=nanomolar
nm=nanometer
Pd$_2$dba$_3$=tris(dibenzylideneacetone)dipalladium(0)
PE=petroleum ether
PMBCl=4-methoxybenzyl chloride
p.s.i.=pound per square inch
quant.=quantitative
RP=reverse phase
RT or r.t.=room temperature
Sat.=saturated
TEA=triethylamine
TFA=trifluoroacetic acid
TLC=thin layer chromatography
T$_3$P=propylphosphonic anhydride
μL=microliter
μM=micromolar Example 1

Synthesis of (R)-1-(3-(4-(4-chlorophenoxy)-1H-pyrazolo[3,4-b]pyridin-3-ylamino)pyrrolidin-1-yl)prop-2-en-1-one (10) (Compound ID 1)

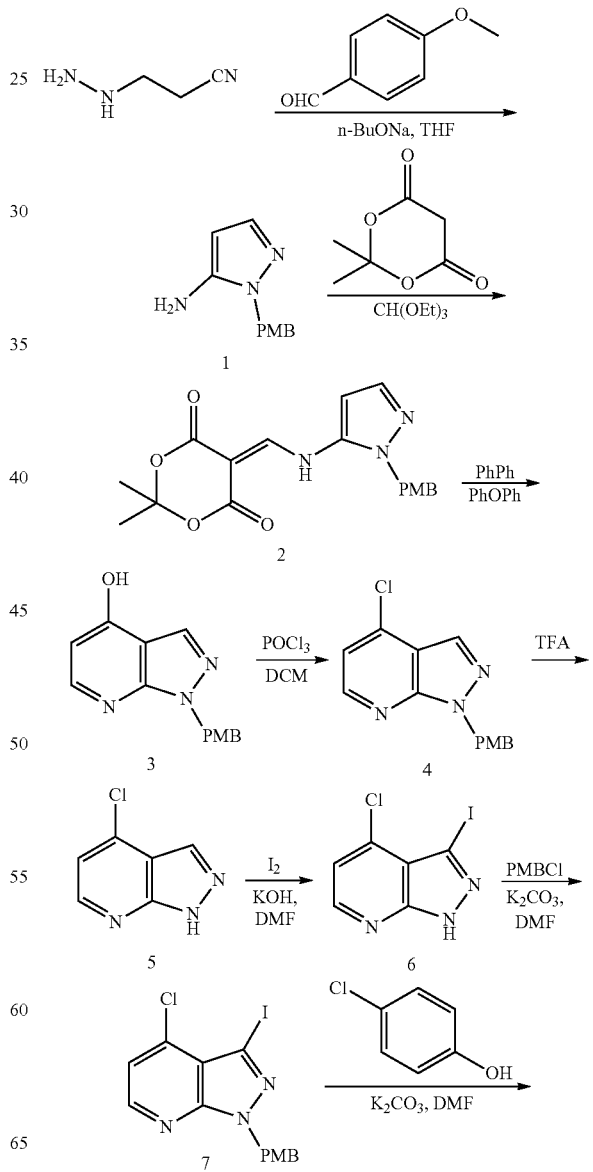

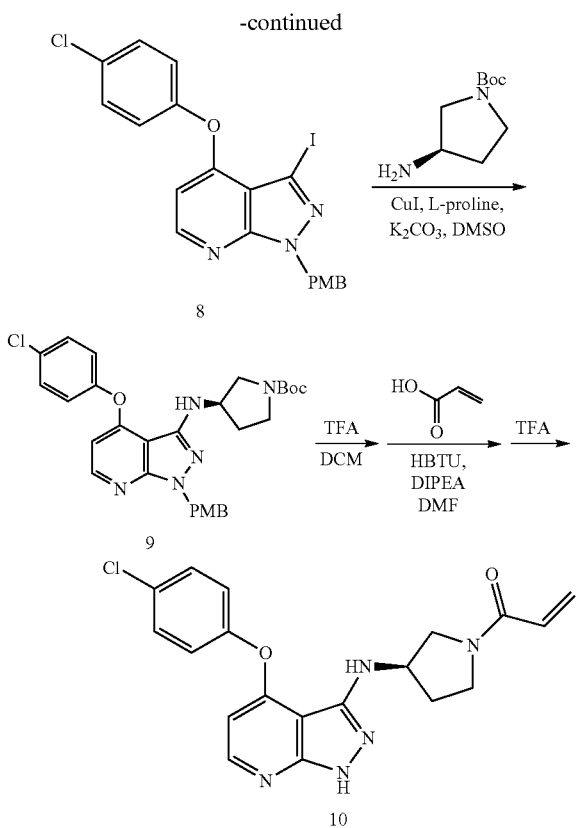

To a solution of 3-hydrazinylpropanenitrile (15.0 g, 0.176 mol) in anhydrous THF (60 mL) was added 4-methoxybenzaldehyde (25.4 g, 0.187 mol) dropwise. The resulting mixture was stirred at r.t. for 3 hrs. The volatiles were evaporated and the residue was diluted with n-BuOH (38 mL). A freshly prepared solution of n-BuONa (0.176 mol) in n-BuOH (88 mL) was added dropwise to the resulting mixture, which was then heated to 120° C. under $N_2$ atmosphere and kept for 3 hrs. After cooling to r.t., the reaction mixture was quenched with ice water (375 mL) and extracted with DCM (375 mL). The organic phase was washed with brine, dried over $Na_2SO_4$ and concentrated under reduced pressure. The crude product was purified by flash chromatography (silica gel, 0 to 50% ethyl acetate in petroleum ether) to afford 1-(4-methoxybenzyl)-1H-pyrazol-5-amine (1) (20.5 g, 57% yield) as a yellow solid. LC-MS (ESI): m/z (M+1) 204.1.

A mixture of 2,2-dimethyl-1,3-dioxane-4,6-dione (23.9 g, 0.165 mol) in $CH(OEt)_3$ (240 mL) was heated to 80° C. for 1 hr. A solution of 1-(4-methoxybenzyl)-1H-pyrazol-5-amine (1) (20.5 g, 0.10 mol) in $CH(OEt)_3$ (240 mL) was added in one portion to the reaction mixture. The stirring was continued at 80° C. under $N_2$ atmosphere overnight. After cooling to r.t., the reaction was diluted with toluene and concentrated to remove ethanol. The resulting suspension was diluted with ether (500 mL). 5-((1-(4-Methoxybenzyl)-1H-pyrazol-5-ylamino)methylene)-2,2-dimethyl-1,3-dioxane-4,6-dione (2) (17.5 g, 49% yield) was obtained as a yellow solid by filtration. LC-MS (ESI): m/z (M−1) 356.0.

A suspension of 5-((1-(4-methoxybenzyl)-1H-pyrazol-5-ylamino)methylene)-2,2-di methyl-1,3-dioxane-4,6-dione (2) (17.5 g, 49 mmol) in PhPh-PhOPh (53 mL) was heated to 240° C. for 10 min under $N_2$ atmosphere. After cooling to r.t., the reaction mixture was washed with PE (500 mL) and ether (500 mL) respectively to give the crude product which was purified by flash chromatography (silica gel, 0 to 100% ethyl acetate in petroleum ether) to afford 1-(4-methoxybenzyl)-1H-pyrazolo[3,4-b]pyridin-4-ol (3) (7.9 g, 63% yield) as yellow solid. LC-MS (ESI): m/z (M+1) 256.1.

To a solution of 1-(4-methoxybenzyl)-1H-pyrazolo[3,4-b]pyridin-4-ol (3) (7.9 g, 31 mmol) in anhydrous DCM (100 mL) was added $POCl_3$ (30 g, 186 mmol). The resulting mixture was heated to reflux under $N_2$ atmosphere overnight. After cooling to r.t., the reaction mixture was slowly poured into ice water (500 mL). Sat. $NaHCO_3$ solution was slowly added until the mixture became neutral. The resulting mixture was extracted with DCM (200 mL×2). The combined organic phase was washed with brine, dried over $Na_2SO_4$, filtered and concentrated to give the crude product which was purified by flash chromatography (silica gel, 0 to 10% ethyl acetate in petroleum ether) to afford 4-chloro-1-(4-methoxybenzyl)-1H-pyrazolo[3,4-b]pyridine (4) (8.2 g, 97% yield) as a red solid. LC-MS (ESI): m/z (M+1) 273.9.

A solution of 4-chloro-1-(4-methoxybenzyl)-1H-pyrazolo[3,4-b]pyridine (4) (8.2 g, 32 mmol) in TFA (50 mL) was heated to 75° C. for 2 hrs. The reaction mixture was concentrated to give the crude product which was partitioned between DCM (200 mL) and sat. $NaHCO_3$ aqueous (200 mL). The organic phase was washed with brine, dried over $Na_2SO_4$, filtered and concentrated to afford 4-chloro-1H-pyrazolo[3,4-b]pyridine (5) (quant. yield) as a yellow solid. LC-MS (ESI): m/z (M+1) 154.2.

To a solution of 4-chloro-1H-pyrazolo[3,4-b]pyridine (5) (32 mmol) in DMF (90 mL) was added KOH (8.7 g, 155 mmol) and $I_2$ (26 g, 103 mmol). The resulting mixture was heated to 50° C. for 1.5 hr. After cooling to r.t., the reaction was quenched with 10% $Na_2S_2O_3$ solution until the dark color disappeared. The resulting suspension was diluted with water (250 mL) and filtered to afford 4-chloro-3-iodo-1H-pyrazolo[3,4-b]pyridine (6) (12.8 g, 89% yield) as a yellow solid. LC-MS (ESI): m/z (M+1) 279.8.

To a solution of 4-chloro-3-iodo-1H-pyrazolo[3,4-b]pyridine (6) (12.8 g, 46 mmol) in DMF (100 mL) were added $K_2CO_3$ (12.9 g, 92 mmol) and PMBCl (7.5 mL, 55 mmol). After stirring at r.t. overnight, the reaction mixture was diluted with water (500 mL) and extracted with EA (300 mL×2). The combined organic phase was washed with brine, dried over $Na_2SO_4$, filtered and concentrated to give the crude product which was purified by flash chromatography (silica gel, 0 to 30% ethyl acetate in petroleum ether and then eluted with DCM/MeOH/THF=10:1:1) to afford 4-chloro-3-iodo-1-(4-methoxybenzyl)-1H-pyrazolo[3,4-b]pyridine (7) (7.8 g, 43% yield) as a yellow solid. LC-MS (ESI): m/z (M+1) 399.9.

To a stirred solution of 4-chloro-3-iodo-1-(4-methoxybenzyl)-1H-pyrazolo[3,4-b]pyridine (7) (4.5 g, 11.3 mmol) in DMF (40 mL) were added $K_2CO_3$ (15.5 g, 113 mmol) and 4-chlorophenol (2.9 g, 22.5 mmol). The mixture was stirred at 150° C. under $N_2$ atmosphere overnight. After cooling to r.t., the resulting mixture was diluted with water (300 mL) and extracted with EA (200 mL×2). The combined organic phase was washed with brine, dried over $Na_2SO_4$, filtered and concentrated to give the crude product which was purified by flash chromatography (silica gel, 0 to 50% DCM in petroleum ether) to afford 4-(4-chlorophenoxy)-3-iodo-1-(4-methoxybenzyl)-1H-pyrazolo[3,4-b]pyridine (8) (2.7 g, 49% yield) as a yellow solid. LC-MS (ESI): m/z (M+1) 492.0.

To a stirred solution of 4-(4-chlorophenoxy)-3-iodo-1-(4-methoxybenzyl)-1H-pyrazolo[3,4-b]pyridine (8) (800 mg, 1.6 mmol) in DMSO (20 mL) were added (R)-tert-butyl 3-aminopyrrolidine-1-carboxylate (909 mg, 4.9 mmol), CuI (155 mg, 0.82 mmol), L-proline (750 mg, 6.5 mmol) and $K_2CO_3$ (1.1 g, 8.1 mmol). The resulting mixture was heated at 60° C. under $N_2$ atmosphere for 2 hr. After cooling to r.t., the reaction mixture was diluted with water (200 mL) and extracted with DCM (100 mL×2). The combined organic phase was washed with brine, dried over $Na_2SO_4$, filtered and concentrated to give the crude product which was purified by flash chromatography (silica gel, 0 to 40% EA in petroleum ether) to afford (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) (192 mg, 22% yield) as a white solid. LC-MS (ESI): m/z (M+1) 550.1.

To a solution of (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) (77 mg, 0.14 mmol) in DCM (4 mL) was added TFA (1 mL). The resulting mixture was stirred at r.t. for 30 min and then concentrated under reduced pressure to afford the de-Boc product. The intermediate was reacted with acrylic acid (20 mg, 0.28 mmol) under typical HBTU condensation condition and purified by flash chromatography (silica gel, 0 to 100% ethyl acetated in petroleum ether) to afford the corresponding amide which was then heated to 60° C. in TFA (4 mL) under $N_2$ atmosphere for 4 hr. The reaction mixture was then concentrated under reduced pressure to give the crude product which was purified by preparative HPLC (RP, C18, 10 to 95% acetonitrile in water (0.2% $NH_3.H_2O$)) to afford (R)-1-(3-(4-(4-chlorophenoxy)-1H-pyrazolo[3,4-b]pyridin-3-ylamino)pyrrolidin-1-yl)prop-2-en-1-one (10) (10 mg, 62% yield) as a white solid. LC-MS (ESI): m/z (M+1) 384.1. $^1$H NMR (400 MHz, DMSO) δ 12.23 (s, 1H), 8.13 (d, J=5.4 Hz, 1H), 7.55 (d, J=8.0 Hz, 2H), 7.32 (d, J=8.0 Hz, 2H), 6.63-6.45 (m, 1H), 6.15-6.06 (m, 1H), 6.02 (dd, J=6.6, 3.5 Hz, 1H), 5.70-5.62 (m, 1H), 5.61-5.44 (m, 1H), 4.47-4.10 (m, 1H), 4.01-3.72 (m, 1H), 3.69-3.50 (m, 2H), 2.32-2.06 (m, 2H).

Example 2

Synthesis of (R)-1-(3-((4-(4-chlorophenoxy)-1H-pyrazolo[3,4-b]pyridin-3-yl)(methyl)amino)pyrrolidin-1-yl)prop-2-en-1-one (12) (Compound ID 2)

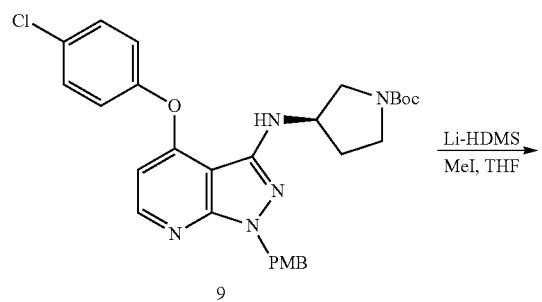

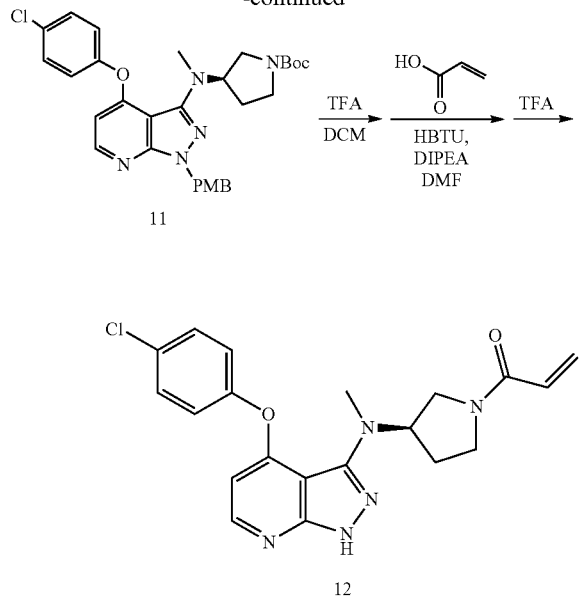

At −35° C. and under $N_2$ atmosphere, to a solution of (R)-tert-butyl 3-(4-(4-chlorophenoxy)-1-(4-methoxybenzyl)-1H-pyrazolo[3,4-b]pyridin-3-ylamino)pyrrolidine-1-carboxylate (291-9) (400 mg, 0.73 mmol) in anhydrous THF (10 mL) was added LiHMDS (1M in THF, 1.5 mL) dropwise. After stirring for 30 min, MeI (156 mg, 1.1 mmol) was added dropwise to the reaction mixture, which was then slowly warmed up to r.t. and stirred for 1 hr. The reaction was quenched with water (20 mL) and extracted with EA (30 mL×2). The combined organic phase was washed with brine, dried over $Na_2SO_4$, filtered and concentrated to give the crude product which was purified by flash chromatography (silica gel, 0 to 40% EA in petroleum ether) to afford (R)-tert-butyl 3-((4-(4-chlorophenoxy)-1-(4-methoxybenzyl)-1H-pyrazolo[3,4-b]pyridin-3-yl)(methyl)amino)pyrrolidine-1-carboxylate (11) (257 mg, 63% yield) as a yellow solid. LC-MS (ESI): m/z (M+1) 564.1.

(R)-1-(3-((4-(4-Chlorophenoxy)-1H-pyrazolo[3,4-b]pyridin-3-yl)(methyl)amino)pyrrolidin-1-yl)prop-2-en-1-one (12) (57 mg, 57% yield) was obtained as a white solid from (R)-tert-butyl 3-((4-(4-chlorophenoxy)-1-(4-methoxybenzyl)-1H-pyrazolo[3,4-b]pyridin-3-yl)(methyl)amino)pyrrolidine-1-carboxylate (11) (257 mg, 0.53 mmol) and acrylic acid (105 mg, 1.06 mmol), following a similar procedure as described in Example 1. LC-MS (ESI): m/z (M+1) 564.1. LC-MS (ESI): m/z (M+1) 398.0. $^1$H NMR (400 MHz, DMSO) δ 12.75 (br, 1H), 8.22 (dd, J=5.4, 2.3 Hz, 1H), 7.62-7.49 (m, 2H), 7.32 (dd, J=8.8, 1.3 Hz, 2H), 6.69-6.46 (m, 1H), 6.19 (dd, J=5.4, 3.1 Hz, 1H), 6.14-6.00 (m, 1H), 5.71-5.58 (m, 1H), 4.51-4.31 (m, 1H), 3.90-3.69 (m, 1H), 3.65-3.49 (m, 1H), 3.39-3.15 (m, 1H), 2.85 (d, J=7.1 Hz, 3H), 2.25-1.85 (m, 2H).

Example 3

Synthesis of (R,E)-1-(3-(4-(4-chlorophenoxy)-1H-pyrazolo[3,4-b]pyridin-3-ylamino)pyrrolidin-1-yl)-4-(dimethylamino)but-2-en-1-one (13) (Compound ID 3)

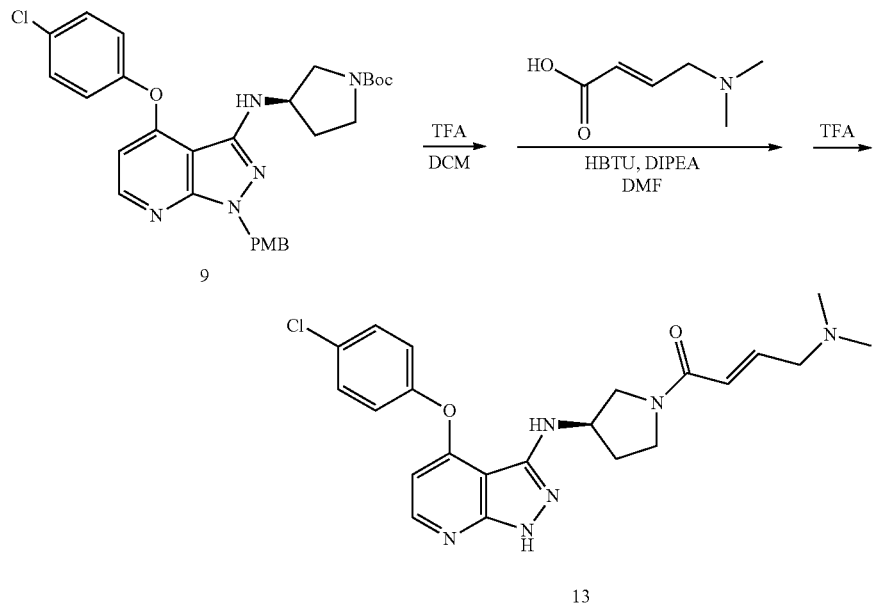

(R,E)-1-(3-(4-(4-Chlorophenoxy)-1H-pyrazolo[3,4-b]pyridin-3-ylamino)pyrrolidin-1-yl)-4-(dimethylamino)but-2-en-1-one (13) (58 mg, 28% yield) was obtained as a white solid from (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) (240 mg, 0.44 mmol) and (E)-4-(dimethylamino)but-2-enoic acid (145 mg, 0.88 mmol), following a similar procedure as described in Example 1. $^1$H NMR (400 MHz, DMSO) δ 12.35 (br, 1H), 10.00 (br, 1H), 8.15 (d, J=5.3 Hz, 1H), 7.62-7.50 (m, 2H), 7.32 (d, J=8.8 Hz, 2H), 6.73-6.56 (m, 2H), 6.04 (dd, J=5.4, 3.5 Hz, 1H), 4.41-4.28 (m, 1H), 4.23-3.93 (m, 1H), 3.90-3.82 (m, 2H), 3.79-3.65 (m, 1H), 3.62-3.39 (m, 2H), 2.78-2.68 (m, 6H), 2.31-1.97 (m, 2H). LC-MS (ESI): m/z (M+1) 441.2.

Example 4

Synthesis of (R)-1-(3-(4-(4-chlorophenoxy)-1H-pyrrolo[2,3-b]pyridin-3-ylamino)pyrrolidin-1-yl)prop-2-en-1-one (18) (Compound ID 7)

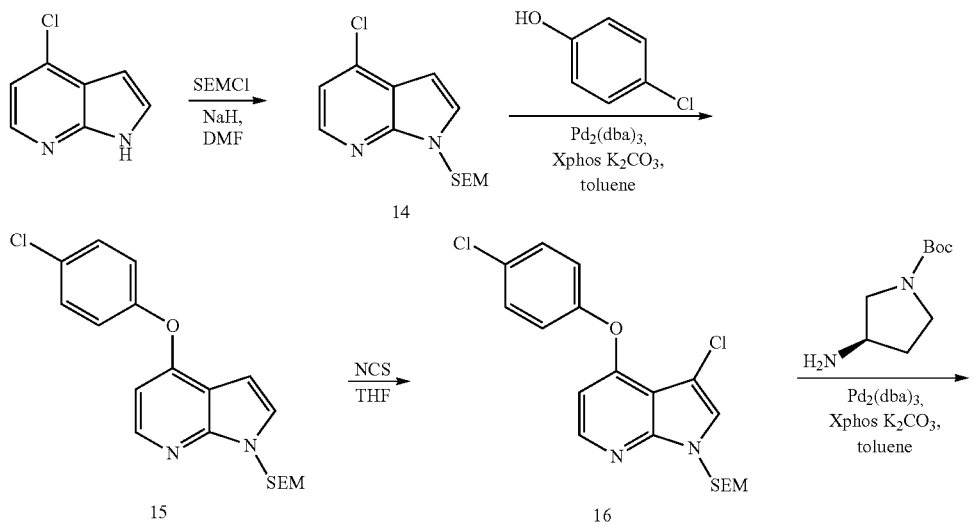

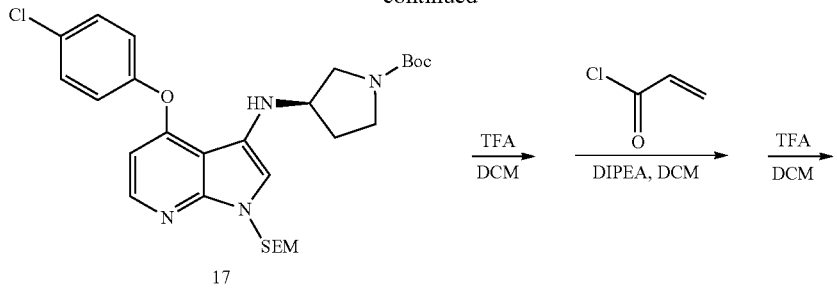

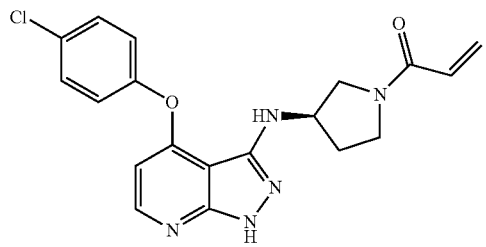

To a solution of 4-chloro-1H-pyrrolo[2,3-b]pyridine (0.83 g, 5.5 mmol) and SEMCl (1.0 g, 6.0 mmol) in DMF (10 mL) was added NaH (60%, 0.28 g, 7.0 mmol) portionwise. After stirred at r.t. overnight, the resulting mixture was quenched with $H_2O$ (20 mL) and extracted with EtOAc (20 mL×2). The combined organic phase was washed with water (30 mL) and brine, dried over $Na_2SO_4$, filtered and concentrated to give the crude product which was purified by flash chromatography (silica gel, 0 to 15% EA in petroleum ether) to afford 4-chloro-1-((2-(trimethylsilyl)ethoxy)methyl)-1H-pyrrolo[2,3-b]pyridine (14) (940 mg, 61% yield) as a yellow solid. LC-MS (ESI): m/z (M/M+2) 282.0/284.0.

A mixture of 4-chloro-1-((2-(trimethylsilyl)ethoxy)methyl)-1H-pyrrolo[2,3-b]pyridine (14) (2.3 g, 8.1 mmol), 4-chlorophenol (2.1 g, 16.2 mmol), $Pd_2(dba)_3$ (740 mg, 0.81 mmol), Xphos (386 mg, 0.81 mmol) and $K_2CO_3$ (3.4 g, 24.3 mmol) was stirred at 110° C. overnight. After cooling to r.t., the resulting mixture was filtered through celite pad. The filtrate was concentrated to give the crude product which was purified by flash chromatography (silica gel, 0 to 40% EA in petroleum ether) to afford 4-(4-chlorophenoxy)-1-((2-(trimethylsilyl)ethoxy)methyl)-1H-pyrrolo[2,3-b]pyridine (15) (1.5 g, 52% yield) as a yellow solid. LC-MS (ESI): m/z (M/M+2) 374.1/376.1.

To a solution of 4-(4-chlorophenoxy)-1-((2-(trimethylsilyl)ethoxy)methyl)-1H-pyrrolo[2,3-b]pyridine (15) (343 mg, 0.92 mmol) in THF (10 mL) was added NCS (135 mg, 1.0 mol). After stirred at r.t. for 1 hr, the reaction mixture was diluted with EtOAc (20 mL) and $H_2O$ (20 mL). The organic phase was washed with brine, dried over $Na_2SO_4$, filtered and concentrated to give the crude product which was purified by flash chromatography (silica gel, 0 to 10% EA in a mixture of DCM and petroleum ether (1:1)) to afford 3-chloro-4-(4-chlorophenoxy)-1-((2-(trimethylsilyl)ethoxy)methyl)-1H-pyrrolo[2,3-b]pyridine (16) (140 mg, 37% yield) as a yellow oil. LC-MS (ESI): m/z (M/M+2) 408.1/410.1.

Under an $N_2$ atmosphere, a mixture of 3-chloro-4-(4-chlorophenoxy)-1- ((2-(trimethylsilyl)ethoxy)methyl)-1H-pyrrolo[2,3-b]pyridine (16) (110 mg, 0.27 mmol), (R)-tert-butyl 3-aminopyrrolidine-1-carboxylate (200 mg, 1.08 mmol), $Pd_2(dba)_3$ (24.7 mg, 0.027 mmol), Xphos (13.0 mg, 0.027 mmol) and $K_2CO_3$ (112 mg, 0.81 mmol) was stirred at 110° C. overnight. After cooling to r.t., the resulting mixture was filtered through a celite pad. The filtrate was concentrated to give the crude product which was purified by flash chromatography (silica gel, 0 to 50% EA in petroleum ether) to afford (R)-tert-butyl 3-(4-(4-chlorophenoxy)-1-((2-(trimethylsilyl)ethoxy)methyl)-1H-pyrrolo[2,3-b]pyridin-3-ylamino)pyrrolidine-1-carboxylate (17) (85 mg, 86% yield) as a yellow solid. LC-MS (ESI): m/z (M/M+2) 558.1/560.1.

Under (R)-1-(3-(4-(4-Chlorophenoxy)-1H-pyrrolo[2,3-b]pyridin-3-ylamino)pyrrolidin-1-yl)prop-2-en-1-one (18) (4.0 mg, 5% yield) was obtained as a white solid from (R)-tert-butyl 3-(4-(4-chlorophenoxy)-1-((2-(trimethylsilyl)ethoxy)methyl)-1H-pyrrolo[2,3-b]pyridin-3-ylamino)pyrrolidine-1-carboxylate (17) (85 mg, 0.15 mmol), following a similar procedure as described in Example 1. LC-MS (ESI): m/z (M/M+2) 382.1/384.1.

Example 5

Synthesis of (R)-1-(3-(4-(4-phenoxyphenoxy)-1H-pyrazolo[3,4-b]pyridin-3-ylamino)pyrrolidin-1-yl)prop-2-en-1-one (21) (Compound ID 4)

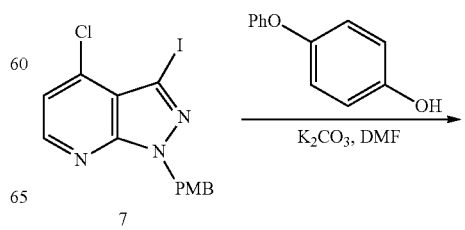

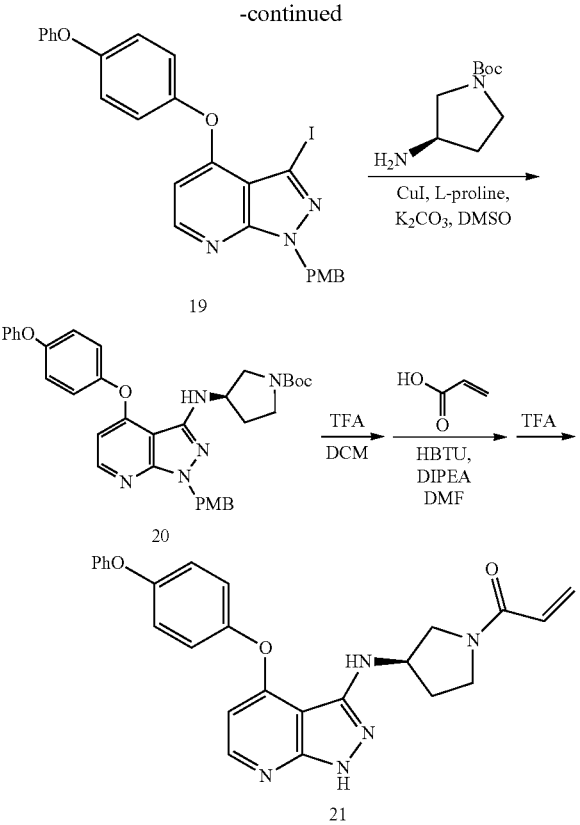

4-(4-chlorophenoxy)-3-iodo-1-(4-methoxybenzyl)-1H-pyrazolo[3,4-b]pyridine (8) in Example 1. LC-MS (ESI): m/z (M+1) 550.0.

(R)-tert-Butyl 3-(1-(4-methoxybenzyl)-4-(4-phenoxyphenoxy)-1H-pyrazolo[3,4-b]pyridin-3-ylamino)pyrrolidine-1-carboxylate (20) (1.3 g, 43% yield) was obtained as a yellow solid from 3-iodo-1-(4-methoxybenzyl)-4-(4-phenoxyphenoxy)-1H-pyrazolo[3,4-b]pyridine (19) (2.7 g, 4.9 mmol) and (R)-tert-butyl 3-aminopyrrolidine-1-carboxylate (2.7 g, 14.8 mmol), following a similar procedure outlined in the preparation of (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) in Example 1. LC-MS (ESI): m/z (M+1) 608.0.

To (R)-1-(3-(4-(4-Phenoxyphenoxy)-1H-pyrazolo[3,4-b]pyridin-3-ylamino)pyrrolidin-1-yl)prop-2-en-1-one (21) (25 mg, 35% yield) was obtained as a white solid from (R)-tert-butyl 3-(1-(4-methoxybenzyl)-4-(4-phenoxyphenoxy)-1H-pyrazolo[3,4-b]pyridin-3-ylamino)pyrrolidine-1-carboxylate (20) (250 mg, 0.41 mmol) and acrylic acid (50 mg, 0.69 mmol), following a similar three-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 442.1. $^1$H NMR (400 MHz, DMSO) δ 12.24 (s, 1H), 8.13 (d, J=5.4 Hz, 1H), 7.47-7.35 (m, 2H), 7.35-7.24 (m, 2H), 7.14 (dd, J=10.5, 8.5 Hz, 3H), 7.04 (d, J=8.1 Hz, 2H), 6.66-6.46 (m, 1H), 6.16-6.08 (m, 1H), 6.04 (dd, J=5.4, 1.7 Hz, 1H), 5.69-5.53 (m, 2H), 4.40-4.12 (m, 1H), 4.03-3.62 (m, 2H), 3.60-3.42 (m, 2H), 2.29-2.16 (m, 1H), 2.12-1.99 (m, 1H).

Example 6

Synthesis of (R,E)-4-(dimethylamino)-1-(3-(4-(4-phenoxyphenoxy)-1H-pyrazolo[3,4-b]pyridin-3-ylamino)pyrrolidin-1-yl)but-2-en-1-one (22) (Compound ID 5)

3-Iodo-1-(4-methoxybenzyl)-4-(4-phenoxyphenoxy)-1H-pyrazolo[3,4-b]pyridine (19) (3.7 g, 68% yield) was obtained as a yellow solid from 4-chloro-3-iodo-1-(4-methoxybenzyl)-1H-pyrazolo[3,4-b]pyridine (7) (4.0 g, 10.0 mmol) and 4-phenoxy phenol (2.8 g, 15.0 mmol), following a similar procedure outlined in the preparation of (R,E)-4-(Dimethylamino)-1-(3-(4-(4-phenoxyphenoxy)-1H-pyrazolo[3,4-b]pyridin-3-ylamino)pyrrolidin-1-yl)but-2-en-1-one (22) (25 mg, 39% yield) was obtained as a white solid from (R)-tert-butyl 3-(1-(4-methoxybenzyl)-4-(4-phenoxy phenoxy)-1H-pyrazolo[3,4-b]pyridin-3-ylamino)pyrrolidine-1-carboxylate (20) (250 mg, 0.41 mmol) and (E)-4-(dimethylamino)but-2-enoic acid (114 mg, 0.69 mmol), following a similar procedure outlined in the preparation of (R)-1-(3-(4-(4-chloro phenoxy)-1H-pyrazolo[3,4-b]pyridin-3-ylamino)pyrrolidin-1-yl)prop-2-en-1-one (10) in Example 1. LC-MS (ESI): m/z (M+1) 499.4. ¹H NMR (400 MHz, DMSO) δ 12.24 (br, 1H), 8.13 (d, J=5.4 Hz, 1H), 7.49-7.36 (m, 2H), 7.35-7.25 (m, 2H), 7.20-7.10 (m, 3H), 7.04 (d, J=8.3 Hz, 2H), 6.67-6.50 (m, 1H), 6.34 (dd, J=20.8, 15.2 Hz, 1H), 6.04 (dd, J=5.4, 0.8 Hz, 1H), 5.59 (dd, J=26.0, 5.7 Hz, 1H), 4.39-4.15 (m, 1H), 3.95-3.59 (m, 2H), 3.56-3.37 (m, 2H), 3.00 (d, J=6.2 Hz, 2H), 2.27-2.19 (m, 1H), 2.11 (d, J=6.5 Hz, 6H), 2.05-1.95 (m, 1H).

Example 7

Synthesis of (R)-1-(3-(4-(4-phenoxyphenoxy)-1H-pyrazolo[3,4-b]pyridin-3-ylamino)piperidin-1-yl)prop-2-en-1-one (24) (Compound ID 6)

(R)-tert-Butyl 3-(1-(4-methoxybenzyl)-4-(4-phenoxyphenoxy)-1H-pyrazolo[3,4-b]pyridin-3-ylamino)piperidine-1-carboxylate (23) (200 mg, 20% yield) was obtained as a yellow solid from 3-iodo-1-(4-methoxybenzyl)-4-(4-phenoxyphenoxy)-1H-pyrazolo[3,4-b]pyridine (19) (900 mg, 1.6 mmol) and (R)-tert-butyl 3-amino piperidine-1-carboxylate (3.1 g, 16.4 mmol), following a similar procedure outlined in the preparation of (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) in Example 1. LC-MS (ESI): m/z (M+1) 623.1.

(R)-1-(3-(4-(4-Phenoxyphenoxy)-1H-pyrazolo[3,4-b]pyridin-3-ylamino)piperidin-1-yl)prop-2-en-1-one (24) (11 mg, 21% yield) was obtained as a white solid from (R)-tert-butyl 3-(1-(4-methoxybenzyl)-4-(4-phenoxyphenxy)-1H-pyrazolo[3,4-b]pyridin-3-ylamino)piperidine-1-carboxylate (23) (217 mg, 0.35 mmol) and acrylic acid (50 mg, 0.69 mmol), following a similar three-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 456.2. ¹H NMR (400 MHz, DMSO) δ 12.18 (s, 1H), 8.13 (d, J=5.3 Hz, 1H), 7.41 (t, J=7.8 Hz, 2H), 7.29 (d, J=8.7 Hz, 2H), 7.20-7.09 (m, 3H), 7.05 (d, J=7.8 Hz, 2H), 6.88-6.55 (m, 1H), 6.16-5.91 (m, 2H), 5.69-5.47 (m, 1H), 5.20 (d, J=7.2 Hz, 1H), 4.55-3.80 (m, 2H), 3.74-3.55 (m, 1H), 3.14-2.92 (m, 1H), 2.10-1.97 (m, 1H), 1.79-1.61 (m, 2H), 1.58-1.29 (m, 1H)

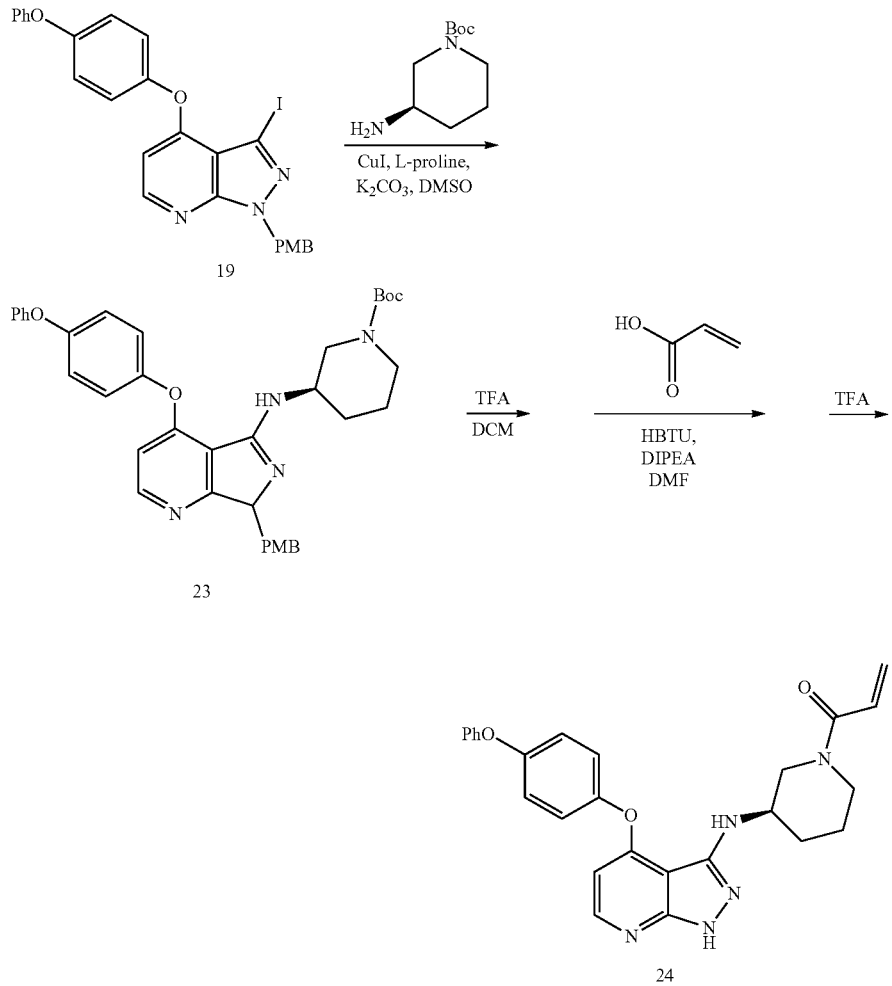

Example 8

Synthesis of (R,E)-4-(cyclopropyl(methyl)amino)-1-(3-(4-(4-phenoxyphenoxy)-1H-pyrazolo[3,4-b]pyridin-3-ylamino)piperidin-1-yl)but-2-en-1-one (25) (Compound ID 8)

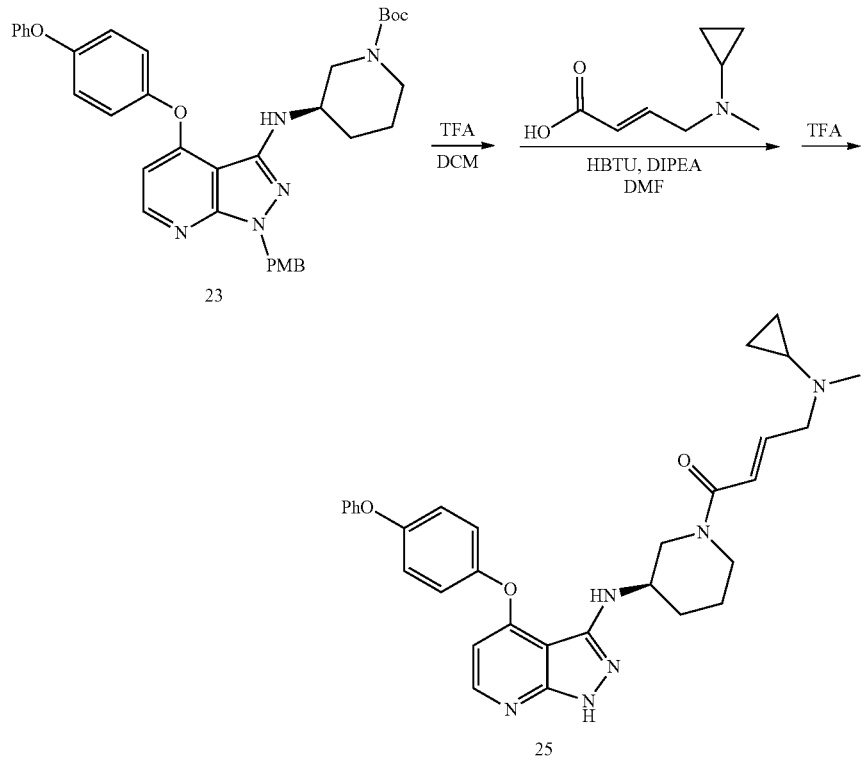

(R,E)-4-(cyclopropyl(methyl)amino)-1-(3-(4-(4-phenoxyphenoxy)-1H-pyrazolo[3,4-b]pyridin-3-ylamino)piperidin-1-yl)but-2-en-1-one (25) (45 mg, 10% yield) was obtained as a white solid from (R)-tert-butyl 3-(1-(4-methoxybenzyl)-4-(4-phenoxyphenoxy)-1H-pyrazolo[3,4-b]pyridin-3-ylamino)piperidine-1-carboxylate (23) (260 mg, mmol) and (E)-4-(cyclopropyl(methyl)amino)but-2-enoic acid (268 mg, 0.84 mmol), following a similar three-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 539.1. $^1$H NMR (400 MHz, DMSO) δ 12.31-12.16 (m, 1H), 8.13 (d, J=5.3 Hz, 1H), 7.41 (t, J=8.0 Hz, 2H), 7.28 (d, J=8.2 Hz, 2H), 7.20-7.09 (m, 3H), 7.05 (d, J=8.4 Hz, 2H), 6.65-6.32 (m, 2H), 6.04 (d, J=5.4 Hz, 1H), 5.27-5.10 (m, 1H), 4.44-3.40 (m, 3H), 3.25-2.92 (m, 3H), 2.33-1.95 (m, 4H), 1.80-1.55 (m, 3H), 1.49-1.21 (m, 1H), 0.50-0.11 (m, 4H).

Example 9

Synthesis of (R,E)-4-(dimethylamino)-1-(3-(4-(4-phenoxyphenylamino)-1H-pyrazolo[3,4-b]pyridin-3-yloxy)pyrrolidin-1-yl)but-2-en-1-one (28) (Compound ID 14)

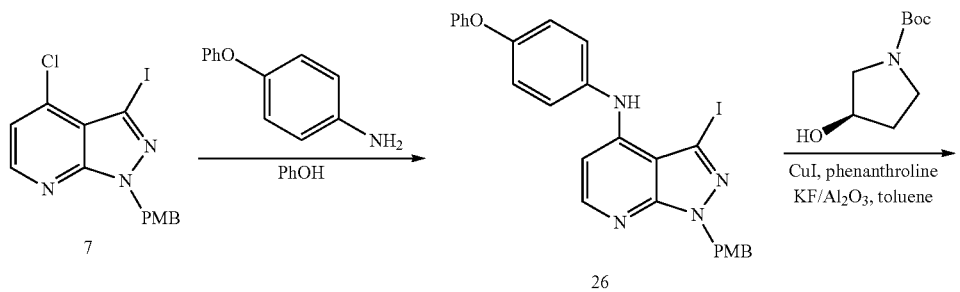

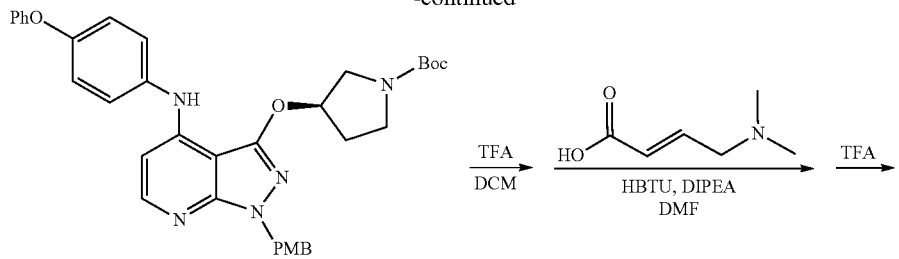

27

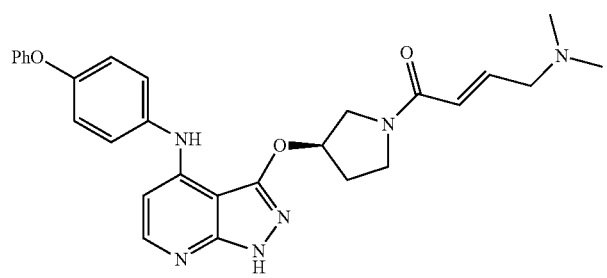

28

A mixture of 4-chloro-3-iodo-1-(4-methoxybenzyl)-1H-pyrazolo[3,4-b]pyridine (7) (1.0 g, 2.5 mmol), 4-phenoxyaniline (925 mg, 5.0 mmol) and phenol (3.8 g, 40 mmol) was heated at 100° C. under $N_2$ atmosphere overnight. After cooling to r.t., the reaction mixture was diluted with EA (40 mL) and washed with 1M NaOH (20 mL) three times. The organic phase was washed with brine, dried over $Na_2SO_4$, filtered and concentrated under reduced pressure to give the crude product which was purified by flash chromatography (silica gel, 0 to 100% PE in DCM) to afford 3-iodo-1-(4-methoxybenzyl)-N-(4-phenoxyphenyl)-1H-pyrazolo[3,4-b]pyridin-4-amine (26) (600 mg, 44% yield) as a pink solid. LC-MS (ESI): m/z (M+1) 548.9.

A mixture of 3-iodo-1-(4-methoxybenzyl)-N-(4-phenoxyphenyl)-1H-pyrazolo[3,4-b]pyri din-4-amine (26) (550 mg, 1.0 mmol), (R)-tert-butyl 3-hydroxypyrrolidine-1-carboxylate (3.7 g, 20 mmol), CuI (190 mg, 1.0 mmol), phenanthroline (180 mg, 1.0 mmol) and $KF/Al_2O_3$ (46% wt. 884 mg, 7.0 mmol) in toluene (20 mL) was heated to 120° C. under $N_2$ atmosphere overnight. After cooling to r.t., the reaction mixture was concentrated under reduced pressure to give the crude product which was purified by flash chromatography (silica gel, 0 to 35% EA in PE) to afford (R)-tert-butyl 3-(1-(4-methoxybenzyl)-4-(4-phenoxyphenylamino)-1H-pyrazolo[3,4-b]pyridin-3-yloxy)pyrrolidine-1-carboxylate (27) (376 mg, 62% yield) as a white solid. LC-MS (ESI): m/z (M+1) 607.2.

(R,E)-4-(dimethylamino)-1-(3-(4-(4-phenoxyphenylamino)-1H-pyrazolo[3,4-b]pyridin-3-yloxy)pyrrolidin-1-yl)but-2-en-1-one (28) (22 mg, 29% yield) was obtained as a white solid from (R)-tert-butyl 3-(1-(4-methoxybenzyl)-4-(4-phenoxyphenylamino)-1H-pyrazolo[3,4-b]pyridin-3-yloxy)pyrrolidine-1-carboxylate (27) (106 mg, 0.21 mmol) and (E)-4-(dimethylamino)but-2-enoic acid (69 mg, 0.42 mmol), following a similar three-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 499.9. $^1$H NMR (400 MHz, DMSO) δ 12.23 (s, 1H), 7.96 (d, J=5.5 Hz, 1H), 7.88 (s, 1H), 7.38 (t, J=7.8 Hz, 2H), 7.32 (d, J=8.6 Hz, 2H), 7.12 (t, J=7.1 Hz, 1H), 7.08-6.96 (m, 3H), 6.65-6.52 (m, 1H), 6.39 (dd, J=25.4, 15.3 Hz, 1H), 6.25 (t, J=6.1 Hz, 1H), 5.47-5.18 (m, 1H), 3.96-3.49 (m, 4H), 3.07 (d, J=3.9 Hz, 2H), 2.40-2.23 (m, 2H), 2.16 (s, 6H).

Example 10

Synthesis of (R,E)-4-((2-methoxyethyl)(methyl)amino)-1-(3-(4-(4-phenoxyphenoxy)-1H-pyrazolo[3, 4-b]pyridin-3-ylamino)pyrrolidin-1-yl)but-2-en-1-one (29) (Compound ID 9)

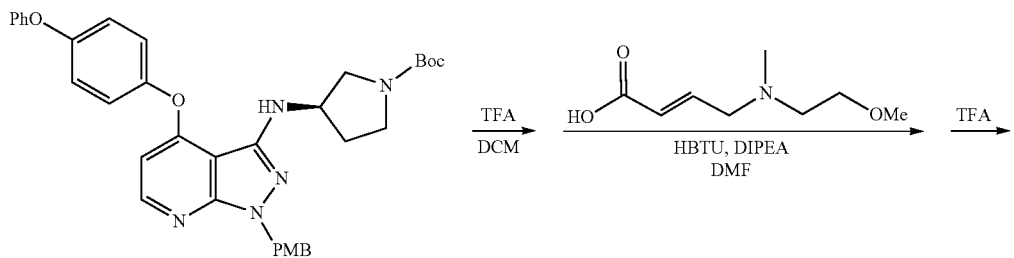

20

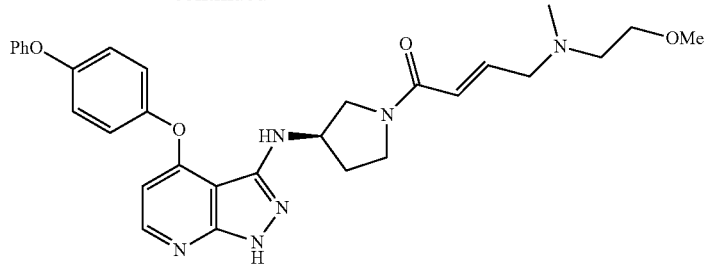

29

(R,E)-4-((2-Methoxyethyl)(methyl)amino)-1-(3-(4-(4-phenoxyphenoxy)-1H-pyrazolo[3,4-b]pyridin-3-ylamino)pyrrolidin-1-yl)but-2-en-1-one (29) (60 mg, 19% yield) was obtained as a white solid from (R)-tert-butyl 3-(1-(4-methoxy benzyl)-4-(4-phenoxyphenoxy)-1H-pyrazolo[3,4-b]pyridin-3-ylamino)pyrrolidine-1-carboxylate (20) (300 mg, 0.5 mmol) and (E)-4-((2-methoxyethyl)(methyl)amino)but-2-enoic acid (495 mg, 1.2 mmol), following a similar three-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 543.4. ¹H NMR (400 MHz, DMSO) δ 12.24 (s, 1H), 8.13 (d, J=5.4 Hz, 1H), 7.40 (t, J=7.8 Hz, 2H), 7.30 (d, J=8.9 Hz, 2H), 7.18-7.10 (m, 3H), 7.04 (d, J=8.1 Hz, 2H), 6.68-6.51 (m, 1H), 6.37 (t, J=16.4 Hz, 1H), 6.04 (d, J=5.4 Hz, 1H), 5.59 (dd, J=24.8, 5.8 Hz, 1H), 4.41-3.44 (m, 4H), 3.42-3.36 (m, 2H), 3.19 (d, J=10.3 Hz, 3H), 3.11 (t, J=6.4 Hz, 2H), 2.47-2.38 (m, 2H), 2.35-2.19 (m, 1H), 2.15 (d, J=6.9 Hz, 3H), 2.11-1.95 (m, 1H).

Example 11

Synthesis of (R,E)-4-(cyclopropyl(methyl)amino)-1-(3-(4-(4-phenoxyphenoxy)-1H-pyrazolo[3,4-b]pyridin-3-ylamino)pyrrolidin-1-yl)but-2-en-1-one (30) (Compound ID 10)

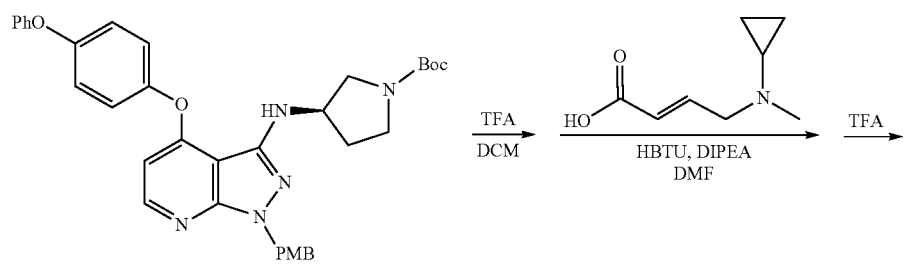

20

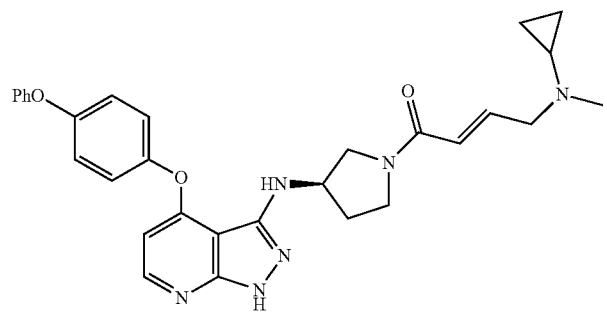

30

(R,E)-4-(Cyclopropyl(methyl)amino)-1-(3-(4-(4-phenoxyphenoxy)-1H-pyrazolo[3,4-b]pyridin-3-ylamino)pyrrolidin-1-yl)but-2-en-1-one (30) (22 mg, 25% yield) was obtained as a white solid from (R)-tert-butyl 3-(1-(4-methoxy benzyl)-4-(4-phenoxyphenoxy)-1H-pyrazolo[3,4-b]pyridin-3-ylamino)pyrrolidine-1-carboxylate (20) (200 mg, 0.4 mmol) and (E)-4-(cyclopropyl(methyl)amino)but-2-enoic acid (255 mg, 0.8 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 525.0. $^1$H NMR (400 MHz, DMSO) δ 12.24 (s, 1H), 8.13 (d, J=5.4 Hz, 1H), 7.40 (t, J=7.9 Hz, 2H), 7.30 (d, J=8.9 Hz, 2H), 7.14 (t, J=9.8 Hz, 3H), 7.04 (t, J=7.9 Hz, 2H), 6.73-6.54 (m, 1H), 6.32 (dd, J=22.2, 15.1 Hz, 1H), 6.04 (d, J=5.4 Hz, 1H), 5.58 (dd, J=25.9, 5.7 Hz, 1H), 4.48-3.35 (m, 5H), 3.23 (t, J=6.7 Hz, 2H), 2.34-1.91 (m, 6H), 1.73-1.60 (m, 1H), 0.46-0.34 (m, 2H), 0.32-0.22 (m, 2H).

Example 12

Synthesis of (R,E)-4-(cyclopropyl(methyl)amino)-1-(3-(4-(3-phenoxyphenoxy)-1H-pyrazolo[3,4-b]pyridin-3-ylamino)pyrrolidin-1-yl)but-2-en-1-one (33) (Compound ID 11)

3-Iodo-1-(4-methoxybenzyl)-4-(3-phenoxyphenoxy)-1H-pyrazolo[3,4-b]pyridine (31) (914 mg, 60% yield) was obtained as a white solid from 4-chloro-3-iodo-1-(4-methoxybenzyl)-1H-pyrazolo[3,4-b]pyridine (7) (1.1 g, 2.76 mmol) and 3-phenoxyphenol (770 mg, 4.14 mmol), following a similar procedure outlined in the preparation of 4-(4-chlorophenoxy)-3-iodo-1-(4-methoxybenzyl)-1H-pyrazolo[3,4-b]pyridine (8) in Example 1. LC-MS (ESI): m/z (M+1) 549.8.

(R)-tert-Butyl 3-(1-(4-methoxybenzyl)-4-(3-phenoxyphenoxy)-1H-pyrazolo[3,4-b]pyridin-3-ylamino)pyrrolidine-1-carboxylate (32) (492 mg, 48% yield) was obtained as a yellow solid from 3-iodo-1-(4-methoxybenzyl)-4-(3-phenoxyphenoxy)-1H-pyrazolo[3,4-b]pyridine (31) (914 mg, 1.67 mmol) and (R)-tert-butyl 3-aminopyrrolidine-1-carboxylate (929 mg, 5.00 mmol), following a similar procedure outlined in the preparation of (R)-tert-butyl3-(4-(4-chlorophenoxy)-1-(4-methoxybenzyl)-1H-pyrazolo[3,4-b]pyridin-3-ylamino)pyrrolidine-1-carboxylate (9) in Example 1. LC-MS (ESI): m/z (M+1) 605.1.

(R,E)-4-(Cyclopropyl(methyl)amino)-1-(3-(4-(3-phenoxyphenoxy)-1H-pyrazolo[3,4-b]pyridin-3-ylamino)pyrrolidin-1-yl)but-2-en-1-one (33) (85 mg, 11% yield) was obtained as a white solid from (R)-tert-butyl 3-(1-(4-methoxybenzyl)-4- (3-phenoxyphenoxy)-1H-pyrazolo[3,4-

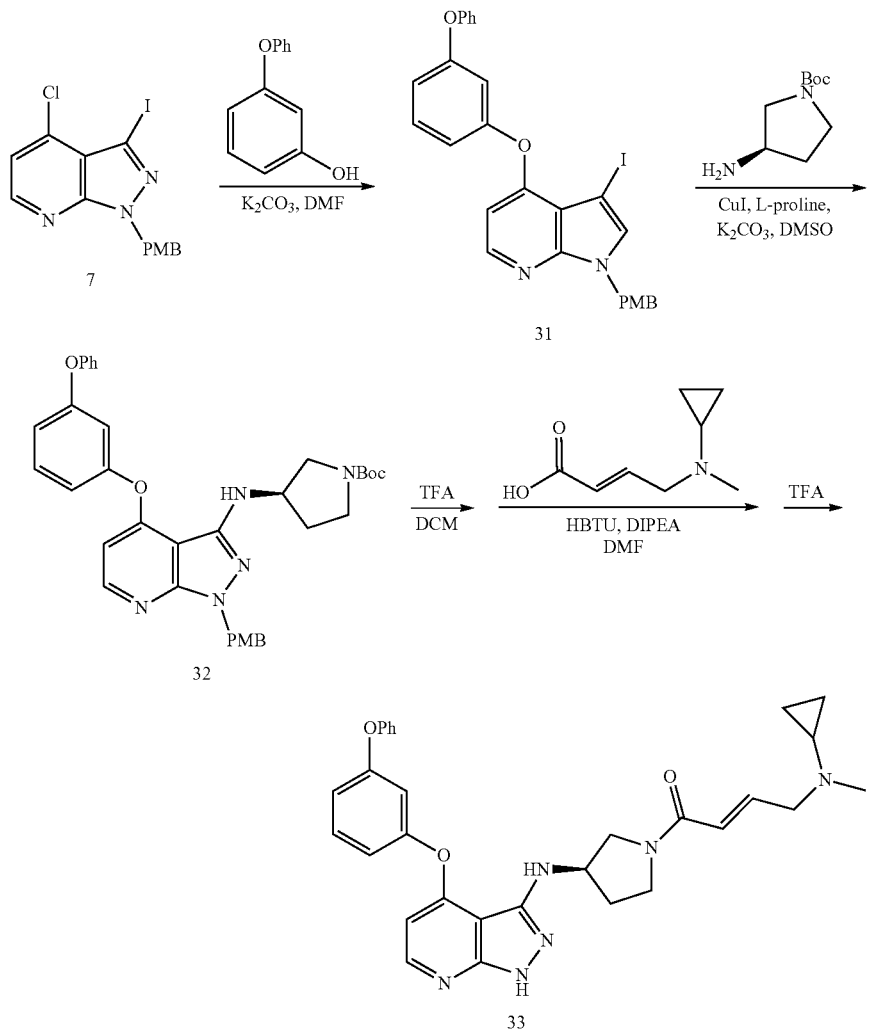

b]pyridin-3-ylamino)pyrrolidine-1-carboxylate (32) (344 mg, 0.57 mmol) and (E)-4-(cyclopropyl(methyl)amino)but-2-enoic acid (363 mg, 1.13 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) Example 1. LC-MS (ESI): m/z (M+1) 525.1. ¹H NMR (400 MHz, DMSO) δ 12.26 (s, 1H), 8.14 (d, J=5.4 Hz, 1H), 7.48 (td, J=8.2, 4.1 Hz, 1H), 7.40 (t, J=7.9 Hz, 2H), 7.16 (t, J=7.4 Hz, 1H), 7.08 (d, J=8.1 Hz, 2H), 7.02 (d, J=8.1 Hz, 1H), 6.95-6.90 (m, 1H), 6.87 (s, 1H), 6.70-6.52 (m, 1H), 6.31 (dd, J=21.4, 15.3 Hz, 1H), 6.14-6.03 (m, 1H), 5.55 (dd, J=31.7, 5.7 Hz, 1H), 4.33-3.35 (m, 4H), 3.28-3.16 (m, 2H), 2.34-1.89 (m, 5H), 1.67 (m, 1H), 0.33 (m, 4H).

Example 13

Synthesis of (R,E)-1-benzyl-4-(3-(1-(4-(dimethylamino)but-2-enoyl)pyrrolidin-3-ylamino)-1H-pyrazolo[3,4-b]pyridin-4-yloxy)pyridin-2(1H)-one (39) (Compound ID 15)

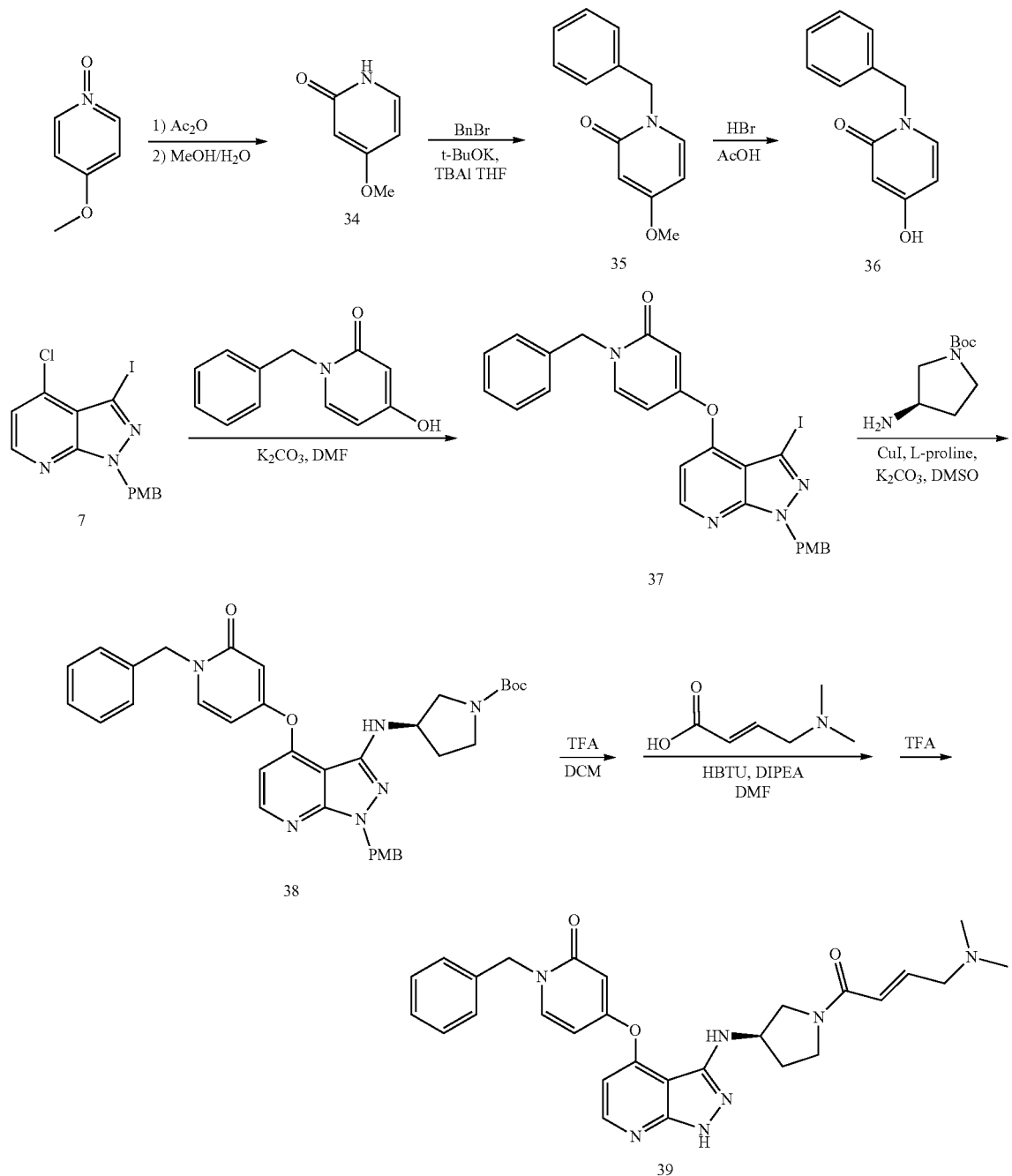

A solution of 4-methoxypyridine 1-oxide (1.5 g, 1.98 mmol) in $Ac_2O$ (45 mL) was heated to reflux under $N_2$ atmosphere overnight. After cooling to r.t., the reaction mixture was concentrated under reduced pressure to remove $Ac_2O$. The residue was diluted with water (15 mL) and MeOH (15 mL) and the resulting mixture was stirred at r.t. overnight. All volatiles were removed and the residue was purified by flash chromatography (silica gel, 0 to 10% MeOH in DCM) to afford 4-methoxy pyridin-2(1H)-one (34) (1.1 g, 71% yield) as a brown solid. LC-MS (ESI): m/z (M+1) 126.0.

To a solution of 4-methoxy pyridin-2(1H)-one (34) (1.06 g, 8.5 mmol) in THF (100 mL) was added t-BuOK (1.05 g, 9.3 mmol) and TBAI (157 mg, 0.43 mmol). After cooling to 0° C., BnBr (1.5 mL, 12.7 mmol) was added dropwise to the resulting mixture, which was stirred at r.t. overnight. The reaction mixture was then concentrated under reduced pressure and the residue was diluted with 1N NaOH solution (20 mL) and DCM (20 mL). The organic phase was washed with brine, dried over $Na_2SO_4$, filtered and concentrated under reduced pressure to give the crude product which was purified by flash chromatography (silica gel, 0 to 100% EA in PE) to afford 1-benzyl-4-methoxypyridin-2(1H)-one (35) (1.6 g, 87% yield) as a yellow solid. LC-MS (ESI): m/z (M+1) 216.3.

1-Benzyl-4-methoxypyridin-2(1H)-one (35) (800 mg, 3.7 mmol) was heated in a solution of HBr in AcOH (30 mL) in a sealed tube at 120° C. overnight. After cooling to r.t., the solvents was evaporated under reduce pressure to give the crude product which was purified by flash chromatography (silica gel, 0 to 50% EA in PE) to afford 1-benzyl-4-hydroxypyridin-2(1H)-one (36) (400 mg, 53% yield) as a white solid. LC-MS (ESI): m/z (M+1) 202.1.

1-Benzyl-4-(3-iodo-1-(4-methoxybenzyl)-1H-pyrazolo [3,4-b]pyridin-4-yloxy)pyridin-2(1H)-one (37) (300 mg, 67% yield) was obtained as a white solid from 4-chloro-3-iodo-1-(4-methoxybenzyl)-1H-pyrazolo[3,4-b]pyridine (318 mg, 0.80 mmol) (7) and 1-benzyl-4-hydroxypyridin-2 (1H)-one (36) (240 mg, 1.19 mmol), following a similar procedure outlined in the preparation of 4-(4-chlorophenoxy)-3-iodo-1-(4-methoxybenzyl)-1H-pyrazolo[3,4-b] pyridine (8) in Example 1. LC-MS (ESI): m/z (M+1) 564.8.

(R)-tert-Butyl 3-(4-(1-benzyl-2-oxo-1,2-dihydropyridin-4-yloxy)-1-(4-methoxybenzyl)-1H-pyrazolo[3,4-b]pyridin-3-ylamino)pyrrolidine-1-carboxylate (38) (150 mg, 12% yield) was obtained as a yellow solid from 1-benzyl-4-(3-iodo-1-(4-methoxybenzyl)-1H-pyrazolo[3,4-b]pyridin-4-yloxy)pyridin-2(1H)-one (37) (1.1 g, 1.95 mmol) and (R)-tert-butyl 3-aminopyrrolidine-1-carboxylate (1.0 g, 7.8 mmol), following a similar procedure outlined in the preparation of (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) in Example 1. LC-MS (ESI): m/z (M+1) 623.0.

(R,E)-1-Benzyl-4-(3-(1-(4-(dimethylamino)but-2-enoyl) pyrrolidin-3-ylamino)-1H-pyrazolo[3,4-b]pyridin-4-yloxy) pyridin-2(1H)-one (39) (30 mg, 21% yield) was obtained as a white solid from (R)-tert-butyl 3-(4-(1-benzyl-2-oxo-1,2-dihydropyridin-4-yloxy)-1-(4-methoxybenzyl)-1H-pyrazolo [3,4-b]pyridin-3-ylamino)pyrrolidine-1-carboxylate (38) (164 mg, 0.26 mmol) and (E)-4-(dimethylamino)but-2-enoic acid (66 mg, 0.39 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 514.0. $^1$H NMR (400 MHz, DMSO) δ 12.42 (s, 1H), 8.27 (d, J=5.3 Hz, 1H), 7.99-7.79 (m, 1H), 7.45-7.12 (m, 4H), 6.67-6.47 (m, 2H), 6.46-5.96 (m, 2H), 5.52 (dd, J=19.0, 5.7 Hz, 1H), 5.10 (s, 2H), 4.32-3.45 (m, 4H), 3.11 (s, 2H), 2.20 (d, J=3.6 Hz, 6H), 2.15-1.88 (m, 2H).

Example 14

Synthesis of (R,E)-1-(3-(4-(3-chloro-4-(oxazol-2-yl) phenoxy)-1H-pyrazolo[3,4-b]pyridin-3-ylamino) pyrrolidin-1-yl)-4-(dimethylamino)but-2-en-1-one (44) (Compound ID 16)

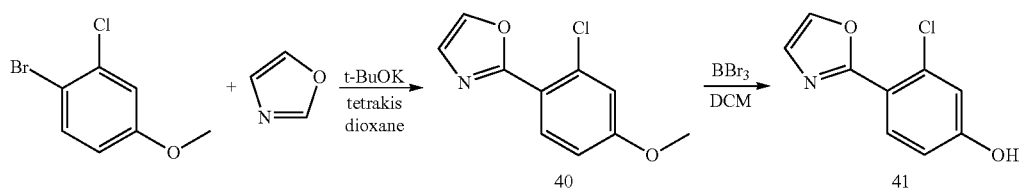

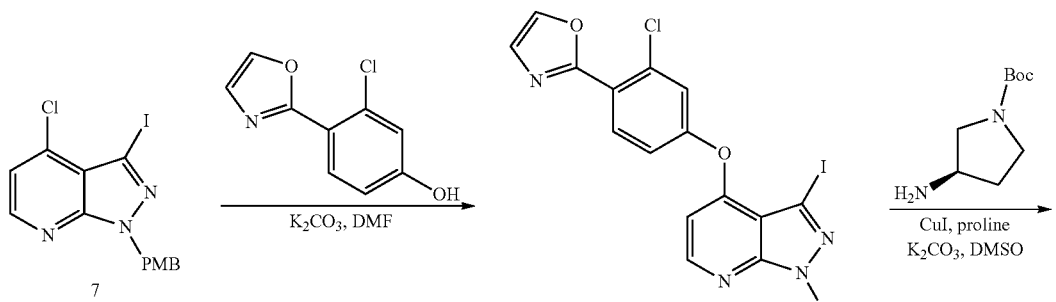

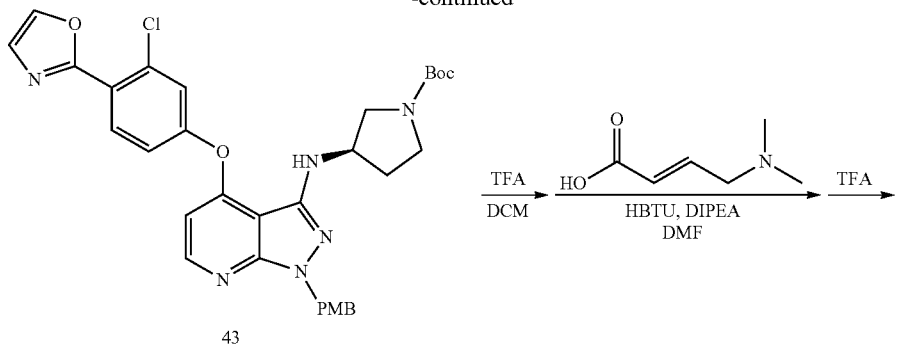

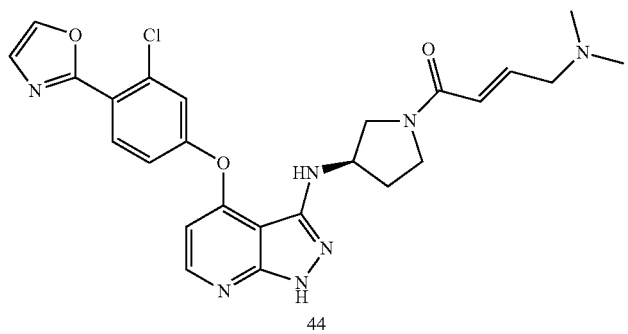

A mixture of 1-bromo-2-chloro-4-methoxybenzene (1.5 g, 6.8 mmol), oxazole (878 mg, 12.7 mmol), t-BuOK (1.52 g, 13.5 mmol) and tetrakis (1.56 g, 1.35 mmol) in dioxane (10 mL) was heated to 100° C. under $N_2$ atmosphere for 4 hr. After cooling to r.t., the reaction mixture was concentrated under reduced pressure to give the crude product which was purified by flash chromatography (silica gel, 0 to 25% EA in PE) to afford 2-(2-chloro-4-methoxyphenyl) oxazole (40) (600 mg, 42% yield) as a yellow solid. LC-MS (ESI): m/z (M+1) 210.0.

To a solution of 2-(2-chloro-4-methoxyphenyl)oxazole (40) (500 mg, 2.38 mmol) in DCM (10 mL) was added $BBr_3$ (1.8 g, 7.1 mmol) dropwise at −78° C. under $N_2$ atmosphere. The reaction was kept at −78° C. for 1.5 hr and then slowly warmed up to r.t. and stirred overnight. The reaction mixture was poured into ice water (20 mL) and the organic phase was dried over $Na_2SO_4$, filtered and concentrated under reduced pressure to give the crude product which was purified by flash chromatography (silica gel, 0 to 30% MeOH in DCM) to afford 3-chloro-4-(oxazol-2-yl) phenol (41) (350 mg, 75% yield) as a white solid. LC-MS (ESI): m/z (M+1) 196.0.

2-(2-Chloro-4-(3-iodo-1-(4-methoxybenzyl)-1H-pyrazolo[3,4-b]pyridin-4-yloxy)phenyl)oxazole (42) (900 mg, 83% yield) was obtained as a white solid from 4-chloro-3-iodo-1-(4-methoxybenzyl)-1H-pyrazolo[3,4-b]pyridine (723 mg, 1.81 mmol) (7) and 3-chloro-4-(oxazol-2-yl) phenol (41) (530 mg, 2.7 mmol), following a similar procedure outlined in the preparation of 4-(4-chlorophenoxy)-3-iodo-1-(4-methoxybenzyl)-1H-pyrazolo[3,4-b]pyridine (8) in Example 1. LC-MS (ESI): m/z (M/M+2) 558.7/560.7.

(R)-tert-Butyl 3-(4-(3-chloro-4-(oxazol-2-yl)phenoxy)-1-(4-methoxybenzyl)-1H-pyrazolo[3,4-b]pyridin-3-ylamino) pyrrolidine-1-carboxylate (43) (138 mg, 23% yield) was obtained as a white solid from 2-(2-chloro-4-(3-iodo-1-(4-methoxybenzyl)-1H-pyrazolo[3,4-b]zpyridin-4-yloxy)phenyl)oxazole (42) (500 mg, 0.90 mmol) and (R)-tert-butyl 3-aminopyrrolidine-1-carboxylate (1.7 g, 8.95 mmol), following a similar procedure outlined in the preparation of (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) in Example 1. LC-MS (ESI): m/z (M+1) 617.1.

To (R,E)-1-(3-(4-(3-Chloro-4-(oxazol-2-yl)phenoxy)-1H-pyrazolo[3,4-b]pyridin-3-ylamino)pyrrolidin-1-yl)-4-(dimethylamino)but-2-en-1-one (44) (35 mg, 31% yield) was obtained as a white solid from (R)-tert-butyl 3-(4-(3-chloro-4-(oxazol-2-yl) phenoxy)-1-(4-methoxybenzyl)-1H-pyrazolo[3,4-b]pyridin-3-ylamino)pyrrolidine-1-carboxylate (43) (138 mg, 0.22 mmol) and (E)-4-(dimethylamino)but-2-enoic acid (74 mg, 0.45 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 508.2. $^1$H NMR (400 MHz, DMSO) δ 12.35 (s, 1H), 8.33 (s, 1H), 8.19 (d, J=5.0 Hz, 1H), 8.07 (dd, J=8.6, 4.2 Hz, 1H), 7.69-7.58 (m, 1H), 7.47 (s, 1H), 7.43-7.37 (m, 1H), 6.66-6.49 (m, 1H), 6.33 (t, J=14.1 Hz, 1H), 6.25 (t, J=5.3 Hz, 1H), 5.67 (dd, J=29.9, 5.6 Hz, 1H), 4.39-3.38 (m, 4H), 2.99 (d, J=6.1 Hz, 2H), 2.30-2.14 (m, 1H), 2.11 (d, J=4.7 Hz, 6H), 2.07-1.89 (m, 1H).

Example 15

Synthesis of (R,E)-4-(dimethylamino)-1-(3-(4-(3-phenoxyphenoxy)-1H-pyrazolo[3,4-b]pyridin-3-ylamino)pyrrolidin-1-yl)but-2-en-1-one (45) (Compound ID 12)

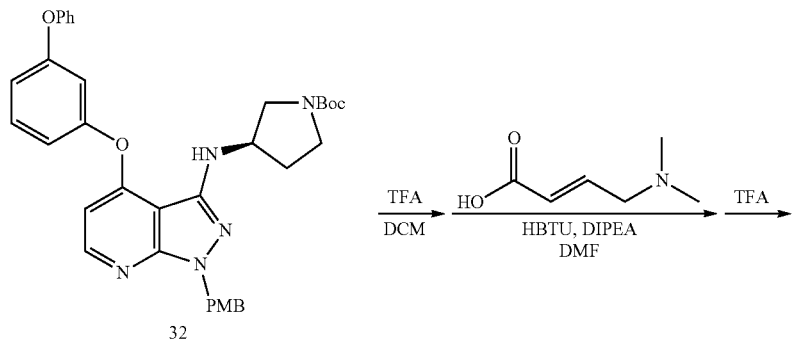

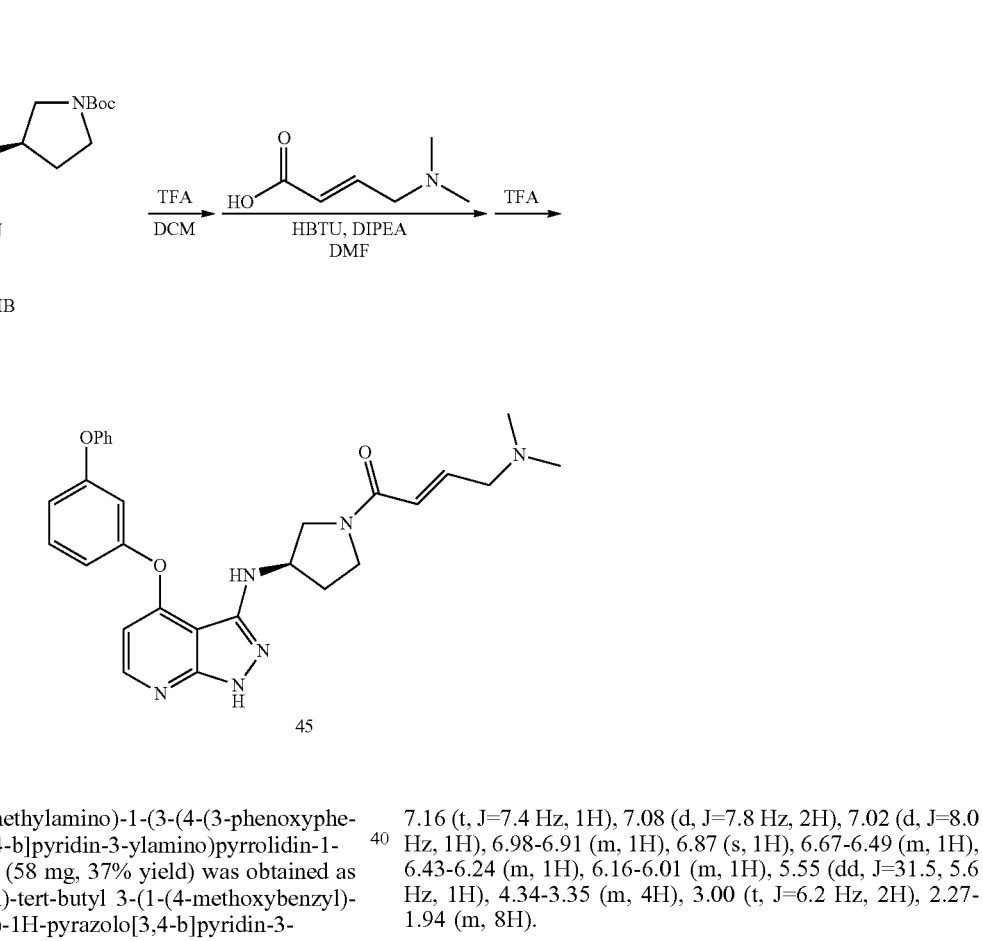

In (R,E)-4-(Dimethylamino)-1-(3-(4-(3-phenoxyphenoxy)-1H-pyrazolo[3,4-b]pyridin-3-ylamino)pyrrolidin-1-yl)but-2-en-1-one (45) (58 mg, 37% yield) was obtained as a white solid from (R)-tert-butyl 3-(1-(4-methoxybenzyl)-4-(3-phenoxyphenoxy)-1H-pyrazolo[3,4-b]pyridin-3-ylamino)pyrrolidine-1-carboxylate (32) (231 mg, 0.38 mmol) and (E)-4-(dimethylamino)but-2-enoic acid (126 mg, 0.76 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 499.4. $^1$H NMR (400 MHz, DMSO) δ 12.26 (s, 1H), 8.14 (d, J=5.4 Hz, 1H), 7.48 (td, J=8.2, 3.6 Hz, 1H), 7.41 (t, J=7.9 Hz, 2H), 7.16 (t, J=7.4 Hz, 1H), 7.08 (d, J=7.8 Hz, 2H), 7.02 (d, J=8.0 Hz, 1H), 6.98-6.91 (m, 1H), 6.87 (s, 1H), 6.67-6.49 (m, 1H), 6.43-6.24 (m, 1H), 6.16-6.01 (m, 1H), 5.55 (dd, J=31.5, 5.6 Hz, 1H), 4.34-3.35 (m, 4H), 3.00 (t, J=6.2 Hz, 2H), 2.27-1.94 (m, 8H).

Example 16

Synthesis of (R,E)-4-(dimethylamino)-1-(3-(4-(3-phenoxyphenylamino)-1H-pyrazolo[3,4-b]pyridin-3-yloxy)pyrrolidin-1-yl)but-2-en-1-one (48) (Compound ID 17)

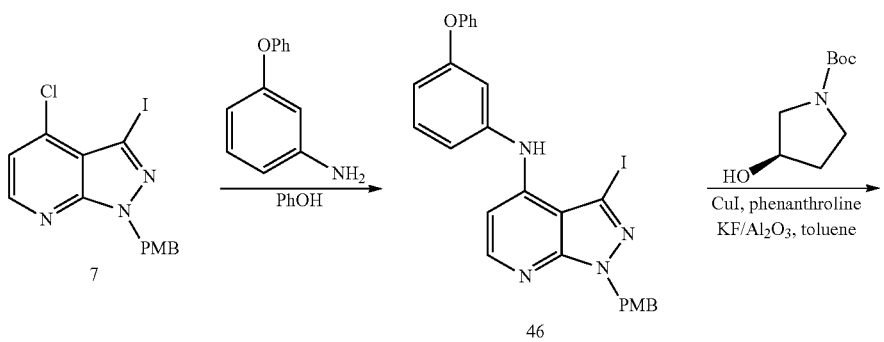

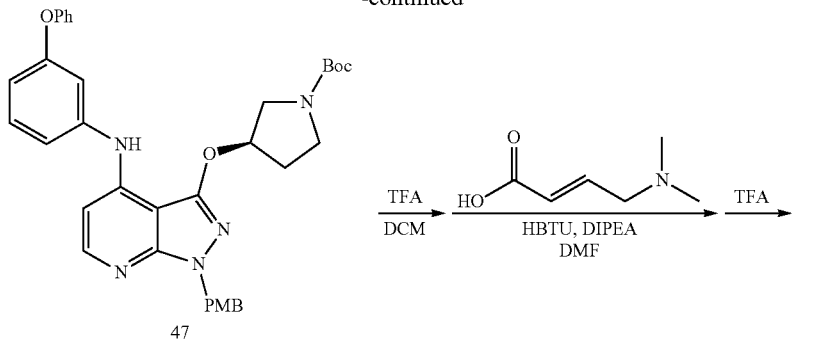

3-Iodo-1-(4-methoxybenzyl)-N-(3-phenoxyphenyl)-1H-pyrazolo[3,4-b]pyridin-4-amine (46) (826 mg, 62% yield) was obtained as a yellow solid from 4-chloro-3-iodo-1-(4-methoxybenzyl)-1H-pyrazolo[3,4-b]pyridine (7) (974 mg, 2.4 mmol) and 4-phenoxyaniline (904 mg, 4.9 mmol), following a similar procedure outlined in the preparation of 3-iodo-1-(4-methoxybenzyl)-N-(4-phenoxyphenyl)-1H-pyrazolo[3,4-b]pyridin-4-amine (31) in Example 12. LC-MS (ESI): m/z (M+1) 548.8.

(R)-tert-butyl 3-(1-(4-methoxybenzyl)-4-(3-phenoxyphenylamino)-1H-pyrazolo[3,4-b]pyridin-3-yloxy)pyrrolidine-1-carboxylate (47) (250 mg, 75% yield) was obtained as a yellow solid from 3-iodo-1-(4-methoxybenzyl)-N-(3-phenoxyphenyl)-1H-pyrazolo[3,4-b]pyridin-4-amine (46) (250 mg, 0.46 mmol) and (R)-tert-butyl 3-hydroxypyrrolidine-1-carboxylate (1.7 g, 9.1 mmol), following a similar procedure outlined in the preparation of (R)-tert-butyl 3-(1-(4-methoxybenzyl)-4-(4-phenoxyphenylamino)-1H-pyrazolo[3,4-b]pyridin-3-yloxy)pyrrolidine-1-carboxylate (32) in Example 12. LC-MS (ESI): m/z (M+1) 607.6.

(R,E)-4-(dimethylamino)-1-(3-(4-(3-phenoxyphenylamino)-1H-pyrazolo[3,4-b]pyridin-3- yloxy)pyrrolidin-1-yl)but-2-en-1-one (48) (14 mg, 31% yield) was obtained as a white solid from (R)-tert-butyl 3-(1-(4-methoxybenzyl)-4-(3-phenoxy phenylamino)-1H-pyrazolo[3,4-b]pyridin-3-yloxy)pyrrolidine-1-carboxylate (47) (250 mg, 0.5 mmol) and (E)-4-(di methylamino)but-2-enoic acid (165 mg, 1.0 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 498.9. $^1$H NMR (400 MHz, DMSO) δ 12.28 (br, 1H), 8.03 (dd, J=12.4, 5.4 Hz, 2H), 7.35 (dt, J=15.1, 7.8 Hz, 3H), 7.14 (t, J=7.4 Hz, 1H), 7.05 (d, J=8.1 Hz, 3H), 6.90 (s, 1H), 6.71 (t, J=8.5 Hz, 1H), 6.63-6.54 (m, 1H), 6.45 (t, J=5.6 Hz, 1H), 6.33 (dd, J=23.6, 15.2 Hz, 1H), 5.51-5.11 (m, 1H), 3.98-3.41 (m, 4H), 2.97 (t, J=5.7 Hz, 2H), 2.32-2.13 (m, 2H), 2.09 (d, J=6.9 Hz, 6H).

Example 17

Synthesis of (R,E)-4-(dimethylamino)-1-(3-(4-(3-phenoxyphenoxy)-1H-pyrazolo[3,4-b]pyridin-3-ylamino)piperidin-1-yl)but-2-en-1-one (50) (Compound ID 13)

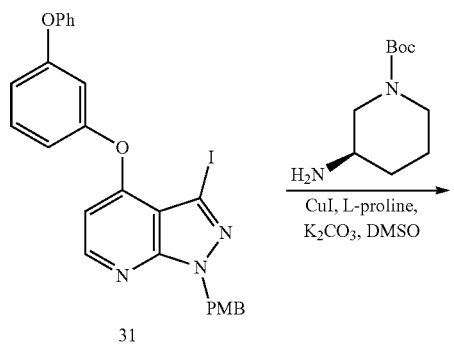

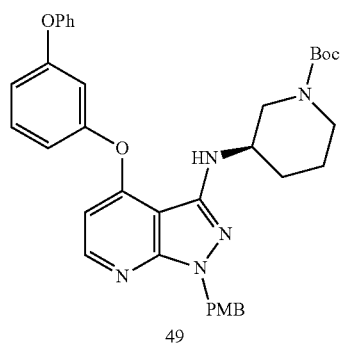
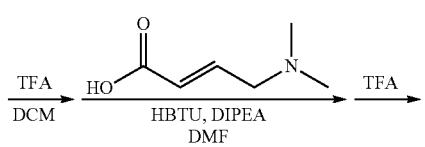

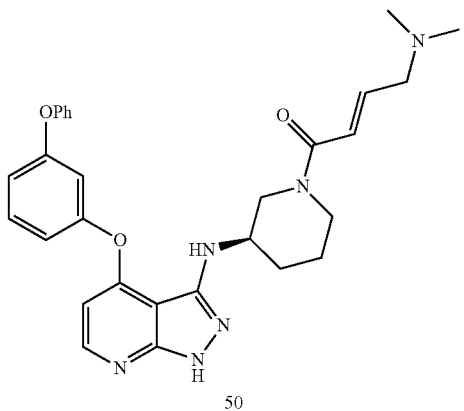

(R)-tert-butyl 3-(1-(4-methoxybenzyl)-4-(3-phenoxyphenoxy)-1H-pyrazolo[3,4-b]pyridin-3-ylamino)piperidine-1-carboxylate (49) (230 mg, 26% yield) was obtained as a yellow oil from 3-iodo-1-(4-methoxybenzyl)-4-(3-phenoxyphenoxy)-1H-pyrazolo[3,4-b]pyridine (31) (780 mg, 1.42 mmol) and (R)-tert-butyl 3-aminopiperidine-1-carboxylate (2.6 g, 14.2 mmol), following a similar procedure outlined in the preparation of (R)-tert-butyl 3-(4-(4-chlorophenoxy)-1-(4-methoxybenzyl)-1H-pyrazolo[3,4-b]pyridin-3-ylamino)pyrrolidine-1-carboxylate (9) in Example 1. LC-MS (ESI): m/z (M+1) 622.4.

(R,E)-4-(dimethylamino)-1-(3-(4-(3-phenoxyphenoxy)-1H-pyrazolo[3,4-b]pyridin-3-ylamino)piperidin-1-yl)but-2-en-1-one (50) (58 mg, 43% yield) was obtained as a white solid from (R)-tert-butyl 3-(1-(4-methoxybenzyl)-4-(3-phenoxyphenoxy)-1H-pyrazolo[3,4-b]pyridin-3-ylamino)piperidine-1-carboxylate (49) (230 mg, 0.37 mmol) and (E)-4-(dimethylamino)but-2-enoic acid (123 mg, 0.74 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 513.4. $^1$H NMR (400 MHz, DMSO) δ 12.22 (d, J=25.4 Hz, 1H), 8.14 (d, J=5.5 Hz, 1H), 7.49 (t, J=8.3 Hz, 1H), 7.41 (t, J=7.9 Hz, 2H), 7.17 (t, J=7.4 Hz, 1H), 7.09 (d, J=7.9 Hz, 2H), 7.01 (d, J=7.1 Hz, 1H), 6.93 (d, J=8.4 Hz, 1H), 6.88 (s, 1H), 6.63-6.31 (m, 2H), 6.10 (d, J=5.4 Hz, 1H), 5.24-5.05 (m, 1H), 4.47-2.63 (m, 5H), 2.21-1.90 (m, 8H), 1.82-1.58 (m, 2H), 1.53-1.32 (m, 1H).

Example 18

Synthesis of (E)-4-(dimethylamino)-N-methyl-N-((1s,4s)-4-(4-(3-phenoxyphenoxy)-1H-pyrazolo[3,4-b]pyridin-3-ylamino)cyclohexyl)but-2-enamide (52) (Compound ID 21)

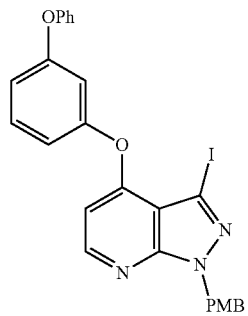
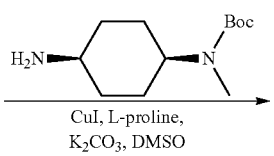

-continued

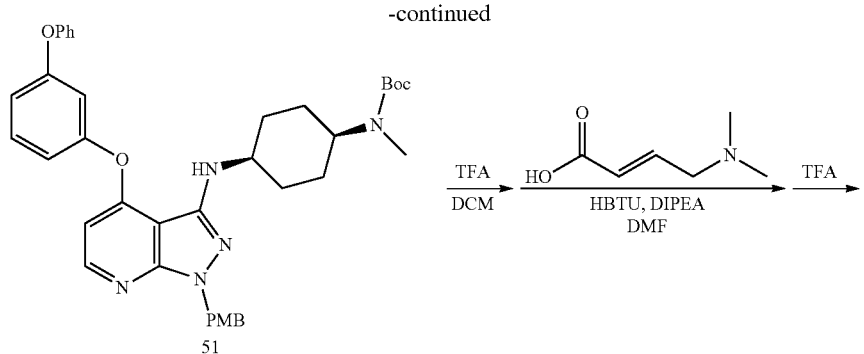

51

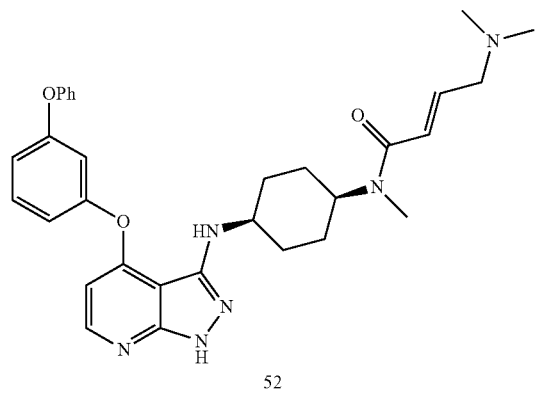

52 tert-Butyl (1s,4s)-4-(1-(4-methoxybenzyl)-4-(3-phenoxyphenoxy)-1H-pyrazolo[3,4-b]pyridin-3-ylamino)cyclohexyl(methyl)carbamate (51) (40 mg, 5.5% yield) was obtained as a colorless oil from 3-iodo-1-(4-methoxybenzyl)-4-(3-phenoxyphenoxy)-1H-pyrazolo[3,4-b]pyridine (31) (460 mg, 0.84 mmol) and tert-butyl (1s,4s)-4-aminocyclohexyl(methyl)carbamate (960 mg, 4.2 mmol), following a similar procedure outlined in the preparation of (R)-tert-butyl3-(4-(4-chlorophenoxy)-1-(4-methoxybenzyl)-1H-pyrazolo[3,4-b]pyridin-3-ylamino)pyrrolidine-1-carboxylate (9) in Example 1. LC-MS (ESI): m/z (M+1) 650.0.

(E)-4-(Dimethylamino)-N-methyl-N-((1s,4s)-4-(4-(3-phenoxyphenoxy)-1H-pyrazolo[3,4-b]pyridin-3-ylamino)cyclohexyl)but-2-enamide (52) (8.0 mg, 25% yield) was obtained as a white solid from tert-butyl (1s,4s)-4-(1-(4-methoxybenzyl)-4-(3-phenoxyphenoxy)-1H-pyrazolo[3,4-b]pyridin-3-ylamino)cyclohexyl(methyl)carbamate (51) (40 mg, 0.06 mmol) and (E)-4-(dimethylamino)but-2-enoic acid (20 mg, 0.12 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 541.0. $^1$H NMR (400 MHz, DMSO) δ 12.26 (s, 1H), 8.19 (d, J=6.1 Hz, 1H), 7.48 (t, J=8.5 Hz, 1H), 7.40 (t, J=7.5 Hz, 2H), 7.17 (t, J=8.0 Hz, 1H), 7.09-6.99 (m, 3H), 6.94-6.87 (m, 2H), 6.65-6.42 (m, 2H), 6.28-6.16 (m, 1H), 4.79 (dd, J=6.4, 2.0 Hz, 1H), 4.30 (br, 1H), 3.82 (dd, J=5.1, 2.7 Hz, 1H), 3.12-3.01 (m, 2H), 2.67 (d, J=47.9 Hz, 3H), 2.17 (s, 6H), 2.07 (d, J=10.8 Hz, 2H), 1.74-1.56 (m, 3H), 1.44-1.21 (m, 3H).

Example 19

Synthesis of (R,E)-3-cyclopropyl-2-(3-(4-(4-phenoxyphenoxy)-1H-pyrazolo[3,4-b]pyridin-3-ylamino)pyrrolidine-1-carbonyl)acrylonitrile (53) (Compound ID 18)

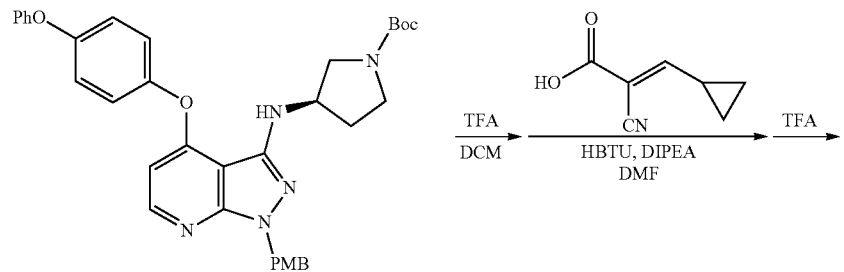

20

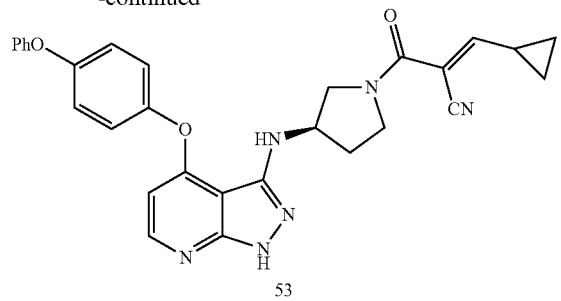

(R,E)-3-Cyclopropyl-2-(3-(4-(4-phenoxyphenoxy)-1H-pyrazolo[3,4-b]pyridin-3-ylamino)pyrrolidine-1-carbonyl)acrylonitrile (53) (30 mg, 30% yield) was obtained as a white solid from (R)-tert-butyl 3-(1-(4-methoxybenzyl)-4-(4-phenoxy phenoxy)-1H-pyrazolo[3,4-b]pyridin-3-ylamino)pyrrolidine-1-carboxylate (20) (200 mg, 0.33 mmol) and (E)-2-cyano-3-cyclopropylacrylic acid (91 mg, 0.66 mmol), following a similar three-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 507.0. 1H NMR (400 MHz, DMSO) δ 12.27 (s, 1H), 8.14 (d, J=5.4 Hz, 1H), 7.41 (t, J=7.8 Hz, 2H), 7.31 (d, J=8.8 Hz, 2H), 7.14 (t, J=8.4 Hz, 3H), 7.05 (d, J=7.8 Hz, 2H), 6.79 (d, J=11.0 Hz, 1H), 6.04 (d, J=5.3 Hz, 1H), 5.69 (dd, J=19.2, 4.8 Hz, 1H), 4.31-3.42 (m, 4H), 2.32-2.00 (m, 2H), 1.96-1.81 (m, 1H), 1.25-1.11 (m, 2H), 1.00-0.82 (m, 2H).

Example 20

Synthesis of (R,E)-2-(3-(4-(4-phenoxyphenoxy)-1H-pyrazolo[3,4-b]pyridin-3-ylamino)pyrrolidine-1-carbonyl)-3-phenylacrylonitrile (56) (Compound ID 19)

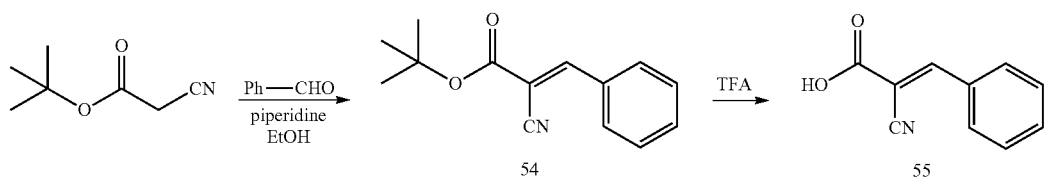

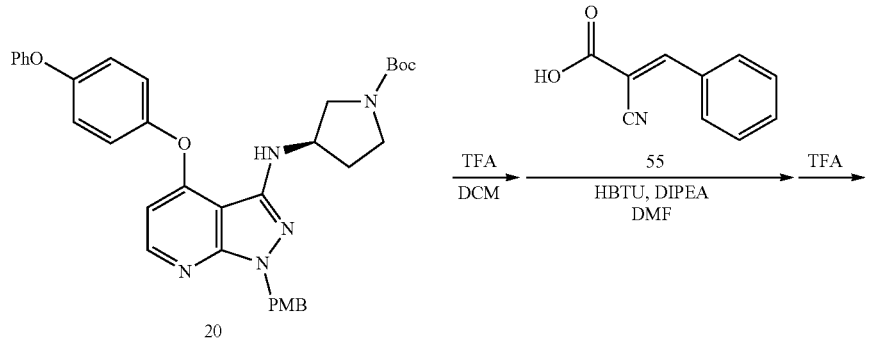

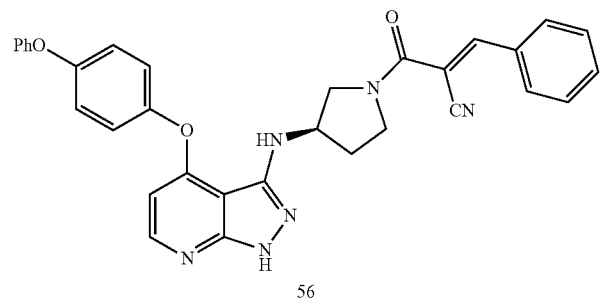

To a stirred solution of tert-butyl 2-cyanoacetate (2.8 g, 20 mmol) and benzaldehyde (1.5 g, 14 mmol) in EtOH (100 mL) was added 10 drops of piperidine. The resulting mixture was heated to reflux. After the reaction was completed, the reaction mixture was poured into ice water (100 mL) and extracted with EA (150 mL×2). The combined organic phase was washed with brine, dried over Na$_2$SO$_4$, filtered and concentrated under reduced pressure to give the crude product which was purified by flash chromatography (silica gel, 0 to 10% EA in PE) to afford (E)-tert-butyl 2-cyano-3-phenylacrylate (54) (2.3 g, 70% yield) as a colorless oil. The product was dissolved in TFA (20 mL) and stirred at r.t. for 1 hr. The precipitated white solid was filtered, washed with ice water and dried to afford (E)-2-cyano-3-phenylacrylic acid (55) (1.5 g, 87% yield) as a white solid. LC-MS (ESI): m/z (M−1) 172.0.

(R,E)-2-(3-(4-(4-Phenoxyphenoxy)-1H-pyrazolo[3,4-b]pyridin-3-ylamino)pyrrolidine-1-carbonyl)-3-phenylacrylonitrile (56) (14 mg, 11% yield) was obtained as a white solid from (R)-tert-butyl 3-(1-(4-methoxybenzyl)-4-(4-phenoxyphenoxy)-1H-pyrazolo[3,4-b]pyridin-3-ylamino)pyrrolidine-1-carboxylate (20) (140 mg, 0.23 mmol) and (E)-2-cyano-3-phenylacrylic acid (55) (80 mg, 0.46 mmol), following a similar three-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (10) in Example 1. LC-MS (ESI): m/z (M+1) 543.0. $^1$H NMR (400 MHz, DMSO) δ 12.26 (d, J=17.8 Hz, 1H), 8.13 (d, J=6.2 Hz, 1H), 8.01-7.81 (m, 3H), 7.62-7.47 (m, 3H), 7.40 (t, J=7.9 Hz, 2H), 7.30 (d, J=7.6 Hz, 2H), 7.20-7.10 (m, 3H), 7.04 (d, J=7.8 Hz, 2H), 6.14-5.93 (m, 1H), 5.79-5.69 (m, 1H), 4.39-4.23 (m, 1H), 4.11-3.53 (m, 4H), 2.29-2.08 (m, 2H).

Example 22

(R,E)-4-(cyclopropyl(methyl)amino)-1-(3-(4-(4-phenoxyphenoxy)-1H-pyrazolo[3,4-b]pyridin-3-yloxy)pyrrolidin-1-yl)but-2-en-1-one (Compound ID 22)

Preparation of (R)-tert-butyl 3-(1-(4-methoxybenzyl)-4-(4-phenoxyphenoxy)-1H-pyrazolo[3,4-b]pyridin-3-yloxy)pyrrolidine-1-carboxylate (488-1)

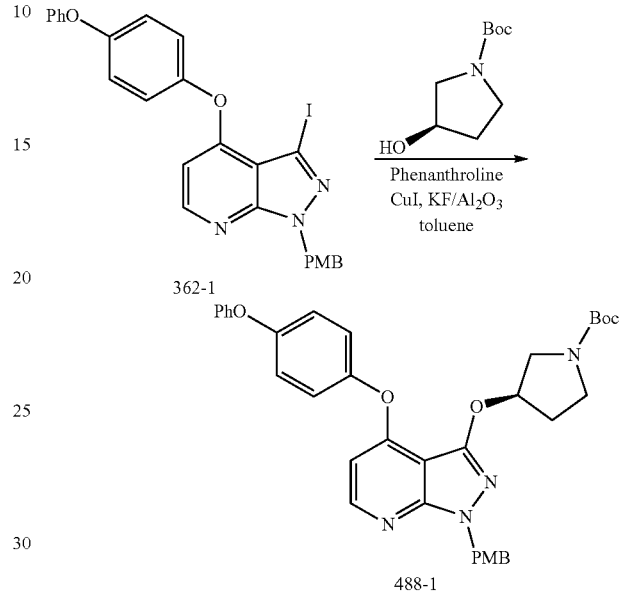

(R)-tert-butyl 3-(1-(4-methoxybenzyl)-4-(4-phenoxyphenoxy)-1H-pyrazolo[3,4-b]pyridin-3-yloxy)pyrrolidine-1-carboxylate (488-1) (306 mg, 75% yield) was obtained as a yellow solid from 3-iodo-1-(4-methoxybenzyl)-4-(4-phenoxyphenoxy)-1H-pyrazolo[3,4-b]pyridine (362-1) (370 mg, 0.67 mmol), following a similar procedure outlined in the preparation of (R)-tert-butyl 3-(1-(4-methoxybenzyl)-4-(4-phenoxyphenylamino)-1H-pyrazolo[3,4-b]pyridin-3-yloxy)pyrrolidine-1-carboxylate (386-2) (Ex. 23). LC-MS (ESI): m/z (M+1) 609.1.

Preparation of (R,E)-4-(cyclopropyl(methyl)amino)-1-(3-(4-(4-phenoxyphenoxy)-1H-pyrazolo[3,4-b]pyridin-3-yloxy)pyrrolidin-1-yl)but-2-en-1-one (488)

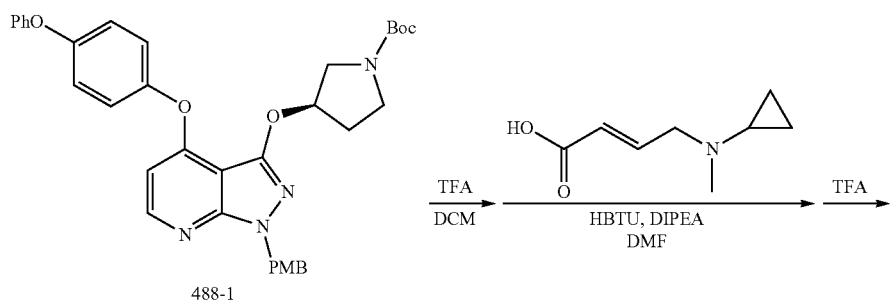

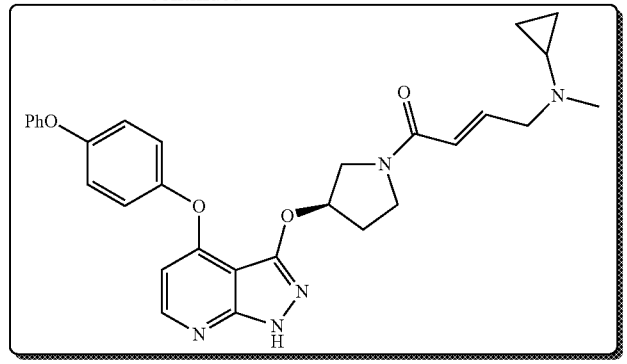

488

(R,E)-4-(cyclopropyl(methyl)amino)-1-(3-(4-(4-phenoxyphenoxy)-1H-pyrazolo[3,4-b]pyridin-3-yloxy)pyrrolidin-1-yl)but-2-en-1-one (488) (90 mg, 34% yield) was obtained as a white powder from (R)-tert-butyl 3-(1-(4-methoxybenzyl)-4-(4-phenoxy phenoxy)-1H-pyrazolo[3,4-b]pyridin-3-yloxy)pyrrolidine-1-carboxylate (488-1) (306 mg, 0.6 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 527.0. $^1$H NMR (400 MHz, DMSO) δ 12.75 (d, J=3.8 Hz, 1H), 8.26 (d, J=5.4 Hz, 1H), 7.40 (t, J=7.8 Hz, 2H), 7.23 (d, J=8.9 Hz, 2H), 7.14 (t, J=7.4 Hz, 1H), 7.10-6.97 (m, 4H), 6.71-6.61 (m, 1H), 6.53 (br, 1H), 6.24 (dd, J=5.3, 2.6 Hz, 1H), 5.36 (d, J=31.9 Hz, 1H), 3.67 (m, 6H), 2.48 (s, 3H), 2.32-2.09 (m, 3H), 0.88-0.25 (m, 4H).

Example 23

(R,E)-4-(cyclopropyl(methyl)amino)-1-(3-(4-(4-phenoxyphenylamino)-1H-pyrazolo[3,4-b]pyridin-3-ylamino)pyrrolidin-1-yl)but-2-en-1-one (Compound ID 23)

Preparation of (R)-tert-butyl 3-(1-(4-methoxybenzyl)-4-(4-phenoxyphenylamino)-1H-pyrazolo[3,4-b]pyridin-3-ylamino)pyrrolidine-1-carboxylate (489-1)

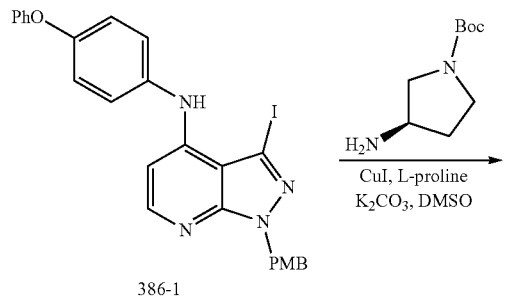

386-1

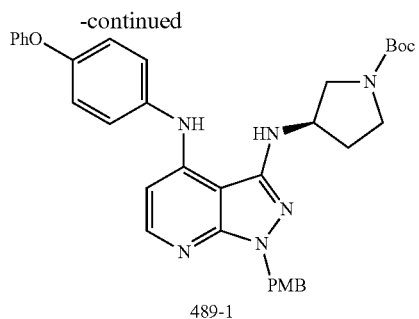

489-1

(R)-tert-butyl 3-(1-(4-methoxybenzyl)-4-(4-phenoxyphenylamino)-1H-pyrazolo[3,4-b]pyridin-3-ylamino)pyrrolidine-1-carboxylate (489-1) (274 mg, 41% yield) was obtained as a yellow solid from 3-iodo-1-(4-methoxybenzyl)-N-(4-phenoxyphenyl)-1H-pyrazolo[3,4-b]pyridin-4-amine (386-1) (600 mg, 1.1 mmol), following a similar procedure outlined in the preparation of (R)-tert-butyl3-(4-(4-chlorophenoxy)-1-(4-methoxy benzyl)-1H-pyrazolo[3,4-b]pyridin-3-ylamino)pyrrolidine-1-carboxylate (291-9) (Ex. 1). LC-MS (ESI): m/z (M+1) 608.16.

Preparation of (R,E)-4-(cyclopropyl(methyl)amino)-1-(3-(4-(4-phenoxyphenylamino)-1H-pyrazolo[3,4-b]pyridin-3-ylamino)pyrrolidin-1-yl)but-2-en-1-one (489)

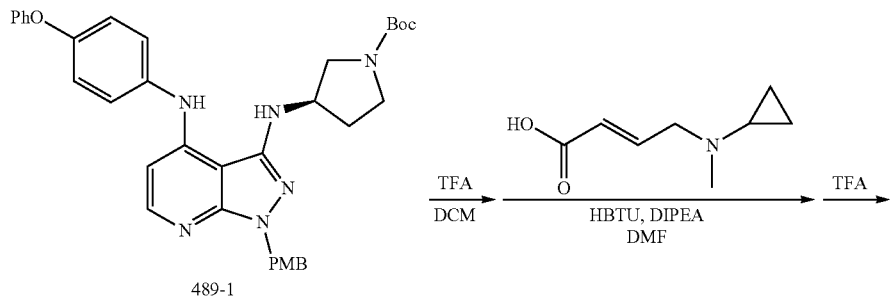

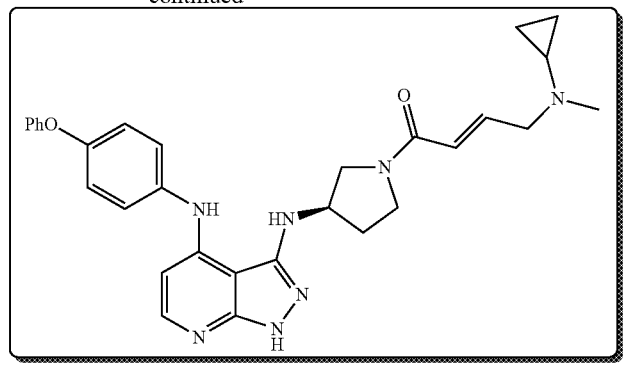
489

(R,E)-4-(cyclopropyl(methyl)amino)-1-(3-(4-(4-phenoxyphenylamino)-1H-pyrazolo[3,4-b]pyridin-3-ylamino)pyrrolidin-1-yl)but-2-en-1-one (489) (40 mg, 42% yield) was obtained as a white powder from (R)-tert-butyl 3-(1-(4-methoxybenzyl)-4-(4-phenoxyphenylamino)-1H-pyrazolo[3,4-b]pyridin-3-ylamino)pyrrolidine-1-carboxylate (489-1) (110 mg, 0.18 mmol), following a similar procedure outlined in the preparation of (R)-1-(3-(4-(4-chlorophenoxy)-1H-pyrazolo[3,4-b]pyridin-3-ylamino) pyrrolidin-1-yl)prop-2-en-1-one (291) (Ex. 1). LC-MS (ESI): m/z (M+1) 524.1. $^1$H NMR (400 MHz, DMSO) δ 12.90 (br, 1H), 9.55 (br, 1H), 8.10-7.76 (m, 1H), 7.50-7.32 (m, 4H), 7.22-7.11 (m, 3H), 7.06 (d, J=7.9 Hz, 2H), 6.74-6.58 (m, 2H), 6.21 (br, 1H), 4.42-4.20 (m, 1H), 4.02-3.45 (m, 4H), 2.89-2.65 (m, 4H), 2.37-2.18 (m, 1H), 2.13-1.92 (m, 1H), 1.01-0.65 (m, 4H).

Example 24

(E)-4-(Dimethylamino)-1-((R)-3-(4-((S)-1-phenylpyrrolidin-3-yloxy)-1H-pyrazolo[3,4-b]pyridin-3-ylamino)pyrrolidin-1-yl)but-2-en-1-one (Compound ID 24)

Preparation of (S)-tert-butyl 3-acetoxypyrrolidine-1-carboxylate (394-1)

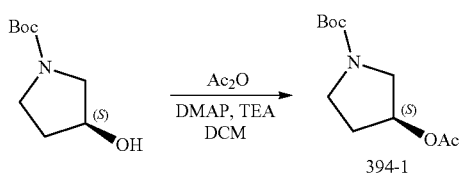

To a solution of (S)-tert-butyl 3-hydroxypyrrolidine-1-carboxylate (4.0 g, 21.3 mmol) in DCM (100 mL) were added DMAP (520 mg, 4.3 mmol), TEA (4.0 mL, 23.5 mmol) and Ac$_2$O (3.0 mL, 21.3 mmol). After a stirring at r.t. overnight, the reaction mixture was diluted with DCM (100 mL) and washed with brine (100 mL×2). The organic phase was dried over Na$_2$SO$_4$ and concentrated under reduced pressure to give the crude product which was purified by flash chromatography (silica gel, 0-40% EA in PE) to afford (S)-tert-butyl 3-acetoxypyrrolidine-1-carboxylate (394-1) (4.8 g, 97% yield) as a yellow oil. LC-MS (ESI): m/z (M+1) 230.4.

Preparation of (S)-1-phenylpyrrolidin-3-yl acetate (394-2)

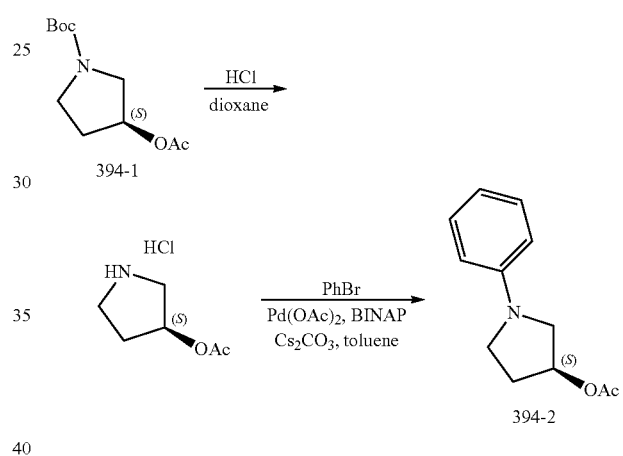

(S)-tert-Butyl 3-acetoxypyrrolidine-1-carboxylate (394-1) (4.0 g, 17.4 mmol) was de-protected with HCl in dioxane (4 N) to give the crude de-Boc product, which was directly reacted with PhBr (1.35 mL, 12.9 mmol) under typical Buchwald reaction condition to afford (S)-1-phenylpyrrolidin-3-yl acetate (830 mg, 26% yield over two steps) as a yellow oil. LC-MS (ESI): m/z (M+1) 206.5.

Preparation of (S)-1-phenylpyrrolidin-3-ol (394-3)

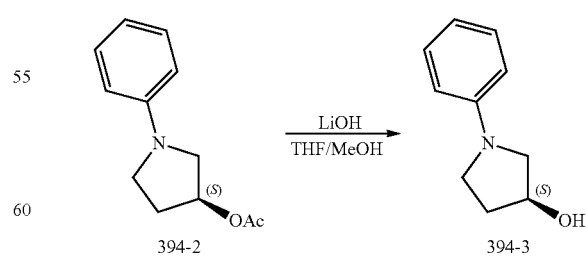

To a solution of (S)-1-phenylpyrrolidin-3-yl acetate (830 mg, 4.1 mmol) in THF (15 mL) and MeOH (5 mL) was added 1M LiOH solution (6.7 mL) dropwise. After stirred at r.t. for 1 hr, the reaction mixture was concentrated under reduced pressure and the residue was diluted with DCM (30 mL) and water (30 mL). The organic phase was washed with brine, dried over Na₂SO₄ and concentrated under reduced pressure to afford (S)-1-phenylpyrrolidin-3-ol (394-3) (656 mg, 99% yield) as a yellow oil. LC-MS (ESI): m/z (M+1) 164.4.

Preparation of (S)-3-iodo-1-(4-methoxybenzyl)-4-(1-phenylpyrrolidin-3-yl oxy)-1H-pyrazolo[3,4-b]pyridine (394-4)

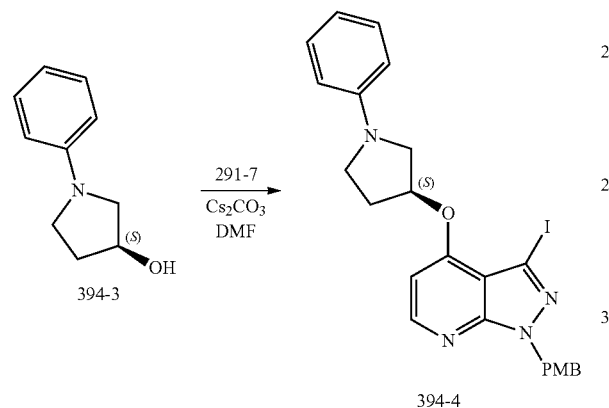

(S)-3-Iodo-1-(4-methoxybenzyl)-4-(1-phenylpyrrolidin-3-yloxy)-1H-pyrazolo[3,4-b]pyridine (394-4) (713 mg, 56% yield) was obtained as a white solid from (S)-1-phenylpyrrolidin-3-ol (394-3) (585 mg, 3.64 mmol) and 291-7 (968 mg, 2.43 mmol), following a similar procedure outlined in the preparation of 4-(4-chlorophenoxy)-3-iodo-1-(4-methoxybenzyl)-1H-pyrazolo[3,4-b]pyridine (291-8) (Ex. 1). LC-MS (ESI): m/z (M+1) 527.1.

Preparation of (R)-tert-butyl 3-(1-(4-methoxybenzyl)-4-((S)-1-phenylpyrrolidin-3-yloxy)-1H-pyrazolo[3,4-b]pyridin-3-ylamino)pyrrolidine-1-carboxylate (394-5)

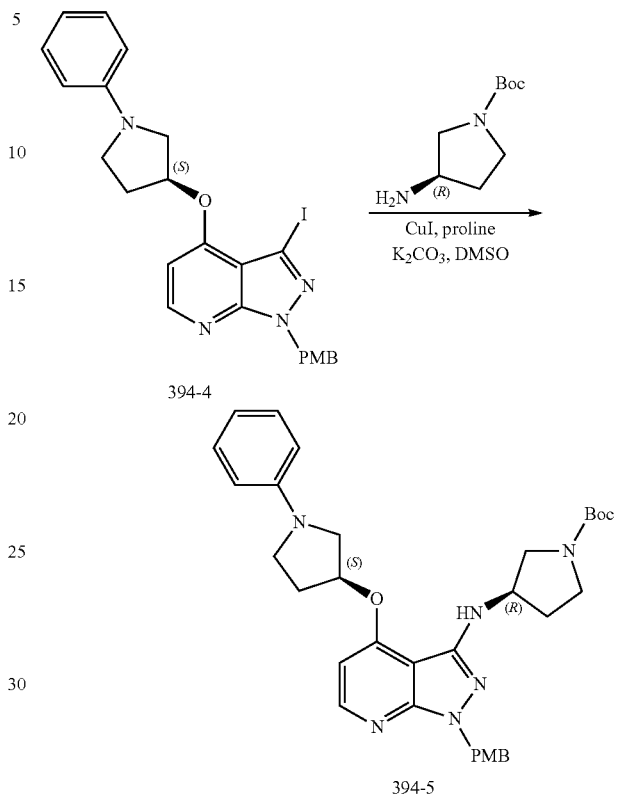

(R)-tert-butyl 3-(1-(4-methoxybenzyl)-4-((S)-1-phenylpyrrolidin-3-yloxy)-1H-pyrazolo[3,4-b]pyridin-3-ylamino)pyrrolidine-1-carboxylate (394-5) (145 mg, 18% yield) was obtained as a yellow solid from (S)-3-iodo-1-(4-methoxybenzyl)-4-(1-phenylpyrrolidin-3-yloxy)-1H-pyrazolo[3,4-b]pyridine (394-4) (392 mg, 0.74 mmol), following a similar procedure outlined in the preparation of (R)-tert-butyl3-(4-(4-chlorophenoxy)-1-(4-methoxybenzyl)-1H-pyrazolo[3,4-b]pyridin-3-ylamino)pyrrolidine-1-carboxylate (291-9) (Ex. 1). LC-MS (ESI): m/z (M+1) 586.1.

Preparation of (E)-4-(dimethylamino)-1-((R)-3-(4-((S)-1-phenylpyrrolidin-3-yloxy)-1H-pyrazolo[3,4-b]pyridin-3-ylamino)pyrrolidin-1-yl)but-2-en-1-one (394)

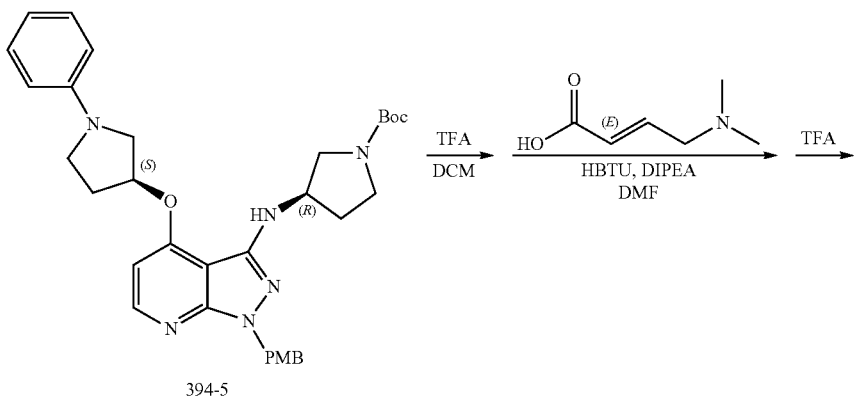

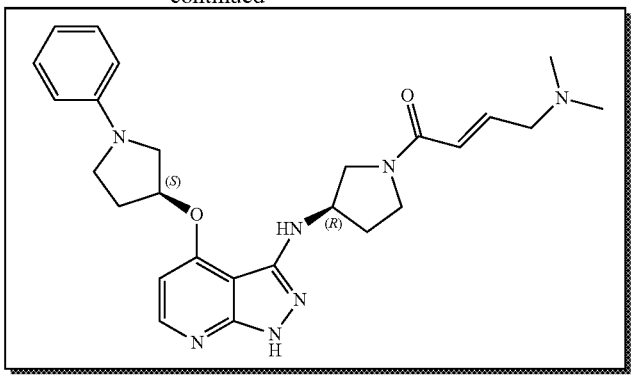

394

(E)-4-(dimethylamino)-1-((R)-3-(4-((S)-1-phenylpyrrolidin-3-yloxy)-1H-pyrazolo[3,4-b]pyridin-3-ylamino)pyrrolidin-1-yl)but-2-en-1-one (394) (47 mg, 35% yield) was obtained as a white solid from (R)-tert-butyl 3-(1-(4-methoxybenzyl)-4-((S)-1-phenylpyrrolidin-3-yloxy)-1H-pyrazolo[3,4-b]pyridin-3-ylamino)pyrrolidine-1-carboxylate (394-5) (145 mg, 0.25 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 476.9. $^1$H NMR (400 MHz, DMSO) δ 12.10 (s, 1H), 8.30-8.09 (m, 1H), 7.14 (t, J=7.7 Hz, 2H), 6.69-6.46 (m, 5H), 6.28 (dd, J=21.4, 15.2 Hz, 1H), 5.45-5.27 (m, 1H), 4.93-4.80 (m, 1H), 4.27-3.29 (m, 10H), 3.03 (dd, J=12.7, 6.2 Hz, 2H), 2.41-2.33 (m, 2H), 2.14 (d, J=12.3 Hz, 6H), 2.12-1.68 (m, 2H).

Example 25

(R,E)-2-(3-(1-(4-(dimethylamino)but-2-enoyl)pyrrolidin-3-ylamino)-1H-pyrazolo[3,4-b]pyridin-4-yloxy)-5-phenoxybenzenesulfonamide (Compound ID 25)

Preparation of 2-methoxy-5-phenoxybenzenesulfonic acid (462-1)

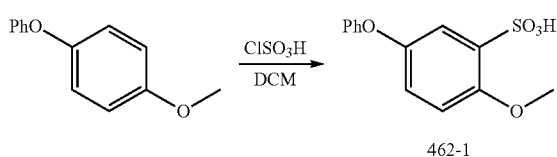 [SMILES: COc1ccc(Oc2ccccc2)cc1 ; "ClSO3H" ; COc1ccc(Oc2ccccc2)cc1S(=O)(=O)O]

At 0° C. and under N$_2$ atmosphere, to a solution of 1-methoxy-4-phenoxybenzene (1.0 g, 5.0 mmol) in DCM (10 mL) was added a solution of chlorosulfonic acid (0.35 mL, 5.25 mmol) in DCM (10 mL) dropwise. After stirred for 15 min, the reaction mixture was added slowly to ice water (100 mL) and the resulting mixture was concentrated to give the crude product which was washed with DCM (100 mL) to afford 2-methoxy-5-phenoxybenzenesulfonic acid (462-1) (1.0 g, 74% yield) as a white solid. LC-MS (ESI): m/z (M−1) 279.1.

Preparation of 2-methoxy-5-phenoxybenzene-1-sulfonyl chloride (462-2)

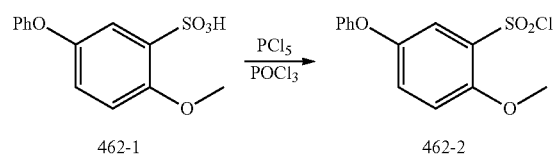

A solution of 2-methoxy-5-phenoxybenzenesulfonic acid (462-1) (1.0 g, 3.7 mmol) and PCl$_5$ (1.2 g, 5.6 mmol) in POCl$_3$ (12 mL) was heated at 90° C. under N$_2$ atmosphere for 1 hr. The reaction mixture was carefully added to ice water (100 mL) and extracted with DCM (50 mL×2). The combined organic phase was washed with brine, dried over Na$_2$SO$_4$, filtered and concentrated to afford 2-methoxy-5-phenoxy benzene-1-sulfonyl chloride (462-2) (945 mg, 86% yield) as a yellow oil. LC-MS (ESI): m/z (M+1) 299.8.

Preparation of 2-methoxy-5-phenoxybenzenesulfonamide (462-3)

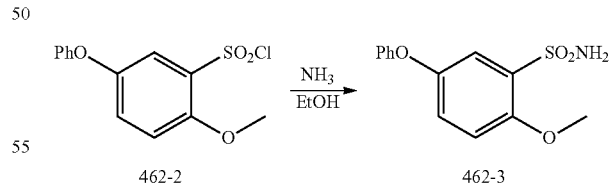

At 0° C., to a solution of 2-methoxy-5-phenoxy benzene-1-sulfonyl chloride (462-2) (945 mg, 3.2 mmol) in anhydrous DCM (20 mL) was added NH$_3$ in EtOH (4N, 35 mL) dropwise. After stirred at r.t. for 48 hrs, the reaction mixture was concentrated to give crude product which was purified by flash chromatography (silica gel, 0 to 20% MeOH in DCM) to afford 2-methoxy-5-phenoxybenzenesulfonamide (462-3) (883 mg, 100% yield) as a white solid. LC-MS (ESI): m/z (M+1) 279.9.

Preparation of 2-hydroxy-5-phenoxybenzenesulfonamide (462-4)

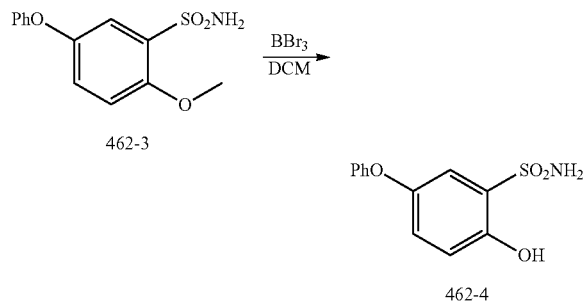

At 0° C., to a suspension of 2-methoxy-5-phenoxybenzenesulfonamide (462-3) (2.6 g, 9.3 mmol) in anhydrous DCM (10 mL) was added BBr$_3$ (1.3 mL, 14 mmol) dropwise. After stirred at r.t. for 1 hr, the reaction mixture was quenched with 1N HCl (20 mL) and extracted with EA (20 mL×3). The combined organic phase was washed with brine, dried over Na$_2$SO$_4$, filtered and concentrated to afford 2-hydroxy-5-phenoxybenzene sulfonamide (462-4) (552 mg, 66% yield) as a brown solid. LC-MS (ESI): m/z (M+1) 265.9.

Preparation of 2-(3-iodo-1-(4-methoxybenzyl)-1H-pyrazolo[3,4-b]pyridin-4-yloxy)-5-phenoxybenzenesulfonamide (462-5)

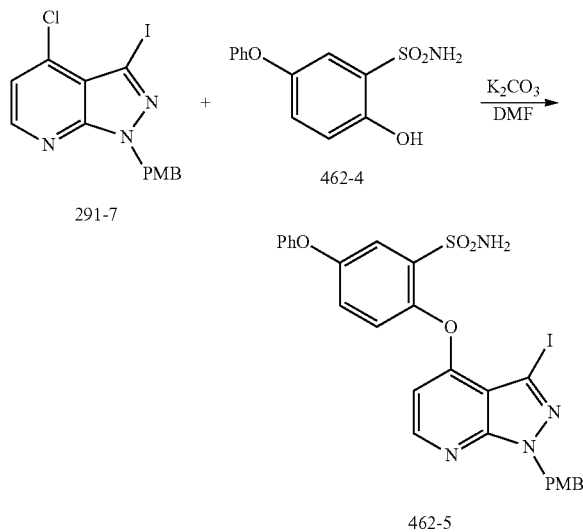

2-(3-Iodo-1-(4-methoxybenzyl)-1H-pyrazolo[3,4-b]pyridin-4-yloxy)-5-phenoxybenzenesulfonamide (462-5) (300 mg, 35% yield) was obtained as a yellow solid from 4-chloro-3-iodo-1-(4-methoxybenzyl)-1H-pyrazolo[3,4-b]pyridine (291-7) (550 mg, 1.4 mmol) and 2-hydroxy-5-phenoxybenzenesulfonamide (462-4) (550 mg, 2.1 mmol), following a similar procedure outlined in the preparation of 4-(4-chlorophenoxy)-3-iodo-1-(4-methoxybenzyl)-1H-pyrazolo[3,4-b]pyridine (291-8) (Ex. 1). LC-MS (ESI): m/z (M+1) 629.2.

Preparation of (R)-tert-butyl 3-(1-(4-methoxybenzyl)-4-(4-phenoxy-2-sulfamoylphenoxy)-1H-pyrazolo[3,4-b]pyridin-3-ylamino)pyrrolidine-1-carboxylate (462-6)

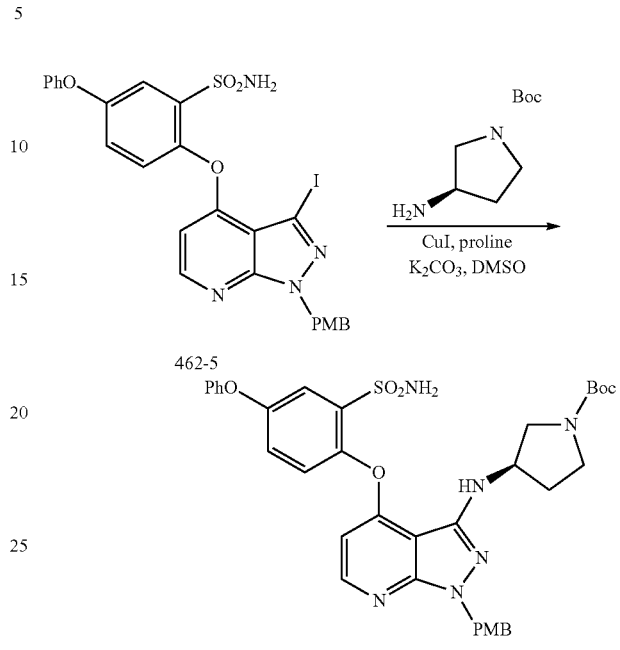

(R)-tert-butyl 3-(1-(4-methoxybenzyl)-4-(4-phenoxy-2-sulfamoylphenoxy)-1H-pyrazolo[3,4-b]pyridin-3-ylamino)pyrrolidine-1-carboxylate (462-6) (32 mg, 10% yield) was obtained as a yellow oil from 2-(3-iodo-1-(4-methoxybenzyl)-1H-pyrazolo[3,4-b]pyridin-4-yloxy)-5-phenoxybenzenesulfonamide (462-5) (300 mg, 0.48 mmol), following a similar procedure outlined in the preparation of (R)-tert-butyl3-(4-(4-chlorophenoxy)-1-(4-methoxybenzyl)-1H-pyrazolo[3,4-b]pyridin-3-ylamino)pyrrolidine-1-carboxylate (291-9) (Ex. 1). LC-MS (ESI): m/z (M+1) 688.2.

Preparation of (R,E)-2-(3-(1-(4-(dimethylamino)but-2-enoyl)pyrrolidin-3-ylamino)-1-(4-methoxybenzyl)-1H-pyrazolo[3,4-b]pyridin-4-yloxy)-5-phenoxybenzenesulfonamide (462-8)

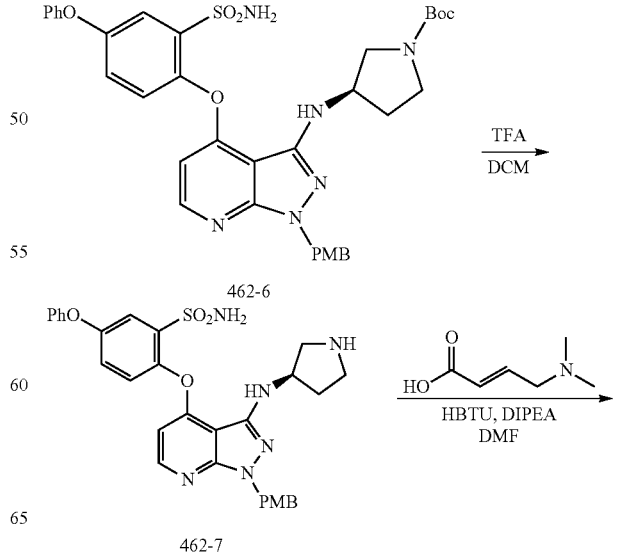

-continued

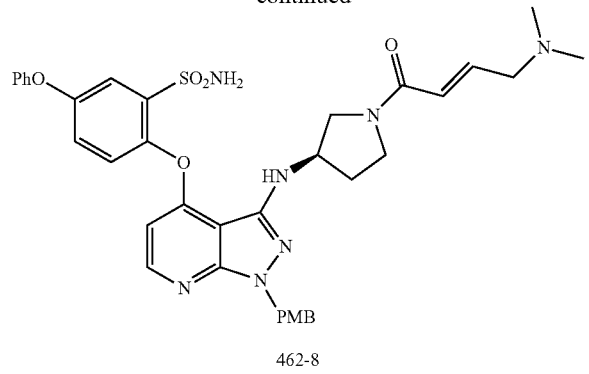

462-8

-continued

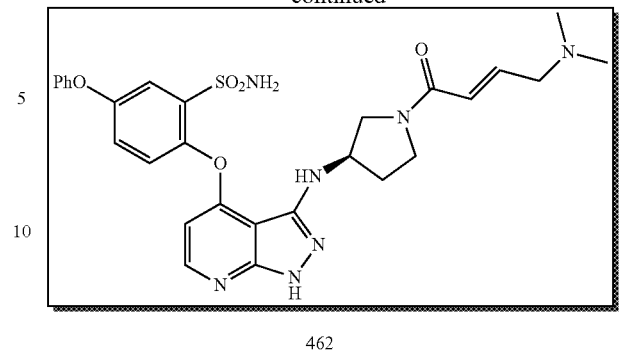

462

(R,E)-2-(3-(1-(4-(dimethylamino)but-2-enoyl)pyrrolidin-3-ylamino)-1-(4-methoxybenzyl)-1H-pyrazolo[3,4-b]pyridin-4-yloxy)-5-phenoxybenzenesulfonamide (462-8) (38 mg, 98% yield) was obtained as a yellow oil from (R)-tert-butyl 3-(1-(4-methoxybenzyl)-4-(4-phenoxy-2-sulfamoyl-phenoxy)-1H-pyrazolo[3,4-b]pyridin-3-ylamino)pyrrolidine-1-carboxylate (462-6) (32 mg, 0.05 mmol), following a similar two-step procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 699.2.

Preparation of (R,E)-2-(3-(1-(4-(dimethylamino)but-2-enoyl)pyrrolidin-3-yl amino)-1H-pyrazolo[3,4-b]pyridin-4-yloxy)-5-phenoxybenzenesulfonamide (462)

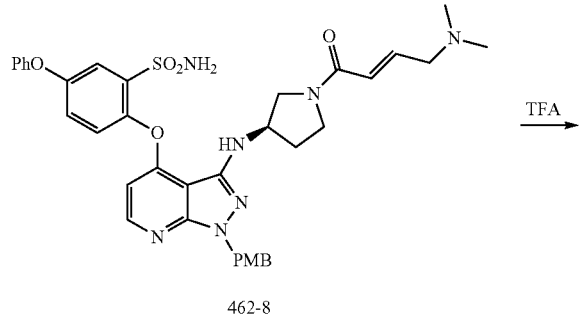

462-8

TFA →

(R,E)-2-(3-(1-(4-(dimethylamino)but-2-enoyl)pyrrolidin-3-ylamino)-1H-pyrazolo[3,4-b]pyridin-4-yloxy)-5-phenoxybenzenesulfonamide (462) (19 mg, 60% yield) was obtained as a white powder from (R,E)-2-(3-(1-(4-(dimethylamino)but-2-enoyl)pyrrolidin-3-ylamino)-1-(4-methoxybenzyl)-1H-pyrazolo[3,4-b]pyridin-4-yloxy)-5-phenoxybenzenesulfonamide (462-8) (38 mg, 0.05 mol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 578.9. $^1$H NMR (400 MHz, DMSO) δ 12.28 (s, 1H), 8.22 (s, 1H), 8.15 (d, J=5.5 Hz, 1H), 7.82 (d, J=8.4 Hz, 2H), 7.42-7.29 (m, 4H), 7.24 (d, J=8.5 Hz, 2H), 7.16 (d, J=8.5 Hz, 2H), 6.66-6.51 (m, 1H), 6.41-6.28 (m, 1H), 6.08 (d, J=5.3 Hz, 1H), 5.63 (d, J=20.8 Hz, 1H), 4.35-3.36 (m, 4H), 3.01 (t, J=5.5 Hz, 2H), 2.32-2.20 (m, 1H), 2.13 (d, J=6.0 Hz, 6H), 2.05-1.97 (m, 1H).

Example 26

(R,E)-2-(3-(4-(4-phenoxyphenoxy)-1H-pyrazolo[3,4-b]pyridin-3-ylamino)pyrrolidine-1-carbonyl)-3-(pyridin-2-yl)acrylonitrile (Compound ID 26)

Preparation of (R)-3-oxo-3-(3-(4-(4-phenoxyphenoxy)-1H-pyrazolo[3,4-b]pyridin-3-ylamino)pyrrolidin-1-yl)propanenitrile (483-1)

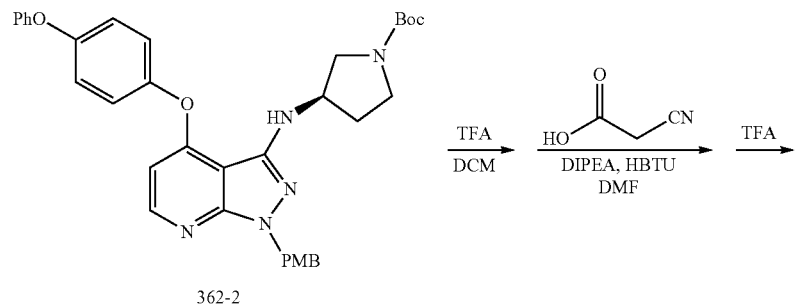

362-2

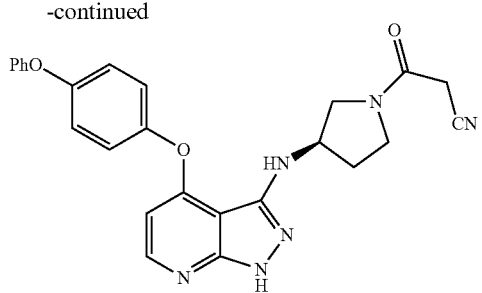

483-1

(R)-3-oxo-3-(3-(4-(4-phenoxyphenoxy)-1H-pyrazolo[3,4-b]pyridin-3-ylamino)pyrrolidin-1-yl)propanenitrile (483-1) (475 mg, 83% yield) was obtained as a white solid from (R)-tert-butyl 3-(1-(4-methoxybenzyl)-4-(4-phenoxyphenoxy)-1H-pyrazolo[3,4-b]pyri din-3-ylamino)pyrrolidine-1-carboxylate (362-2) (780 mg, 1.3 mmol) and 2-cyanoacetic acid (163 mg, 1.9 mmol), following a similar procedure outlined in the preparation of (R)-1-(3-(4-(4-chlorophenoxy)-1H-pyrazolo[3,4-b]pyridin-3-ylamino) pyrrolidin-1-yl)prop-2-en-1-one (291) (Ex. 1). LC-MS (ESI): m/z (M+1) 454.9.

Preparation of (R,E)-2-(3-(4-(4-phenoxyphenoxy)-1H-pyrazolo[3,4-b]pyridin-3-ylamino)pyrrolidine-1-carbonyl)-3-(pyridin-2-yl)acrylonitrile (483)

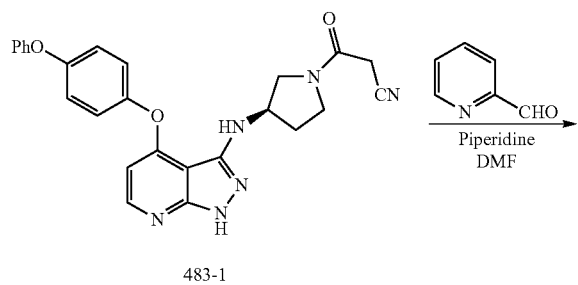

483-1

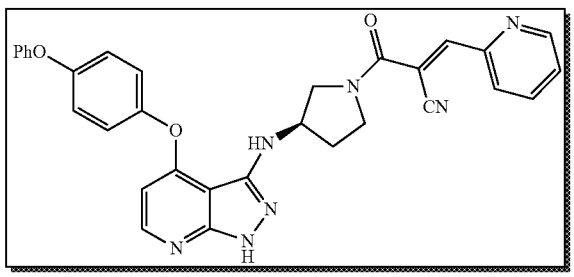

483

To a solution of (R)-3-oxo-3-(3-(4-(4-phenoxyphenoxy)-1H-pyrazolo[3,4-b]pyridin-3-ylamino)pyrrolidin-1-yl)propanenitrile (483-1) (100 mg, 0.17 mmol) and picolin aldehyde (18.5 mg, 0.17 mmol) in DMF (4.0 mL) was added one drop of piperidine. The resulting mixture was stirred at 50° C. for 4 hr. The mixture was concentrated under reduced pressure and the residue was portioned between DCM (10 mL) & H$_2$O (10 mL). The layers were separated and the organic phase was washed with brine, dried over Na$_2$SO$_4$, filtered and concentrated to give the crude product which was purified by prep. HPLC to afford (R,E)-2-(3-(4-(4-phenoxyphenoxy)-1H-pyrazolo[3,4-b]pyridin-3-ylamino)pyrrolidine-1-carbonyl)-3-(pyridin-2-yl)acrylonitrile (483) (20 mg, 21% yield) as a white powder. LC-MS (ESI): m/z (M+1) 543.9. $^1$H NMR (400 MHz, DMSO) δ 12.28 (d, J=21.7 Hz, 1H), 8.73 (t, J=5.5 Hz, 1H), 8.20-8.09 (m, 1H), 7.95 (dd, J=14.0, 6.6 Hz, 1H), 7.87 (s, 1H), 7.75 (dd, J=11.9, 8.0 Hz, 1H), 7.58-7.47 (m, 1H), 7.40 (t, J=7.9 Hz, 2H), 7.31 (dd, J=8.8, 6.9 Hz, 2H), 7.20-7.10 (m, 3H), 7.04 (d, J=7.9 Hz, 2H), 6.09-5.98 (m, 1H), 5.82-5.68 (m, 1H), 4.38-4.23 (m, 1H), 4.13-3.49 (m, 4H), 2.32-2.24 (m, 1H), 2.19-2.08 (m, 1H).

Example 27

(R,E)-3-cyclobutyl-2-(3-(4-(4-phenoxyphenoxy)-1H-pyrazolo[3,4-b]pyridin-3-ylamino)pyrrolidine-1-carbonyl)acrylonitrile (Compound ID 27)

Preparation of cyclobutanecarbaldehyde (484-1)

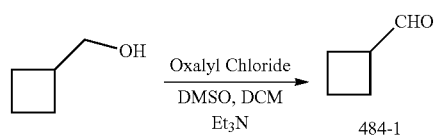 [SMILES: OCC1CCC1 ; O=CC1CCC1]

484-1

Cyclobutanecarbaldehyde (484-1) was obtained as a colorless oil from cyclobutylmethanol, following typical Swern Oxidation procedure and the product was purified by distillation.

Preparation of (R,E)-3-cyclobutyl-2-(3-(4-(4-phenoxyphenoxy)-1H-pyrazolo[3,4-b]pyridin-3-ylamino)pyrrolidine-1-carbonyl)acrylonitrile (484)

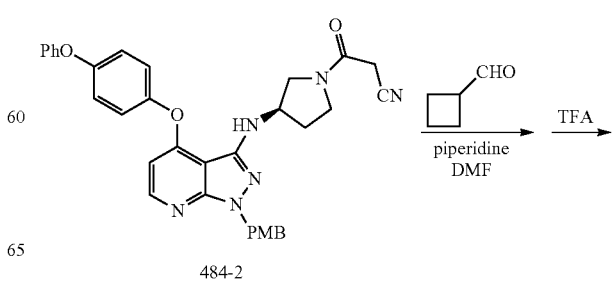

484-2

-continued

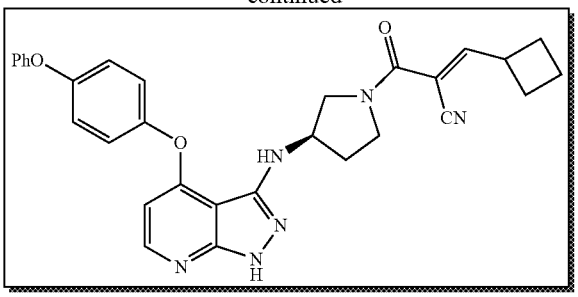

484

(R,E)-3-cyclobutyl-2-(3-(4-(4-phenoxyphenoxy)-1H-pyrazolo[3,4-b]pyridin-3-ylamino)pyrrolidine-1-carbonyl)acrylonitrile (484) (10 mg, 9% yield) was obtained as a white powder from (R)-3-(3-(1-(4-methoxybenzyl)-4-(4-phenoxyphenoxy)-1H-pyrazolo[3,4-b]pyridin-3-ylamino)pyrrolidin-1-yl)-3-oxopropanenitrile (484-2) (40 mg, 0.07 mmol) and cyclobutanecarbaldehyde (484-1) (11.6 mg, 0.07 mmol), following a similar procedure outlined in the preparation of (R,E)-2-(3-(4-(4-phenoxyphenoxy)-1H-pyrazolo[3,4-b]pyridin-3-ylamino)pyrrolidine-1-carbonyl)-3-(pyridin-2-yl)acrylonitrile (483) (Ex. 26). LC-MS (ESI): m/z (M+1) 522.0. $^1$H NMR (400 MHz, DMSO) δ 12.26 (s, 1H), 8.14 (d, J=5.1 Hz, 1H), 7.46-7.35 (m, 2H), 7.36-7.26 (m, 3H), 7.17-7.11 (m, 3H), 7.05 (d, J=8.0 Hz, 2H), 6.04 (dd, J=4.8, 2.2 Hz, 1H), 5.69 (dd, J=13.0, 6.4 Hz, 1H), 4.32-3.45 (m, 4H), 2.26-1.86 (m, 9H).

Example 28

(R,E)-3-(1H-imidazol-2-yl)-2-(3-(4-(4-phenoxyphenoxy)-1H-pyrazolo[3,4-b]pyridin-3-ylamino)pyrrolidine-1-carbonyl)acrylonitrile (Compound ID 28)

Preparation of (R,E)-3-(1H-imidazol-2-yl)-2-(3-(4-(4-phenoxyphenoxy)-1H-pyrazolo[3,4-b]pyridin-3-ylamino)pyrrolidine-1-carbonyl)acrylonitrile (486)

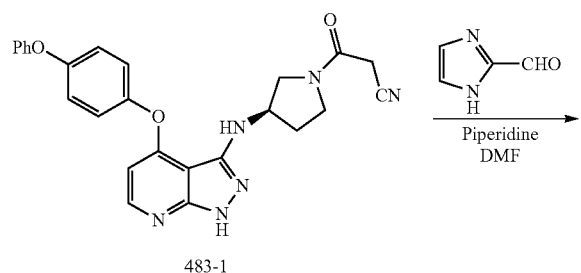

483-1

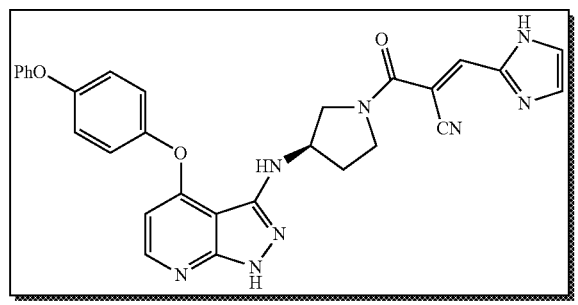

486

(R,E)-3-(1H-imidazol-2-yl)-2-(3-(4-(4-phenoxyphenoxy)-1H-pyrazolo[3,4-b]pyridin-3-ylamino)pyrrolidine-1-carbonyl)acrylonitrile (486) (25 mg, 17% yield) was obtained as a white powder from (R)-3-oxo-3-(3-(4-(4-phenoxyphenoxy)-1H-pyrazolo[3,4-b]pyridin-3-ylamino)pyrrolidin-1-yl)propanenitrile (483-1) (150 mg, 0.33 mmol) and 1H-imidazole-2-carbaldehyde (32 mg, 0.33 mmol), following a similar procedure outlined in the preparation of (R,E)-2-(3-(4-(4-phenoxyphenoxy)-1H-pyrazolo[3,4-b]pyridin-3-ylamino)pyrrolidine-1-carbonyl)-3-(pyridin-2-yl)acrylonitrile (483) (Ex. 26). LC-MS (ESI): m/z (M+1) 543.9. $^1$H NMR (400 MHz, DMSO) δ 12.28 (d, J=12.5 Hz, 1H), 8.13 (d, J=5.0 Hz, 1H), 7.69 (s, 1H), 7.50-7.24 (m, 6H), 7.14 (t, J=7.9 Hz, 3H), 7.04 (d, J=7.8 Hz, 2H), 6.03 (dd, J=8.9, 4.1 Hz, 1H), 5.76 (dd, J=15.3, 5.3 Hz, 1H), 4.36-4.22 (m, 1H), 4.12-3.50 (m, 4H), 2.30-2.02 (m, 2H).

Example 29

(Z)-2-cyano-N-methyl-3-(3-(4-(4-phenoxyphenoxy)-1H-pyrazolo[3,4-b]pyridin-3-ylamino)phenyl)acrylamide (Compound ID 29)

Preparation of (E)-tert-butyl 2-cyano-3-(3-nitrophenyl)acrylate (472-1)

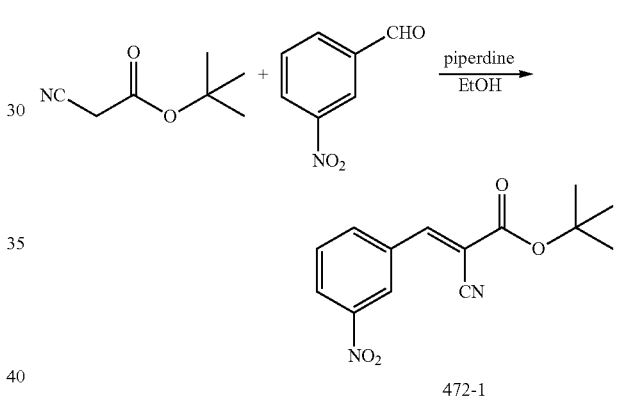

472-1

To a solution of tert-butyl 2-cyanoacetate (2.8 mL, 19.8 mmol) and 3-nitrobenzaldehyde (2.0 mg, 13.2 mmol) in EtOH (20 mL) was added 5 drops of piperidine. After stirred at 70° C. overnight, the reaction mixture was quenched with H$_2$O (100 mL) and extracted with EA (100 mL×3). The combined organic phase was washed with brine, dried over Na$_2$SO$_4$, filtered and concentrated to give the crude product which was purified by flash chromatography (silica gel, 0 to 30% EA in PE) to afford (E)-tert-butyl 2-cyano-3-(3-nitrophenyl)acrylate (472-1) (1.2 g, 33% yield) as a yellow oil.

Preparation of (E)-tert-butyl 3-(3-aminophenyl)-2-cyanoacrylate (472-2)

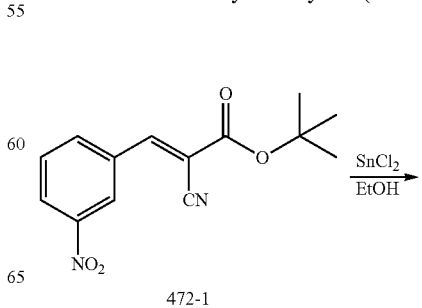

472-1

-continued

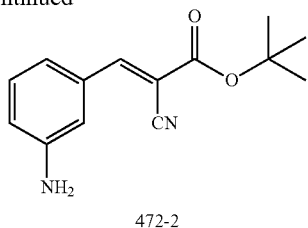

472-2

To a solution of (E)-tert-butyl 2-cyano-3-(3-nitrophenyl) acrylate (472-1) (1.2 g, 4.4 mmol) in EtOH (50 mL) was added SnCl₂ (4.9 g, 21.7 mmol). The resulting mixture was heated up to reflux under N₂ atmosphere for 1 hr. After cooled down to the r.t., the reaction was quenched with sat. NaHCO₃ aq. (100 mL) and extracted with EA (200 mL×2). The combined organic phase was washed with brine, dried over Na₂SO₄, filtered and concentrated to give the crude product which was purified by flash chromatography (silica gel, 0 to 50% EA in PE) to afford (E)-tert-butyl 3-(3-aminophenyl)-2-cyanoacrylate (472-2) (1.0 g, containing some SnCl₂) as a yellow solid. LC-MS (ESI): m/z (M+1) 245.4.

Preparation of (E)-tert-butyl 2-cyano-3-(3-(1-(4-methoxybenzyl)-4-(4-phenoxyphenoxy)-1H-pyrazolo[3,4-b]pyridin-3-ylamino)phenyl)acrylate (472-4)

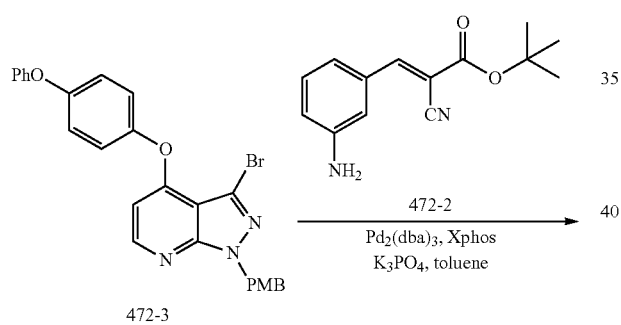

A mixture of 3-bromo-1-(4-methoxybenzyl)-4-(4-phenoxyphenoxy)-1H-pyrazolo[3,4-b]pyridine (472-3) (550 mg, 1.1 mmol), (E)-tert-butyl 3-(3-aminophenyl)-2-cyanoacrylate (472-2) (400 mg, 1.6 mmol), Pd₂(dba)₃ (100 mg, 0.11 mmol), Xphos (157 mg, 0.33 mmol) and K₃PO₄ (586 mg, 2.2 mmol) in toluene (20 mL) was purged with N₂ (×3). The resulting mixture was heated up to 120° C. overnight. After cooled down to rt., the reaction mixture was filtered through a celite pad. The filtrate was concentrated under reduced pressure to give the crude product which was purified by flash chromatography (silica gel, 0 to 30% EA in PE) to afford (E)-tert-butyl 2-cyano-3-(3-(1-(4-methoxybenzyl)-4-(4-phenoxyphenoxy)-1H-pyrazolo[3,4-b]pyridin-3-ylamino)phenyl)acrylate (472-4) (200 mg, 34% yield) as a yellow solid. LC-MS (ESI): m/z (M+1) 666.1.

Preparation of (E)-2-cyano-3-(3-(1-(4-methoxybenzyl)-4-(4-phenoxyphenoxy)-1H-pyrazolo[3,4-b]pyridin-3-ylamino)phenyl)acrylic acid (472-5)

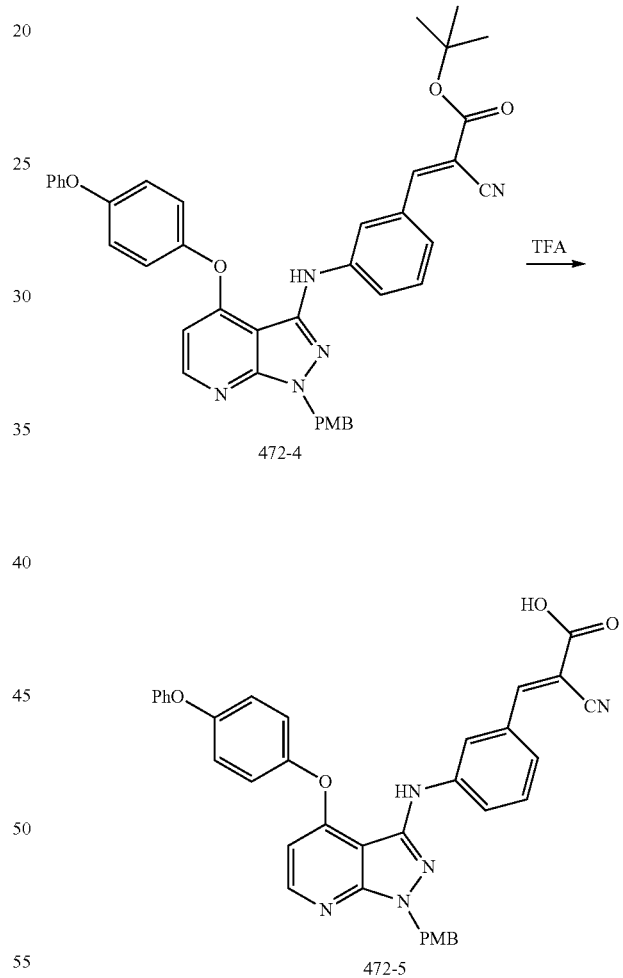

(E)-tert-butyl 2-cyano-3-(3-(1-(4-methoxybenzyl)-4-(4-phenoxyphenoxy)-1H-pyrazolo[3,4-b]pyridin-3-ylamino) phenyl)acrylate (472-4) (150 mg, 0.23 mmol) was treated with TFA (10 mL). The reaction mixture was stirred at r.t. for 2 hr and concentrated under reduced pressure to give (E)-2-cyano-3-(3-(1-(4-methoxybenzyl)-4-(4-phenoxy phenoxy)-1H-pyrazolo[3,4-b]pyridin-3-ylamino)phenyl)acrylic acid (472-5) (quantitative yield) as a yellow oil, which was directly used in next step without further purification. LC-MS (ESI): m/z (M+1) 609.9.

181

Preparation of (E)-2-cyano-3-(3-(1-(4-methoxybenzyl)-4-(4-phenoxyphenoxy)-1H-pyrazolo[3,4-b]pyridin-3-ylamino)phenyl)-N-methylacrylamide (472-6)

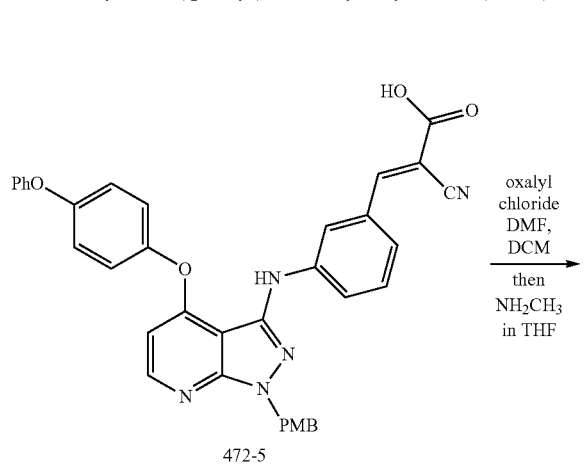

At 0° C., to a solution of (E)-2-cyano-3-(3-(1-(4-methoxybenzyl)-4-(4-phenoxyphenoxy)-1H-pyrazolo[3,4-b]pyridin-3-ylamino)phenyl)acrylic acid (472-5) (0.23 mmol) in anhydrous DCM (10 mL) was added oxalyl chloride (0.026 mL, 0.28 mmol) and DMF (1 drop) under $N_2$ atmosphere. The resulting mixture was stirred at 0° C. for 30 min before a solution of $NH_2Me$ in THF (5 mL, 1 M) was introduced. Stirring was continued at 0° C. for another 30 min. The reaction mixture was then quenched with $H_2O$ (20 mL) and extracted with DCM (10 mL×3). The combined organic phases was washed with brine, dried over $Na_2SO_4$, filtered and concentrated to give the crude product which was purified by flash chromatography (silica gel, 0 to 50% EA in PE) to afford (E)-2-cyano-3-(3-(1-(4-methoxybenzyl)-4-(4-phenoxyphenoxy)-1H-pyrazolo[3,4-b]pyridin-3-ylamino)phenyl)-N-methylacrylamide (472-6) (85 mg, 60% yield) as a yellow oil. LC-MS (ESI): m/z (M+1) 622.9.

182

Preparation of (E)-2-cyano-N-methyl-3-(3-(4-(4-phenoxyphenoxy)-1H-pyrazolo[3,4-b]pyridin-3-ylamino)phenyl)acrylamide (472)

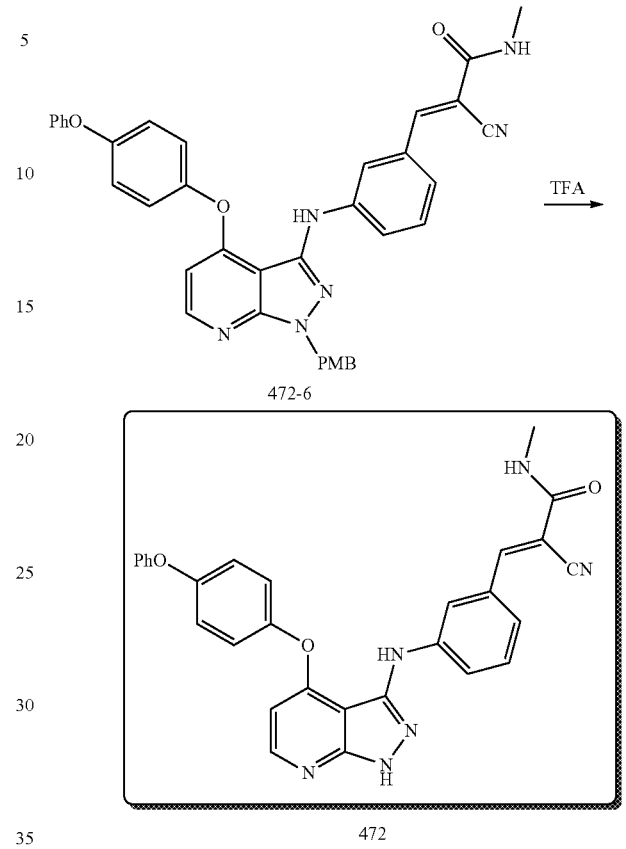

(E)-2-Cyano-3-(3-(1-(4-methoxybenzyl)-4-(4-phenoxyphenoxy)-1H-pyrazolo[3,4-b]pyridin-3-ylamino)phenyl)-N-methylacrylamide (472-6) (85 mg, 0.14 mmol) was treated with TFA (5 mL) at 60° C. to afford (E)-2-cyano-N-methyl-3-(3-(4-(4-phenoxyphenoxy)-1H-pyrazolo[3,4-b]pyridin-3-ylamino)phenyl)acrylamide (472) (14 mg, 20% yield) as a white powder. LC-MS (ESI): m/z (M+1) 503.1. $^1$H NMR (400 MHz, DMSO) δ 12.89 (s, 1H), 8.48-8.35 (m, 2H), 8.25 (d, J=5.4 Hz, 1H), 8.04 (d, J=7.0 Hz, 2H), 7.69 (d, J=7.9 Hz, 1H), 7.48-7.35 (m, 4H), 7.29 (d, J=9.0 Hz, 2H), 7.18-7.09 (m, 3H), 7.04 (d, J=7.7 Hz, 2H), 6.18 (d, J=5.4 Hz, 1H), 2.73 (d, J=4.5 Hz, 3H).

Example 30

4-(4-(4-phenoxyphenoxy)-1H-pyrazolo[3,4-b]pyridin-3-ylamino)picolinonitrile (Compound ID 30)

Preparation of 4-(4-(4-phenoxyphenoxy)-1H-pyrazolo[3,4-b]pyridin-3-ylamino)picolinonitrile

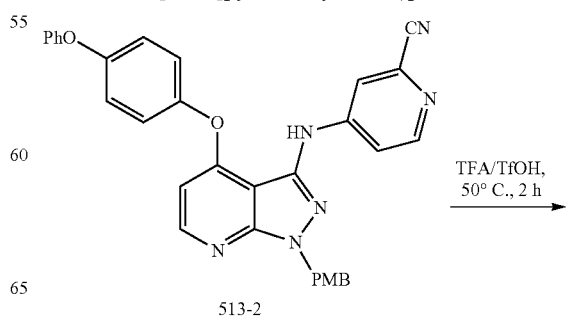

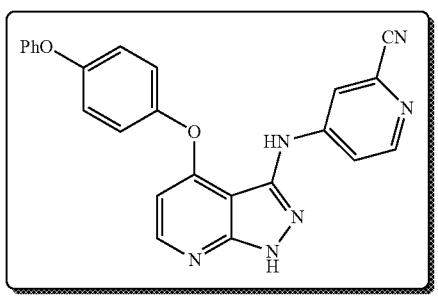

494

To a solution of 4-(1-(4-methoxybenzyl)-4-(4-phenoxyphenoxy)-1H-pyrazolo[3,4-b]pyridin-3-ylamino)picolinonitrile (513-2) (150 mg, 0.28 mmol) in TFA (2 mL) was add TfOH (5 drops). The resulting mixture was stirred at 50° C. for 2 hrs. The solvents were removed in vacuo. The residue was suspended in aqueous of NaHCO$_3$, extracted with DCM (5 mL×3). The combined organic layers were washed with brine, dried over Na$_2$SO$_4$ and concentrated in vacuo. The residue was purified by preparative HPLC (RP, C18, 10 to 95% acetonitrile in water (0.2% HCOOH)) to give 4-(4-(4-phenoxyphenoxy)-1H-pyrazolo[3,4-b]pyridin-3-ylamino) picolinonitrile (494) (28 mg, 24%) as a white solid. LC-MS (ESI): m/z (M+1) 421.0. $^1$H NMR (400 MHz, DMSO) δ 13.30 (s, 1H), 9.36 (s, 1H), 8.33 (dd, J=21.0, 5.6 Hz, 2H), 7.93 (d, J=2.0 Hz, 1H), 7.65 (dd, J=5.7, 2.2 Hz, 1H), 7.40 (t, J=8.0 Hz, 2H), 7.28 (d, J=8.9 Hz, 2H), 7.14 (dd, J=14.3, 8.2 Hz, 3H), 7.04 (d, J=7.8 Hz, 2H), 6.25 (d, J=5.4 Hz, 1H).

Example 31

(Z)-2-fluoro-N-methyl-3-(3-(4-(4-phenoxyphenoxy)-1H-pyrazolo[3,4-b]pyridin-3-ylamino)phenyl)acrylamide (Compound ID 31)

Preparation of ethyl 2-(diethoxyphosphoryl)-2-fluoroacetate (473-1)

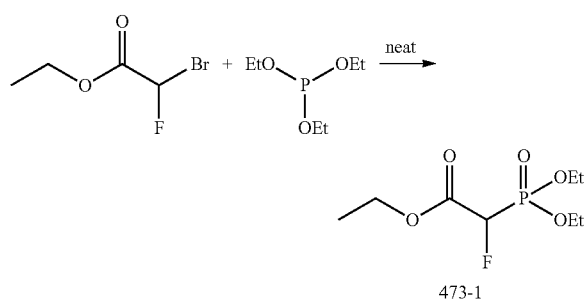

A mixture of ethyl 2-bromo-2-fluoroacetate (2.5 g, 13.5 mmol) and triethyl phosphate (5.8 mL, 32.8 mmol) was heated at 130° C. for 24 hr. The excess of triethyl phosphate was removed by distillation under reduced pressure to afford ethyl 2-(diethoxyphosphoryl)-2-fluoroacetate (473-1) (3.0 g, 92% yield) as a colorless oil.

Preparation of ethyl 2-(diethoxyphosphoryl)-2-fluoroacetic acid (473-2)

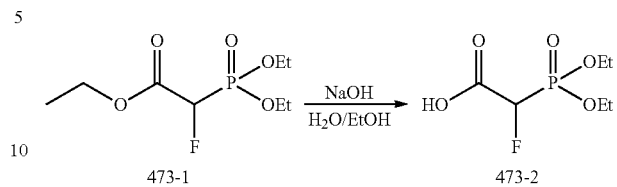

To a solution of 2-(diethoxyphosphoryl)-2-fluoroacetate (473-1) (3.0 g, 12.4 mmol) in ethanol (30 mL) was added a solution of NaOH (496 mg, 12.4 mmol) in H$_2$O (15 mL) dropwise. After stirred at r.t. overnight, the reaction mixture was acidified to pH ~1 with 1M HCl and extracted with ether (100 mL×3). The combined organic phase was dried over Na$_2$SO$_4$, filtered and concentrated to afford 2-(diethoxyphosphoryl)-2-fluoroacetic acid (473-2) (2.9 g, quantitative yield) as colorless oil.

Preparation of ethyl (Z)-2-fluoro-3-(3-nitrophenyl) acrylic acid (473-3)

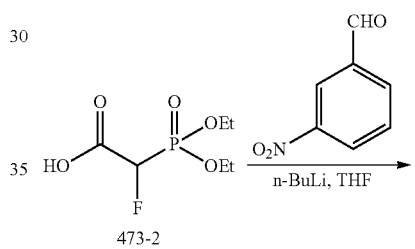

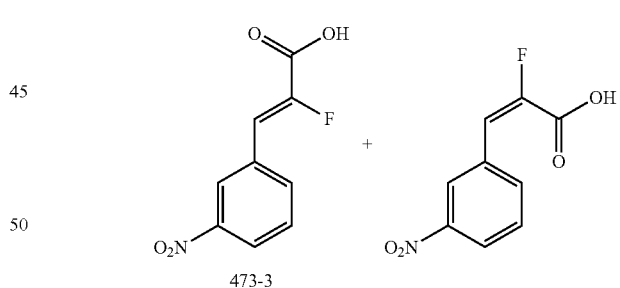

At −78° C. and under N$_2$ atmosphere, to a solution of 2-(diethoxyphosphoryl)-2-fluoroacetic acid (473-2) (2.4 g, 10 mmol) in anhydrous THF (60 mL) was added n-BuLi (2.4M, 8.0 mL) dropwise. After stirred for 30 min, a solution of 3-nitrobenzaldehyde (1.5 g, 10 mmol) in anhydrous THF (10 mL) was introduced dropwise. Stirring was continued at −78° C. for 1 hr before the reaction was quenched with sat. NH$_4$Cl aq. and extracted with EA (100 mL×2). The combined organic phase was washed with brine, dried over Na$_2$SO$_4$, filtered and concentrated to afford a mixture of (Z)-2-fluoro-3-(3-nitrophenyl)acrylic acid (473-3) and its E-isomer as a white solid (2.0 g, 91% yield). LC-MS (ESI): m/z (M−1) 209.9

Preparation of ethyl (Z)-methyl 2-fluoro-3-(3-nitrophenyl)acrylate (473-4)

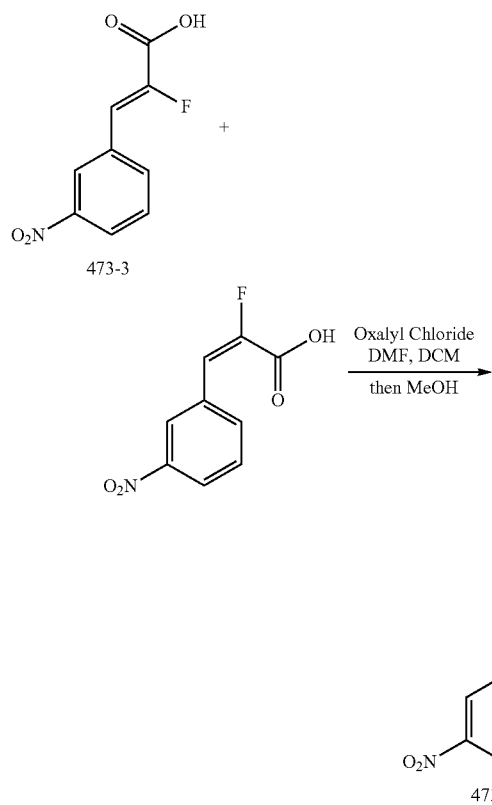

At 0° C., to a solution of (Z/E)-2-fluoro-3-(3-nitrophenyl) acrylic acid (2.0 g, 9.5 mmol) in anhydrous DCM (20 mL) was added oxalyl chloride (1.1 mL, 11.4 mmol) dropwise and 1 drop of DMF under $N_2$ atmosphere. The resulting mixture was stirred at 0° C. for 30 min before MeOH (1.0 mL) was introduced. Stirring was continued for another 30 min. and the reaction was then quenched with $H_2O$ (20 mL). The layers were separated and the aqueous layer was extracted with DCM (2×20 mL). The combined organic phase was washed with brine, dried over $Na_2SO_4$, filtered and concentrated to give the crude product which was purified by flash chromatography (silica gel, 0 to 30% EA in PE) to afford (Z)-methyl 2-fluoro-3-(3-nitrophenyl)acrylate (473-4) (confirmed by $^1$H-NMR analysis) (219 mg, 10.3% yield) as a colorless oil.

Preparation of ethyl (Z)-methyl 3-(3-aminophenyl)-2-fluoroacrylate (473-5)

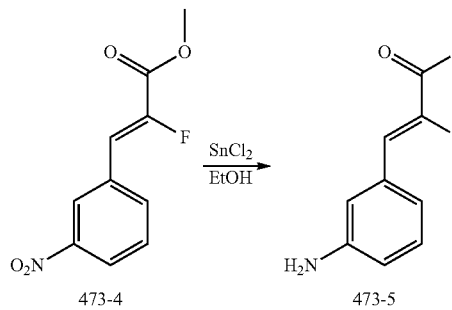

(Z)-Methyl 3-(3-aminophenyl)-2-fluoroacrylate (473-5) (154 mg, 81% yield) was obtained as a yellow solid from (Z)-methyl 2-fluoro-3-(3-nitrophenyl)acrylate (473-4) (219 mg, 0.97 mmol), following a similar procedure outlined in the preparation of (E)-tert-butyl 3-(3-aminophenyl)-2-cyanoacrylate (472-2) (Ex. 25). LC-MS (ESI): m/z (M+1) 196.3.

$^1$H NMR (400 MHz, CDCl$_3$) δ 7.19 (t, J=8.1 Hz, 1H), 7.05-6.98 (m, 2H), 6.85 (d, J$_{F-H}$=35.4 Hz, 1H), 6.74-6.67 (m, 1H), 3.89 (s, 3H), 3.74 (br, 2H).

Preparation of (Z)-methyl 2-fluoro-3-(3-(1-(4-methoxybenzyl)-4-(4-phenoxyphenoxy)-1H-pyrazolo[3,4-b]pyridin-3-ylamino)phenyl)acrylate (473-6)

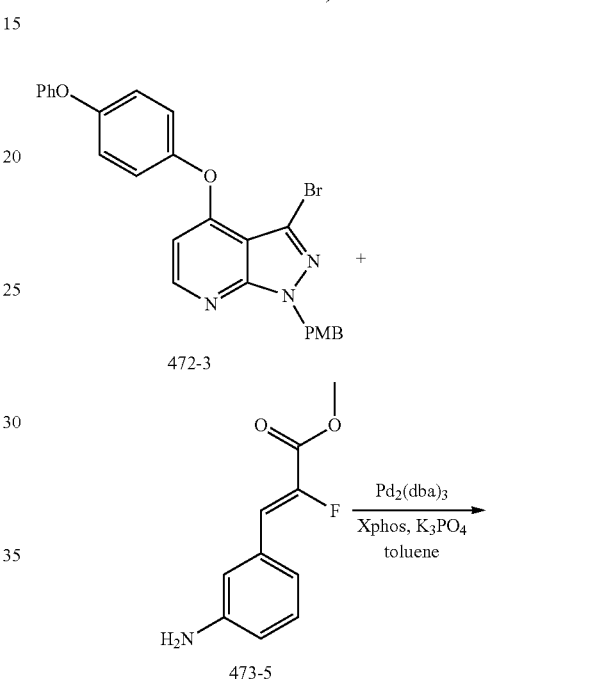

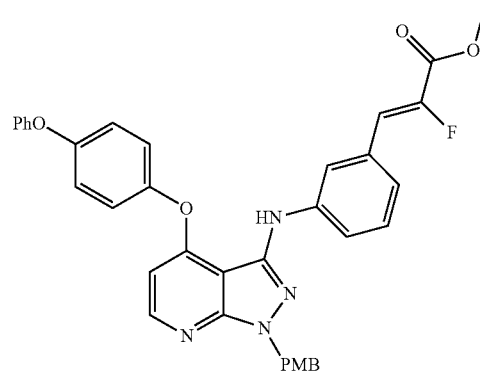

(Z)-Methyl 2-fluoro-3-(3-(1-(4-methoxybenzyl)-4-(4-phenoxyphenoxy)-1H-pyrazolo[3,4-b]pyridin-3-ylamino) phenyl)acrylate (473-6) (263 mg, 81% yield) was obtained as a yellow solid from 3-bromo-1-(4-methoxybenzyl)-4-(4-phenoxyphenoxy)-1H-pyrazolo[3,4-b]pyridine (472-3) (264 mg, 0.53 mmol) and (Z)-methyl 3-(3-aminophenyl)-2-fluoroacrylate (473-5) (154 mg, 0.79 mmol), following a similar procedure outlined in the preparation of (E)-tert-butyl 2-cyano-3-(3-(1-(4-methoxybenzyl)-4-(4-phenoxyphenoxy)-1H-pyrazolo[3,4-b]pyridin-3-ylamino)phenyl)acrylate (472-3) (Ex. 25). LC-MS (ESI): m/z (M+1) 617.4.

187

Preparation of (Z)-2-fluoro-3-(3-(1-(4-methoxybenzyl)-4-(4-phenoxyphenoxy)-1H-pyrazolo[3,4-b]pyridin-3-ylamino)phenyl)acrylic acid (473-7)

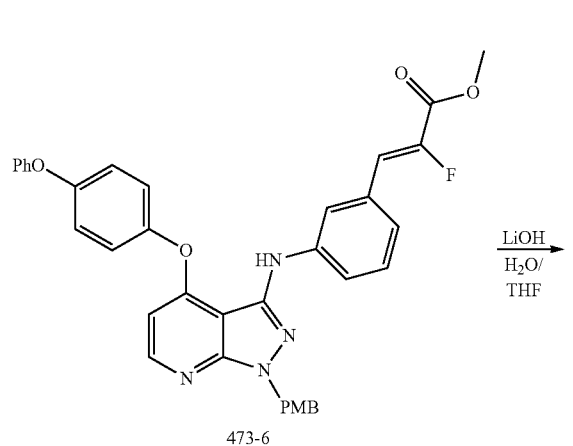
473-6

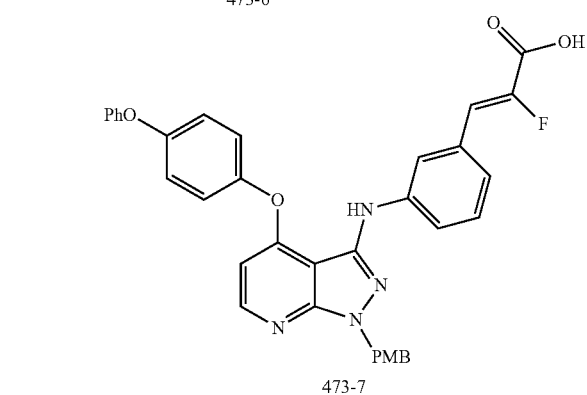
473-7

(Z)-Methyl 2-fluoro-3-(3-(1-(4-methoxybenzyl)-4-(4-phenoxyphenoxy)-1H-pyrazolo[3,4-b]pyridin-3-ylamino)phenyl)acrylate (473-6) (263 mg, 0.43 mmol) was hydrolyzed with 1M LiOH (3 mL) in THF (4 mL) to afford (Z)-2-fluoro-3-(3-(1-(4-methoxybenzyl)-4-(4-phenoxyphenoxy)-1H-pyrazolo[3,4-b]pyridin-3-ylamino)phenyl)acrylic acid (473-7) (quant. yield) as a yellow solid which was directly used in the next step.

Preparation of (Z)-2-fluoro-3-(3-(1-(4-methoxybenzyl)-4-(4-phenoxyphenoxy)-1H-pyrazolo[3,4-b]pyridin-3-ylamino)phenyl)-N-methylacrylamide (473-8)

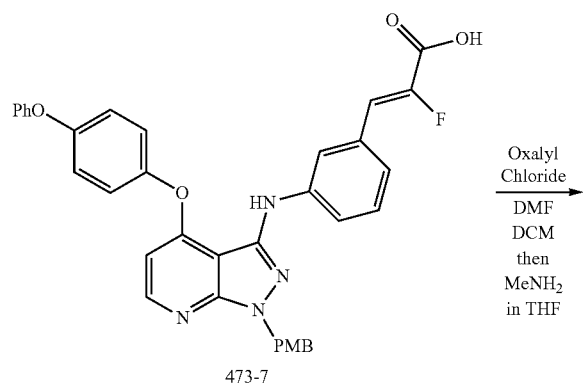
473-7

188

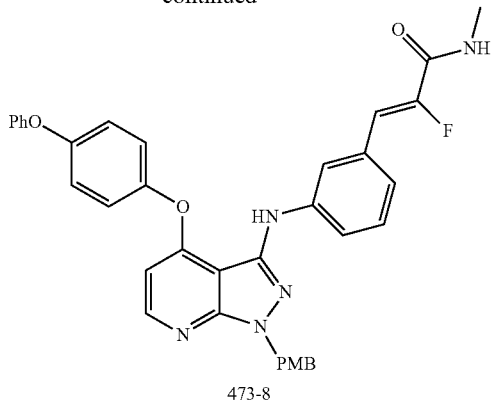
473-8

(Z)-2-Fluoro-3-(3-(1-(4-methoxybenzyl)-4-(4-phenoxyphenoxy)-1H-pyrazolo[3,4-b]pyridin-3-ylamino)phenyl)-N-methylacrylamide (473-8) (46 mg, 90% yield) was obtained from (Z)-2-fluoro-3-(3-(1-(4-methoxybenzyl)-4-(4-phenoxyphenoxy)-1H-pyrazolo[3,4-b]pyridin-3-ylamino)phenyl)acrylic acid (473-7) (50 mg, 0.08 mmol), following a similar procedure outlined in the preparation of (E)-2-cyano-3-(3-(1-(4-methoxybenzyl)-4-(4-phenoxyphenoxy)-1H-pyrazolo[3,4-b]pyridin-3-ylamino)phenyl)-N-methylacrylamide (472-5) (Ex. 25). LC-MS (ESI): m/z (M+1) 616.3.

Preparation of (Z)-2-fluoro-N-methyl-3-(3-(4-(4-phenoxyphenoxy)-1H-pyrazolo[3,4-b]pyridin-3-ylamino)phenyl)acrylamide (473)

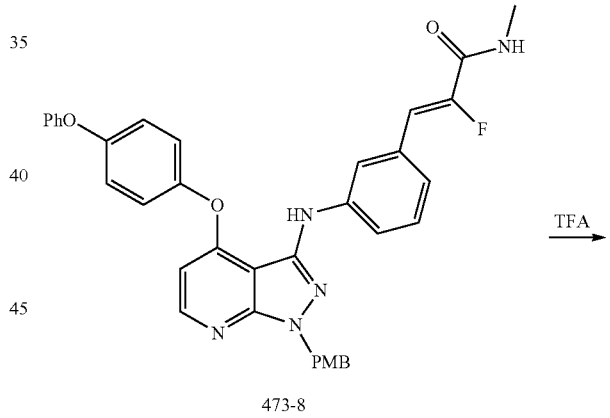
473-8

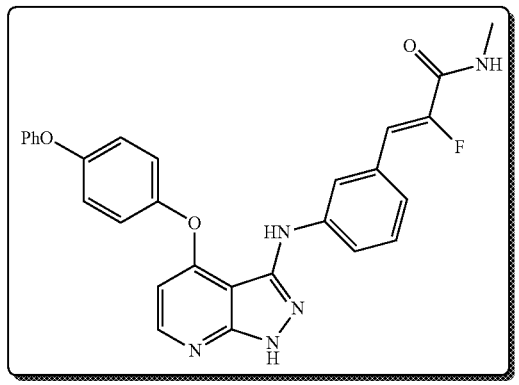
473

(Z)-2-Fluoro-N-methyl-3-(3-(4-(4-phenoxyphenoxy)-1H-pyrazolo[3,4-b]pyridin-3-ylamino)phenyl)acrylamide (473) (12 mg, 32% yield) was obtained as a white powder from (Z)-2-fluoro-3-(3-(1-(4-methoxybenzyl)-4-(4-phenoxyphenoxy)-1H-pyrazolo[3,4-b]pyridin-3-ylamino)phenyl)-N-methylacrylamide (473-8) (46 mg, 0.08 mmol), following a similar procedure outlined in the preparation of (E)-2-cyano-3-(3-(1-(4-methoxybenzyl)-4-(4-phenoxyphenoxy)-1H-pyrazolo[3,4-b]pyridin-3-ylamino)phenyl)-N-methylacrylamide (472-5) (Ex. 25). LC-MS (ESI): m/z (M+1) 496.3. $^1$H NMR (400 MHz, DMSO) δ 12.78 (s, 1H), 8.50 (d, J=4.6 Hz, 1H), 8.24 (d, J=5.4 Hz, 1H), 8.20 (s, 1H), 7.86 (s, 1H), 7.58 (d, J=8.2 Hz, 1H), 7.40 (t, J=8.0 Hz, 2H), 7.33-7.25 (m, 3H), 7.19-7.00 (m, 6H), 6.73 (d, $J_{F-H}$=38.9 Hz, 1H), 6.17 (d, J=5.4 Hz, 1H), 2.71 (d, J=4.6 Hz, 3H).

Example 32

(E)-4-(dimethylamino)-1-(3-(4-(4-phenoxyphenoxy)-1H-pyrazolo[3,4-b]pyridin-3-yl)piperidin-1-yl)but-2-en-1-one (Compound ID 32)

Preparation of tert-butyl 3-(trifluoromethylsulfonyloxy)-5,6-dihydropyridine-1(2H)-carboxylate (503-2)

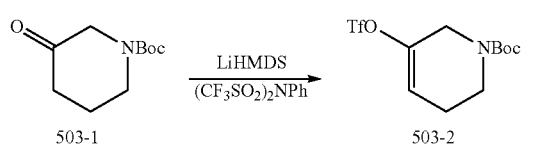 [SMILES: CC(C)(C)OC(=O)N1CCCC(=O)C1 ; CC(C)(C)OC(=O)N1CCC=C(OS(=O)(=O)C(F)(F)F)C1 ; "(CF3SO2)2NPh"]

At −70° C. and under N$_2$ atmosphere, to a solution of LiHMDS (1M, 11 mL, 11 mmol) in anhydrous THF (20 mL) was added a solution of tert-butyl 3-oxopiperidine-1-carboxylate (503-1) (2 g, 10 mmol) in THF (10 mL) dropwise over 15 min. The resulting mixture was stirred at −70° C. for 30 min. A solution of 1,1,1-trifluoro-N-phenyl-N-(trifluoromethylsulfonyl)-methanesulfonamide (4.64 g, 13 mmol) in THF (10 mL) was added and the resulting mixture was stirred at −70° C. for an additional 30 min. before being allowed to warm up to room temperature over 2 hr. The reaction was quenched with NaHCO$_3$ aq., extracted with EA (15 mL×3). The combined organic layer was washed with brine, dried over Na$_2$SO$_4$ and concentrated in vacuo. The residue was purified by column chromatography (silica gel, 0 to 10% EA in PE) to give tert-butyl 3-(trifluoromethylsulfonyloxy)-5,6-dihydropyridine-1(2H)-carboxylate (503-2) (1.4 g, 42.3%) as a colorless oil.

Preparation of tert-butyl 3-(4,4,5,5-tetramethyl-1,3,2-dioxaborolan-2-yl)-5,6-dihydropyridine-1(2H)-carboxylate (503-3)

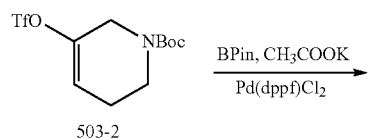

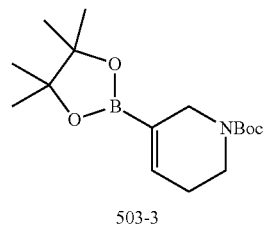

To a solution of tert-butyl 3-(trifluoromethylsulfonyloxy)-5,6-dihydropyridine-1(2H)-carboxylate (503-2) (1.4 g, 4.3 mmol), BPin (1.3 g, 5.1 mmol) and KOAc (1.26 g, 12.9 mmol) in dioxane (10 mL) was added Pd(dppf)Cl$_2$.DCM (351 mg, 0.43 mmol). The resulting mixture was purged with N$_2$×3 and heated to 80° C. overnight. The solvent was removed in vacuo and the residue was purified by column chromatography (silica gel, 0 to 10% EA in PE) to give tert-butyl 3-(4,4,5,5-tetramethyl-1,3,2-dioxaborolan-2-yl)-5,6-dihydropyridine-1(2H)-carboxylate (503-3) (850 mg, 64%) as a yellow oil.

Preparation of tert-butyl 3-(1-(4-methoxybenzyl)-4-(4-phenoxyphenoxy)-1H-pyrazolo[3,4-b]pyridin-3-yl)-5,6-dihydropyridine-1(2H)-carboxylate (503-4)

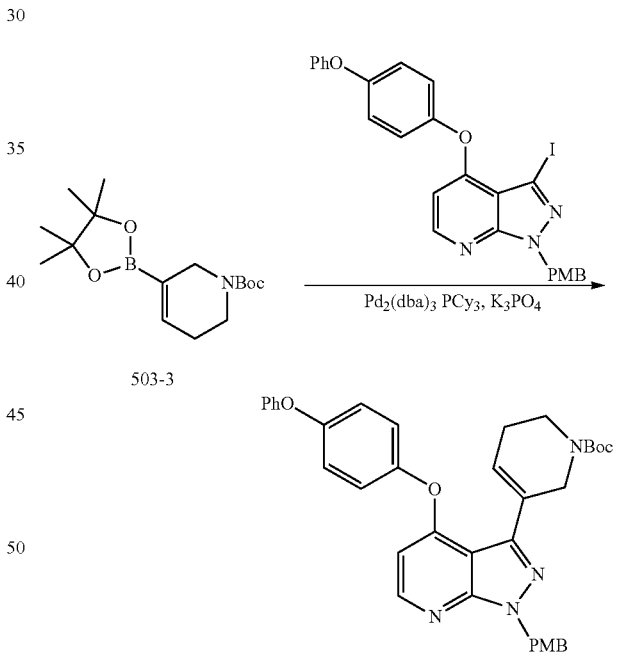

tert-Butyl 3-(1-(4-methoxybenzyl)-4-(4-phenoxyphenoxy)-1H-pyrazolo[3,4-b]pyridin-3-yl)-5,6-dihydropyridine-1(2H)-carboxylate (503-4) (50 mg, 83%) was obtained as a yellow solid from tert-butyl 3-(4,4,5,5-tetramethyl-1,3,2-dioxaborolan-2-yl)-5,6-dihydropyridine-1(2H)-carboxylate (503-3) (36 mg, 0.12 mmol) and 3-iodo-1-(4-methoxybenzyl)-4-(4-phenoxyphenoxy)-1H-pyrazolo[3,4-b]pyridine (58 mg, 0.1 mmol), following a similar procedure outlined in Ex 24. LC-MS (ESI): m/z (M+1) 605.2.

Preparation of tert-butyl 3-(1-(4-methoxybenzyl)-4-(4-phenoxyphenoxy)-1H-pyrazolo[3,4-b]pyridin-3-yl)piperidine-1-carboxylate (503-5)

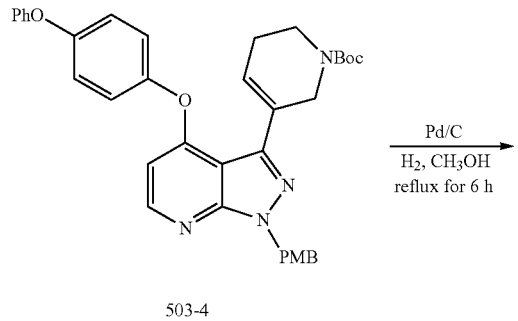

503-4

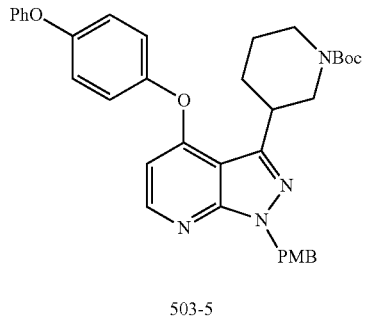

503-5

To a suspension of Pd/C (50 mg) in MeOH (10 mL) was added tert-butyl 3-(1-(4-methoxybenzyl)-4-(4-phenoxyphenoxy)-1H-pyrazolo[3,4-b]pyridin-3-yl)-5,6-dihydropyridine-1(2H)-carboxylate (503-4) (50 mg, 0.08 mmol). The resulting mixture was stirred at 60° C. under $H_2$ atmosphere for 6 h. The mixture was filtered and concentrated in vacuo to give tert-butyl 3-(1-(4-methoxybenzyl)-4-(4-phenoxyphenoxy)-1H-pyrazolo[3,4-b]pyridin-3-yl)piperidine-1-carboxylate (503-5) (50 mg, quant.) as a yellow solid. LC-MS (ESI): m/z (M+1) 607.2

Preparation of (E)-4-(dimethylamino)-1-(3-(4-(4-phenoxyphenoxy)-1H-pyrazolo[3,4-b]pyridin-3-yl)piperidin-1-yl)but-2-en-1-one (503)

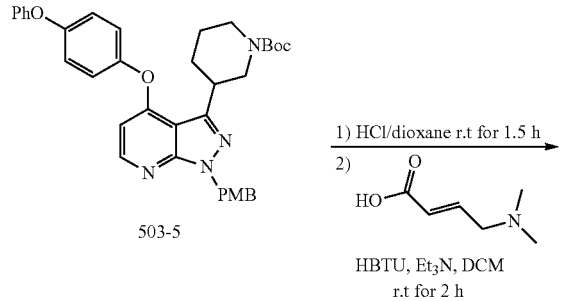

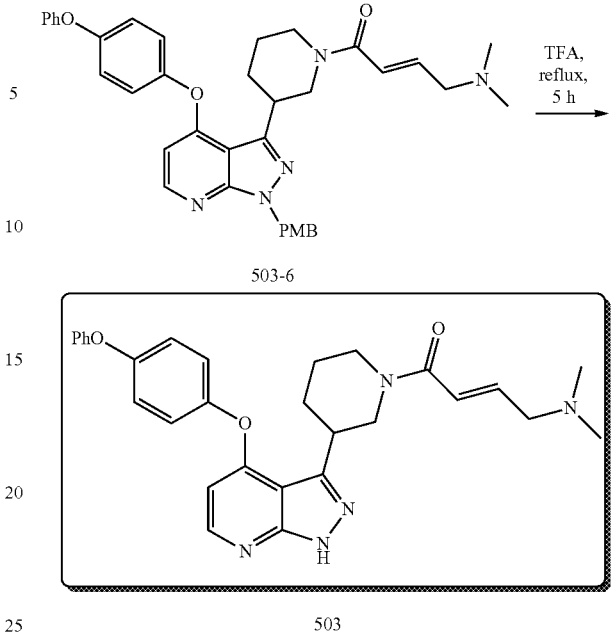

503

(E)-4-(Dimethylamino)-1-(3-(4-(4-phenoxyphenoxy)-1H-pyrazolo[3,4-b]pyridin-3-yl)piperidin-1-yl)but-2-en-1-one (503) (30 mg, %) was obtained as a white solid from tert-butyl 3-(1-(4-methoxybenzyl)-4-(4-phenoxyphenoxy)-1H-pyrazolo[3,4-b]pyridin-3-yl)piperidine-1-carboxylate (503-5) (50 mg, 0.08 mmol), following a similar procedure outlined in Ex. 1. LC-MS (ESI): m/z (M+1) 498.2. $^1$H NMR (400 MHz, DMSO) δ 13.41 (s, 1H), 8.16 (HCOOH), 8.27 (d, J=5.4 Hz, 1H), 7.46-7.28 (m, 4H), 7.20-7.01 (m, 5H), 6.66-6.46 (m, 2H), 6.29-6.16 (m, 1H), 4.84-3.95 (m, 2H), 3.27-2.57 (m, 5H), 2.19-1.94 (m, 8H), 1.85-1.78 (m, 1H), 1.51-1.39 (m, 1H).

Example 33

(R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-(trifluoromethyl)pyridin-2-yl)benzamide (Compound ID 33)

Preparation of 4-acetoxybenzoic acid (500-1)

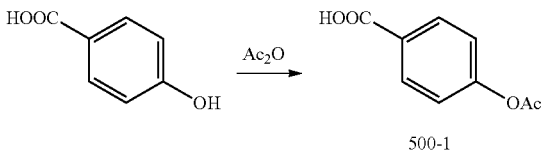 [SMILES: "Ac2O" ; O=C(O)c1ccc(O)cc1 ; CC(=O)Oc1ccc(C(=O)O)cc1]

500-1

To a solution of 4-hydroxybenzoic acid (5 g, 36 mmol) in acetic anhydride (10 mL) was added 3 drops of conc. $H_2SO_4$. The reaction mixture was heated at 80° C. under $N_2$ for 3 hr. After cooled down to room temperature, the mixture was concentrated, and then poured into ice-water. The resulting precipitate was filtered and washed with water and petroleum ether to give 4-acetoxybenzoic acid (500-1) (5.6 g, 86%) as a white solid. LC-MS (ESI): m/z (M+1) 181.2.

Preparation of 4-(4-(trifluoromethyl)pyridin-2-ylcarbamoyl)phenyl acetate (500-2)

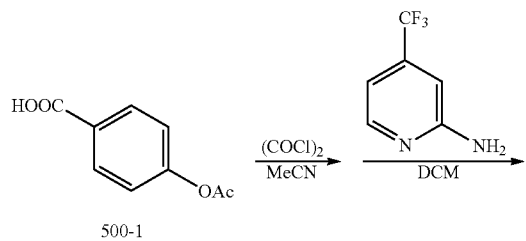

500-1

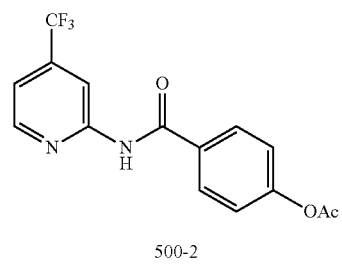

500-2

To a suspension of 4-acetoxybenzoic acid (500-1) (1.6 g, 8.9 mmol) in anhydrous acetonitrile (10 mL) was added 1 drop of DMF before introducing (COCl)$_2$ (2 mL, 21 mmol). The resulting mixture was stirred at room temperature for 1 hr. The solvent was evaporated. The freshly generated acid chloride was dissolved in anhydrous DCM (3 mL) and the solution was introduced to a solution of 4-(trifluoromethyl) pyridin-2-amine (700 mg, 4.3 mmol) in DCM (3 mL). The reaction mixture was stirred at room temperature for 1 hr before being quenched with MeOH (5 mL). Solvents were removed and the residue was purified by column chromatography (silica gel, 0 to 30% ethyl acetate in petroleum ether) to give 4-(4-(trifluoromethyl)pyridin-2-ylcarbamoyl) phenyl acetate (500-2) (697 mg, 50%) as a solid. LC-MS (ESI): m/z (M+1) 325.2.

Preparation of 4-hydroxy-N-(4-(trifluoromethyl) pyridin-2-yl)benzamide (500-3)

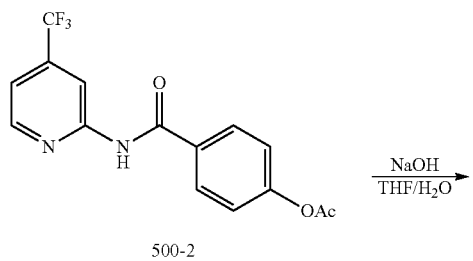

500-2

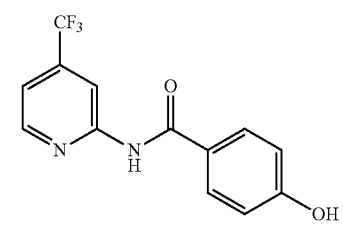

500-3

To a mixture of 4-(4-(trifluoromethyl)pyridin-2-ylcarbamoyl)phenyl acetate (500-2) (697 mg, 2.2 mmol) in THF/H$_2$O (5 mL/5 mL) was added NaOH (103 mg, 2.6 mmol). The resulting mixture was heated at 45° C. for 3 hr under N$_2$. After being cooled to room temperature, the mixture was neutralized to pH=7 with 1N HCl solution, and extracted with EtOAc (50 mL×3). The combined organic layer was washed with water and brine, dried over Na$_2$SO$_4$, and concentrated. 4-Hydroxy-N-(4-(trifluoromethyl)pyridin-2-yl)benzamide (500-3) (550 mg, 91%) was afforded as a white solid. LC-MS (ESI): m/z (M−1) 281.2.

Preparation of 4-(3-bromo-1-(4-methoxybenzyl)-1H-pyrazolo[3,4-b]pyridin-4-yloxy)-N-(4-(trifluoromethyl)pyridin-2-yl)benzamide (500-4)

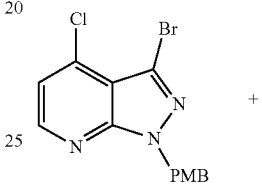

+

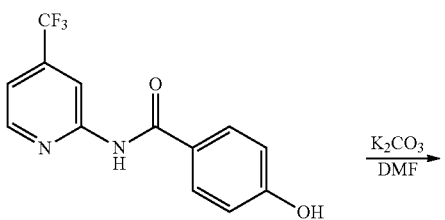

500-3

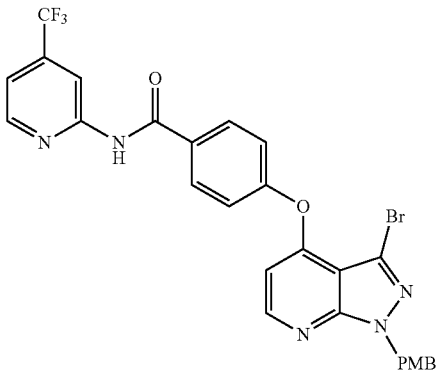

500-4

To a mixture of 3-bromo-4-chloro-1-(4-methoxybenzyl)-1H-pyrazolo[3,4-b]pyridine (1.0 g, 2.8 mmol) and 4-hydroxy-N-(4-(trifluoromethyl)pyridin-2-yl)benzamide (500-3) (550 mg, 1.95 mmol) in DMF (10 mL) was added $K_2CO_3$ (1.0 g, 7.2 mmol). The resulting mixture was heated at 80° C. under $N_2$ for 4 h. After being cooled down to room temperature, the reaction was diluted with water (100 mL), and extracted with EtOAc (50 mL×3). The combined organic layer was washed with water and brine, dried over $Na_2SO_4$, and concentrated. The residue was purified by column chromatography (silica gel, 0 to 50% ethyl acetate in petroleum ether) to give 4-(3-bromo-1-(4-methoxybenzyl)-1H-pyrazolo[3,4-b]pyridin-4-yloxy)-N-(4-(trifluoromethyl)pyridin-2-yl)benzamide (500-4) (1.0 g, 85%) as a brown solid. LC-MS (ESI): m/z (M+1) 599.1.

Preparation of (R)-tert-butyl 3-(1-(4-methoxybenzyl)-4-(4-(4-(trifluoromethyl)pyridin-2-ylcarbamoyl)phenoxy)-1H-pyrazolo[3,4-b]pyridin-3-ylamino)pyrrolidine-1-carboxylate (500-5)

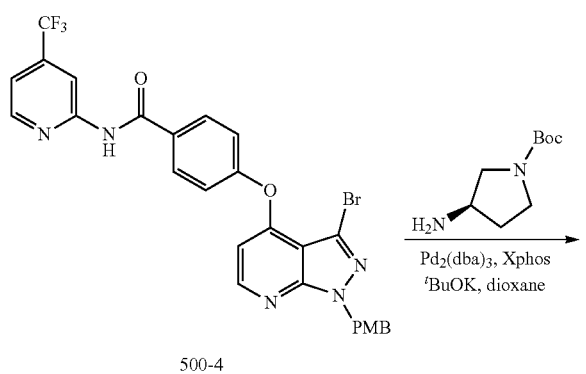

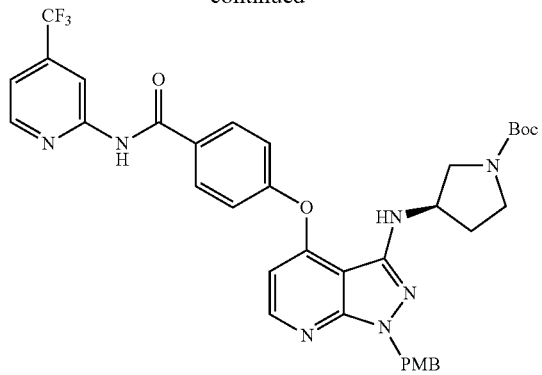

500-5

To a mixture of 4-(3-bromo-1-(4-methoxybenzyl)-1H-pyrazolo[3,4-b]pyridin-4-yloxy)-N-(4-(trifluoromethyl)pyridin-2-yl)benzamide (500-4) (1.0 g, 1.7 mmol), (R)-tert-butyl 3-aminopyrrolidine-1-carboxylate (1.56 g, 8.4 mmol) and $^tBuOK$ (562 mg, 5.0 mmol) in dioxane (10 mL) were added $Pd_2(dba)_3$ (153 mg, 0.17 mmol) and Xphos (238 mg, 0.5 mmol). The resulting mixture was purged with $N_2$ (3×) before heated at 120° C. for 2 days under $N_2$ atmosphere. After cooled to rt, the reaction was concentrated under vacuum. The residue was purified by column chromatography (silica gel, 0 to 50% ethyl acetate in petroleum ether) to give (R)-tert-butyl 3-(1-(4-methoxybenzyl)-4-(4-(4-(trifluoromethyl)pyridin-2-ylcarbamoyl)phenoxy)-1H-pyrazolo[3,4-b]pyridin-3-ylamino)pyrrolidine-1-carboxylate (500-5) (300 mg, 26%) as a brown solid. LC-MS (ESI): m/z (M+1) 704.1.

Preparation of (R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-(trifluoromethyl)pyridin-2-yl)benzamide (500)

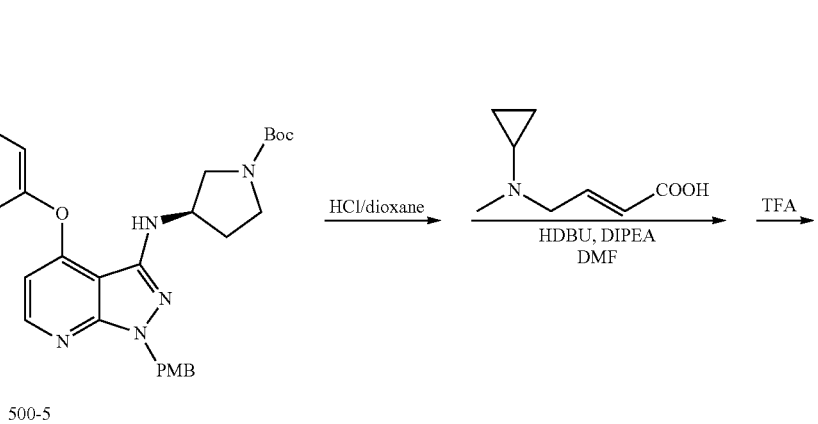

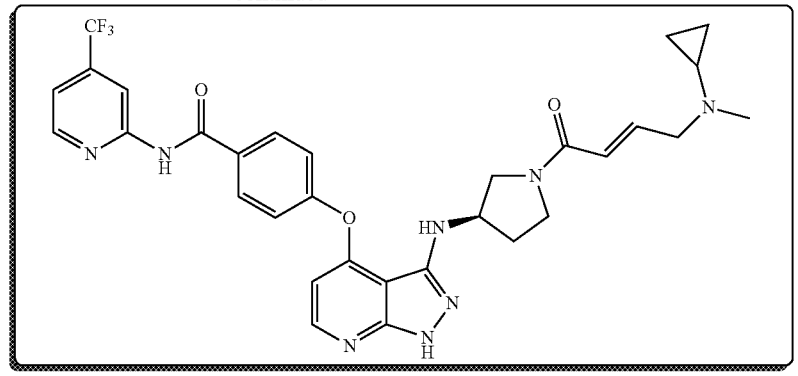

500

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(4-(trifluoromethyl)pyridin-2-yl)benzamide (500) (15 mg, 6%) was obtained as a white solid from (R)-tert-butyl 3-(1-(4-methoxybenzyl)-4-(4-(4-(trifluoromethyl)pyridin-2-ylcarbamoyl)phenoxy)-1H-pyrazolo[3,4-b]pyridin-3-ylamino)pyrrolidine-1-carboxylate (500-5) (300 mg, 0.43 mmol) and (E)-4-(cyclopropyl(methyl)amino)but-2-enoic acid, HCl salt (100 mg, 0.52 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 621.0. $^1$H NMR (400 MHz, DMSO) δ 12.34 (s, 1H), 11.37 (s, 1H), 8.67 (d, J=5.0 Hz, 1H), 8.54 (s, 1H), 8.23-8.09 (m, 3H), 7.54 (d, J=4.5 Hz, 1H), 7.44-7.34 (m, 2H), 6.68-6.52 (m, 1H), 6.37-6.23 (m, 1H), 6.14 (dd, J=8.8, 5.3 Hz, 1H), 5.72-5.51 (m, 1H), 4.35-4.12 (m, 1H), 3.94-3.46 (m, 3H), 3.20 (t, J=5.8 Hz, 2H), 2.24-2.12 (m, 4H), 2.10-1.91 (m, 1H), 1.68-1.60 (m, 1H), 0.42-0.32 (m, 2H), 0.30-0.20 (m, 2H).

Example 34

(R,E)-2-(3-(1-(4-(dimethylamino)but-2-enoyl)pyrrolidin-3-ylamino)-1H-pyrazolo[3,4-b]pyridin-4-yloxy)-5-phenoxybenzonitrile (Compound ID 34)

Preparation of 2-hydroxy-5-phenoxybenzaldehyde oxime (515-2)

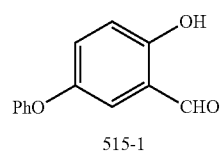

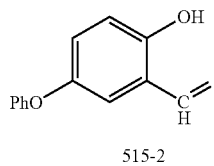

To a solution of 2-hydroxy-5-phenoxybenzaldehyde (515-1) (1.6 g, 7.5 mmol) and KOAc (806 mg, 8.2 mmol) in THF (20 mL) was added hydroxylamine hydrochloride (519 mg, 7.5 mmol). The resulting mixture was stirred at r.t. for 1 h. The solvent was removed in vacuum and the residue was portioned between DCM (50 mL) and water (50 mL). The layers were separated and the water layer was extracted with DCM (20 mL×2). The combined organic was washed with brine dried over Na$_2$SO$_4$ and concentrated in vacuo to give 2-hydroxy-5-phenoxybenzaldehyde oxime (515-2) (1.4 g, 82%) as a colorless oil. LC-MS (ESI): m/z (M+1) 230.1.

Preparation of 2-hydroxy-5-phenoxybenzonitrile (515-3)

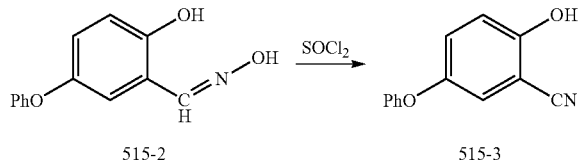

2-Hydroxy-5-phenoxybenzaldehyde oxime (515-2) (2 g, 8.7 mmol) was dissolved in SOCl$_2$ (30 mL). The resulting mixture was stirred at room temperature for 2 hr. The mixture was poured into ice and extracted with DCM (20 mL×3). Combined organic layers were washed with brine, dried over Na$_2$SO$_4$ and concentrated in vacuo. The residue was purified by column chromatography (silica gel, 0 to 20% EA in PE) to give 2-hydroxy-5-phenoxybenzonitrile (515-3) (940 mg, 52%) as a white solid. LC-MS (ESI): m/z (M−1) 210.1.

Preparation of 2-(3-bromo-1-(4-methoxybenzyl)-1H-pyrazolo[3,4-b]pyridin-4-yloxy)-5-phenoxybenzonitrile (515-4)

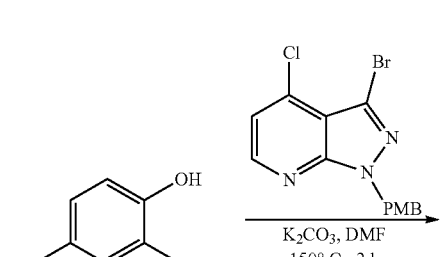

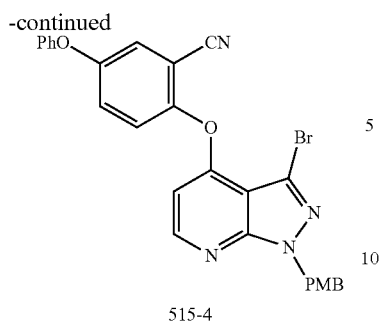

515-4

2-(3-Bromo-1-(4-methoxybenzyl)-1H-pyrazolo[3,4-b]pyridin-4-yloxy)-5-phenoxybenzonitrile (515-4) (595 mg, 99%) was obtained as a yellow solid from 2-hydroxy-5-phenoxybenzonitrile (515-3) (288 mg, 1.36 mmol) and 3-bromo-4-chloro-1-(4-methoxybenzyl)-1H-pyrazolo[3,4-b]pyridine (400 mg, 1.13 mmol), following a similar procedure outlined in Ex. 1. LC-MS (ESI): m/z (M/M+1) 526.8/528.8.

Preparation of (R)-tert-butyl 3-(4-(2-cyano-4-phenoxyphenoxy)-1-(4-methoxybenzyl)-1H-pyrazolo[3,4-b]pyridin-3-ylamino)pyrrolidine-1-carboxylate (515-5)

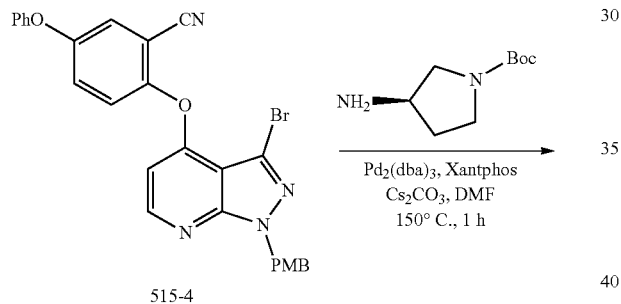

515-4

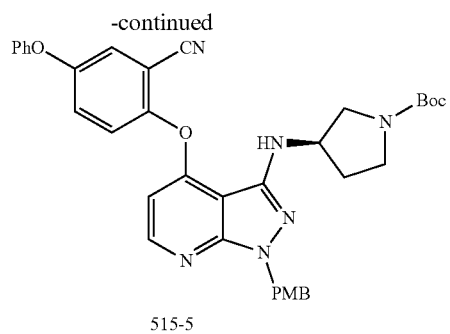

515-5

(R)-tert-butyl 3-(4-(2-cyano-4-phenoxyphenoxy)-1-(4-methoxybenzyl)-1H-pyrazolo[3,4-b]pyridin-3-ylamino)pyrrolidine-1-carboxylate (515-5) (480 mg, 67% yield) was obtained from 2-(3-bromo-1-(4-methoxybenzyl)-1H-pyrazolo[3,4-b]pyridin-4-yloxy)-5-phenoxybenzonitrile (515-4) (600 mg, 1.13 mmol), following a similar procedure outlined in the preparation of (R)-tert-butyl3-(4-(4-chlorophenoxy)-1-(4-methoxy benzyl)-1H-pyrazolo[3,4-b]pyridin-3-ylamino)pyrrolidine-1-carboxylate (291-9) (Ex. 1). LC-MS (ESI): m/z (M+1) 633.2.

Preparation of (R,E)-2-(3-(1-(4-(dimethylamino)but-2-enoyl)pyrrolidin-3-ylamino)-1H-pyrazolo[3,4-b]pyridin-4-yloxy)-5-phenoxybenzonitrile (515)

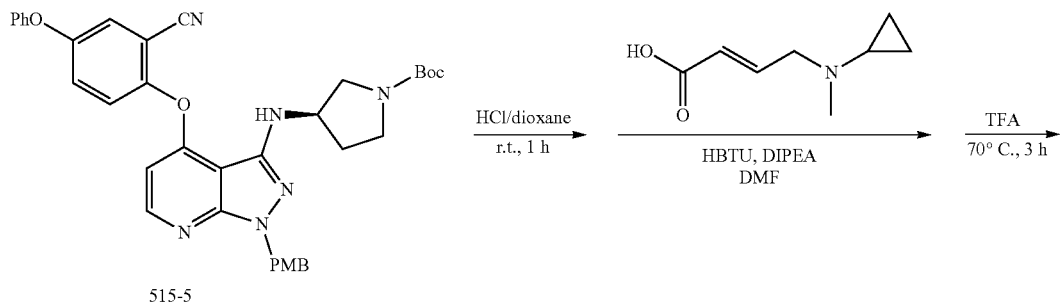

515-5

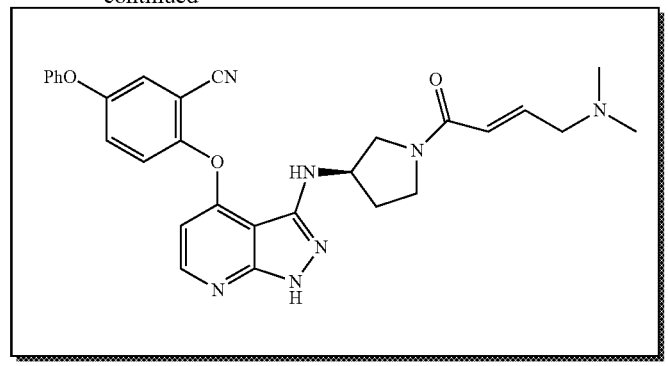

515

(R,E)-2-(3-(1-(4-(dimethylamino)but-2-enoyl)pyrrolidin-3-ylamino)-1H-pyrazolo[3,4-b]pyridin-4-yloxy)-5-phenoxybenzonitrile (515) (30 mg, 12% yield) was obtained as a white solid from (R)-tert-butyl 3-(4-(2-cyano-4-phenoxyphenoxy)-1-(4-methoxybenzyl)-1H-pyrazolo[3,4-b]pyridin-3-ylamino)pyrrolidine-1-carboxylate (515-5) (300 mg, 0.47 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 524.2. $^1$H NMR (400 MHz, DMSO) δ 12.38 (s, 1H), 8.19 (d, J=5.4 Hz, 1H), 7.71 (t, J=2.7 Hz, 1H), 7.54 (d, J=9.0 Hz, 1H), 7.44 (t, J=7.7 Hz, 3H), 7.20 (t, J=7.3 Hz, 1H), 7.11 (d, J=8.4 Hz, 2H), 6.56 (s, 1H), 6.36 (d, J=18.2 Hz, 1H), 6.15 (t, J=5.8 Hz, 1H), 5.71 (dd, J=30.3, 6.1 Hz, 1H), 4.39-4.16 (m, 1H), 3.59 (dd, J=34.4, 28.7 Hz, 4H), 2.99 (t, J=5.5 Hz, 2H), 2.31-2.16 (m, 1H), 2.11 (d, J=5.7 Hz, 6H), 2.06-1.88 (m, 1H).

Example 35

(R,E)-2-(3-(1-(4-(cyclopropyl(methyl)amino)but-2-enoyl)pyrrolidin-3-ylamino)-1H-pyrazolo[3,4-b]pyridin-4-yloxy)-5-phenoxybenzonitrile (Compound ID 35)

Preparation of (R,E)-2-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-5-phenoxybenzonitrile (509-1)

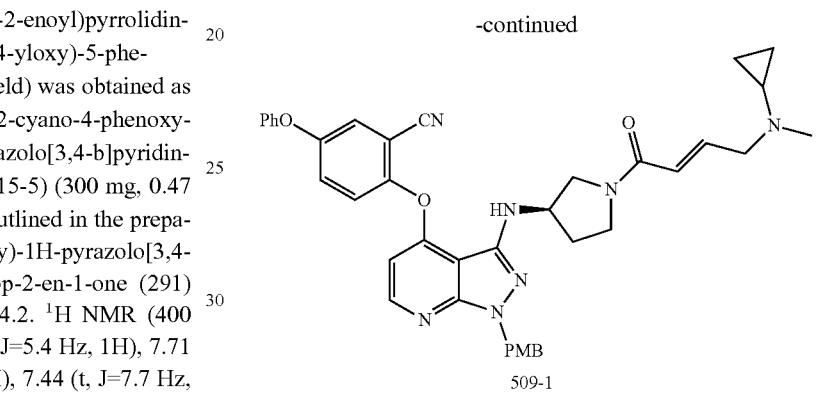

509-1

(R,E)-2-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-5-phenoxybenzonitrile (509-1) (120 mg, 47%) was obtained as a yellow solid from (R)-2-(1-(4-methoxybenzyl)-3-(pyrrolidin-3-ylamino)-1H-pyrazolo[3,4-b]pyridin-4-yloxy)-5-phenoxybenzonitrile (515-6) (200 mg, 0.38 mmol) and (E)-4-(cyclopropyl(methyl)amino)but-2-enoic acid hydrochloride (132 mg, 0.41 mmol), following a similar procedure outlined in Ex. 8. LC-MS (ESI): m/z (M+1) 670.2.

Preparation of (R,E)-2-(3-(1-(4-(cyclopropyl(methyl)amino)but-2-enoyl)pyrrolidin-3-ylamino)-1H-pyrazolo[3,4-b]pyridin-4-yloxy)-5-phenoxybenzonitrile (509)

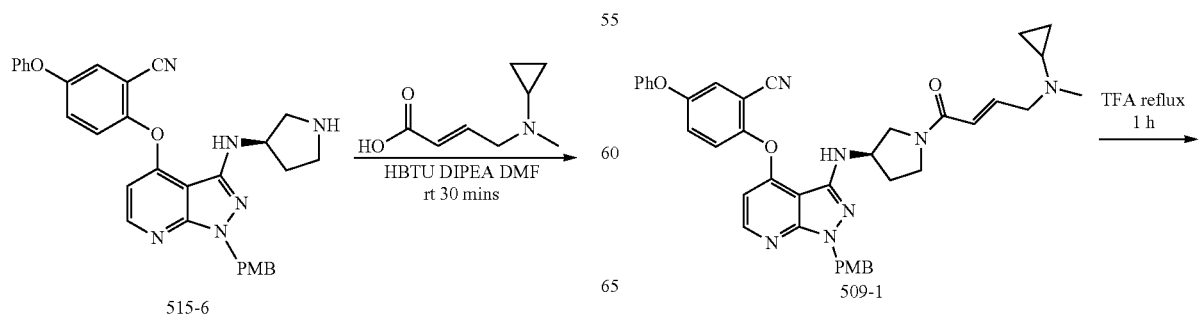

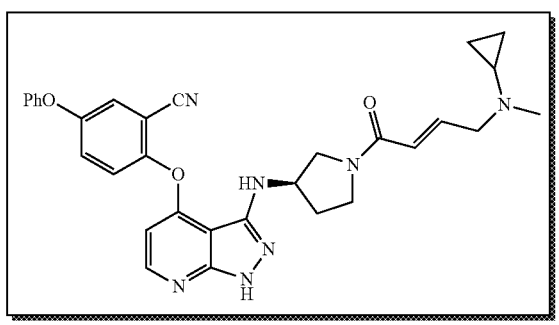

509

(R,E)-2-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-5-phenoxybenzonitrile (509-1) (120 mg, 0.18 mmol) was treated with TFA at 70° C. for 1 h to give (R,E)-2-(3-(1-(4-(cyclopropyl(methyl)-amino)but-2-enoyl)pyrrolidin-3-ylamino)-1H-pyrazolo[3,4-b]pyridin-4-yloxy)-5-phenoxybenzonitrile (509) (50 mg, 51%) as a white solid. LC-MS (ESI): m/z (M+1) 550.2. $^1$H NMR (400 MHz, DMSO) δ 12.42 (s, 1H), 8.22 (d, J=5.2 Hz, 1H), 7.74 (s, 1H), 7.56 (d, J=9.1 Hz, 1H), 7.46 (t, J=7.2 Hz, 3H), 7.23 (t, J=7.3 Hz, 1H), 7.13 (d, J=7.8 Hz, 2H), 6.75-6.49 (m, 2H), 6.18 (t, J=5.2 Hz, 1H), 5.75 (dd, J=30.2, 5.5 Hz, 1H), 4.32 (dd, J=43.8, 5.1 Hz, 1H), 4.05-3.93 (m, 1H), 3.79-3.69 (m, 1H), 3.64-3.47 (m, 2H), 3.35 (s, 3H), 2.98-2.64 (m, 2H), 2.31-2.03 (m, 3H), 0.97-0.28 (m, 4H).

Example 36

(S,E)-4-(cyclopropyl(methyl)amino)-1-(2-((4-(4-phenoxyphenoxy)-1H-pyrazolo[3,4-b]pyridin-3-ylamino)methyl)pyrrolidin-1-yl)but-2-en-1-one (Compound ID 36)

Preparation of (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1)

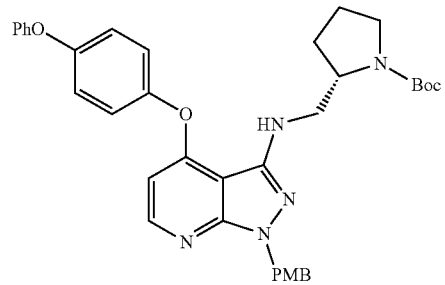

504-1

A mixture of 3-bromo-1-(4-methoxybenzyl)-4-(4-phenoxyphenoxy)-1H-pyrazolo[3,4-b]pyridine (472-3) (200 mg, 0.40 mmol), (S)-tert-butyl 2-(aminomethyl)pyrrolidine-1-carboxylate (240 mg, 1.2 mmol), Pd$_2$(dba)$_3$ (18 mg, 0.02 mmol), xantphos (23 mg, 0.04 mmol) and Cs$_2$CO$_3$ (294 mg, 1.2 mmol) in DMF (10 mL) was heated at 150° C. under N$_2$ atmosphere for 1 hr. After being cooled down to room temperature, the reaction mixture was concentrated under reduced pressure to give the crude product which was purified by flash chromatography (silica gel, 0 to 40% EA in PE) to afford (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1) (180 mg, 58% yield) as a light yellow oil. LC-MS (ESI): m/z (M+1) 623.4.

Preparation of (S,E)-4-(cyclopropyl(methyl)amino)-1-(2-((1-(4-methoxybenzyl)-4-(4-phenoxyphenoxy)-1H-pyrazolo[3,4-b]pyridin-3-ylamino)methyl)pyrrolidin-1-yl)but-2-en-1-one (504-3)

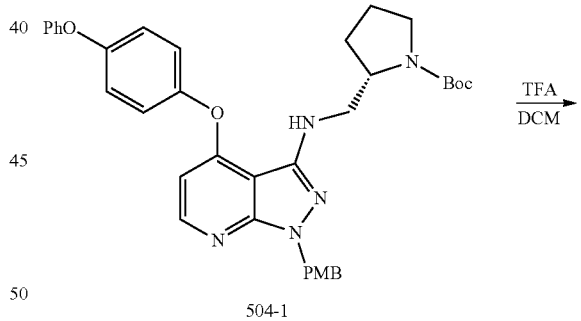

504-1

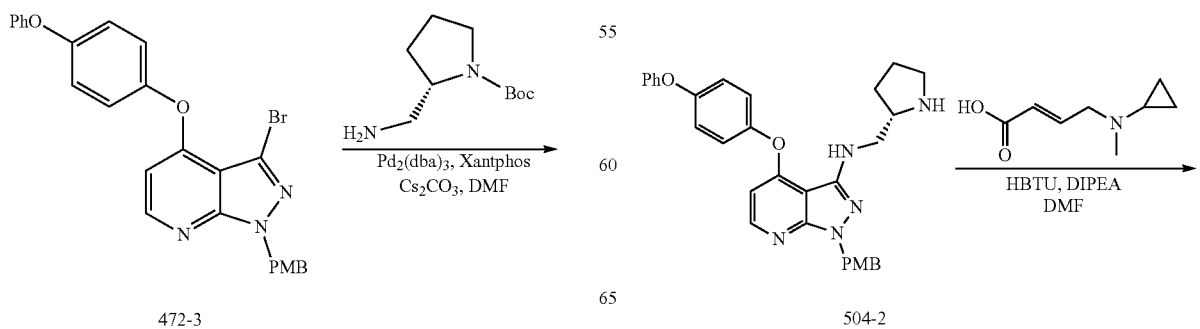

472-3          504-2

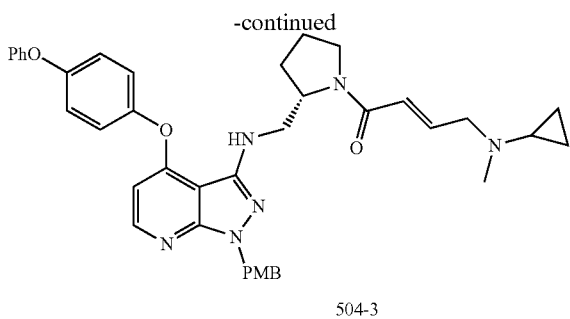

504-3

(S,E)-4-(Cyclopropyl(methyl)amino)-1-(2-((1-(4-methoxybenzyl)-4-(4-phenoxyphenoxy)-1H-pyrazolo[3,4-b]pyridin-3-ylamino)methyl)pyrrolidin-1-yl)but-2-en-1-one (504-3) (66 mg, 69% yield) was obtained as a light yellow oil from (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1) (90 mg, 0.14 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 659.32.

Preparation of (S,E)-4-(cyclopropyl(methyl)amino)-1-(2-((4-(4-phenoxyphenoxy)-1H-pyrazolo[3,4-b]pyridin-3-ylamino)methyl)pyrrolidin-1-yl)but-2-en-1-one (504)

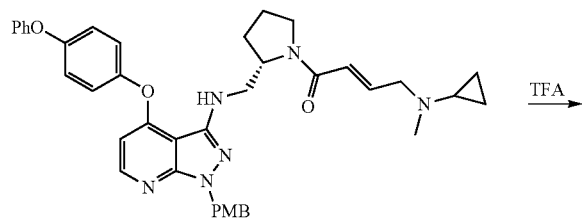

504-3

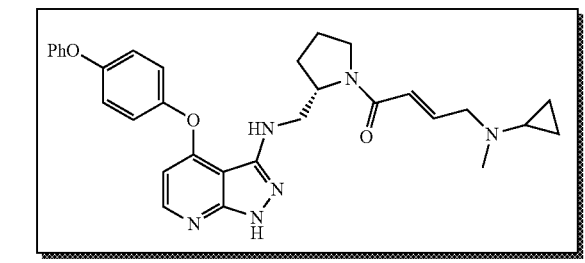

504

(S,E)-4-(Cyclopropyl(methyl)amino)-1-(2-((4-(4-phenoxyphenoxy)-1H-pyrazolo[3,4-b]pyridin-3-ylamino)methyl)pyrrolidin-1-yl)but-2-en-1-one (504) (24 mg, 43% yield) was obtained was a white powder from (S,E)-4-(cyclopropyl(methyl)amino)-1-(2-((1-(4-methoxybenzyl)-4-(4-phenoxyphenoxy)-1H-pyrazolo[3,4-b]pyridin-3-ylamino)methyl)pyrrolidin-1-yl)but-2-en-1-one (504-3) (66 mg, 0.10 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 539.3. ¹H NMR (400 MHz, DMSO) δ 12.25 (s, 1H), 8.13 (dd, J=11.4, 5.5 Hz, 1H), 7.42 (t, J=7.9 Hz, 2H), 7.31 (d, J=8.9 Hz, 2H), 7.15 (dt, J=14.7, 7.2 Hz, 3H), 7.06 (d, J=7.8 Hz, 2H), 6.85 (d, J=14.7 Hz, 1H), 6.70-6.60 (m, 1H), 6.58-6.27 (m, 1H), 6.05 (dd, J=12.3, 5.2 Hz, 2H), 4.47-4.36 (m, 1H), 3.59-3.28 (m, 3H), 3.24-3.07 (m, 3H), 2.16 (d, J=11.9 Hz, 3H), 2.07-1.98 (m, 1H), 1.96-1.82 (m, 3H), 1.70-1.58 (m, 1H), 0.43-0.32 (m, 2H), 0.30-0.22 (m, 2H).

Example 37

(S,E)-4-(cyclopropyl(methyl)amino)-1-(2-((4-(4-phenoxyphenoxy)-1H-pyrazolo[3,4-b]pyridin-3-ylamino)methyl)piperidin-1-yl)but-2-en-1-one
(Compound ID 37)

Preparation of (S)-tert-butyl 2-((1-(4-methoxybenzyl)-4-(4-phenoxyphenoxy)-1H-pyrazolo[3,4-b]pyridin-3-ylamino)methyl)piperidine-1-carboxylate (507-1)

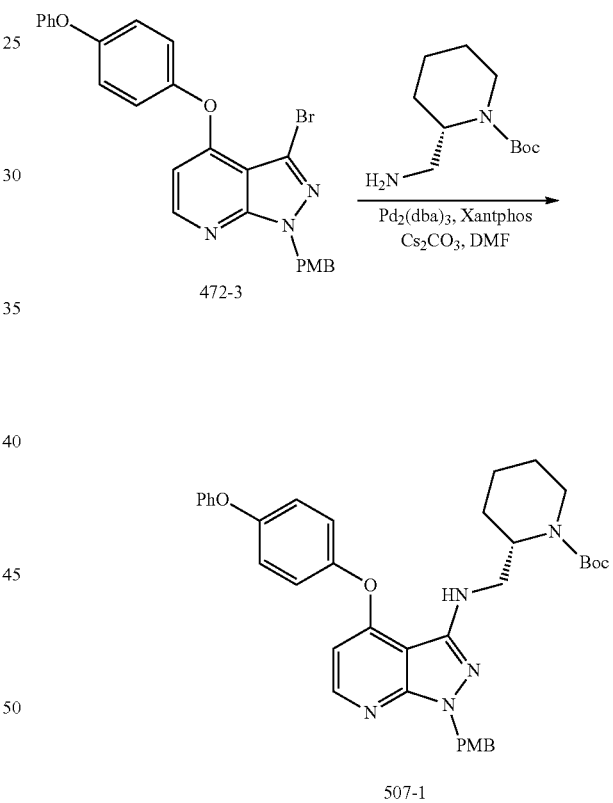

472-3

507-1

(S)-tert-Butyl 2-((1-(4-methoxybenzyl)-4-(4-phenoxyphenoxy)-1H-pyrazolo[3,4-b]pyridin-3-ylamino)methyl)piperidine-1-carboxylate (507-1) (158 mg, 50% yield) was obtained as a light yellow oil from 3-bromo-1-(4-methoxybenzyl)-4-(4-phenoxyphenoxy)-1H-pyrazolo[3,4-b]pyridine (472-3) (200 mg, 0.40 mmol) and (S)-tert-butyl 2-(aminomethyl)piperidine-1-carboxylate (256 mg, 1.20 mmol), following a similar procedure outlined in the preparation of (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1) (Ex. 1). LC-MS (ESI): m/z (M+1) 637.3.

207

Preparation of (S,E)-4-(cyclopropyl(methyl)amino)-1-(2-((1-(4-methoxybenzyl)-4-(4-phenoxyphenoxy)-1H-pyrazolo[3,4-b]pyridin-3-ylamino)methyl)piperidin-1-yl)but-2-en-1-one (507-3)

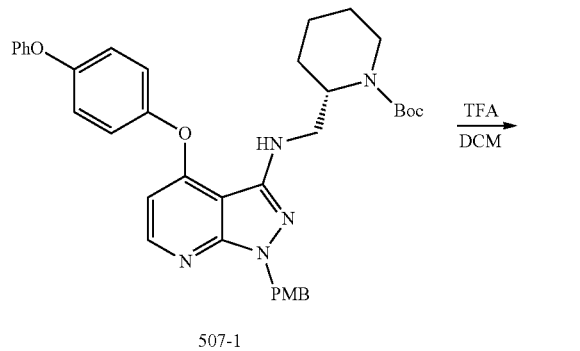

507-1

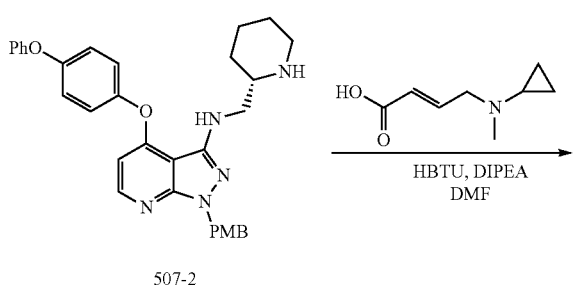

507-2

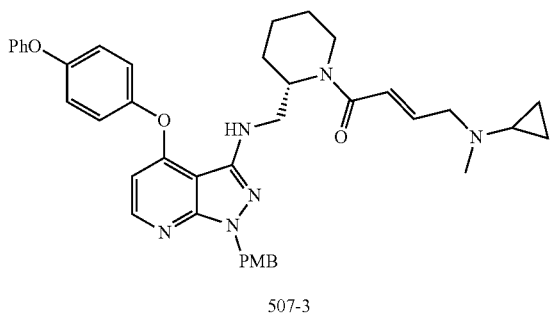

507-3

(S,E)-4-(Cyclopropyl(methyl)amino)-1-(2-((1-(4-methoxybenzyl)-4-(4-phenoxyphenoxy)-1H-pyrazolo[3,4-b]pyridin-3-ylamino)methyl)piperidin-1-yl)but-2-en-1-one (507-3) (59 mg, 62% yield) was obtained as a light yellow oil from (S)-tert-butyl 2-((1-(4-methoxybenzyl)-4-(4-phenoxyphenoxy)-1H-pyrazolo[3,4-b]pyridin-3-ylamino)methyl)piperidine-1-carboxylate (507-1) (90 mg, 0.14 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 673.2.

208

Preparation of (S,E)-4-(cyclopropyl(methyl)amino)-1-(2-((4-(4-phenoxyphenoxy)-1H-pyrazolo[3,4-b]pyridin-3-ylamino)methyl)piperidin-1-yl)but-2-en-1-one (507)

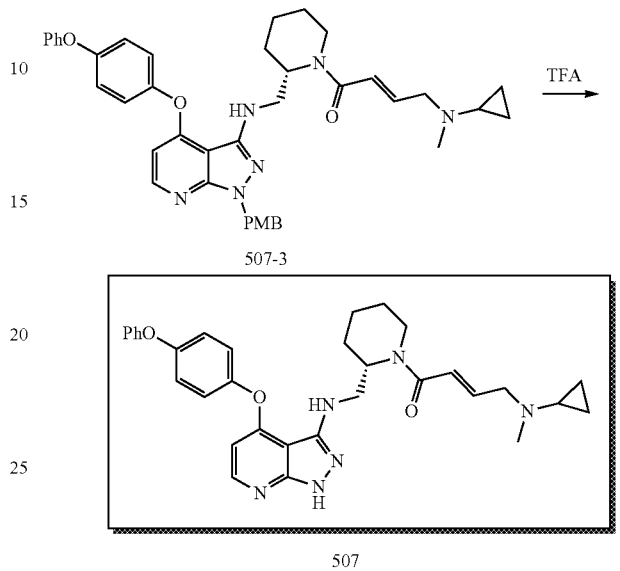

(S,E)-4-(Cyclopropyl(methyl)amino)-1-(2-((4-(4-phenoxyphenoxy)-1H-pyrazolo[3,4-b]pyridin-3-ylamino)methyl)piperidin-1-yl)but-2-en-1-one (507) (23 mg, 47% yield) was obtained was a white powder from (S,E)-4-(cyclopropyl(methyl)amino)-1-(2-((1-(4-methoxybenzyl)-4-(4-phenoxyphenoxy)-1H-pyrazolo[3,4-b]pyridin-3-ylamino)methyl)piperidin-1-yl)but-2-en-1-one (507-3) (59 mg, 0.09 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 553.0. $^1$H NMR (400 MHz, DMSO) δ 12.17 (s, 1H), 8.13 (d, J=5.4 Hz, 1H), 7.42 (t, J=7.7 Hz, 2H), 7.26 (d, J=8.1 Hz, 2H), 7.16 (t, J=7.5 Hz, 3H), 7.06 (d, J=8.1 Hz, 2H), 6.46-6.35 (m, 2H), 6.01 (d, J=5.1 Hz, 1H), 5.77 (t, J=6.4 Hz, 1H), 4.66-4.51 (m, 1H), 4.46-4.29 (m, 1H), 3.68-3.55 (m, 1H), 3.21-3.07 (m, 1H), 2.93-2.64 (m, 2H), 2.20-2.06 (m, 1H), 1.94 (s, 2H), 1.84-1.40 (m, 7H), 1.33-1.17 (m, 1H), 0.39-0.09 (m, 4H).

Example 38

(E)-4-(cyclopropyl(methyl)amino)-N-methyl-N-(3-(4-(4-phenoxyphenoxy)-1H-pyrazolo[3,4-b]pyridin-3-ylamino)phenyl)but-2-enamide (Compound ID 38)

Preparation of N-methyl-3-nitroaniline (505-2)

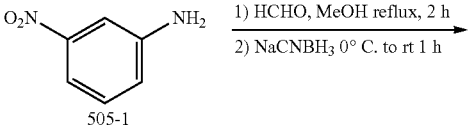

-continued

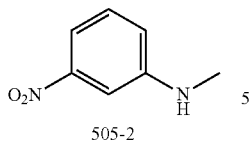
505-2

N-Methyl-3-nitroaniline (505-2) (210 mg, 19%) was obtained as a yellow solid from 3-nitroaniline (505-1) (1 g, 7.25 mmol), following a similar procedure outlined in Ex. 29. LC-MS (ESI): m/z (M+1) 153.3.

Preparation of (E)-4-(cyclopropyl(methyl)amino)-N-methyl-N-(3-nitrophenyl)but-2-enamide (505-3)

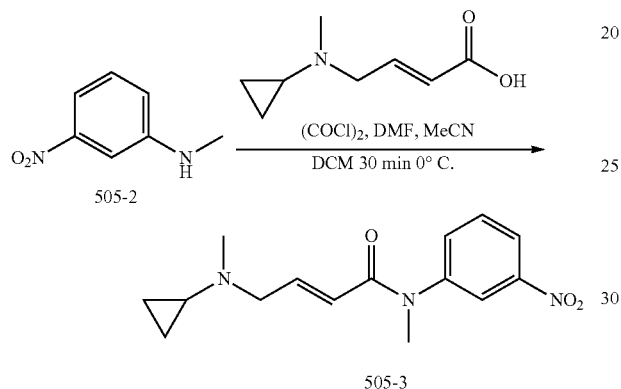

(E)-4-(Cyclopropyl(methyl)amino)-N-methyl-N-(3-nitrophenyl)but-2-enamide (505-3) (200 mg, 50%) was obtained as a white solid from N-methyl-3-nitroaniline (505-2) (210 mg, 1.38 mmol) and (E)-4-(cyclopropyl(methyl)amino)but-2-enoic acid hydrochloride (397 mg, 2.07 mmol), following a similar procedure outlined in Ex.1. LC-MS (ESI): m/z (M+1) 290.2.

Preparation of (E)-N-(3-aminophenyl)-4-(cyclopropyl(methyl)amino)-N-methylbut-2-enamide (505-4)

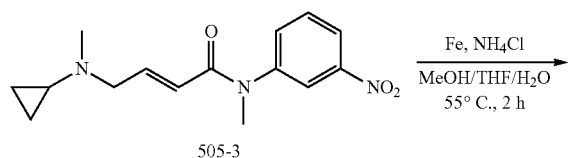

(E)-N-(3-Aminophenyl)-4-(cyclopropyl(methyl)amino)-N-methylbut-2-enamide (505-4) (500 mg, 93%) was obtained as a light yellow solid from (E)-4-(cyclopropyl(methyl)amino)-N-methyl-N-(3-nitrophenyl)but-2-enamide (505-3) (600 mg, 2.08 mmol), following a similar procedure outline in Ex. 28. LC-MS (ESI): m/z (M+1) 260.2.

Preparation of (E)-4-(cyclopropyl(methyl)amino)-N-(3-(1-(4-methoxybenzyl)-4-(4-phenoxyphenoxy)-1H-pyrazolo[3,4-b]pyridin-3-ylamino)phenyl)-N-methylbut-2-enamide (505-6)

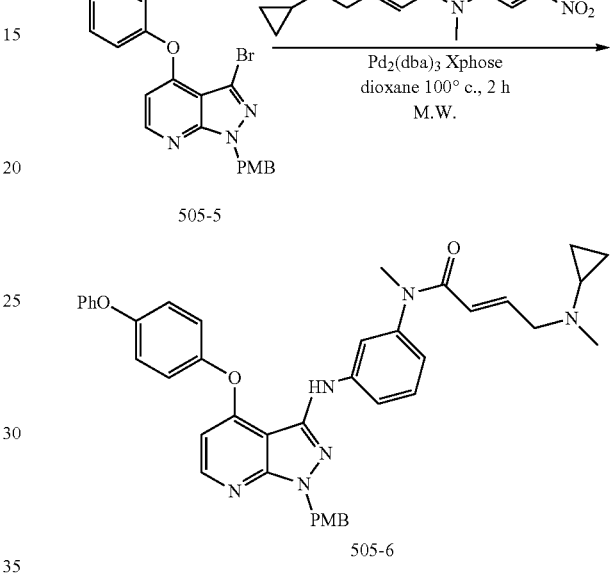

(E)-4-(Cyclopropyl(methyl)amino)-N-(3-(1-(4-methoxybenzyl)-4-(4-phenoxyphenoxy)-1H-pyrazolo[3,4-b]pyridin-3-ylamino)phenyl)-N-methylbut-2-enamide (505-6) (130 mg 52%) was obtained as a light yellow solid from 3-bromo-1-(4-methoxybenzyl)-4-(4-phenoxyphenoxy)-1H-pyrazolo[3,4-b]pyridine (505-5) (200 mg, 0.4 mmol) and (E)-N-(3-aminophenyl)-4-(cyclopropyl(methyl)amino)-N-methylbut-2-enamide (505-4) (206 mg, 0.8 mmol), following a similar procedure outlined in Ex. 29. LC-MS (ESI): m/z (M+1) 260.2.

Preparation of (E)-4-(cyclopropyl(methyl)amino)-N-methyl-N-(3-(4-(4-phenoxyphenoxy)-1H-pyrazolo[3,4-b]pyridin-3-ylamino)phenyl)but-2-enamide (505)

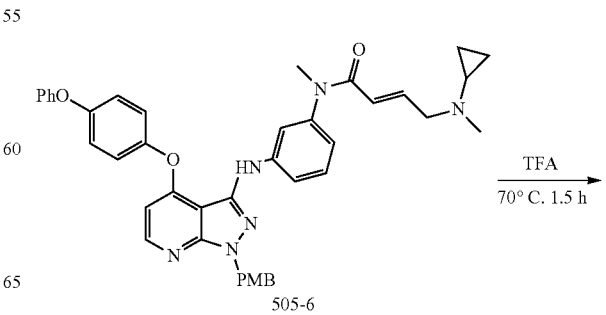

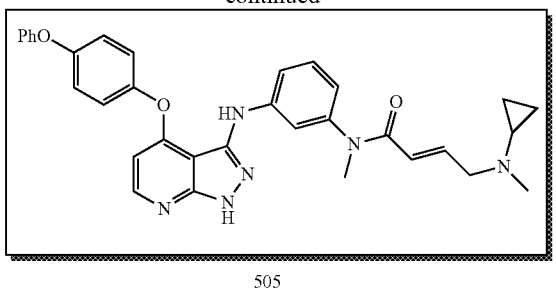

(E)-4-(Cyclopropyl(methyl)amino)-N-(3-(1-(4-methoxybenzyl)-4-(4-phenoxyphenoxy)-1H-pyrazolo[3,4-b]pyridin-3-ylamino)phenyl)-N-methylbut-2-enamide (505-6) (130 mg, 0.176 mmol) was treated with TFA at 70° C. for 1.5 hr to give (E)-4-(cyclopropyl(methyl)amino)-N-methyl-N-(3-(4-(4-phenoxyphenoxy)-1H-pyrazolo[3,4-b]pyridin-3-ylamino)phenyl)but-2-enamide (505) (29 mg, 30%) as a white solid. LC-MS (ESI): m/z (M+1) 561.2. 505 (-1)$^1$H NMR (400 MHz, DMSO) δ 12.81 (s, 1H), 8.42-8.12 (m, 2H), 7.63-7.55 (m, 2H), 7.42 (t, J=8.0 Hz, 2H), 7.35-7.24 (m, 3H), 7.17 (t, J=8.0 Hz, 3H), 7.06 (d, J=8.4 Hz, 2H), 6.75-6.55 (m, 2H), 6.19 (d, J=5.4 Hz, 1H), 5.95-5.80 (m, 1H), 3.22 (s, 3H), 3.05 (d, J=6.2 Hz, 2H), 2.09 (s, 3H), 1.63-1.49 (m, 1H), 0.35-0.24 (m, 2H), 0.21-0.09 (m, 2H).

Example 39

(R,E)-4-(Dimethylamino)-1-(3-(4-(4-phenoxyphenoxy)-1H-pyrazolo[3,4-d]pyrimidin-3-ylamino)pyrrolidin-1-yl)but-2-en-1-one (Compound ID 39)

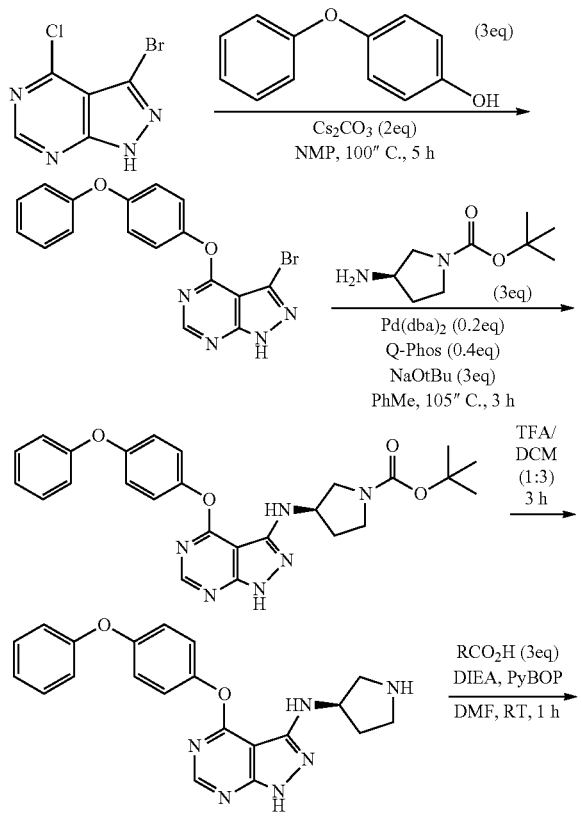

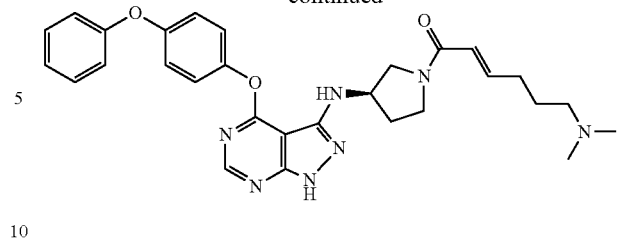

3-Bromo-4-chloro-1H-pyrazolo[3,4-d]pyrimidine (720 mg, 3.1 mmol) and 4-phenoxyphenol (1.73 g, 9.3 mmol) were dissolved in 20 mL NMP. To it was added powder cesium carbonate (2.02 g, 6.2 mmol). The mixture was then stirred at 100° C. for 5 h. It was diluted with ethyl acetate, washed with brine and 1N NaOH, dried, concentrated in vacuo, subjected to flash column with 0-40% ethyl acetate in DCM to isolate 3-bromo-4-(4-phenoxyphenoxy)-1H-pyrazolo[3,4-d]pyrimidine (0.97 g, 82%).

3-Bromo-4-(4-phenoxyphenoxy)-1H-pyrazolo[3,4-d]pyrimidine (150 mg, 0.39 mmol), (R)-tert-butyl 3-aminopyrrolidine-1-carboxylate (218 mg, 1.17 mmol), Q-Phos (1,2,3,4,5-Pentaphenyl-1'-(di-tert-butylphosphino)ferrocene, 114 mg, 0.16 mmol) and Pd(dba)$_2$ (46 mg, 0.08 mmol) were charged into a dry flask. To it were added anhydrous toluene (15 mL) and sodium tert-butoxide (2.0 M in THF, 0.59 mL, 1.17 mmol). The mixture was degassed with dry nitrogen stream for 3 min and sent to 105° C. bath under nitrogen atmosphere for 3 h. The mixture was cooled to RT, diluted with ethyl acetate (120 mL), washed with water and brine, dried, concentrated in vacuo, and subjected to flash column with 0-80% ethyl acetate in DCM to isolate (R)-tert-butyl 3-(4-(4-phenoxyphenoxy)-1H-pyrazolo[3,4-d]pyrimidin-3-ylamino)pyrrolidine-1-carboxylate (90 mg, 35%). It was treated with 3:1 DCM/TFA (9 mL+3 mL) at RT for 3 h. The mixture was concentrated in vacuo to dryness to afford the deprotected pyrrolidine. It was dissolved in DMF (4 mL). To the solution were added diisopropylethylamine (DIEA, 175 µL, 1.0 mmol), (E)-4-(dimethylamino)but-2-enoic acid hydrochloride (50 mg, 0.30 mmol) and PyBOP (156 mg, 0.30 mmol). The mixture was stirred for 3 h, acidified with TFA (0.2 mL), diluted with water, and subjected to reverse phase preparative HPLC to isolate (R,E)-4-(dimethylamino)-1-(3-(4-(4-phenoxyphenoxy)-1H-pyrazolo[3,4-d]pyrimidin-3-ylamino)pyrrolidin-1-yl)but-2-en-1-one as HCl salt (23 mg). LC-MS (ESI): m/z (M+1)$^+$ 500.1.

Example 40

(R,E)-1-(3-(4-(4-((1H-1,2,3-triazol-5-yl)methoxy)phenoxy)-1H-pyrazolo[3,4-b]pyridin-3-ylamino)pyrrolidin-1-yl)-4-(cyclopropyl(methyl)amino)but-2-en-1-one (Compound ID 40)

Preparation of (5-((4-methoxyphenoxy)methyl)-1H-1,2,3-triazol-1-yl)methylpivalate (421-1)

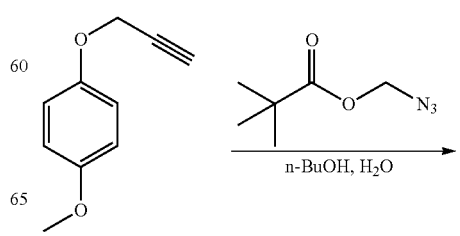

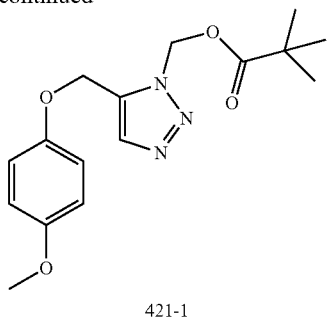

421-1

To a solution of 1-methoxy-4-(prop-2-ynyloxy)benzene (4.4 g, 25 mmol) in n-BuOH (40 mL) and H₂O (40 mL) was added azidomethyl pivalate (3.3 g, 25 mmol), CuSO₄ (813 mg, 5.1 mmol) and sodium ascorbate (1.0 g, 5.1 mmol). After stirred at 25° C. for 3 days, the reaction mixture was diluted with EA (100 mL) and H₂O (100 mL). The aq. phase was washed with EA (50 mL×2) and the combined organic phase was washed with brine, dried over Na₂SO₄, filtered and concentrated to give the crude product which was purified by flash chromatography (silica gel, 0 to 40% EA in PE) to afford (5-((4-methoxyphenoxy)methyl)-1H-1,2,3-triazol-1-yl)methyl pivalate (421-1) (2.2 g, 26% yield) as a colorless oil.

Preparation of (5-((4-hydroxyphenoxy)methyl)-1H-1,2,3-triazol-1-yl)methyl pivalate (421-2)

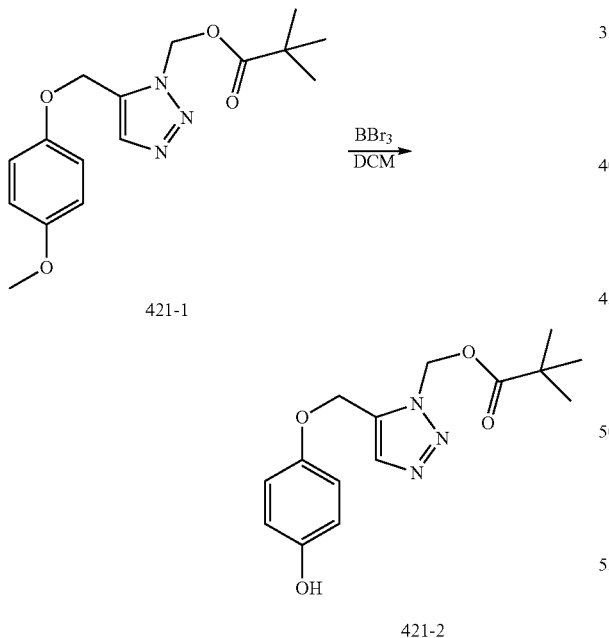

To a solution of (5-((4-methoxyphenoxy)methyl)-1H-1,2,3-triazol-1-yl)methyl pivalate (421-1) (3.0 g, 9.4 mmol) in anhydrous DCM (30 mL) was added BBr₃ (0.9 mL, 14.1 mmol) at 0° C. under N₂ atmosphere. After stirred at 0° C. for 2 hr, the resulting mixture was diluted with DCM (50 mL) and washed with H₂O, brine, dried over Na₂SO₄, and concentrated to give the crude product which was purified by flash chromatography (silica gel, 0 to 5% MeOH in DCM) to afford (5-((4-hydroxyphenoxy)methyl)-1H-1,2,3-triazol-1-yl)methyl pivalate (421-2) (1.5 g, 51% yield) as a white solid. LC-MS (ESI): m/z (M+1) 305.9.

Preparation of (5-((4-(3-iodo-1-(4-methoxybenzyl)-1H-pyrazolo[3,4-b]pyridin-4-yloxy)phenoxy)methyl)-1H-1,2,3-triazol-1-yl)methyl pivalate (421-3)

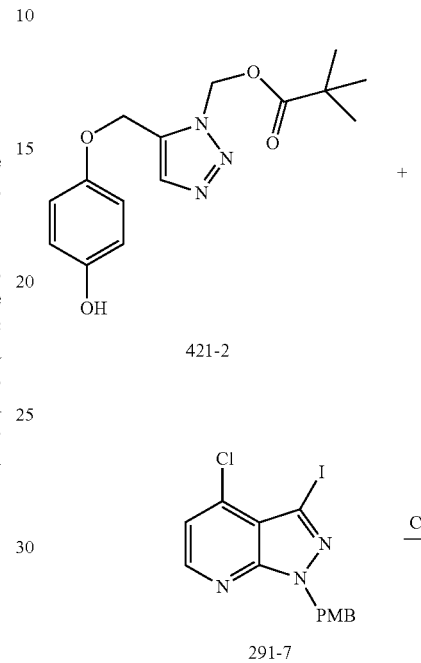

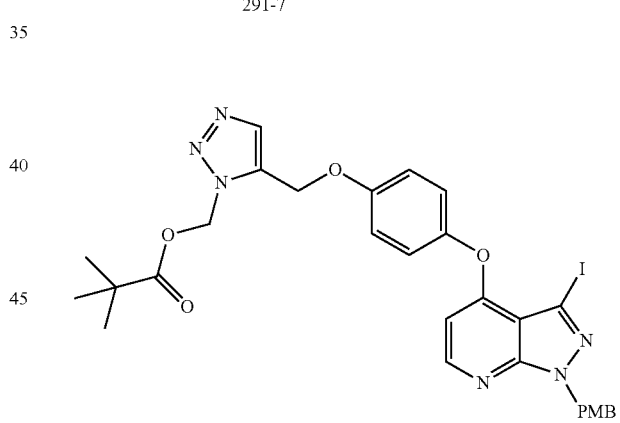

421-3

Under N₂ atmosphere, a mixture of (5-((4-hydroxyphenoxy)methyl)-1H-1,2,3-triazol-1-yl)methyl pivalate (421-2) (1.0 g, 3.4 mmol), 4-chloro-3-iodo-1-(4-methoxybenzyl)-1H-pyrazolo[3,4-b]pyridine (291-7) (900 mg, 2.3 mmol) and Cs2CO3 (2.2 g, 6.7 mmol) in DMF (20 mL) was stirred at 80° C. overnight. After cooled down to r.t., the resulting mixture was diluted with EA (100 mL) and H₂O (200 mL). The aq. phase was washed with EA (100 mL×2) and the combined organic phase was washed with brine, dried over Na₂SO₄, filtered and concentrated to give the crude product which was purified by flash chromatography (silica gel, 0 to 40% EA in PE) to afford (5-((4-(3-iodo-1-(4-methoxybenzyl)-1H-pyrazolo[3,4-b]pyridin-4-yloxy)phenoxy)methyl)-1H-1,2,3-triazol-1-yl)methyl pivalate (421-3) (125 mg, 8% yield) as a white solid. LC-MS (ESI): m/z (M+1) 668.9.

Preparation of (R)-tert-butyl 3-(1-(4-methoxybenzyl)-4-(4-((1-(pivaloyloxymethyl)-1H-1,2,3-triazol-5-yl)methoxy)phenoxy)-1H-pyrazolo[3,4-b]pyridin-3-ylamino)pyrrolidine-1-carboxylate (421-4)

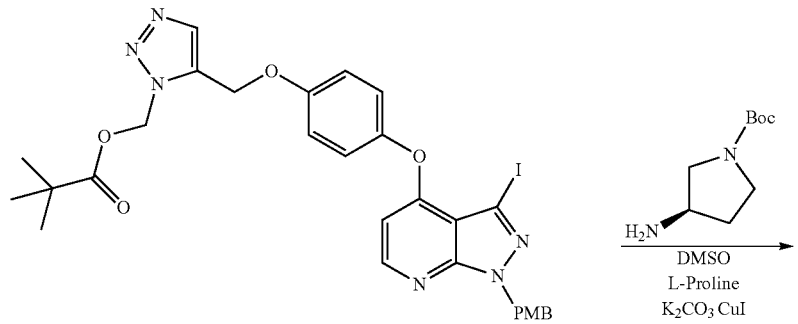

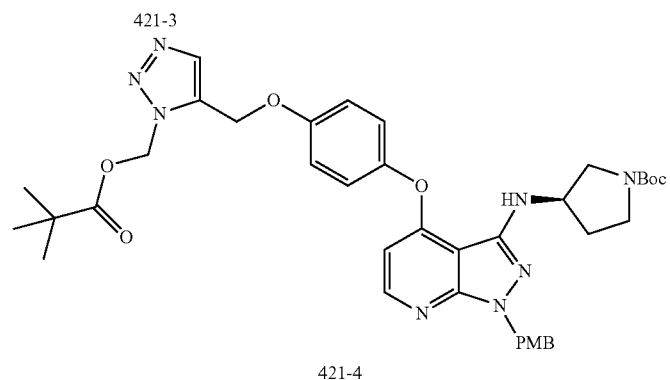

(R)-tert-Butyl 3-(1-(4-methoxybenzyl)-4-(4-((1-(pivaloyloxymethyl)-1H-1,2,3-triazol-5-yl)methoxy)phenoxy)-1H-pyrazolo[3,4-b]pyridin-3-ylamino)pyrrolidine-1-carboxylate (421-4) (65 mg, not pure, 60% yield) was obtained as a yellow oil from (5-((4-(3-iodo-1-(4-methoxybenzyl)-1H-pyrazolo[3,4-b]pyridin-4-yloxy)phenoxy)methyl)-1H-1,2,3-triazol-1-yl)methyl pivalate (421-3) (125 mg, 0.19 mmol), following a similar procedure outlined in the preparation of (R)-tert-butyl3-(4-(4-chlorophenoxy)-1-(4-methoxybenzyl)-1H-pyrazolo[3,4-b]pyridin-3-ylamino)pyrrolidine-1-carboxylate (291-9) (Ex. 1). LC-MS (ESI): m/z (M+1) 727.2.

Preparation of (R,E)-(5-((4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)phenoxy)methyl)-1H-1,2,3-triazol-1-yl)methyl pivalate (421-5)

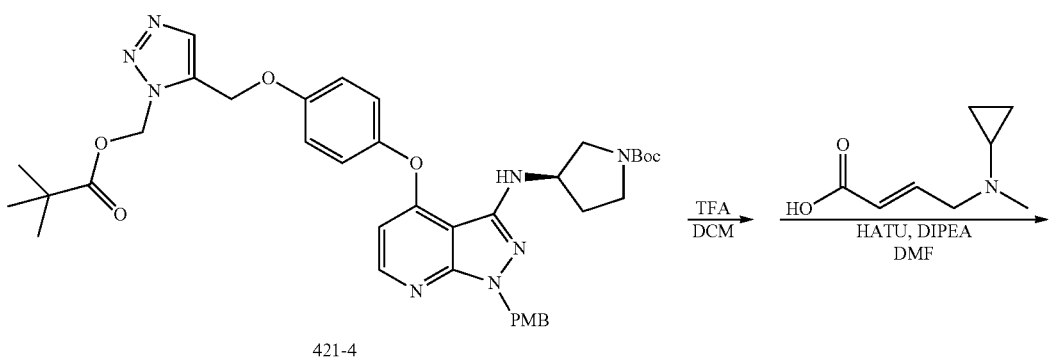

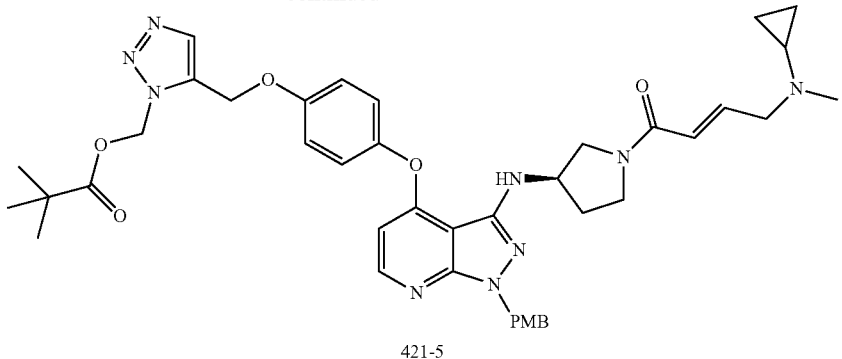

421-5

(R,E)-(5-((4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)phenoxy)methyl)-1H-1,2,3-triazol-1-yl)methyl pivalate (421-5) (14 mg, 34% yield) was obtained as a yellow oil from (R)-tert-butyl 3-(1-(4-methoxybenzyl)-4-(4-(((1-(pivaloyloxymethyl)-1H-1,2,3-triazol-5-yl)methoxy)phenoxy)-1H-pyrazolo[3,4-b]pyridin-3-ylamino)pyrrolidine-1-carboxylate (421-4) (65 mg, not pure, 0.02 mmol) and (E)-4-(dimethylamino)but-2-enoic acid (13 mg, 0.02 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 764.4.

Preparation of (R,E)-1-(3-(4-(4-((1H-1,2,3-triazol-5-yl)methoxy)phenoxy)-1H-pyrazolo[3,4-b]pyridin-3-ylamino)pyrrolidin-1-yl)-4-(cyclopropyl(methyl)amino)but-2-en-1-one (421)

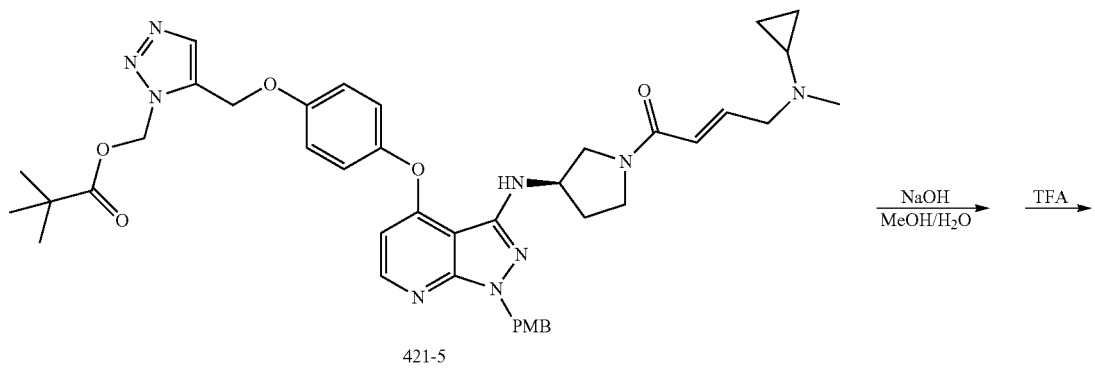

421-5

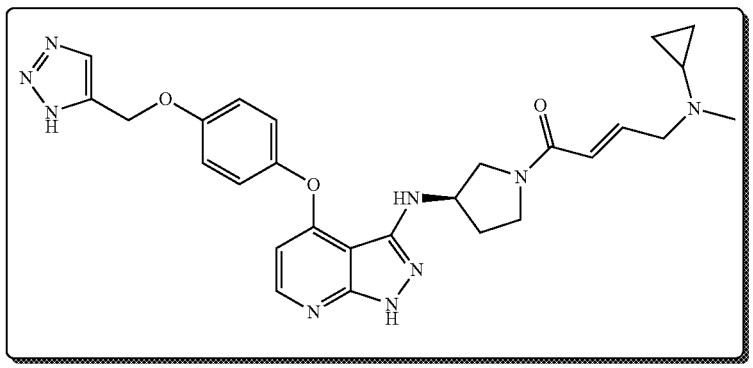

421

To a solution of (R,E)-(5-((4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)phenoxy)methyl)-1H-1,2,3-triazol-1-yl)methyl pivalate (421-5) (14 mg, 0.02 mmol) in MeOH (2.0 mL) was added 1M NaOH (2.0 mL). After stirred at r.t. for 0.5 hr, the resulting mixture was neutralized with 1M HCl and extracted with DCM (20 mL×2). The combined organic phase was washed with brine, dried over Na$_2$SO$_4$, filtered and concentrated to give the intermediate which was treated with TFA (10 mL) and heated up to 60° C. under N$_2$ atmosphere for 2 hr. After cooled down to r.t., the reaction mixture was concentrated under reduced pressure to give the crude product which was purified by prep. HPLC to afford (R,E)-1-(3-(4-(4-((1H-1,2,3-triazol-5-yl)methoxy)phenoxy)-1H-pyrazolo[3,4-b]pyridin-3-ylamino)pyrrolidin-1-yl)-4-(cyclopropyl(methyl)amino)but-2-en-1-one (421) (9 mg, 92% yield) as a white powder. LC-MS (ESI): m/z (M+1) 530.22. $^1$H NMR (400 MHz, DMSO) δ 12.23 (s, 1H), 8.28-8.22 (m, 1H), 8.11 (d, J=5.6 Hz, 1H), 8.00 (d, J=3.5 Hz, 1H), 7.22 (d, J=9.0 Hz, 2H), 7.15 (d, J=8.9 Hz, 2H), 6.68-6.59 (m, 1H), 6.33 (dd, J=21.9, 14.6 Hz, 1H), 5.94 (d, J=5.8 Hz, 1H), 5.59 (dd, J=25.2, 5.4 Hz, 1H), 5.22 (s, 2H), 4.38-3.54 (m, 6H), 3.26-3.23 (m, 2H), 2.21 (d, J=8.4 Hz, 3H), 2.11-1.96 (m, 1H), 1.75-1.62 (m, 1H), 0.46-0.37 (m, 2H), 0.36-0.24 (m, 2H).

Example 41

(R,E)-2-(3-(1-(4-(dimethylamino)but-2-enoyl)pyrrolidin-3-ylamino)-1H-pyrazolo[3,4-b]pyridin-4-yloxy)-5-phenoxybenzamide (Compound ID 41)

Preparation of (R)-2-(1-(4-methoxybenzyl)-3-(pyrrolidin-3-ylamino)-1H-pyrazolo[3,4-b]pyridin-4-yloxy)-5-phenoxybenzamide (463-1)

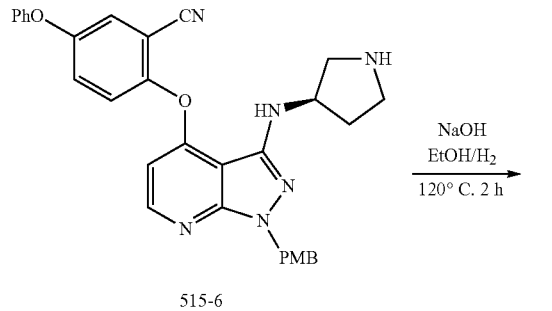

To a suspension of (R)-2-(1-(4-methoxybenzyl)-3-(pyrrolidin-3-ylamino)-1H-pyrazolo[3,4-b]pyridin-4-yloxy)-5-phenoxybenzonitrile (515-6) (200 mg, 0.37 mmol) in EtOH/H$_2$O (3 mL/3 mL) was added NaOH (148 mg, 3.7 mmol). The resulting mixture was stirred at 100° C. for 2 hrs. After the reaction was completed, the mixture was concentrated in vacuo. The residue was suspended in MeOH (10 mL) and filtered through a celite pad. The filtrate was concentrated in vacuo to give (R)-2-(1-(4-methoxybenzyl)-3-(pyrrolidin-3-ylamino)-1H-pyrazolo[3,4-b]pyridin-4-yloxy)-5-phenoxybenzamide (463-1) (200 mg, quant.) as yellow oil. LC-MS (ESI): m/z (M+1) 551.2.

Preparation of (R,E)-2-(3-(1-(4-(dimethylamino)but-2-enoyl)pyrrolidin-3-ylamino)-1-(4-methoxybenzyl)-1H-pyrazolo[3,4-b]pyridin-4-yloxy)-5-phenoxybenzamide (463-2)

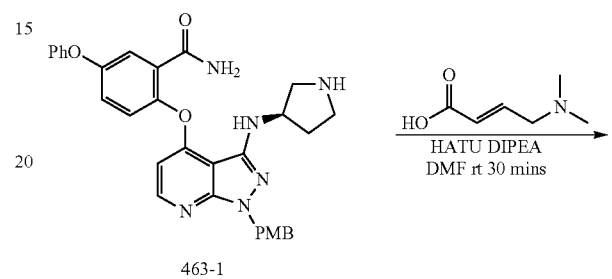

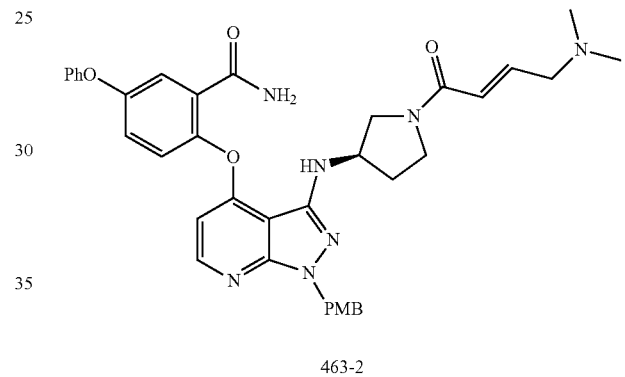

(R,E)-2-(3-(1-(4-(Dimethylamino)but-2-enoyl)pyrrolidin-3-ylamino)-1-(4-methoxybenzyl)-1H-pyrazolo[3,4-b]pyridin-4-yloxy)-5-phenoxybenzamide (463-2) (130 mg, 55%) was obtained as an oil from (R)-2-(1-(4-methoxybenzyl)-3-(pyrrolidin-3-ylamino)-1H-pyrazolo[3,4-b]pyridin-4-yloxy)-5-phenoxybenzamide (463-1) (200 mg, 0.36 mml) and (E)-4-(dimethylamino)but-2-enoic acid hydrochloride (83 mg, 0.5 mmol), following a similar procedure outlined in Ex. 8. LC-MS (ESI): m/z (M+1) 662.3.

Preparation of (R,E)-2-(3-(1-(4-(dimethylamino)but-2-enoyl)pyrrolidin-3-ylamino)-1H-pyrazolo[3,4-b]pyridin-4-yloxy)-5-phenoxybenzamide (463)

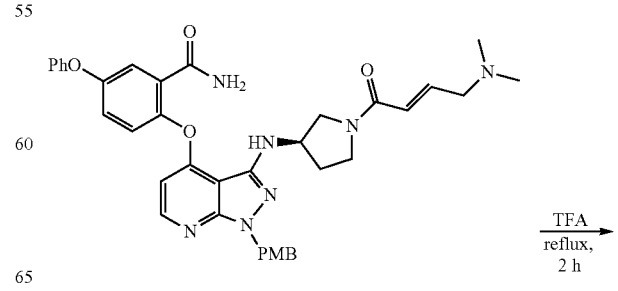

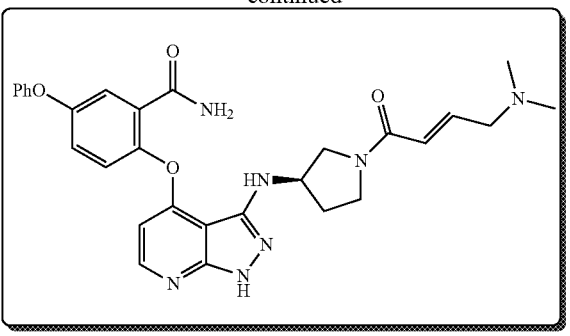

463

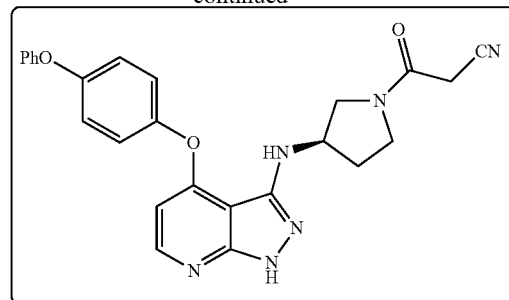

514

(R,E)-2-(3-(1-(4-(Dimethylamino)but-2-enoyl)pyrrolidin-3-ylamino)-1-(4-methoxybenzyl)-1H-pyrazolo[3,4-b]pyridin-4-yloxy)-5-phenoxybenzamide (463-2) (130 mg, 0.2 mmol) was treated with TFA at 70° C. for 2 hrs to give (R,E)-2-(3-(1-(4-(dimethylamino) but-2-enoyl)pyrrolidin-3-ylamino)-1H-pyrazolo[3,4-b]pyridin-4-yloxy)-5-phenoxybenzamide (463) (30 mg, 28%) as a white solid. LC-MS (ESI): m/z (M+1) 542.2. $^1$H NMR (400 MHz, DMSO) δ 12.13 (s, 1H), 8.17 (d, J=5.4 Hz, 1H), 8.14 (s, 1H), 7.87 (s, 1H), 7.44 (s, 1H), 7.33 (t, J=7.5 Hz, 2H), 7.06-6.97 (m, 2H), 6.91 (d, J=8.1 Hz, 2H), 6.76 (d, J=8.2 Hz, 1H), 6.68-6.40 (m, 4H), 4.35-4.22 (m, 1H), 3.97-3.89 (m, 1H), 3.71-3.65 (m, 2H), 3.55-3.49 (m, 1H), 3.43-3.37 (m, 2H), 2.42 (s, 3H), 2.40 (s, 3H), 2.37-2.11 (m, 2H).

Example 44

(R)-3-oxo-3-(3-(4-(4-phenoxyphenoxy)-1H-pyrazolo[3,4-b]pyridin-3-ylamino)pyrrolidin-1-yl)propanenitrile (Compound ID 44)

Preparation of (R)-3-oxo-3-(3-(4-(4-phenoxyphenoxy)-1H-pyrazolo[3,4-b]pyridin-3-ylamino)pyrrolidin-1-yl)propanenitrile (514)

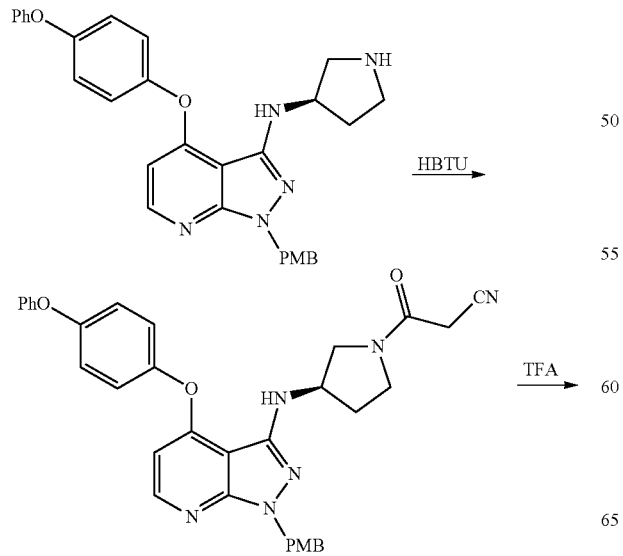

(R)-3-oxo-3-(3-(4-(4-Phenoxyphenoxy)-1H-pyrazolo[3,4-b]pyridin-3-ylamino)pyrrolidin-1-yl)propanenitrile (514) was obtained as a white solid, following a similar procedure outlined in Ex. 26. LC-MS (ESI): m/z (M+1) 455.0. $^1$H NMR (400 MHz, DMSO) δ 12.28 (s, 1H), 8.15 (s, 1H), 7.56-6.79 (m, 9H), 6.06 (s, 1H), 5.81-5.50 (m, 1H), 4.42-4.14 (m, 1H), 4.01-3.52 (m, 4H), 3.02-2.90 (m, 1H), 2.34-1.99 (m, 2H), 1.68-1.47 (m, 1H).

Example 45

(R)—N-(1-methylpyrrolidin-3-yl)-4-(4-phenoxyphenoxy)-1H-pyrazolo[3,4-b]pyridin-3-amine (Compound ID 45)

Preparation of (R)-tert-butyl 3-(1-(4-methoxybenzyl)-4-(4-phenoxyphenoxy)-1H-pyrazolo[3,4-b]pyridin-3-ylamino)pyrrolidine-1-carboxylate (516-1)

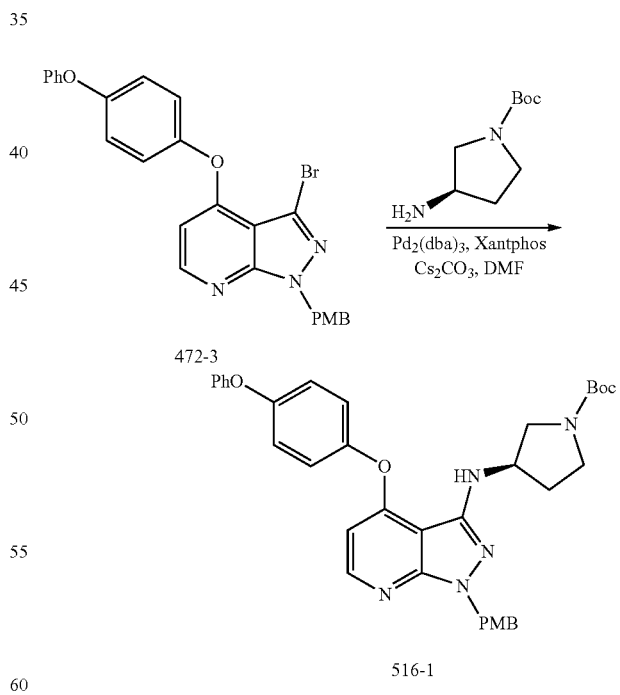

516-1

(R)-tert-Butyl 3-(1-(4-methoxybenzyl)-4-(4-phenoxyphenoxy)-1H-pyrazolo[3,4-b]pyridin-3-ylamino)pyrrolidine-1-carboxylate (516-1) (244 mg, 57% yield) was obtained as a light yellow solid from 3-bromo-1-(4-methoxybenzyl)-4-(4-phenoxyphenoxy)-1H-pyrazolo[3,4-b]pyridine (472-3) (300 mg, 0.6 mmol), following a similar procedure outlined in the preparation of (S)-tert-butyl 2-((1-(4-methoxybenzyl)-4-(4-phenoxy phenoxy)-1H-pyrazolo[3,4-b]pyridin-3-ylamino)methyl)pyrrolidine-1-carboxylate (504-1) (Ex. 1). LC-MS (ESI): m/z (M+1) 609.4.

Preparation of (R)-1-(4-methoxybenzyl)-4-(4-phenoxyphenoxy)-N-(pyrrolidin-3-yl)-1H-pyrazolo[3,4-b]pyridin-3-amine (516-2)

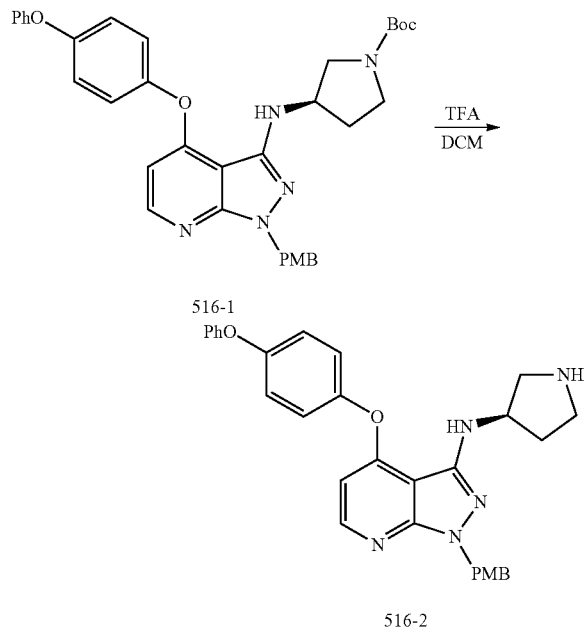

(R)-tert-Butyl 3-(1-(4-methoxybenzyl)-4-(4-phenoxyphenoxy)-1H-pyrazolo[3,4-b]pyridin-3-ylamino)pyrrolidine-1-carboxylate (516-1) (100 mg, 0.16 mmol) was treated with TFA (2 mL) in DCM (4 mL) and stirred at r.t. for 30 min. The resulting mixture was concentrated under reduced pressure to afford (R)-1-(4-methoxybenzyl)-4-(4-phenoxyphenoxy)-N-(pyrrolidin-3-yl)-1H-pyrazolo[3,4-b]pyridin-3-amine (516-2) (quant. yield) as a yellow oil which was directly used in next step.

Preparation of (R)-1-(4-methoxybenzyl)-N-(1-methylpyrrolidin-3-yl)-4-(4-phenoxyphenoxy)-1H-pyrazolo[3,4-b]pyridin-3-amine (516-3)

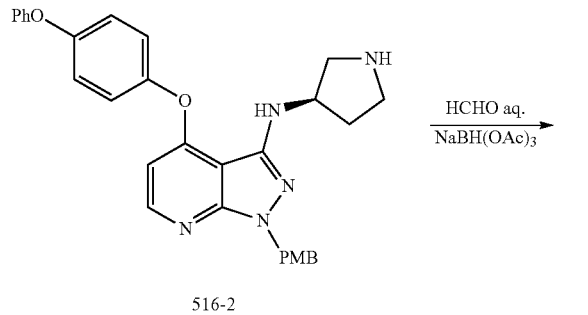

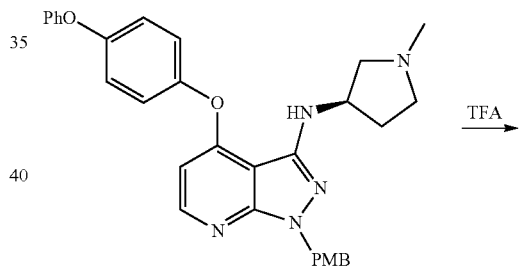

(R)-1-(4-Methoxybenzyl)-4-(4-phenoxyphenoxy)-N-(pyrrolidin-3-yl)-1H-pyrazolo[3,4-b]pyridin-3-amine (516-2) (90 mg, 0.16 mmol) in DCM (5 mL) were added aq. HCHO (0.12 mL) and NaBH(OAc)$_3$ (20 mg, 0.1 mmol). After stirred at r.t. overnight, the resulting mixture was filtered and the filtrate was concentrated under reduced pressure to give the crude product which was purified by flash chromatography (silica gel, 0 to 50% EA in PE) to give (R)-1-(4-methoxybenzyl)-N-(1-methylpyrrolidin-3-yl)-4-(4-phenoxyphenoxy)-1H-pyrazolo[3,4-b]pyridin-3-amine (516-3) (60 mg, 65% yield) as a colorless oil. LC-MS (ESI): m/z (M+1) 522.08.

Preparation of (R)—N-(1-methylpyrrolidin-3-yl)-4-(4-phenoxyphenoxy)-1H-pyrazolo[3,4-b]pyridin-3-amine (516)

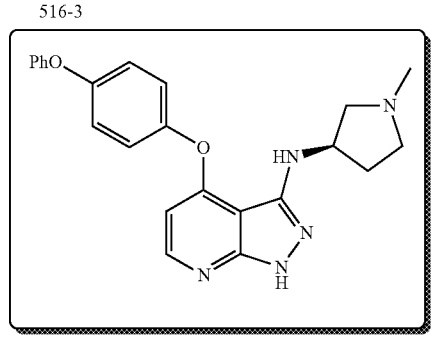

(R)—N-(1-Methylpyrrolidin-3-yl)-4-(4-phenoxyphenoxy)-1H-pyrazolo[3,4-b]pyridin-3-amine (516) (25 mg, 54% yield) was obtained as a white powder from (R)-1-(4-methoxybenzyl)-N-(1-methylpyrrolidin-3-yl)-4-(4-phenoxyphenoxy)-1H-pyrazolo[3,4-b]pyridin-3-amine (516-3) (60 mg, 0.12 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 402.1. $^1$H NMR (400 MHz, DMSO) δ 12.24 (s, 1H), 8.14 (d, J=5.4 Hz, 1H), 7.42 (t, J=7.7 Hz, 2H), 7.32 (d, J=8.8 Hz, 2H), 7.20-7.11 (m, 3H), 7.06 (d, J=8.4 Hz, 2H), 6.04 (d, J=5.4 Hz, 1H), 5.46 (d, J=7.1 Hz, 1H), 4.31-4.21 (m, 1H), 3.00-2.89 (m, 1H), 2.86-2.81 (m, 1H), 2.79-2.71 (m, 1H), 2.66-2.54 (m, 1H), 2.39 (s, 3H), 2.34-2.21 (m, 1H), 1.88-1.75 (m, 1H).

Example 46

(R)-1-(3-(4-(4-phenoxyphenoxy)-1H-pyrazolo[3,4-b]pyridin-3-ylamino)pyrrolidin-1-yl)ethanone (Compound ID 46)

Preparation of (R)-1-(3-(1-(4-methoxybenzyl)-4-(4-phenoxyphenoxy)-1H-pyrazolo[3,4-b]pyridin-3-ylamino)pyrrolidin-1-yl)ethanone (517-1)

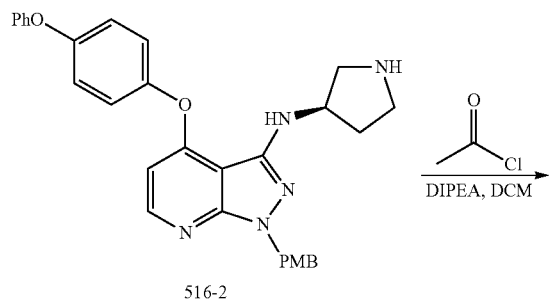

At 0° C., to a solution of (R)-1-(4-methoxybenzyl)-4-(4-phenoxyphenoxy)-N-(pyrrolidin-3-yl)-1H-pyrazolo[3,4-b]pyridin-3-amine (516-2) (90 mg, 0.16 mmol), DIPEA (0.07 mL, 0.90 mol) in DCM (5 mL) was added a solution of acetic chloride (13 mg, 0.16 mmol) in DCM (1 mL) dropwise. After stirred for 30 min, the reaction mixture was quenched with H$_2$O (10 mL) and extracted with DCM (3×20 mL). The combined organic phase was washed with brine, dried over Na$_2$SO$_4$, filtered and concentrated to afford (R)-1-(3-(1-(4-methoxybenzyl)-4-(4-phenoxyphenoxy)-1H-pyrazolo[3,4-b]pyridin-3-ylamino)pyrrolidin-1-yl)ethanone (517-1) (90 mg, 92% yield) as a light yellow oil. LC-MS (ESI): m/z (M+1) 551.1.

Preparation of (R)-1-(3-(4-(4-phenoxyphenoxy)-1H-pyrazolo[3,4-b]pyridin-3-ylamino)pyrrolidin-1-yl)ethanone (517)

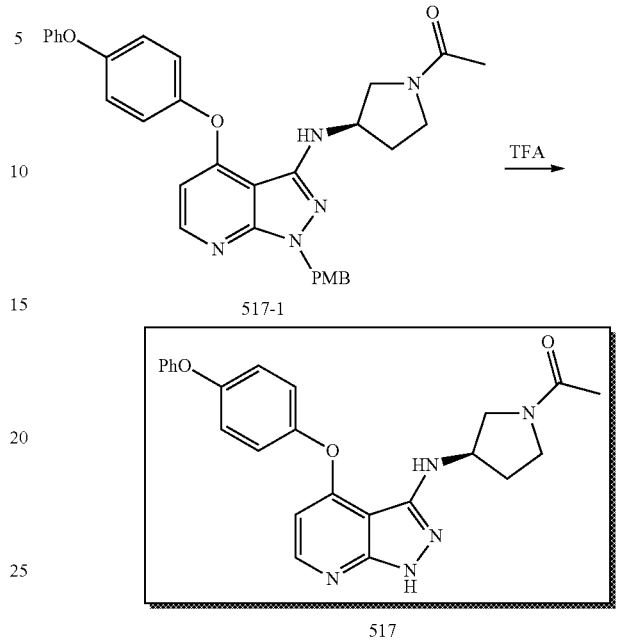

(R)-1-(3-(4-(4-Phenoxyphenoxy)-1H-pyrazolo[3,4-b]pyridin-3-ylamino)pyrrolidin-1-yl)ethanone (517) (45 mg, 64% yield) was obtained as a white powder from (R)-1-(3-(1-(4-methoxybenzyl)-4-(4-phenoxyphenoxy)-1H-pyrazolo[3,4-b]pyridin-3-ylamino)pyrrolidin-1-yl)ethanone (517-1) (90 mg, 0.16 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 431.0. $^1$H NMR (400 MHz, DMSO) δ 12.27 (s, 1H), 8.15 (d, J=5.4 Hz, 1H), 7.43 (t, J=7.9 Hz, 2H), 7.33 (d, J=9.0 Hz, 2H), 7.20-7.12 (m, 3H), 7.07 (d, J=8.0 Hz, 2H), 6.06 (dd, J=5.5, 1.6 Hz, 1H), 5.61 (dd, J=27.7, 5.8 Hz, 1H), 4.25 (ddd, J=17.5, 12.0, 6.0 Hz, 1H), 3.96-3.39 (m, 4H), 2.32-1.98 (m, 2H), 1.93 (d, J=7.8 Hz, 3H).

Example 47

4-(4-phenoxyphenoxy)-N-(tetrahydro-2H-pyran-4-yl)-1H-pyrazolo[3,4-b]pyridin-3-amine (Compound ID 47)

Preparation of 1-(4-methoxybenzyl)-4-(4-phenoxyphenoxy)-N-(tetrahydro-2H-pyran-4-yl)-1H-pyrazolo[3,4-b]pyridin-3-amine (518-1)

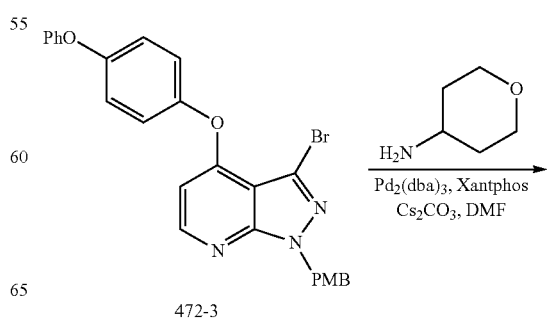

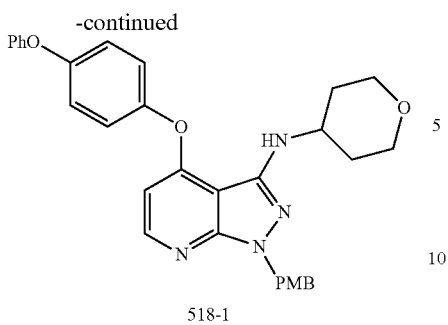

518-1

1-(4-Methoxybenzyl)-4-(4-phenoxyphenoxy)-N-(tetrahydro-2H-pyran-4-yl)-1H-pyrazolo[3,4-b]pyridin-3-amine (518-1) (120 mg, 58% yield) was obtained as a light yellow oil from 3-bromo-1-(4-methoxybenzyl)-4-(4-phenoxyphenoxy)-1H-pyrazolo[3,4-b]pyridine (472-3) (200 mg, 0.4 mmol), following a similar procedure outlined in the preparation of (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1) (Ex. 1). LC-MS (ESI): m/z (M+1) 524.3.

Preparation of 4-(4-phenoxyphenoxy)-N-(tetrahydro-2H-pyran-4-yl)-1H-pyrazolo[3,4-b]pyridin-3-amine (518)

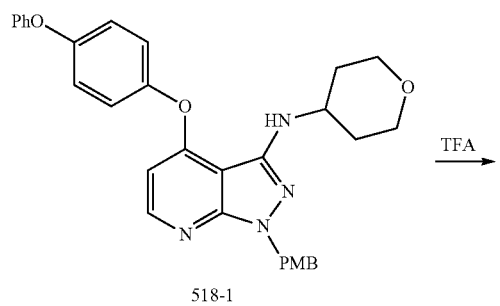

4-(Phenoxyphenoxy)-N-(tetrahydro-2H-pyran-4-yl)-1H-pyrazolo[3,4-b]pyridin-3-amine (518) (40 mg, 43% yield) was obtained as a white powder from 1-(4-methoxybenzyl)-4-(4-phenoxyphenoxy)-N-(tetrahydro-2H-pyran-4-yl)-1H-pyrazolo[3,4-b]pyridin-3-amine (518-1) (120 mg, 0.23 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 404.0. $^1$H NMR (400 MHz, DMSO) δ 12.16 (s, 1H), 8.14 (d, J=5.4 Hz, 1H), 7.43 (t, J=7.9 Hz, 2H), 7.36-7.30 (m, 2H), 7.20-7.12 (m, 3H), 7.07 (d, J=8.3 Hz, 2H), 6.05 (d, J=5.4 Hz, 1H), 5.19 (d, J=7.7 Hz, 1H), 3.88 (d, J=10.9 Hz, 2H), 3.83-3.69 (m, 1H), 3.48-3.29 (m, 2H), 2.07-1.92 (m, 2H), 1.65-1.48 (m, 2H).

Example 48

(R,E)-4-(Cyclopropyl(methyl)amino)-1-(3-(4-(4-phenoxyphenoxy)-1H-pyrazolo[3,4-d]pyrimidin-3-ylamino)pyrrolidin-1-yl)but-2-en-1-one (Compound ID 48)

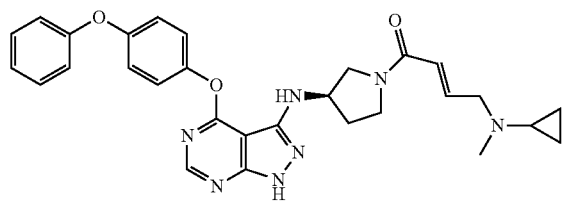 [SMILES: CN(C/C=C/C(=O)N1CC[C@@H](Nc2n[nH]c3ncnc(Oc4ccc(Oc5ccccc5)cc4)c23)C1)C1CC1]

Compound (R,E)-4-(cyclopropyl(methyl)amino)-1-(3-(4-(4-phenoxyphenoxy)-1H-pyrazolo[3,4-d]pyrimidin-3-ylamino)pyrrolidin-1-yl)but-2-en-1-one was prepared by the same scheme illustrated for Example 39. LC-MS (ESI): m/z (M+1)$^+$ 526.2.

Example 49

(E)-4-(Cyclopropyl(methyl)amino)-N—((R)-1-((E)-4-(cyclopropyl(methyl)amino)but-2-enoyl)pyrrolidin-3-yl)-N-(4-(4-phenoxyphenoxy)-1H-pyrazolo[3,4-d]pyrimidin-3-yl)but-2-enamide (Compound ID 49)

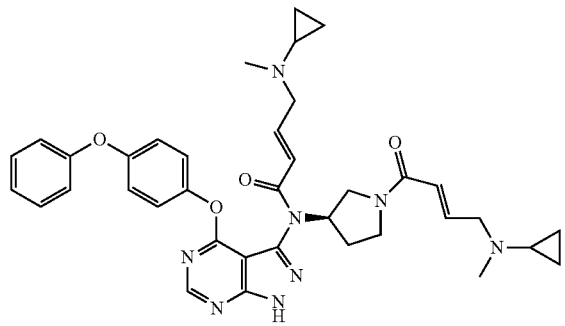 [SMILES: CN(C/C=C/C(=O)N1CC[C@@H](N(C(=N)c2c(N)ncnc2Oc2ccc(Oc3ccccc3)cc2)C(=O)/C=C/CN(C)C2CC2)C1)C1CC1]

Compound (E)-4-(cyclopropyl(methyl)amino)-N—((R)-1-((E)-4-(cyclopropyl(methyl)amino)but-2-enoyl)pyrrolidin-3-yl)-N-(4-(4-phenoxyphenoxy)-1H-pyrazolo[3,4-d]pyrimidin-3-yl)but-2-enamide was isolated as a by-product during the preparation of compound (R,E)-4-(cyclopropyl(methyl)amino)-1-(3-(4-(4-phenoxyphenoxy)-1H-pyrazolo[3,4-d]pyrimidin-3-ylamino)pyrrolidin-1-yl)but-2-en-1-one (Example 48) by the same scheme illustrated for Example 39. LC-MS (ESI): m/z (M+1)$^+$ 663.3.

Example 50

(R)-4-(4-Phenoxyphenoxy)-N-(piperidin-3-yl)-1H-pyrazolo[3,4-d]pyrimidin-3-amine (Compound ID 50)

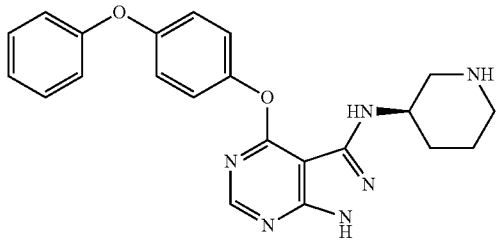 [SMILES: N=C(N[C@@H]1CCCNC1)c1c(N)ncnc1Oc1ccc(Oc2ccccc2)cc1]

Compound (R)-4-(4-phenoxyphenoxy)-N-(piperidin-3-yl)-1H-pyrazolo[3,4-d]pyrimidin-3-amine was prepared by the same scheme illustrated for Example 39. LC-MS (ESI): m/z (M+1)⁺ 403.1.

Example 51

(R)-1-(3-(4-(4-Phenoxyphenoxy)-1H-pyrazolo[3,4-d]pyrimidin-3-ylamino)piperidin-1-yl)propan-1-one (Compound ID 51)

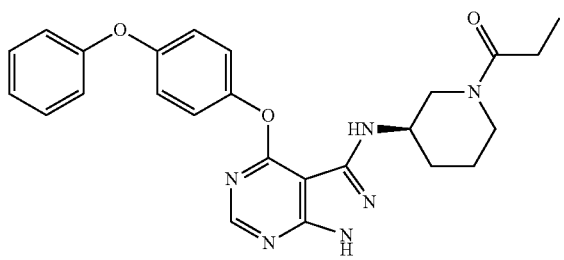 [SMILES: CCC(=O)N1CCC[C@@H](NC(=N)c2c(N)ncnc2Oc2ccc(Oc3ccccc3)cc2)C1]

Compound (R)-4-(4-phenoxyphenoxy)-N-(piperidin-3-yl)-1H-pyrazolo[3,4-d]pyrimidin-3-amine (65 mg, 0.16 mmol) was dissolved in 2 mL DMF. To it were added DIEA (85 µL, 0.48 mmol) and then propionyl chloride (21 µL, 0.24 mmol). The mixture was stirred at RT for 1 h, acidified with 0.2 mL TFA, subjected to reverse phase preparative HPLC to isolate (R)-1-(3-(4-(4-phenoxyphenoxy)-1H-pyrazolo[3,4-d]pyrimidin-3-ylamino)piperidin-1-yl)propan-1-one as HCl salt (27 mg). LC-MS (ESI): m/z (M+1)⁺ 459.1.

Example 52

(R)—N-(4-(4-Phenoxyphenoxy)-1H-pyrazolo[3,4-d]pyrimidin-3-yl)-N-(1-propionylpiperidin-3-yl)propionamide (Compound ID 52)

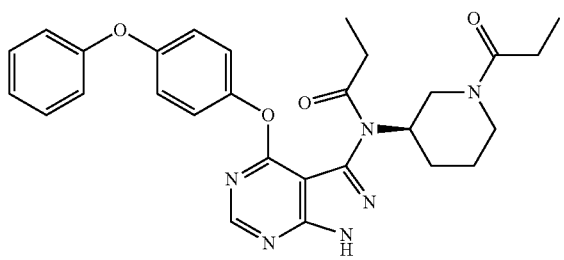 [SMILES: CCC(=O)N1CCC[C@@H](N(C(=N)c2c(N)ncnc2Oc2ccc(Oc3ccccc3)cc2)C(=O)CC)C1]

Compound (R)—N-(4-(4-phenoxyphenoxy)-1H-pyrazolo[3,4-d]pyrimidin-3-yl)-N-(1-propionylpiperidin-3-yl)propionamide was isolated as a by-product during the preparation of compound (R)-1-(3-(4-(4-phenoxyphenoxy)-1H-pyrazolo[3,4-d]pyrimidin-3-ylamino)piperidin-1-yl)propan-1-one (Example 51) by the same scheme illustrated for Example 39. LC-MS (ESI): m/z (M+1)⁺ 515.2.

Example 53

(R,E)-4-(Dimethylamino)-1-(3-(4-(4-phenoxyphenoxy)-1H-pyrazolo[3,4-d]pyrimidin-3-ylamino)piperidin-1-yl)but-2-en-1-one (Compound ID 53)

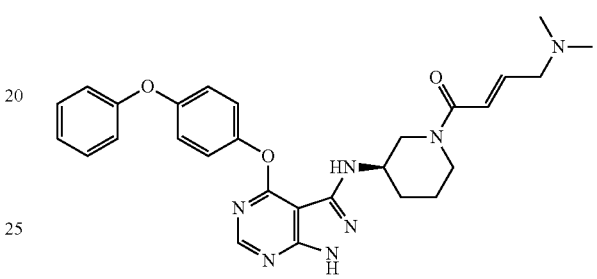

Compound (R,E)-4-(dimethylamino)-1-(3-(4-(4-phenoxyphenoxy)-1H-pyrazolo[3,4-d]pyrimidin-3-ylamino)piperidin-1-yl)but-2-en-1-one was prepared by the same scheme illustrated for Example 39. LC-MS (ESI): m/z (M+1)⁺ 514.1.

Example 54

(E)-4-(dimethylamino)-1-((3R)-3-(4-(2-hydroxy-3-phenoxypropoxy)-1H-pyrazolo[3,4-b]pyridin-3-ylamino)pyrrolidin-1-yl)but-2-en-1-one (Compound ID 54)

Preparation of 3-phenoxypropane-1,2-diol (453-1)

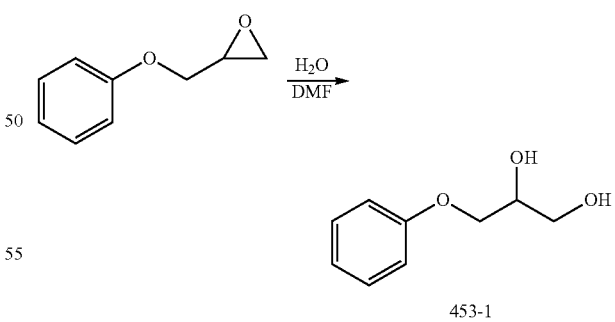

453-1

A solution of 2-(phenoxymethyl)oxirane (5.0 g, 33 mmol) in H₂O (0.6 mL) and DMF (0.3 mL) was heated at 110° C. overnight. After cooled down to r.t., the reaction mixture was diluted with EA (100 mL), dried over Na₂SO₄, filtered and concentrated to give 3-phenoxypropane-1,2-diol (453-1) (5.2 g, 93% yield) as a yellow oil which was directly used in the next step without purification. LC-MS (ESI): m/z (M+1) 169.1.

Preparation of 1-(tert-butyldimethylsilyloxy)-3-phenoxypropan-2-ol (453-2)

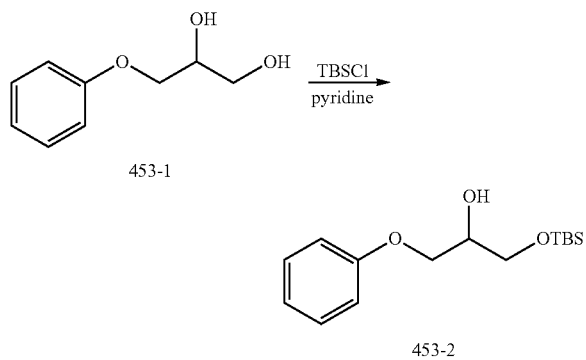

At 0° C., to a solution of 3-phenoxypropane-1,2-diol (453-1) (910 mg, 5.4 mmol) in pyridine (3.0 mL) was added TBSCl (896 mg, 5.9 mmol). After stirred at r.t. for 2 hr, the reaction mixture was concentrated under reduced pressure and co-evaporated with toluene. The residue was diluted with EA (50 mL) and washed with $H_2O$, brine, dried over $Na_2SO_4$, and concentrated to give the crude product which was purified by flash chromatography (silica gel, 0 to 20% EA in PE) to afford 1-(tert-butyldimethylsilyloxy)-3-phenoxypropan-2-ol (453-2) (760 mg, 51% yield) as a colorless oil. LC-MS (ESI): m/z (M+1) 282.5.

Preparation of 1-(tert-butyldimethylsilyloxy)-3-phenoxypropan-2-yl acetate (453-3)

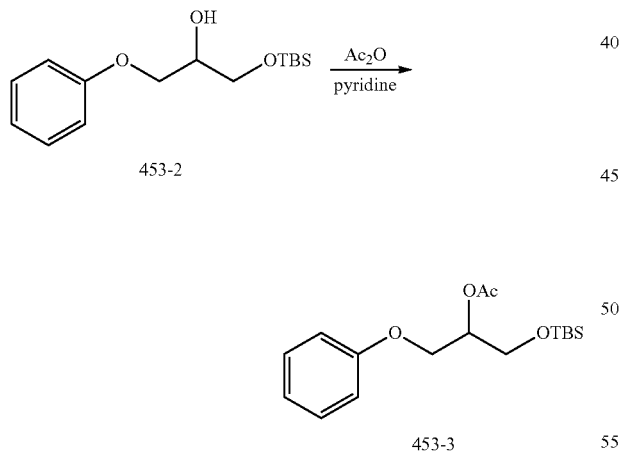

To a solution of 1-(tert-butyldimethylsilyloxy)-3-phenoxypropan-2-ol (453-2) (100 mg, 0.35 mmol) in pyridine (4.0 mL) was added $Ac_2O$ (0.5 mL). After stirred at r.t. overnight, the reaction mixture was quenched with sat. $NH_4Cl$ aq. and extracted with EA (20 mL×2). The combined organic phase was washed with brine, dried over $Na_2SO_4$, filtered and concentrated to afford 1-(tert-butyldimethylsilyloxy)-3-phenoxy propan-2-yl acetate (453-3) (208 mg, 90% yield) as a colorless oil which was directly used in the next step without purification.

Preparation of 1-hydroxy-3-phenoxypropan-2-yl acetate (453-4)

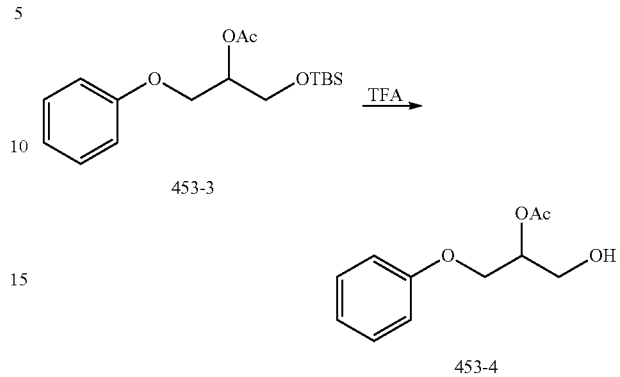

A solution of 1-(tert-butyldimethylsilyloxy)-3-phenoxy propan-2-yl acetate (453-3) (208 mg, 0.64 mmol) in TFA (7 mL) and $H_2O$ (7 mL) was stirred at r.t. for 3 hr. The reaction mixture was concentrated and purified by flash chromatography (silica gel, 0-50% EA in PE) to afford 1-hydroxy-3-phenoxypropan-2-yl acetate (453-4) (56 mg, 41% yield) as a colorless oil. LC-MS (ESI): m/z (M+1)=210.9.

Preparation of 1-(3-iodo-1-(4-methoxybenzyl)-1H-pyrazolo[3,4-b]pyridin-4-yloxy)-3-phenoxypropan-2-ol (453-5)

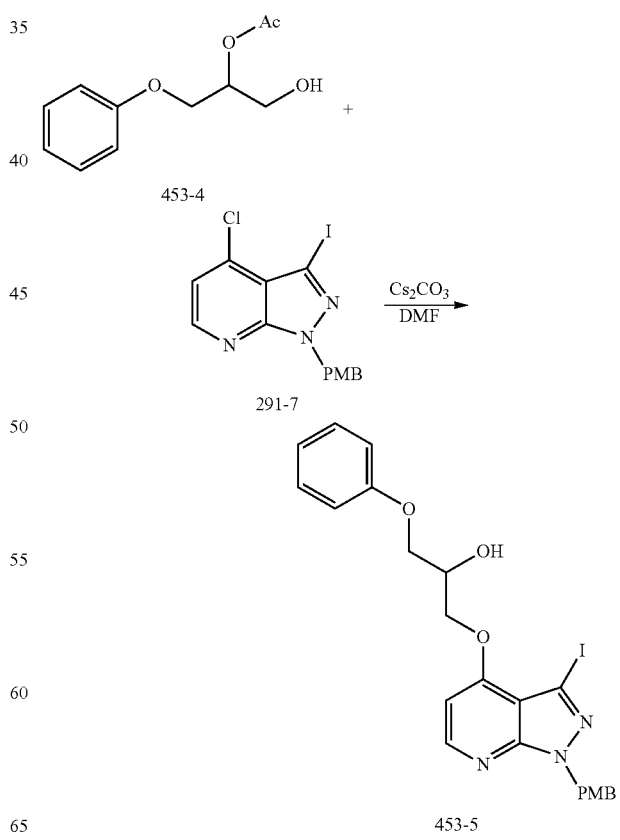

At 85° C., a mixture of 1-hydroxy-3-phenoxypropan-2-yl acetate (453-4) (20 mg, 0.09 mmol), 4-chloro-3-iodo-1-(4-methoxybenzyl)-1H-pyrazolo[3,4-b]pyridine (291-7) (25 mg, 0.06 mmol) and $Cs_2CO_3$ (203 mg, 0.6 mmol) in DMF (2.0 mL) was stirred under $N_2$ atmosphere for 1.5 hr. After cooled down to r.t., the reaction mixture was quenched with $H_2O$ (50 mL) and extracted with EA (50 mL×2). The combined organic phase was wash with brine, dried over $Na_2SO_4$, filtered and concentrated to give the crude product which was purified by flash chromatography (silica gel, 0 to 50% EA in PE) to afford 1-(3-iodo-1-(4-methoxybenzyl)-1H-pyrazolo[3,4-b]pyridin-4-yloxy)-3-phenoxypropan-2-ol (453-5) (14 mg, 42% yield) as a colorless oil. LC-MS (ESI): m/z (M+1) 532.2.

Preparation of (3R)-tert-butyl 3-(4-(2-hydroxy-3-phenoxypropoxy)-1-(4-methoxybenzyl)-1H-pyrazolo[3,4-b]pyridin-3-ylamino)pyrrolidine-1-carboxylate (453-6)

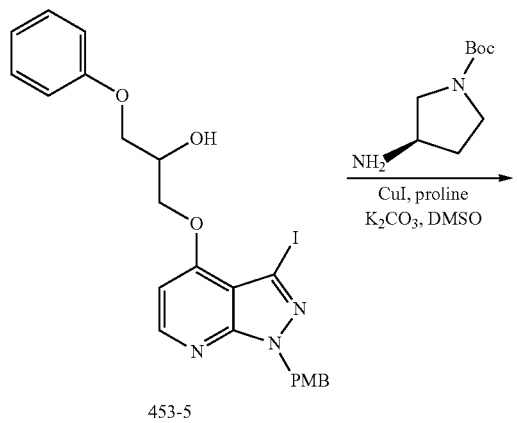

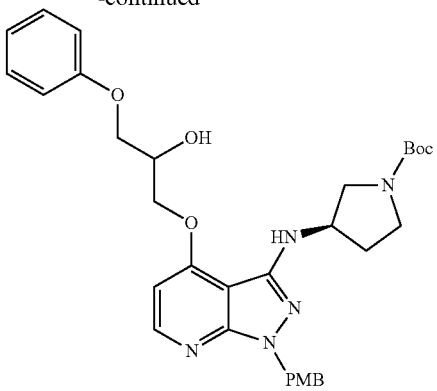

(3R)-tert-Butyl 3-(4-(2-hydroxy-3-phenoxypropoxy)-1-(4-methoxybenzyl)-1H-pyrazolo[3,4-b]pyridin-3-ylamino)pyrrolidine-1-carboxylate (453-6) (122 mg, 55% yield) was obtained as a yellow oil from 1-(3-iodo-1-(4-methoxybenzyl)-1H-pyrazolo[3,4-b]pyridin-4-yloxy)-3-phenoxypropan-2-ol (453-5) (200 mg, 0.38 mmol), following a similar procedure outlined in the preparation of (R)-tert-butyl3-(4-(4-chlorophenoxy)-1-(4-methoxybenzyl)-1H-pyrazolo[3,4-b]pyridin-3-ylamino)pyrrolidine-1-carboxylate (291-9) (Ex. 1). LC-MS (ESI): m/z (M+1) 591.3.

Preparation of (E)-4-(dimethylamino)-1-((3R)-3-(4-(2-hydroxy-3-phenoxy propoxy)-1H-pyrazolo[3,4-b]pyridin-3-ylamino)pyrrolidin-1-yl)but-2-en-1-one (453)

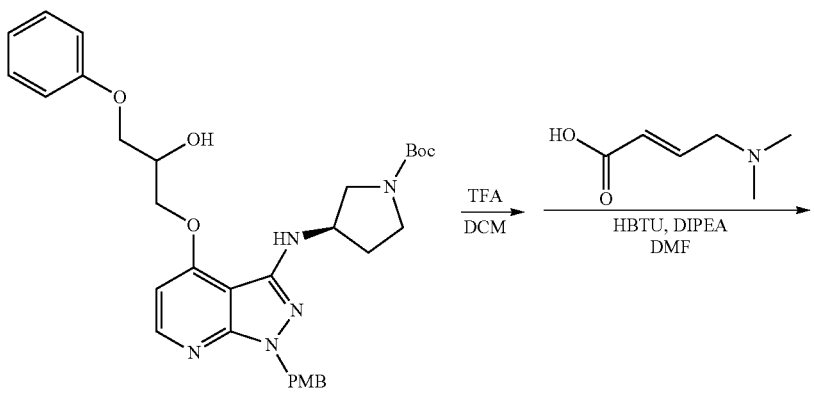

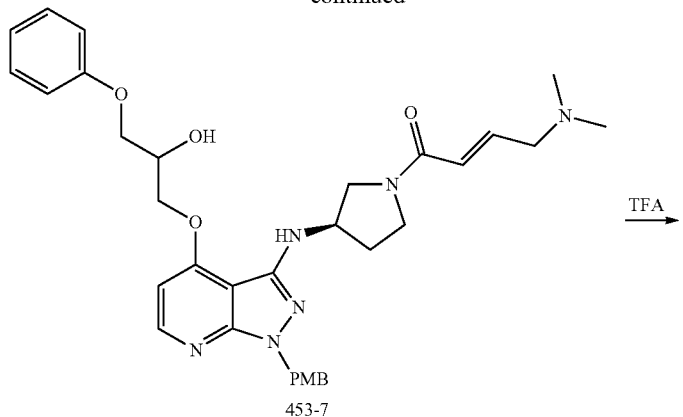

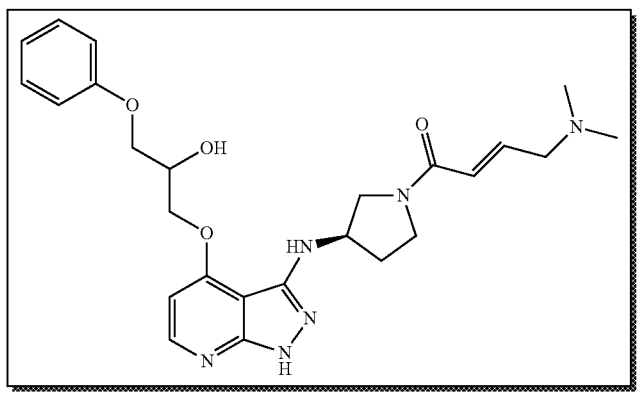

(E)-4-(Dimethylamino)-1-((3R)-3-(4-(2-hydroxy-3-phenoxypropoxy)-1H-pyrazolo[3,4-b]pyridin-3-ylamino)pyrrolidin-1-yl)but-2-en-1-one (453) (15 mg, 11% yield) was obtained as a white powder from (3R)-tert-butyl 3-(4-(2-hydroxy-3-phenoxypropoxy)-1-(4-methoxybenzyl)-1H-pyrazolo[3,4-b]pyridin-3-ylamino)pyrrolidine-1-carboxylate (453-6) (170 mg, 0.29 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1).

LC-MS (ESI): m/z (M+1) 601.1 for 453-7
LC-MS (ESI): m/z (M+1) 482.0 for 453
453 $^1$H NMR (400 MHz, DMSO) δ 12.10 (s, 1H), 8.19 (s, 1H), 7.28 (t, J=7.9 Hz, 2H), 7.03-6.85 (m, 3H), 6.68-6.57 (m, 1H), 6.55 (t, J=7.3 Hz, 1H), 6.43-6.29 (m, 1H), 5.23 (dd, J=16.3, 4.9 Hz, 1H), 4.41-3.38 (m, 10H), 3.12-3.04 (m, 2H), 2.37-2.22 (m, 1H), 2.20 (d, J=10.1 Hz, 6H), 2.04-1.84 (m, 1H).

Example 55

(R,E)-4-(3-(1-(4-(cyclopropyl(methy)amino)but-2-enoyl)pyrrolidin-3-ylamino)-1H-pyrazolo[3,4-b]pyridin-4-yloxy)-N-(pyridin-2-yl)benzamide (Compound ID 55)

Preparation of methyl 4-(3-iodo-1-(4-methoxybenzyl)-1H-pyrazolo[3,4-b]pyridin-4-yloxy)benzoate (499-1)

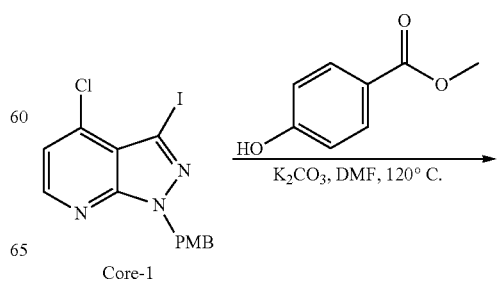

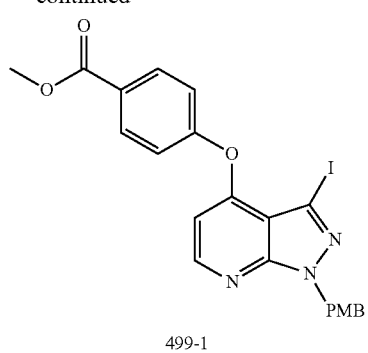

499-1

Methyl 4-(3-iodo-1-(4-methoxybenzyl)-1H-pyrazolo[3,4-b]pyridin-4-yloxy)benzoate (499-1) (3.8 g, 98%) was obtained as a white solid from 4-chloro-3-iodo-1-(4-methoxybenzyl)-1H-pyrazolo[3,4-b]pyridine (Core-1) (3 g, 7.5 mmol) and methyl 4-hydroxybenzoate (1.14 g, 7.5 mmol), following a similar procedure outline in Ex. 1. LC-MS (ESI): m/z (M+1) 516.0.

Preparation of (R)-tert-butyl 3-(1-(4-methoxybenzyl)-4-(4-(methoxycarbonyl)phenoxy)-1H-pyrazolo[3,4-b]pyridin-3-ylamino)pyrrolidine-1-carboxylate (499-2)

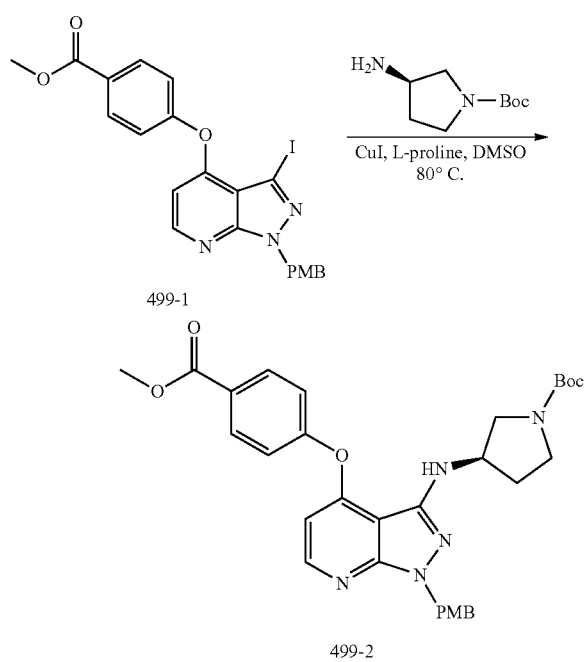

(R)-tert-Butyl 3-(1-(4-methoxybenzyl)-4-(4-(methoxycarbonyl)phenoxy)-1H-pyrazolo[3,4-b]pyridin-3-ylamino)pyrrolidine-1-carboxylate (499-2) was obtained as a light yellow solid from methyl 4-(3-iodo-1-(4-methoxybenzyl)-1H-pyrazolo[3,4-b]pyridin-4-yloxy)benzoate (499-1) (1 g, 1.94 mmol) and (R)-tert-butyl 3-aminopyrrolidine-1-carboxylate (1.8 g, 9.7 mmol), following a similar procedure outlined in Ex. 1. LC-MS (ESI): m/z (M+1) 574.2.

Preparation of (R)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (499-3)

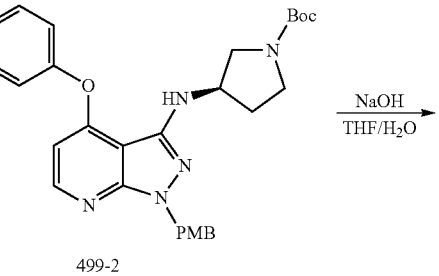

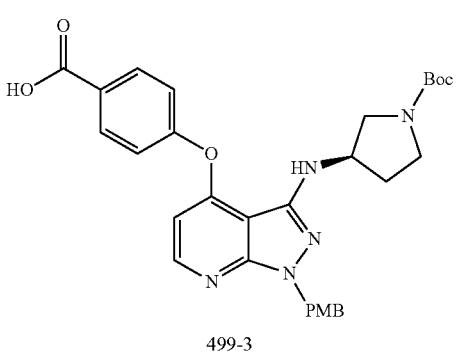

499-3

(R)-tert-Butyl 3-(1-(4-methoxybenzyl)-4-(4-(methoxycarbonyl)phenoxy)-1H-pyrazolo[3,4-b]pyridin-3-ylamino)pyrrolidine-1-carboxylate (499-2) (600 mg, 1.05 mmol) was treated with NaOH in THF and water to give (R)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (499-3) (550 mg, 94%). LC-MS (ESI): m/z (M+1) 560.2.

Preparation of (R)-tert-butyl 3-(1-(4-methoxybenzyl)-4-(4-(pyridin-2 ylcarbamoyl)phenoxy)-1H-pyrazolo[3,4-b]pyridin-3-ylamino)pyrrolidine-1-carboxylate (499-4)

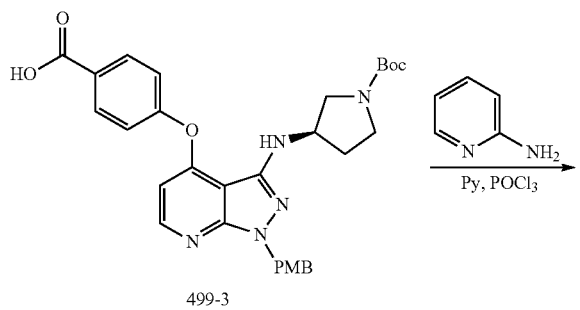

499-3

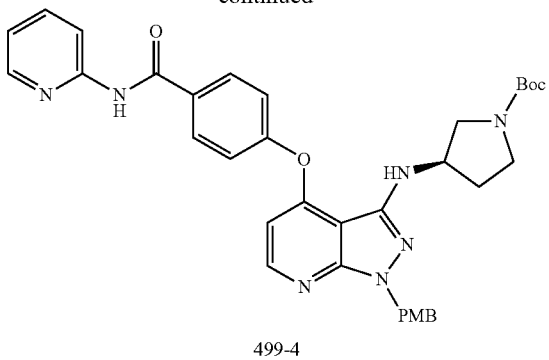

499-4

To a solution of (R)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (499-3) (100 g, 0.18 mmol) and pyridin-2-amine (51 mg, 0.54 mmol) in pyridine (1 mL) was added POCl$_3$ (414 mg, 2.7 mmol) dropwise. The resulting mixture was stirred at r.t. for 0.5 h. The reaction was quenched with ice water (2 mL). The mixture was extracted with EA (2 mL×3). Combine organic layers were washed with water, brine, dried over Na$_2$SO$_4$ and concentrated in vacuo to give (R)-tert-butyl 3-(1-(4-methoxybenzyl)-4-(4-(pyridin-2-ylcarbamoyl)phenoxy)-1H-pyrazolo[3,4-b]pyridin-3-ylamino)pyrrolidine-1-carboxylate (499-4) (100 mg, 88%). LC-MS (ESI): m/z (M+1) 636.2.

Preparation of (R,E)-4-(3-(1-(4-(cyclopropyl(methyl)amino)but-2-enoyl)pyrrolidin-3-ylamino)-1H-pyrazolo[3,4-b]pyridin-4-yloxy)-N-(pyridin-2-yl)benzamide (499)

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(pyridin-2-yl)benzamide (499) (32 mg, 24%) was obtained as a white solid from (R)-tert-butyl 3-(1-(4-methoxybenzyl)-4-(4-(pyridin-2-ylcarbamoyl)phenoxy)-1H-pyrazolo[3,4-b]pyridin-3-ylamino)pyrrolidine-1-carboxylate (499-4) (150 mg, 0.24 mmol), following a similar procedure outlined in Ex. 1. LC-MS (ESI): m/z (M+1) 553.2. $^1$H NMR (400 MHz, DMSO) δ 12.34 (s, 1H), 10.87 (s, 1H), 8.49-8.29 (m, 2H), 8.19 (dd, J=12.3, 6.8 Hz, 4H), 7.86 (t, J=7.5 Hz, 1H), 7.39 (dd, J=8.6, 2.6 Hz, 2H), 7.23-7.14 (m, 1H), 6.62 (s, 1H), 6.32 (t, J=14.4 Hz, 1H), 6.15 (t, J=5.7 Hz, 1H), 5.62 (dd, J=32.9, 5.6 Hz, 1H), 4.35-3.44 (m, 4H), 3.23 (d, J=6.5 Hz, 2H), 2.34-2.22 (m, 1H), 2.21 (d, J=3.3 Hz, 3H), 2.14-1.93 (m, 1H), 1.73-1.59 (m, 1H), 0.46-0.35 (m, 2H), 0.33-0.23 (m, 2H).

Example 56

(R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-propylpyridin-2-yl)benzamide (Compound ID 56)

Preparation of 4-propylpyridine 1-oxide (501-1)

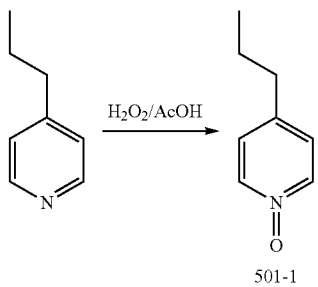

501-1

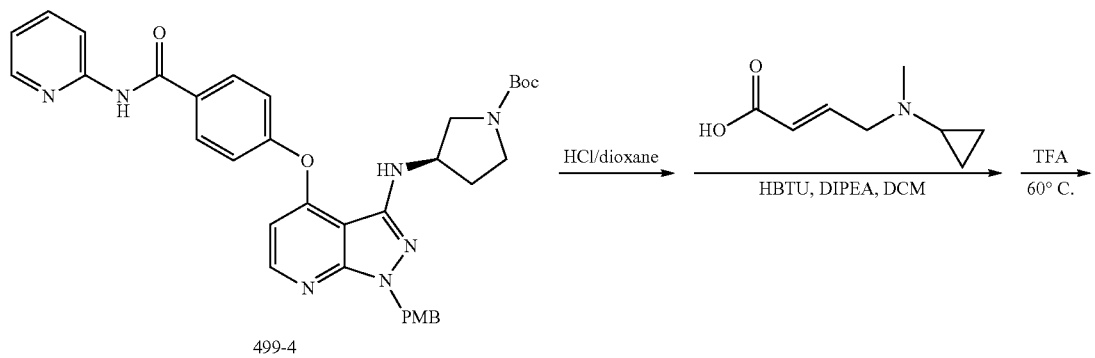

499-4

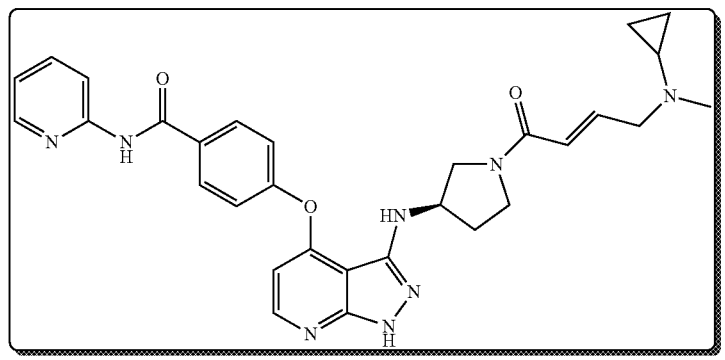

499

To a solution of 4-propylpyridine (1.21 g, 10 mmol) in AcOH (10 mL) was added $H_2O_2$ (0.97 mL, 10 mmol). The resulting mixture was stirred at 60° C. for 48 hrs under $N_2$ atmosphere before quenched with aq. $Na_2SO_3$ and neutralized with sat. $NaHCO_3$. The mixture was extracted with EA (30 mL×3). The combined organic phase was dried over $Na_2SO_4$, filtered and concentrated. The residue was purified by flash chromatography (silica gel, 0 to 50% EA in PE) to provide 4-propylpyridine 1-oxide (501-1) (1.4 g, 100%) as a yellow oil. LC-MS (ESI): m/z (M+1) 138.1.

Preparation of 2-chloro-4-propylpyridine (501-2)

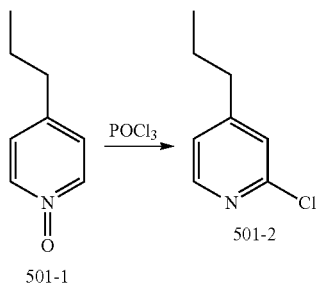

A solution of 4-propylpyridine 1-oxide (510-1) (1.4 g, 10 mmol) in $POCl_3$ (60 mL) was heated to 100° C. under $N_2$ atmosphere overnight. Excess $POCl_3$ was removed under vacuum and the residue was quenched with sat. $NaHCO_3$. The resulting mixture was extracted with EA (30 mL×3). The combined organic phases was dried over $Na_2SO_4$, filtered and concentrated. The residue was purified by flash chromatography (silica gel, 0 to 50% EA in PE) to provide 2-chloro-4-propylpyridine (501-2) (750 mg, 48%) as a yellow oil. LC-MS (ESI): m/z (M/M+2) 156.1/158.1

Preparation of N-(4-methoxybenzyl)-4-propylpyridin-2-amine (501-3)

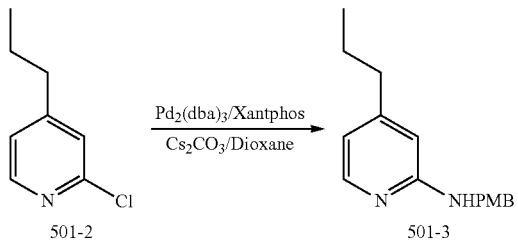

To a solution of 2-chloro-4-propylpyridine (510-2) (750 mg, 4.83 mmol) in dioxane (4 mL) was added $PMBNH_2$ (1.1 g, 8.0 mmol), $Pd_2(dba)_3$ (443 mg, 0.48 mmol), Xantphos (419 mg, 0.72 mmol) and $Cs_2CO_3$ (4.63 g, 14.2 mmol). The resulting mixture was purged with $N_2$ (3×) and the reaction was then heated to 110° C. overnight. The solvents were removed under vacuum and the residue was purified by flash chromatography (silica gel, 0 to 50% EA in PE) to provide N-(4-methoxybenzyl)-4-propylpyridin-2-amine (501-3) (523 mg, 42%) as a yellow oil. LC-MS (ESI): m/z (M+1) 257.2.

Preparation of 4-propylpyridin-2-amine (501-4)

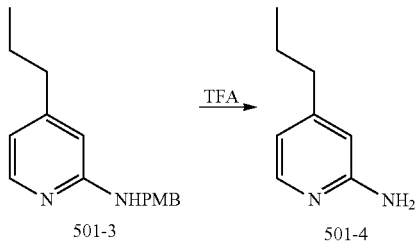

4-Propylpyridin-2-amine (501-4) (360 mg, 100%) was obtained as a yellow oil by treating N-(4-methoxybenzyl)-4-propylpyridin-2-amine (523 mg, 2 mmol) with TFA (10 mL). LC-MS (ESI): m/z (M+1) 137.2

Preparation of (S)-tert-butyl 3-(1-(4-methoxybenzyl)-4-(4-(4-(4-propylpyridin-2-ylcarbamoyl)phenoxy)-1H-pyrazolo[3,4-b]pyridin-3-ylamino)pyrrolidine-1-carboxylate (501-5)

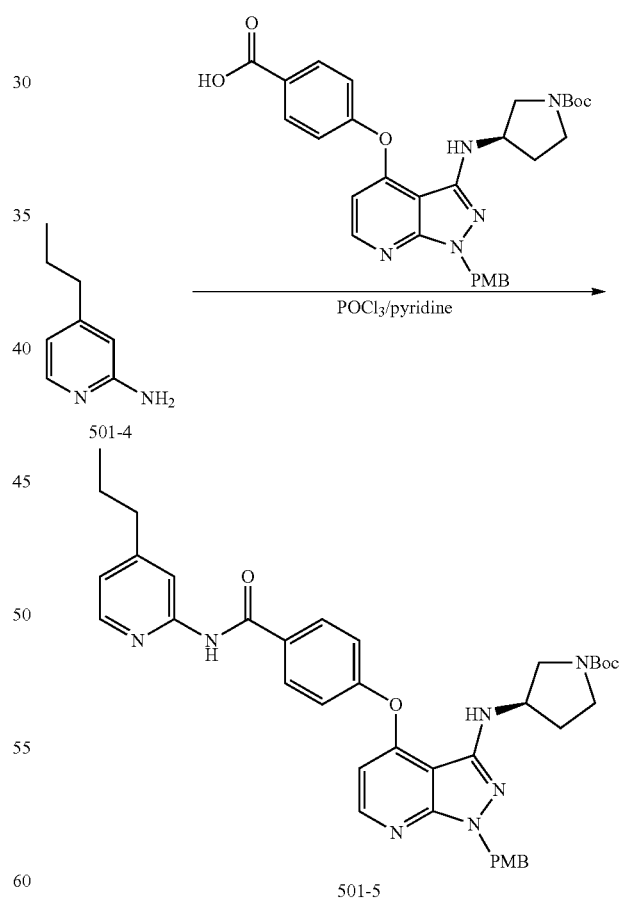

To a solution of 4-propylpyridin-2-amine (58 mg, 0.43 mmol) and (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (510-4) (80 mg, 0.14 mmol) in pyridine (2 mL) was added $POCl_3$ (110 mg, 0.72 mmol) at r.t.

The resulting mixture was then stirred at r.t. for 20 min before carefully poured into ice-water. The mixture was extracted with EA (10 mL×3). The combined organic phase was dried over Na₂SO₄, filtered and concentrated. The residue was purified by flash chromatography (silica gel, 0 to 50% EA in PE) to provide (S)-tert-butyl 3-(1-(4-methoxybenzyl)-4-(4-(4-propylpyridin-2-ylcarbamoyl)phenoxy)-1H-pyrazolo[3,4-b]pyridin-3-ylamino)pyrrolidine-1-carboxylate (501-5) (65 mg, 67%) as a yellow oil. LC-MS (ESI): m/z (M+1) 678.1

Preparation of (R,E)-4-(3-(1-(4-(cyclopropyl (methyl)amino)but-2-enoyl) pyrrolidin-3-ylamino)-1-(4-methoxybenzyl)-1H-pyrazolo[3,4-b]pyridin-4-yloxy)-N-(4-propylpyridin-2-yl)benzamide (501-7)

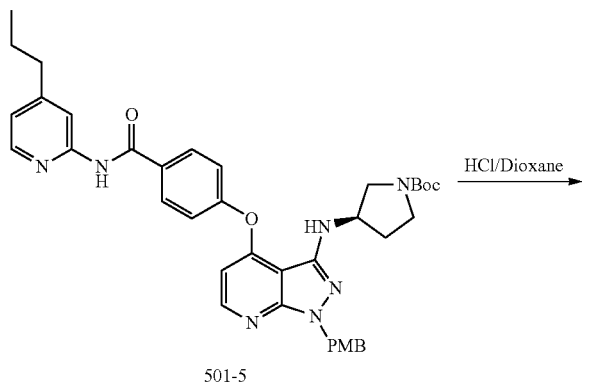

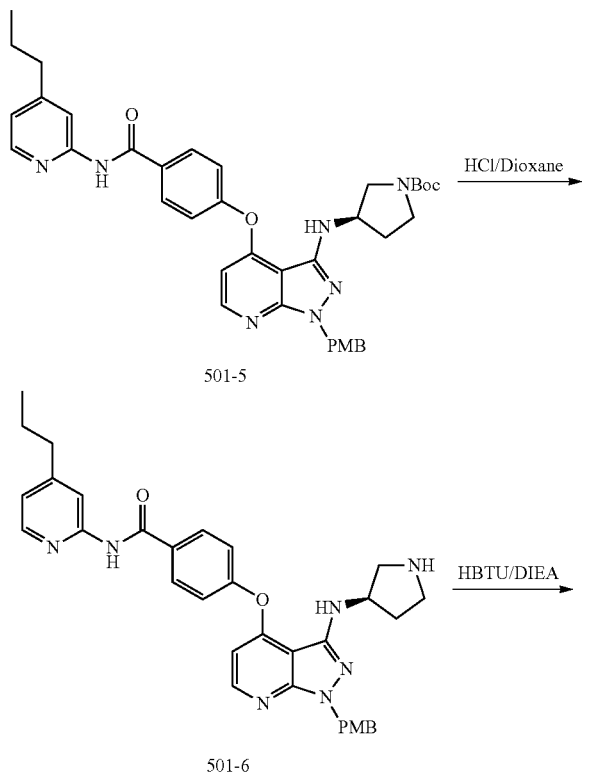

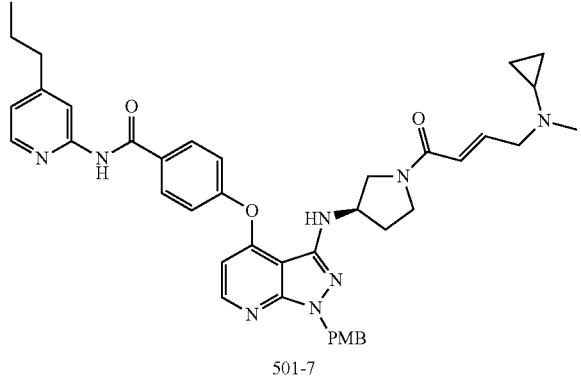

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(4-propylpyridin-2-yl)benzamide (501-7) (64 mg, 100%) was obtained as a yellow solid from (S)-tert-butyl 3-(1-(4-methoxybenzyl)-4-(4-(4-propylpyridin-2-ylcarbamoyl)phenoxy)-1H-pyrazolo[3,4-b]pyridin-3-ylamino)pyrrolidine-1-carboxylate (65 mg, 0.096 mmol) and (E)-4-(cyclopropyl(methyl)amino)but-2-enoic acid HCl salt (mg, mmol), following a similar procedure outlined in Ex. 8. LC-MS (ESI): m/z (M+1) 715.2.

Preparation of (R,E)-4-(3-(1-(4-(cyclopropyl (methyl)amino)but-2-enoylpyrrolidin-3-ylamino)-1H-pyrazolo[3,4-b]pyridin-4-yloxy)-N-(4-propylpyridin-2-yl)benzamide (501)

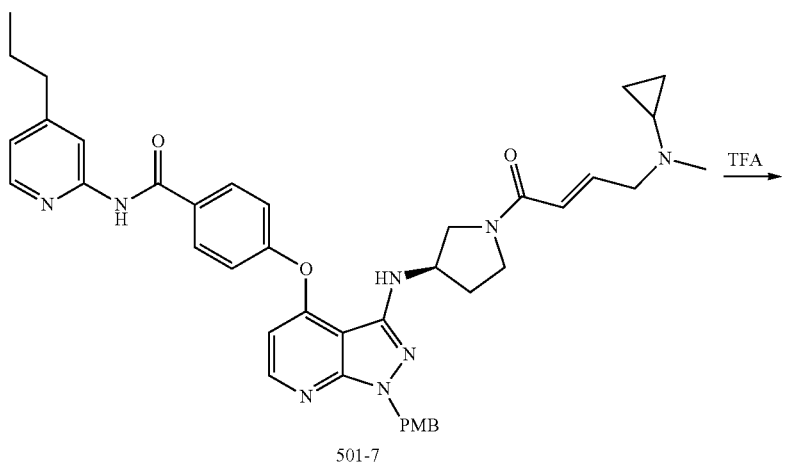

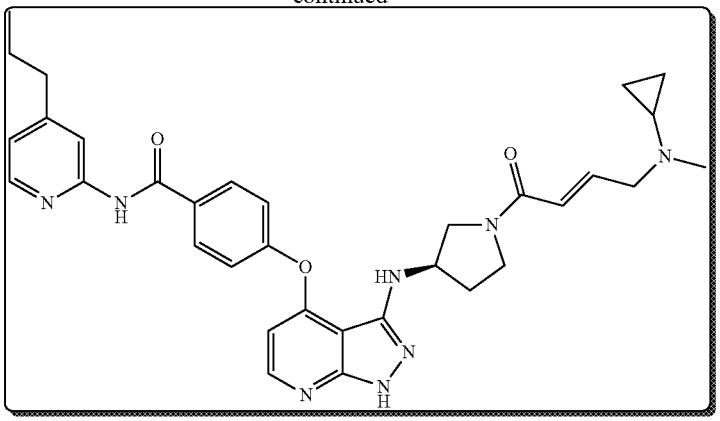

501

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(4-propylpyridin-2-yl)benzamide (501) (10 mg, 19%) was obtained as a white solid by treating (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(4-propylpyridin-2-yl)benzamide (64 mg, 0.09 mmol) with TFA (2 mL) at 60° C. for 2 hr. LC-MS (ESI): m/z (M+1) 595.2. $^1$H NMR (400 MHz, DMSO) δ 12.33 (s, 1H), 10.79 (d, J=2.6 Hz, 1H), 8.28 (d, J=5.1 Hz, 1H), 8.22-8.15 (m, 3H), 8.08 (s, 1H), 7.39 (dd, J=8.7, 3.6 Hz, 1H), 7.04 (d, J=3.9 Hz, 1H), 6.67-6.60 (m, 1H), 6.37-6.28 (m, 1H), 6.17-6.12 (m, 1H), 4.67-3.51 (m, 4H), 3.23 (d, J=6.5 Hz, 2H), 2.62 (t, J=7.5 Hz, 2H), 2.28-2.16 (m, 4H), 2.08-1.94 (m, 1H), 1.71-1.60 (m, 3H), 0.93 (t, J=7.3 Hz, 3H), 0.43-0.36 (m, 2H), 0.32-0.26 (m, 2H).

Example 57

(E)-4-(cyclopropyl(methyl)amino)-N-(2-(4-(4-phenoxyphenoxy)-1H-pyrazolo[3,4-b]pyridin-3-ylamino)phenyl)but-2-enamide (Compound ID 57)

Preparation of 1-(4-methoxybenzyl)-N-(2-nitrophenyl)-4-(4-phenoxyphenoxy)-1H-pyrazolo[3,4-b]pyridin-3-amine (508-2)

To a solution of 1-(4-methoxybenzyl)-4-(4-phenoxyphenoxy)-1H-pyrazolo[3,4-b]pyridin-3-amine (508-1) (300 mg, 0.68 mmol) and 1-fluoro-2-nitrobenzene (127 mg, 0.9 mmol) in DMF (5 mL) was added NaH (60%, 80 mg, 2 mmol). The resulting mixture was stirred at r.t. overnight. The reaction was quenched with water and partitioned between EA and water. The layer was separated and the aqueous phase was extracted with EA (10 mL×3). The combined organic layers were washed with brine, dried over Na$_2$SO$_4$ and concentrated in vacuo. The residue was purified by column chromatography (silica gel, 0 to 50% EA in PE) to give 1-(4-methoxybenzyl)-N-(2-nitrophenyl)-4-(4-phenoxyphenoxy)-1H-pyrazolo[3,4-b]pyridin-3-amine (508-2) (120 mg, 32%) as a yellow solid. LC-MS (ESI): m/z (M+1) 560.2.

Preparation of N1-(1-(4-methoxybenzyl)-4-(4-phenoxyphenoxy)-1H-pyrazolo[3,4-b]pyridin-3-yl)benzene-1,2-diamine (508-3)

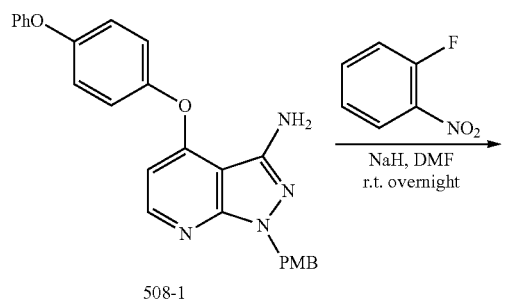

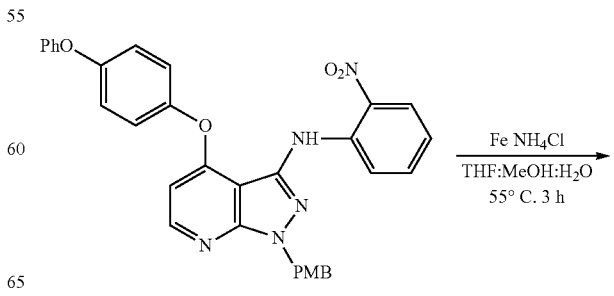

-continued

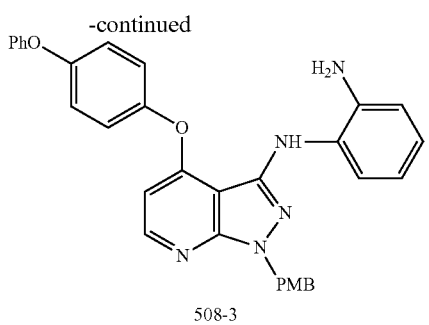
508-3

N1-(1-(4-Methoxybenzyl)-4-(4-phenoxyphenoxy)-1H-pyrazolo[3,4-b]pyridin-3-yl)benzene-1,2-diamine (508-3) (70 mg, 66%) was obtained as a light yellow solid from 1-(4-methoxybenzyl)-N-(2-nitrophenyl)-4-(4-phenoxyphenoxy)-1H-pyrazolo[3,4-b]pyridin-3-amine (508-2) (120 mg, 0.2 mmol), following a similar procedure outlined in Ex. 28. LC-MS (ESI): m/z (M+1) 530.2.

Preparation of (E)-4-(cyclopropyl(methyl)amino)-N-(2-(1-(4-methoxybenzyl)-4-(4-phenoxyphenoxy)-1H-pyrazolo[3,4-b]pyridin-3-ylamino)phenyl)but-2-enamide (508-4)

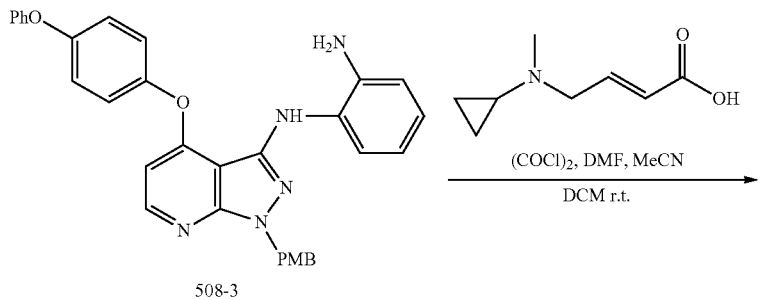

(E)-4-(Cyclopropyl(methyl)amino)-N-(2-(1-(4-methoxybenzyl)-4-(4-phenoxyphenoxy)-1H-pyrazolo[3,4-b]pyridin-3-ylamino)phenyl)but-2-enamide (508-4) (55 mg, 63%) was obtained as a light yellow solid from N1-(1-(4-methoxybenzyl)-4-(4-phenoxyphenoxy)-1H-pyrazolo[3,4-b]pyridin-3-yl)benzene-1,2-diamine (508-3) (70 mg, 0.13 mmol), following a similar procedure outlined in Ex. 1. LC-MS (ESI): m/z (M+1) 667.3.

Preparation of (E)-4-(cyclopropyl(methyl)amino)-N-(2-(4-(4-phenoxyphenoxy)-1H-pyrazolo[3,4-b]pyridin-3-ylamino)phenyl)but-2-enamide (508)

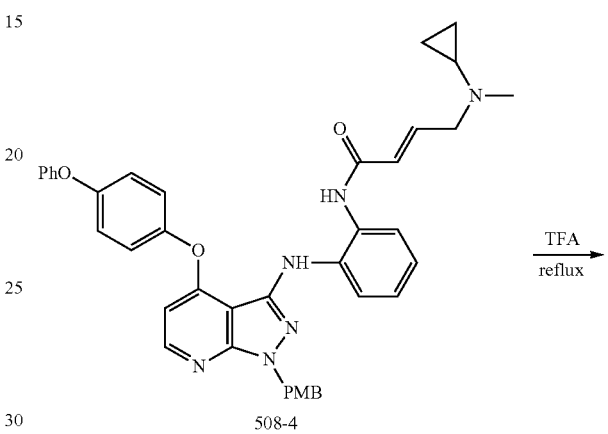

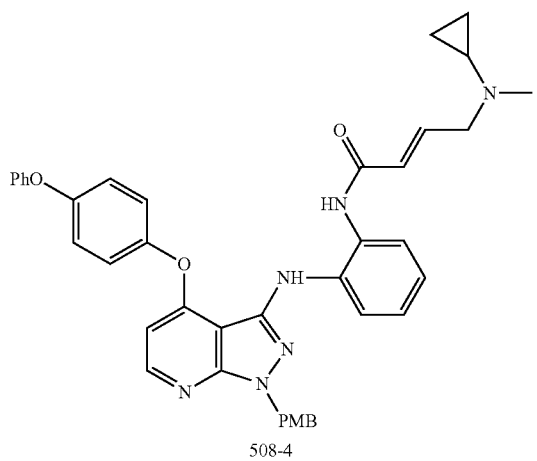
508-4

-continued

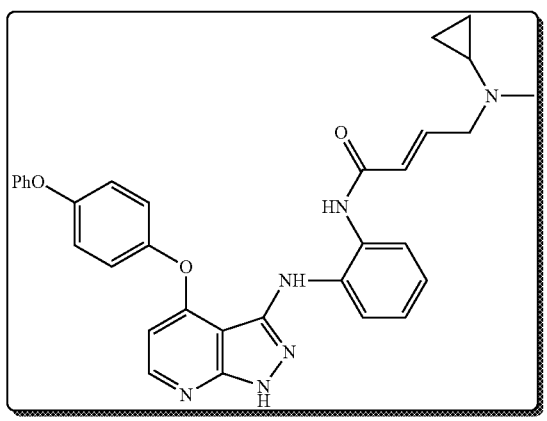

HDBPCYC-508

(E)-4-(Cyclopropyl(methyl)amino)-N-(2-(1-(4-methoxybenzyl)-4-(4-phenoxyphenoxy)-1H-pyrazolo[3,4-b]pyridin-3-ylamino)phenyl)but-2-enamide (508-4) (55 mg, 0.08 mmol) was treated with TFA at 70° C. for 1 hr to give (E)-4-(cyclopropyl(methyl)amino)-N-(2-(4-(4-phenoxyphenoxy)-1H-pyrazolo[3,4-b]pyridin-3-ylamino)phenyl)but-2-enamide (508) (30 mg, 68%) as a white solid. LC-MS (ESI): m/z (M+1) 547.2. $^1$H NMR (400 MHz, DMSO) δ 12.63 (s, 1H), 9.96 (s, 1H), 8.36 (d, J=7.7 Hz, 1H), 8.23 (d, J=5.4 Hz, 1H), 7.84 (s, 1H), 7.45 (t, J=8.0 Hz, 2H), 7.28 (d, J=8.9 Hz, 3H), 7.21-7.08 (m, 6H), 6.97-6.87 (m, 1H), 6.54-6.38 (m, 1H), 6.16-6.05 (m, 2H), 3.01 (d, J=5.8 Hz, 2H), 2.13 (s, 3H), 1.70-1.61 (m, 1H), 0.43-0.37 (m, 2H), 0.29-0.24 (m, 2H).

Example 58

(R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-methoxypyridin-2-yl)benzamide (Compound ID 58)

Preparation of (R)-tert-butyl 3-(1-(4-methoxybenzyl)-4-(4-(4-methoxypyridin-2-ylcarbamoyl)phenoxy)-1H-pyrazolo[3,4-b]pyridin-3-ylamino)pyrrolidine-1-carboxylate (530-1)

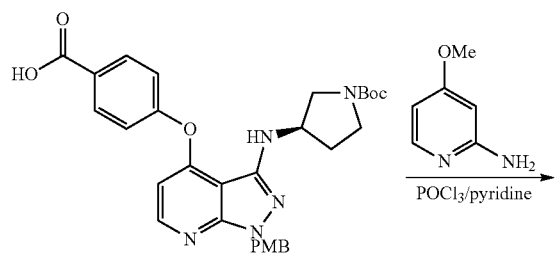

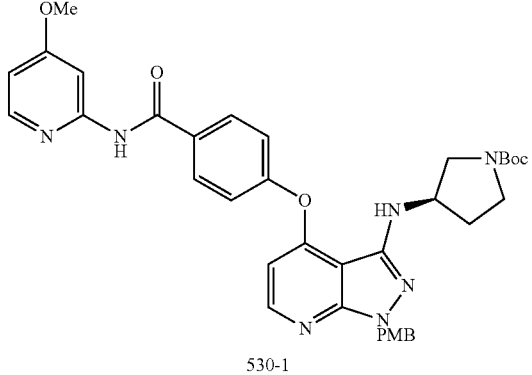

530-1

(R)-tert-Butyl 3-(1-(4-methoxybenzyl)-4-(4-(4-methoxypyridin-2-ylcarbamoyl) phenoxy)-1H-pyrazolo[3,4-b]pyridin-3-ylamino)pyrrolidine-1-carboxylate (530-1) (120 mg, 67%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (150 mg, 0.27 mmol) and 4-methoxypyridin-2-amine (99 mg, 0.8 mmol), following a similar procedure outlined in Ex. 26. LC-MS (ESI): m/z (M+1) 666.2.

Preparation (R)-4-(1-(4-methoxybenzyl)-3-(pyrrolidin-3-(pyrrolidin-3-ylamino)-1H-pyrazolo[3,4-b]pyridin-4-yloxy)-N-(4-methoxypyridin-2-yl)benzamide (530-2)

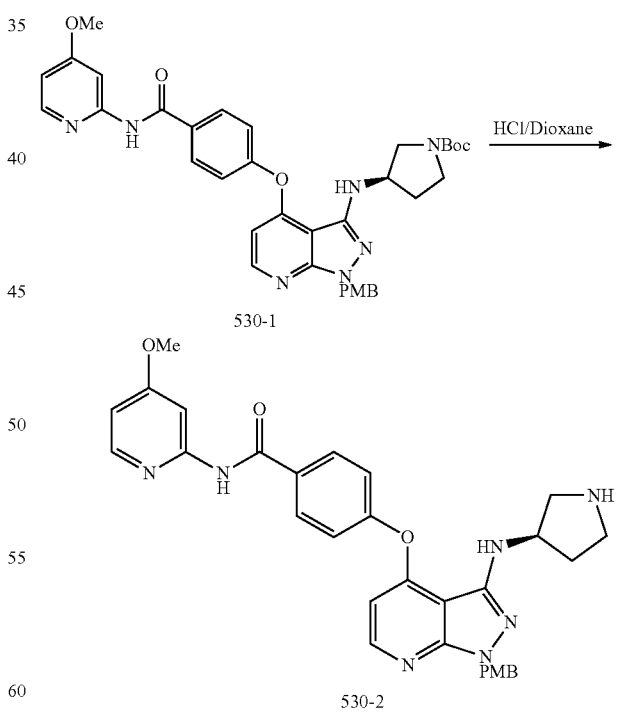

(R)-tert-Butyl 3-(1-(4-methoxybenzyl)-4-(4-(4-methoxypyridin-2-ylcarbamoyl) phenoxy)-1H-pyrazolo[3,4-b]pyridin-3-ylamino)pyrrolidine-1-carboxylate (530-1) (120 mg, 0.18 mmol) was treated with HCl/dioxane (4N) at r.t. for 1 hour to give (R)-4-(1-(4-methoxybenzyl)-3-(pyrrolidin-3- ylamino)-1H-pyrazolo[3,4-b]pyridin-4-yloxy)-N-(4-methoxypyridin-2-yl)benzamide (530-2) (quant.). LC-MS (ESI): m/z (M+1) 566.3.

Preparation of (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(4-methoxypyridin-2-yl)benzamide (530-3)

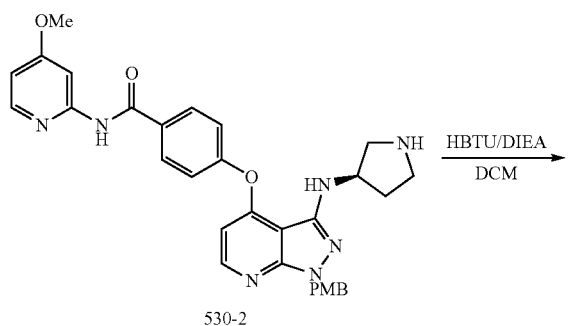

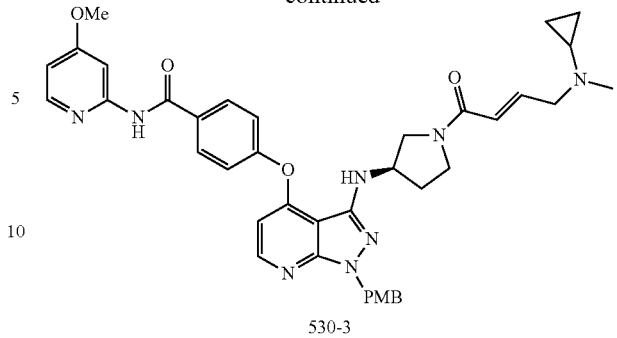

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(4-methoxypyridin-2-yl)benzamide (530-3) (70 mg, 55%) was prepared from (R)-4-(1-(4-methoxybenzyl)-3-(pyrrolidin-3-ylamino)-1H-pyrazolo[3,4-b]pyridin-4-yloxy)-N-(4-methoxypyridin-2-yl)benzamide (530-2) (102 mg, 0.18 mmol) and (E)-4-(cyclopropyl(methyl)amino)but-2-enoic acid HCl salt (64 mg, 0.23 mmol), following a similar procedure outlined in Ex. 26. LC-MS (ESI): m/z (M+1) 703.2.

Preparation of (R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-methoxy-pyridin-2-yl)benzamide (530)

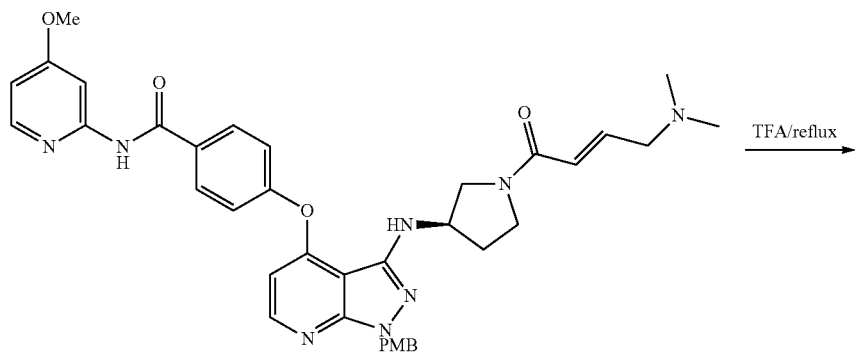

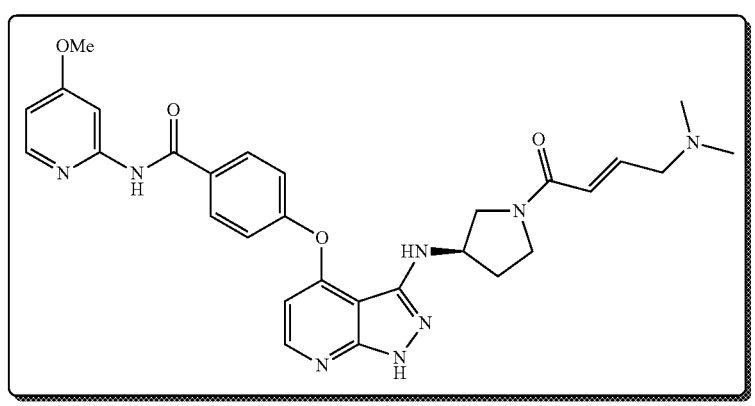

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(4-methoxypyridin-2-yl)benzamide (530-3) (70 mg, 0.1 mmol) was treated with TFA at 70° C. for 3 hr to give (R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-methoxypyridin-2-yl)benzamide (530) (23 mg, 39%). LC-MS (ESI): m/z (M+1) 583.2. ¹H NMR (400 MHz, DMSO) δ 12.31 (s, 1H), 10.82 (s, 1H), 8.20-8.15 (m, 4H), 7.86 (s, 1H), 7.46-7.33 (m, 3H), 6.82-6.76 (m, 1H), 6.70-6.54 (m, 1H), 6.38-6.25 (m, 1H), 6.18-6.06 (m, 1H), 5.69-5.53 (m, 1H), 4.36-3.45 (m, 7H), 3.23 (d, J=6.4 Hz, 2H), 2.29-2.23 (m, 1H), 2.20 (s, 3H), 2.14-1.95 (m, 1H), 1.75-1.61 (m, 1H), 0.41-0.39 (m, 2H), 0.30-0.27 (m, 2H).

Example 59

4-(4-(4-phenoxyphenoxy)-1H-pyrazolo[3,4-b]pyridin-3-ylamino)picolinamide (Compound ID 59)

Preparation of 1-(4-methoxybenzyl)-4-(4-phenoxyphenoxy)-1H-pyrazolo[3,4-b]pyridin-3-amine (513-1)

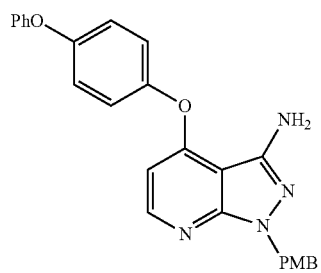

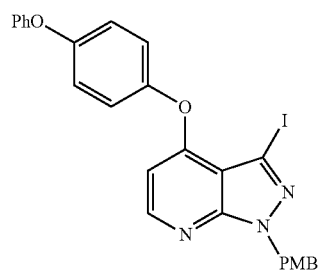

1-(4-Methoxybenzyl)-4-(4-phenoxyphenoxy)-1H-pyrazolo[3,4-b]pyridin-3-amine (513-1) (500 mg, 64%) was obtained as a white solid from 3-iodo-1-(4-methoxybenzyl)-4-(4-phenoxyphenoxy)-1H-pyrazolo[3,4-b]pyridine (1.0 g, 1.8 mmol) and NH₂Boc (2.13 g, 18 mmol), following a similar procedure outlined in Ex. 1, then treated with HCl/dioxane. LC-MS (ESI): m/z (M+1) 439.1.

Preparation of 4-(1-(4-methoxybenzyl)-4-(4-phenoxyphenoxy)-1H-pyrazolo[3,4-b]pyridin-3-ylamino)picolinonitrile (513-2)

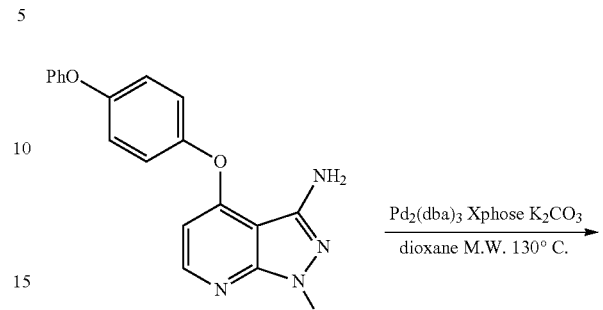

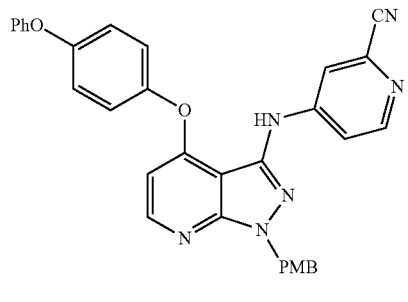

4-(1-(4-Methoxybenzyl)-4-(4-phenoxyphenoxy)-1H-pyrazolo[3,4-b]pyridin-3-ylamino)picolinonitrile (513-2) (195 mg, 50%) was obtained as a white solid from 1-(4-methoxybenzyl)-4-(4-phenoxyphenoxy)-1H-pyrazolo[3,4-b]pyridin-3-amine (513-1) (380 mg, 0.866 mmol) and 2-chloro-5-phenoxypyrimidine (132 mg, 0.96 mmol), following a similar procedure outlined in Ex. 29. LC-MS (ESI): m/z (M+1) 541.2.

Preparation of 4-(1-(4-methoxybenzyl)-4-(4-phenoxyphenoxy)-1H-pyrazolo[3,4-b]pyridin-3-ylamino)picolinamide (513-3)

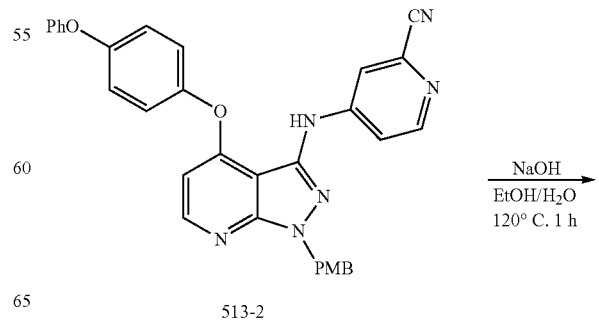

-continued

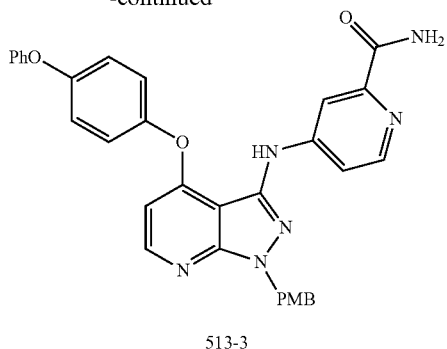

513-3

To a suspension of 4-(1-(4-methoxybenzyl)-4-(4-phenoxyphenoxy)-1H-pyrazolo[3,4-b]pyridin-3-ylamino)picolinonitrile (513-2) (195 mg, 0.36 mmol) in EtOH/H$_2$O (3 mL/3 mL) was added NaOH (145 mg, 3.6 mmol). The resulting mixture was heated at 120° C. for 1 hr. After the reaction was completed, the mixture was filtered and the filter cake was washed with cold water, dried in vacuo to give 4-(1-(4-methoxybenzyl)-4-(4-phenoxyphenoxy)-1H-pyrazolo[3,4-b]pyridin-3-ylamino)picolinamide (513-3) (100 mg, 50%) as a white solid. LC-MS (ESI): m/z (M+1) 559.2.

Preparation of 4-(4-(4-phenoxyphenoxy)-1H-pyrazolo[3,4-b]pyridin-3-ylamino)picolinamide (513)

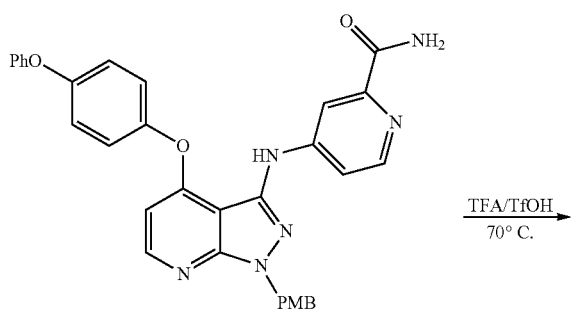

To a solution of 4-(1-(4-methoxybenzyl)-4-(4-phenoxyphenoxy)-1H-pyrazolo[3,4-b]pyridin-3-ylamino)picolinamide (513-3) (100 mg, 0.18 mmol) in TFA (3 mL) was added one drop of TfOH. The resulting mixture was heated to 70° C. for 1 hr. The mixture was concentrated in vacuo to give crude product which was purified by preparative HPLC (RP, C18, 10 to 95% acetonitrile in water (0.2% HCOOH)) to give 4-(4-(4-phenoxyphenoxy)-1H-pyrazolo[3,4-b]pyridin-3-ylamino)picolinamide (513) (25 mg, 35%) as a white solid. LC-MS (ESI): m/z (M+1) 439.1. $^1$H NMR (400 MHz, DMSO) δ 13.21 (s, 1H), 9.14 (s, 1H), 8.30 (dd, J=8.5, 5.6 Hz, 2H), 8.16-8.00 (m, 2H), 7.54 (d, J=5.9 Hz, 2H), 7.42 (t, J=7.9 Hz, 2H), 7.29 (d, J=8.9 Hz, 2H), 7.21-6.96 (m, 5H), 6.23 (d, J=5.4 Hz, 1H).

Example 60

(R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-cyclopropylpyridin-2-yl)benzamide (Compound ID 60)

Preparation of 4-cyclopropylpyridin-2-amine (526-1)

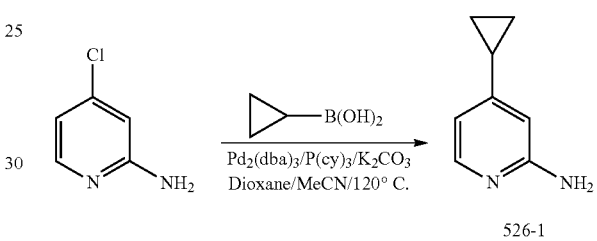

To a solution of 4-chloropyridin-2-amine (514 mg, 4 mmol) in dioxane/MeCN (5 mL/5 mL) was added cyclopropylboronic acid (687 mg, 8 mmol), Pd$_2$(dba)$_3$ (366 mg, 0.4 mmol), P(Cy)$_3$ (168 mg, 0.6 mmol) and K$_2$CO$_3$ (1.66 g, 12 mmol). The resulting mixture was purged with N$_2$ (3×) and heated to 120° C. overnight. The solvents were removed in vacuo and the residue was purified by flash chromatography (silica gel, 0-50% ethyl acetate in petroleum ether) to provide 4-cyclopropylpyridin-2-amine (526-1) (530 mg, 99%) as a light yellow oil. LC-MS (ESI): m/z (M+1) 135.2.

Preparation of (S)-tert-butyl 3-(4-(4-(4-cyclopropylpyridin-2-ylcarbamoyl) phenoxy)-1-(4-methoxybenzyl)-1H-pyrazolo[3,4-b]pyridin-3-ylamino)pyrrolidine-1-carboxylate (526-2)

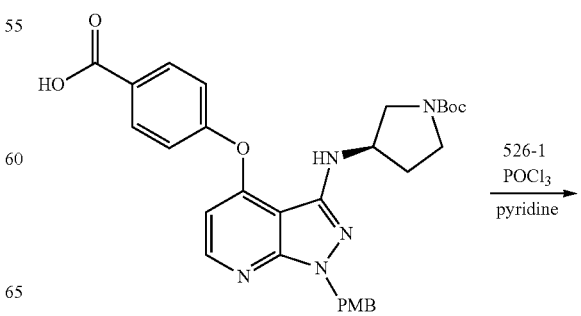

-continued

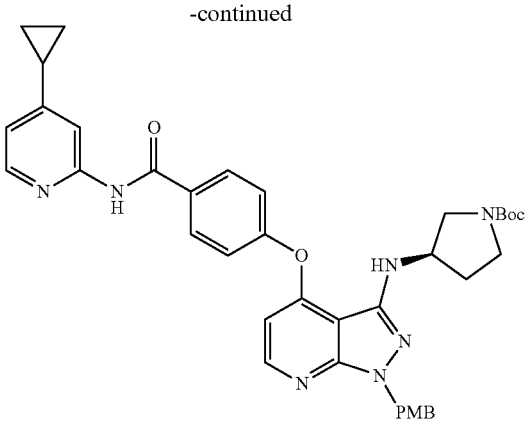

526-2

(S)-tert-Butyl 3-(4-(4-(4-cyclopropylpyridin-2-ylcarbamoyl)phenoxy)-1-(4-methoxybenzyl)-1H-pyrazolo[3,4-b]pyridin-3-ylamino)pyrrolidine-1-carboxylate (526-2) (95 mg, 83%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (133 mg, 0.17 mmol) and 4-cyclopropylpyridin-2-amine (70 mg, 0.52 mmol), following a similar procedure outlined in Ex. 26. LC-MS (ESI): m/z (M+1) 676.0.

Preparation of (R)—N-(4-cyclopropylpyridin-2-yl)-4-(1-(4-methoxybenzyl)-3-(pyrrolidin-3-ylamino)-1H-pyrazolo[3,4-b]pyridin-4-yloxy)benzamide (526-3)

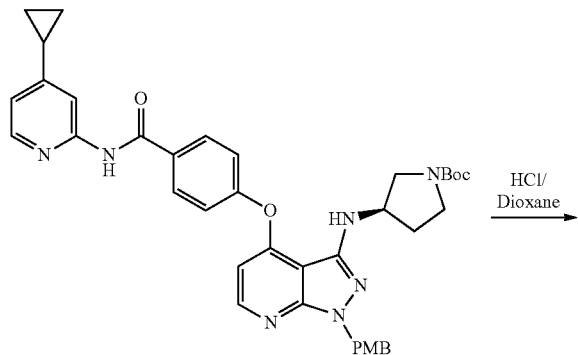

526-2

HCl/Dioxane

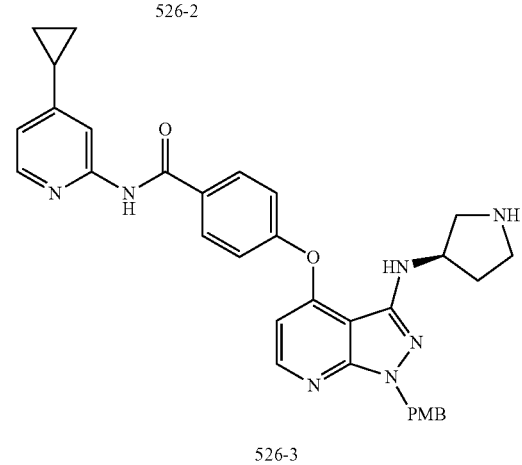

526-3

(R)—N-(4-Cyclopropylpyridin-2-yl)-4-(1-(4-methoxybenzyl)-3-(pyrrolidin-3-ylamino)-1H-pyrazolo[3,4-b]pyridin-4-yloxy)benzamide (526-3) (81 mg, 100%) was obtained as a yellow solid by treating (S)-tert-butyl 3-(4-(4-(4-cyclopropylpyridin-2-ylcarbamoyl) phenoxy)-1-(4-methoxybenzyl)-1H-pyrazolo[3,4-b]pyridin-3-ylamino)pyrrolidine-1-carboxylate (95 mg, 0.14 mmol) with 4N HCl/Dioxane (2 mL). LC-MS (ESI): m/z (M+1) 576.0.

Preparation of (R,E)-4-(3-(1-(4-(cyclopropyl (methyl)amino)but-2-enoyl)pyrrolidin-3-ylamino)-1-(4-methoxybenzyl)-1H-pyrazolo[3,4-b]pyridin-4-yloxy)-N-(4-cyclopropylpyridin-2-yl)benzamide (526-4)

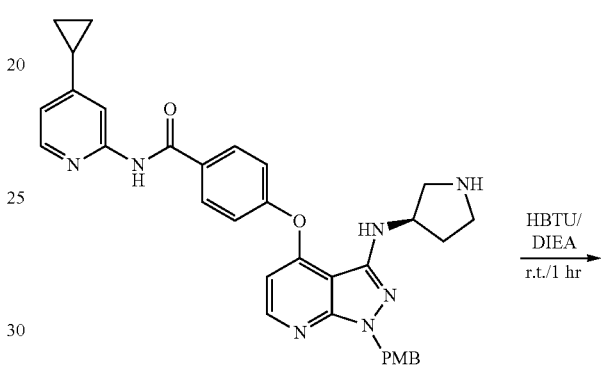

526-3

HBTU/DIEA
r.t./1 hr

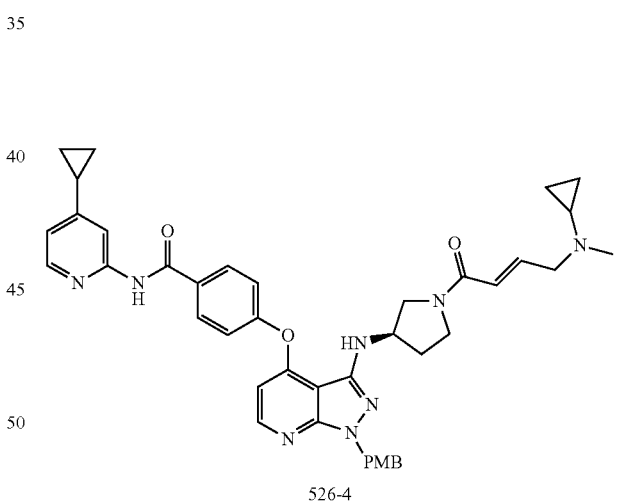

526-4

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(4-cyclopropylpyridin-2-yl)benzamide (526-4) (47 mg, 47%) was obtained as a yellow solid from (R)—N-(4-cyclopropylpyridin-2-yl)-4-(1-(4-methoxybenzyl)-3-(pyrrolidin-3-ylamino)-1H-pyrazolo[3,4-b]pyridin-4-yloxy)benzamide (526-3) (81 mg, 0.14 mmol) and (E)-4-(cyclopropyl(methyl)amino)but-2-enoic acid hydrochloride (30 mg, 0.15 mmol), following a similar procedure in Ex. 26. LC-MS (ESI): m/z (M+1) 713.1.

Preparation of (R,E)-4-(3-(1-(4-(cyclopropyl (methyl)amino)but-2-enoyl)pyrrolidin-3-ylamino)- 1H-pyrazolo[3,4-b]pyridin-4-yloxy)-N-(4-cyclopropylpyridin-2-yl)benzamide (526)

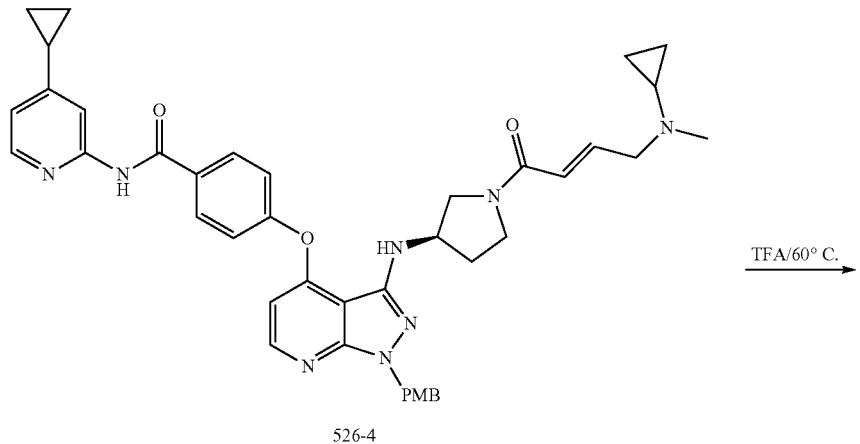

526-4

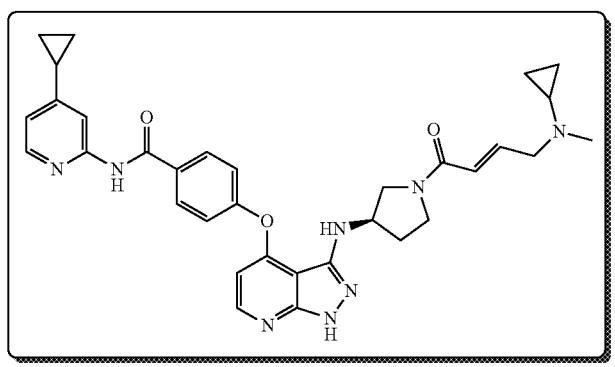

526

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(4-cyclopropylpyridin-2-yl)benzamide (526) (24 mg, 61%) was obtained as a white solid from (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(4-cyclopropylpyridin-2-yl)benzamide (526-4) (39 mg, 0.055 mmol), following a similar procedure in Ex. 26. LC-MS (ESI): m/z (M+1) 593.2. $^1$H NMR (400 MHz, DMSO) δ 12.34 (s, 1H), 10.76 (s, 1H), 8.24-8.15 (m, 5H), 7.96 (s, 1H), 7.39-7.37 (m, 2H), 6.87 (d, J=5.1 Hz, 1H), 6.62-6.60 (m, 1H), 6.34-6.32 (m, 1H), 6.18-6.11 (m, 1H), 5.62 (dd, J=35.1, 5.7 Hz, 0H), 4.31-3.33 (m, 4H), 3.23 (d, J=6.7 Hz, 2H), 2.35-2.04 (m, 5H), 2.01-1.98 (m, 1H), 1.68-1.66 (m, 1H), 1.11-1.09 (m, 2H), 0.82-0.78 (m, 2H), 0.42-0.38 (m, 2H), 0.30-0.28 (m, 2H).

Example 61

(R,E)-4-(3-(1-(4-(cyclopropyl(methyl)amino)but-2-enoyl)pyrrolidin-3-ylamino)-1H-pyrazolo[3,4-b] pyridin-4-yloxy)-N-(4-isopropylpyridin-2-yl)benzamide (Compound ID 61)

Preparation of 4-(prop-1-en-2-yl)pyridin-2-amine (527-1)

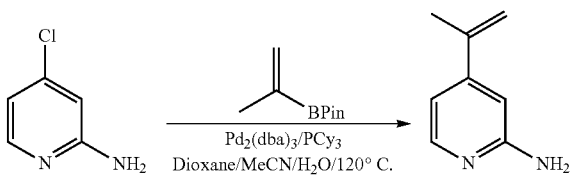

4-(Prop-1-en-2-yl)pyridin-2-amine (527-1) (670 mg, 100%) was obtained as a yellow oil from 4-chloropyridin- 2-amine (642 mg, 5 mmol) and 4,4,5,5-tetramethyl-2-(prop-1-en-2-yl)-1,3,2-dioxaborolane (1.68 g, 10 mmol), following a similar procedure in Ex. 3.3.1. LC-MS (ESI): m/z (M+1) 135.2.

Preparation of 4-isopropylpyridin-2-amine (527-2)

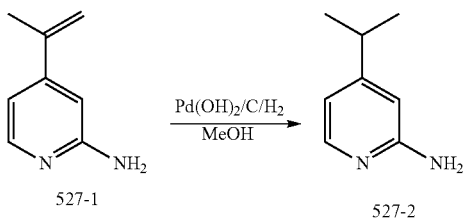

4-(Prop-1-en-2-yl)pyridin-2-amine (527-1) (670 mg, 5 mmol) was treated with Pd(OH)₂/C (200 mg) in MeOH (10 mL) under H₂ atmosphere to provide 4-isopropylpyridin-2-amine (527-2) (630 mg, 94%) as a yellow oil. LC-MS (ESI): m/z (M+1) 137.2.

Preparation of (S)-tert-butyl 3-(4-(4-(4-isopropylpyridin-2-ylcarbamoyl)phenoxy)-1-(4-methoxybenzyl)-1H-pyrazolo[3,4-b]pyridin-3-ylamino)pyrrolidine-1-carboxylate (527-3)

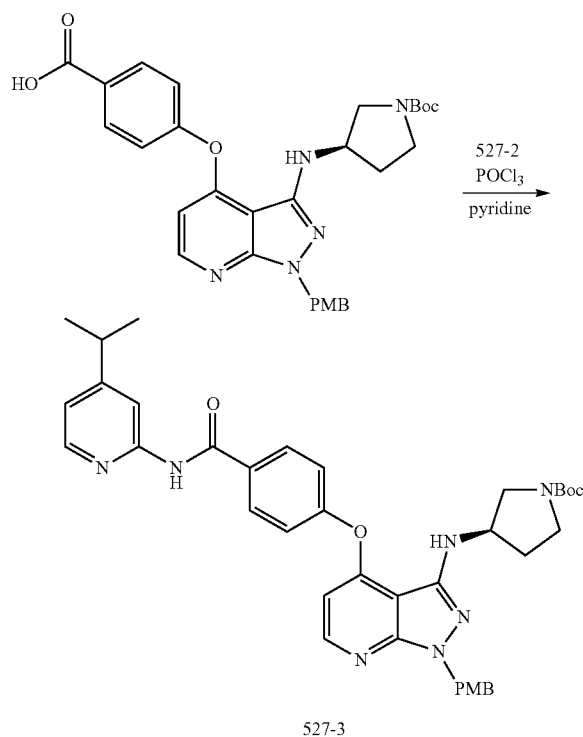

(S)-tert-Butyl 3-(4-(4-(4-isopropylpyridin-2-ylcarbamoyl)phenoxy)-1-(4-methoxybenzyl)-1H-pyrazolo[3,4-b]pyridin-3-ylamino)pyrrolidine-1-carboxylate (527-3) (115 mg, 99%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (100 mg, 0.18 mmol) and 4-isopropylpyridin-2-amine (527-2) (72 mg, 0.53 mmol), following a similar procedure outlined in Ex. 26. LC-MS (ESI): m/z (M+1) 678.2.

Preparation of (R)—N-(4-isopropylpyridin-2-yl)-4-(1-(4-methoxybenzyl)-3-(pyrrolidin-3-ylamino)-1H-pyrazolo[3,4-b]pyridin-4-yloxy)benzamide (527-4)

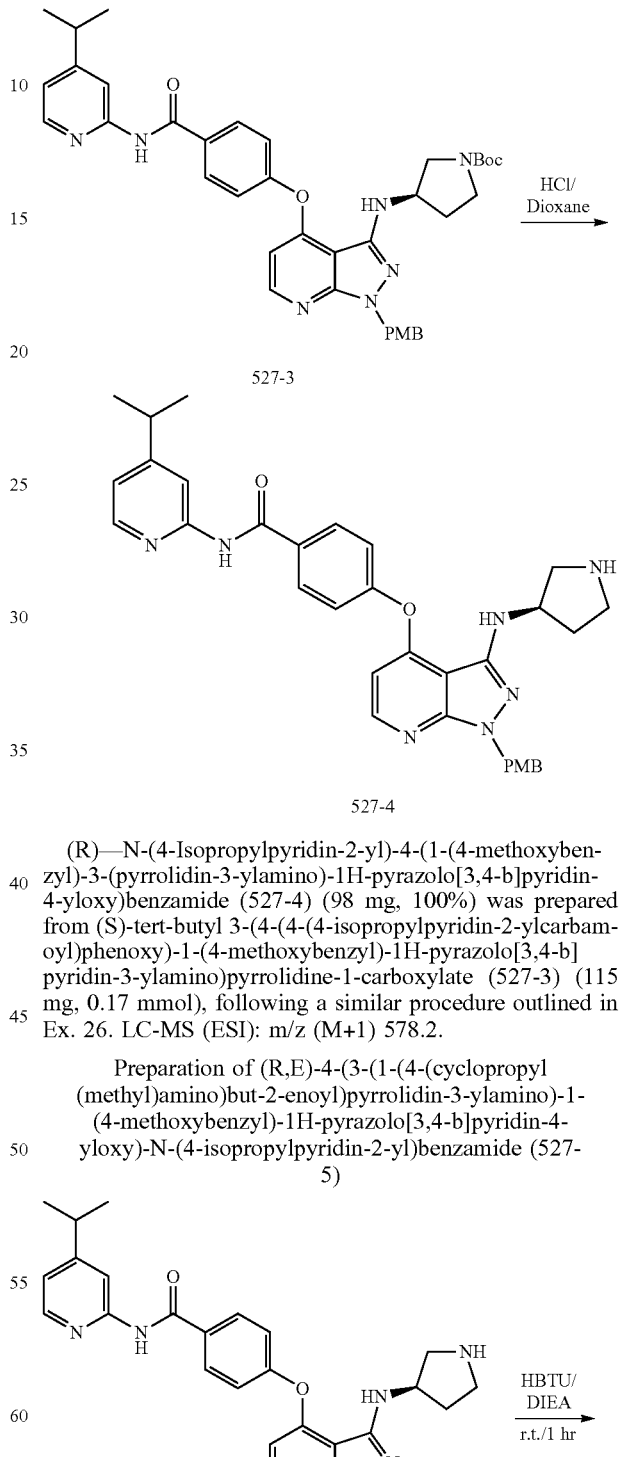

(R)—N-(4-Isopropylpyridin-2-yl)-4-(1-(4-methoxybenzyl)-3-(pyrrolidin-3-ylamino)-1H-pyrazolo[3,4-b]pyridin-4-yloxy)benzamide (527-4) (98 mg, 100%) was prepared from (S)-tert-butyl 3-(4-(4-(4-isopropylpyridin-2-ylcarbamoyl)phenoxy)-1-(4-methoxybenzyl)-1H-pyrazolo[3,4-b]pyridin-3-ylamino)pyrrolidine-1-carboxylate (527-3) (115 mg, 0.17 mmol), following a similar procedure outlined in Ex. 26. LC-MS (ESI): m/z (M+1) 578.2.

Preparation of (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(4-isopropylpyridin-2-yl)benzamide (527-5)

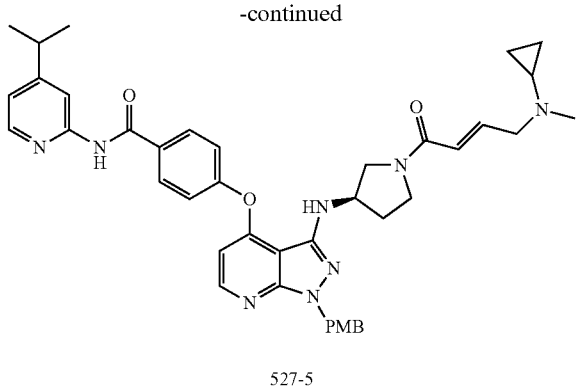

527-5

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(4-isopropylpyridin-2-yl)benzamide (527-5) (64 mg, 53%) was prepared from (R)—N-(4-isopropylpyridin-2-yl)-4-(1-(4-methoxybenzyl)-3-(pyrrolidin-3-ylamino)-1H-pyrazolo[3,4-b]pyridin-4-yloxy)benzamide (527-4) (98 mg, 0.17 mmol) and (E)-4-(cyclopropyl(methyl)amino)but-2-enoic acid (57 mg, 0.21 mmol, HCl salt, mixed with LiCl), following a similar procedure in Ex. 26. LC-MS (ESI): m/z (M+1) 715.3.

Preparation of (R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-isopropylpyridin-2-yl)benzamide (527)

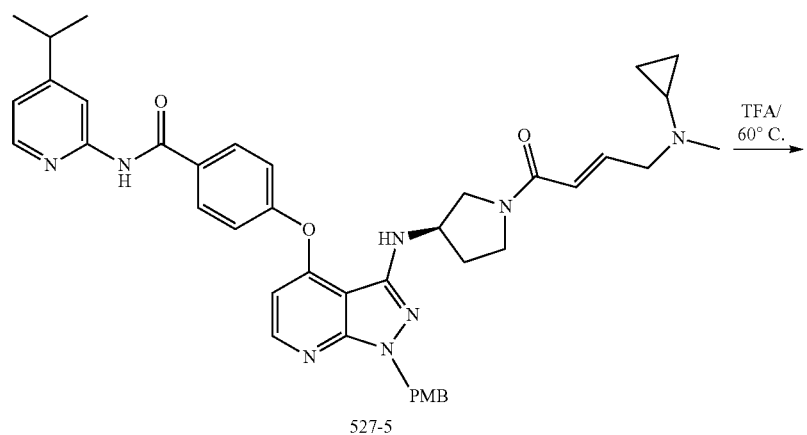

527-5

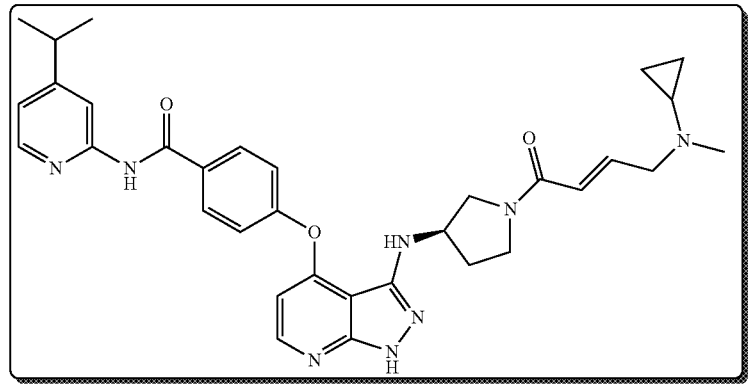

527

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(4-isopropylpyridin-2-yl)benzamide (527) (25 mg, 49%) was obtained as a white solid from (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(4-isopropylpyridin-2-yl)benzamide (527-5) (59 mg, 0.083 mmol), following a similar procedure in Ex. 26. LC-MS (ESI): m/z (M+1) 595.1. ¹H NMR (400 MHz, DMSO) δ 12.34 (s, 1H), 10.80 (s, 1H), 8.29 (d, J=5.2 Hz, 1H), 8.24-8.10 (m, 5H), 7.39 (dd, J=8.7, 3.8 Hz, 2H), 7.09 (d, J=5.4 Hz, 1H), 6.68-6.58 (m, 1H), 6.37-6.27 (m, 1H), 6.15 (s, 1H), 5.62 (dd, J=34.4, 5.9 Hz, 1H), 4.36-4.17 (m, 1H), 3.96-3.41 (m, 4H), 3.23 (d, J=6.6 Hz, 2H), 2.98-2.91 (m, 1H), 2.27-1.99 (m, 5H), 1.73-1.62 (m, 1H), 1.25 (s, 3H), 1.23 (s, 3H), 0.43-0.36 (m, 2H), 0.31-0.25 (m, 2H).

Example 62

(R,E)-N-(4-cyanopyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide (Compound ID 62)

Preparation of (R)-tert-butyl 3-(4-(4-(4-cyanopyridin-2-ylcarbamoyl)phenoxy)-1-(4-methoxybenzyl)-1H-pyrazolo[3,4-b]pyridin-3-ylamino)pyrrolidine-1-carboxylate (529-1)

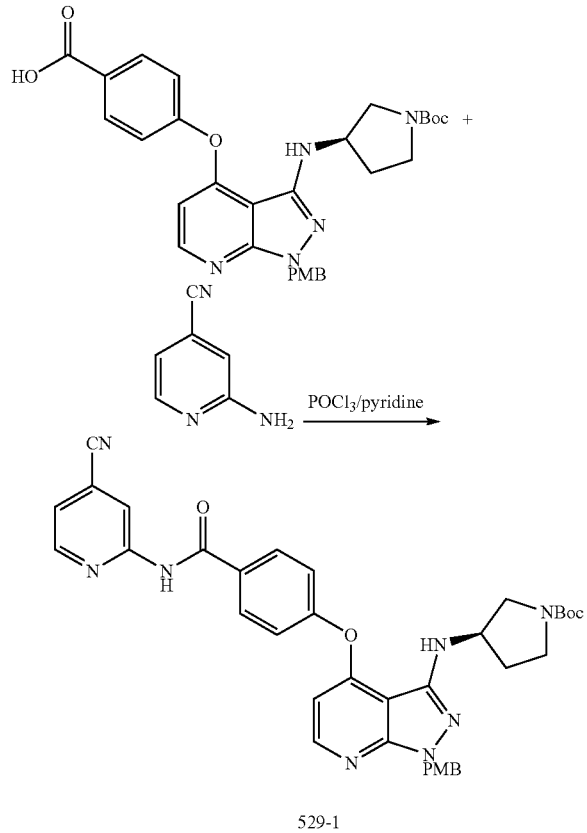

(R)-tert-Butyl 3-(4-(4-(4-cyanopyridin-2-ylcarbamoyl)phenoxy)-1-(4-methoxybenzyl)-1H-pyrazolo[3,4-b]pyridin-3-ylamino)pyrrolidine-1-carboxylate (529-1) (149 mg, 37%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (350 mg, 0.62 mmol) and 2-aminoisonicotinonitrile (224 mg, 1.88 mmol), following a similar procedure outlined in Ex. 26. LC-MS (ESI): m/z (M+1) 661.2.

Preparation of (R)—N-(4-cyanopyridin-2-yl)-4-(1-(4-methoxybenzyl)-3-(pyrrolidin-3-ylamino)-1H-pyrazolo[3,4-b]pyridin-4-yloxy)benzamide (529-2)

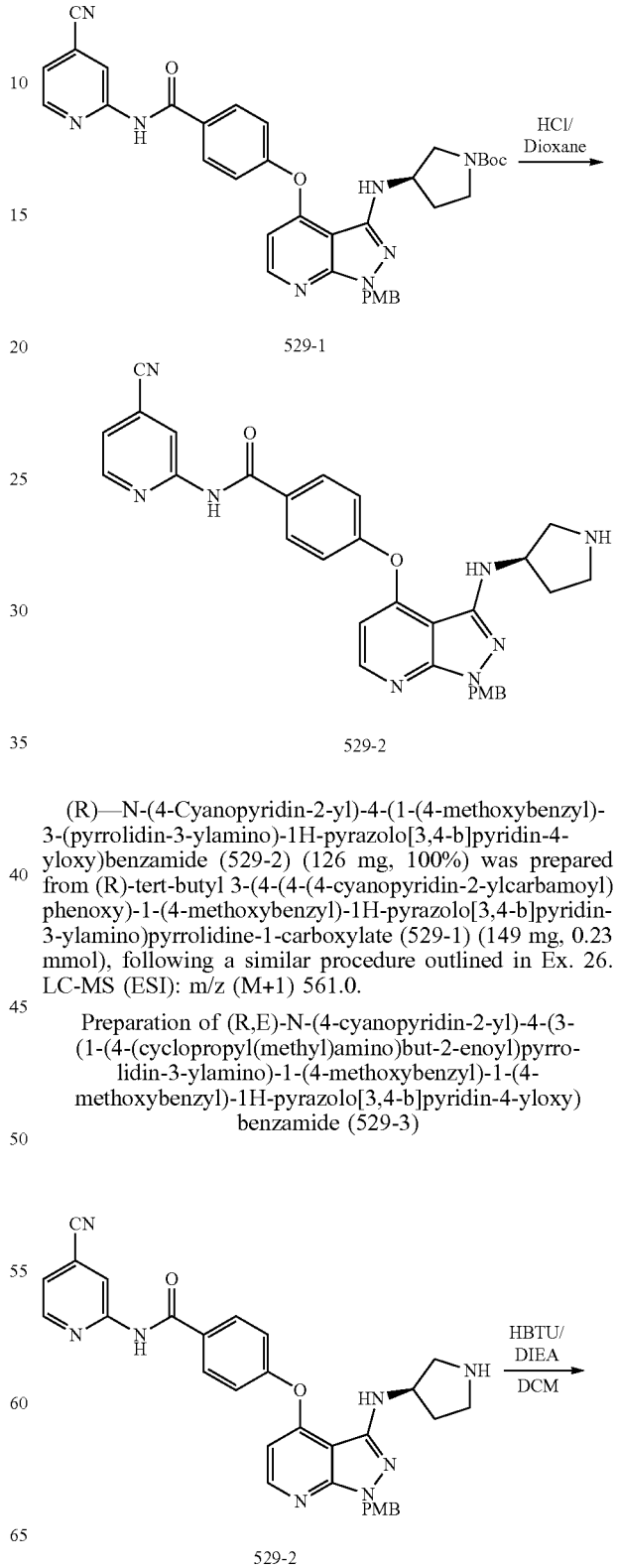

(R)—N-(4-Cyanopyridin-2-yl)-4-(1-(4-methoxybenzyl)-3-(pyrrolidin-3-ylamino)-1H-pyrazolo[3,4-b]pyridin-4-yloxy)benzamide (529-2) (126 mg, 100%) was prepared from (R)-tert-butyl 3-(4-(4-(4-cyanopyridin-2-ylcarbamoyl)phenoxy)-1-(4-methoxybenzyl)-1H-pyrazolo[3,4-b]pyridin-3-ylamino)pyrrolidine-1-carboxylate (529-1) (149 mg, 0.23 mmol), following a similar procedure outlined in Ex. 26. LC-MS (ESI): m/z (M+1) 561.0.

Preparation of (R,E)-N-(4-cyanopyridin-2-yl)-4-(3-(1-(4-(cyclopropyl(methyl)amino)but-2-enoyl)pyrrolidin-3-ylamino)-1-(4-methoxybenzyl)-1-(4-methoxybenzyl)-1H-pyrazolo[3,4-b]pyridin-4-yloxy)benzamide (529-3)

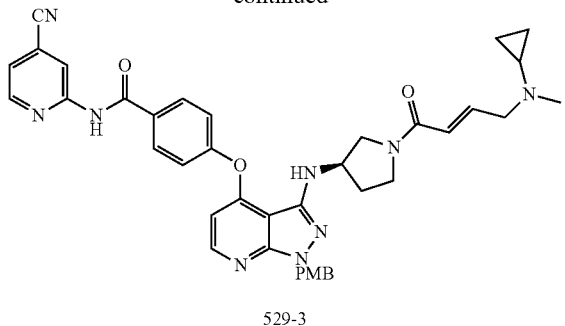

529-3

(R,E)-N-(4-Cyanopyridin-2-yl)-4-(3-(1-(4-(cyclopropyl (methyl)amino)but-2-enoyl)pyrrolidin-3-ylamino)-1-(4-methoxybenzyl)-1H-pyrazolo[3,4-b]pyridin-4-yloxy)benzamide (529-3) (16 mg, 12%) was prepared from (R)—N-(4-cyanopyridin-2-yl)-4-(1-(4-methoxybenzyl)-3-(pyrrolidin-3-ylamino)-1H-pyrazolo[3,4-b]pyridin-4-yloxy) benzamide (529-2) (106 mg, 0.19 mmol) and (E)-4-(cyclopropyl(methyl)amino)but-2-enoic acid HCl salt (64 mg, 0.23 mmol), following a similar procedure outlined in Ex. 26. LC-MS (ESI): m/z (M+1) 698.0.

Preparation of (R,E)-N-(4-cyanopyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide (529)

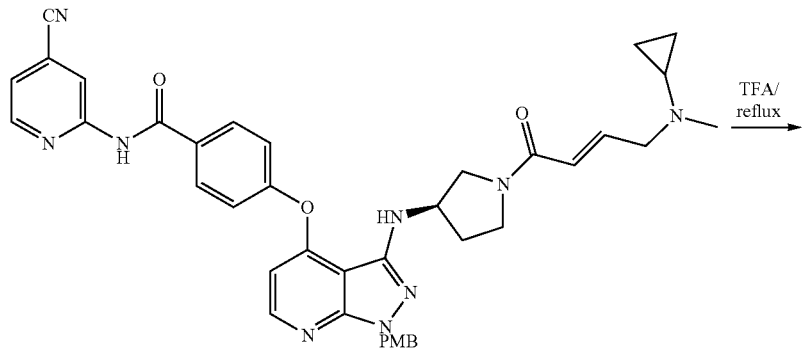

529

(R,E)-N-(4-Cyanopyridin-2-yl)-4-(3-(1-(4-(cyclopropyl (methyl)amino)but-2-enoyl)pyrrolidin-3-ylamino)-1H-pyrazolo[3,4-b]pyridin-4-yloxy)benzamide (529) (28 mg, 49%) was obtained as a white solid from (R,E)-N-(4-cyanopyridin-2-yl)-4-(3-(1-(4-(cyclopropyl(methyl)amino) but-2-enoyl)pyrrolidin-3-ylamino)-1-(4-methoxybenzyl)-1H-pyrazolo[3,4-b]pyridin-4-yloxy)benzamide (70 mg, 0.1 mmol) following a similar procedure outlined in Ex. 26. LC-MS (ESI): m/z (M+1) 578.3. $^1$H NMR (400 MHz, DMSO) δ 12.34 (s, 1H), 11.36 (s, 1H), 8.67 (d, J=4.7 Hz, 1H), 8.53 (s, 1H), 8.19 (t, J=7.4 Hz, 4H), 7.64 (d, J=5.0 Hz, 1H), 7.41 (d, J=5.8 Hz, 2H), 6.67-6.58 (m, 1H), 6.32 (t, J=14.0 Hz, 1H), 6.16 (d, J=5.9 Hz, 1H), 5.69-5.54 (m, 1H), 4.35-4.18 (m, 1H), 3.91-3.54 (m, 3H), 3.23 (s, 2H), 2.30-2.23 (m, 1H), 2.21 (d, J=2.5 Hz, 3H), 2.13-2.01 (m, 1H), 1.70-1.65 (m, 1H), 0.42-0.38 (m, 2H), 0.31-0.28 (m, 2H).

Example 63

(R,E)-4-(3-(1-(4-(cyclopropyl(methyl)amino)but-2-enoyl)pyrrolidin-3-ylamino)-1H-pyrazolo[3,4-b] pyridin-4-yloxy)-N-(pyrimidin-2-yl)benzamide (Compound ID 63)

Preparation of (R)-tert-butyl 3-(1-(4-methoxybenzyl)-4-(4-(pyrimidin-2-ylcarbamoyl)phenoxy)-1H-pyrazolo[3,4-b]pyridin-3-ylamino)pyrrolidine-1-carboxylate (532-1)

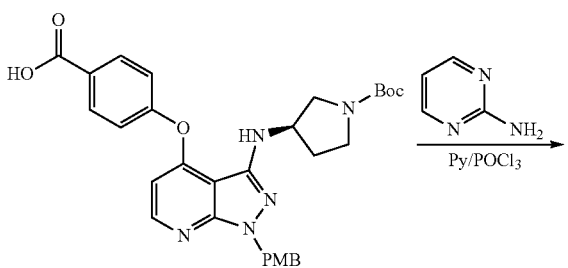

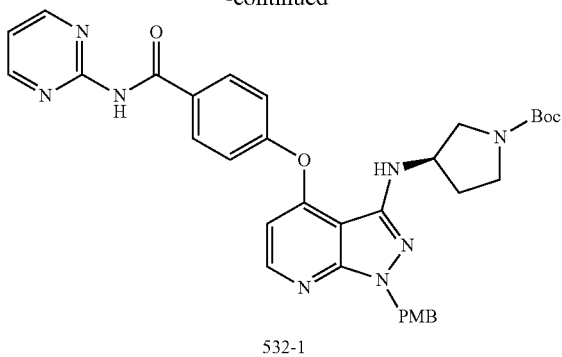

532-1

(R)-tert-Butyl 3-(1-(4-methoxybenzyl)-4-(4-(pyrimidin-2-ylcarbamoyl)phenoxy)-1H-pyrazolo[3,4-b]pyridin-3-ylamino)pyrrolidine-1-carboxylate (532-1) (115 mg, 53%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (190 mg, 0.34 mmol) and pyrimidin-2-amine (96 mg, 1.04 mmol), following a similar procedure outlined in Ex. 26. LC-MS (ESI): m/z (M+1) 637.1.

Preparation of (R)-4-(1-(4-methoxybenzyl)-3-(pyrrolidin-3-ylamino)-1H-pyrazolo[3,4-b]pyridin-4-yloxy)-N-(pyrimidin-2-yl)benzamide (532-2)

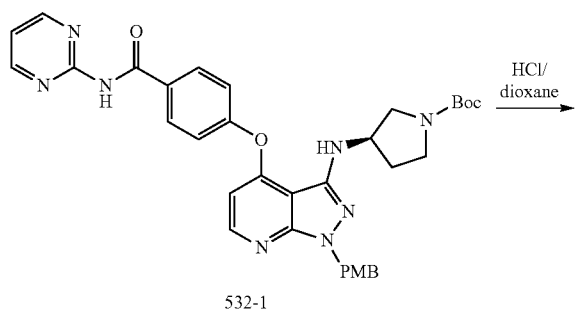

532-1

HCl/ dioxane

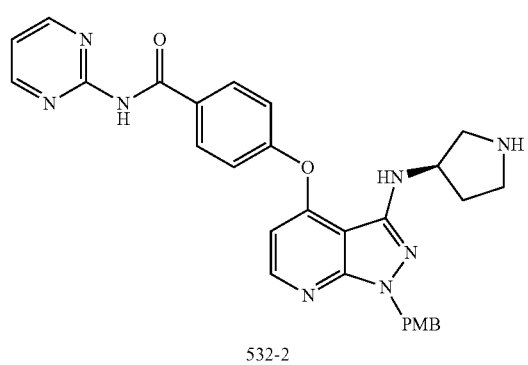

532-2

(R)-4-(1-(4-Methoxybenzyl)-3-(pyrrolidin-3-ylamino)-1H-pyrazolo[3,4-b]pyridin-4-yloxy)-N-(pyrimidin-2-yl)benzamide (532-2) (96 mg, 100%) was prepared from (R)-tert-butyl 3-(1-(4-methoxybenzyl)-4-(4-(pyrimidin-2-ylcarbamoyl)phenoxy)-1H-pyrazolo[3,4-b]pyridin-3-ylamino)pyrrolidine-1-carboxylate (532-1) (115 mg, 0.18 mmol), following a similar procedure outlined in Ex. 26. LC-MS (ESI): m/z (M+1) 537.0.

Preparation of (R,E)-4-(3-(1-(4-(cyclopropyl (methyl)amino)but-2-enoyl)pyrrolidin-3-ylamino)-1-(4-methoxybenzyl)-1H-pyrazolo[3,4-b]pyridin-4-yloxy)-N-(pyrimidin-2-yl)benzamide (532-3)

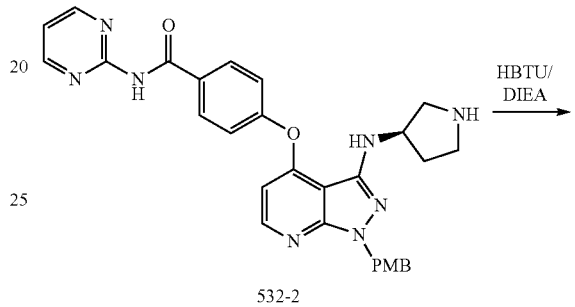

532-2

HBTU/ DIEA

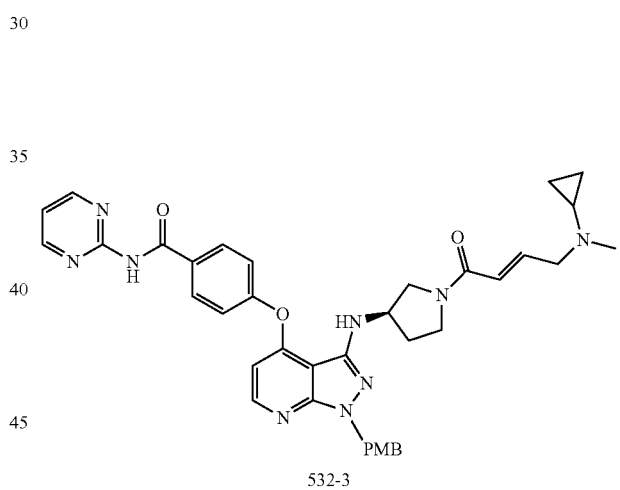

532-3

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(pyrimidin-2-yl)benzamide (532-3) (76 mg, 60%) was prepared from (R)-4-(1-(4-methoxybenzyl)-3-(pyrrolidin-3-ylamino)-1H-pyrazolo[3,4-b]pyridin-4-yloxy)-N-(pyrimidin-2-yl)benzamide (532-2) (96 mg, 0.19 mmol) and (E)-4-(cyclopropyl(methyl)amino)but-2-enoic acid HCl salt (85 mg, 0.275 mmol), following a similar procedure outlined in Ex. 26. LC-MS (ESI): m/z (M+1) 674.1.

Preparation of (R,E)-4-(3-(1-(4-(cyclopropyl (methyl)amino)but-2-enoyl)pyrrolidin-3-ylamino)-1H-pyrazolo[3,4-b]pyridin-4-yloxy)-N-(pyrimidin-2-yl)benzamide (532)

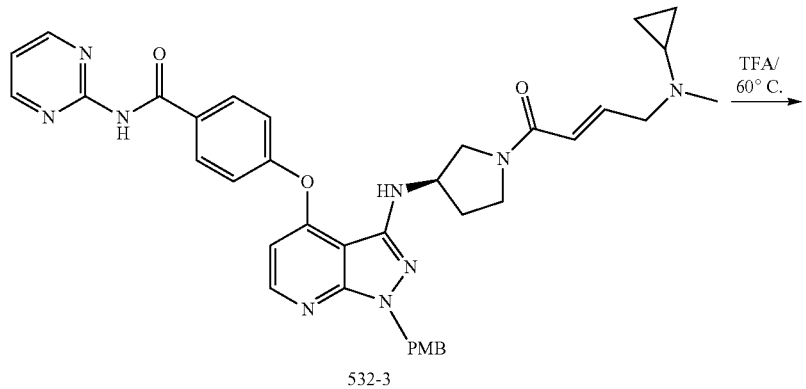

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(pyrimidin-2-yl)benzamide (532) (25 mg, 40%) was obtained as white solid from (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(pyrimidin-2-yl)benzamide (76 mg, 0.11 mmol) following a similar procedure outlined in Ex. 26. LC-MS (ESI): m/z (M+1) 554.0. $^1$H NMR (400 MHz, DMSO) δ 12.34 (s, 1H), 11.09 (s, 1H), 8.75 (d, J=4.8 Hz, 2H), 8.29-8.17 (m, 2H), 8.11 (d, J=8.6 Hz, 2H), 7.39 (d, J=8.6 Hz, 2H), 7.27 (t, J=4.8 Hz, 1H), 6.70-6.57 (m, 1H), 6.33 (s, 1H), 6.14 (dd, J=5.3, 2.5 Hz, 1H), 5.73-3.39 (m, 5H), 3.24 (d, J=6.0 Hz, 2H), 2.25-2.20 (m, 4H), 2.18-1.89 (m, 1H), 1.73-1.62 (m, 1H), 0.43-0.36 (m, 2H), 0.33-0.26 (m, 2H).

Example 64
(R,E)-4-(3-(1-(4-(cyclopropyl(methyl)amino)but-2-enoyl)pyrrolidin-3-ylamino)-1H-pyrazolo[3,4-b] pyridin-4-yloxy)-N-(pyrimidin-4-yl)benzamide (Compound ID 64)

Preparation of (R)-tert-butyl 3-(1-(4-methoxybenzyl)-4-(4-(pyrimidin-4-ylcarbamoyl)phenoxy)-1H-pyrazolo[3,4-b]pyridin-3-ylamino)pyrrolidine-1-carboxylate (533-1)

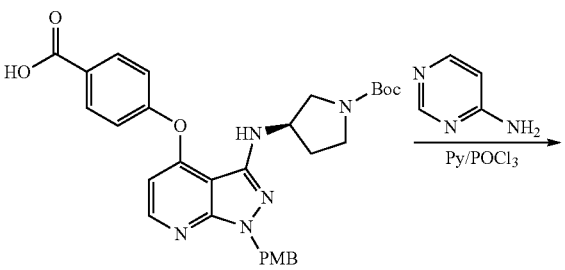

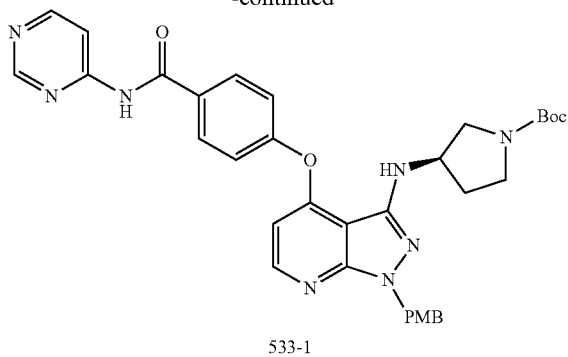

533-1

(R)-tert-Butyl 3-(1-(4-methoxybenzyl)-4-(4-(pyrimidin-4-ylcarbamoyl)phenoxy)-1H-pyrazolo[3,4-b]pyridin-3-ylamino)pyrrolidine-1-carboxylate (533-1) (110 mg, 39%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (250 mg, 0.44 mmol) and pyrimidin-4-amine (127 mg, 1.62 mmol), following a similar procedure outlined in Ex. 26. LC-MS (ESI): m/z (M+1) 637.2.

Preparation of (R)-4-(1-(4-methoxybenzyl)-3-(pyrrolidin-3-ylamino)-1H-pyrazolo[3,4-b]pyridin-4-yloxy)-N-(pyrimidin-4-yl)benzamide (533-2)

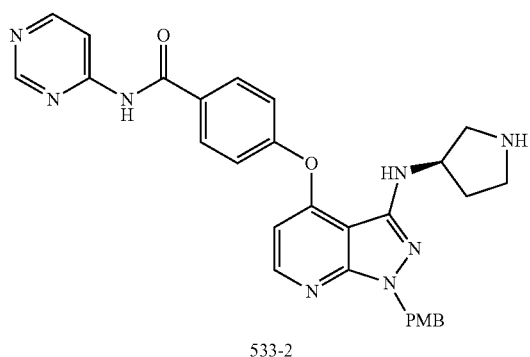

533-2

(R)-4-(1-(4-Methoxybenzyl)-3-(pyrrolidin-3-ylamino)-1H-pyrazolo[3,4-b]pyridin-4-yloxy)-N-(pyrimidin-4-yl)benzamide (533-2) (93 mg, 100%) was prepared from (R)-tert-butyl 3-(1-(4-methoxybenzyl)-4-(4-(pyrimidin-4-ylcarbamoyl)phenoxy)-1H-pyrazolo[3,4-b]pyridin-3-ylamino)pyrrolidine-1-carboxylate (533-1) (110 mg, 0.17 mmol), following a similar procedure outlined in Ex. 26. LC-MS (ESI): m/z (M+1) 537.1.

Preparation of (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(pyrimidin-4-yl)benzamide (533-3)

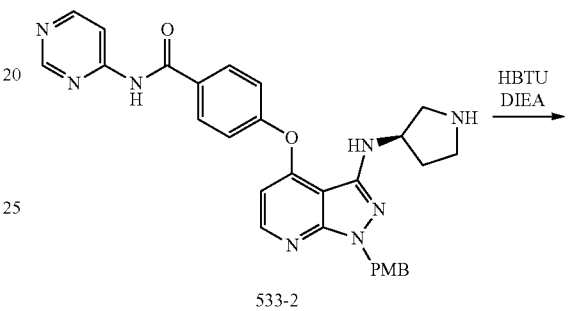

533-2

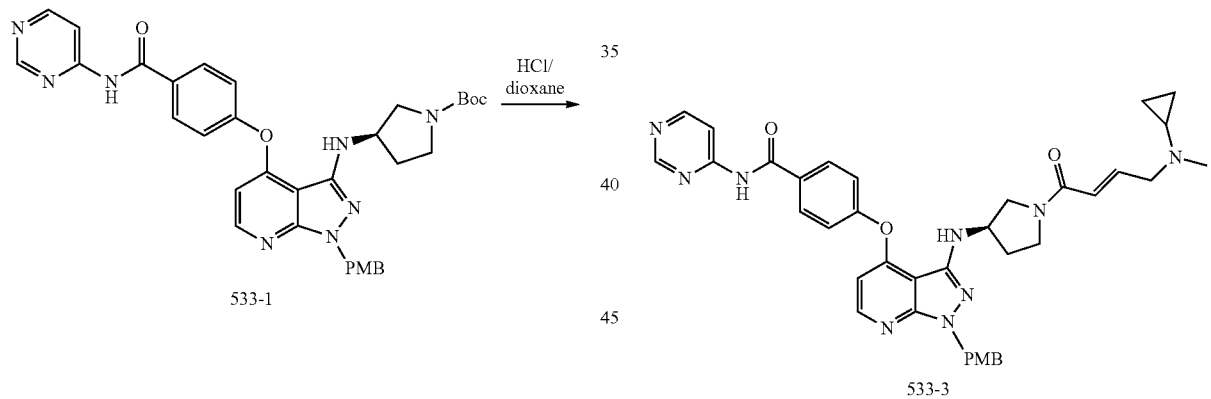

533-3

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(pyrimidin-4-yl)benzamide (533-3) (110 mg, 96%) was prepared from (R)-4-(1-(4-methoxybenzyl)-3-(pyrrolidin-3-ylamino)-1H-pyrazolo[3,4-b]pyridin-4-yloxy)-N-(pyrimidin-4-yl)benzamide (533-2) (93 mg, 0.17 mmol) and (E)-4-(cyclopropyl(methyl)amino)but-2-enoic acid HCl salt (83 mg, 0.26 mmol) following a similar procedure outlined in Ex. 26. LC-MS (ESI): m/z (M+1) 674.1.

Preparation of (R,E)-4-(3-(1-(4-(cyclopropyl (methyl)amino)but-2-enoyl)pyrrolidin-3-ylamino)-1H-pyrazolo[3,4-b]pyridin-4-yloxy)-N-(pyrimidin-4-yl)benzamide (533)

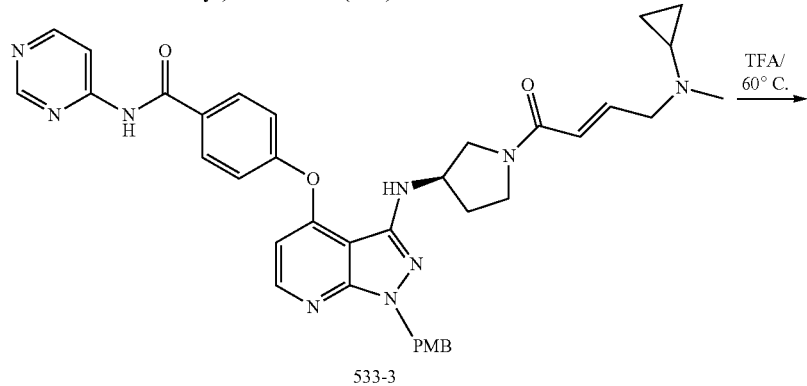

533-3

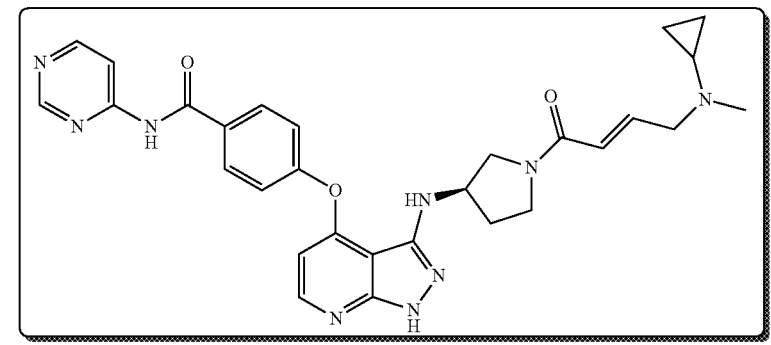

HDBPCYC-533

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(pyrimidin-4-yl)benzamide (533) (34 mg, 39%) was obtained as white solid from (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(pyrimidin-4-yl)benzamide (533-3) (110 mg, 0.16 mmol), following a similar procedure outlined in Ex. 26. LC-MS (ESI): m/z (M+1) 554.1.

Example 65
N-(cyanomethyl)-4-(4-(4-phenoxyphenoxy)-1H-pyrazolo[3,4-b]pyridin-3-ylamino)picolinamide (Compound ID 65)

Preparation of methyl 4-(1-(4-methoxybenzyl)-4-(4-phenoxyphenoxy)-1H-pyrazolo[3,4-b]pyridin-3-ylamino)picolinate (496-2)

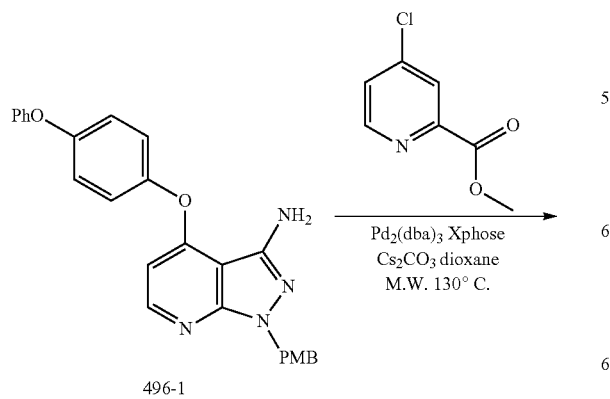

496-1

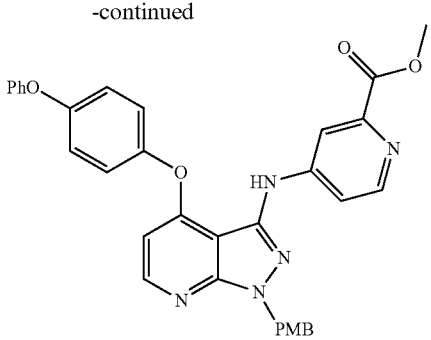

496-2

Methyl 4-(1-(4-methoxybenzyl)-4-(4-phenoxyphenoxy)-1H-pyrazolo[3,4-b]pyridin-3-ylamino)picolinate (496-2) (200 mg, 50%) was obtained as a yellow solid from 1-(4-methoxybenzyl)-4-(4-phenoxyphenoxy)-1H-pyrazolo[3,4-b]pyridin-3-amine (496-1) (390 mg, 0.89 mmol) and methyl 4-chloropicolinate (168 mg, 0.98 mmol), following a similar procedure outlined in Ex. 29. LC-MS (ESI): m/z (M+1) 574.2.

277

Preparation of methyl 4-(4-(4-phenoxyphenoxy)-1H-pyrazolo[3,4-b]pyridin-3-ylamino)picolinate (496-3)

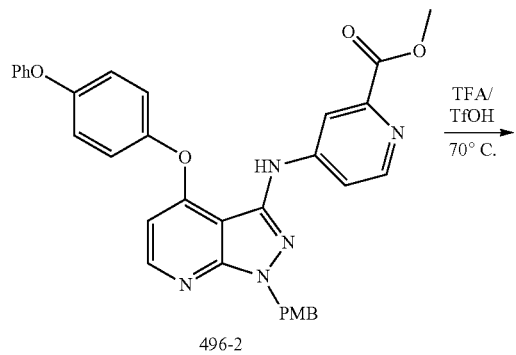

Methyl 4-(4-(4-phenoxyphenoxy)-1H-pyrazolo[3,4-b]pyridin-3-ylamino)picolinate (496-3) (90 mg, 60%) was obtained as a yellow solid from methyl 4-(1-(4-methoxybenzyl)-4-(4-phenoxyphenoxy)-1H-pyrazolo[3,4-b]pyridin-3-ylamino)picolinate (496-2) (200 mg, 0.35 mmol), following a similar procedure outlined in Ex. 23. LC-MS (ESI): m/z (M+1) 454.2.

Preparation of 4-(4-(4-phenoxyphenoxy)-1H-pyrazolo[3,4-b]pyridin-3-ylamino)picolinic acid (496-4)

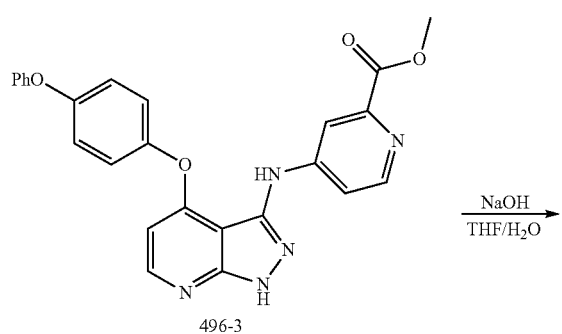

278

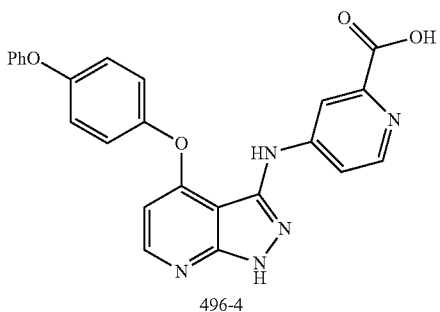

Methyl 4-(4-(4-phenoxyphenoxy)-1H-pyrazolo[3,4-b]pyridin-3-ylamino)picolinate (496-3) (90 mg, 0.2 mmol) was treated with NaOH in THF/H$_2$O to give 4-(4-(4-phenoxyphenoxy)-1H-pyrazolo[3,4-b]pyridin-3-ylamino)picolinic acid (496-4) (87 mg, quant.) as a yellow solid. LC-MS (ESI): m/z (M+1) 440.1.

Preparation of N-(cyanomethyl)-4-(4-(4-phenoxyphenoxy)-1H-pyrazolo[3,4-b]pyridin-3-ylamino)picolinamide (496)

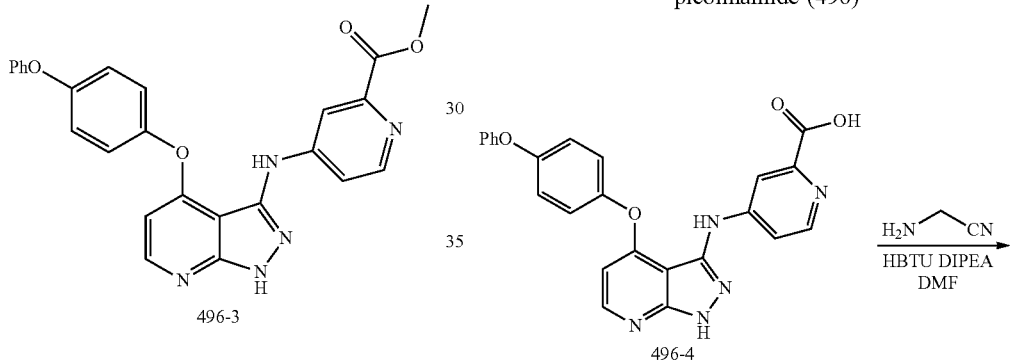

N-(Cyanomethyl)-4-(4-(4-phenoxyphenoxy)-1H-pyrazolo[3,4-b]pyridin-3-ylamino)picolinamide (496) (10 mg, 13%) was obtained as a white solid from 4-(4-(4-phenoxyphenoxy)-1H-pyrazolo[3,4-b]pyridin-3-ylamino)picolinic acid (496-4) (70 mg, 0.16 mmol) and 2-aminoacetonitrile sulfate (240 mg, 1.6 mmol), following a similar procedure outlined in Ex. 8. LC-MS (ESI): m/z (M+1) 478.1. $^1$H NMR (400 MHz, DMSO) δ 13.22 (s, 1H), 9.43-9.34 (m, 1H), 8.32 (d, J=5.4 Hz, 2H), 8.08 (s, 1H), 7.65-7.53 (m, 1H), 7.46-7.36 (m, 2H), 7.27 (d, J=8.8 Hz, 2H), 7.19-7.09 (m, 3H), 7.05 (d, J=8.6 Hz, 2H), 6.25 (d, J=5.4 Hz, 1H), 4.28 (d, J=5.8 Hz, 2H).

Example 66

(R)-4-(3-(1-propionylpyrrolidin-3-ylamino)-1H-pyrazolo[3,4-b]pyridin-4-yloxy)-N-(4-(trifluoromethyl)pyridin-2-yl)benzamide (Compound ID 66)

Preparation of (R)-tert-butyl 3-(1-(4-methoxybenzyl)-4-(4-(4-(trifluoromethyl)pyridin-2-ylcarbamoyl)phenoxy)-1H-pyrazolo[3,4-b]pyridin-3-ylamino)pyrrolidine-1-carboxylate (541-1)

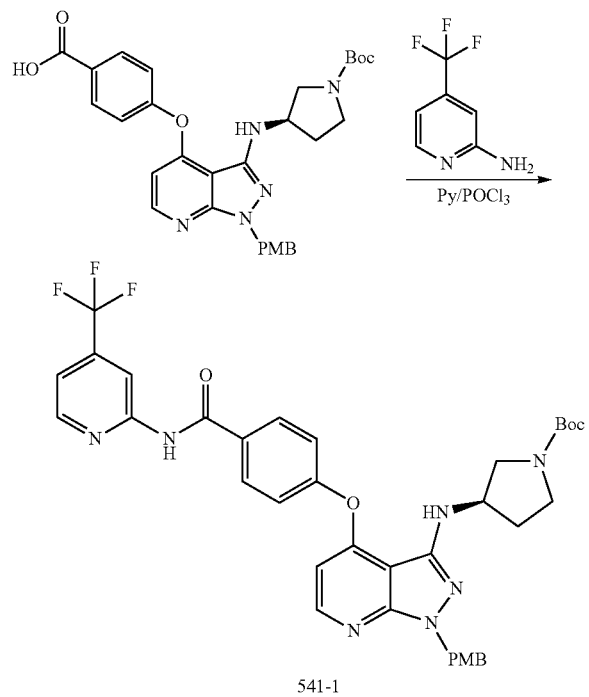

541-1

(R)-tert-Butyl 3-(1-(4-methoxybenzyl)-4-(4-(4-(trifluoromethyl)pyridin-2-ylcarbamoyl)phenoxy)-1H-pyrazolo[3,4-b]pyridin-3-ylamino)pyrrolidine-1-carboxylate (541-1) (90 mg, 47%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (150 mg, 0.27 mmol) and 4-(trifluoromethyl)pyridin-2-amine (130 mg, 0.8 mmol), following a similar procedure outlined in Ex. 26. LC-MS (ESI): m/z (M+1) 704.1.

Preparation of (R)-4-(1-(4-methoxybenzyl)-3-(pyrrolidin-3-ylamino)-1H-pyrazolo[3,4-b]pyridin-4-yloxy)-N-(4-(trifluoromethyl)pyridin-2-yl)benzamide (541-2)

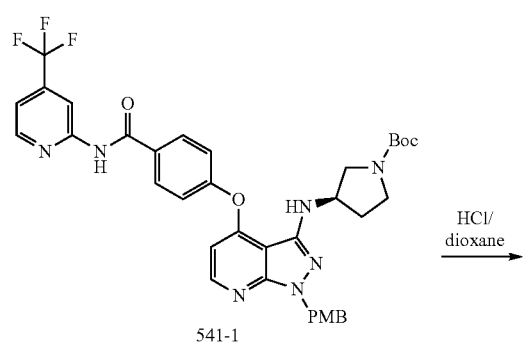

541-1

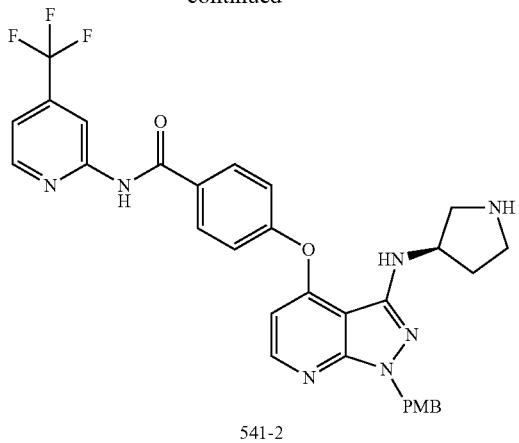

541-2

(R)-4-(1-(4-Methoxybenzyl)-3-(pyrrolidin-3-ylamino)-1H-pyrazolo[3,4-b]pyridin-4-yloxy)-N-(4-(trifluoromethyl)pyridin-2-yl)benzamide (541-2) (77 mg, 100%) was obtained as a yellow solid by treating (R)-tert-butyl 3-(1-(4-methoxybenzyl)-4-(4-(4-(trifluoromethyl)pyridin-2-ylcarbamoyl)phenoxy)-1H-pyrazolo[3,4-b]pyridin-3-ylamino)pyrrolidine-1-carboxylate (541-1) (90 mg, 0.13 mmol) with 4N HCl/Dioxane (mL) following a similar procedure in Ex. 26. LC-MS (ESI): m/z (M+1) 604.1.

Preparation of (R)-4-(1-(4-methoxybenzyl)-3-(1-propionylpyrrolidin-3-ylamino)-1H-pyrazolo[3,4-b]pyridin-4-yloxy)-N-(4-(trifluoromethyl)pyridin-2-yl)benzamide (541-3)

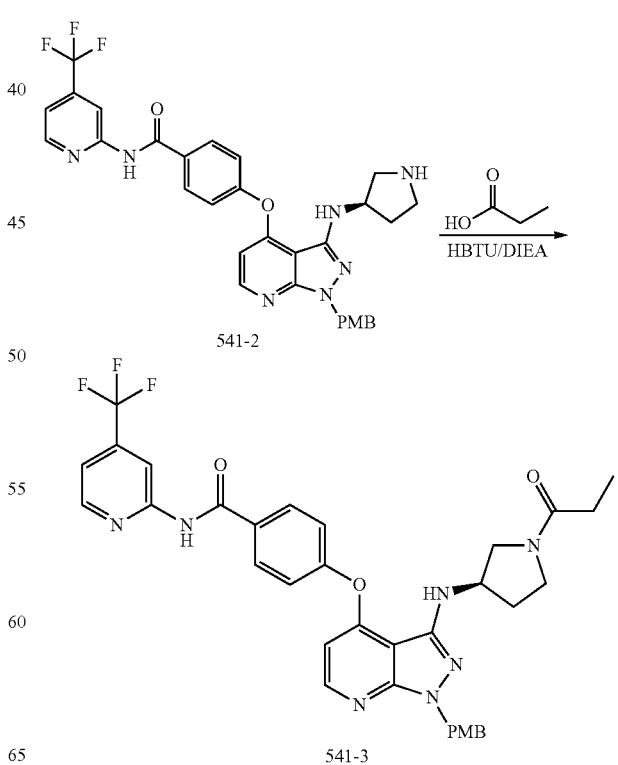

541-2

541-3

(R)-4-(1-(4-Methoxybenzyl)-3-(1-propionylpyrrolidin-3-ylamino)-1H-pyrazolo[3,4-b]pyridin-4-yloxy)-N-(4-(trifluoromethyl)pyridin-2-yl)benzamide (541-3) (80 mg, 95%) was obtained as a yellow solid from (R)-4-(1-(4-methoxybenzyl)-3-(pyrrolidin-3-ylamino)-1H-pyrazolo[3,4-b]pyridin-4-yloxy)-N-(4-(trifluoromethyl)pyridin-2-yl)benzamide (541-2) (77 mg, 0.12 mmol) and propionic acid (15 mg, 0.20 mmol), following a similar procedure in Ex. 26. LC-MS (ESI): m/z (M+1) 660.2.

Preparation of (R)-4-(3-(1-propionylpyrrolidin-3-ylamino)-1H-pyrazolo[3,4-b]pyridin-4-yloxy)-N-(4-(trifluoromethyl)pyridin-2-yl)benzamide (541)

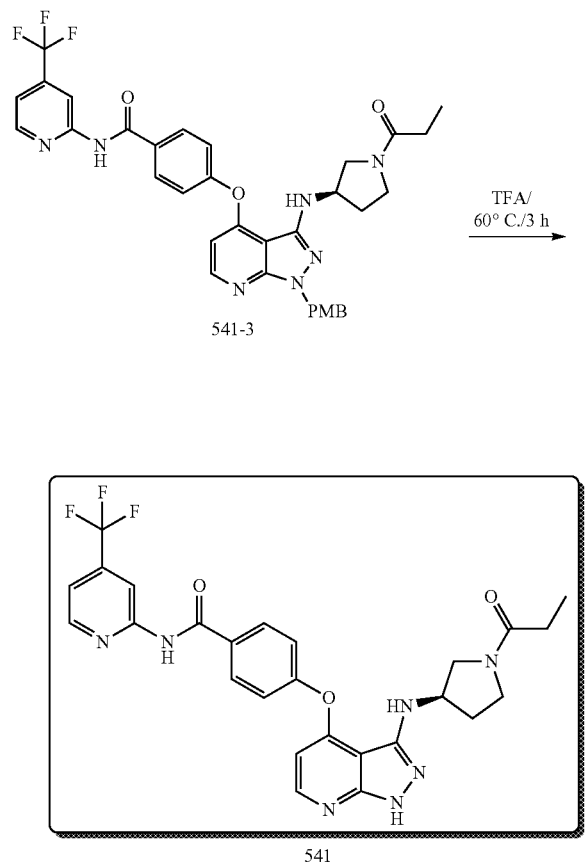

(R)-4-(3-(1-Propionylpyrrolidin-3-ylamino)-1H-pyrazolo[3,4-b]pyridin-4-yloxy)-N-(4-(trifluoromethyl)pyridin-2-yl)benzamide (541) (40 mg, 62%) was obtained as a white solid from (R)-4-(1-(4-methoxybenzyl)-3-(1-propionylpyrrolidin-3-ylamino)-1H-pyrazolo[3,4-b]pyridin-4-yloxy)-N-(4-(trifluoromethyl)pyridin-2-yl)benzamide (541-3) (80 mg, 0.12 mmol), following a similar procedure in Ex. 26. LC-MS (ESI): m/z (M+1) 540.1. $^1$H NMR (400 MHz, DMSO) δ 12.34 (s, 1H), 11.37 (s, 1H), 8.69 (d, J=5.2 Hz, 1H), 8.56 (s, 1H), 8.45 (s, 1H), 8.23-8.16 (m, 3H), 7.56 (d, J=5.1 Hz, 1H), 7.46-7.39 (m, 2H), 6.20-6.13 (m, 1H), 5.58 (dd, J=32.8, 5.7 Hz, 1H), 4.31-4.15 (m, 1H), 3.85-3.77 (m, 1H), 3.70-3.64 (m, 1H), 3.57-3.45 (m, 2H), 2.25-1.95 (m, 4H), 0.96 (td, J=7.3, 2.5 Hz, 3H).

Example 67

(R,E)-4-(3-(1-(4-(cyclopropyl(methyl)amino)but-2-enoyl)pyrrolidin-3-ylamino)-1H-pyrazolo[3,4-b]pyridin-4-yloxy)-N-(1H-imidazol-2-yl)benzamide (Compound ID 67)

Preparation of (S)-tert-butyl 3-(4-(4-(1H-imidazol-2-ylcarbamoyl)phenoxy)-1-(4-methoxybenzyl)-1H-pyrazolo[3,4-b]pyridin-3-ylamino)pyrrolidine-1-carboxylate (550-1)

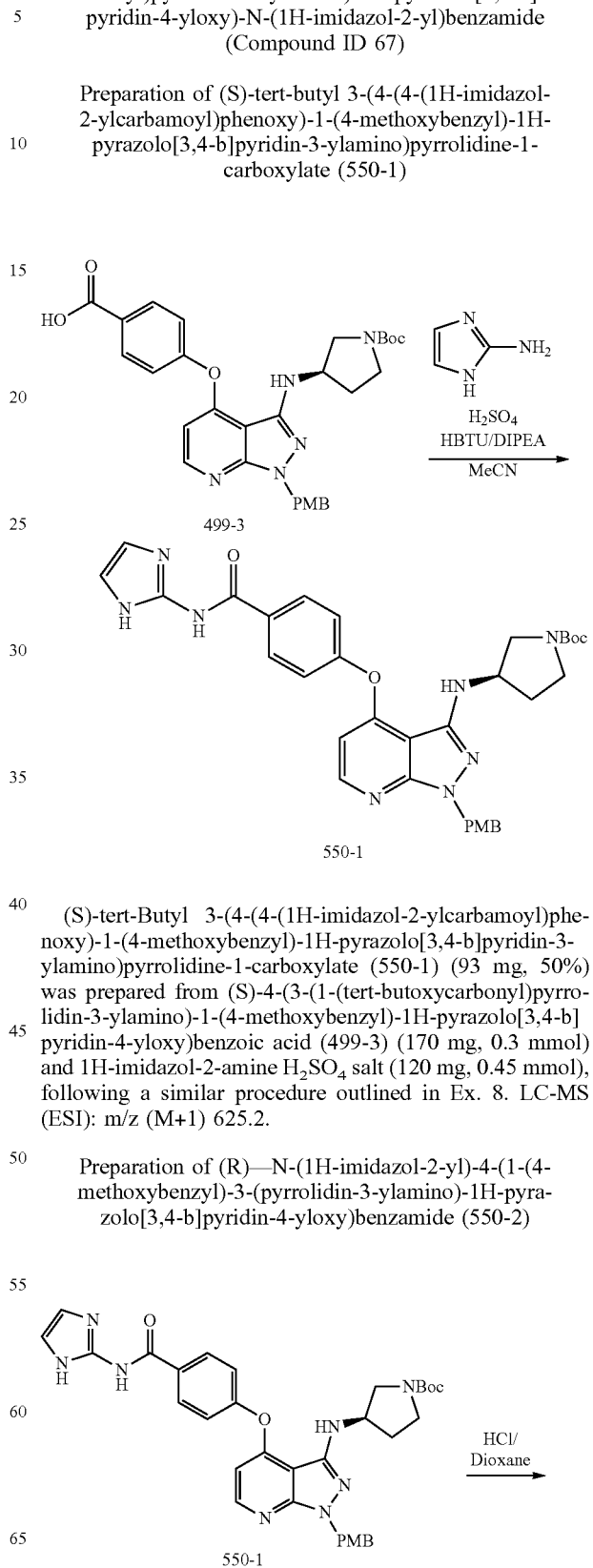

(S)-tert-Butyl 3-(4-(4-(1H-imidazol-2-ylcarbamoyl)phenoxy)-1-(4-methoxybenzyl)-1H-pyrazolo[3,4-b]pyridin-3-ylamino)pyrrolidine-1-carboxylate (550-1) (93 mg, 50%) was prepared from (S)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (499-3) (170 mg, 0.3 mmol) and 1H-imidazol-2-amine H$_2$SO$_4$ salt (120 mg, 0.45 mmol), following a similar procedure outlined in Ex. 8. LC-MS (ESI): m/z (M+1) 625.2.

Preparation of (R)—N-(1H-imidazol-2-yl)-4-(1-(4-methoxybenzyl)-3-(pyrrolidin-3-ylamino)-1H-pyrazolo[3,4-b]pyridin-4-yloxy)benzamide (550-2)

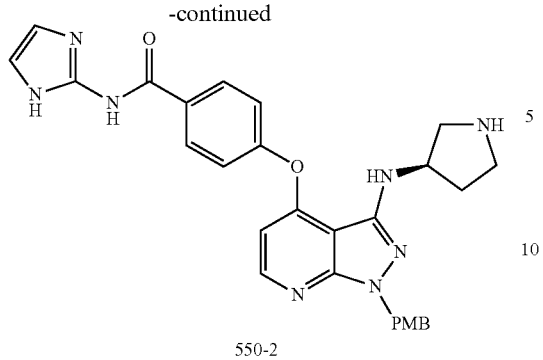

550-2

(R)—N-(1H-Imidazol-2-yl)-4-(1-(4-methoxybenzyl)-3-(pyrrolidin-3-ylamino)-1H-pyrazolo[3,4-b]pyridin-4-yloxy)benzamide (550-2) (78 mg, 100%) was obtained as a yellow solid from (S)-tert-butyl 3-(4-(4-(1H-imidazol-2-ylcarbamoyl)phenoxy)-1-(4-methoxybenzyl)-1H-pyrazolo[3,4-b]pyridin-3-ylamino)pyrrolidine-1-carboxylate (550-1) (93 mg, 0.15 mmol), following a similar procedure outlined in Ex. 26. LC-MS (ESI): m/z (M+1) 525.2.

Preparation of (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(1H-imidazol-2-yl)benzamide (550-3)

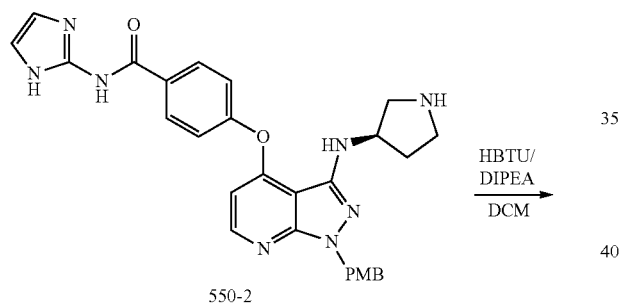

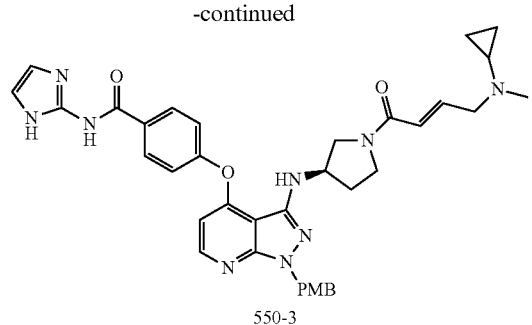

550-3

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(1H-imidazol-2-yl)benzamide (550-3) (90 mg, 92%) was obtained as a yellow solid from (R)—N-(1H-imidazol-2-yl)-4-(1-(4-methoxybenzyl)-3-(pyrrolidin-3-ylamino)-1H-pyrazolo[3,4-b]pyridin-4-yloxy)benzamide (550-2) (78 mg, 0.15 mmol), following a similar procedure outlined in Ex. 26. LC-MS (ESI): m/z (M+1) 662.3.

Preparation of (R,E)-4-(3-(1-(4-(cyclopropyl(methyl)amino)but-2-enoyl)pyrrolidin-3-ylamino)-1H-pyrazolo[3,4-b]pyridin-4-yloxy)-N-(1H-imidazol-2-yl)benzamide (550)

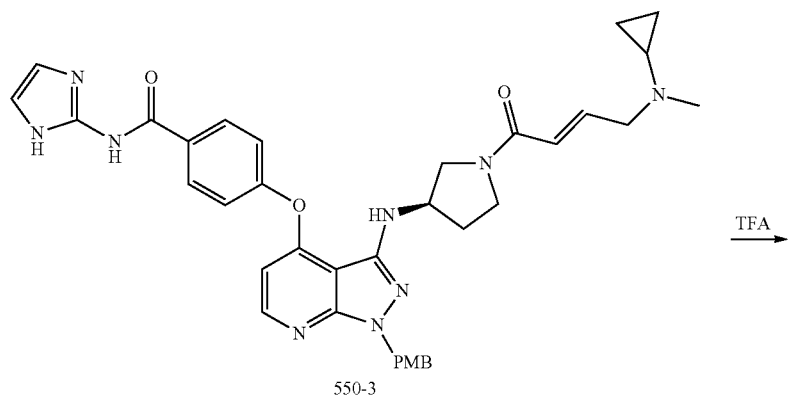

550-3

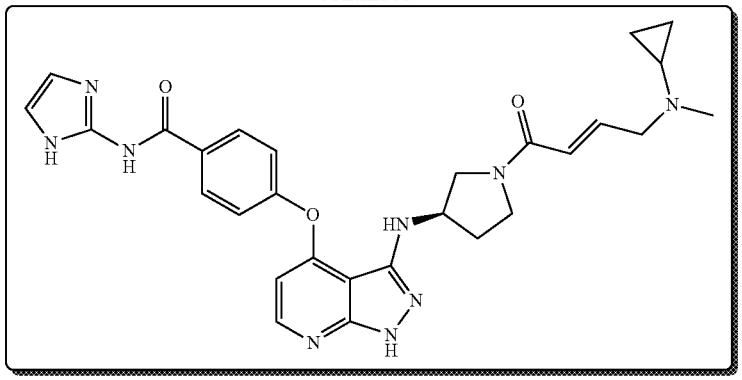

550

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(1H-imidazol-2-yl)benzamide (550) (28 mg, 38%) was obtained as a white solid from (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(1H-imidazol-2-yl)benzamide (550-3) (90 mg, 0.13 mmol) following a similar procedure outlined in Ex. 26. LC-MS (ESI): m/z (M+1) 542.1. $^1$H NMR (400 MHz, DMSO) δ 12.32 (s, 1H), 8.23-8.15 (m, 3H), 7.41-7.32 (m, 2H), 6.83 (s, 2H), 6.68-6.58 (m, 1H), 6.33 (t, J=15.0 Hz, 1H), 6.13 (t, J=5.9 Hz, 1H), 5.63 (dd, J=33.7, 5.7 Hz, 1H), 4.34-4.19 (m, 1H), 3.95-3.50 (m, 4H), 3.23 (d, J=6.4 Hz, 2H), 2.26-1.99 (m, 5H), 1.73-1.63 (m, 1H), 0.44-0.37 (m, 2H), 0.33-0.26 (m, 2H).

Example 68

(R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-(dimethylamino)pyridin-2-yl)benzamide (Compound ID 68)

Preparation of N$^4$,N$^4$-dimethylpyridine-2,4-diamine (528-1)

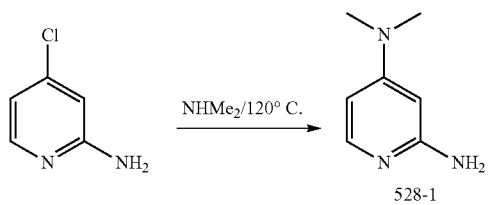

528-1

A stirred solution of 4-chloropyridin-2-amine (514 mg, 4 mmol) in NHMe$_2$ (10 mL, 30% in H$_2$O) was heated to 120° C. under MW. The reaction mixture was concentrated and the residue was purified by flash chromatography (silica gel, 0-50% ethyl acetate in petroleum ether) to provide N$^4$,N$^4$-dimethylpyridine-2,4-diamine (528-1) (540 mg, 99%) as a yellow solid. LC-MS (ESI): m/z (M+1) 138.2.

Preparation of (R)-tert-butyl 3-(4-(4-(4-(dimethylamino)pyridin-2-ylcarbamoyl)phenoxy)-1-(4-methoxybenzyl)-1H-pyrazolo[3,4-b]pyridin-3-ylamino)pyrrolidine-1-carboxylate (528-2)

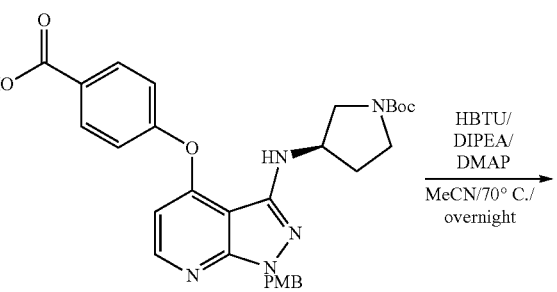

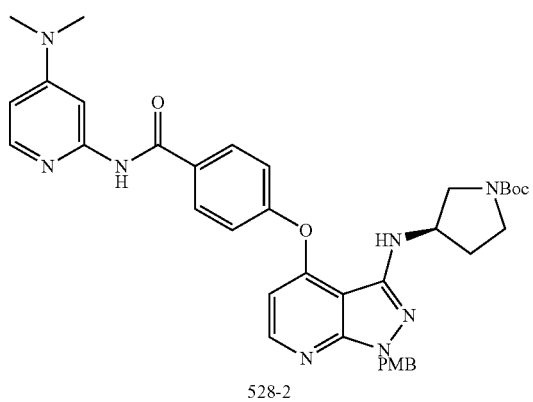

528-2

(R)-tert-Butyl 3-(4-(4-(4-(dimethylamino)pyridin-2-ylcarbamoyl)phenoxy)-1-(4-methoxybenzyl)-1H-pyrazolo[3,4-b]pyridin-3-ylamino)pyrrolidine-1-carboxylate (528-2) (150 mg, 60%) was obtained as a white solid from (R)-4-(3-(1-(tert-butoxycarbonyl) pyrrolidin-3-ylamino)-1-(4-methoxybenzyl)-1H-pyrazolo[3,4-b]pyridin-4-yloxy)benzoic acid (206 mg, 0.54 mmol) and N$^4$,N$^4$-dimethylpyridine-2,4-diamine (62 mg, 0.45 mmol), following a similar procedure in Ex. 8. LC-MS (ESI): m/z (M+1) 679.3.

287

Preparation of (R)—N-(4-(dimethylamino)pyridin-2-yl)-4-(1-(4-methoxybenzyl)-3-(pyrrolidin-3-ylamino)-1H-pyrazolo[3,4-b]pyridin-4-yloxy)benzamide (528-3)

288

Preparation of (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(4-(dimethylamino)pyridin-2-yl)benzamide (528-4)

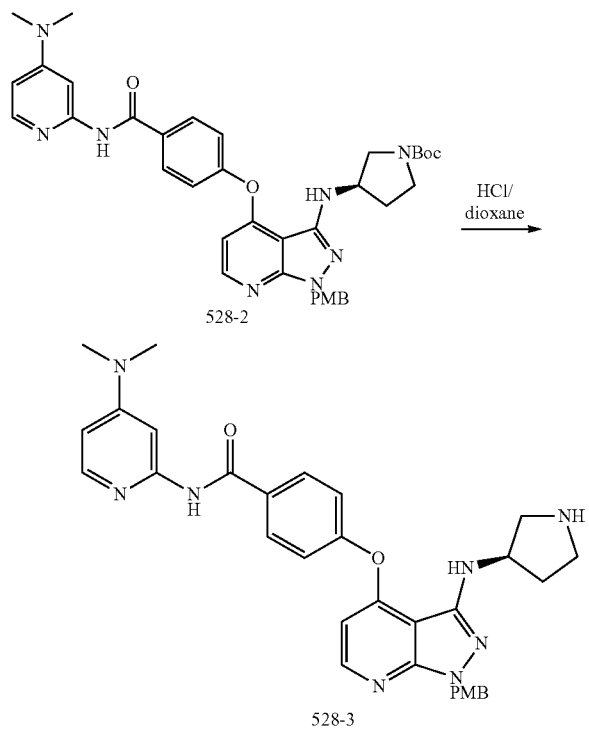

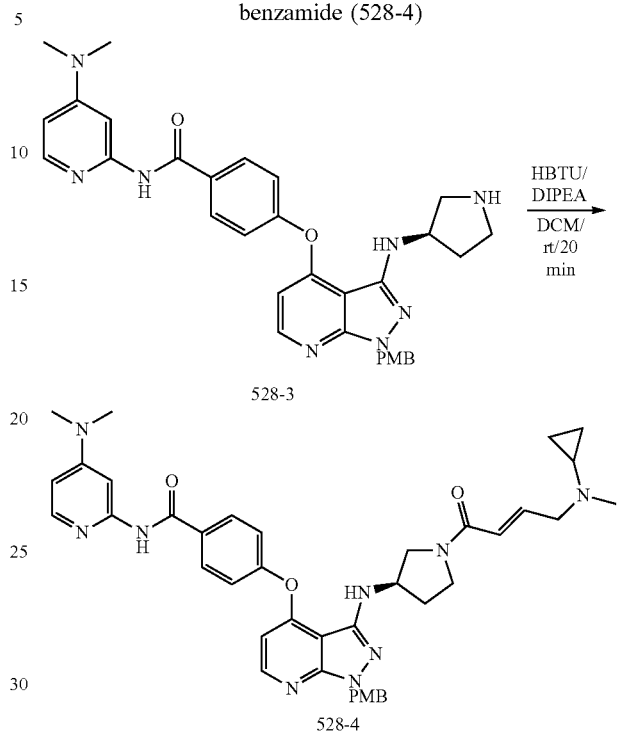

(R)—N-(4-(Dimethylamino)pyridin-2-yl)-4-(1-(4-methoxybenzyl)-3-(pyrrolidin-3-ylamino)-1H-pyrazolo[3,4-b]pyridin-4-yloxy)benzamide (528-3) (127 mg, 100%) was prepared from (R)-tert-butyl 3-(4-(4-(4-(dimethylamino)pyridin-2-ylcarbamoyl)phenoxy)-1-(4-methoxybenzyl)-1H-pyrazolo[3,4-b]pyridin-3-ylamino)pyrrolidine-1-carboxylate (528-2) (150 mg, 0.22 mmol), following a similar procedure outlined in Ex. 26. LC-MS (ESI): m/z (M+1) 579.2.

(R,E)-4-(3-(1-(4-(Cyclopropyl(methyl)amino)but-2-enoyl)pyrrolidin-3-ylamino)-1-(4-methoxybenzyl)-1H-pyrazolo[3,4-b]pyridin-4-yloxy)-N-(4-(dimethylamino)pyridin-2-yl)benzamide (528-4) (76 mg, 48%) was prepared from (R)—N-(4-(dimethylamino)pyridine-2-yl)-4-(1-(4-methoxybenzyl)-3-(pyrrolidin-3-ylamino)-1H-pyrazolo[3,4-b]pyridin-4-yloxy)benzamide (127 mg, 0.22 mmol) (528-3) and (E)-4-(cyclopropyl(methyl)amino)but-2-enoic acid HCl salt (48 mg, 0.24 mmol), following a similar procedure outlined in Ex. 26. LC-MS (ESI): m/z (M+1) 716.2.

Preparation of (R,E)-4-(3-(1-(4-(cyclopropyl(methyl)amino)but-2-enoyl)pyrrolidin-3-ylamino)-1H-pyrazolo[3,4-b]pyridin-4-yloxy)-N-(4-(dimethylamino)pyridin-2-yl)benzamide (528)

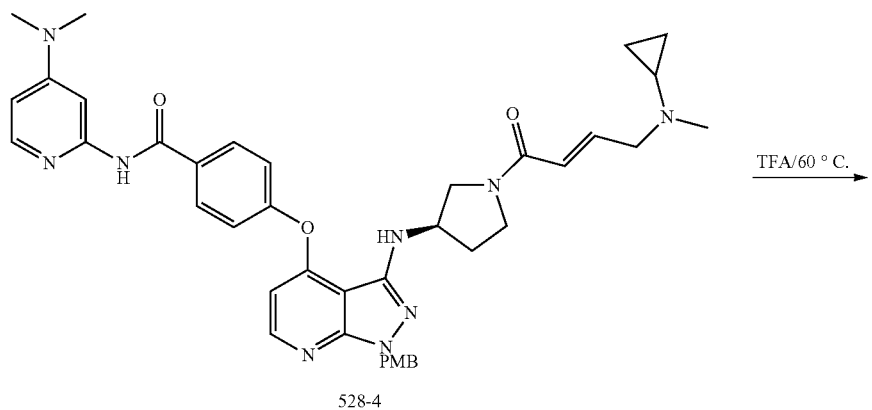

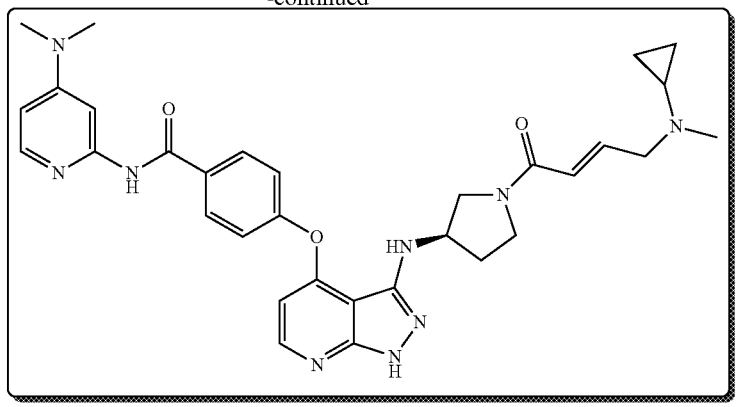

528

(R,E)-4-(3-(1-(4-(Cyclopropyl(methyl)amino)but-2-enoyl)pyrrolidin-3-ylamino)-1H-pyrazolo[3,4-b]pyridin-4-yloxy)-N-(4-(dimethylamino)pyridin-2-yl)benzamide (528) (22 mg, 33%) was obtained as a white solid from (R,E)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)-N-(4-(dimethylamino)pyridin-2-yl)benzamide (528-4) (76 mg, 0.11 mmol), following a similar procedure outlined in Ex. 26. LC-MS (ESI): m/z (M+1) 596.2. $^1$H NMR (400 MHz, DMSO) δ 12.36 (s, 1H), 8.22-8.14 (m, 3H), 7.98 (d, J=6.2 Hz, 1H), 7.45 (d, J=7.0 Hz, 2H), 7.18 (s, 1H), 6.72-6.60 (m, 2H), 6.51-6.43 (m, 1H), 6.17 (s, 1H), 5.63 (d, J=23.4 Hz, 1H), 4.35-4.21 (m, 1H), 3.99-3.44 (m, 3H), 3.10 (s, 8H), 2.46-1.96 (m, 5H), 1.24 (s, 1H), 0.71-0.38 (m, 4H).

Example 69

(R)—N-(1H-benzo[d]imidazol-2-yl)-4-(3-(1-propionylpyrrolidin-3-ylamino)-1H-pyrazolo[3,4-b]pyridin-4-yloxy)benzamide (Compound ID 69)

Preparation of (R)—N-(1H-benzo[d]imidazol-2-yl)-4-(1-(4-methoxybenzyl)-3-(1-propionylpyrrolidin-3-ylamino)-1H-pyrazolo[3,4-b]pyridin-4-yloxy)benzamide (543-1)

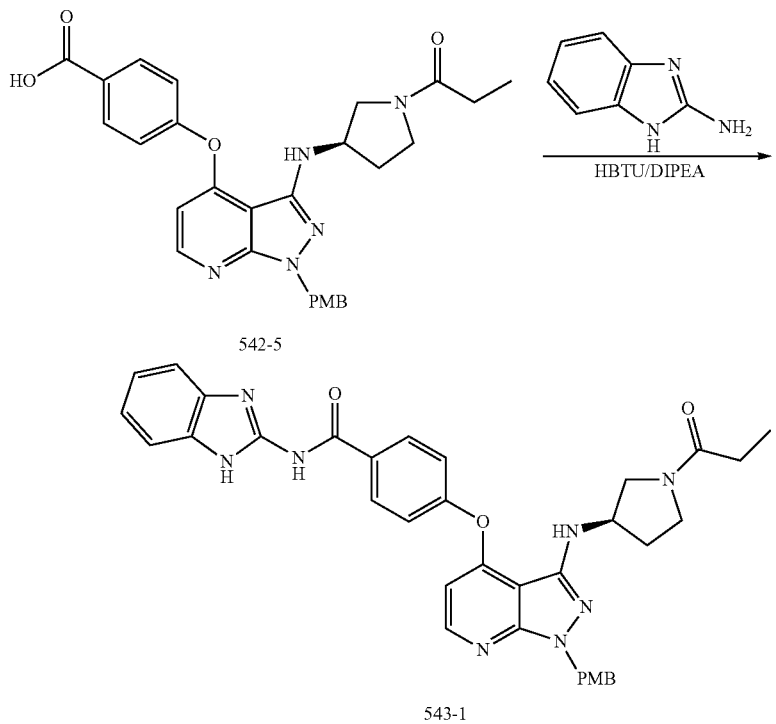

(R)—N-(1H-Benzo[d]imidazol-2-yl)-4-(1-(4-methoxybenzyl)-3(1-propionylpyrrolidin-3-ylamino)-1H-pyrazolo[3,4-b]pyridin-4-yloxy)benzamide (543-1) (95 mg, 52%) was prepared from (R)-4-(1-(4-methoxybenzyl)-3-(1-propionylpyrrolidin-3-ylamino)-1H-pyrazolo[3,4-b]pyridin-4-yloxy)benzoic acid (542-5) (150 mg, 0.29 mmol) and 1H-benzo[d]imidazol-2-amine (58 mg, 0.44 mmol), following a similar procedure in Ex. 26. LC-MS (ESI): m/z (M+1) 631.3.

Preparation of (R)—N-(1H-benzo[d]imidazol-2-yl)-4-(3-(1-propionylpyrrolidin-3-ylamino)-1H-pyrazolo[3,4-b]pyridin-4-yloxy)benzamide (543)

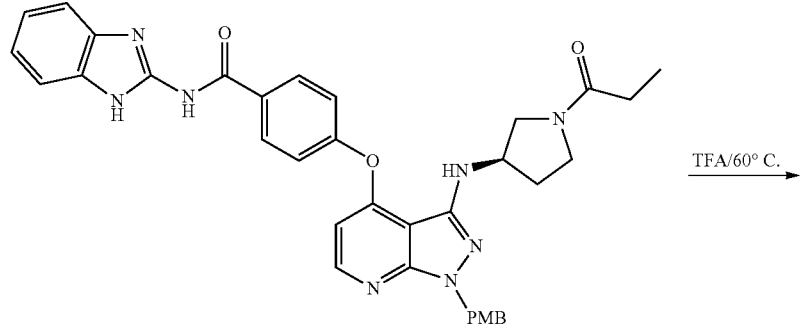

543-1

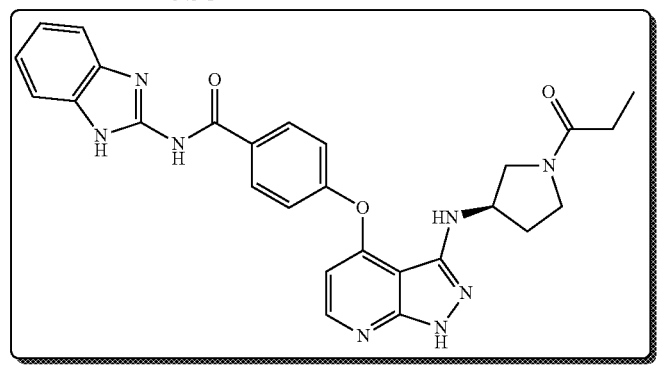

543

(R)—N-(1H-Benzo[d]imidazol-2-yl)-4-(3-(1-propionylpyrrolidin-3-ylamino)-1H-pyrazolo[3,4-b]pyridin-4-yloxy)benzamide (543) (35 mg, 45%) was obtained as a white solid from (R)—N-(1H-Benzo[d]imidazol-2-yl)-4-(1-(4-methoxybenzyl)-3-(1-propionylpyrrolidin-3-ylamino)-1H-pyrazolo[3,4-b]pyridin-4-yloxy)benzamide (543-1) (95 mg, 0.15 mmol), following a similar procedure in Ex. 26. LC-MS (ESI): m/z (M+1) 511.1. $^{1}$H NMR (400 MHz, DMSO) δ 12.32 (s, 2H), 8.29 (d, J=7.5 Hz, 2H), 8.19 (s, 1H), 7.45-7.40 (m, 4H), 7.15 (s, 2H), 6.16 (s, 1H), 5.62-5.54 (m, 1H), 4.24-3.82 (m, 4H), 2.22-1.92 (m, 4H), 1.03-0.89 (m, 3H).

Example 70

(R)-4-(3-(1-propionylpyrrolidin-3-ylamino)-1H-pyrazolo[3,4-b]pyridin-4-ylamino)-N-(4-(trifluoromethyl)pyridin-2-yl)benzamide (Compound ID 70)

Preparation of methyl 4-(3-iodo-1-(4-methoxybenzyl)-1H-pyrazolo[3,4-b]pyridin-4-ylamino)benzoate (547-1)

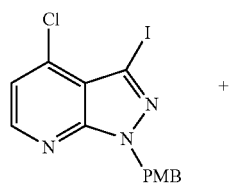

291-7

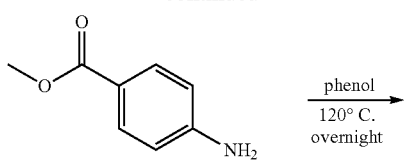

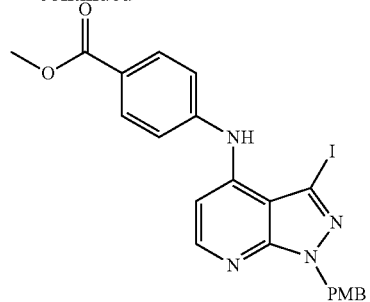

547-1

Methyl 4-(3-iodo-1-(4-methoxybenzyl)-1H-pyrazolo[3,4-b]pyridin-4-ylamino)benzoate (547-1) (645 mg, 50% yield) was obtained as a light yellow solid from 4-chloro-3-iodo-1-(4-methoxybenzyl)-1H-pyrazolo[3,4-b]pyridine (291-7) (1.0 g, 2.5 mmol) and methyl 4-aminobenzoate (456 mg, 3.0 mmol), following a similar procedure outlined in the preparation of 3-iodo-1-(4-methoxybenzyl)-N-(4-phenoxyphenyl)-1H-pyrazolo[3,4-b]pyridin-4-amine (386-1) (Ex. 23). LC-MS (ESI): m/z (M+1) 515.4.

Preparation of (R)-tert-butyl 3-(1-(4-methoxybenzyl)-4-(4-(methoxycarbonyl)phenylamino)-1H-pyrazolo[3,4-b]pyridin-3-ylamino)pyrrolidine-1-carboxylate (547-2)

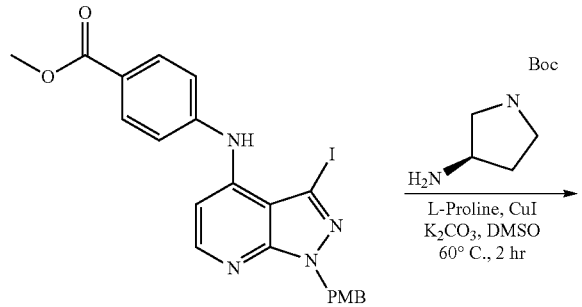

(R)-tert-Butyl 3-(1-(4-methoxybenzyl)-4-(4-(methoxycarbonyl)phenylamino)-1H-pyrazolo[3,4-b]pyridin-3-ylamino)pyrrolidine-1-carboxylate (547-2) (100 mg, 36% yield) was obtained as a light yellow oil from methyl 4-(3-iodo-1-(4-methoxybenzyl)-1H-pyrazolo[3,4-b]pyridin-4-ylamino)benzoate (547-1) (250 mg, 0.49 mmol), and (R)-tert-butyl 3-aminopyrrolidine-1-carboxylate (360 mg, 1.9 mmol), following a similar procedure outlined in the preparation of (R)-tert-butyl3-(4-(4-chlorophenoxy)-1-(4-methoxybenzyl)-1H-pyrazolo[3,4-b]pyridin-3-ylamino)pyrrolidine-1-carboxylate (291-9) (Ex. 1). LC-MS (ESI): m/z (M+1) 573.3.

Preparation of (R)-methyl 4-(1-(4-methoxybenzyl)-3-(1-propionylpyrrolidin-3-ylamino)-1H-pyrazolo[3,4-b]pyridin-4-ylamino)benzoate (547-3)

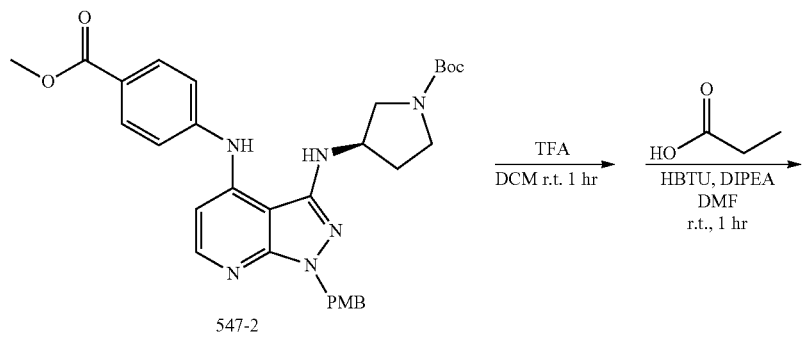

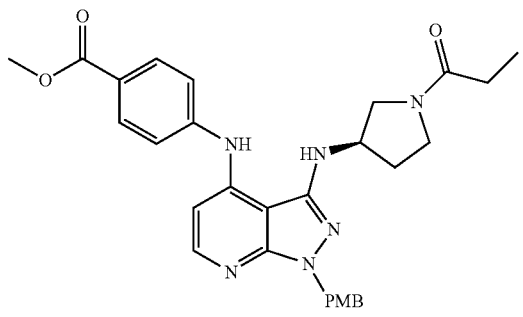

(R)-Methyl 4-(1-(4-methoxybenzyl)-3-(1-propionylpyrrolidin-3-ylamino)-1H-pyrazolo[3,4-b]pyridin-4-ylamino)benzoate (547-3) (67 mg, 73% yield) was obtained as a colorless oil from (R)-tert-butyl 3-(1-(4-methoxybenzyl)-4-(4-(methoxycarbonyl)phenyl amino)-1H-pyrazolo[3,4-b]pyridin-3-ylamino)pyrrolidine-1-carboxylate (547-2) (100 mg, 0.18 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 529.3.

Preparation of (R)-4-(1-(4-methoxybenzyl)-3-(1-propionylpyrrolidin-3-ylamino)-1H-pyrazolo[3,4-b]pyridin-4-ylamino)benzoic acid (547-4)

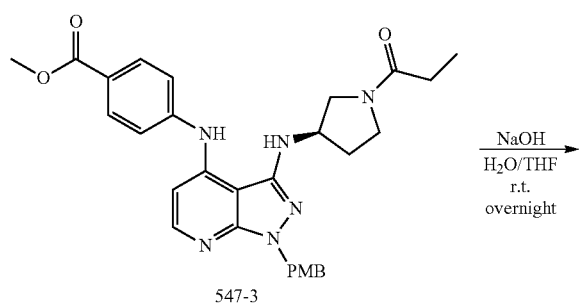

547-3

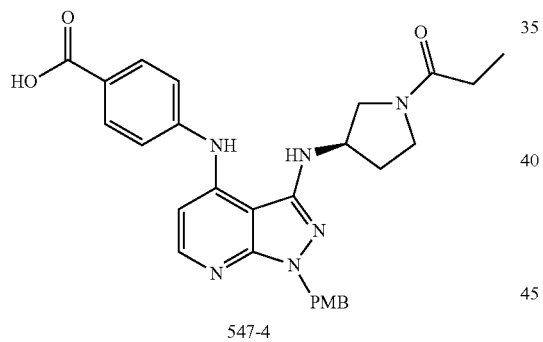

547-4

To a solution of (R)-methyl 4-(1-(4-methoxybenzyl)-3-(1-propionylpyrrolidin-3-yl amino)-1H-pyrazolo[3,4-b]pyridin-4-ylamino)benzoate (547-3) (64 mg, 0.12 mmol) in THF (2 mL) and H$_2$O (1 mL) was added NaOH (15 mg, 0.36 mmol). After stirred at r.t. overnight, the reaction mixture was acidified to pH ~3 with 1N HCl and extracted with 15% i-PrOH in DCM (10 mL×3). The combined organic phase was washed with brine, dried over Na$_2$SO$_4$, filtered and concentrated under reduced pressure to afford (R)-4-(1-(4-methoxybenzyl)-3-(1-propionylpyrrolidin-3-ylamino)-1H-pyrazolo[3,4-b]pyridin-4-ylamino)benzoic acid (547-4) (62 mg, quant. yield) as a colorless oil. LC-MS (ESI): m/z (M+1) 515.5.

Preparation of (R)-4-(1-(4-methoxybenzyl)-3-(1-propionylpyrrolidin-3-ylamino)-1H-pyrazolo[3,4-b]pyridin-4-ylamino)-N-(4-(trifluoromethyl)pyridin-2-yl)benzamide (547-5)

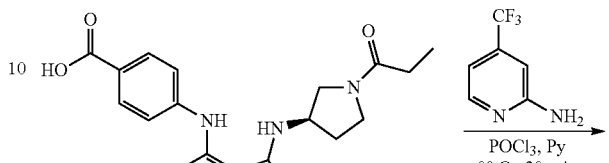

547-4

547-5

At 0° C., to a solution of (R)-4-(1-(4-methoxybenzyl)-3-(1-propionylpyrrolidin-3-ylamino)-1H-pyrazolo[3,4-b]pyridin-4-ylamino)benzoic acid (547-4) (140 mg, 0.27 mmol) and 4-(trifluoromethyl)pyridin-2-amine (118 mg, 0.72 mmol) in anhydrous pyridine (4 mL) was added POCl$_3$ (0.11 mL, 1.2 mmol) dropwise. After stirred at 0° C. for 30 min, the reaction mixture was quenched with sat. NaHCO$_3$ solution (10 mL) and extracted with 15% i-PrOH in DCM (10 mL×3). The combined organic phase was washed with brine, dried over Na$_2$SO$_4$, filtered and concentrated under reduced pressure to give the crude product which was purified by flash chromatography (0 to 10% MeOH in DCM) to afford (R)-4-(1-(4-methoxybenzyl)-3-(1-propionylpyrrolidin-3-ylamino)-1H-pyrazolo[3,4-b]pyridin-4-ylamino)-N-(4-(trifluoromethyl)pyridin-2-yl)benzamide (547-5) (42 mg, 23% yield) as a light yellow oil. LC-MS (ESI): m/z (M+1) 659.1.

297

Preparation of (R)-4-(3-(1-propionylpyrrolidin-3-ylamino)-1H-pyrazolo[3,4-b]pyridin-4-ylamino)-N-(4-(trifluoromethyl)pyridin-2-yl)benzamide (547)

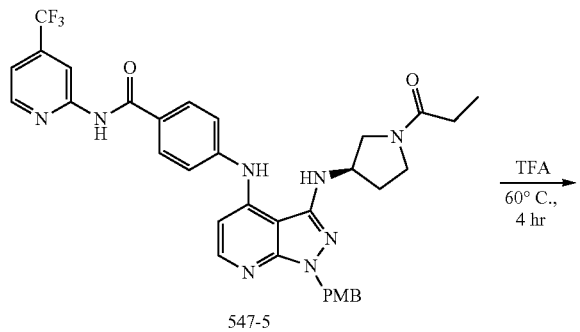
547-5

TFA
60° C., 4 hr

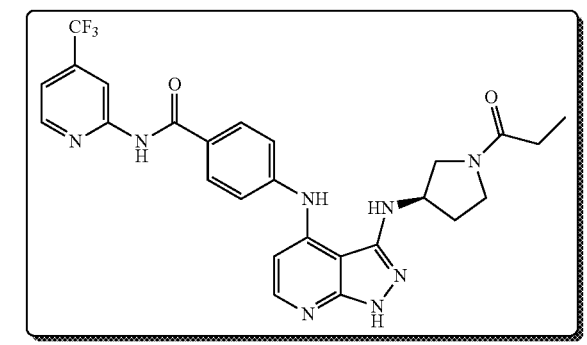
547

(R)-4-(3-(1-propionylpyrrolidin-3-ylamino)-1H-pyrazolo[3,4-b]pyridin-4-ylamino)-N-(4-(trifluoromethyl)pyridin-2-yl)benzamide (547) (20 mg, 58% yield) was obtained as a white powder from (R)-4-(1-(4-methoxybenzyl)-3-(1-propionylpyrrolidin-3-ylamino)-1H-pyrazolo[3,4-b]pyridin-4-ylamino)-N-(4-(trifluoromethyl)pyridin-2-yl)benzamide (547-5) (42 mg, 0.06 mmol), following a similar procedure outlined in the preparation of (R)-1-(3-(4-(4-chlorophenoxy)-1H-pyrazolo[3,4-b]pyridin-3-ylamino) pyrrolidin-1-yl)prop-2-en-1-one (291) (Ex. 1). LC-MS (ESI): m/z (M+1) 539.4. $^1$H NMR (400 MHz, DMSO) δ 12.11 (s, 1H), 11.16 (s, 1H), 8.69 (d, J=10.2 Hz, 2H), 8.56 (s, 1H), 8.30 (s, 1H), 8.13-8.02 (m, 2H), 7.53 (d, J=6.0 Hz, 1H), 7.38 (d, J=9.6 Hz, 2H), 6.66 (d, J=5.0 Hz, 1H), 5.91 (d, J=34.8 Hz, 1H), 4.36-3.49 (m, 4H), 2.30-2.17 (m, 2H), 2.13-1.84 (m, 2H), 0.96 (t, J=6.6 Hz, 3H).

298

Example 71

(R)-4-(3-(1-propionylpyrrolidin-3-yloxy)-1H-pyrazolo[3,4-b]pyridin-4-ylamino)-N-(4-(trifluoromethyl)pyridin-2-yl)benzamide (Compound ID 71)

Preparation of (R)-tert-butyl 3-(1-(4-methoxybenzyl)-4-(4-(methoxycarbonyl)phenylamino)-1H-pyrazolo[3,4-b]pyridin-3-yloxy)pyrrolidine-1-carboxylate (548-1)

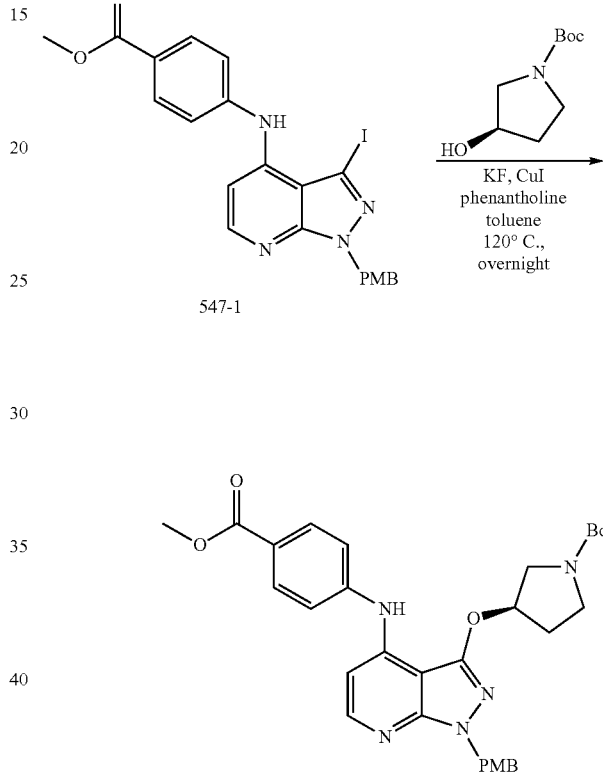

(R)-tert-Butyl 3-(1-(4-methoxybenzyl)-4-(4-(methoxycarbonyl)phenylamino)-1H-pyrazolo[3,4-b]pyridin-3-yloxy)pyrrolidine-1-carboxylate (548-1) (crude) was obtained as a yellow oil together with (R)-tert-butyl 3-hydroxypyrrolidine-1-carboxylate from methyl 4-(3-iodo-1-(4-methoxybenzyl)-1H-pyrazolo[3,4-b]pyridin-4-ylamino) benzoate (547-1) (950 mg, 1.8 mmol) and (R)-tert-butyl 3-hydroxypyrrolidine-1-carboxylate (6.8 g, 37 mmol), following a similar procedure outlined in the preparation of (R)-tert-butyl 3-(1-(4-methoxybenzyl)-4-(4-phenoxyphenylamino)-1H-pyrazolo[3,4-b]pyridin-3-yloxy)pyrrolidine-1-carboxylate (386-2) (Ex. 23). LC-MS (ESI): m/z (M+1) 574.3.

Preparation of (R)-methyl 4-(1-(4-methoxybenzyl)-3-(1-propionylpyrrolidin-3-yloxy)-1H-pyrazolo[3,4-b]pyridin-4-ylamino)benzoate (548-2)

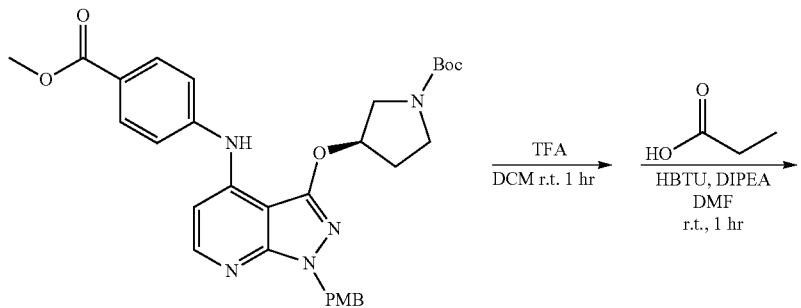

(R)-Methyl 4-(1-(4-methoxybenzyl)-3-(1-propionylpyrrolidin-3-yloxy)-1H-pyrazolo[3,4-b]pyridin-4-ylamino)benzoate (548-2) (152 mg, 16% yield for three steps) was obtained as a light yellow oil from (R)-tert-butyl 3-(1-(4-methoxybenzyl)-4-(4-(methoxy carbonyl)phenylamino)-1H-pyrazolo[3,4-b]pyridin-3-yloxy)pyrrolidine-1-carboxylate (548-1) (crude, directly used in this step), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 530.2.

Preparation of (R)-4-(1-(4-methoxybenzyl)-3-(1-propionylpyrrolidin-3-yloxy)-1H-pyrazolo[3,4-b]pyridin-4-ylamino)benzoic acid (548-3)

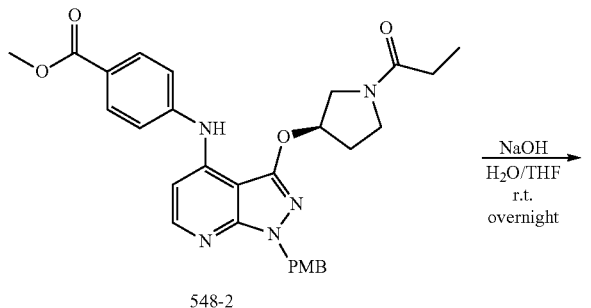

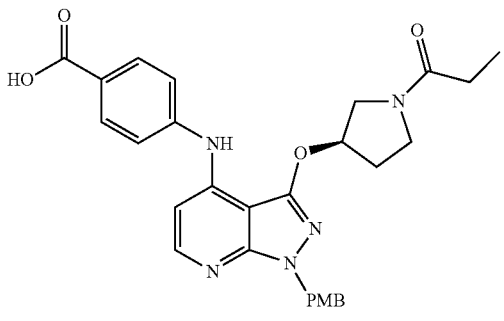

(R)-4-(1-(4-Methoxybenzyl)-3-(1-propionylpyrrolidin-3-yloxy)-1H-pyrazolo[3,4-b]pyridin-4-ylamino)benzoic acid (548-3) (145 mg, quant. yield) was obtained as a white solid from (R)-methyl 4-(1-(4-methoxybenzyl)-3-(1-propionylpyrrolidin-3-yloxy)-1H-pyrazolo[3,4-b]pyridin-4-ylamino)benzoate (548-2) (152 mg, 0.28 mmol), following a similar procedure outlined in the preparation of (R)-4-(1-(4-methoxybenzyl)-3-(1-propionyl pyrrolidin-3-ylamino)-1H-pyrazolo[3,4-b]pyridin-4-ylamino)benzoic acid (547-4) (Ex. 28). LC-MS (ESI): m/z (M+1) 516.5.

Preparation of (R)-4-(1-(4-methoxybenzyl)-3-(1-propionylpyrrolidin-3-yloxy)-1H-pyrazolo[3,4-b]pyridin-4-ylamino)-N-(4-(trifluoromethyl)pyridin-2-yl)benzamide (548-4)

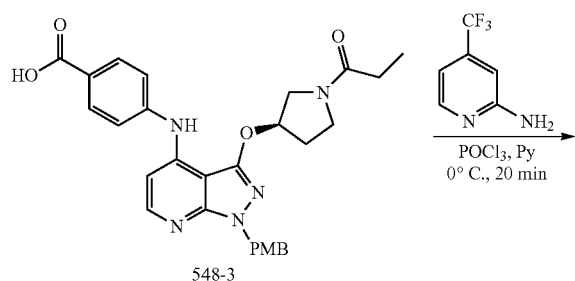

548-3

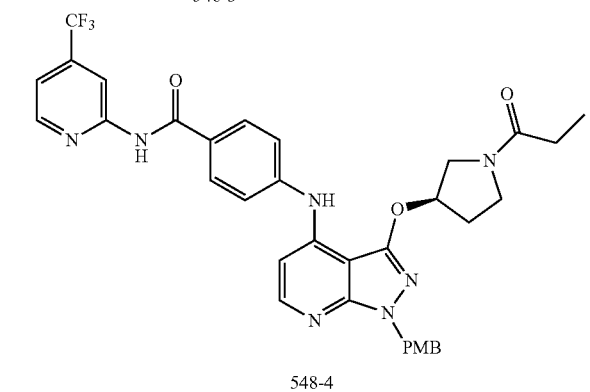

548-4

(R)-4-(1-(4-Methoxybenzyl)-3-(1-propionylpyrrolidin-3-yloxy)-1H-pyrazolo[3,4-b]pyridin-4-ylamino)-N-(4-(trifluoromethyl)pyridin-2-yl)benzamide (548-4) (80 mg, 45% yield) was obtained as a light yellow solid from (R)-4-(1-(4-methoxybenzyl)-3-(1-propionylpyrrolidin-3-yloxy)-1H-pyrazolo[3,4-b]pyridin-4-ylamino)benzoic acid (548-3) (145 mg, 0.28 mmol) and 4-(trifluoromethyl)pyridin-2-amine (223 mg, 1.4 mmol), following a similar procedure outlined in the preparation of (R)-4-(1-(4-methoxybenzyl)-3-(1-propionyl pyrrolidin-3-ylamino)-1H-pyrazolo[3,4-b]pyridin-4-ylamino)-N-(4-(trifluoromethyl)pyridin-2-yl)benzamide (547-5) (Ex. 28). LC-MS (ESI): m/z (M+1) 660.3.

Preparation of (R)-4-(3-(1-propionylpyrrolidin-3-yloxy)-1H-pyrazolo[3,4-b]pyridin-4-ylamino)-N-(4-(trifluoromethyl)pyridin-2-yl)benzamide (548)

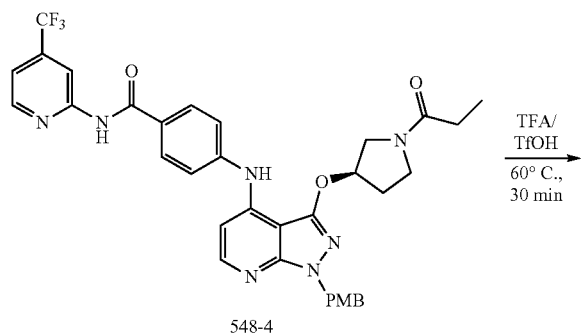

548-4

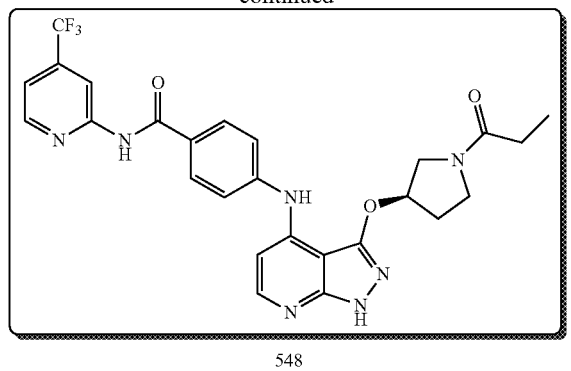

548

(R)-4-(3-(1-Propionylpyrrolidin-3-yloxy)-1H-pyrazolo[3,4-b]pyridin-4-ylamino)-N-(4-(trifluoromethyl)pyridin-2-yl)benzamide (548) (32 mg, 49% yield) was obtained as a white powder from (R)-4-(1-(4-methoxybenzyl)-3-(1-propionylpyrrolidin-3-yloxy)-1H-pyrazolo[3,4-b]pyridin-4-ylamino)-N-(4-(trifluoromethyl)pyridin-2-yl)benzamide (548-4) (80 mg, 0.12 mmol) with TFA (5 mL) and one drop of TfOH, following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 540.3. $^1$H NMR (400 MHz, DMSO) δ 12.41 (s, 1H), 11.15 (s, 1H), 8.67 (d, J=4.8 Hz, 1H), 8.56 (s, 1H), 8.45 (s, 1H), 8.16 (d, J=5.6 Hz, 1H), 8.06 (d, J=8.0 Hz, 2H), 7.52 (d, J=5.0 Hz, 1H), 7.35 (d, J=7.7 Hz, 2H), 6.71 (d, J=5.5 Hz, 1H), 5.30 (d, J=33.0 Hz, 1H), 3.84-3.42 (m, 3H), 2.31-2.02 (m, 5H), 0.92 (dd, J=14.0, 6.7 Hz, 3H).

Example 72

(R)—N-(5-methylthiazol-2-yl)-4-(3-(1-propionylpyrrolidin-3-ylamino)-1H-pyrazolo[3,4-b]pyridin-4-yloxy)benzamide (Compound ID 72)

Preparation of (R)-4-(1-(4-methoxybenzyl)-3-(1-propionylpyrrolidin-3-ylamino)-1H-pyrazolo[3,4-b]pyridin-4-yloxy)-N-(5-methylthiazol-2-yl)benzamide (549-1)

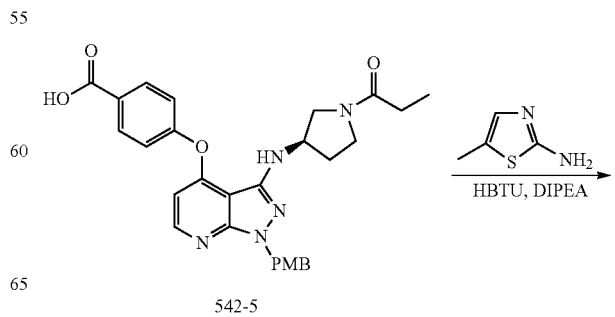

542-5

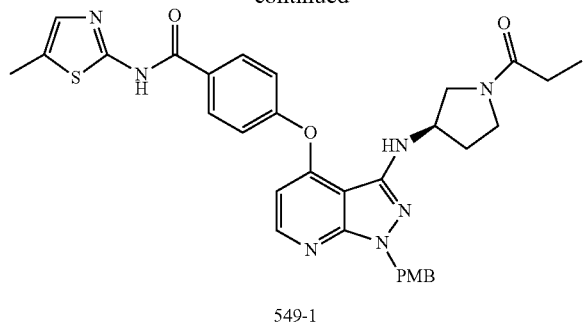

549-1

(R)-4-(1-(4-Methoxybenzyl)-3-(1-propionylpyrrolidin-3-ylamino)-1H-pyrazolo[3,4-b]pyridin-4-yloxy)-N-(5-methylthiazol-2-yl)benzamide (549-1) (120 mg, 68%) was prepared from (R)-4-(1-(4-methoxybenzyl)-3-(1-propionylpyrrolidin-3-ylamino)-1H-pyrazolo[3,4-b]pyridin-4-yloxy)benzoic acid (542-5) (150 mg, 0.29 mmol) and 5-methylthiazol-2-amine (50 mg, 0.44 mmol), following a similar procedure in Ex. 26. LC-MS (ESI): m/z (M−1) 610.3.

Preparation of (R)—N-(5-methylthiazol-2-yl)-4-(3-(1-propionylpyrrolidin-3-ylamino)-1H-pyrazolo[3,4-b]pyridin-4-yloxy)benzamide (549)

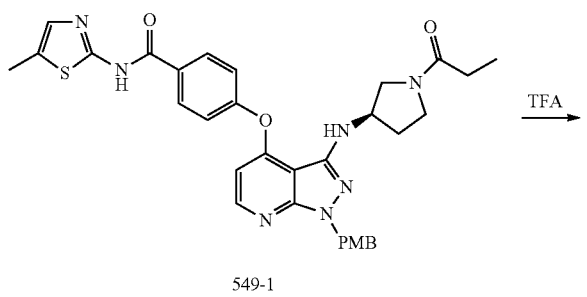

549-1

TFA →

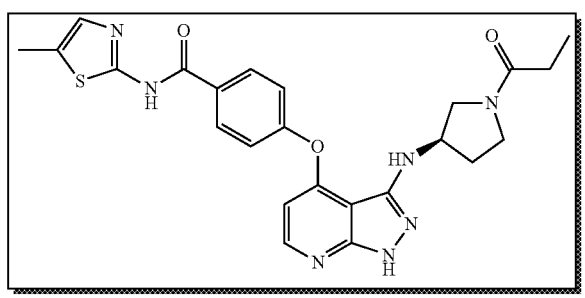

549

(R)—N-(5-Methylthiazol-2-yl)-4-(3-(1-propionylpyrrolidin-3-ylamino)-1H-pyrazolo[3,4-b]pyridin-4-yloxy)benzamide (549) (66 mg, 67%) was obtained as a white solid from (R)-4-(1-(4-methoxybenzyl)-3-(1-propionylpyrrolidin-3-ylamino)-1H-pyrazolo[3,4-b]pyridin-4-yloxy)-N-(5-methylthiazol-2-yl)benzamide (549-1) (120 mg, 0.20 mmol), following a similar procedure outlined in Ex. 26.

LC-MS (ESI): m/z (M+1) 492.1. $^1$H NMR (400 MHz, DMSO) δ 12.52 (br, 1H), 12.33 (s, 1H), 8.28-8.09 (m, 3H), 7.48-7.32 (m, 2H), 7.23 (s, 1H), 6.24-6.07 (m, 1H), 5.70-5.44 (m, 1H), 4.35-4.14 (m, 1H), 3.87-3.61 (m, 1H), 3.58-3.41 (m, 2H), 2.38 (s, 3H), 2.26-1.89 (m, 4H), 0.96 (d, J=2.0 Hz, 3H).

Example 73

(R)—N-(1-methyl-1H-imidazol-2-yl)-4-(3-(1-propionylpyrrolidin-3-ylamino)-1H-pyrazolo[3,4-b]pyridin-4-yloxy)benzamide (Compound ID 73)

Preparation of 1-methyl-2-nitro-1H-imidazole (542-1)

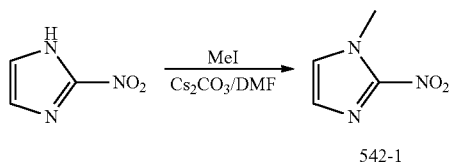

542-1

To a stirred solution of 2-nitro-1H-imidazole (500 mg, 4.42 mmol) in DMF (6 mL) was added Cs$_2$CO$_3$ (4.3 g, 13.3 mmol) before introduction of MeI (942 mg, 6.63 mmol). The resulting mixture was heated to 50° C. under N$_2$ overnight. The reaction was quenched with aqueous NaHCO$_3$ (sat.) and extracted with EA (25 mL×3). The combined organic layers was dried over Na$_2$SO$_4$, filtered and concentrated. The crude product was purified by flash chromatography (silica gel, 0-50% ethyl acetate in petroleum ether) to provide 1-methyl-2-nitro-1H-imidazole (542-1) (530 mg, 100%) as a yellow solid. LC-MS (ESI): m/z (M+1) 128.1.

Preparation of 1-methyl-1H-imidazol-2-amine (542-2)

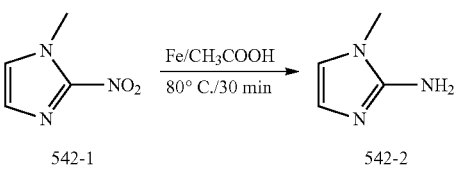

542-1        542-2

To a stirred solution of 1-methyl-2-nitro-1H-imidazole (542-1) (500 mg, 3.9 mmol) in AcOH (15 mL) was added Fe (1.34 g, 24 mmol). The resulting mixture was stirred at 80° C. overnight. The reaction was filtered through a pad of celite and the filtrate was concentrate under vacuum. The residue was purified by prep. HPLC (C18, 10 to 90% acetonitrile in H$_2$O (with 0.1% HCOOH)) to give 1-methyl-1H-imidazol-2-amine (542-2) (66 mg, 17%) as a yellow solid.

Preparation of (R)-methyl 4-(1-(4-methoxybenzyl)-3-(pyrrolidin-3-ylamino)-1H-pyrazolo[3,4-b]pyridin-4-yloxy)benzoate (542-3)

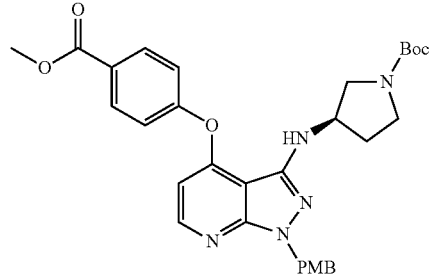

HCl/Dioxane

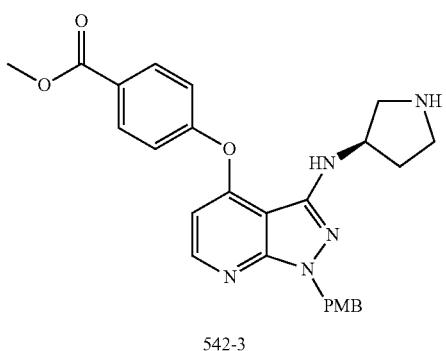

542-3

(R)-Methyl 4-(1-(4-methoxybenzyl)-3-(pyrrolidin-3-ylamino)-1H-pyrazolo[3,4-b]pyridin-4-yloxy)benzoate (542-3) (784 mg, 100%) was prepared from ((R)-tert-butyl 3-(1-(4-methoxybenzyl)-4-(4-(methoxycarbonyl)phenoxy)-1H-pyrazolo[3,4-b]pyridin-3-ylamino)pyrrolidine-1-carboxylate (950 mg, 1.6 mmol), following a similar procedure outlined in Ex. 26. LC-MS (ESI): m/z (M+1) 474.2.

Preparation of (R)-methyl 4-(1-(4-methoxybenzyl)-3-(1-propionylpyrrolidin-3-ylamino)-1H-pyrazolo[3,4-b]pyridin-4-yloxy)benzoate (542-4)

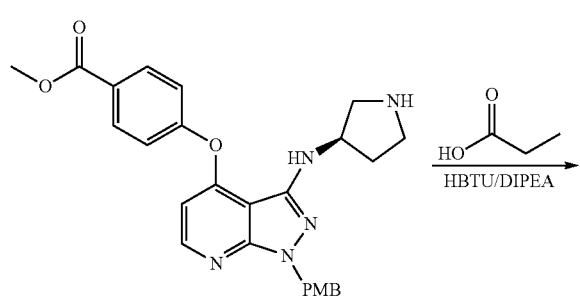

HBTU/DIPEA

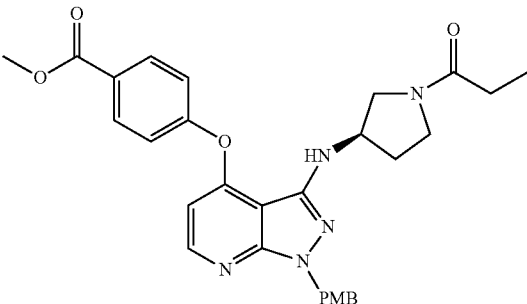

542-4

(R)-Methyl 4-(1-(4-methoxybenzyl)-3-(1-propionylpyrrolidin-3-ylamino)-1H-pyrazolo[3,4-b]pyridin-4-yloxy)benzoate (542-4) (900 mg, 100%) was prepared from (R)-methyl 4-(1-(4-methoxybenzyl)-3-(pyrrolidin-3-ylamino)-1H-pyrazolo[3,4-b]pyridin-4-yloxy)benzoate (542-3) (784 mg, 1.6 mmol) and propionic acid (184 mg, 2.5 mmol), following a similar procedure in Ex. 26. LC-MS (ESI): m/z (M+1) 530.3.

Preparation of (R)-4-(1-(4-methoxybenzyl)-3-(1-propionylpyrrolidin-3-ylamino)-1H-pyrazolo[3,4-b]pyridin-4-yloxy)benzoic acid (542-5)

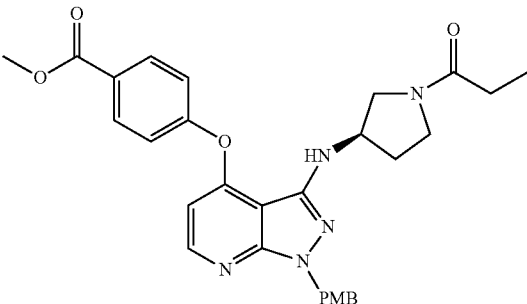

NaOH
THF/
H₂O

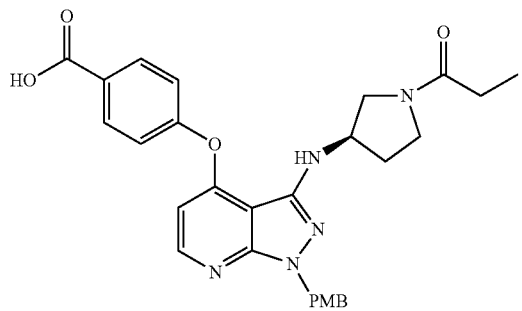

542-5

307

To a stirred solution of (R)-methyl 4-(1-(4-methoxybenzyl)-3-(1-propionylpyrrolidin-3-ylamino)-1H-pyrazolo[3,4-b]pyridin-4-yloxy)benzoate (524-4) (900 mg, 1.7 mmol) in THF/H$_2$O (5 mL/5 mL) was added NaOH (204 mg, 5.1 mmol). The resulting mixture was stirred at r.t overnight before acidified to pH-1. The layers were separated and the aqueous layer was extracted with DCM (10 mL×3). The combined organic layers were dried, filtered and concentrated to provide (R)-4-(1-(4-methoxybenzyl)-3-(1-propionylpyrrolidin-3-ylamino)-1H-pyrazolo[3,4-b]pyridin-4-yloxy)benzoic acid (542-5) (800 mg, 91%) as a yellow solid. LC-MS (ESI): m/z (M−1) 514.2.

Preparation of (R)-4-(1-(4-methoxybenzyl)-3-(1-propionylpyrrolidin-3-ylamino)-1H-pyrazolo[3,4-b]pyridin-4-yloxy)-N-(1-methyl-1H-imidazol-2-yl)benzamide (542-6)

308

Preparation of (R)—N-(1-methyl-1H-imidazol-2-yl)-4-(3-(1-propionylpyrrolidin-3-ylamino)-1H-pyrazolo[3,4-b]pyridin-4-yloxy)benzamide (542)

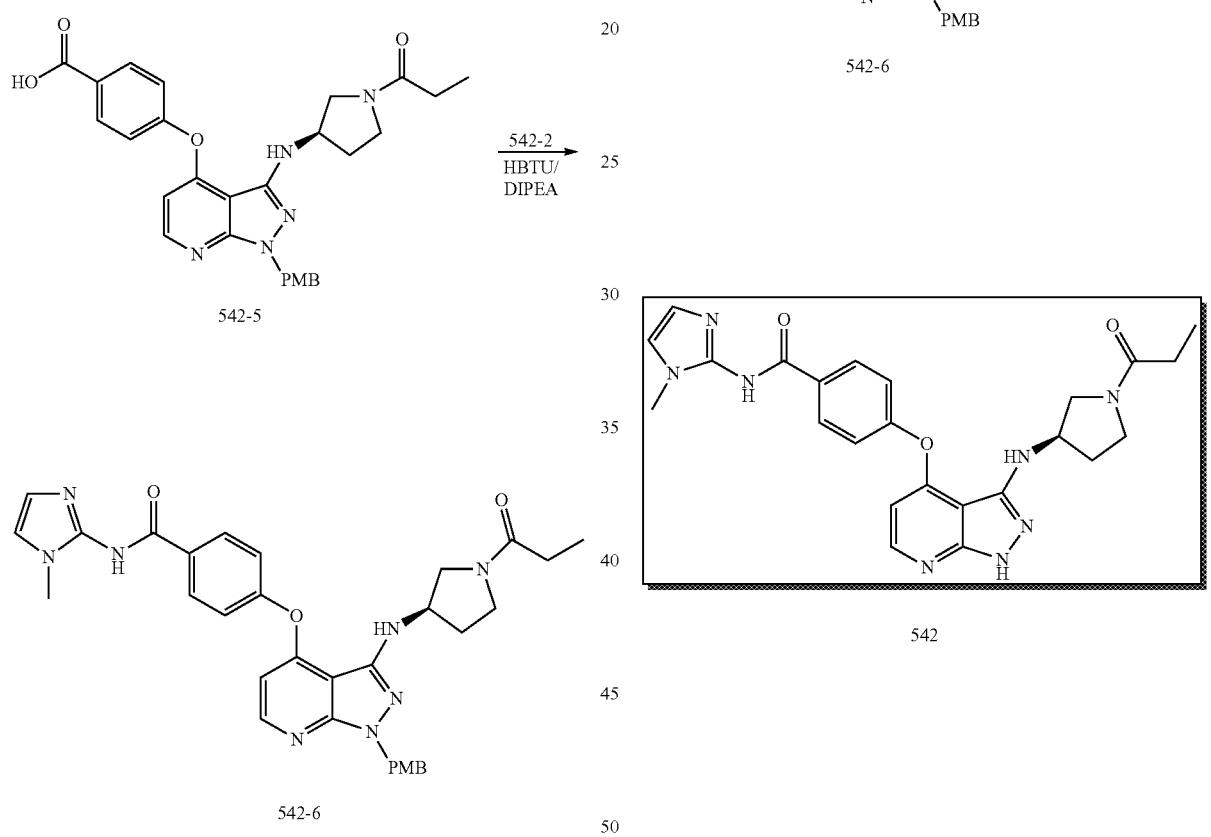

(R)-4-(1-(4-Methoxybenzyl)-3-(1-propionylpyrrolidin-3-ylamino)-1H-pyrazolo[3,4-b]pyridin-4-yloxy)-N-(1-methyl-1H-imidazol-2-yl)benzamide (542-6) (80 mg, 47%) was prepared from (R)-4-(1-(4-methoxybenzyl)-3-(1-propionylpyrrolidin-3-ylamino)-1H-pyrazolo[3,4-b]pyridin-4-yloxy)benzoic acid (542-5) (150 mg, 0.29 mmol) and 1-methyl-1H-imidazol-2-amine (41 mg, 0.44 mmol), following a similar procedure in Ex. 26. LC-MS (ESI): m/z (M+1) 595.2.

(R)—N-(1-Methyl-1H-imidazol-2-yl)-4-(3-(1-propionylpyrrolidin-3-ylamino)-1H-pyrazolo[3,4-b]pyridin-4-yloxy)benzamide (542) (45 mg, 72%) was obtained as a white solid from (R)-4-(1-(4-methoxybenzyl)-3-(1-propionylpyrrolidin-3-ylamino)-1H-pyrazolo[3,4-b]pyridin-4-yloxy)-N-(1-methyl-1H-imidazol-2-yl)benzamide (542-6) (80 mg, 0.13 mmol), following a similar procedure in Ex. 26. LC-MS (ESI): m/z (M+1) 475.1. $^1$H NMR (400 MHz, DMSO) δ 12.26 (s, 2H), 8.33-8.06 (m, 3H), 7.29 (s, 2H), 7.02 (s, 1H), 6.82 (s, 1H), 6.06 (s, 1H), 5.56 (d, J=34.4 Hz, 1H), 4.33-3.42 (m, 7H), 2.25-1.95 (m, 4H), 0.95 (t, J=7.3 Hz, 3H).

Example 74

(R)—N-(6-oxo-1,6-dihydropyrimidin-2-yl)-4-(3-(1-propionylpyrrolidin-3-ylamino)-1H-pyrazolo[3,4-b]pyridin-4-yloxy)benzamide (Compound ID 74)

Preparation of (R)—N-(4-hydroxypyrimidin-2-yl)-4-(1-(4-methoxybenzyl)-3-(1-propionylpyrrolidin-3-ylamino)-1H-pyrazolo[3,4-b]pyridin-4-yloxy)benzamide (544-1)

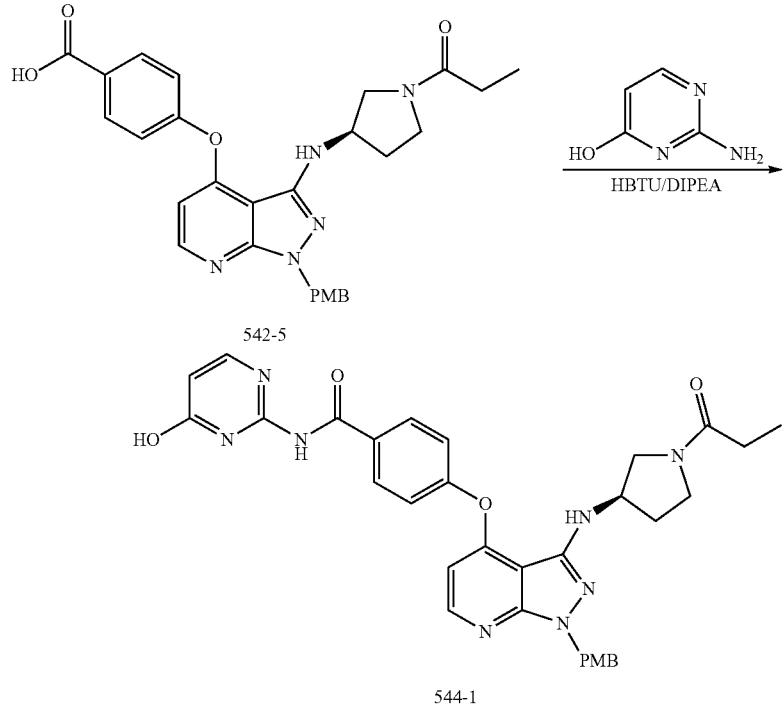

(R)—N-(4-hydroxypyrimidin-2-yl)-4-(1-(4-methoxybenzyl)-3-(1-propionylpyrrolidin-3-ylamino)-1H-pyrazolo[3,4-b]pyridin-4-yloxy)benzamide (544-1) (70 mg, 30%) was prepared from (R)-4-(1-(4-methoxybenzyl)-3-(1-propionylpyrrolidin-3-ylamino)-1H-pyrazolo[3,4-b]pyridin-4-yloxy)benzoic acid (542-5) (200 mg, 0.39 mmol) and 2-aminopyrimidin-4-ol (70 mg, 0.63 mmol), following a similar procedure in Ex. 26. LC-MS (ESI): m/z (M+1) 609.3.

Preparation of (R)—N-(4-hydroxypyrimidin-2-yl)-4-(3-(1-propionylpyrrolidin-3-ylamino)-1H-pyrazolo[3,4-b]pyridin-4-yloxy)benzamide (544)

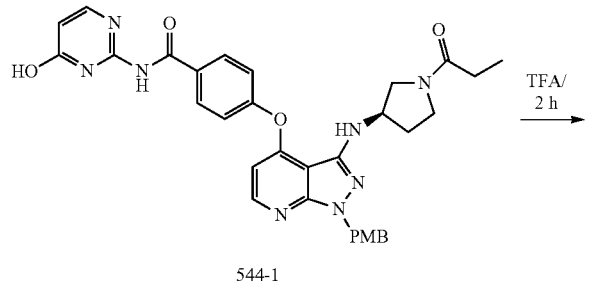

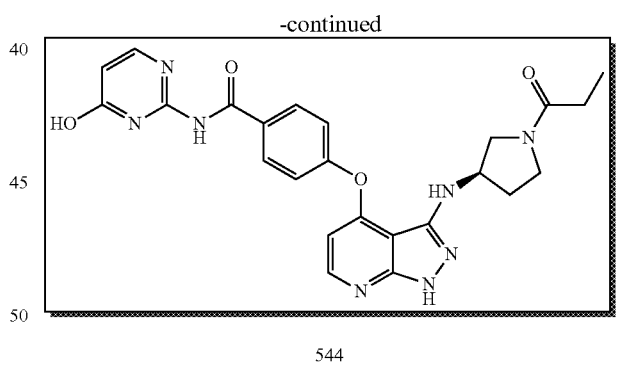

(R)—N-(4-Hydroxypyrimidin-2-yl)-4-(3-(1-propionylpyrrolidin-3-ylamino)-1H-pyrazolo[3,4-b]pyridin-4-yloxy)benzamide (544) (17 mg, 29%) was obtained as a white solid from (R)—N-(4-hydroxypyrimidin-2-yl)-4-(1-(4-methoxybenzyl)-3-(1-propionylpyrrolidin-3-ylamino)-1H-pyrazolo[3,4-b]pyridin-4-yloxy)benzamide (544-1) (70 mg, 0.12 mmol), following a similar procedure in Ex. 26. LC-MS (ESI): m/z (M+1) 489.1. $^1$H NMR (400 MHz, DMSO) δ 12.32 (br, 2H), 8.27-8.13 (m, 3H), 7.76 (d, J=6.3 Hz, 1H), 7.44-7.31 (s, 2H), 6.15-6.10 (m, 1H), 5.97 (d, J=6.9 Hz, 1H), 5.64-5.51 (m, 1H), 4.36-4.13 (m, 1H), 3.82-3.52 (m, 1H), 3.47-3.32 (s, 2H), 2.29-1.88 (s, 5H), 0.96 (t, J=7.3 Hz, 3H).

Example 75

(R)—N-(5-methyl-4H-1,2,4-triazol-3-yl)-4-(3-(1-propionylpyrrolidin-3-ylamino)-1H-pyrazolo[3,4-b]pyridin-4-yloxy)benzamide (Compound ID 75)

Preparation of (R)-tert-butyl 3-(1-(4-methoxybenzyl)-4-(4-(5-methyl-4H-1,2,4-triazol-3-ylcarbamoyl)phenoxy)-1H-pyrazolo[3,4-b]pyridin-3-ylamino)pyrrolidine-1-carboxylate (546-1)

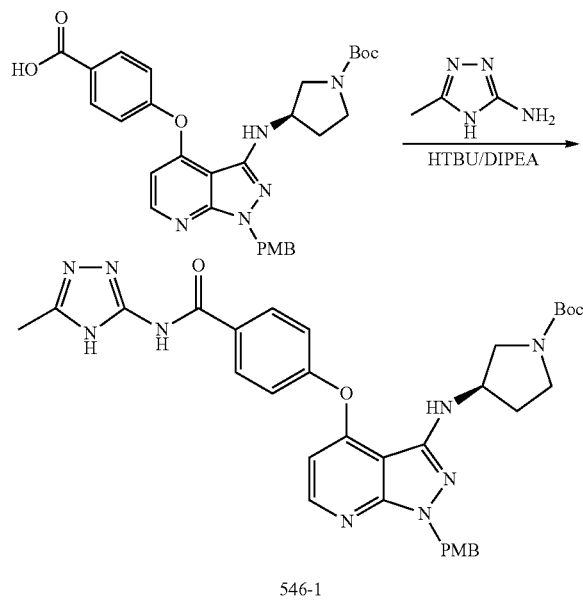

546-1

(R)-tert-Butyl 3-(1-(4-methoxybenzyl)-4-(4-(5-methyl-4H-1,2,4-triazol-3-ylcarbamoyl)phenoxy)-1H-pyrazolo[3,4-b]pyridin-3-ylamino)pyrrolidine-1-carboxylate (546-1) (142 mg, 49%) was obtained as a white solid from (R)-4-(3-(1-(tert-Butoxycarbonyl)pyrrolidin-3-ylamino)-1-(4-methoxybenzyl)-1H-pyrazolo[3,4-b]pyridin-4-yloxy)benzoic acid (250 mg, 0.45 mmol) and 5-methyl-4H-1,2,4-triazol-3-amine (178 mg, 1.82 mmol), following a similar procedure in Ex. 8. LC-MS (ESI): m/z (M+1) 640.6.

Preparation of (R)-4-(1-(4-methoxybenzyl)-3-(pyrrolidin-3-ylamino)-1H-pyrazolo[3,4-b]pyridin-4-yloxy)-N-(5-methyl-4H-1,2,4-triazol-3-yl)benzamide (546-2)

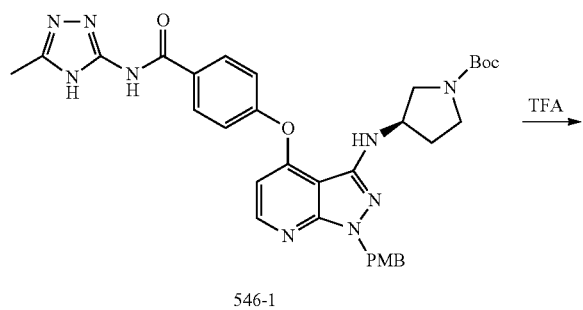

546-1

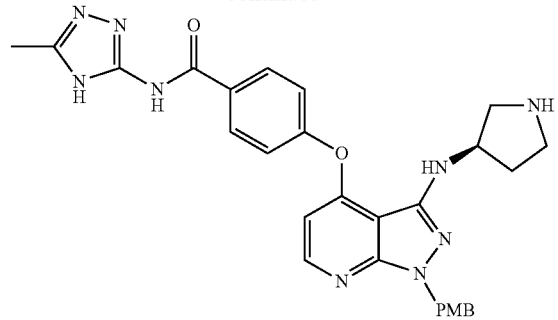

546-2

(R)-4-(1-(4-Methoxybenzyl)-3-(pyrrolidin-3-ylamino)-1H-pyrazolo[3,4-b]pyridin-4-yloxy)-N-(5-methyl-4H-1,2,4-triazol-3-yl)benzamide (546-2) (120 mg, 100%) was obtained as a yellow solid from (R)—N-(4-hydroxypyrimidin-2-yl)-4-(1-(4-methoxybenzyl)-3-(1-propionylpyrrolidin-3-ylamino)-1H-pyrazolo[3,4-b]pyridin-4-yloxy)benzamide (546-1) (142 mg, 0.22 mmol), following a similar procedure in Ex. 26. LC-MS (ESI): m/z (M+1) 540.3.

Preparation of (R)-4-(1-(4-methoxybenzyl)-3-(1-propionylpyrrolidin-3-ylamino)-1H-pyrazolo[3,4-b]pyridin-4-yloxy)-N-(5-methyl-4H-1,2,4-triazol-3-yl)benzamide (546-3)

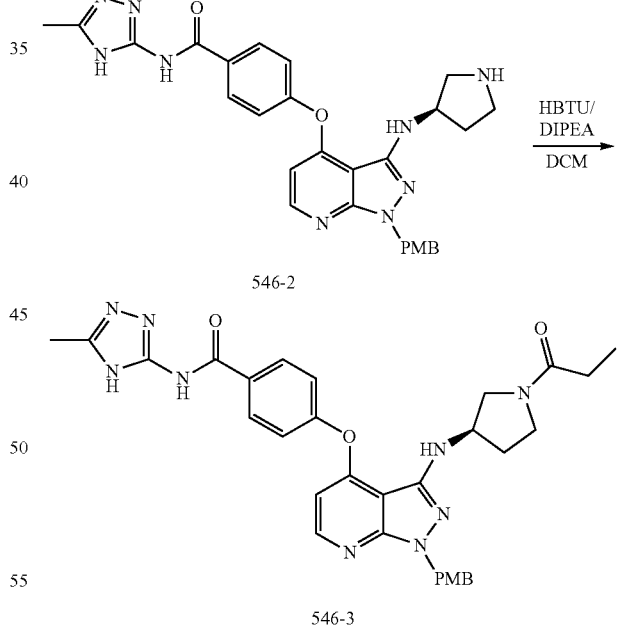

(R)-4-(1-(4-Methoxybenzyl)-3-(1-propionylpyrrolidin-3-ylamino)-1H-pyrazolo[3,4-b]pyridin-4-yloxy)-N-(5-methyl-4H-1,2,4-triazol-3-yl)benzamide (546-3) (115 mg, 88%) was prepared from (R)-4-(1-(4-methoxybenzyl)-3-(pyrrolidin-3-ylamino)-1H-pyrazolo[3,4-b]pyridin-4-yloxy)-N-(5-methyl-4H-1,2,4-triazol-3-yl)benzamide (546-2) (120 mg, 0.22 mmol) and propionic acid (19 mg, 0.25 mmol) following a similar procedure outlined in Ex. 26. LC-MS (ESI): m/z (M+1) 596.2.

Preparation of (R)—N-(5-methyl-4H-1,2,4-triazol-3-yl)-4-(3-(1-propionyl pyrrolidin-3-ylamino)-1H-pyrazolo[3,4-b]pyridin-4-yloxy)benzamide (546)

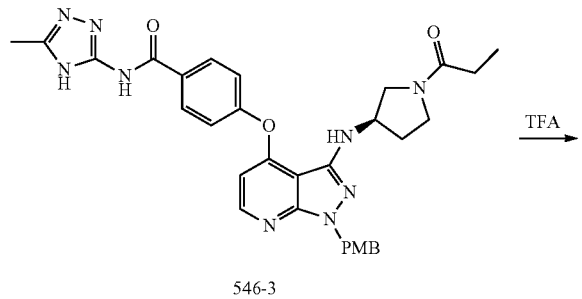

546-3

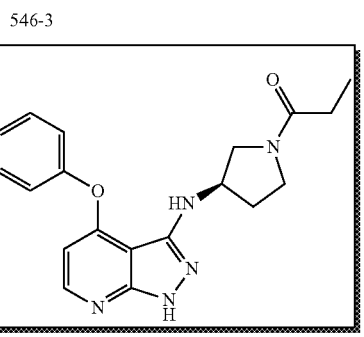

546

(R)—N-(5-Methyl-4H-1,2,4-triazol-3-yl)-4-(3-(1-propionylpyrrolidin-3-ylamino)-1H-pyrazolo[3,4-b]pyridin-4-yloxy)benzamide (546) (42 mg, 47%) was obtained as a white solid from (R)-4-(1-(4-methoxybenzyl)-3-(1-propionylpyrrolidin-3-ylamino)-1H-pyrazolo[3,4-b]pyridin-4-yloxy)-N-(5-methyl-4H-1,2,4-triazol-3-yl)benzamide (546-3) (115 mg, 0.19 mmol), following a similar procedure in Ex. 26. LC-MS (ESI): m/z (M+1) 476.1. $^1$H NMR (400 MHz, DMSO) δ 12.31 (s, 2H), 8.22-8.04 (m, 3H), 7.43-7.34 (m, 2H), 6.18-6.10 (m, 1H), 5.63-5.50 (m, 1H), 4.30-4.13 (m, 1H), 3.82-3.48 (m, 3H), 2.61-1.92 (m, 7H), 0.98-0.93 (m, 3H).

Example 76

(R,E)-N-(4-cyclopropoxypyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide (Compound ID 76)

Preparation of 4-cyclopropoxypyridin-2-amine (531-1)

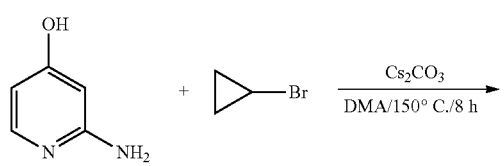

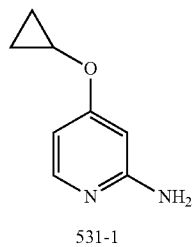

531-1

To a solution of 2-aminopyridin-4-ol (110 mg, 1 mmol) in DMA (5 mL) was added bromocyclopropane (181 mg, 1.5 mmol) and $Cs_2CO_3$ (1.6 g, 5 mmol). The resulting mixture was heated to 150° C. for 8 hr. The reaction mixture was quenched with $H_2O$ and extracted with EA (10 mL×3). The combined organic layers was dried over $Na_2SO_4$, filtered and concentrated. The crude product was purified by flash chromatography (silica gel, 0-50% ethyl acetate in petroleum ether) to provide 4-cyclopropoxypyridin-2-amine (531-1) (93 mg, 62%) as a yellow oil. LC-MS (ESI): m/z (M+1) 151.2.

Preparation of (R)-tert-butyl 3-(4-(4-(4-cyclopropoxypyridin-2-ylcarbamoyl)phenoxy)-1-(4-methoxybenzyl)-1H-pyrazolo[3,4-b]pyridin-3-ylamino)pyrrolidine-1-carboxylate (531-2)

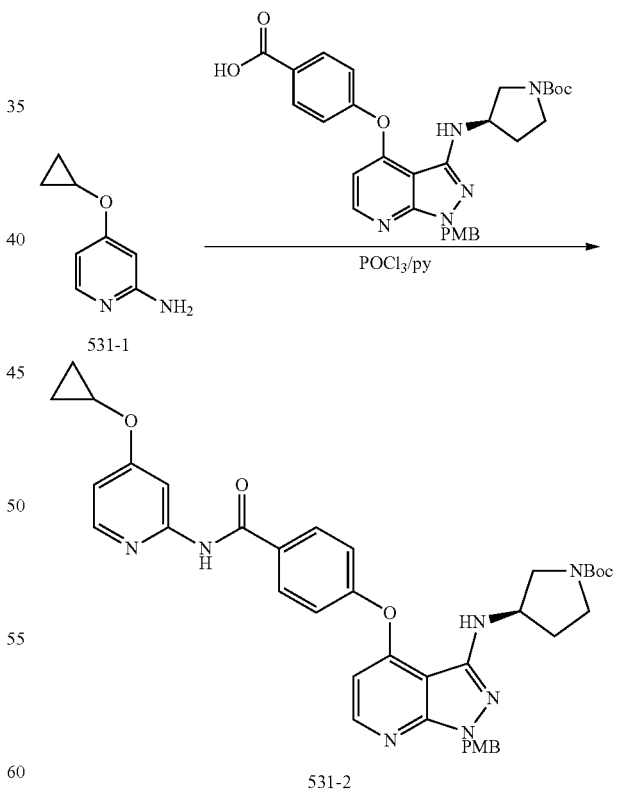

(R)-tert-Butyl 3-(4-(4-(4-cyclopropoxypyridin-2-ylcarbamoyl)phenoxy)-1-(4-methoxybenzyl)-1H-pyrazolo[3,4-b]pyridin-3-ylamino)pyrrolidine-1-carboxylate (531-2) (100 mg, 81%) was obtained as a yellow solid from (R)-4-(3-(1-(tert-butoxycarbonyl)pyrrolidin-3-ylamino)-1-(4-methoxybenzyl)-1H-pyrazolo[3,4-b]pyridin-4-yloxy)benzoic acid (100 mg, 0.18 mmol) and 4-cyclopropoxypyridin-2-amine (531-1) (80 mg, 0.53 mmol), following a similar procedure in Ex 26. LC-MS (ESI): m/z (M+1) 692.3.

Preparation of (R,E)-N-(4-cyclopropoxypyridin-2-yl)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)benzamide (531-3)

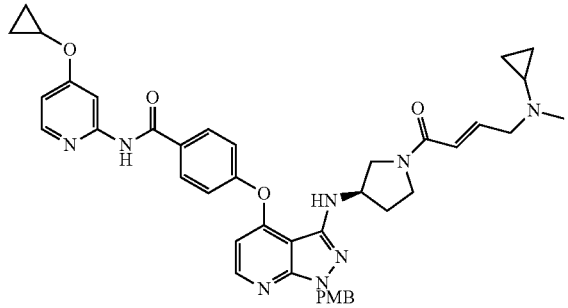

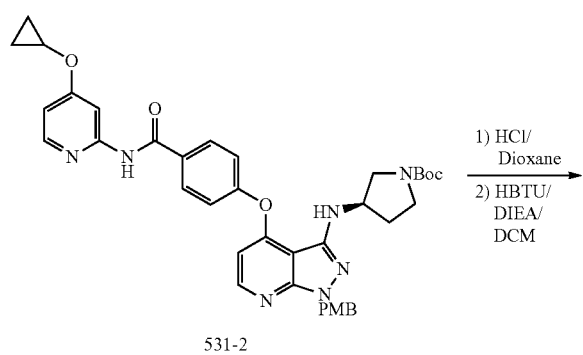

531-2

(R,E)-N-(4-Cyclopropoxypyridin-2-yl)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)benzamide (531-3) (45 mg, 44%) was prepared from (R)-tert-butyl 3-(4-(4-(4-cyclopropoxypyridin-2-ylcarbamoyl)phenoxy)-1-(4-methoxybenzyl)-1H-pyrazolo[3,4-b]pyridin-3-ylamino)pyrrolidine-1-carboxylate (531-2) (100 mg, 0.145 mmol) and (E)-4-(cyclopropyl(methyl)amino)but-2-enoic acid HCl salt (48 mg, 0.17 mmol), following a similar procedure outlined in Ex. 26. LC-MS (ESI): m/z (M+1) 729.4.

Preparation of (R,E)-N-(4-cyclopropoxypyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide (531)

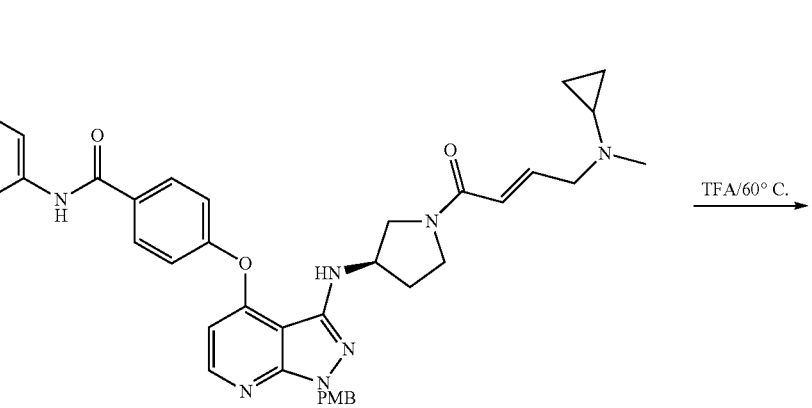

531-3

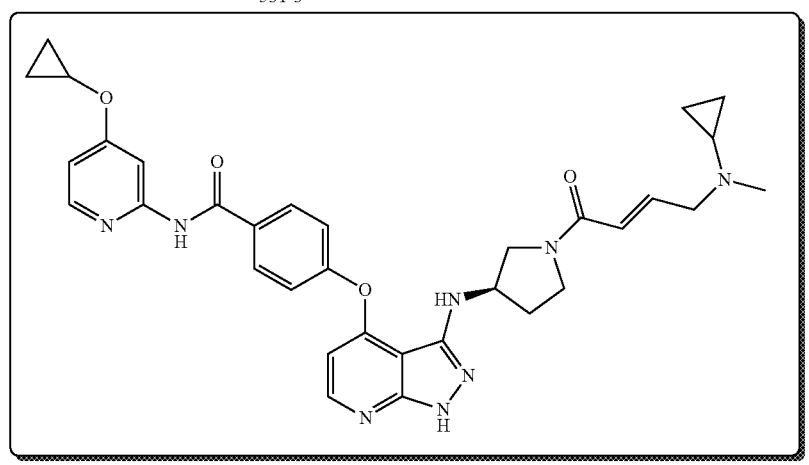

531

(R,E)-N-(4-Cyclopropoxypyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide (531) (25 mg, 66%) was obtained as white solid from (R,E)-N-(4-cyclopropoxypyridin-2-yl)-4-(3-(1-(4-(cyclopropyl(methyl)amino)but-2-enoyl)pyrrolidin-3-ylamino)-1-(4-methoxybenzyl)-1H-pyrazolo[3,4-b]pyridin-4-yloxy)benzamide (531-3) (45 mg, 0.06 mmol), following a similar procedure outlined in Ex. 26. LC-MS (ESI): m/z (M+1) 609.3. $^{1}$H NMR (400 MHz, DMSO) δ 12.32 (s, 1H), 10.81 (s, 1H), 8.27-8.07 (m, 5H), 7.98 (s, 1H), 7.37 (d, J=6.5 Hz, 2H), 6.89-6.85 (m, 1H), 6.66-6.58 (m, 1H), 6.15-6.10 (m, 1H), 5.68-5.54 (m, 1H), 4.35-4.17 (m, 1H), 4.00-3.47 (m, 5H), 3.21-3.10 (m, 2H), 2.42-2.14 (m, 5H), 1.28-1.19 (m, 1H), 0.85-0.81 (m, 2H), 0.75-0.71 (m, 2H), 0.62-0.30 (m, 4H).

Example 77

N-(4-cyanopyridin-2-yl)-4-(3-(tetrahydro-2H-pyran-4-ylamino)-1H-pyrazolo[3,4-b]pyridin-4-yloxy)benzamide (Compound ID 77)

Preparation of methyl 4-(1-(4-methoxybenzyl)-3-(tetrahydro-2H-pyran-4-ylamino)-1H-pyrazolo[3,4-b]pyridin-4-yloxy)benzoate (588-1)

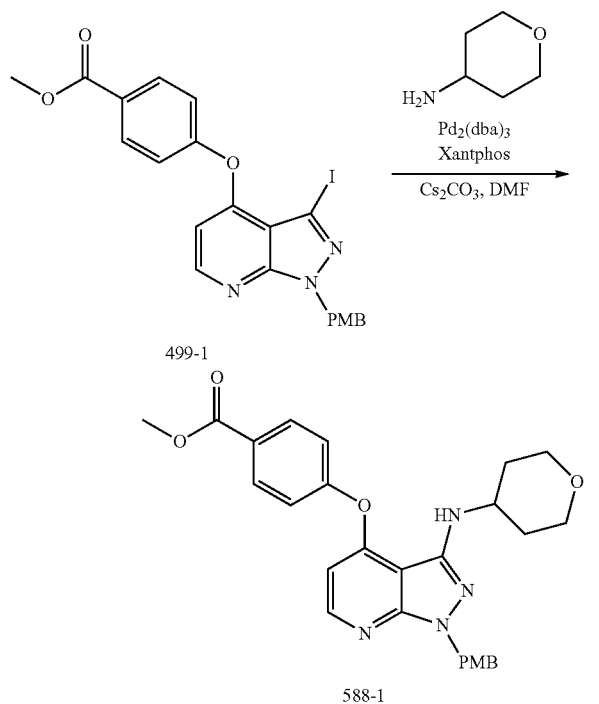

Methyl 4-(1-(4-methoxybenzyl)-3-(tetrahydro-2H-pyran-4-ylamino)-1H-pyrazolo[3,4-b]pyridin-4-yloxy)benzoate (588-1) (180 mg, 32% yield) was obtained as a yellow solid from methyl 4-(3-iodo-1-(4-methoxybenzyl)-1H-pyrazolo[3,4-b]pyridin-4-yloxy)benzoate (499-1) (600 mg, 1.2 mmol) and tetrahydro-2H-pyran-4-amine (468 mg, 4.6 mmol), following a similar procedure outlined in the preparation of (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1) (Ex. 1). LC-MS (ESI): m/z (M+1) 490.3.

Preparation of 4-(1-(4-methoxybenzyl)-3-(tetrahydro-2H-pyran-4-ylamino)-1H-pyrazolo[3,4-b]pyridin-4-yloxy)benzoic acid (588-2)

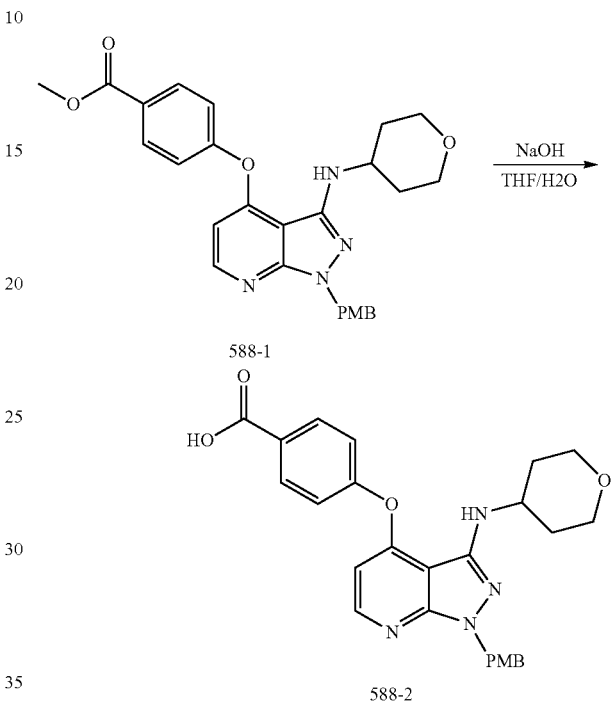

4-(1-(4-Methoxybenzyl)-3-(tetrahydro-2H-pyran-4-ylamino)-1H-pyrazolo[3,4-b]pyridin-4-yloxy)benzoic acid (588-2) (170 mg, 98% yield) was obtained as a yellow solid from methyl 4-(1-(4-methoxybenzyl)-3-(tetrahydro-2H-pyran-4-ylamino)-1H-pyrazolo[3,4-b]pyridin-4-yloxy)benzoate (588-1) (180 mg, 0.37 mmol), following a similar procedure outlined in the preparation of 4-(3-((1r,4r)-4-(tert-butyldimethylsilyloxy)cyclohexylamino)-1-(4-methoxybenzyl)-1H-pyrazolo[3,4-b]pyridin-4-yloxy)benzoic acid (587-3) (Ex. 1). LC-MS (ESI): m/z (M+1) 476.5.

Preparation of N-(4-cyanopyridin-2-yl)-4-(1-(4-methoxybenzyl)-3-(tetrahydro-2H-pyran-4-ylamino)-1H-pyrazolo[3,4-b]pyridin-4-yloxy)benzamide (588-3)

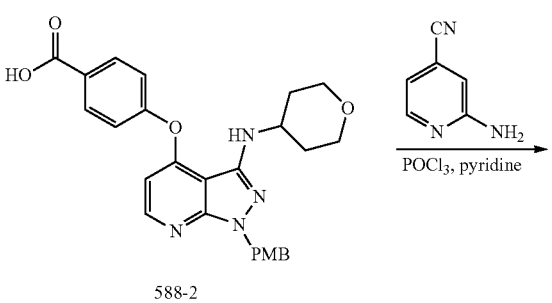

319

-continued

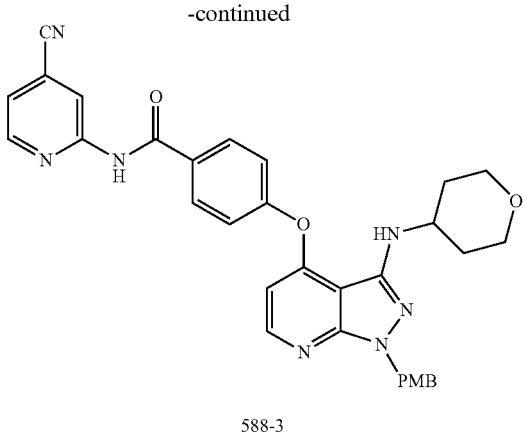

588-3

N-(4-Cyanopyridin-2-yl)-4-(1-(4-methoxybenzyl)-3-(tetrahydro-2H-pyran-4-ylamino)-1H-pyrazolo[3,4-b]pyridin-4-yloxy)benzamide (588-3) (76 mg, 63% yield) was obtained as a yellow oil from 4-(1-(4-methoxybenzyl)-3-(tetrahydro-2H-pyran-4-ylamino)-1H-pyrazolo[3,4-b]pyridin-4-yloxy)benzoic acid (588-2) (100 mg, 0.21 mmol) and 2-aminoisonicotinonitrile (75 mg, 0.63 mmol), following a similar procedure outlined in the preparation of 4-(3-((1 r,4r)-4-(tert-butyldimethylsilyloxy)cyclohexylamino)-1-(4-methoxybenzyl)-1H-pyrazolo[3,4-b]pyridin-4-yloxy)-N-(4-cyanopyridin-2-yl)benzamide (587-4) (Ex. 1). LC-MS (ESI): m/z (M+1) 576.3.

Preparation of N-(4-cyanopyridin-2-yl)-4-(3-(tetrahydro-2H-pyran-4-ylamino)-1H-pyrazolo[3,4-b]pyridin-4-yloxy)benzamide (588)

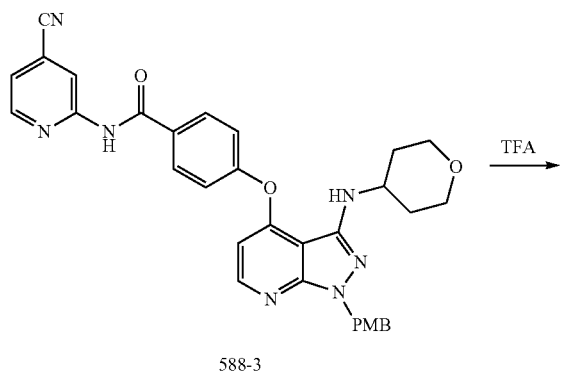

320

N-(4-Cyanopyridin-2-yl)-4-(3-(tetrahydro-2H-pyran-4-ylamino)-1H-pyrazolo[3,4-b]pyridin-4-yloxy)benzamide (588) (20 mg, 33% yield) was obtained as a white powder from N-(4-cyanopyridin-2-yl)-4-(1-(4-methoxybenzyl)-3-(tetrahydro-2H-pyran-4-ylamino)-1H-pyrazolo[3,4-b]pyridin-4-yloxy)benzamide (588-3) (76 mg, 0.13 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 456.4. $^1$H NMR (400 MHz, DMSO) δ 12.21 (s, 1H), 11.34 (s, 1H), 8.67 (d, J=4.6 Hz, 1H), 8.53 (s, 1H), 8.28-8.10 (m, 3H), 7.64 (d, J=3.7 Hz, 1H), 7.54-7.29 (m, 2H), 6.15 (d, J=5.2 Hz, 1H), 5.18 (d, J=5.5 Hz, 1H), 3.92-3.82 (m, 2H), 3.82-3.72 (m, 1H), 3.42-3.37 (m, 2H), 2.07-1.89 (m, 2H), 1.66-1.43 (m, 2H).

Example 78

(R)-ethyl 3-(4-(4-(4-cyanopyridin-2-ylcarbamoyl)phenoxy)-1H-pyrazolo[3,4-b]pyridin-3-ylamino)piperidine-1-carboxylate (Compound ID 78)

Preparation of (R)-tert-butyl 3-(1-(4-methoxybenzyl)-4-(4-(methoxycarbonyl)phenoxy)-1H-pyrazolo[3,4-b]pyridin-3-ylamino)piperidine-1-carboxylate (590-1)

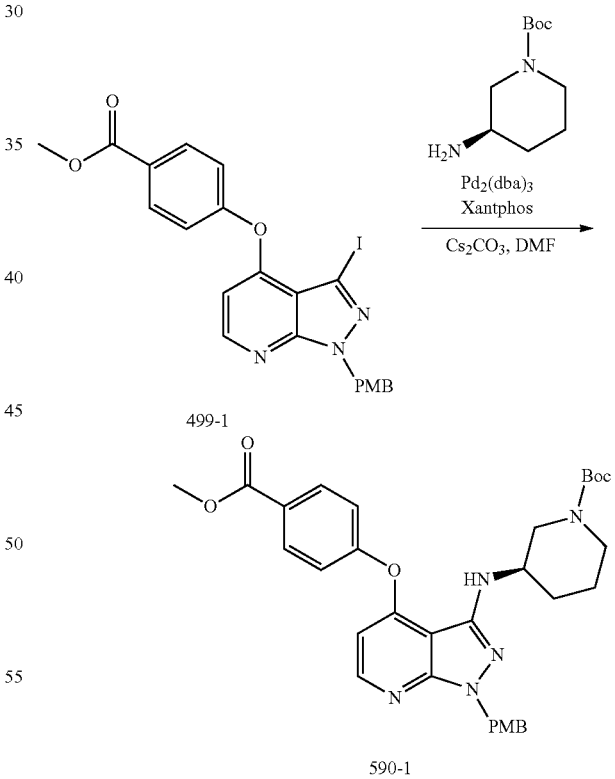

(R)-tert-Butyl 3-(1-(4-methoxybenzyl)-4-(4-(methoxycarbonyl)phenoxy)-1H-pyrazolo[3,4-b]pyridin-3-ylamino)piperidine-1-carboxylate (590-1) (1.0 g, 63% yield) was obtained as a light yellow solid from methyl 4-(3-iodo-1-(4-methoxybenzyl)-1H-pyrazolo[3,4-b]pyridin-4-yloxy)benzoate (499-1) (1.4 g, 2.7 mmol) and (R)-tert-butyl 3-aminopiperidine-1-carboxylate (1.75 g, 8.8 mmol), following a similar procedure outlined in the preparation of (S)-tert-butyl 2-((1-(4-methoxybenzyl)-4-(4-phenoxy phenoxy)-1H-pyrazolo[3,4-b]pyridin-3-ylamino)methyl)pyrrolidine-1-carboxylate (504-1) (Ex. 1). LC-MS (ESI): m/z (M+1) 589.3.

Preparation of (R)-4-(3-(1-(tert-butoxycarbonyl)piperidin-3-ylamino)-1-(4-methoxybenzyl)-1H-pyrazolo[3,4-b]pyridin-4-yloxy)benzoic acid (590-2)

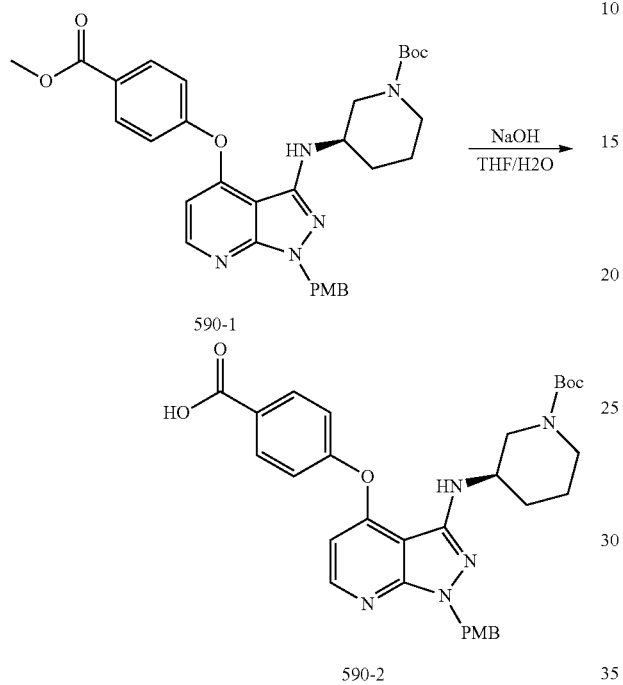

(R)-4-(3-(1-(tert-Butoxycarbonyl)piperidin-3-ylamino)-1-(4-methoxybenzyl)-1H-pyrazolo[3,4-b]pyridin-4-yloxy)benzoic acid (590-2) (980 mg, quant. yield) was obtained as a yellow solid from (R)-tert-butyl 3-(1-(4-methoxybenzyl)-4-(4-(methoxycarbonyl)phenoxy)-1H-pyrazolo[3,4-b]pyridin-3-ylamino)piperidine-1-carboxylate (590-1) (1.0 g, 1.7 mmol), following a similar procedure outlined in the preparation of 4-(3-((1r,4r)-4-(tert-butyldimethylsilyloxy)cyclohexylamino)-1-(4-methoxybenzyl)-1H-pyrazolo[3,4-b]pyridin-4-yloxy)benzoic acid (587-3) (Ex. 1). LC-MS (ESI): m/z (M+1) 575.6.

Preparation of (R)-tert-butyl 3-(4-(4-(4-cyanopyridin-2-ylcarbamoyl)phenoxy)-1-(4-methoxybenzyl)-1H-pyrazolo[3,4-b]pyridin-3-ylamino)piperidine-1-carboxylate (590-3)

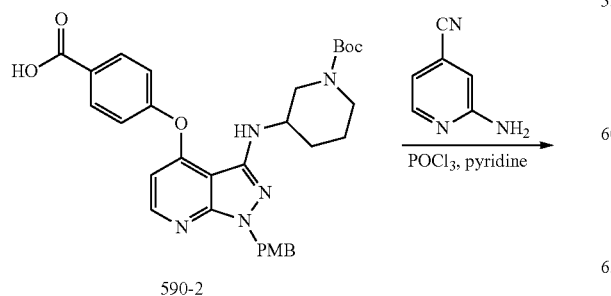

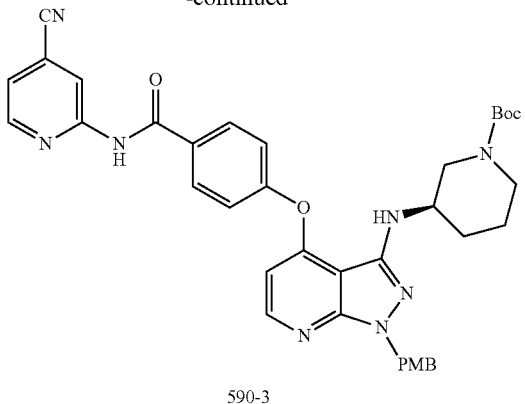

(R)-tert-Butyl 3-(4-(4-(4-cyanopyridin-2-ylcarbamoyl)phenoxy)-1-(4-methoxybenzyl)-1H-pyrazolo[3,4-b]pyridin-3-ylamino)piperidine-1-carboxylate (590-3) (640 mg, 54% yield) was obtained as yellow solid from (R)-4-(3-(1-(tert-butoxycarbonyl)piperidin-3-ylamino)-1-(4-methoxybenzyl)-1H-pyrazolo[3,4-b]pyridin-4-yloxy)benzoic acid (590-2) (1.0 g, 1.7 mmol) and 2-aminoisonicotinonitrile (620 mg, 5.1 mmol), following a similar procedure outlined in the preparation of 4-(3-((1r,4r)-4-(tert-butyldimethylsilyloxy)cyclohexylamino)-1-(4-methoxybenzyl)-1H-pyrazolo[3,4-b]pyridin-4-yloxy)-N-(4-cyanopyridin-2-yl)benzamide (587-4) (Ex. 1). LC-MS (ESI): m/z (M+1) 675.4.

Preparation of (R)—N-(4-cyanopyridin-2-yl)-4-(1-(4-methoxybenzyl)-3-(piperidin-3-ylamino)-1H-pyrazolo[3,4-b]pyridin-4-yloxy)benzamide, TFA salt (590-4)

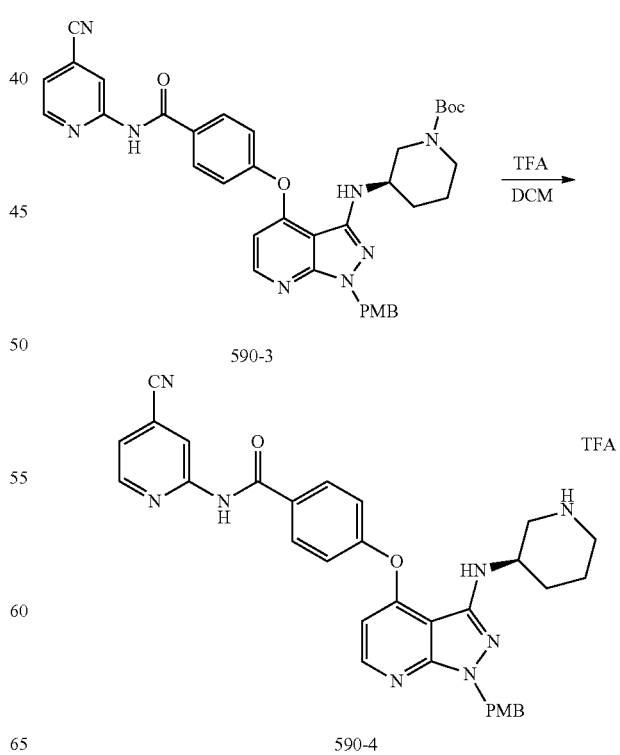

To a solution of (R)-tert-butyl 3-(4-(4-(4-cyanopyridin-2-ylcarbamoyl)phenoxy)-1-(4-methoxybenzyl)-1H-pyrazolo[3,4-b]pyridin-3-ylamino)piperidine-1-carboxylate (590-3) (80 mg, 0.12 mmol) in DCM (2 mL) was added TFA (0.5 mL). After stirred at r.t. for 30 min, the reaction mixture was concentrated under reduced pressure to afford (R)—N-(4-cyanopyridin-2-yl)-4-(1-(4-methoxybenzyl)-3-(piperidin-3-ylamino)-1H-pyrazolo[3,4-b]pyridin-4-yloxy)benzamide, TFA salt (590-4) (0.12 mmol, quant. yield), which was used in next step without purification.

Preparation of (R)-ethyl 3-(4-(4-(4-cyanopyridin-2-ylcarbamoyl)phenoxy)-1H-pyrazolo[3,4-b]pyridin-3-ylamino)piperidine-1-carboxylate (590)

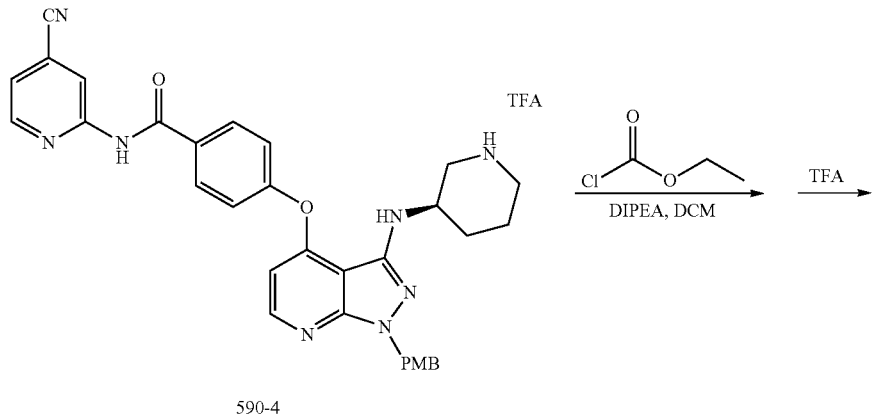

590-4 carbonochloridate (0.017 mL, 0.18 mmol). The resulting mixture was stirred at room temperature for 30 min. The reaction mixture was concentrated to give the crude product which was purified by flash chromatography (silica gel, 0 to 50% EA in PE) to give the corresponding amide. LC-MS (ESI): m/z (M+1) 647.3.

The intermediate was heated in TFA (5 mL) at 60° C. under $N_2$ atmosphere for 1 hr and concentrated under reduced pressure to give the crude product which was purified by prep. HPLC to afford (R)-ethyl 3-(4-(4-(4-cyanopyridin-2-ylcarbamoyl)phenoxy)-1H-pyrazolo[3,4-b]pyridin-3-ylamino)piperidine-1-carboxylate (590) (28 mg, 44% yield) as a white powder. LC-MS (ESI): m/z (M+1) 527.2. $^1$H NMR (400 MHz, DMSO) δ 12.27 (s, 1H), 11.34

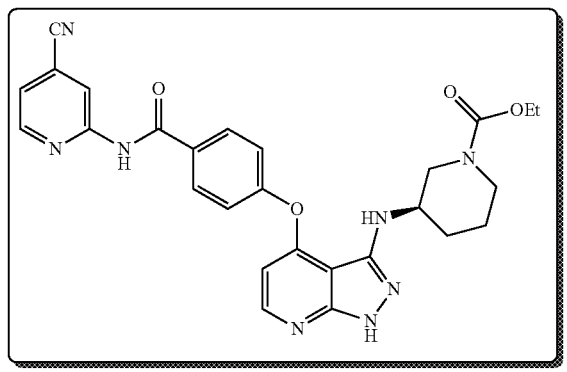

590

At 0° C., to a solution of (R)—N-(4-cyanopyridin-2-yl)-4-(1-(4-methoxybenzyl)-3-(piperidin-3-ylamino)-1H-pyrazolo[3,4-b]pyridin-4-yloxy)benzamide, TFA salt (590-4) (0.12 mmol, the crude product from previous step) in DCM (2 mL) were added DIPEA (0.12 mL, 0.64 mmol), ethyl (s, 1H), 8.67 (d, J=4.1 Hz, 1H), 8.53 (s, 1H), 8.28-8.12 (m, 3H), 7.64 (d, J=3.5 Hz, 1H), 7.42 (d, J=7.4 Hz, 2H), 6.16 (d, J=5.2 Hz, 1H), 5.22-5.12 (m, 1H), 4.20-3.82 (m, 4H), 3.70 (m, 2H), 3.02-2.93 (m, 1H), 2.08-1.92 (m, 1H), 1.72-1.52 (m, 2H), 1.49-1.37 (m, 1H), 1.20-0.95 (m, 3H).

Example 79

(R)-3-(4-(4-(4-cyanopyridin-2-ylcarbamoyl)phenoxy)-1H-pyrazolo[3,4-b]pyridin-3-ylamino)-N-ethylpiperidine-1-carboxamide (Compound ID 79)

Preparation of (R)-3-(4-(4-(4-cyanopyridin-2-ylcarbamoyl)phenoxy)-1H-pyrazolo[3,4-b]pyridin-3-ylamino)-N-ethylpiperidine-1-carboxamide (591)

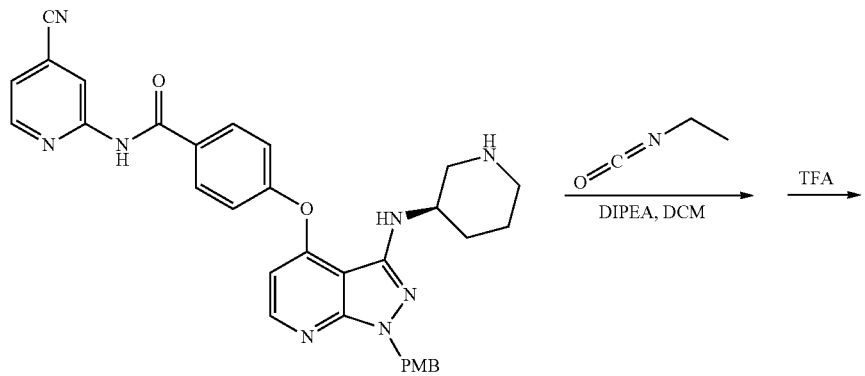

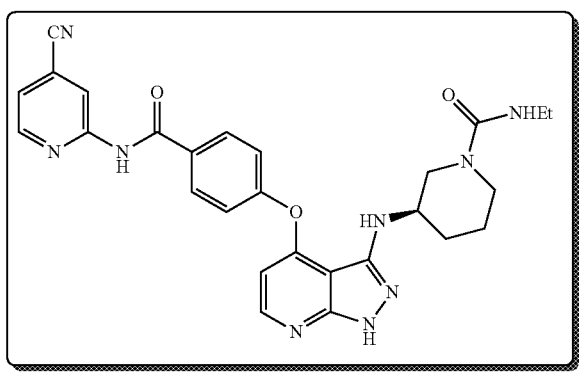

591

(R)-3-(4-(4-(4-Cyanopyridin-2-ylcarbamoyl)phenoxy)-1H-pyrazolo[3,4-b]pyridin-3-ylamino)-N-ethylpiperidine-1-carboxamide (591) (34 mg, 54% yield) was obtained as a white solid from (R)—N-(4-cyanopyridin-2-yl)-4-(1-(4-methoxybenzyl)-3-(piperidin-3-ylamino)-1H-pyrazolo[3,4-b]pyridin-4-yloxy)benzamide, TFA salt (590-4) (0.12 mmol, the crude product from previous step) and isocyanatoethane (0.014 mL, 0.18 mmol), following a similar procedure outlined in the preparation of (R)-ethyl 3-(4-(4-(4-cyanopyridin-2-ylcarbamoyl)phenoxy)-1H-pyrazolo[3,4-b]pyridin-3-ylamino)piperidine-1-carboxylate (590) (Ex. 3.4.5). LC-MS (ESI): m/z (M+1) 526.6. $^1$H NMR (400 MHz, DMSO) δ 12.25 (s, 1H), 11.35 (s, 1H), 8.66 (d, J=4.6 Hz, 1H), 8.52 (s, 1H), 8.19 (d, J=7.1 Hz, 3H), 7.64 (d, J=4.8 Hz, 1H), 7.41 (d, J=7.9 Hz, 2H), 6.47-6.28 (m, 1H), 6.16 (d, J=5.0 Hz, 1H), 5.19 (d, J=8.1 Hz, 1H), 4.08-3.84 (m, 1H), 3.79-3.54 (m, 2H), 3.06-2.97 (m, 2H), 2.92-2.79 (m, 2H), 2.03-1.94 (m, 1H), 1.68-1.54 (m, 2H), 1.47-1.36 (m, 1H), 0.96 (t, J=7.0 Hz, 3H).

Example 80

(R)—N-(4-cyanopyridin-2-yl)-4-(3-(1-(3-methoxypropanoyl)piperidin-3-ylamino)-1H-pyrazolo[3,4-b]pyridin-4-yloxy)benzamide (Compound ID 80)

Preparation of 3-methoxypropanoic acid (593-1)

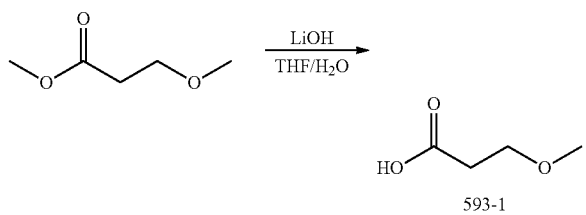

To a solution of methyl 3-methoxypropanoate (1.0 g, 8.5 mmol) in THF (7 mL) and water (7 mL) was added LiOH (533 mg, 12.7 mmol). The resulting mixture was stirred at roomtemperature overnight. The solvent was removed under reduced pressure and the residue was acidified with 1N HCl to pH 3-4 and concentrated to afford 3-methoxypropanoic acid (593-1) (quant. yield, together with LiCl) which was directly used in the next step. LC-MS (ESI): m/z (M−1) 105.4.

Preparation of (R)—N-(4-cyanopyridin-2-yl)-4-(3-(1-(3-methoxypropanoyl)piperidin-3-ylamino)-1H-pyrazolo[3,4-b]pyridin-4-yloxy)benzamide (593)

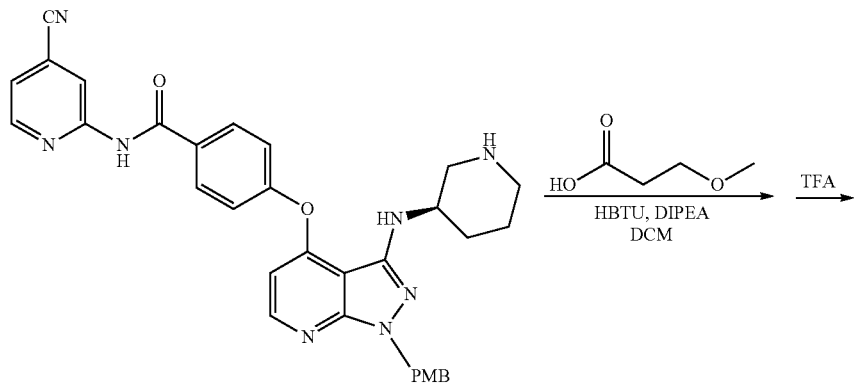

590-4

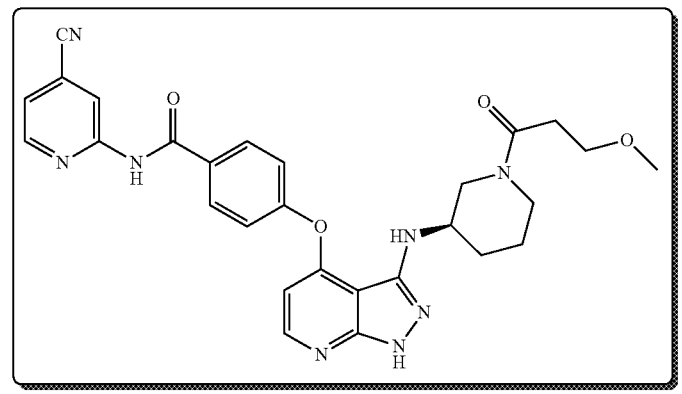

593

(R)—N-(4-Cyanopyridin-2-yl)-4-(3-(1-(3-methoxypropanoyl)piperidin-3-ylamino)-1H-pyrazolo[3,4-b]pyridin-4-yloxy)benzamide (593) (29 mg, 45% yield) was obtained as a white powder from (R)—N-(4-cyanopyridin-2-yl)-4-(1-(4-methoxy benzyl)-3-(piperidin-3-ylamino)-1H-pyrazolo[3,4-b]pyridin-4-yloxy)benzamide, TFA salt (590-4) (0.12 mmol, the crude product from previous step), following a similar procedure outlined in the preparation of (R)-1-(3-(4-(4-chlorophenoxy)- 1H-pyrazolo[3,4-b]pyridin-3-ylamino)pyrrolidin-1-yl)prop-2-en-1-one (291) (Ex. 1). LC-MS (ESI): m/z (M+1) 541.3. $^1$H NMR (400 MHz, DMSO) δ 12.28 (d, J=32.5 Hz, 1H), 11.33 (s, 1H), 8.66 (d, J=5.0 Hz, 1H), 8.52 (s, 1H), 8.19 (d, J=6.0 Hz, 3H), 7.64 (d, J=4.9 Hz, 1H), 7.41 (d, J=7.3 Hz, 2H), 6.17 (dd, J=9.3, 4.5 Hz, 1H), 5.19 (dd, J=19.0, 5.5 Hz, 1H), 4.47-3.89 (m, 2H), 3.73-3.48 (m, 3H), 3.19 (d, J=9.4 Hz, 3H), 2.94-2.77 (m, 1H), 2.60-2.52 (m, 2H), 2.11-1.89 (m, 1H), 1.80-1.55 (m, 2H), 1.49-1.27 (m, 1H), 1.14-0.82 (m, 1H).

Example 81

(R)—N-(4-cyanopyridin-2-yl)-4-(3-(1-(cyclopropanecarbonyl)piperidin-3-ylamino)-1H-pyrazolo[3,4-b]pyridin-4-yloxy)benzamide (Compound ID 81)

Preparation of (R)—N-(4-cyanopyridin-2-yl)-4-(3-(1-(cyclopropanecarbonyl)piperidin-3-ylamino)-1H-pyrazolo[3,4-b]pyridin-4-yloxy)benzamide (595)

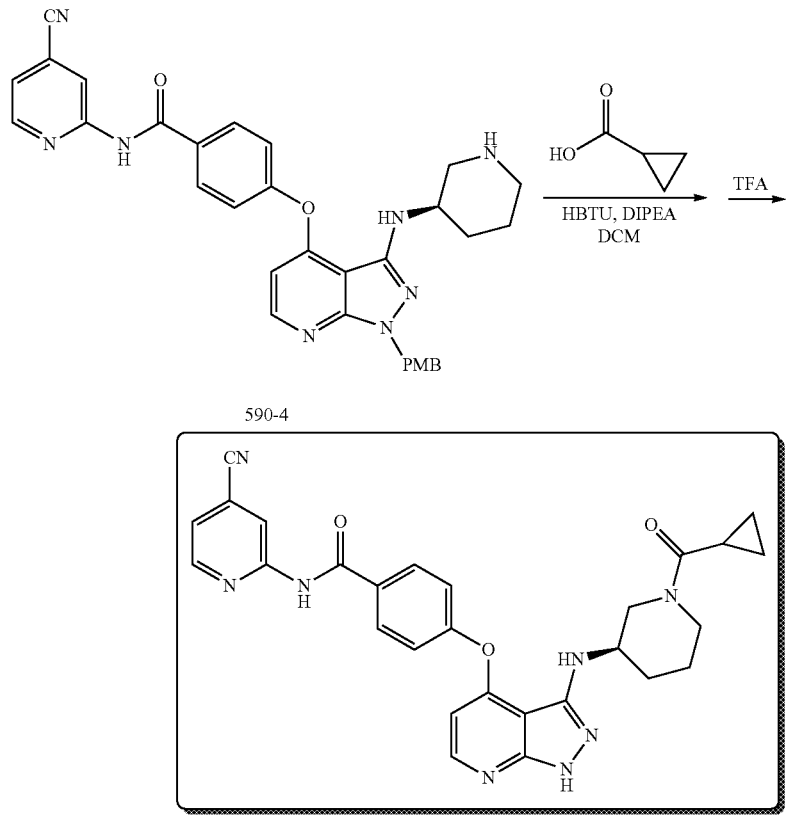

(R)—N-(4-Cyanopyridin-2-yl)-4-(3-(1-(cyclopropanecarbonyl)piperidin-3-ylamino)-1H-pyrazolo[3,4-b]pyridin-4-yloxy)benzamide (595) (26 mg, 41% yield) was obtained as a white powder from (R)—N-(4-cyanopyridin-2-yl)-4-(1-(4-methoxy benzyl)-3-(piperidin-3-ylamino)-1H-pyrazolo[3,4-b]pyridin-4-yloxy)benzamide, TFA salt (590-4) (0.12 mmol, the crude product from previous step) and cyclopropanecarboxylic acid (15 mg, 0.18 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 523.2. $^1$H NMR (400 MHz, DMSO) δ 12.27 (s, 1H), 11.30 (s, 1H), 8.66 (d, J=4.2 Hz, 1H), 8.53 (d, J=2.1 Hz, 1H), 8.20 (d, J=7.6 Hz, 3H), 7.64 (d, J=3.4 Hz, 1H), 7.42 (d, J=7.5 Hz, 2H), 6.17 (s, 1H), 5.29-5.13 (m, 1H), 4.40-4.14 (m, 1H), 4.01-3.64 (m, 2H), 3.14-2.97 (m, 1H), 2.10-1.86 (m, 2H), 1.81-1.59 (m, 2H), 1.53-1.39 (m, 1H), 1.31-1.14 (m, 1H), 0.85-0.51 (m, 4H).

Example 82

N-(4-cyanopyridin-2-yl)-4-(3-((1r,4r)-4-hydroxycyclohexylamino)-1H-pyrazolo[3,4-b]pyridin-4-yloxy)benzamide (Compound ID 82)

Preparation of (1r,4r)-4-(tert-butyldimethylsilyloxy)cyclohexanamine (587-1)

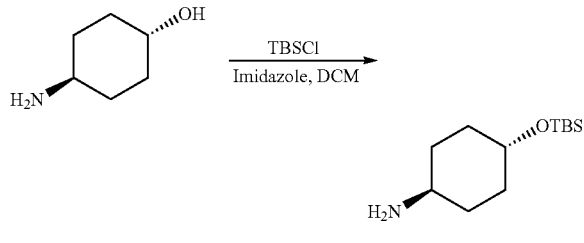

To a solution of (1r,4r)-4-aminocyclohexanol (5.0 g, 43 mmol) in DCM (100 mL) were added imidazole (14.8 g, 217 mmol) and TBSCl (19.6 g, 130 mmol). The resulting mixture was stirred at room temperature overnight before being concentrated in vacuo. The residue was diluted with EA (200 mL), washed with 1N NaOH aq. solution (100 mL), water and brine, dried over $Na_2SO_4$, filtered and concentrated under reduced pressure to afford (1 r,4r)-4-(tert-butyldimethylsilyloxy)cyclohexanamine (587-1) (7.0 g, 70% yield) as a yellow oil. LC-MS (ESI): m/z (M+1) 231.1.

Preparation of methyl 4-(3-((1r,4r)-4-(tert-butyldimethylsilyloxy)cyclohexylamino)-1-(4-methoxybenzyl)-1H-pyrazolo[3,4-b]pyridin-4-yloxy)benzoate (587-2)

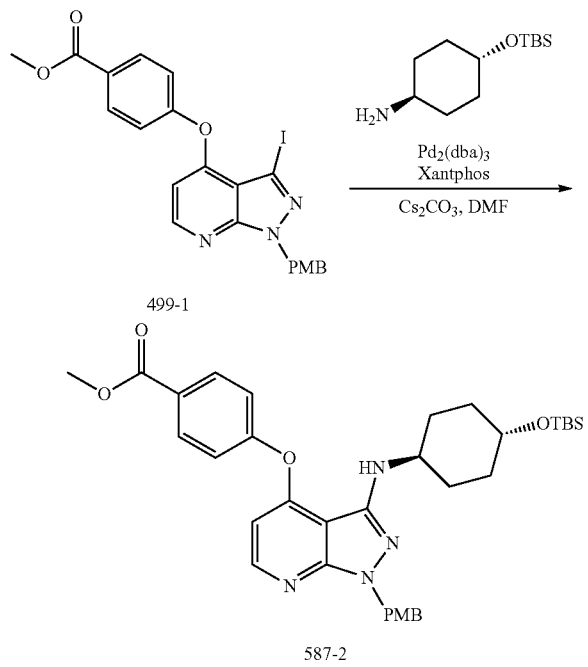

587-2

Methyl 4-(3-((1 r,4r)-4-(tert-butyldimethylsilyloxy)cyclohexylamino)-1-(4-methoxybenzyl)-1H-pyrazolo[3,4-b]pyridin-4-yloxy)benzoate (587-2) (371 mg, 62% yield) was obtained as a yellow solid from methyl 4-(3-iodo-1-(4-methoxybenzyl)-1H-pyrazolo[3,4-b]pyridin-4-yloxy)benzoate (499-1) (500 mg, 0.97 mmol) and (1r,4r)-4-(tert-butyldimethylsilyloxy)cyclohexanamine (587-1) (890 mg, 3.98 mmol), following a similar procedure outlined in the preparation of (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1) (Ex. 1). LC-MS (ESI): m/z (M+1) 617.3.

Preparation of 4-(3-((1r,4r)-4-(tert-butyldimethylsilyloxy)cyclohexylamino)-1-(4-methoxybenzyl)-1H-pyrazolo[3,4-b]pyridin-4-yloxy)benzoic acid (587-3)

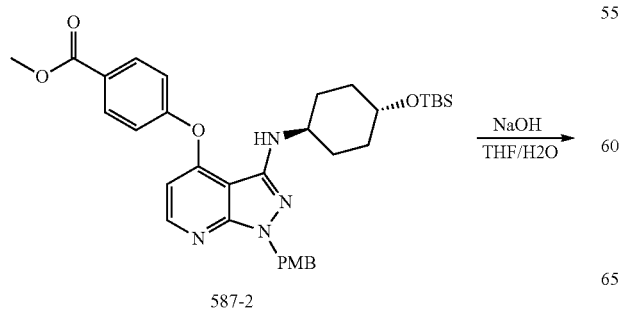

587-2

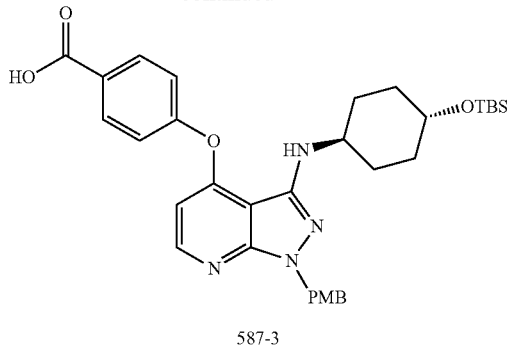

587-3

To a solution of methyl 4-(3-((1r,4r)-4-(tert-butyldimethylsilyloxy)cyclohexylamino)-1-(4-methoxybenzyl)-1H-pyrazolo[3,4-b]pyridin-4-yloxy)benzoate (587-2) (371 mg, 0.60 mmol) in THF (4 mL) and $H_2O$ (2 mL) was added NaOH (72 mg, 1.8 mmol). The resulting mixture was stirred at room temperature overnight. The reaction mixture was acidified to pH ~3 with 1N HCl and extracted with 10% i-PrOH in DCM (×3). The combined organic phase was washed with brine, dried over $Na_2SO_4$ and concentrated to afford 4-(3-((1r,4r)-4-(tert-butyldimethylsilyloxy)cyclohexylamino)-1-(4-methoxybenzyl)-1H-pyrazolo[3,4-b]pyridin-4-yloxy)benzoic acid (587-3) (368 mg, 98% yield) as a yellow solid. LC-MS (ESI): m/z (M+1) 604.3.

Preparation of 4-(3-((1r,4r)-4-(tert-butyldimethylsilyloxy)cyclohexylamino)-1-(4-methoxybenzyl)-1H-pyrazolo[3,4-b]pyridin-4-yloxy)-N-(4-cyanopyridin-2-yl)benzamide (587-4)

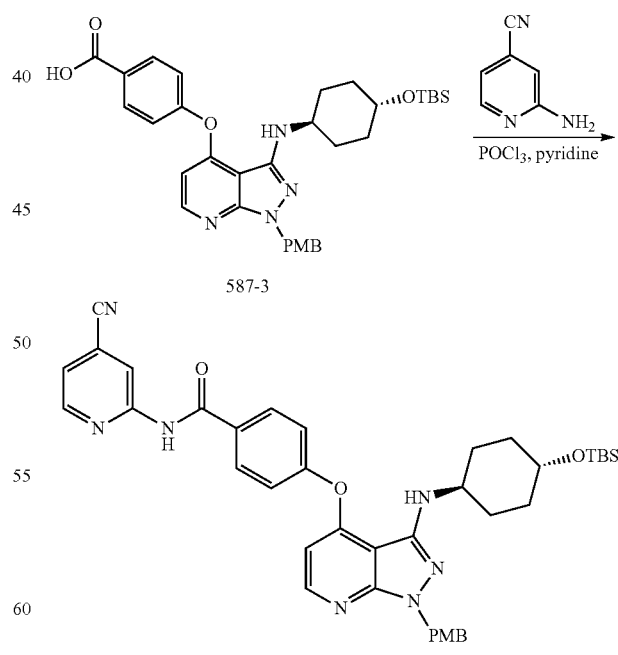

587-4

At 0° C., to a solution of 4-(3-((1r,4r)-4-(tert-butyldimethylsilyloxy)cyclohexylamino)-1-(4-methoxybenzyl)-1H-pyrazolo[3,4-b]pyridin-4-yloxy)benzoic acid (587-3) (180 mg, 0.30 mmol) and 2-aminoisonicotinonitrile (107 mg, 0.90 mmol) in anhydrous pyridine (2 mL) was added POCl₃ (0.14 mL, 1.50 mmol) dropwise. After stirred at 0° C. for 30 min, the reaction mixture was quenched with ice water and extracted with EA (50 mL×3). The combined organic phase was washed with brine, dried over Na₂SO₄ and filtered to give the crude product which was purified by flash chromatography (silica gel, 0 to 50% EA in PE) to afford 4-(3-((1r,4r)-4-(tert-butyldimethylsilyloxy) cyclohexylamino)-1-(4-methoxybenzyl)-1H-pyrazolo[3,4-b]pyridin-4-yloxy)-N-(4-cyanopyridin-2-yl)benzamide (587-4) (125 mg, 60% yield) as a yellow solid. LC-MS (ESI): m/z (M+1) 704.4.

Preparation of (1r,4r)-4-(4-(4-(4-cyanopyridin-2-ylcarbamoyl)phenoxy)-1H-pyrazolo[3,4-b]pyridin-3-ylamino)cyclohexyl 2,2,2-trifluoroacetate (587-5)

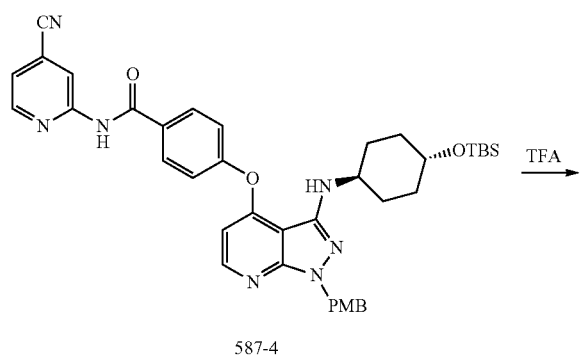

587-4

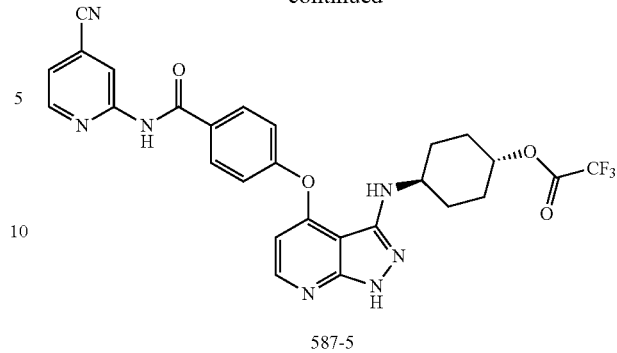

587-5

A solution of 4-(3-((1 r,4r)-4-(tert-butyldimethylsilyloxy) cyclohexylamino)-1-(4-methoxy benzyl)-1H-pyrazolo[3,4-b]pyridin-4-yloxy)-N-(4-cyanopyridin-2-yl)benzamide (587-4) (125 mg, 0.18 mmol) in TFA was heated at 60° C. under N₂ atmosphere for 2 hr. After being cooled down to room temperature, the reaction mixture was concentrated under reduced pressure to afford (1r,4r)-4-(4-(4-(4-cyanopyridin-2-ylcarbamoyl)phenoxy)-1H-pyrazolo[3,4-b]pyridin-3-ylamino)cyclohexyl 2,2,2-trifluoroacetate (587-5) as a crude product which was directly used in next step without purification.

Preparation of N-(4-cyanopyridin-2-yl)-4-(3-((1r, 4r)-4-hydroxycyclohexylamino)-1H-pyrazolo[3,4-b] pyridin-4-yloxy)benzamide (587)

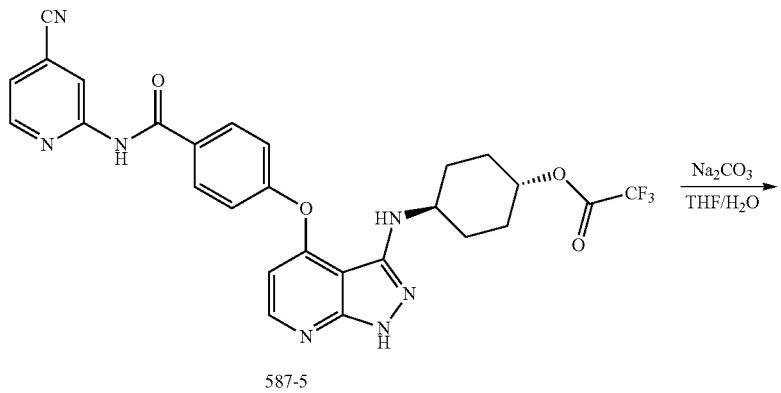

587-5

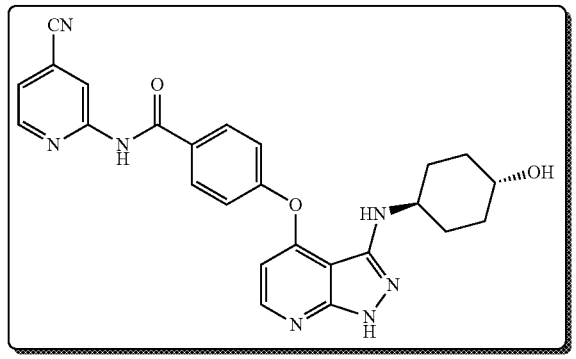

587

335

To a solution of (1R,4R)-4-(4-(4-(4-cyanopyridin-2-yl-carbamoyl)phenoxy)-1H-pyrazolo[3,4-b]pyridin-3-ylamino)cyclohexyl 2,2,2-trifluoroacetate (587-5) (crude product obtained from previous step) in THF (9 mL) was added 0.5N $Na_2CO_3$ aq. (4 mL). After being stirred at room temperature for 30 min, the reaction mixture was extracted with DCM and the organic phase was dried over $Na_2SO_4$ and filtered to give the crude product which was purified by prep. HPLC to afford N-(4-cyanopyridin-2-yl)-4-(3-((1r,4r)-4-hydroxycyclohexylamino)-1H-pyrazolo[3,4-b]pyridin-4-yloxy)benzamide (587) (30 mg, 36% yield over 2 steps) as a white powder. LC-MS (ESI): m/z (M+1) 470.2. $^1$H NMR (400 MHz, DMSO) δ 12.17 (s, 1H), 11.34 (s, 1H), 8.66 (d, J=5.0 Hz, 1H), 8.52 (s, 1H), 8.44 (br, 1H), 8.18 (t, J=7.1 Hz, 3H), 7.72-7.56 (m, 1H), 7.41 (d, J=8.5 Hz, 2H), 6.13 (d, J=5.3 Hz, 1H), 4.93 (d, J=7.4 Hz, 1H), 4.76-4.27 (m, 1H), 3.54-3.46 (m, 1H), 2.13-1.95 (m, 2H), 1.93-1.72 (m, 2H), 1.43-1.14 (m, 4H).

Example 83

(R)—N-(4-cyanopyridin-2-yl)-4-(3-(1-(3-methyloxetane-3-carbonyl)piperidin-3-ylamino)-1H-pyrazolo[3,4-b]pyridin-4-yloxy)benzamide (Compound ID 83)

Preparation of 3-methyloxetane-3-carboxylic acid (592-1)

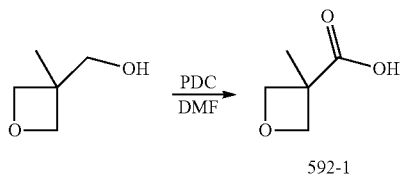

592-1

To a stirred solution of (3-methyloxetan-3-yl)methanol (2.04 g, 20 mmol) in DMF (20 mL) was added PDC (37.6 g, 100 mmol). The resulting mixture was stirred at room temperature overnight before being quenched with $H_2O$ and extracted with ethyl acetate (30 mL×3). The combined organic layers were dried over $Na_2SO_4$, filtered and concentrated to provide 3-methyloxetane-3-carboxylic acid (592-1) (2.1 g, quant. yield) as a brown oil.

Preparation of (R)—N-(4-cyanopyridin-2-yl)-4-(1-(4-methoxybenzyl)-3-(1-(3-methyloxetane-3-carbonyl)piperidin-3-ylamino)-1H-pyrazolo[3,4-b]pyridin-4-yloxy)benzamide (592-2)

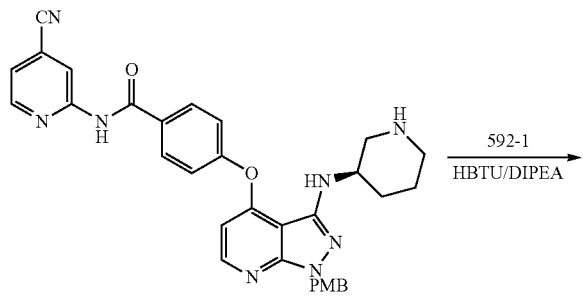

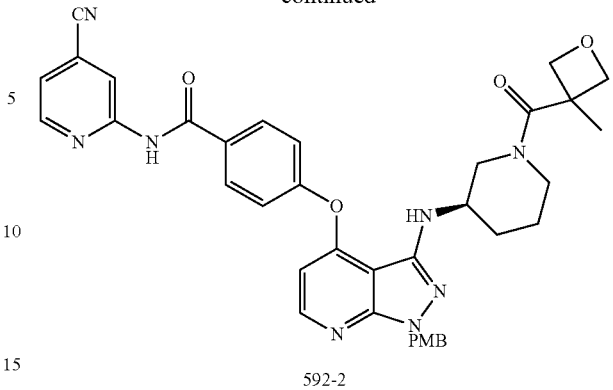

592-2

(R)—N-(4-Cyanopyridin-2-yl)-4-(1-(4-methoxybenzyl)-3-(1-(3-methyloxetane-3-carbonyl)piperidin-3-ylamino)-1H-pyrazolo[3,4-b]pyridin-4-yloxy)benzamide (592-2) (84 mg, quant. yield) was obtained as a yellow oil from (R)—N-(4-cyanopyridin-2-yl)-4-(1-(4-methoxybenzyl)-3-(piperidin-3-ylamino)-1H-pyrazolo[3,4-b]pyridin-4-yloxy)benzamide (72 mg, 0.13 mmol) and 3-methyloxetane-3-carboxylic acid (mg, mmol), following a similar procedure in Ex. 26. LC-MS (ESI): m/z (M+1).

Preparation of (R)—N-(4-cyanopyridin-2-yl)-4-(3-(1-(3-methyloxetane-3-carbonyl)piperidin-3-ylamino)-1H-pyrazolo[3,4-b]pyridin-4-yloxy)benzamide (592)

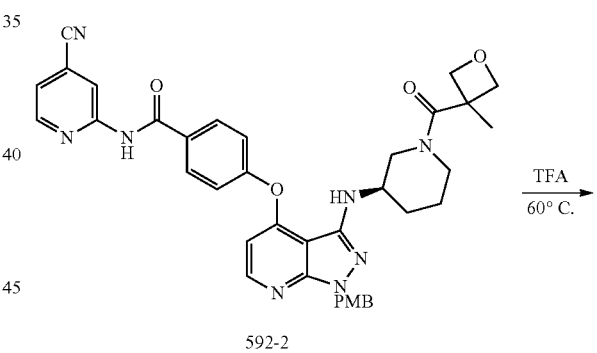

592-2

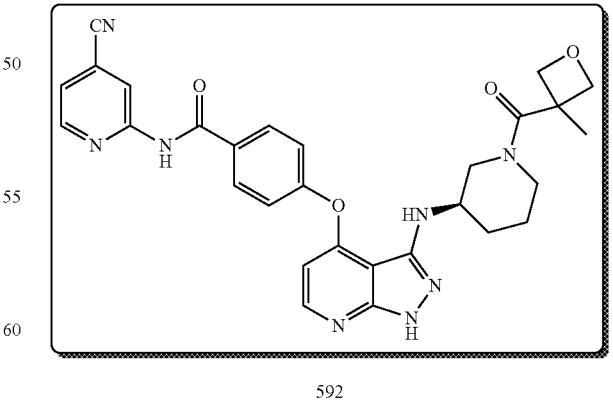

592

(R)—N-(4-Cyanopyridin-2-yl)-4-(3-(1-(3-methyloxetane-3-carbonyl)piperidin-3-ylamino)-1H-pyrazolo[3,4-b]pyridin-4-yloxy)benzamide (592) (31 mg, 43%) was obtained as a white solid from (R)—N-(4-cyanopyridin-2-yl)-4-(1-(4-methoxybenzyl)-3-(1-(3-methyloxetane-3-carbonyl)piperidin-3-ylamino)-1H-pyrazolo[3,4-b]pyridin-4-yloxy)benzamide (84 mg, 0.13 mmol), following a similar procedure in Ex. 26. LC-MS (ESI): m/z (M+1). $^1$H NMR (400 MHz, DMSO) δ 12.38-12.24 (m, 1H), 11.26 (br, 2H), 8.66 (d, J=4.4 Hz, 1H), 8.52 (s, 1H), 8.28-8.10 (m, 3H), 7.70-7.60 (m, 1H), 7.42 (d, J=8.1 Hz, 2H), 6.15 (d, J=5.4 Hz, 1H), 5.35-5.15 (m, 1H), 4.92-4.15 (m, 4H), 3.71-2.58 (m, 4H), 2.06-1.96 (m, 1H), 1.74-1.42 (m, 6H).

Example 84

(R)-4-(3-(1-(3-methyloxetane-3-carbonyl)piperidin-3-ylamino)-1H-pyrazolo[3,4-b]pyridin-4-yloxy)-N-(4-(trifluoromethyl)pyridin-2-yl)benzamide (Compound ID 84)

Preparation of (R)-tert-butyl 3-(1-(4-methoxybenzyl)-4-(4-(4-(trifluoromethyl)pyridin-2-ylcarbamoyl)phenoxy)-1H-pyrazolo[3,4-b]pyridin-3-ylamino)piperidine-1-carboxylate (595)

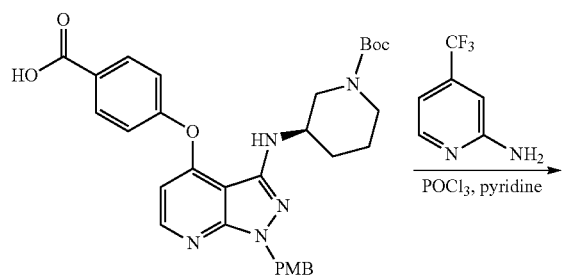

590-2

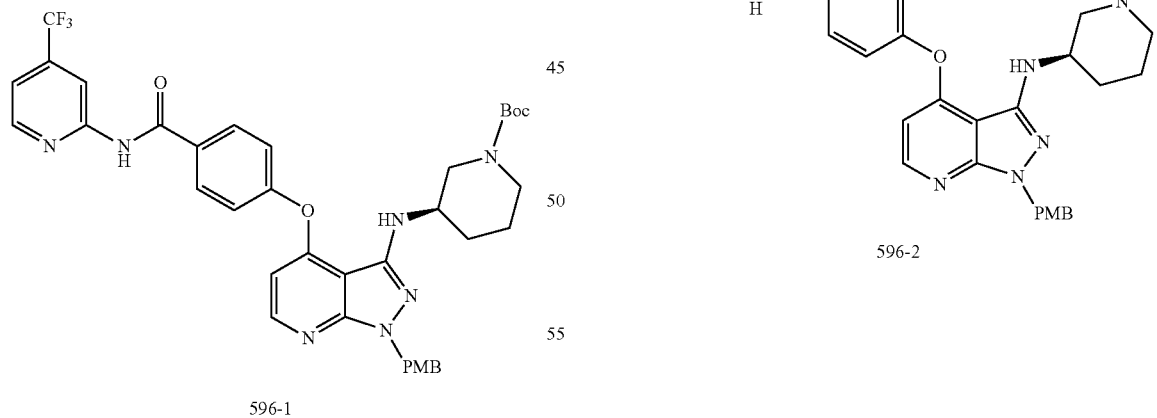

596-1

(R)-tert-Butyl 3-(1-(4-methoxybenzyl)-4-(4-(4-(trifluoromethyl)pyridin-2-ylcarbamoyl) phenoxy)-1H-pyrazolo[3,4-b]pyridin-3-ylamino)piperidine-1-carboxylate (596-1) (100 mg, 54% yield) was obtained as light yellow solid from (R)-4-(3-(1-(tert-butoxycarbonyl)piperidin-3-ylamino)-1-(4-methoxybenzyl)-1H-pyrazolo[3,4-b]pyridin-4-yloxy)benzoic acid (590-2) (150 mg, 0.26 mmol) and 4-(trifluoromethyl)pyridin-2-amine (84 mg, 0.52 mmol), following a similar procedure outlined in the preparation of 4-(3-((1r,4r)-4-(tert-butyldimethylsilyloxy) cyclohexylamino)-1-(4-methoxybenzyl)-1H-pyrazolo[3,4-b]pyridin-4-yloxy)-N-(4-cyanopyridin-2-yl)benzamide (587-4) (Ex. 1). LC-MS (ESI): m/z (M+1) 718.3.

Preparation of (R)-4-(1-(4-methoxybenzyl)-3-(piperidin-3-ylamino)-1H-pyrazolo[3,4-b]pyridin-4-yloxy)-N-(4-(trifluoromethyl)pyridin-2-yl)benzamide (596-2)

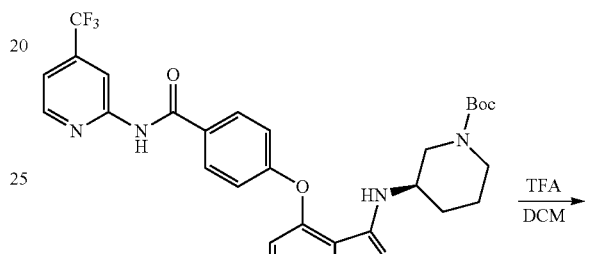

596-1

596-2

(R)-tert-Butyl 3-(1-(4-methoxybenzyl)-4-(4-(4-(trifluoromethyl)pyridin-2-ylcarbamoyl) phenoxy)-1H-pyrazolo[3,4-b]pyridin-3-ylamino)piperidine-1-carboxylate (596-1) (86 mg, 0.12 mmol) was treated with TFA in DCM to give (R)-4-(1-(4-methoxybenzyl)-3-(piperidin-3-ylamino)-1H-pyrazolo[3,4-b]pyridin-4-yloxy)-N-(4-(trifluoromethyl)pyridin-2-yl)benzamide (596-2) (quant.). LC-MS (ESI): m/z (M+1) 618.2.

Preparation of (R)-4-(3-(1-(3-methyloxetane-3-carbonyl)piperidin-3-ylamino)-1H-pyrazolo[3,4-b]pyridin-4-yloxy)-N-(4-(trifluoromethyl)pyridin-2-yl)benzamide (596)

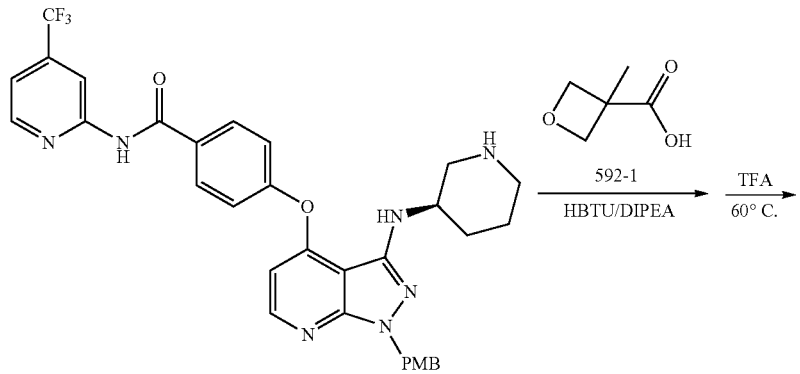

596-2

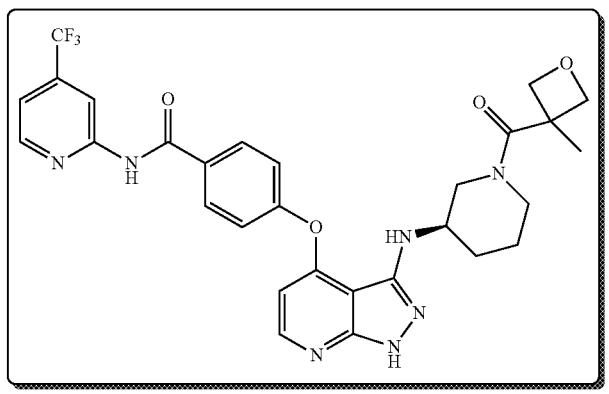

596

(R)-4-(3-(1-(3-Methyloxetane-3-carbonyl)piperidin-3-ylamino)-1H-pyrazolo[3,4-b]pyridin-4-yloxy)-N-(4-(trifluoromethyl)pyridin-2-yl)benzamide (596) (30 mg, 41% yield) was obtained as a white powder from (R)-4-(1-(4-methoxybenzyl)-3-(piperidin-3-ylamino)-1H-pyrazolo[3,4-b]pyridin-4-yloxy)-N-(4-(trifluoromethyl)pyridin-2-yl)benzamide (596-2) (0.12 mmol, the crude product from previous step) and 3-methyloxetane-3-carboxylic acid (21 mg, 0.18 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 596.2. $^1$H NMR (400 MHz, DMSO) δ 12.32 (s, 1H), 12.26 (s, 1H), 11.35 (s, 1H), 8.75-8.61 (m, 1H), 8.55 (s, 1H), 8.27-8.11 (m, 3H), 7.61-7.49 (m, 1H), 7.42 (d, J=8.1 Hz, 2H), 6.15 (d, J=5.3 Hz, 1H), 5.35-5.16 (m, 1H), 4.92-4.71 (m, 2H), 4.38-4.13 (m, 3H), 3.71-3.53 (m, 1H), 3.00-2.60 (m, 3H), 2.05-1.96 (m, 1H), 1.75-1.56 (m, 4H), 1.49-1.39 (m, 1H).

Example 85

N-(4-cyanopyridin-2-yl)-4-(3-((1s,4s)-4-methoxycyclohexylamino)-1H-pyrazolo[3,4-b]pyridin-4-yloxy)benzamide (Compound ID 85)

Preparation of tert-butyl (1r,4r)-4-hydroxycyclohexylcarbamate (589-1)

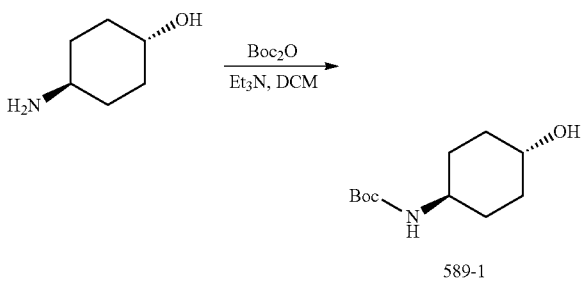

589-1

At 0° C., to a suspension of (1r,4r)-4-aminocyclohexanol (10 g, 87 mmol) and TEA (24 mL, 174 mmol) in DCM (100 mL) was added Boc$_2$O (22 mL, 104 mmol) dropwise. The resulting mixture was stirred at room temperature overnight. The reaction mixture was filtered and the filter cake was washed with water and dried to afford tert-butyl (1r,4r)-4-hydroxycyclohexylcarbamate (589-1) (12 g, 64% yield) as a white solid. LC-MS (ESI): m/z (M+1) 216.4.

Preparation of (1s,4s)-4-(tert-butoxycarbonylamino)cyclohexyl acetate (589-2)

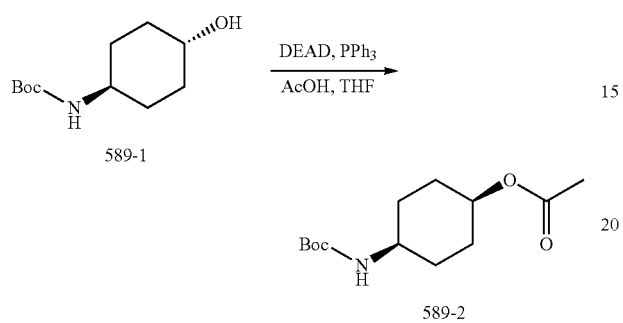

At 0° C. and under N₂ atmosphere, to a mixture of tert-butyl (1r,4r)-4-hydroxycyclohexylcarbamate (589-1) (3.0 g, 14.0 mmol), AcOH (3.2 mL, 55.8 mmol) and PPh₃ (14.6 g, 55.8 mmol) in anhydrous THF (40 mL) was added DEAD (8.8 mL, 55.8 mmol) dropwise. The resulting mixture was stirred at r.t. overnight. The reaction mixture was concentrated and the residue was triturated with ether/PE (1:1) and filtered to remove P(O)Ph₃. The filtrate was concentrated to give the crude product which was purified by flash chromatography (silica gel, 0 to 10% EA in PE) to afford (1s,4s)-4-(tert-butoxycarbonylamino)cyclohexyl acetate (589-2) (230 mg, 6.5% yield) as a colorless oil. LC-MS (ESI): m/z (M+1) 258.3.

Preparation of tert-butyl (1s,4s)-4-hydroxycyclohexylcarbamate (589-3)

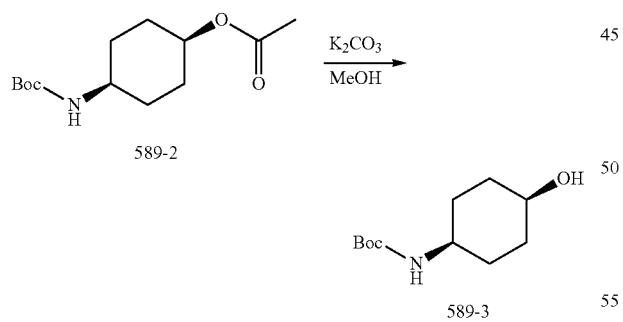

To a solution of (1s,4s)-4-(tert-butoxycarbonylamino)cyclohexyl acetate (589-2) (230 mg, 0.89 mmol) in MeOH (3 mL) was added K₂CO₃ (186 mg, 1.34 mmol). The resulting mixture was stirred at r.t. for 2 hr. before concentrated. The residue was partitioned between DCM/H₂O (30 mL/30 mL). The layers were separated and the organic layer was washed with brine, dried over Na₂SO₄, filtered and concentrated to afford tert-butyl (1s,4s)-4-hydroxycyclohexylcarbamate (589-3) (183 mg, quant.) as a colorless oil. LC-MS (ESI): m/z (M+1) 216.4.

Preparation of tert-butyl (1s,4s)-4-methoxycyclohexylcarbamate (589-4)

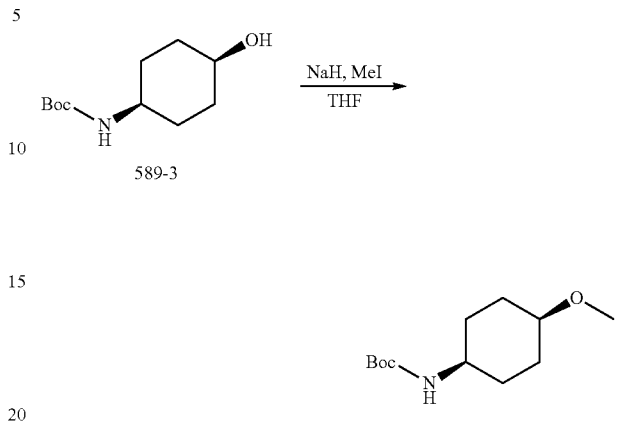

At 0° C., to a solution of tert-butyl (1s,4s)-4-hydroxycyclohexylcarbamate (589-3) (183 mg, 0.85 mmol) in anhydrous THF (2 mL) was added NaH (51 mg, 1.28 mmol). The resulting mixture was stirred at 0° C. for 30 min. After MeI (0.08 mL, 0.85 mL) was added, the resulting mixture was stirred at r.t. overnight. The reaction mixture was quenched with sat. NH₄Cl aq. (5 mL) and extracted with EA (3 mL×3), the organic phase was washed with brine, dried over Na₂SO₄, filtered and concentrated under reduced pressure to give the crude product which was purified by flash chromatography (silica gel, 0 to 20% EA in PE) to afford tert-butyl (1s,4s)-4-methoxycyclohexylcarbamate (589-4) (120 mg, 61% yield) as a colorless oil. LC-MS (ESI): m/z (M+1) 230.1.

Preparation of (1s,4s)-4-methoxycyclohexanamine, HCl salt (589-5)

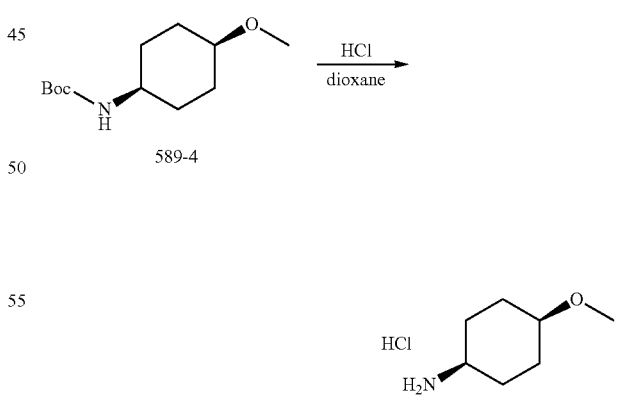

(1S,4S)-4-Methoxycyclohexanamine, HCl salt (589-5) (quant. yield) was obtained as a colorless oil by stirring tert-butyl (1s,4s)-4-methoxycyclohexylcarbamate (589-4) (120 mg, 0.52 mmol) in HCl/dioxane (4N) for 30 min. LC-MS (ESI): m/z (M+1) 130.1.

Preparation of methyl 4-(1-(4-methoxybenzyl)-3-((1s,4s)-4-methoxycyclohexylamino)-1H-pyrazolo[3,4-b]pyridin-4-yloxy)benzoate (589-6)

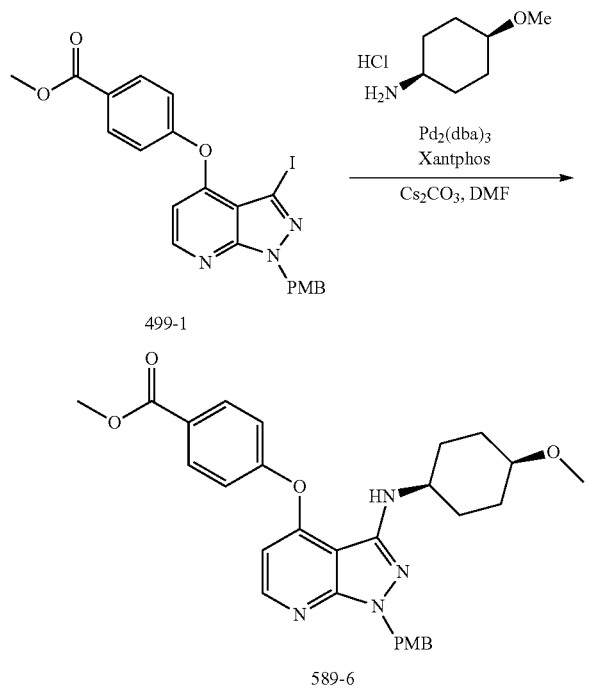

Methyl 4-(1-(4-methoxybenzyl)-3-((1s,4s)-4-methoxycyclohexylamino)-1H-pyrazolo[3,4-b]pyridin-4-yloxy)benzoate (589-6) (23 mg, 17% yield) was obtained as a light yellow oil from methyl 4-(3-iodo-1-(4-methoxybenzyl)-1H-pyrazolo[3,4-b]pyridin-4-yl oxy)benzoate (499-1) (135 mg, 0.26 mmol) and (1s,4s)-4-methoxycyclohexanamine, HCl salt (589-5) (63 mg, 0.52 mmol), following a similar procedure outlined in the preparation of (S)-tert-butyl 2-((1-(4-methoxybenzyl)-4-(4-phenoxyphenoxy)-1H-pyrazolo[3,4-b]pyridin-3-ylamino)methyl)pyrrolidine-1-carboxylate (504-1) (Ex. 1). LC-MS (ESI): m/z (M+1) 517.0.

Preparation of 4-(1-(4-methoxybenzyl)-3-((1s,4s)-4-methoxycyclohexylamino)-1H-pyrazolo[3,4-b]pyridin-4-yloxy)benzoic acid (589-7)

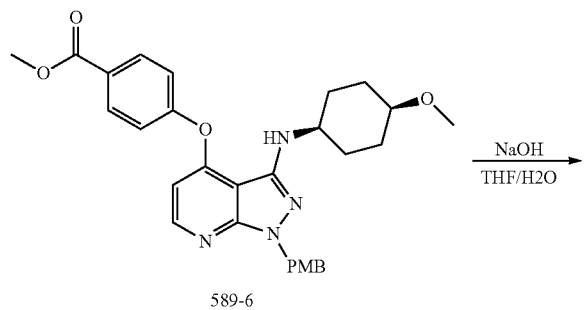

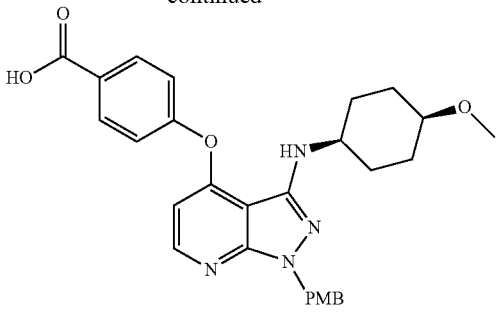

4-(1-(4-Methoxybenzyl)-3-((1s,4s)-4-methoxycyclohexylamino)-1H-pyrazolo[3,4-b]pyridin-4-yloxy)benzoic acid (589-6) (22 mg, quant. yield) was obtained from methyl 4-(1-(4-methoxybenzyl)-3-((1s,4s)-4-methoxycyclohexylamino)-1H-pyrazolo[3,4-b]pyridin-4-yloxy)benzoate (589-6) (23 mg, 0.04 mmol), following a similar procedure outlined in the preparation of 4-(3-((1r,4r)-4-(tert-butyldimethylsilyloxy) cyclohexylamino)-1-(4-methoxybenzyl)-1H-pyrazolo[3,4-b]pyridin-4-yloxy)benzoic acid (587-3) (Ex. 1). LC-MS (ESI): m/z (M+1) 503.5.

Preparation of N-(4-cyanopyridin-2-yl)-4-(1-(4-methoxybenzyl)-3-((1s,4s)-4-methoxycyclohexylamino)-1H-pyrazolo[3,4-b]pyridin-4-yloxy)benzamide (589-8)

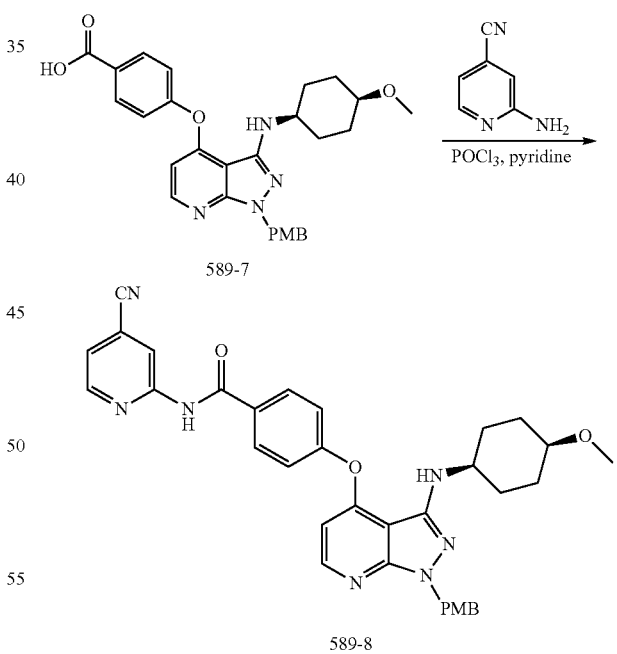

N-(4-Cyanopyridin-2-yl)-4-(1-(4-methoxybenzyl)-3-((1s,4s)-4-methoxycyclohexylamino)-1H-pyrazolo[3,4-b]pyridin-4-yloxy)benzamide (589-8) (25 mg, 83% yield) was obtained as a light yellow oil from 4-(1-(4-methoxybenzyl)-3-((1s,4s)-4-methoxycyclohexylamino)-1H-pyrazolo[3,4-b]pyridin-4-yloxy)benzoic acid (589-6) (22 mg, 0.05 mmol) and 2-aminoisonicotinonitrile (18 mg, 0.15 mmol), following a similar procedure outlined in the preparation of 4-(3-

((1r,4r)-4-(tert-butyldimethylsilyloxy)cyclohexyl amino)-1-(4-methoxybenzyl)-1H-pyrazolo[3,4-b]pyridin-4-yloxy)-N-(4-cyanopyridin-2-yl)benzamide (587-4) (Ex. 1). LC-MS (ESI): m/z (M+1) 604.3.

Preparation of N-(4-cyanopyridin-2-yl)-4-(3-((1s,4s)-4-methoxycyclohexyl amino)-1H-pyrazolo[3,4-b]pyridin-4-yloxy)benzamide (589)

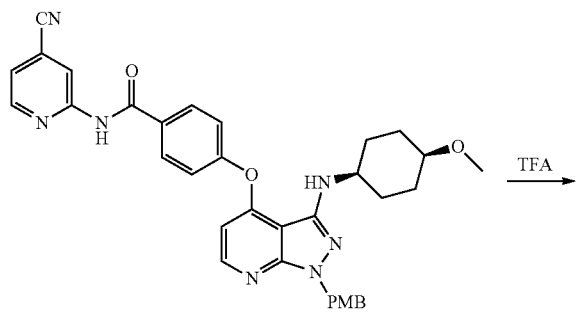

589-8

TFA

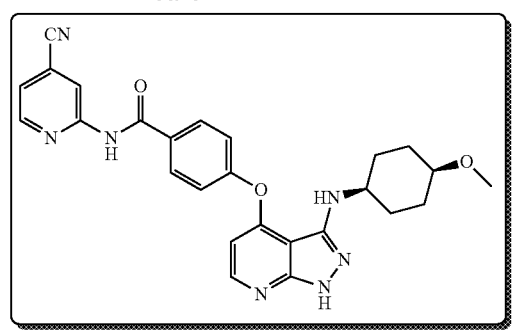

589

N-(4-Cyanopyridin-2-yl)-4-(3-((1s,4s)-4-methoxycyclohexylamino)-1H-pyrazolo[3,4-b]pyridin-4-yloxy)benzamide (589) (8 mg, 40% yield) was obtained as a white powder from N-(4-cyanopyridin-2-yl)-4-(1-(4-methoxybenzyl)-3-((1s,4s)-4-methoxycyclohexylamino)-1H-pyrazolo[3,4-b]pyridin-4-yloxy)benzamide (589-8) (25 mg, 0.04 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one (291) (Ex. 1). LC-MS (ESI): m/z (M+1) 484.2. $^1$H NMR (400 MHz, DMSO) δ 12.15 (s, 1H), 11.31 (s, 1H), 8.64 (d, J=4.2 Hz, 1H), 8.51 (s, 1H), 8.30-8.07 (m, 3H), 7.62 (d, J=3.9 Hz, 1H), 7.40 (d, J=8.6 Hz, 2H), 6.15 (d, J=5.2 Hz, 1H), 4.94 (d, J=8.0 Hz, 1H), 3.74-3.49 (m, 1H), 3.17 (s, 3H), 2.57-2.51 (m, 1H), 1.86-1.63 (m, 4H), 1.65-1.38 (m, 4H).

Synthesis of Intermediates for Preparation of Compound ID 86 and Analogs

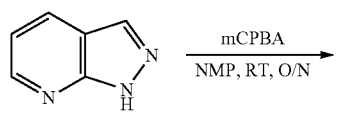

mCPBA
NMP, RT, O/N

1

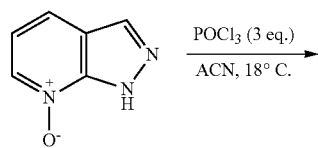

2

POCl$_3$ (3 eq.)
ACN, 18° C.

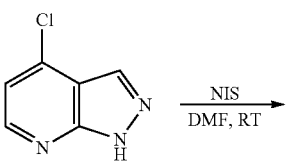

3

NIS
DMF, RT

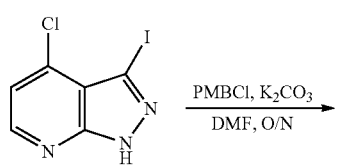

4

PMBCl, K$_2$CO$_3$
DMF, O/N

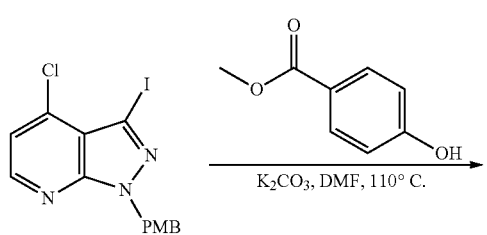

5

K$_2$CO$_3$, DMF, 110° C.

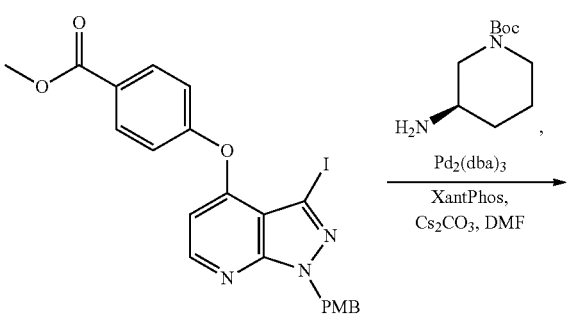

6

Pd$_2$(dba)$_3$
XantPhos,
Cs$_2$CO$_3$, DMF

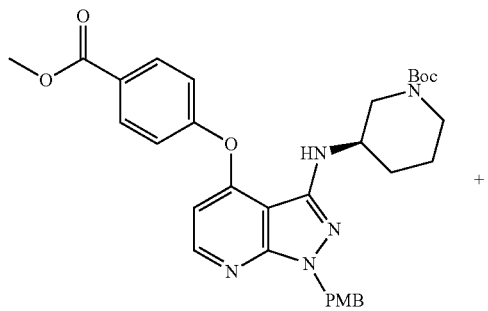

7

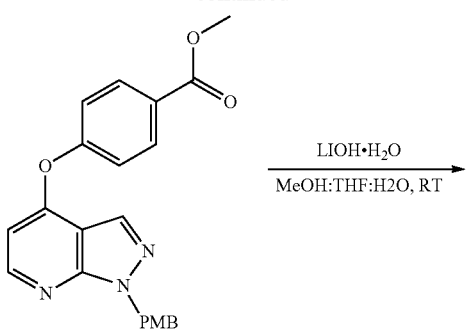

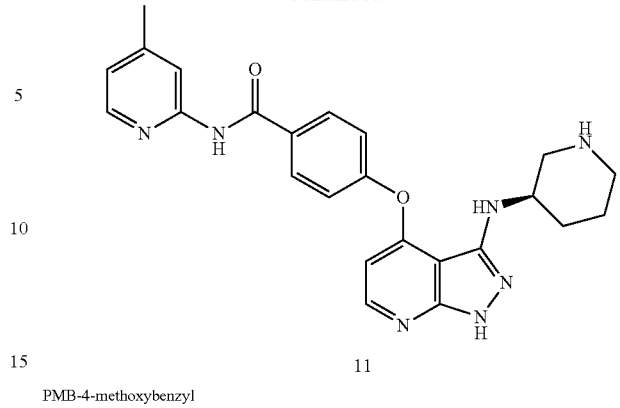

PMB-4-methoxybenzyl

1.1 Preparation of 1H-pyrazolo[3,4-b]pyridine 7-oxide

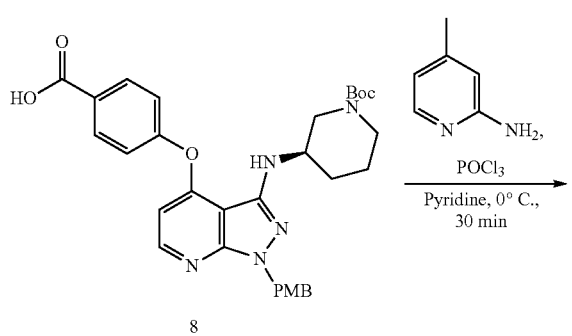

To a solution of 1H-pyrazolo[3,4-b]pyridine (50 g, 0.42 mol) in NMP (300 mL) was added a solution of m-CPBA (84 g, 0.49 mol) in NMP (200 mL) dropwise. After being stirred at room temperature for 1 hr, the reaction mixture was diluted with tert-butyl methyl ether (600 mL) and stirred vigorously for 30 min. The precipitate was collected by filtration and washed with MTBE to afford 1H-pyrazolo[3,4-b]pyridine 7-oxide (47.3 g) as a off-white solid. LC-MS (ESI): m/z, (M+H)$^+$, 136.0.

1.2 Preparation of 4-chloro-1H-pyrazolo[3,4-b]pyridine

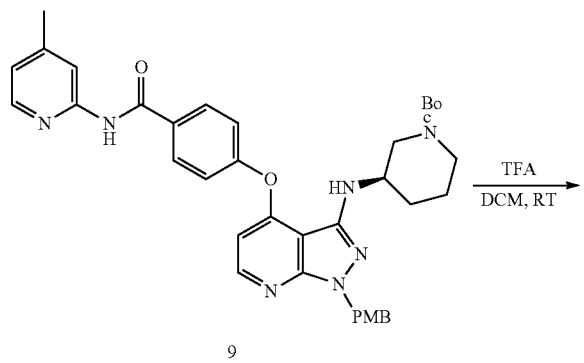

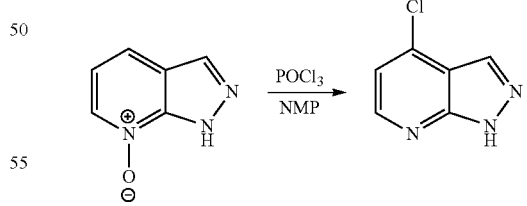

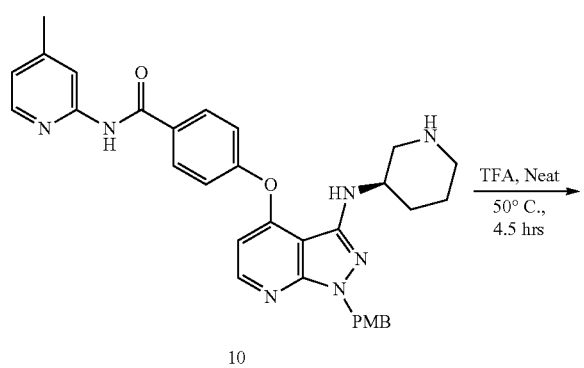

To a solution of 1H-pyrazolo[3,4-b]pyridine 7-oxide (47.3 g, 0.31 mol) in ACN (250 mL) was added POCl$_3$ (130 mL, 1.41 mol) dropwise to maintain the temperature below 30° C. Stirred at r.t. for 3 hrs, the reaction mixture was quenched carefully with 20% NaOH aqueous solution (300 mL). The precipitate was collected by filtration and washed with H$_2$O, dried under high vacuum to give the crude product (a mixture of 4-Cl and 6-Cl isomers) (50 g) as a white solid. LC-MS (ESI): m/z (M+H)$^+$, 154.1.

1.3 Preparation of 4-chloro-3-iodo-1H-pyrazolo[3,4-b]pyridine

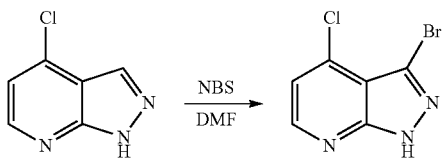

To a solution of 4-chloro-1H-pyrazolo[3,4-b]pyridine and 6-chloro-1H-pyrazolo[3,4-b]pyridine (30 g, 195 mmol) in DMF (20 mL) was added NBS (52 g, 293.0 mmol) in a small portion. The reaction mixture was stirred at room temperature for 6 hr, the resulting mixture was poured into H$_2$O (1000 mL). The precipitate was collected by filtration to afford mixture of 4-chloro-3-bromo-1H-pyrazolo[3,4-b]pyridine and 6-chloro-3-bromo-1H-pyrazolo[3,4-b]pyridine (40 g) as a white solid. LC-MS (ESI): m/z, (M+H)$^+$, 233.7.

1.4 Preparation of 4-chloro-3-iodo-1-(4-methoxybenzyl)-1H-pyrazolo[3,4-b]pyridine To a solution of 4-chloro-3-bromo-1H-pyrazolo[3,4-b]pyridine and 6-chloro-3-bromo-1H-pyrazolo[3,4-b]pyridine (144 g, 0.619 mmol) in DMF (800 mL) was added PMBCl (145.5 g, 0.929 mol) and K$_2$CO$_3$ (171.1 g, 1.238 mol). The reaction mixture was stirred at 30° C. overnight. The reaction mixture was poured into water (3 L) followed by extraction with ethyl acetate (800 mL×3). The combined organic layer was dried over MgSO$_4$ and evaporated 80% of solvent in vacuo to afford the title compound (76.6 g) which was collected by filtration. LC-MS (ESI): m/z (M+1)$^+$, 351.8.

1.5 Preparation of 4-chloro-3-iodo-1-(4-methoxybenzyl)-1H-pyrazolo[3,4-b]pyridine

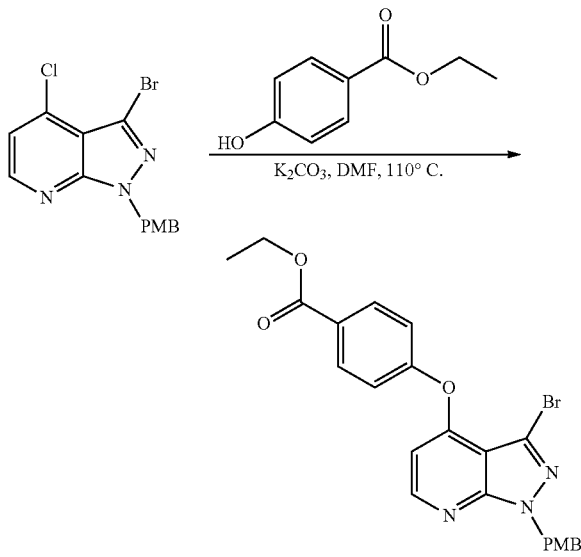

The reaction mixture of 4-Chloro-3-iodo-1-(4-methoxybenzyl)-1H-pyrazolo[3,4-b]pyridine (15.6 g, 67.1 mmol), ethyl 4-hydroxybenzoate (11.15 g, 67.1 mmol) and K$_2$CO$_3$ (18.5 g, 134.2 mmol) in DMF was stirred at 120° C. for 3 hrs. Cooling to room temperature, ice-water was added and the product was extracted with ethyl acetate (200 mL×3). Evaporation of the solvent followed by flash chromatography on silica gel (10-30% EA/hexanes as eluent) afforded the title compound 12.97 g. LC-MS (ESI): m/z (M+1)$^+$, 481.95.

1.6 (R)-tert-butyl 3-(4-(1-(ethoxycarbonyl)phenoxy)-1-(4-methoxybenzyl)-1H-pyrazolo[3,4-b]pyridin-3-ylamino)piperidine-1-carboxylate

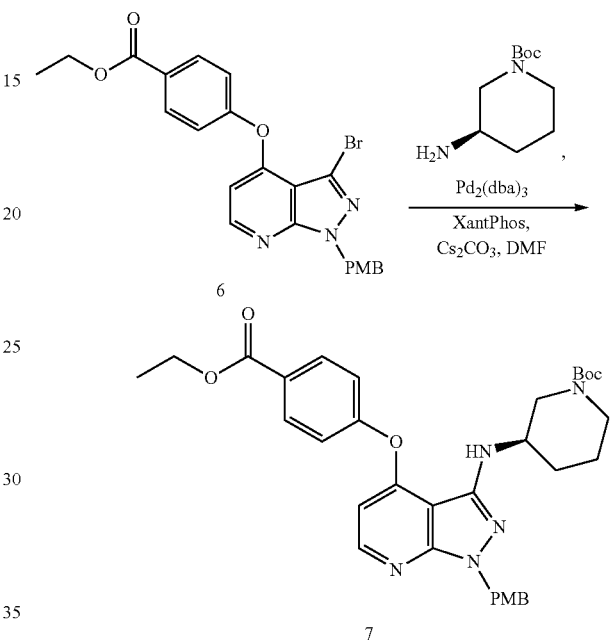

The mixture of ethyl 4-(3-iodo-1-(4-methoxybenzyl)-1H-pyrazolo[3,4-b]pyridin-4-yloxy)benzoate (18.17 g, 37.67 mmol), (R)-tert-butyl 3-aminopiperidine-1-carboxylate (10.56 g, 52.74 mmol), Pd$_2$(dba)$_3$ (1.08 g, 1.18 mmol), Xantphos (3.27 g, 5.65 mmol) and cesium carbonate (24.54 g, 75 mmol) in dioxane was degassed with N$_2$ for 3 min followed by stirring at 120° C. for 16 hrs. Cooling to room temperature, the reaction mixture was partitioned with EA (500 mL) and water (500 mL), extracted with ethyl acetate, dried by MgSO$_4$. Evaporation of solvent followed by flash chromatography on silica gel (10-40% EA/hexanes as eluent) afforded the title compound (20.65 g). LC-MS (ESI): m/z (M+1)$^+$, 602.9.

1.7 (R)-4-(3-(1-(tert-butoxycarbonyl)piperidin-3-ylamino)-1-(4-methoxybenzyl)-1H-pyrazolo[3,4-b]pyridin-4-yloxy)benzoic acid

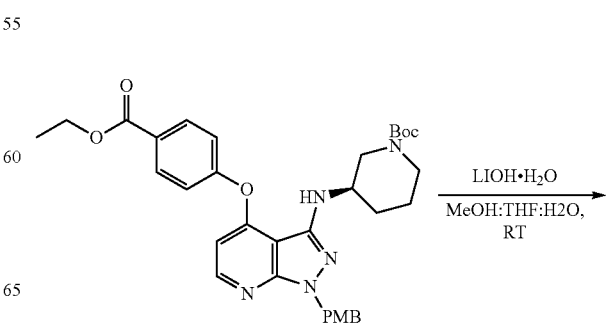

-continued

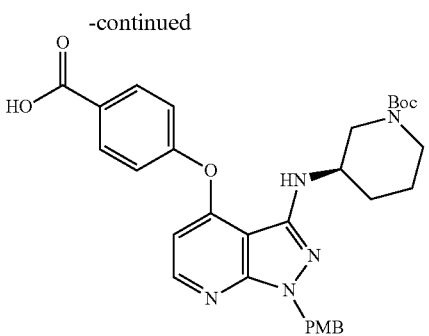

To a solution of (R)-tert-butyl 3-(4-(4-(ethoxycarbonyl)phenoxy)-1-(4-methoxybenzyl)-1H-pyrazolo[3,4-b]pyridin-3-ylamino)piperidine-1-carboxylate (15.01 g, 31.17 mmol) in THF (33 mL) and MeOH (33 mL) was added the solution of LiOH in water (33 mL) dropwise at room temperature. The reaction mixture was stirred at RT for 2 hrs and adjusted pH=2 with 1N HCl with stirring. The product (13.2 g) was collected by filtration, washed with water and dried under high vacuum overnight. LC-MS (ESI): m/z (M+1)$^+$, 574.9.

1.8 (R)-tert-butyl 3-(1-(4-methoxybenzyl)-4-(4-(4-methylpyridin-2-ylcarbamoyl)phenoxy)-1H-pyrazolo[3,4-b]pyridin-3-ylamino)piperidine-1-carboxylate

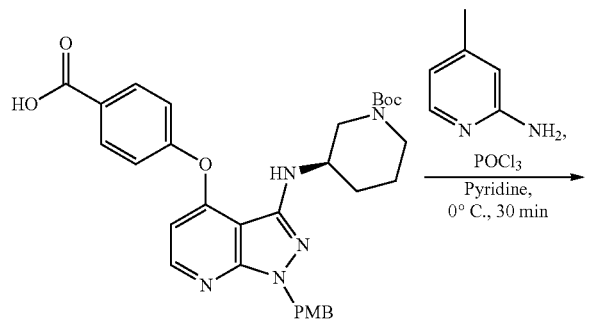

To a solution of (R)-4-(3-(1-(tert-butoxycarbonyl)piperidin-3-ylamino)-1-(4-methoxybenzyl)-1H-pyrazolo[3,4-b]pyridin-4-yloxy)benzoic acid (1.52 g, 2.65 mmol) and 4-methylpyridin-2-amine in pyridine (10 ml) was added POCl3 (1.219 g, 7.95 mmol) dropwise at room temperature. After addition, the reaction mixture was stirred at RT for 10 min. Poured into cold water, the product (1.51 g) was collected by filtration, washed with water and dried under high vacuum overnight. LC-MS (ESI): m/z (M+1)$^+$, 664.2.

1.9 (R)-4-(1-(4-methoxybenzyl)-3-(piperidin-3-ylamino)-1H-pyrazolo[3,4-b]pyridin-4-yloxy)-N-(4-methylpyridin-2-yl)benzamide

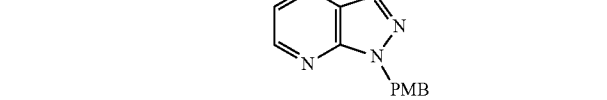
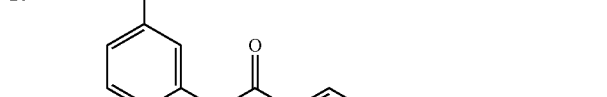
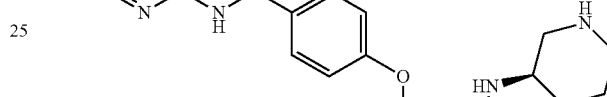

4 M HCl solution (5.31 ml, 21.24 mmol) in dioxane was added dropwise to the solution of (R)-tert-butyl 3-(1-(4-methoxybenzyl)-4-(4-(4-methylpyridin-2-ylcarbamoyl)phenoxy)-1H-pyrazolo[3,4-b]pyridin-3-ylamino)piperidine-1-carboxylate (1.41 g, 2.124 mmol) in methanol at room temperature. The reaction mixture was heated to 40° C. for 3 hrs. Evaporated solvent, the residue was further dried on high vacuum overnight to give the desired product (1.48 g). LC-MS (ESI): m/z (M+1)$^+$, 564.3.

1.10 (R)—N-(4-methylpyridin-2-yl)-4-(3-(piperidin-3-ylamino)-1H-pyrazolo[3,4-b]pyridin-4-yloxy)benzamide

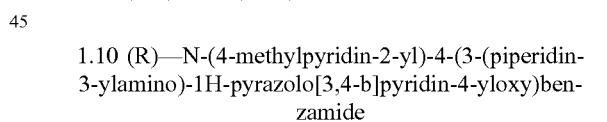
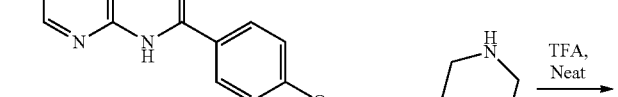
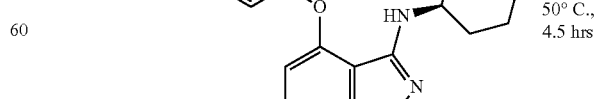
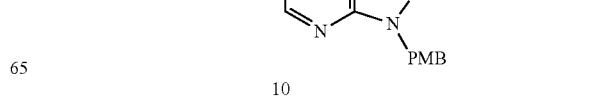

353
-continued

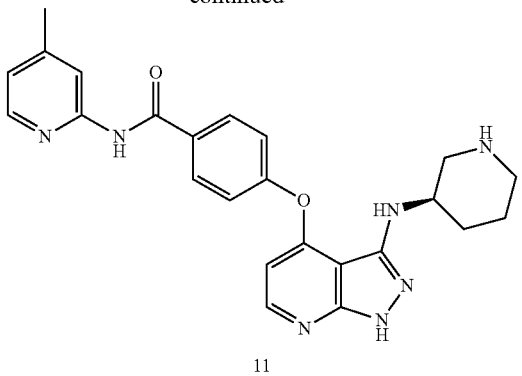

The solution of (R)-4-(1-(4-methoxybenzyl)-3-(piperidin-3-ylamino)-1H-pyrazolo[3,4-b]pyridin-4-yloxy)-N-(4-methylpyridin-2-yl)benzamide (1.48 g, 2.63 mmol) in neat TFA was heated to 50° C. for 5 hrs. Evaporated TFA, the residue was purified by silica gel column chromatography using 10-100% MeOH/DCM as eluent to give desired product (0.57 g). LC-MS (ESI): m/z (M+1)$^+$, 444.2.

Using similar technology the intermediates were also prepared:

1.11 (R)—N-(6-methylpyridin-2-yl)-4-(3-(piperidin-3-ylamino)-1H-pyrazolo[3,4-b]pyridin-4-yloxy)benzamide

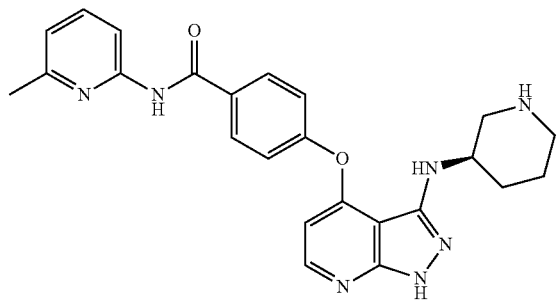 [SMILES: Cc1cccc(NC(=O)c2ccc(Oc3ccnc4[nH]nc(N[C@@H]5CCCNC5)c34)cc2)n1]

LC-MS (ESI): m/z (M+1)$^+$, 444.1.

1.12 (R)-4-(3-(piperidin-3-ylamino)-1H-pyrazolo[3,4-b]pyridin-4-yloxy)-N-(pyridin-2-yl)benzamide

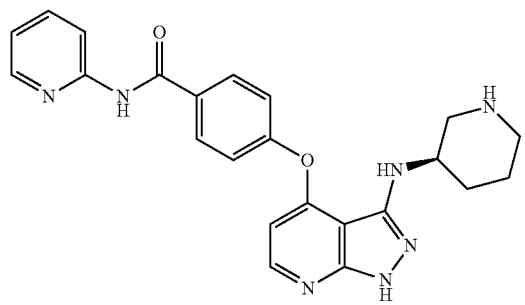 [SMILES: O=C(Nc1ccccn1)c1ccc(Oc2ccnc3[nH]nc(N[C@@H]4CCCNC4)c23)cc1]

LC-MS (ESI): m/z (M+1)$^+$, 430.2.

354

Example 86

(R)-4-(3-(1-(3-methyloxetane-3-carbonyl)piperidin-3-ylamino)-1H-pyrazolo[3,4-b]pyridin-4-yloxy)-N-(4-methylpyridin-2-yl)benzamide (Compound ID 86)

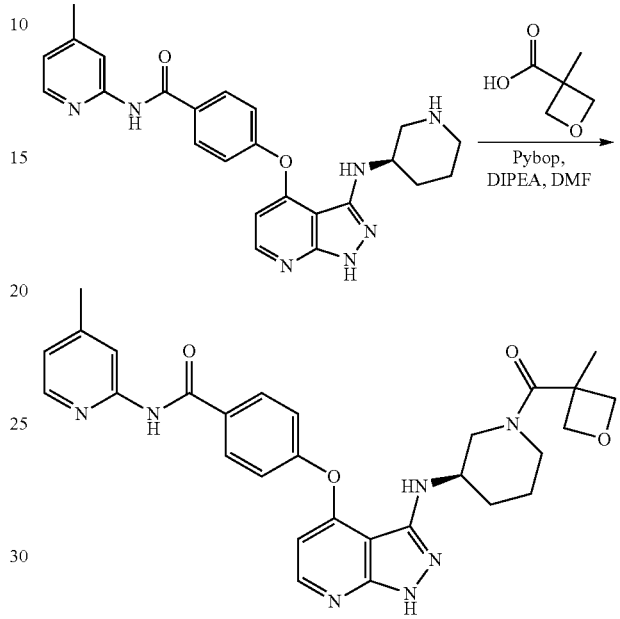

To reaction mixture of (R)—N-(4-methylpyridin-2-yl)-4-(3-(piperidin-3-ylamino)-1H-pyrazolo[3,4-b]pyridin-4-yloxy)benzamide (60 mg, 0.14 mmol), 3-methyloxetane-3-carboxylic acid (19 mg) and Pybop (141 mg, 0.27 mmol) in DMF was added DIPEA (70 mg, 0.54 mmol) at room temperature. After stirring for 10 min, the reaction was purified by reverse phase prep HPLC using 0.1% formic acid aqueous solution and acetonitrile as mobile phase to give product 32.3 mg. LC-MS (ESI): m/z (M+1)$^+$, 542.7.

The following compounds were prepared in the similar method:

Example 87

(R)—N-(4-methylpyridin-2-yl)-4-(3-(1-(4-methyltetrahydro-2H-pyran-4-carbonyl)piperidin-3-ylamino)-1H-pyrazolo[3,4-b]pyridin-4-yloxy)benzamide (Compound ID 87)

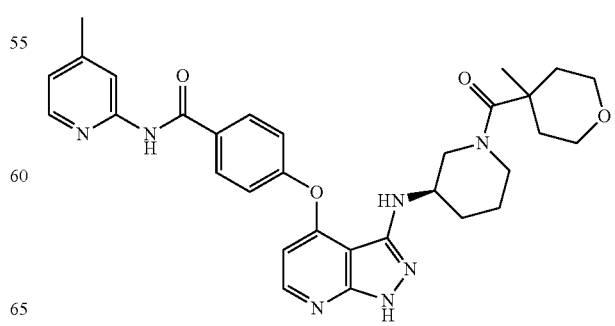

The compound was prepared following the method described for Ex. 86. LC-MS (ESI): m/z (M+1)$^+$, 570.3.

Example 88

(R)-4-(3-(1-(1-methylcyclobutanecarbonyl)piperidin-3-ylamino)-1H-pyrazolo[3,4-b]pyridin-4-yloxy)-N-(4-methylpyridin-2-yl)benzamide (Compound ID 88)

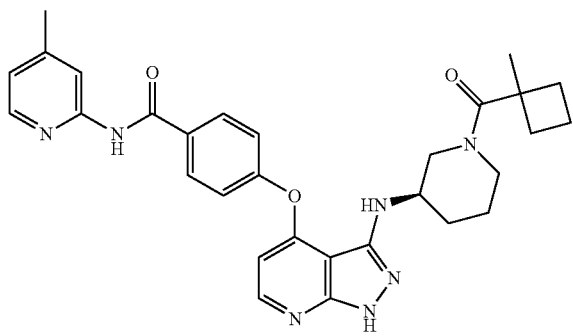 [SMILES: Cc1ccnc(NC(=O)c2ccc(Oc3ccnc4[nH]nc(N[C@@H]5CCCN(C(=O)C6(C)CCC6)C5)c34)cc2)c1]

The compound was prepared following the method described for Ex. 86. LC-MS (ESI): m/z (M+1)$^+$, 540.5.

Example 89

N-(4-methylpyridin-2-yl)-4-(3-((3R)-1-(3-methyltetrahydrofuran-3-carbonyl)piperidin-3-ylamino)-1H-pyrazolo[3,4-b]pyridin-4-yloxy)benzamide (Compound ID 89)

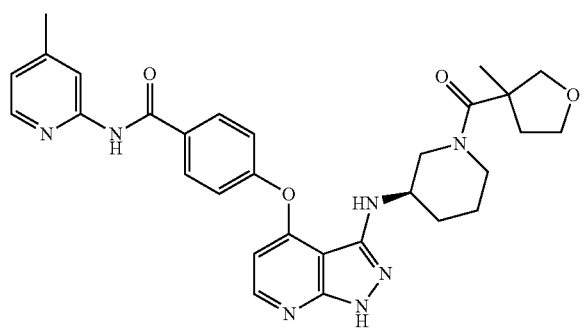 [SMILES: Cc1ccnc(NC(=O)c2ccc(Oc3ccnc4[nH]nc(N[C@@H]5CCCN(C(=O)C6(C)CCOC6)C5)c34)cc2)c1]

The compound was prepared following the method described for Ex. 86. LC-MS (ESI): m/z (M+1)$^+$, 556.4.

Example 90

(R)—N-(4-methylpyridin-2-yl)-4-(3-(1-(oxetane-3-carbonyl)piperidin-3-ylamino)-1H-pyrazolo[3,4-b]pyridin-4-yloxy)benzamide (Compound ID 90)

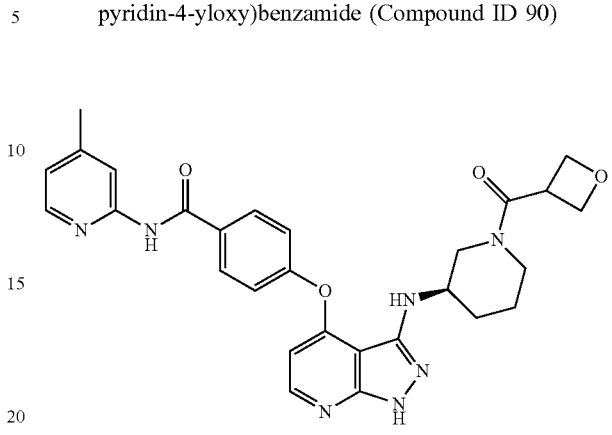

The compound was prepared following the method described for Ex. 86. LC-MS (ESI): m/z (M+1)$^+$, 528.3.

Example 91

(R)—N-(4-methylpyridin-2-yl)-4-(3-(1-(morpholine-4-carbonyl)piperidin-3-ylamino)-1H-pyrazolo[3,4-b]pyridin-4-yloxy)benzamide (Compound ID 91)

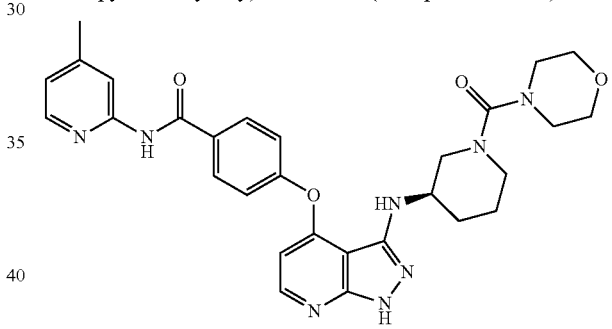

The compound was prepared following the method described for Ex. 86. LC-MS (ESI): m/z (M+1)$^+$, 557.2.

Example 92

(R)-4-(3-(1-(1-methylpiperidine-4-carbonyl)piperidin-3-ylamino)-1H-pyrazolo[3,4-b]pyridin-4-yloxy)-N-(4-methylpyridin-2-yl)benzamide (Compound ID 92)

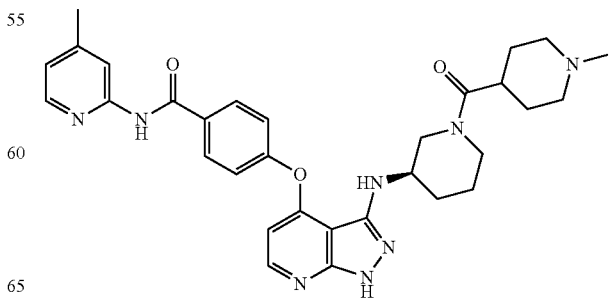

The compound was prepared following the method described for Ex. 86. LC-MS (ESI): m/z (M+1)$^+$, 569.45.

Example 93

(R)-phenyl 3-(4-(4-(4-methylpyridin-2-ylcarbamoyl)phenoxy)-1H-pyrazolo[3,4-b]pyridin-3-ylamino)piperidine-1-carboxylate (Compound ID 93)

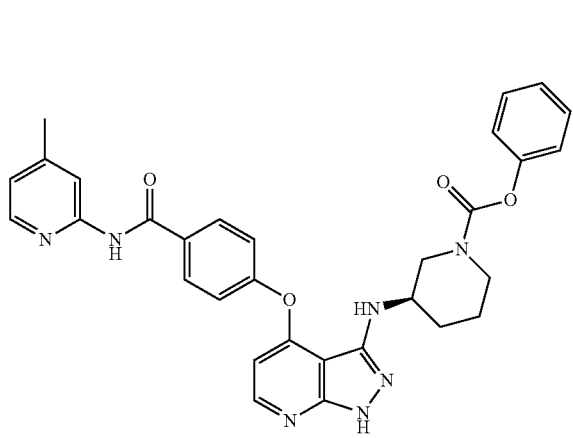 [SMILES: Cc1ccnc(NC(=O)c2ccc(Oc3ccnc4[nH]nc(N[C@@H]5CCCN(C(=O)Oc6ccccc6)C5)c34)cc2)c1]

The compound was prepared following the method described for Ex. 86. LC-MS (ESI): m/z (M+1)$^+$, 564.3.

Example 94

N-(4-methylpyridin-2-yl)-4-(3-((R)-1-((R)-tetrahydrofuran-2-carbonyl)piperidin-3-ylamino)-1H-pyrazolo[3,4-b]pyridin-4-yloxy)benzamide (Compound ID 94)

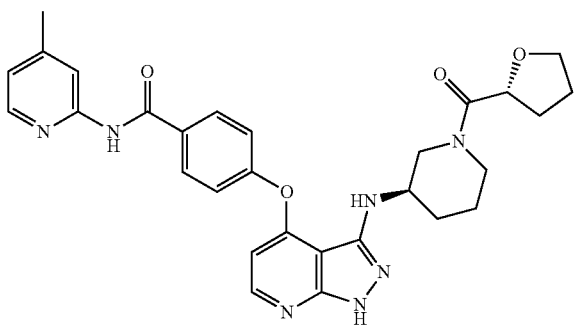 [SMILES: Cc1ccnc(NC(=O)c2ccc(Oc3ccnc4[nH]nc(N[C@@H]5CCCN(C(=O)[C@H]6CCCO6)C5)c34)cc2)c1]

The compound was prepared following the method described for Ex. 86. LC-MS (ESI): m/z (M+1)$^+$, 542.3.

Example 95

(R)-4-(3-(1-(4-(dimethylamino)butanoyl)piperidin-3-ylamino)-1H-pyrazolo[3,4-b]pyridin-4-yloxy)-N-(4-methylpyridin-2-yl)benzamide (Compound ID 95)

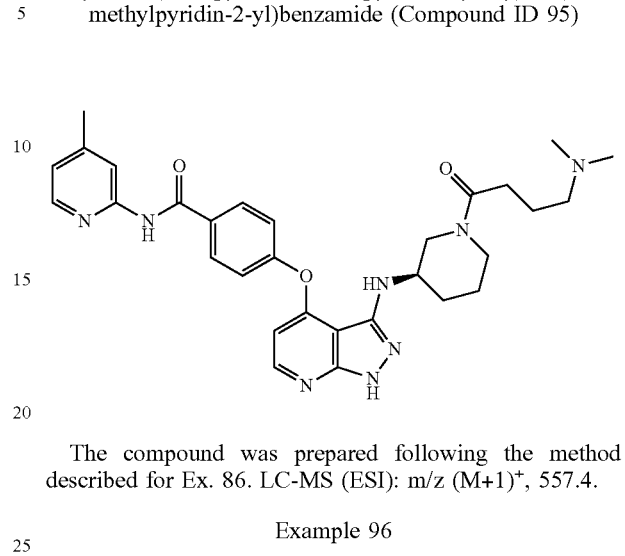

The compound was prepared following the method described for Ex. 86. LC-MS (ESI): m/z (M+1)$^+$, 557.4.

Example 96

(R)—N-(4-methylpyridin-2-yl)-4-(3-(1-(piperidine-4-carbonyl)piperidin-3-ylamino)-1H-pyrazolo[3,4-b]pyridin-4-yloxy)benzamide (Compound ID 96)

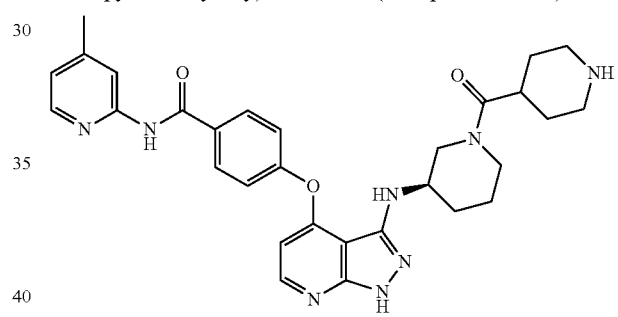

The compound was prepared following the method described for Ex. 104. LC-MS (ESI): m/z (M+1)$^+$, 555.4.

Example 97

(R)-4-(3-(1-(2-(methylamino)-2-oxoacetyl)piperidin-3-ylamino)-1H-pyrazolo[3,4-b]pyridin-4-yloxy)-N-(4-methylpyridin-2-yl)benzamide (Compound ID 97)

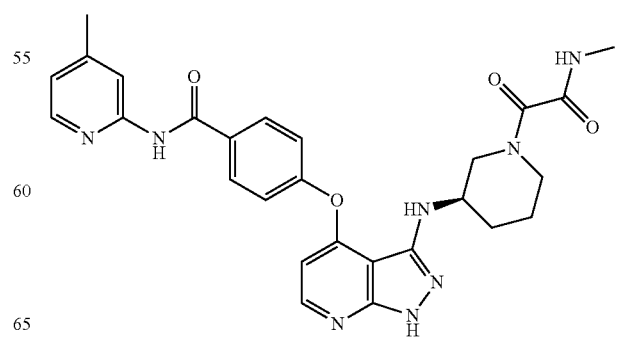

The compound was prepared following the method described for Ex. 86. LC-MS (ESI): m/z (M+1)$^+$, 529.4.

Example 98

(R)-4-(3-(1-(2-(dimethylamino)-2-oxoacetyl)piperidin-3-ylamino)-1H-pyrazolo[3,4-b]pyridin-4-yloxy)-N-(4-methylpyridin-2-yl)benzamide (Compound ID 98)

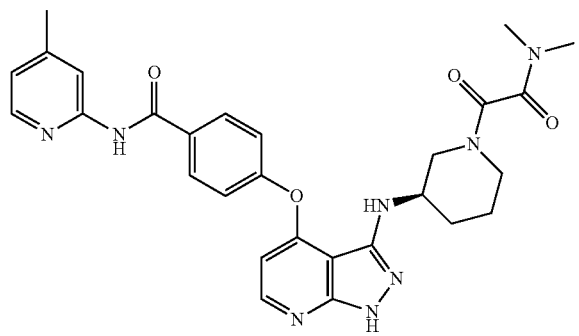 [SMILES: Cc1ccnc(NC(=O)c2ccc(Oc3ccnc4[nH]nc(N[C@@H]5CCCN(C(=O)C(=O)N(C)C)C5)c34)cc2)c1]

The compound was prepared following the method described for Ex. 86. LC-MS (ESI): m/z (M+1)$^+$, 543.3.

Example 99

(R)-4-(3-(1-(1-(methoxymethyl)cyclobutanecarbonyl)piperidin-3-ylamino)-1H-pyrazolo[3,4-b]pyridin-4-yloxy)-N-(4-methylpyridin-2-yl)benzamide (Compound ID 99)

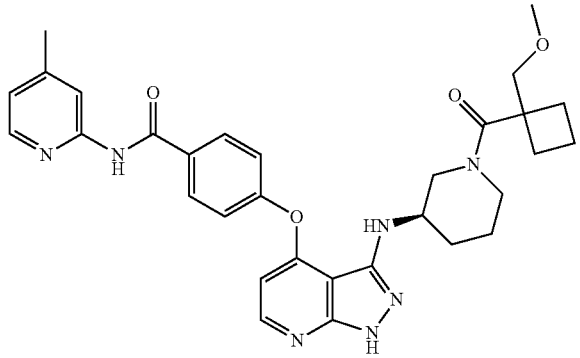 [SMILES: COCC1(C(=O)N2CCC[C@@H](Nc3n[nH]c4nccc(Oc5ccc(C(=O)Nc6cc(C)ccn6)cc5)c34)C2)CCC1]

The compound was prepared following the method described for Ex. 86. LC-MS (ESI): m/z (M+1)$^+$, 570.7.

Example 100

(R)-4-(3-(1-(cyclopropanecarbonyl)piperidin-3-ylamino)-1H-pyrazolo[3,4-b]pyridin-4-yloxy)-N-(4-methylpyridin-2-yl)benzamide (Compound ID 100)

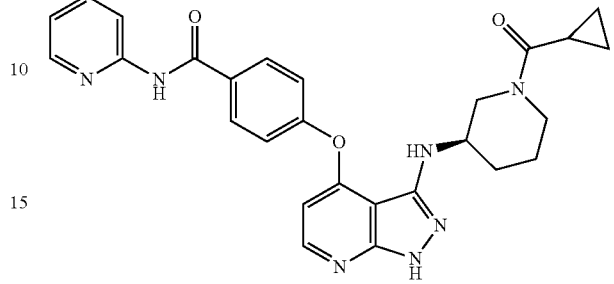

The compound was prepared following the method described for Ex. 86. LC-MS (ESI): m/z (M+1)$^+$, 512.7.

Example 101

(R)-4-(3-(1-(1-cyanocyclopropanecarbonyl)piperidin-3-ylamino)-1H-pyrazolo[3,4-b]pyridin-4-yloxy)-N-(4-methylpyridin-2-yl)benzamide (Compound ID 101)

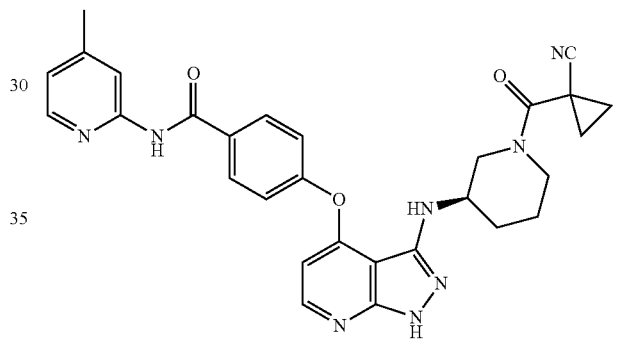

The compound was prepared following the method described for Ex. 86. LC-MS (ESI): m/z (M+1)$^+$, 537.6.

Example 102

(R)-4-(3-(1-(1-cyanocyclopropanecarbonyl)piperidin-3-ylamino)-1H-pyrazolo[3,4-b]pyridin-4-yloxy)-N-(4-methylpyridin-2-yl)benzamide (Compound ID 102)

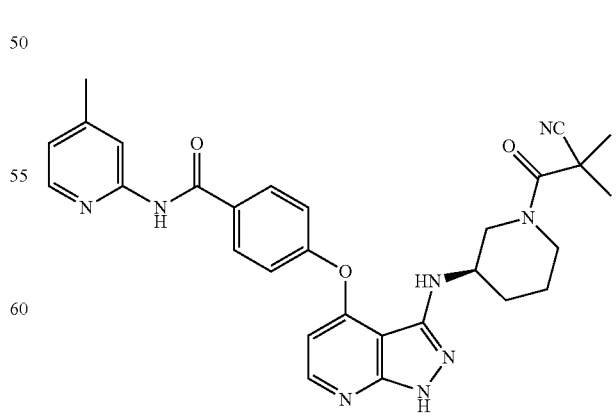

The compound was prepared following the method described for Ex. 86. LC-MS (ESI): m/z (M+1)$^+$, 539.4.

Example 103

(R)-tert-butyl 4-methyl-4-(3-(4-(4-(4-methylpyridin-2-ylcarbamoyl)phenoxy)-1H-pyrazolo[3,4-b]pyridin-3-ylamino)piperidine-1-carbonyl)piperidine-1-carboxylate (Compound ID 103)

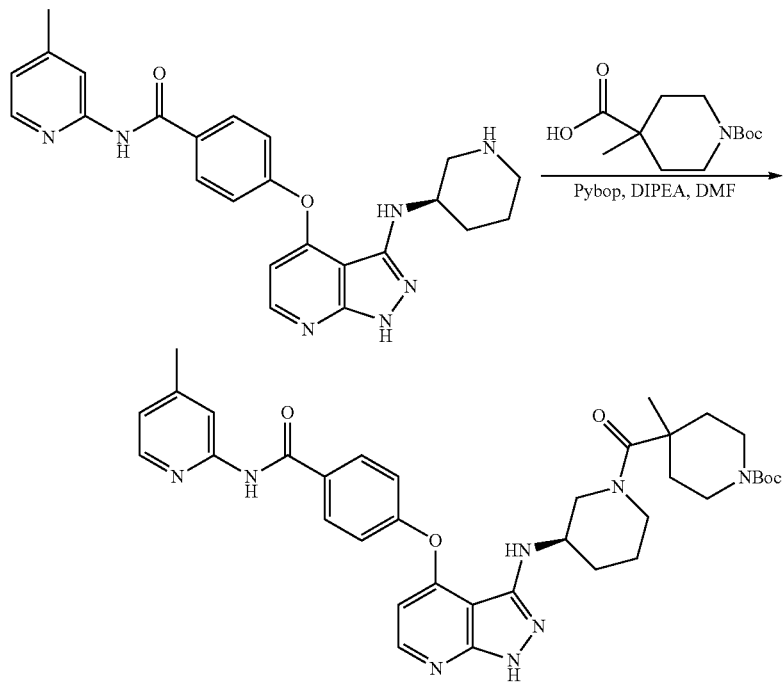 [SMILES: Cc1ccnc(NC(=O)c2ccc(Oc3ccnc4[nH]nc(N[C@@H]5CCCNC5)c34)cc2)c1 ; CC(C)(C)OC(=O)N1CCC(C)(C(=O)O)CC1 ; Cc1ccnc(NC(=O)c2ccc(Oc3ccnc4[nH]nc(N[C@@H]5CCCN(C(=O)C6(C)CCN(C(=O)OC(C)(C)C)CC6)C5)c34)cc2)c1]

To reaction mixture of (R)—N-(4-methylpyridin-2-yl)-4-(3-(piperidin-3-ylamino)-1H-pyrazolo[3,4-b]pyridin-4-yloxy)benzamide (100 mg, 0.23 mmol), 1-(tert-butoxycarbonyl)-4-methylpiperidine-4-carboxylic acid (55 mg, 0.23 mmol) and Pybop (235 mg, 0.45 mmol) in DMF (1 mL) was added DIPEA (117 mg, 0.90 mmol) at room temperature. After stirring for 10 min, the reaction was purified by reverse phase prep HPLC using 0.1% formic acid aqueous solution and acetonitrile as mobile phase to give product 92 mg. LC-MS (ESI): m/z (M+1)$^+$, 670.0.

Example 104

(R)-4-(3-(1-(4-methylpiperidine-4-carbonyl)piperidin-3-ylamino)-1H-pyrazolo[3,4-b]pyridin-4-yloxy)-N-(4-methylpyridin-2-yl)benzamide (Compound ID 104)

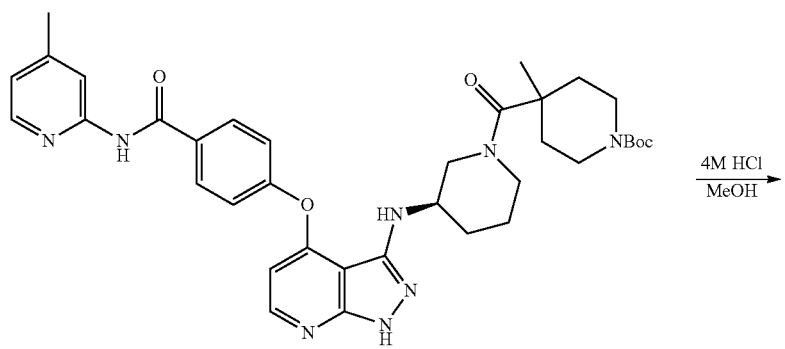

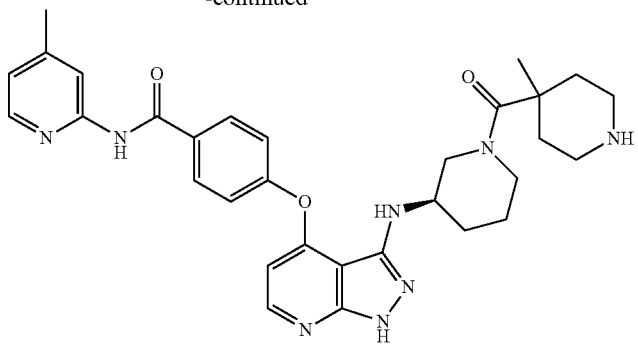

To a solution of (R)-tert-butyl 4-methyl-4-(3-(4-(4-(4-methylpyridin-2-ylcarbamoyl)phenoxy)-1H-pyrazolo[3,4-b]pyridin-3-ylamino)piperidine-1-carbonyl)piperidine-1-carboxylate (90 mg, 0.13 mmol) in MeOH (1 mL) was added 4M HCl in dioxane (0.5 mL) at room temperature. After stirring for 16 hrs, the reaction mixture was purified by reverse phase prep HPLC using 5 mM HCl aqueous solution and acetonitrile as a mobile phase to give 15.5 mg of the product. LC-MS (ESI): m/z (M+1)$^+$, 670.0.

Example 105

(R)—N-(4-methylpyridin-2-yl)-4-(3-(1-(tetrahydro-2H-pyran-4-carbonyl)piperidin-3-ylamino)-1H-pyrazolo[3,4-b]pyridin-4-yloxy)benzamide (Compound ID 105)

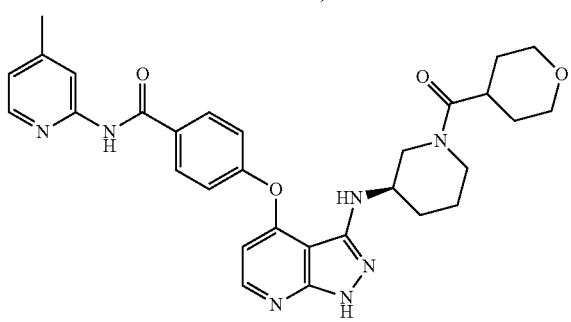

The compound was prepared following the method described for Ex. 86. LC-MS (ESI): m/z (M+1)$^+$, 556.9.

Example 106

(R)—N,N-dimethyl-3-(4-(4-(4-methylpyridin-2-ylcarbamoyl)phenoxy)-1H-pyrazolo[3,4-b]pyridin-3-ylamino)piperidine-1-carboxamide (Compound ID 106)

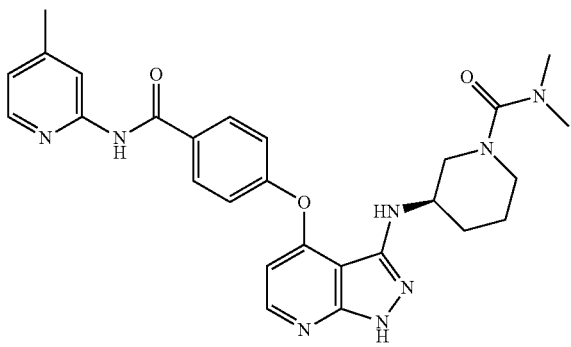 [SMILES: Cc1ccnc(NC(=O)c2ccc(Oc3ccnc4[nH]nc(N[C@@H]5CCCN(C(=O)N(C)C)C5)c34)cc2)c1]

The compound was prepared following the method described for Ex. 86. LC-MS (ESI): m/z (M+1)$^+$, 515.7.

Example 107

(R)-4-(3-(1-(cyclopentanecarbonyl)piperidin-3-ylamino)-1H-pyrazolo[3,4-b]pyridin-4-yloxy)-N-(4-methylpyridin-2-yl)benzamide (Compound ID 107)

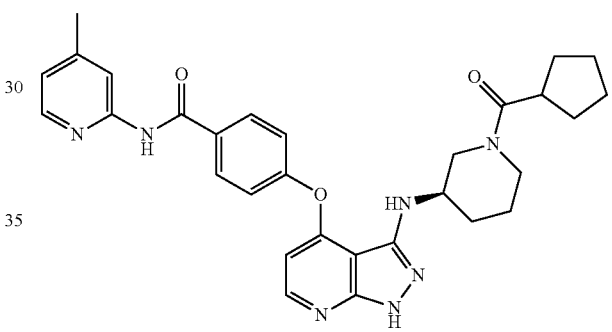

The compound was prepared following the method described for Ex. 86. LC-MS (ESI): m/z (M+1)$^+$, 540.8.

Example 108

(R)-ethyl 3-(4-(4-(4-methylpyridin-2-ylcarbamoyl)phenoxy)-1H-pyrazolo[3,4-b]pyridin-3-ylamino)piperidine-1-carboxylate (Compound ID 108)

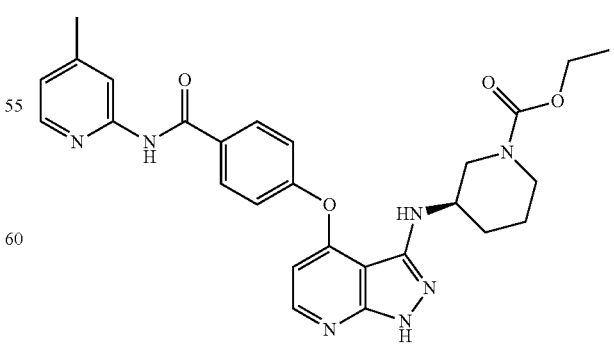

The compound was prepared following the method described for Ex. 86. LC-MS (ESI): m/z (M+1)$^+$, 516.8.

Example 109

(R)-4-(3-(1-benzoylpiperidin-3-ylamino)-1H-pyrazolo[3,4-b]pyridin-4-yloxy)-N-(4-methylpyridin-2-yl)benzamide (Compound ID 109)

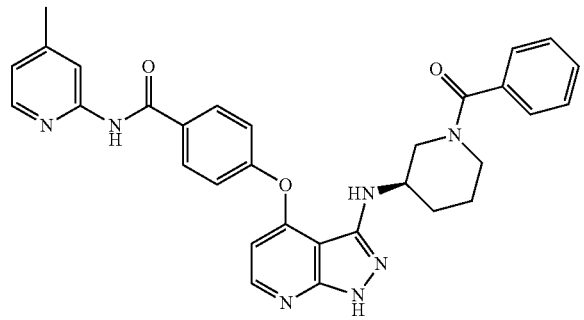 [SMILES: Cc1ccnc(NC(=O)c2ccc(Oc3ccnc4[nH]nc(N[C@@H]5CCCN(C(=O)c6ccccc6)C5)c34)cc2)c1]

The compound was prepared following the method described for Ex. 86. LC-MS (ESI): m/z (M+1)+, 548.3.

Example 110

(R)—N-(4-methylpyridin-2-yl)-4-(3-(1-picolinoylpiperidin-3-ylamino)-1H-pyrazolo[3,4-b]pyridin-4-yloxy)benzamide (Compound ID 110)

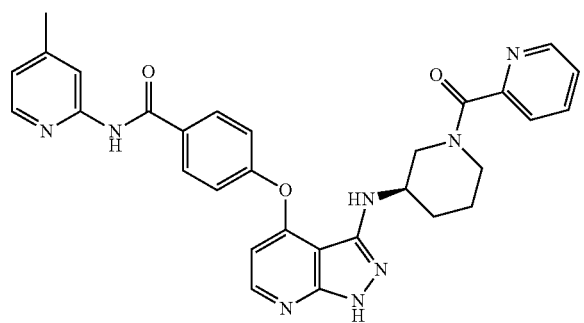 [SMILES: Cc1ccnc(NC(=O)c2ccc(Oc3ccnc4[nH]nc(N[C@@H]5CCCN(C(=O)c6ccccn6)C5)c34)cc2)c1]

The compound was prepared following the method described for Ex. 86. LC-MS (ESI): m/z (M+1)+, 549.3.

Example 111

(R)-4-(3-(1-(3-methyloxetane-3-carbonyl)piperidin-3-ylamino)-1H-pyrazolo[3,4-b]pyridin-4-yloxy)-N-(pyridin-2-yl)benzamide (Compound ID 111)

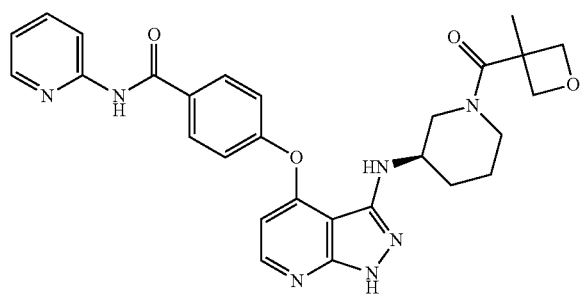 [SMILES: CC1(C(=O)N2CCC[C@@H](Nc3n[nH]c4nccc(Oc5ccc(C(=O)Nc6ccccn6)cc5)c34)C2)COC1]

The compound was prepared following the method described for Ex. 86. LC-MS (ESI): m/z (M+1)+, 542.3.

Example 112

(R)-4-(3-(1-(4-methyltetrahydro-2H-pyran-4-carbonyl)piperidin-3-ylamino)-1H-pyrazolo[3,4-b]pyridin-4-yloxy)-N-(pyridin-2-yl)benzamide (Compound ID 112)

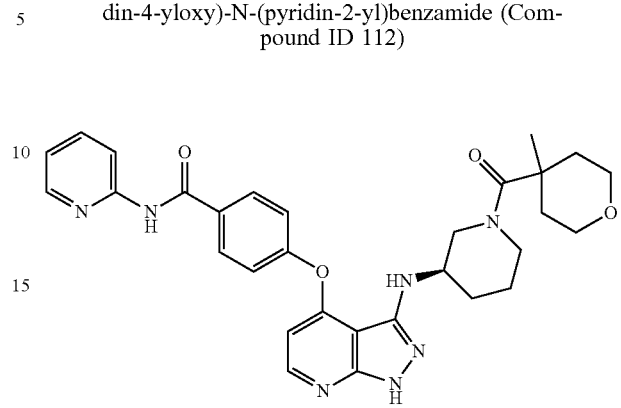

The compound was prepared following the method described for Ex. 86. LC-MS (ESI): m/z (M+1)+, 556.7.

Example 113

(R)-4-(3-(1-(3-methyloxetane-3-carbonyl)piperidin-3-ylamino)-1H-pyrazolo[3,4-b]pyridin-4-yloxy)-N-(6-methylpyridin-2-yl)benzamide (Compound ID 113)

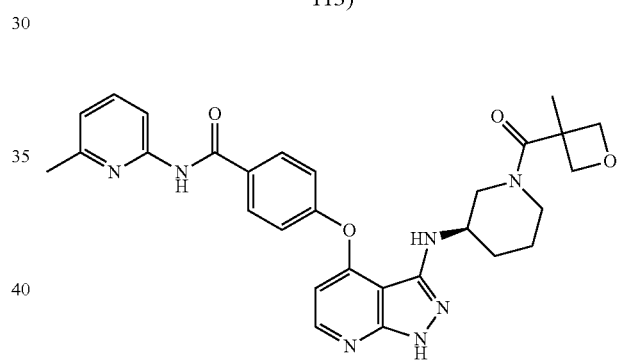

The compound was prepared following the method described for Ex. 86. LC-MS (ESI): m/z (M+1)+, 542.7.

Example 114

(R)—N-(6-methylpyridin-2-yl)-4-(3-(1-(4-methyltetrahydro-2H-pyran-4-carbonyl)piperidin-3-ylamino)-1H-pyrazolo[3,4-b]pyridin-4-yloxy)benzamide (Compound ID 114)

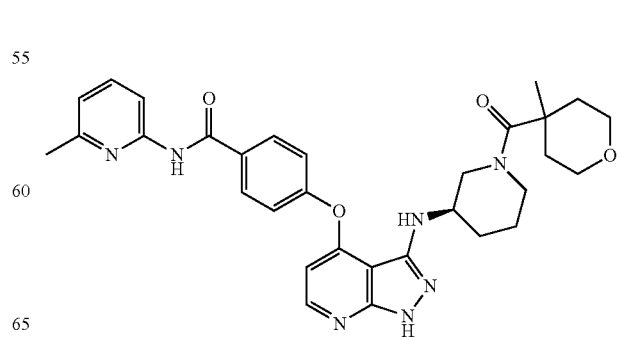

Example 115

N-(4-methylpyridin-2-yl)-4-(3-((R)-1-((R)-tetrahydrofuran-3-carbonyl)piperidin-3-ylamino)-1H-pyrazolo[3,4-b]pyridin-4-yloxy)benzamide (Compound ID 115)

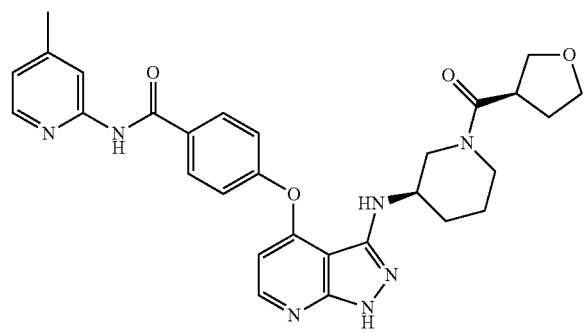 [SMILES: Cc1ccnc(NC(=O)c2ccc(Oc3ccnc4[nH]nc(N[C@@H]5CCCN(C(=O)[C@@H]6CCOC6)C5)c34)cc2)c1]

The compound was prepared following the method described for Ex. 86. LC-MS (ESI): m/z (M+1)$^+$, 542.5.

Example 116

N-(4-methylpyridin-2-yl)-4-(3-((R)-1-((S)-tetrahydrofuran-3-carbonyl)piperidin-3-ylamino)-1H-pyrazolo[3,4-b]pyridin-4-yloxy)benzamide (Compound ID 116)

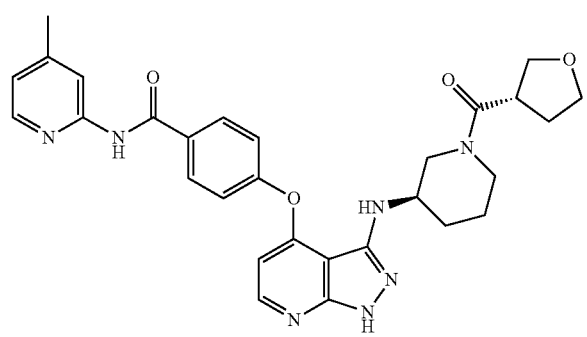 [SMILES: Cc1ccnc(NC(=O)c2ccc(Oc3ccnc4[nH]nc(N[C@@H]5CCCN(C(=O)[C@H]6CCOC6)C5)c34)cc2)c1]

The compound was prepared following the method described for Ex. 86. LC-MS (ESI): m/z (M+1)$^+$, 542.5.

Example 117

N-(4-methylpyridin-2-yl)-4-(3-((R)-1-((S)-tetrahydrofuran-2-carbonyl)piperidin-3-ylamino)-1H-pyrazolo[3,4-b]pyridin-4-yloxy)benzamide (Compound ID 117)

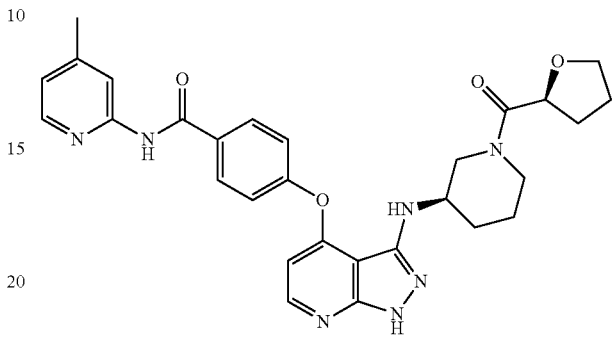

The compound was prepared following the method described for Ex. 86. LC-MS (ESI): m/z (M+1)$^+$, 542.4.

Example 118

(R)-4-(3-(1-(3-(dimethylamino)propanoyl)piperidin-3-ylamino)-1H-pyrazolo[3,4-b]pyridin-4-yloxy)-N-(4-methylpyridin-2-yl)benzamide (Compound ID 118)

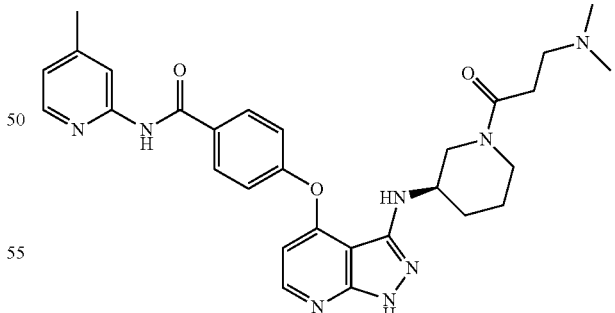

The compound was prepared following the method described for Ex. 86. LC-MS (ESI): m/z (M+1)$^+$, 543.3.

Example 119

(R)-4-(3-(1-(3-methoxypropanoyl)piperidin-3-ylamino)-1H-pyrazolo[3,4-b]pyridin-4-yloxy)-N-(4-methylpyridin-2-yl)benzamide (Compound ID 119)

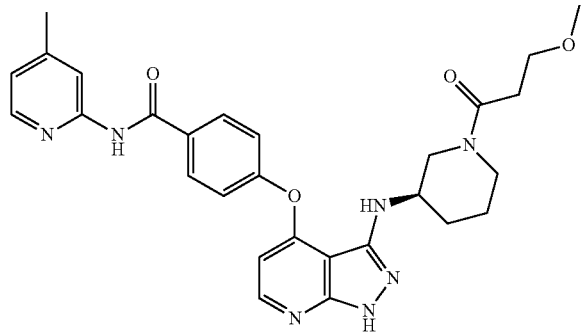 [SMILES: COCCC(=O)N1CCC[C@@H](Nc2n[nH]c3nccc(Oc4ccc(C(=O)Nc5cc(C)ccn5)cc4)c23)C1]

The compound was prepared following the method described for Ex. 86. LC-MS (ESI): m/z (M+1)$^+$, 530.3.

Example 120

(R)-4-(3-(1-(1-methylcyclopropanecarbonyl)piperidin-3-ylamino)-1H-pyrazolo[3,4-b]pyridin-4-yloxy)-N-(4-methylpyridin-2-yl)benzamide (Compound ID 120)

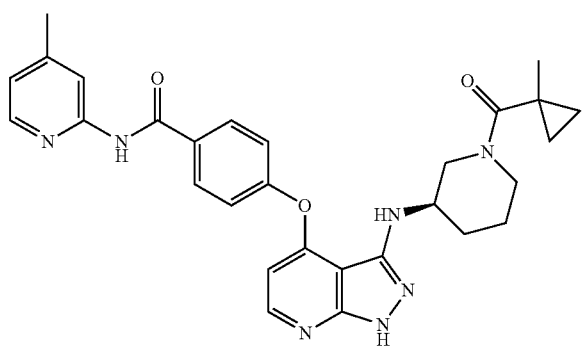 [SMILES: Cc1ccnc(NC(=O)c2ccc(Oc3ccnc4[nH]nc(N[C@@H]5CCCN(C(=O)C6(C)CC6)C5)c34)cc2)c1]

The compound was prepared following the method described for Ex. 86. LC-MS (ESI): m/z (M+1)$^+$, 526.2.

1.13 Preparation of tert-butyl (3R)-3-[(4-{4-[(ethylcarbamoyl)amino]phenoxy}-1-[(4-methoxyphenyl)methyl]-1H-pyrazolo[3,4-b]pyridin-3-yl)amino]piperidine-1-carboxylate

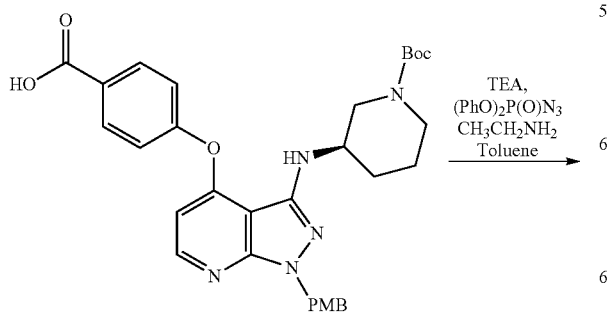

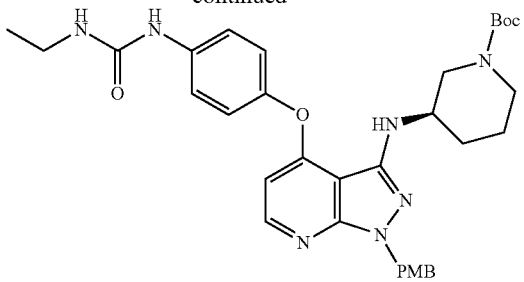

Diphenylphosphonic azide (0.31 mL, 1.464 mmol) was added to a 0 OC cooled solution of 4-[(3-{[(3R)-1-[(tert-butoxy)carbonyl]piperidin-3-yl]amino}-1-[(4-methoxyphenyl)methyl]-1H-pyrazolo[3,4-b]pyridin-4-yl)oxy]benzoic acid (702.1 mg, 1.220 mmol) in toluene (28 mL). TEA (0.2 mL, 1.464 mmol) was added at room temperature and the mixture was heated at 100 OC for 1 hr. 2 M ethyl amine in THF (0.73 mL, 1.464 mmol) was added at room temperature and the mixture was stirred for 15 minutes. Water was added and extracted with ethyl acetate. Organic layers were washed with brine, dried over Na$_2$SO$_4$, filtered and concentrated to give a crude that was purified by gradient flash-chromatography (silica gel, from 30% to 80% ethyl acetate in cyclohexane) to afford tert-butyl (3R)-3-[(4-{4-[(ethylcarbamoyl)amino]phenoxy}-1-[(4-methoxyphenyl)methyl]-1H-pyrazolo[3,4-b]pyridin-3-yl)amino]piperidine-1-carboxylate (270 mg, 25% yield) as a yellow solid. LC-MS (ESI): m/z (M+1)$^+$, 616.2

1.14 Preparation of 3-ethyl-1-[4-({1-[(4-methoxyphenyl)methyl]-3-{[(3R)-piperidin-3-yl]amino}-1H-pyrazolo[3,4-b]pyridin-4-yl}oxy)phenyl]urea trifluoroacetate

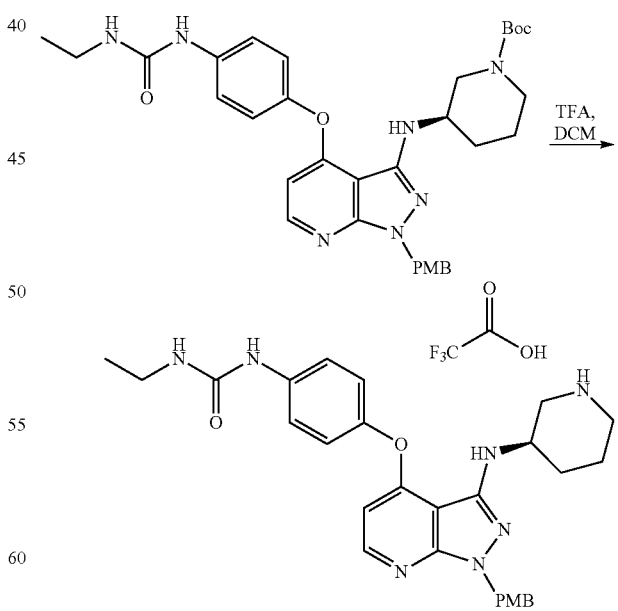

To a solution of tert-butyl (3R)-3-[(4-{4-[(ethylcarbamoyl)amino]phenoxy}-1-[(4-methoxyphenyl)methyl]-1H-pyrazolo[3,4-b]pyridin-3-yl)amino]piperidine-1-carboxylate (270 mg, 0.311 mmol) in DCM (9 mL) TFA (2.2 mL)

was added. The resulting mixture was stirred at room temperature for 15 min and then it was concentrated under reduced pressure to afford 3-ethyl-1-[4-({1-[(4-methoxyphenyl)methyl]-3-{[(3R)-piperidin-3-yl]amino}-1H-pyrazolo[3,4-b]pyridin-4yl}oxy)phenyl]urea trifluoroacetate (413.1 mg, quantitative yield) as a yellow foam. LC-MS (ESI): m/z (M+1)+, 516.2

1.15 Preparation of 3-ethyl-1-{4-[(3-{[(3R)-piperidin-3-yl]amino}-1H-pyrazolo[3,4-b]pyridin-4-yl)oxy]phenyl}urea

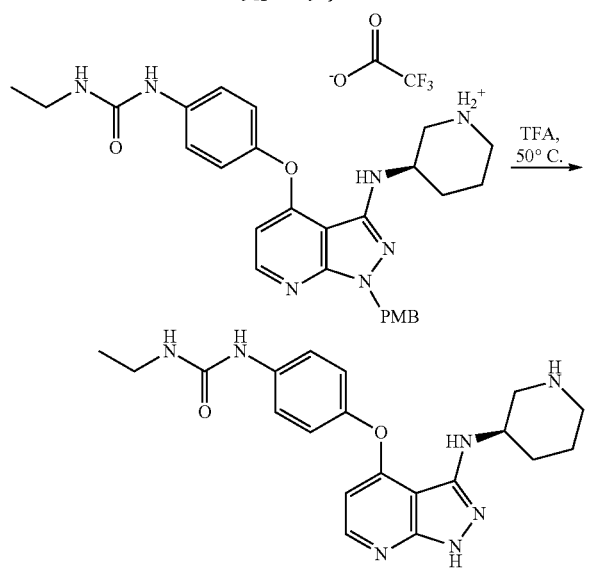

3-Ethyl-1-[4-({1-[(4-methoxyphenyl)methyl]-3-{[(3R)-piperidin-3-yl]amino}-1H-pyrazolo[3,4-b]pyridin-4-yl}oxy)phenyl]urea trifluoroacetate (413.1 mg, 0.311 mmol) in TFA (8.4 mL) was stirred at 50° C. under N₂ atmosphere for 3 hr. The reaction mixture was concentrated unerd reduced pressure to give the crude product (437.8 mg). 1M ammonia in methanol was added and the mixture was concentrated under reduced pressure. The obtained solid was purified by scx-cartridge to afford 3-ethyl-1-{4-[(3-{[(3R)-piperidin-3-yl]amino}-1H-pyrazolo[3,4-b]pyridin-4-yl)oxy]phenyl}urea (146.1 mg, 99% yield) as a yellow solid. LC-MS (ESI): m/z (M+1)+, 396.1.

Example 122

Synthesis of (R)-3-(3-(1-acryloylpyrrolidin-3-ylamino)-1H-pyrazolo[3,4-b]pyridin-4-yloxy)-N-(4-isopropyl-3-methylphenyl)benzamide (Compound ID 122)

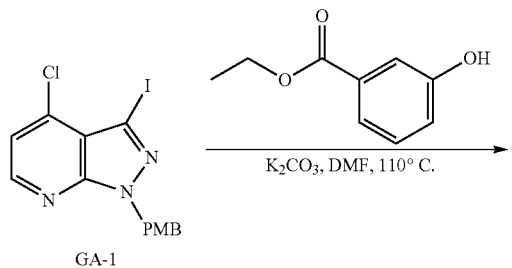

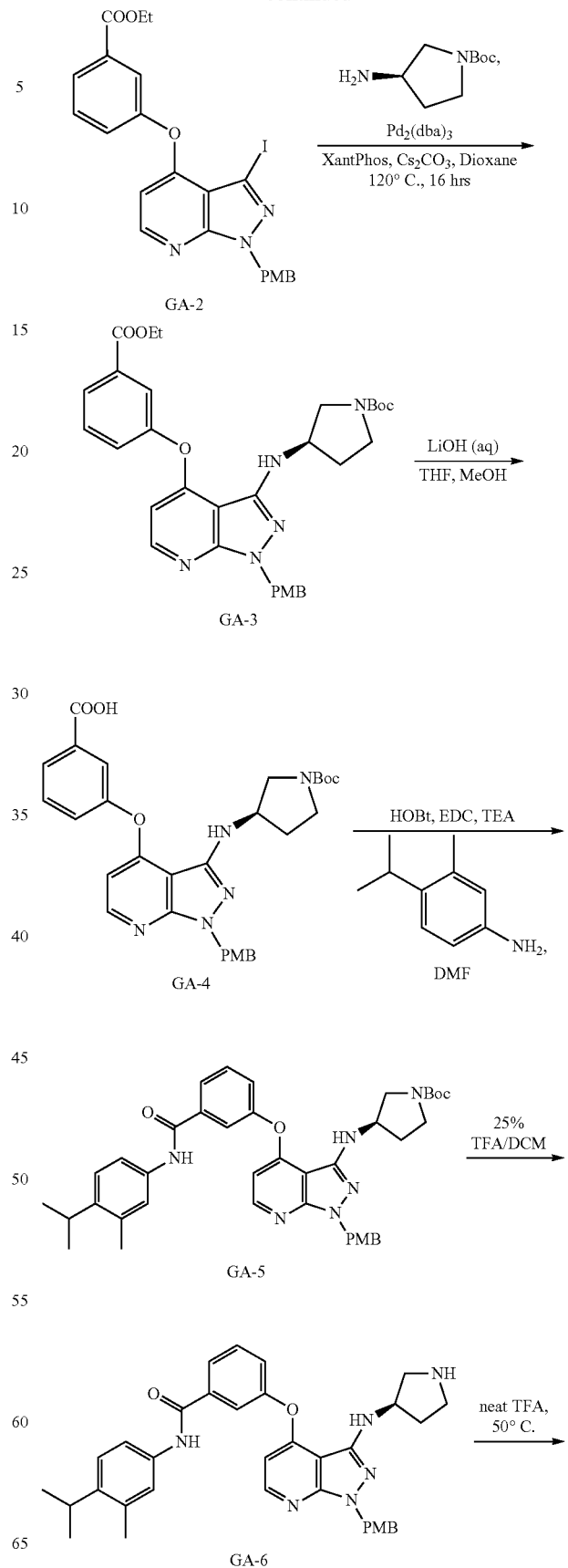

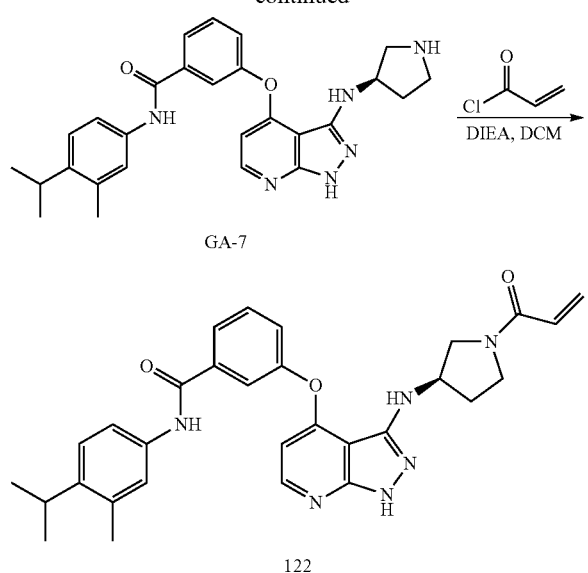

122.1 Preparation of ethyl 3-(3-iodo-1-(4-methoxybenzyl)-1H-pyrazolo[3,4-b]pyridin-4-yloxy)benzoate

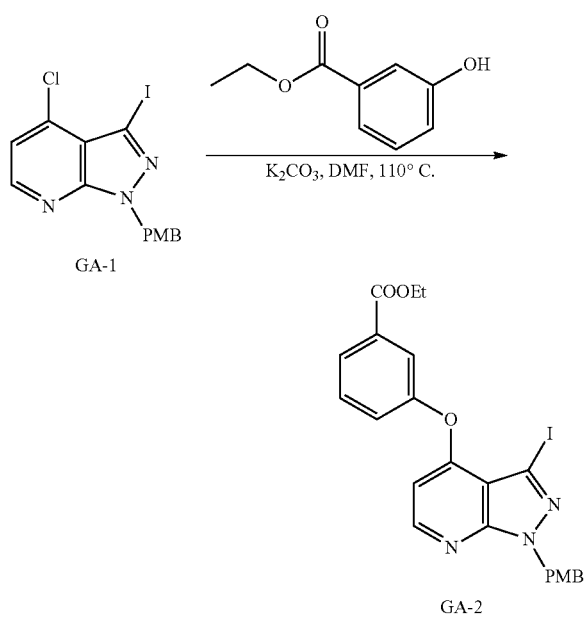

The reaction mixture of 4-chloro-3-iodo-1-(4-methoxybenzyl)-1H-pyrazolo[3,4-b]pyridine (1.0 g, 2.55 mmol), ethyl 3-hydroxybenzoate (467 mg, 2.81 mmol) and $K_2CO_3$ (776 mg, 5.62 mmol) in 14 mL DMF was stirred at 110° C. for 6 hr, then cooled to RT. The mixture was diluted with water and extracted with ethyl acetate (2×100 mL). Evaporation of the solvent, followed by flash chromatography on silica gel (0-50% EtOAc/hexanes as eluent) afforded the title compound, 1.26 g, in 93% yield, as a white solid. MW=529.3, MH+=530.2.

122.2 Preparation of (R)-tert-butyl 3-(4-(3-(ethoxycarbonyl)phenoxy)-1-(4-methoxybenzyl)-1H-pyrazolo[3,4-b]pyridin-3-ylamino)pyrrolidine-1-carboxylate

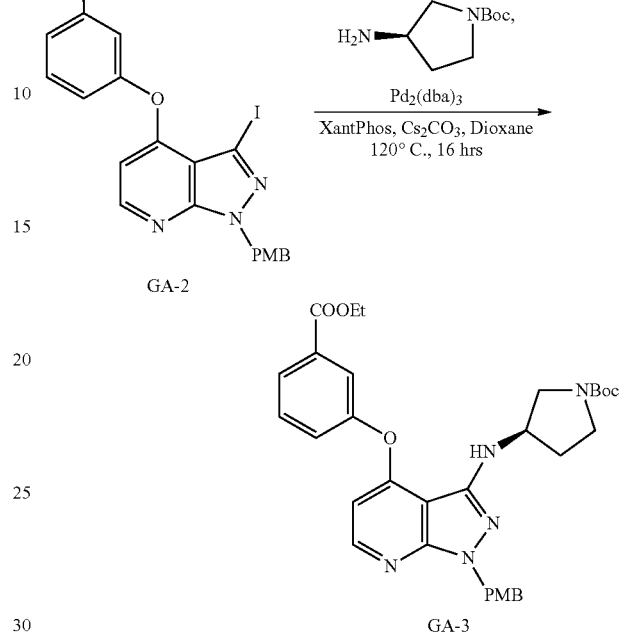

The mixture of 3-(3-iodo-1-(4-methoxybenzyl)-1H-pyrazolo[3,4-b]pyridin-4-yloxy)benzoate (630 mg, 1.19 mmol), (R)-tert-butyl 3-aminopyrrolidine-1-carboxylate (444 mg, 2.38 mmol), $Pd_2(dba)_3$ (54.5 mg, 0.06 mmol), Xantphos (103 mg, 0.18 mmol) and cesium carbonate (776 mg, 2.38 mmol) in dioxane, was degassed by bubbling $N_2$ through for 3 min. It was then capped and heated at 120° C. for 16 hrs. After cooling to room temperature, the reaction mixture was partitioned between EtOAc (80 mL) and water (40 mL). The aqueous layer was re-extracted with EA 1× and the combined organics dried ($Na_2SO_4$), filtered and concentrated. The crude material was purified by flash chromatography on silica gel (0-45% EtOAc/hexanes as eluent) to afford the title compound, 137 mg (20% yield). MW=587.7, MH+=588.8.

122.3 Preparation of (R)-3-(3-(1-(tert-butoxycarbonyl)pyrrolidin-3-ylamino)-1-(4-methoxybenzyl)-1H-pyrazolo[3,4-b]pyridin-4-yloxy)benzoic acid

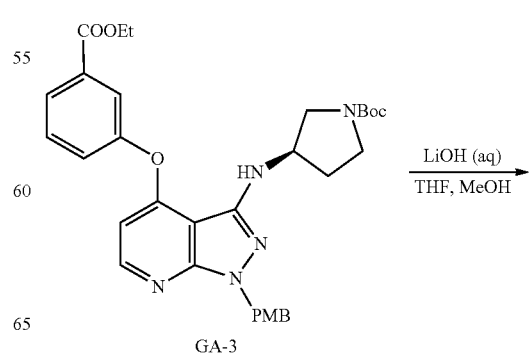

-continued

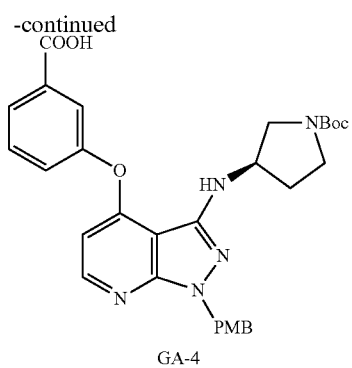

GA-4

To a solution of (R)-tert-butyl 3-(4-(3-(ethoxycarbonyl)phenoxy)-1-(4-methoxybenzyl)-1H-pyrazolo[3,4-b]pyridin-3-ylamino)pyrrolidine-1-carboxylate (137 mg, 0.23 mmol) in THF (0.75 mL) and MeOH (0.75 mL) was added the solution of LiOH (39 mg, 0.93 mmol) in water (0.75 mL). The reaction mixture was stirred at RT for 16 hr, then adjusted pH to pH=5 using 2 N HCl. The mixture was diluted with EtOAc (50 mL) and Water (10 mL), and the aqueous extracted 3×. The combined organics were dried (Na$_2$SO$_4$), filtered, concentrated and dried on house vacuum to yield 138 mg (assume quantitative) crude product acid which was used without further purification. MW=559.6, MH$^+$=560.7.

122.4 Preparation of (R)-tert-butyl 3-(4-(3-(4-isopropyl-3-methylphenylcarbamoyl)phenoxy)-1-(4-methoxybenzyl)-1H-pyrazolo[3,4-b]pyridin-3-ylamino)pyrrolidine-1-carboxylate

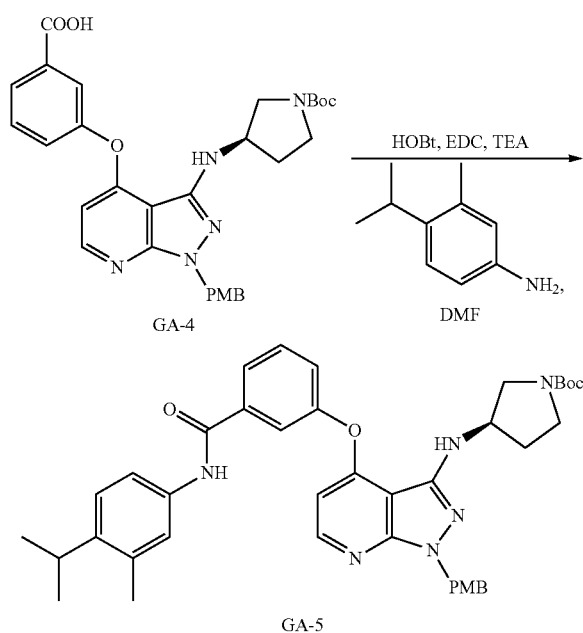

(R)-3-(3-(1-(tert-butoxycarbonyl)pyrrolidin-3-ylamino)-1-(4-methoxybenzyl)-1H-pyrazolo[3,4-b]pyridin-4-yloxy)benzoic acid (138 mg, 0.25 mmol), EDC (142 mg, 0.74 mmol), HOBt.H$_2$O (113 mg, 0.74 mmol) and TEA (172 µL, 1.23 mmol) were stirred in 1.2 mL DMF for 45 minutes. Added 4-isopropyl-3-methylaniline (92 mg, 0.49 mmol) and continued stirring for 16 hours. Quenched with 3 mL water and diluted further with EtOAc (40 mL), water (7 mL) and brine (7 mL). The phases were separated and the aqueous re-extracted 2× with EtOAc. The combined organics were dried over Na$_2$SO$_4$, filtered and concentrated in vacuo to 0.6 g crude liquid. The crude was purified by Flash Chromatography using 0 to 65% EtOAc in hexanes gradient to isolate (R)-tert-butyl 3-(4-(3-(4-isopropyl-3-methylphenylcarbamoyl)phenoxy)-1-(4-methoxybenzyl)-1H-pyrazolo[3,4-b]pyridin-3-ylamino)pyrrolidine-1-carboxylate (GA-5) (142.6 mg, 84%) as a clear yellow film; MW=690.8, MH$^+$=691.8.

122.5 (R)—N-(4-isopropyl-3-methylphenyl)-3-(1-(4-methoxybenzyl)-3-(pyrrolidin-3-ylamino)-1H-pyrazolo[3,4-b]pyridin-4-yloxy)benzamide

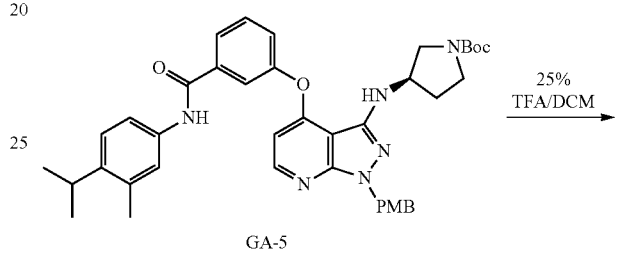

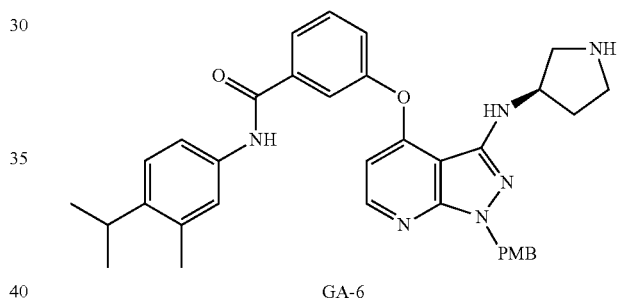

A solution of (R)-tert-butyl 3-(4-(3-(4-isopropyl-3-methylphenylcarbamoyl)phenoxy)-1-(4-methoxybenzyl)-1H-pyrazolo[3,4-b]pyridin-3-ylamino)pyrrolidine-1-carboxylate (142.6 mg, 0.206 mmol) in 2 mL of 25% TFA/DCM was let sit for 1 hr, then concentrated. Used without further purification. Obtained (R)—N-(4-isopropyl-3-methylphenyl)-3-(1-(4-methoxybenzyl)-3-(pyrrolidin-3-ylamino)-1H-pyrazolo[3,4-b]pyridin-4-yloxy)benzamide; MW=590.7, MH$^+$=591.6.

122.6 Preparation of (R)—N-(4-isopropyl-3-methylphenyl)-3-(3-(pyrrolidin-3-ylamino)-1H-pyrazolo[3,4-b]pyridin-4-yloxy)benzamide

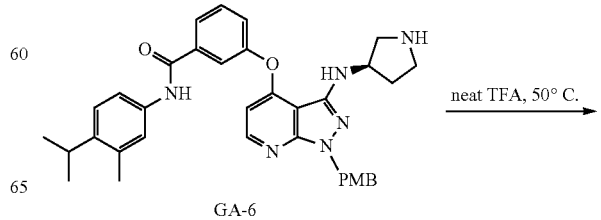

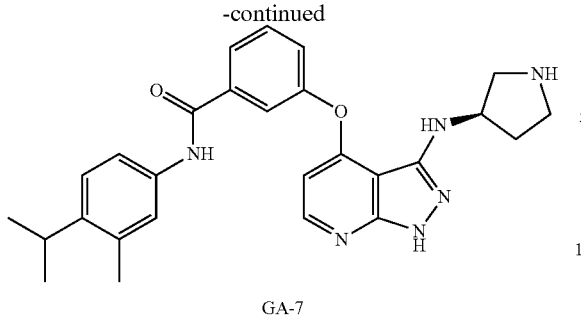

GA-7

The solution of crude (R)—N-(4-isopropyl-3-methylphenyl)-3-(1-(4-methoxybenzyl)-3-(pyrrolidin-3-ylamino)-1H-pyrazolo[3,4-b]pyridin-4-yloxy)benzamide (122 mg, 0.206 mmol) in 1.2 mL neat TFA was heated at 50° C. for 10 hrs. The solvent was evaporated, and the residue purified by flash chromatography using 0-45% MeOH/DCM (+0.1% TEA) as eluent to give the desired product (63.2 mg, 65% yield over 2 steps). MW=470.6, MH$^+$=471.2.

122.7 Preparation of (R)-3-(3-(1-acryloylpyrrolidin-3-ylamino)-1H-pyrazolo[3,4-b]pyridin-4-yloxy)-N-(4-isopropyl-3-methylphenyl)benzamide (Compound ID 122)

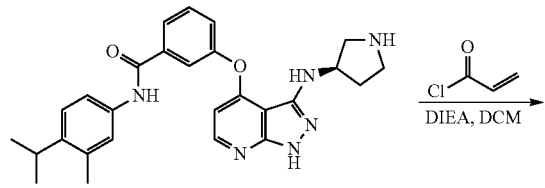

GA-7

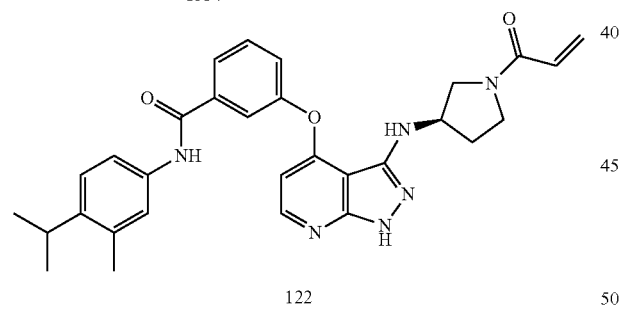

122

To a solution of (R)—N-(4-isopropyl-3-methylphenyl)-3-(3-(pyrrolidin-3-ylamino)-1H-pyrazolo[3,4-b]pyridin-4-yloxy)benzamide (31.6 mg, 0.067 mmol) in 0.5 mL DCM was added Hunig's base (35 µl, 0.20 mmol), and 2 minutes later, acryloyl chloride (8.1 µL, 0.10 mmol). The resulting mixture was allowed to stir for 10 minutes, then quenched with 3 ml water. Added some brine and extracted with DCM (3×10 mL). Combined organics dried over MgSO$_4$, filtered and concentrated. The crude material was purified by Reverse Phase HPLC using 0.1% Formic acid in MQ Water and CH$_3$CN as mobile phases, to yield (R)-3-(3-(1-acryloylpyrrolidin-3-ylamino)-1H-pyrazolo[3,4-b]pyridin-4-yloxy)-N-(4-isopropyl-3-methylphenyl)benzamide (122) as a yellow solid, formic acid salt (5.4 mg, 15%); MW=524.6, MH$^+$=525.5, MH$^-$=523.2, UV: λ=slope-like (223 nm).

Example 123

Preparation of (R)-3-(3-(1-acetylpyrrolidin-3-ylamino)-1H-pyrazolo[3,4-b]pyridin-4-yloxy)-N-(4-isopropyl-3-methylphenyl)benzamide (Compound ID 123)

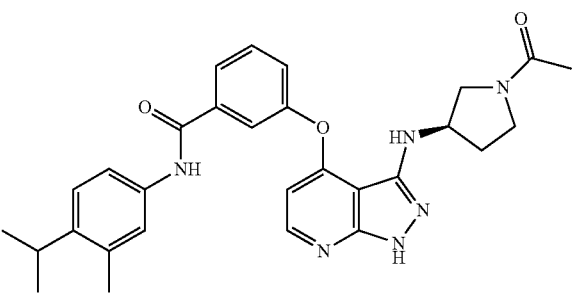

123

Using similar procedure as 122.7 formic acid salt of compound 123 was prepared as a yellow solid (10.6 mg, 31%); MW=512.6, MH$^+$=513.5, MH$^-$=511.2, UV: λ=slope-like (220 nm).

Example 124

Preparation of (S)-3-(3-(1-acetylpyrrolidin-3-ylamino)-1H-pyrazolo[3,4-b]pyridin-4-yloxy)-N-(4-isopropyl-3-methylphenyl)benzamide (Compound ID 124)

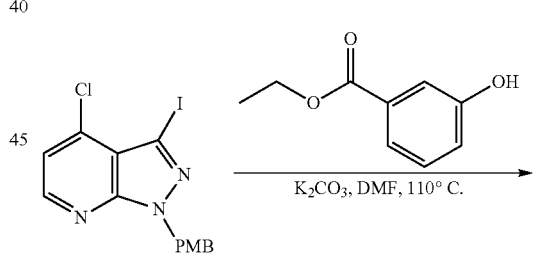

GA-1

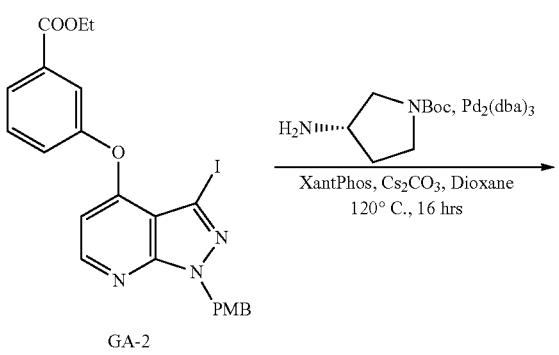

GA-2

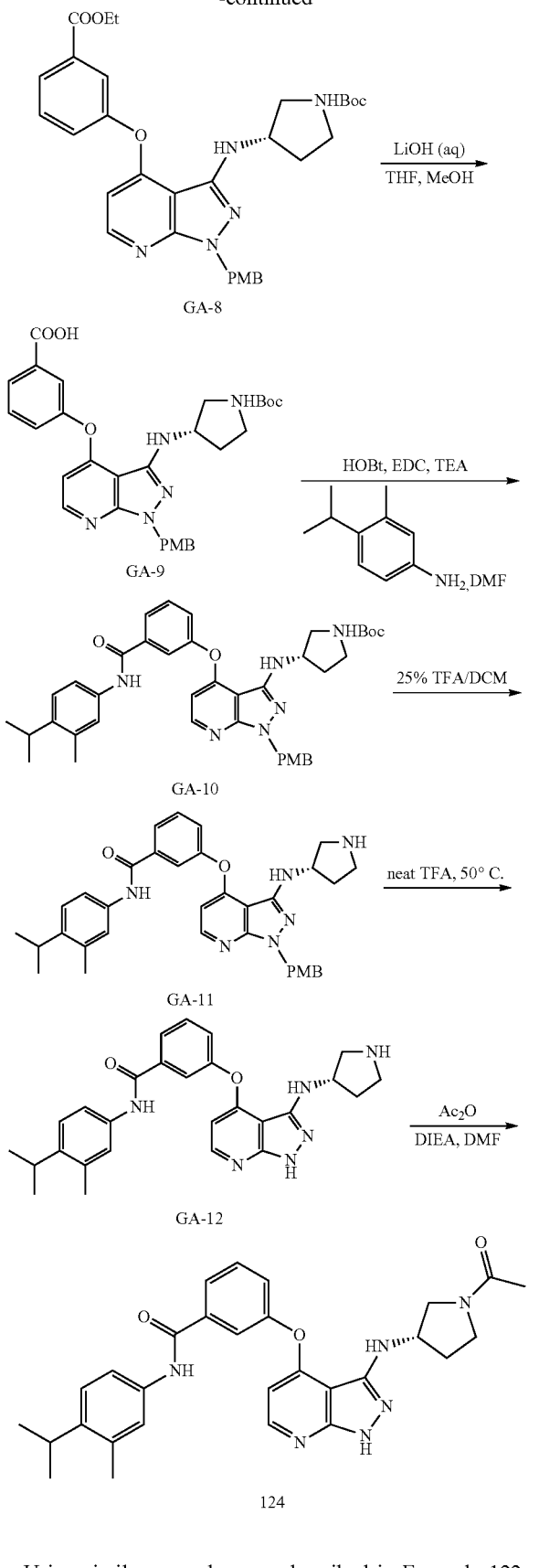

(S)-tert-butyl 3-(4-(3-(ethoxycarbonyl)phenoxy)-1-(4-methoxybenzyl)-1H-pyrazolo[3,4-b]pyridin-3-ylamino)pyrrolidine-1-carboxylate, (GA-8), orange oil, 328.6 mg (47%), MW=587.7, MH⁺=588.7.

(S)-3-(3-(1-(tert-butoxycarbonyl)pyrrolidin-3-ylamino)-1-(4-methoxybenzyl)-1H-pyrazolo[3,4-b]pyridin-4-yloxy)benzoic acid, (GA-9), 303.6 mg (97%), MW=559.6, MH⁺=560.7.

(S)-tert-butyl 3-(4-(3-(4-isopropyl-3-methylphenylcarbamoyl)phenoxy)-1-(4-methoxybenzyl)-1H-pyrazolo[3,4-b]pyridin-3-ylamino)pyrrolidine-1-carboxylate, (GA-10), yellow film, 265.2 mg (71%), MW=690.8, MH⁺=691.6.

(S)—N-(4-isopropyl-3-methylphenyl)-3-(1-(4-methoxybenzyl)-3-(pyrrolidin-3-ylamino)-1H-pyrazolo[3,4-b]pyridin-4-yloxy)benzamide, (GA-11), MW=590.7, MH⁺=591.6.

(S)—N-(4-isopropyl-3-methylphenyl)-3-(3-(pyrrolidin-3-ylamino)-1H-pyrazolo[3,4-b]pyridin-4-yloxy)benzamide, (GA-12), off-white solid, 128.7 (71%), MW=470.6, MH⁺=471.4.

(S)-3-(3-(1-acetylpyrrolidin-3-ylamino)-1H-pyrazolo[3,4-b]pyridin-4-yloxy)-N-(4-isopropyl-3-methylphenyl)benzamide (124); a yellow solid, formic acid salt (13.6 mg, 49%); MW=512.6, MH⁺=513.7, MH⁻=511.2, UV: λ=slope-like (275 nm).

Example 125

(S)-3-(3-(1-(cyclopropanecarbonyl)pyrrolidin-3-ylamino)-1H-pyrazolo[3,4-b]pyridin-4-yloxy)-N-(4-isopropyl-3-methylphenyl)benzamide (Compound ID 125)

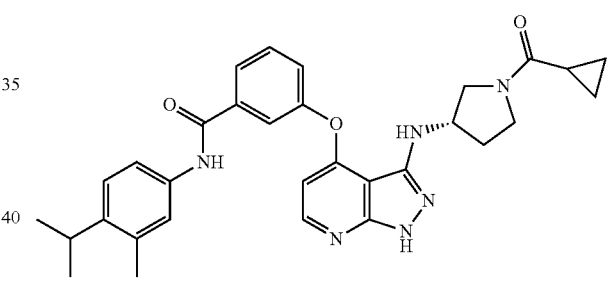

Using procedures similar to that described in Example 124, Compound 125 was made: a yellow solid, formic acid salt (15.0 mg, 51%); MW=538.6, MH⁺=539.7, MH⁻=537.2, UV: λ=slope-like (275 nm).

Example 126

(S)-3-(3-(1-acryloylpyrrolidin-3-ylamino)-1H-pyrazolo[3,4-b]pyridin-4-yloxy)-N-(4-isopropyl-3-methylphenyl)benzamide (Compound ID 126)

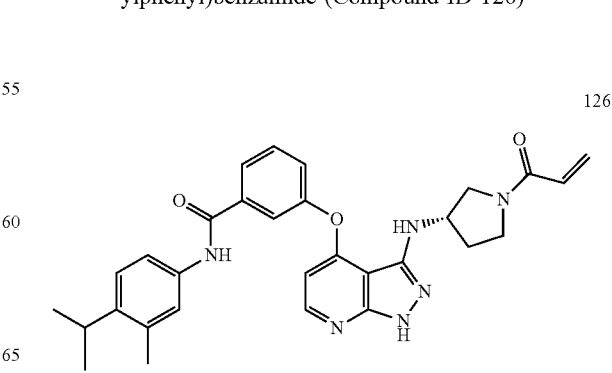

Using similar procedures as described in Example 122, the following compounds were made:

Compound 126 was made using procedures similar to that described in Example 124: a light yellow solid, formic acid salt (10.2 mg, 36%); MW=524.6, MH+=525.6, MH−=523.2, UV: λ=slope-like (270 nm).

Example 127

(R)-3-(3-(1-(cyclopropanecarbonyl)piperidin-3-ylamino)-1H-pyrazolo[3,4-b]pyridin-4-ylamino)-N-(4-isopropyl-3-methylphenyl)benzamide (Compound ID 127)

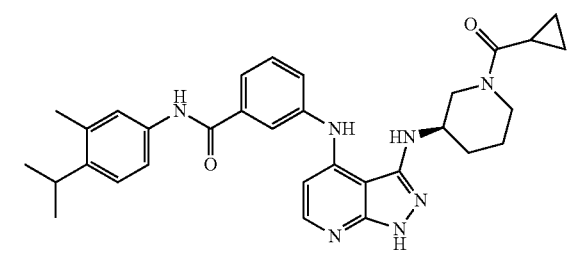 [SMILES: Cc1cc(NC(=O)c2cccc(Nc3ccnc4[nH]nc(N[C@@H]5CCCN(C(=O)C6CC6)C5)c34)c2)ccc1C(C)C]

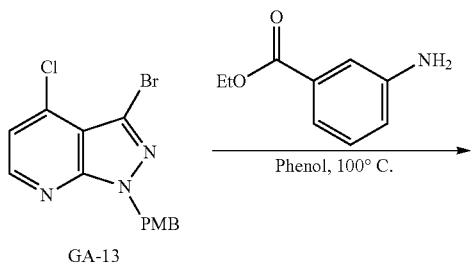

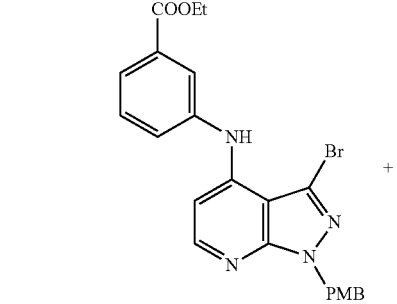

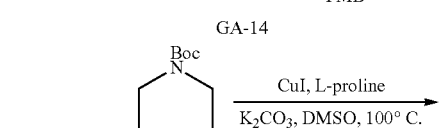

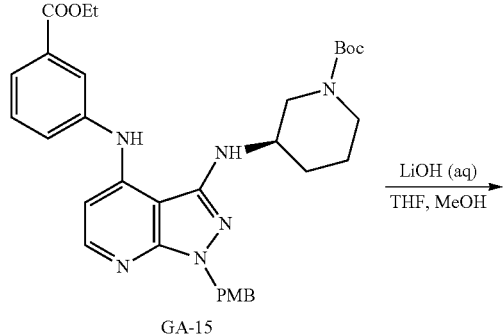

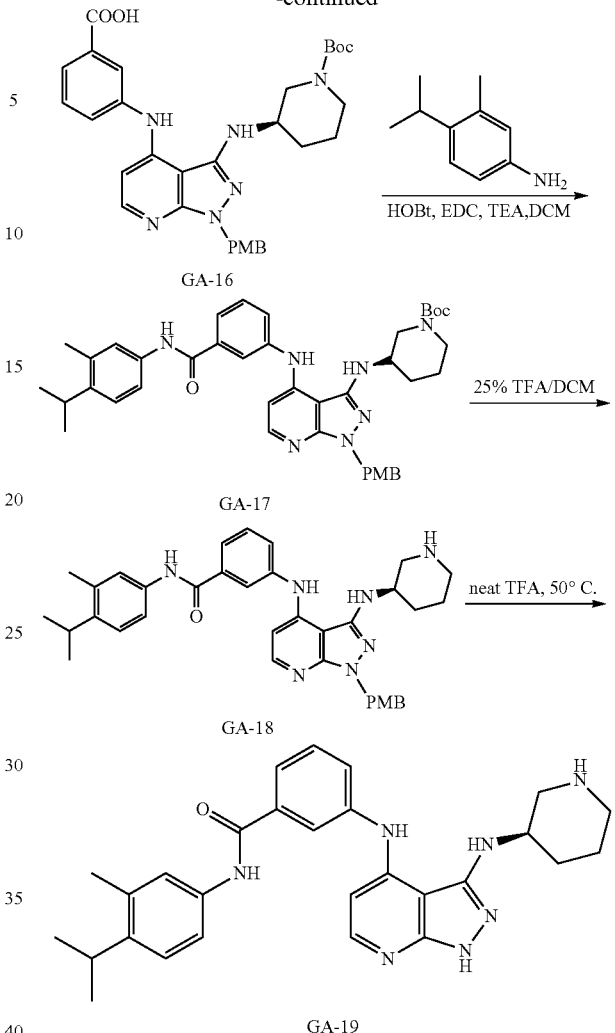

127.1 Preparation of ethyl 3-(3-bromo-1-(4-methoxybenzyl)-1H-pyrazolo[3,4-b]pyridin-4-ylamino)benzoate, (GA-14)

3-bromo-4-chloro-1-(4-methoxybenzyl)-1H-pyrazolo[3,4-b]pyridine (2.5 g, 7.1 mmol), ethyl 3-aminobenzoate (2.34 g, 14.2 mmol) and phenol (10.7 g, 113 mmol) were heated at 100° C., under $N_2$, for 17 hrs. The brown solution was diluted with 80 mL EtOAc and washed with 10% NaOH (aq) (3×25 mL). Organics were then washed with brine, dried ($Na_2SO_4$), filtered and evaporated in vacuo. The title compound was isolated after Flash Chromatography, 0-35% EtOAc/hexanes as eluent, as a yellow crystalline solid, 2.61 g (76%), MW=481.3, MH+=481.0/483.0.

127.2 Preparation of (R)-tert-butyl 3-(4-(3-(ethoxycarbonyl)phenylamino)-1-(4-methoxybenzyl)-1H-pyrazolo[3,4-b]pyridin-3-ylamino)piperidine-1-carboxylate, (GA-15)

A mixture of ethyl 3-(3-bromo-1-(4-methoxybenzyl)-1H-pyrazolo[3,4-b]pyridin-4-ylamino)benzoate (1.0 g, 2.1 mmol), (R)-tert-butyl 3-aminopiperidine-1-carboxylate (1.25 g, 6.2 mmol), copper iodide (200 mg, 1.04 mmol), L-proline (0.96 g, 8.3 mmol), and potassium carbonate (1.44 g, 10.4 mmol), in 20 mL DMSO was heated at 100° C. for 9 hrs under $N_2$. The reaction mixture was diluted with 100 mL water and extracted with DCM (2×150 mL). The combined organics were dried ($Na_2SO_4$), filtered, concentrated and purified by Flash Chromatography using 0-65% EtOAc/hexanes as eluent to yield (R)-tert-butyl 3-(4-(3-(ethoxycarbonyl)phenylamino)-1-(4-methoxybenzyl)-1H-pyrazolo[3,4-b]pyridin-3-ylamino)piperidine-1-carboxylate, (GA-15), 448 mg (36%), MW=600.7, $MH^+$=601.9.

Following procedures similar to that described in Example 122, the following intermediate and final compounds were prepared:

(R)-3-(3-(1-(tert-butoxycarbonyl)piperidin-3-ylamino)-1-(4-methoxybenzyl)-1H-pyrazolo[3,4-b]pyridin-4-ylamino)benzoic acid, (GA-16), 465 mg (99%), MW=572.6, $MH^+$=573.5.

(R)-tert-butyl 3-(4-(3-(4-isopropyl-3-methylphenylcarbamoyl)phenylamino)-1-(4-methoxybenzyl)-1H-pyrazolo[3,4-b]pyridin-3-ylamino)piperidine-1-carboxylate, (GA-17), 465 mg (81%), MW=703.9, $MH^+$=704.9.

(R)—N-(4-isopropyl-3-methylphenyl)-3-(1-(4-methoxybenzyl)-3-(piperidin-3-ylamino)-1H-pyrazolo[3,4-b]pyridin-4-ylamino)benzamide, (GA-18), 366 mg (92%), MW=603.8, $MH^+$=604.6.

(R)—N-(4-isopropyl-3-methylphenyl)-3-(3-(piperidin-3-ylamino)-1H-pyrazolo[3,4-b]pyridin-4-ylamino)benzamide, (GA-19), yellow solid, 257 mg (88%), MW=483.6, $MH^+$=484.3.

Compound 127: a pale yellow solid, formic acid salt (1.5 mg, 5%); MW=551.7, $MH^+$=552.6, $MH^-$=550.3, UV: λ=293 nm.

Example 128

(S)-3-(3-(1-(4-fluorobenzoyl)pyrrolidin-3-ylamino)-1H-pyrazolo[3,4-b]pyridin-4-yloxy)-N-(4-isopropyl-3-methylphenyl)benzamide (Compound ID 128)

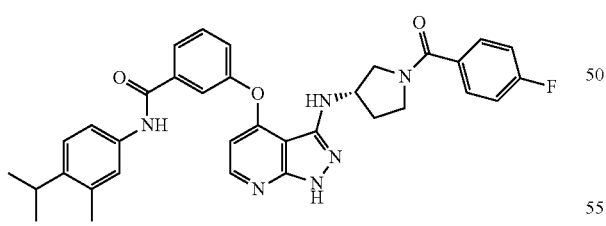

Compound 128 was made using procedures similar to that described in Example 124; a light yellow solid, formic acid salt (13.7 mg, 42%); MW=592.7, $MH^+$=593.5, $MH^-$=591.3, UV: λ=slope-like (270 nm).

Example 129

(R)-3-(3-(1-acryloylpiperidin-3-ylamino)-1H-pyrazolo[3,4-b]pyridin-4-ylamino)-N-(4-isopropyl-3-methylphenyl)benzamide (Compound ID 129)

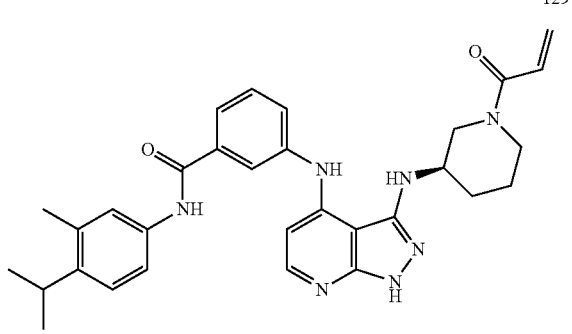

Compound 129 was made using procedures similar to that described in Example 127: a yellow solid, formic acid salt (4.9 mg, 17%); MW=537.7, $MH^+$=538.6, $MH^-$=536.3, UV: λ=293 nm.

Example 130

(R)-3-(3-(1-(4-fluorobenzoyl)piperidin-3-ylamino)-1H-pyrazolo[3,4-b]pyridin-4-ylamino)-N-(4-isopropyl-3-methylphenyl)benzamide (Compound ID 130)

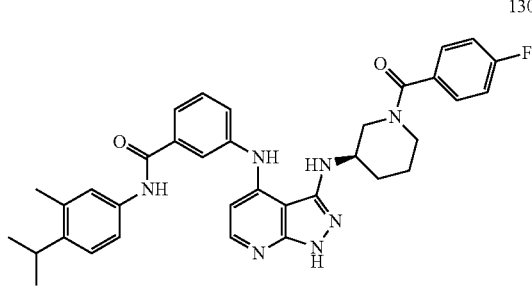 [SMILES: Cc1cc(NC(=O)c2cccc(Nc3ccnc4[nH]nc(N[C@@H]5CCCN(C(=O)c6ccc(F)cc6)C5)c34)c2)ccc1C(C)C]

Compound 130 was made using procedures similar to that described in Example 127: a pale yellow solid, formic acid salt (3.9 mg, 12%); MW=605.7, $MH^+$=606.6, $MH^-$=604.3, UV: λ=292 nm.

Example 131

(R)-3-(3-(1-acetylpiperidin-3-ylamino)-1H-pyrazolo[3,4-b]pyridin-4-ylamino)-N-(4-isopropyl-3-methylphenyl)benzamide (Compound 131)

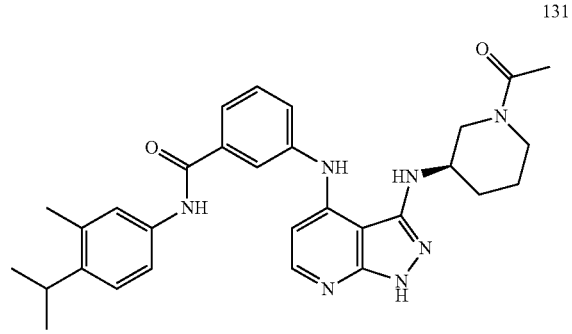 [SMILES: CC(=O)N1CCC[C@@H](Nc2n[nH]c3nccc(Nc4cccc(C(=O)Nc5ccc(C(C)C)c(C)c5)c4)c23)C1]

Compound 131 was made using procedures similar to that of Example 127: a pale yellow solid, formic acid salt (6.4 mg, 23%); MW=525.6, MH⁺=526.5, MH⁻=524.3, UV: λ=292 nm.

Example 132

(R)—N-(4-isopropyl-3-methylphenyl)-3-(3-(1-(morpholine-4-carbonyl)piperidin-3-ylamino)-1H-pyrazolo[3,4-b]pyridin-4-ylamino)benzamide (Compound ID 132)

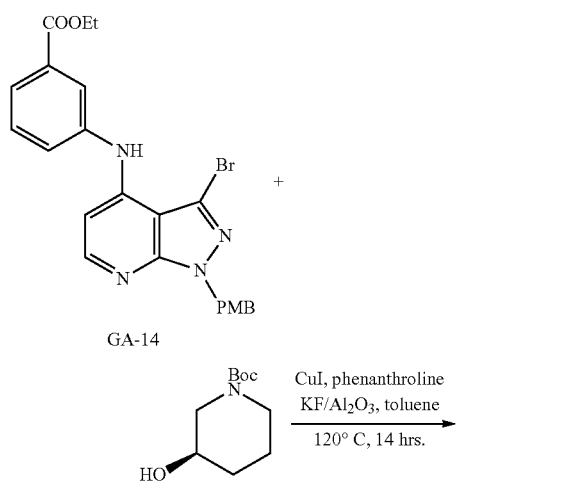

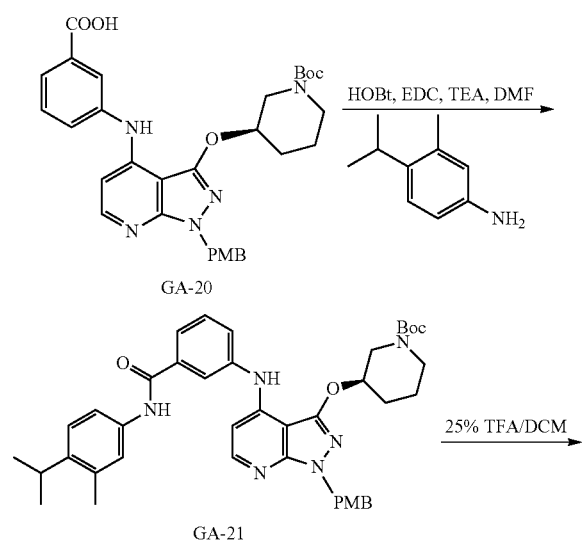

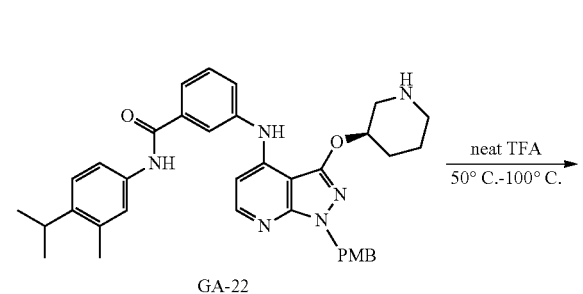

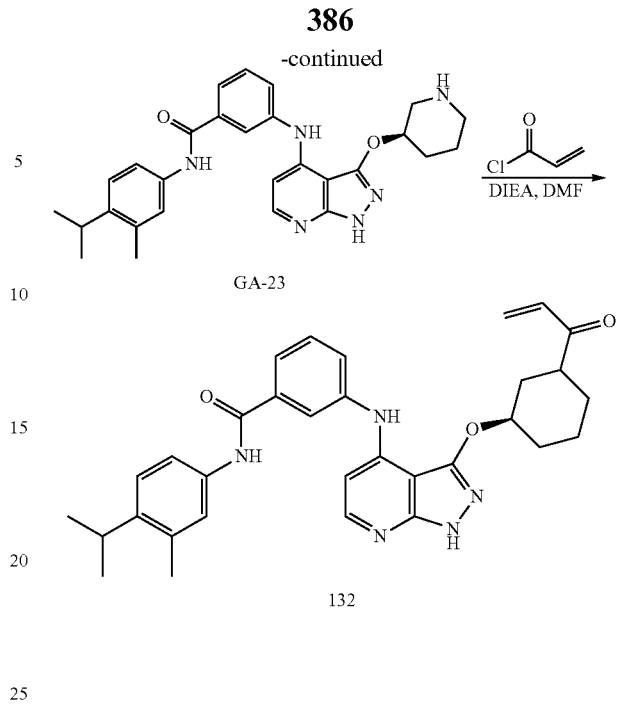

132.1 Preparation of (R)-3-(3-(1-(tert-butoxycarbonyl)piperidin-3-yloxy)-1-(4-methoxybenzyl)-1H-pyrazolo[3,4-b]pyridin-4-ylamino)benzoic acid, (GA-20)

A mixture of ethyl 3-(3-bromo-1-(4-methoxybenzyl)-1H-pyrazolo[3,4-b]pyridin-4-ylamino)benzoate (500 mg, 1.04 mmol), (R)-tert-butyl 3-hydroxypiperidine-1-carboxylate (4.2 g, 20.8 mmol), copper iodide (198 mg, 1.04 mmol), phenanthroline (187 mg, 1.04 mmol) and ~5.5 mmol/g KF/Al₂O₃ (1.32 g, 7.27 mmol) in 20 mL toluene was heated at 120° C. for 14 hrs under N₂. Upon cooling to room temperature, the mixture was filtered and concentrated in vacuo. The residue was subjected to Flash Chromatography, 0-45% MeOH/DCM as eluent, followed by washing with warm EtOAc (3×100 mL). The clean product goes into EtOAc, leaving the phenanthroline impurities behind as solids. The title compound was isolated as a clear film, 322 mg (54%), MW=573.6, MH⁺=574.8.

Following procedures from Example 122, the following intermediates and compounds were prepared:

(R)-tert-butyl 3-(4-(3-(4-isopropyl-3-methylphenylcarbamoyl)phenylamino)-1-(4-methoxybenzyl)-1H-pyrazolo[3,4-b]pyridin-3-yloxy)piperidine-1-carboxylate, (GA-21), 286 mg (72%), MW=704.9, MH⁺=705.9.

(R)-tert-butyl 3-(4-(3-(4-isopropyl-3-methylphenylcarbamoyl)phenylamino)-1-(4-methoxybenzyl)-1H-pyrazolo[3,4-b]pyridin-3-yloxy)piperidine-1-carboxylate, (GA-21), 286 mg (72%), MW=704.9, MH⁺=705.9.

(R)—N-(4-isopropyl-3-methylphenyl)-3-(1-(4-methoxybenzyl)-3-(piperidin-3-yloxy)-1H-pyrazolo[3,4-b]pyridin-4-ylamino)benzamide, (GA-22), MW=604.7, MH⁺=605.5.

(R)—N-(4-isopropyl-3-methylphenyl)-3-(3-(piperidin-3-yloxy)-1H-pyrazolo[3,4-b]pyridin-4-ylamino)benzamide, (GA-23), 110 mg, (56%), MW=484.6, MH⁺=485.5.

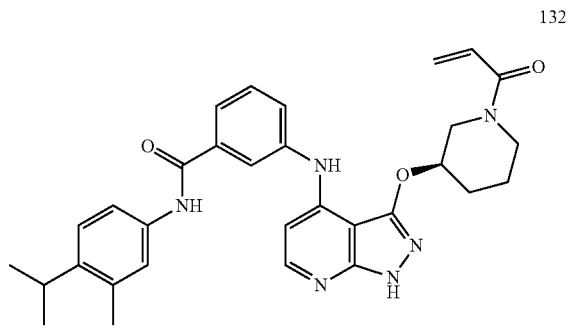 [SMILES: C=CC(=O)N1CCC[C@@H](Oc2n[nH]c3nccc(Nc4cccc(C(=O)Nc5ccc(C(C)C)c(C)c5)c4)c23)C1]

132

(R)-3-(3-(1-acryloylpiperidin-3-yloxy)-1H-pyrazolo[3,4-b]pyridin-4-ylamino)-N-(4-isopropyl-3-methylphenyl)benzamide (132); a white solid, formic acid salt (3.5 mg, 13%); MW=538.6, MH$^+$=539.5, MH$^-$=537.2, UV: λ=283 nm.

Example 133

(R)—N-(4-isopropyl-3-methylphenyl)-3-(3-(1-(morpholine-4-carbonyl)piperidin-3-ylamino)-1H-pyrazolo[3,4-b]pyridin-4-ylamino)benzamide. (Compound ID 133)

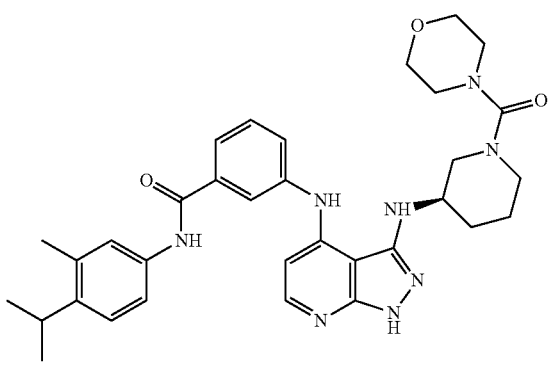

133

Compound 133 was made using procedures similar to that described in Example 127, a yellow solid, formic acid salt (1.1 mg, 4%); MW=596.7, MH$^+$=597.5, MH$^-$=595.3, UV: λ=294 nm.

Example 134

(R)-3-(3-(1-(cyclopropanecarbonyl)piperidin-3-yloxy)-1H-pyrazolo[3,4-b]pyridin-4-ylamino)-N-(4-isopropyl-3-methylphenyl)benzamide. (Compound ID 134)

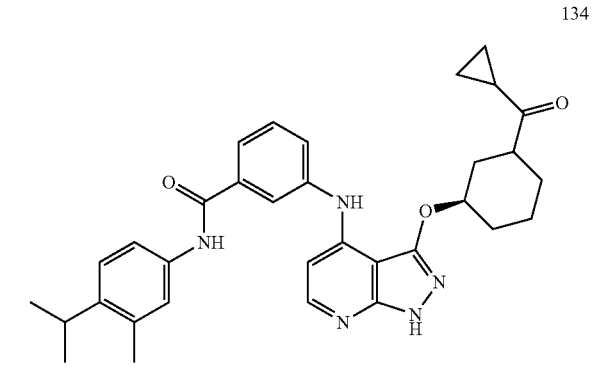 [SMILES: Cc1cc(NC(=O)c2cccc(Nc3ccnc4[nH]nc(O[C@@H]5CCCC(C(=O)C6CC6)C5)c34)c2)ccc1C(C)C]

134

Compound 134 was made using procedures in Example 132: white solid, formic acid salt (10.2 mg, 36%); MW=552.7, MH$^+$=553.6, MH$^-$=551.3, UV: λ=283 nm.

Example 135

(R)-3-(3-(1-acetylpiperidin-3-yloxy)-1H-pyrazolo[3,4-b]pyridin-4-ylamino)-N-(4-isopropyl-3-methylphenyl)benzamide. (Compound ID 135)

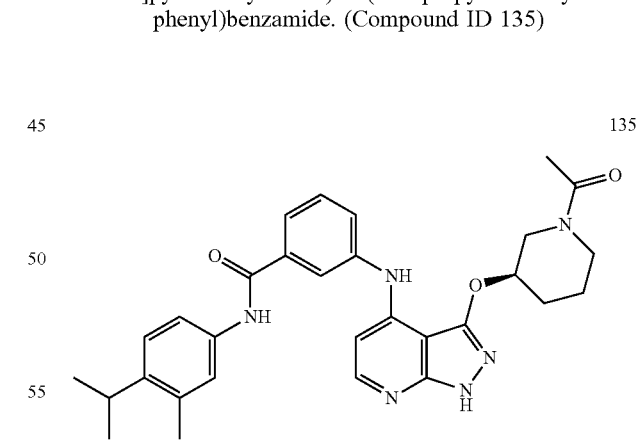

135

Compound 135 was made using procedures similar to that described in Example 132: a white solid, formic acid salt (6.3 mg, 23%); MW=526.6, MH$^+$=527.4, MH$^-$=525.3, UV: λ=283 nm.

Example 136

1-{4-[(3-{[(3R)-1-[(2E)-4-[cyclopropyl(methyl)
amino]but-2-enoyl]piperidin-3-yl]amino}-1H-pyra-
zolo[3,4-b]pyridin-4-yl)oxy]phenyl}-3-ethylurea
(Compound ID 136)

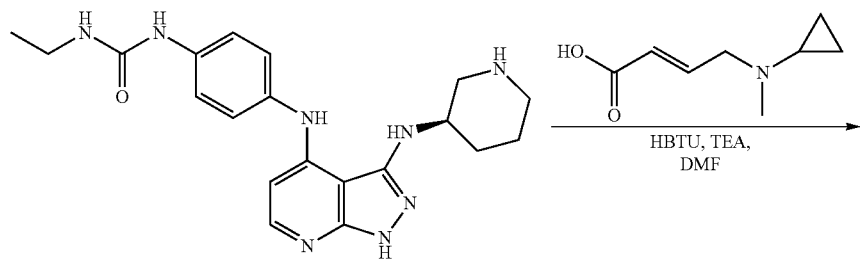

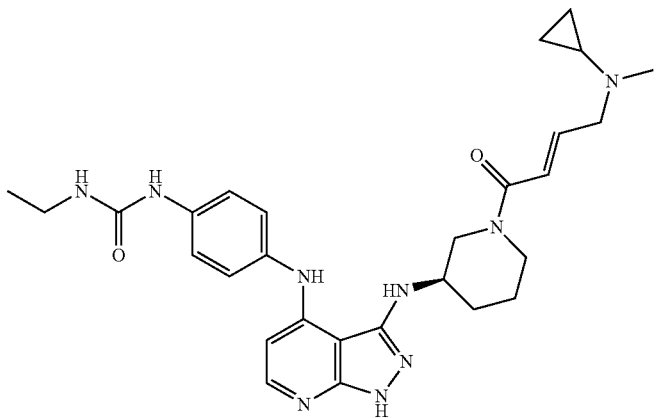

To a solution of (2E)-4-[cyclopropyl(methyl)amino]but-2-enoic acid (30.1 mg, 0.194 mmol) and HBTU (73 mg, 0.191 mmol) in DMF (2 mL) TEA (53 μL) was added and the solution was stirred at room temperature for 30 minutes. A solution of 3-ethyl-1-{4-[(3-{[(3R)-piperidin-3-yl]amino}-1H-pyrazolo[3,4-b]pyridin-4-yl)oxy]phenyl}urea (75.4 mg, 0.191 mmol) in DMF (2 mL) was added and the mixture was stirred at room temperature for 3.5 hours. The reaction mixture was concentrated under reduced pressure to obtain a crude (188.5 mg) which was purified by gradient flash-chromatography (C18, 5% to 95% of acetonitrile in water with 0.1% of NH$_4$OH, then Silica-NH, 3% methanol in DCM) and triturated in Et$_2$O to afford 1-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-3-ethylurea (18.1 mg, 17% yield) as a white solid. LC-MS (ESI): m/z (M+1)$^+$, 533.3. 1H NMR (500 MHz, DMSO) δ 12.21 (br. s., 1H), 8.56 (s, 1H), 8.11 (d, J=5.40 Hz, 1H), 7.50 (d, J=8.80 Hz, 2H), 7.12 (d, J=8.80 Hz, 2H), 6.61-6.46 (m, 1H), 6.44-6.30 (m, 1H), 6.12 (t, J=5.38 Hz, 1H), 5.97 (d, J=5.40 Hz, 1H), 5.21-5.08 (m, 1H), 3.97 (d, J=12.72 Hz, 1H), 3.85-3.59 (m, 2H), 3.49-2.91 (m, 6H), 2.08 (br. s., 3H), 2.01 (br. s., 1H), 1.85-1.53 (m, 3H), 1.50-1.39 (m, 1H), 1.06 (t, J=7.09 Hz, 3H), 0.45-0.18 (m, 4H)

Example 137

4-[(3-{[(3R)-1-[(2E)-4-[cyclopropyl(methyl)amino]
but-2-enoyl]piperidin-3-yl]amino}-1H-pyrazolo[3,4-
b]pyridin-4-yl)oxy]-N-{5-methyl-4H,5H,6H,7H-[1,
3]thiazolo[4,5-c]pyridin-2-yl}benzamide
(Compound 137)

1.16 Preparation of Tert-butyl (3R)-3-({1-[(4-methoxyphenyl)methyl]-4-[4-({5-methyl-4H,5H,6H,7H-[1,3]thiazolo[5,4-c]pyridin-2-yl}carbamoyl)phenoxy]-1H-pyrazolo[3,4-b]pyridin-3-yl}amino)
piperidine-1-carboxylate

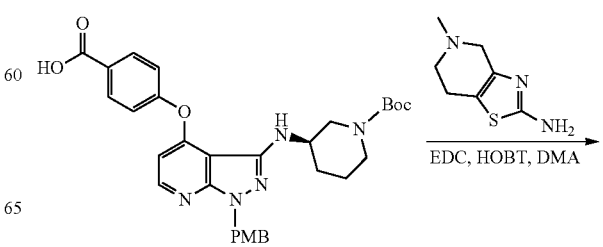

-continued

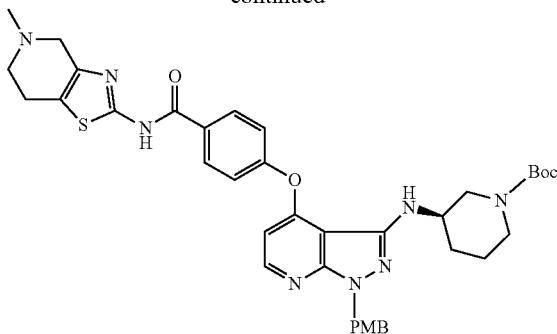

4-[(3-{[(3R)-1-[(tert-Butoxy)carbonyl]piperidin-3-yl]amino}-[(4-methoxyphenyl)methyl]-1H-pyrazolo[3,4-b]pyridin-4-yl)oxy]benzoic acid (0.4156 g, 0.72 mmol) and 5-methyl-4H,5H,6H,7H-[1,3]thiazolo[5,4-c]pyridin-2-amine (255 mg, 1.51 mmol) were dissolved in 5 mL of DMA, then EDC (285 mg, 1.49 mmol) and HOBt (101 mg, 0.75 mol) were added, the mixture was stirred and heated at 50° C. for 1.5 hours. The reaction mixture was cooled to room temperature ethyl acetate and NaHCO₃ saturated aqueous solution were added and the two phases separated. The organic phase was washed with brine, dried over Na₂SO₄, and concentrated to give a crude product that was purified by flash chromatography (silica gel, 50 g, from pure ethyl acetate to methanol/ethyl acetate 15/85). Tert-butyl (3R)-3-({1-[(4-methoxyphenyl)methyl]-4-[4-({5-methyl-4H,5H,6H,7H-[1,3]thiazolo[5,4-c]pyridin-2-yl}carbamoyl)phenoxy]-1H-pyrazolo[3,4-b]pyridin-3-yl}amino)piperidine-1-carboxylate was obtained as a yellow solid (249.5 mg, Yield 46%). LC-MS (ESI): m/z (M+1)⁺, 725.2.

1.17 Preparation of (3R)-3-({1-[(4-methoxyphenyl)methyl]-4-[4-({5-methyl-4H,5H,6H, 7H-[1,3]thiazolo[5,4-c]pyridin-2-yl}carbamoyl)phenoxy]-1H-pyrazolo[3,4-b]pyridin-3-yl}amino)piperidin-1-ium trifluoroacetate

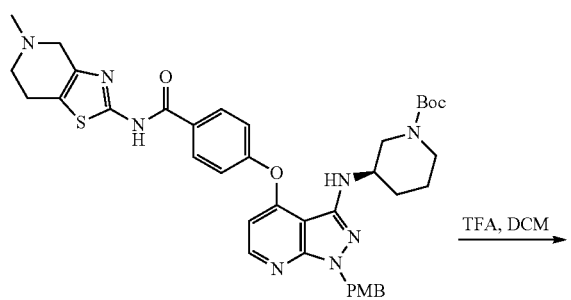

TFA, DCM

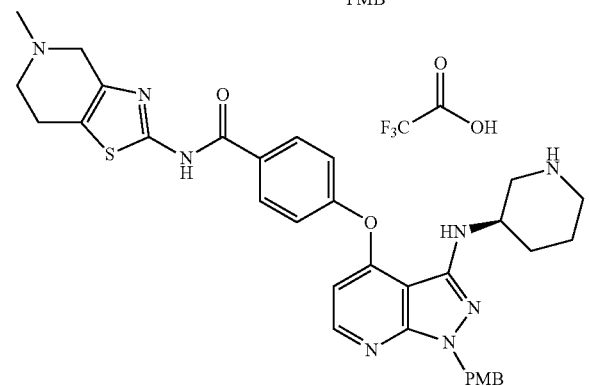

To a solution of tert-butyl (3R)-3-({1-[(4-methoxyphenyl)methyl]-4-[4-({5-methyl-4H,5H,6H,7H-[1,3]thiazolo[5,4-c]pyridin-2-yl}carbamoyl)phenoxy]-1H-pyrazolo[3,4-b]pyridin-3-yl})amino)piperidine-1-carboxylate (249.5 mg, 0.34 mmol) in DCM (9 mL) at r.t. TFA (2 mL) was added. The reaction mixture was stirred at room temperature for 25 min then concentrated to afford (3R)-3-({1-[(4-methoxyphenyl)methyl]-4-[4-({5-methyl-4H,5H,6H,7H-[1,3]thiazolo[5,4-c]pyridin-2-yl}carbamoyl)phenoxy]-1H-pyrazolo[3,4-b]pyridin-3-yl}amino)piperidin-1-ium trifluoroacetate as a yellow oil (410 mg, Yield: quantitative). LC-MS (ESI): m/z (M+1)⁺, 625.6.

1.18 Preparation of N-{5-methyl-4H, 5H, 6H, 7H-[1,3]thiazolo[4,5-c]pyridin-2-yl}-4-[(3-{[(3R)-piperidin-3-yl]amino}-1H-pyrazolo[3,4-b]pyridin-4-yl)oxy]benzamide

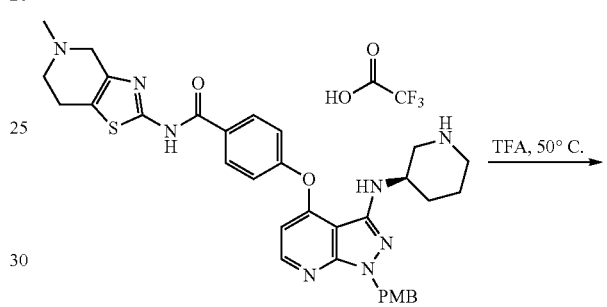

TFA, 50° C.

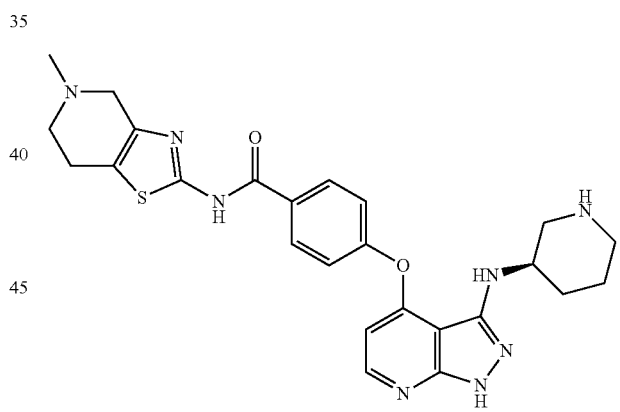

(3R)-3-({1-[(4-Methoxyphenyl)methyl]-4-[4-({5-methyl-4H,5H,6H,7H-[1,3]thiazolo[5,4-c]pyridin-2-yl}carbamoyl)phenoxy]-1H-pyrazolo[3,4-b]pyridin-3-yl}amino)piperidin-1-ium trifluoroacetate (410 g, 0.34 mmol) was dissolved in TFA (10 mL) and stirred at 50° C. for 7.5 hours then the solvent was evaporated. The crude product was purified by SCX cartridge affording N-{5-methyl-4H,5H,6H,7H-[1,3]thiazolo[4,5-c]pyridin-2-yl}-4-[(3-{[(3R)-piperidin-3-yl]amino}-1H-pyrazolo[3,4-b]pyridin-4-yl)oxy]benzamide as a pale yellow powder (140.5 mg, Yield: 80%). LC-MS (ESI): m/z (M+1)⁺, 505.0.

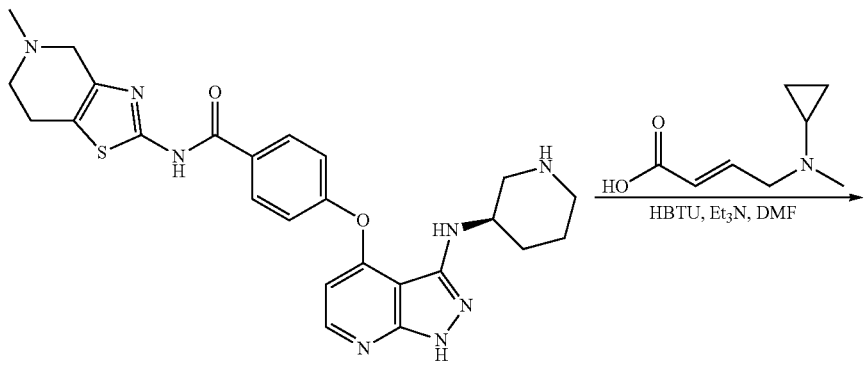

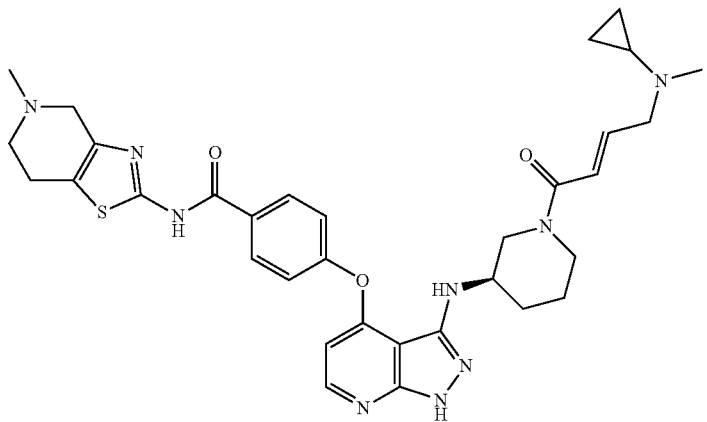

(2E)-4-[Cyclopropyl(methyl)amino]but-2-enoic acid (23 mg, 0.092 mmol), was dissolved in DMF (2 mL), HBTU (56.3 mg, 0.148 mmol) was added followed by Et$_3$N (40 µL, 0.28 mmol). The mixture turned red and was stirred for 15 min. N-{5-methyl-4H,5H,6H,7H-[1,3]thiazolo[4,5-c]pyridin-2-yl}-4-[(3-{[(3R)-piperidin-3-yl]amino}-1H-pyrazolo[3,4-b]pyridin-4-yl)oxy]benzamide (69.7 mg, 0.14 mmol) was added and the mixture stirred for 2 hours. The solvent was evaporated and the crude purified by gradient flash chromatography (silica gel NH, 30 g, DCM/MeOH from 98/2 to 95/5). 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-{5-methyl-4H,5H,6H,7H-[1,3]thiazolo[4,5-c]pyridin-2-yl}benzamide was obtained as a white solid (20.6 mg, Yield: 23%). LC-MS (ESI): m/z (M+1)$^+$, 642.5. $^1$H NMR (600 MHz, DMSO) δ 12.57 (br. s., 1H), 12.33 (br. s., 1H), 8.26-8.15 (m, 3H), 7.49-7.27 (m, 2H), 6.60-6.46 (m, 1H), 6.37 (d, J=15.15 Hz, 1H), 6.23-6.12 (m, 1H), 5.13 (d, J=6.59 Hz, 1H), 3.94 (d, J=12.20 Hz, 1H), 3.83-3.61 (m, 2H), 3.52 (s, 2H), 3.45 (dd, J=12.19, 7.58 Hz, 1H), 3.27-2.92 (m, 3H), 2.77-2.65 (m, 4H), 2.39 (s, 3H), 2.39 (s, 3H), 2.08 (br. s., 3H), 1.99 (br. s., 1H), 1.78-1.54 (m, 3H), 1.43 (br. s., 1H), 0.45-0.18 (m, 4H).

Example 138

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-[3-(trifluoromethyl)phenyl]benzamide (Compound ID 138)

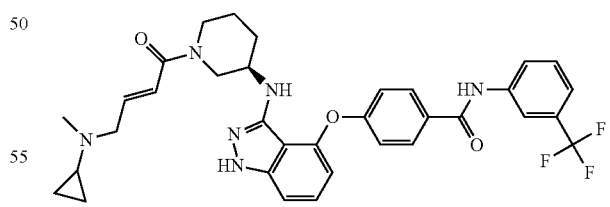

Compound 138 was prepared following the method described for Ex. 137. LC-MS (ESI): m/z (M+1)$^+$, 634.2. $^1$H NMR (500 MHz, DMSO) δ 12.35 (br. s., 1H), 10.61 (s, 1H), 8.29-8.24 (m, 1H), 8.23-8.18 (m, 1H), 8.13 (d, J=7.83 Hz, 2H), 8.07 (d, J=8.31 Hz, 1H), 7.62 (t, J=8.07 Hz, 1H), 7.50-7.39 (m, 3H), 6.62-6.33 (m, 2H), 6.22-6.12 (m, 1H), 5.12 (d, J=6.85 Hz, 1H), 3.92 (d, J=12.72 Hz, 1H), 3.56-3.45 (m, 1H), 3.83-3.23 (m, 3H), 3.22-2.92 (m, 2H), 2.08 (s, 3H), 2.03-1.37 (m, 5H), 0.46-0.15 (m, 4H).

Example 139

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(4-methyl-1,3-thiazol-2-yl)benzamide (Compound ID 139)

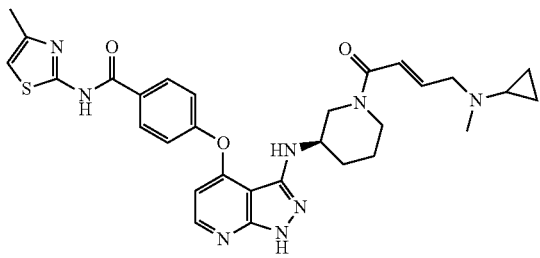 [SMILES: Cc1csc(NC(=O)c2ccc(Oc3ccnc4[nH]nc(N[C@@H]5CCCN(C(=O)/C=C/CN(C)C6CC6)C5)c34)cc2)n1]

1.22 Preparation of tert-butyl (3R)-3-({1-[(4-methoxyphenyl)methyl]-4-{4-[(4-methyl-1,3-thiazol-2-yl)carbamoyl]phenoxy}-1H-pyrazolo[3,4-b]pyridin-3-yl}amino)piperidine-1-carboxylate

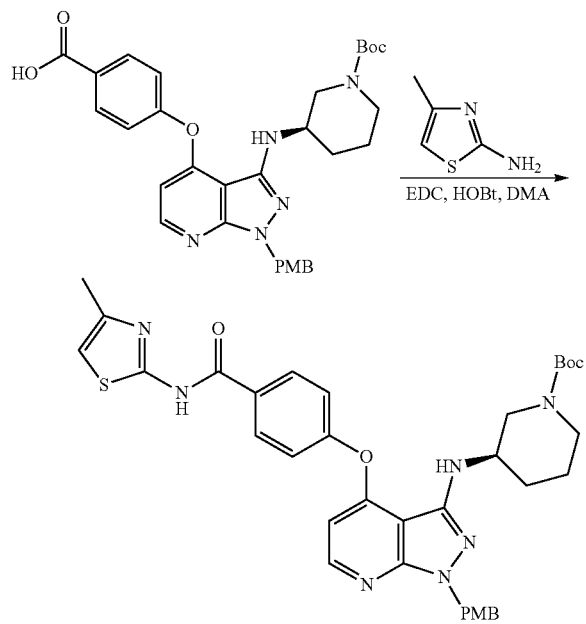

4-[(3-{[(3R)-1-[(tert-Butoxy)carbonyl]piperidin-3-yl]amino}-1-[(4-methoxyphenyl)methyl]-1H-pyrazolo[3,4-b]pyridin-4-yl)oxy]benzoic acid (0.5037 g, 0.88 mmol) and 4-methyl-1,3-thiazol-2-amine (185.3 mg, 1.62 mmol) were dissolved in 6 mL of DMA, then EDC (334.9 mg, 1.75 mmol) and HOBt (114.2 mg, 0.85 mol) were added, the mixture was stirred and heated at 50° C. for 2.0 hours. The reaction mixture was cooled to room temperature ethyl acetate and NaHCO₃ saturated aqueous solution were added and the two phases separated. The organic phase was washed with brine, dried over Na₂SO₄, and concentrated to give a crude product that was purified by flash chromatography (silica gel, 50 g, cyclohexane/ethyl acetate from 3/7 to 7/3). Tert-butyl (3R)-3-({1-[(4-methoxyphenyl)methyl]-4-{4-[(4-methyl-1,3-thiazol-2-yl)carbamoyl]phenoxy}-1H-pyrazolo[3,4-b]pyridin-3-yl}amino)piperidine-1-carboxylate was obtained as a yellow oil (449.8 mg, Yield 77%). LC-MS (ESI): m/z (M+1)⁺, 670.1.

1.23 Preparation of (3R)-3-({1-[(4-methoxyphenyl)methyl]-4-{4-[(4-methyl-1,3-thiazol-2-yl)carbamoyl]phenoxy}-1H-pyrazolo[3,4-b]pyridin-3-yl}amino)piperidin-1-ium trifluoroacetate

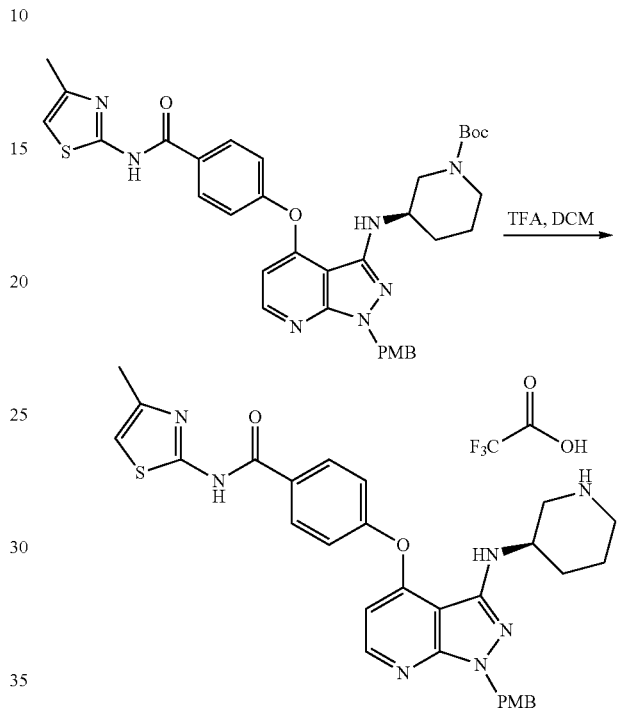

To a solution of tert-butyl (3R)-3-(({1-[(4-methoxyphenyl)methyl]-4-{4-[(4-methyl-1,3-thiazol-2-yl)carbamoyl]phenoxy}-1H-pyrazolo[3,4-b]pyridin-3-yl})amino)piperidine-1-carboxylate (0.445 g, 0.66 mmol) in DCM (18 mL) at room temperature TFA (3.5 mL) was added. The reaction mixture was stirred at this temperature for 15 min then concentrated to afford (3R)-3-({1-[(4-methoxyphenyl)methyl]-4-{4-[(4-methyl-1,3-thiazol-2-yl)carbamoyl]phenoxy}-1H-pyrazolo[3,4-b]pyridin-3-yl}amino)piperidin-1-ium trifluoroacetate as a yellow oil (0.8281 g, Yield: quantitative). LC-MS (ESI): m/z (M+1)⁺, 570.0.

1.24 Preparation of N-(4-methyl-1,3-thiazol-2-yl)-4-[(3-{[(3R)-piperidin-3-yl]amino}-1H-pyrazolo[3,4-b]pyridin-4-yl)oxy]benzamide

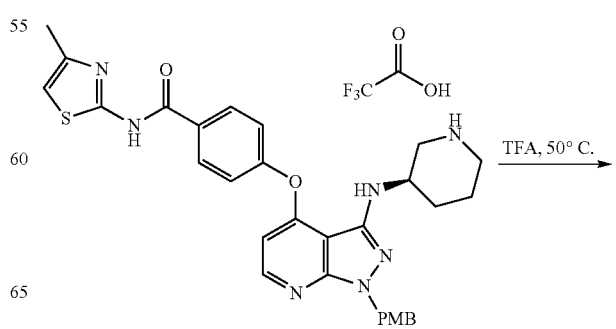

-continued

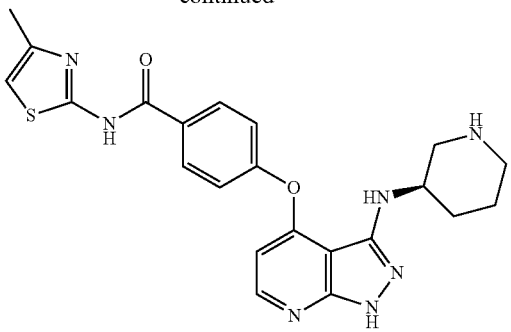

(3R)-3-({1-[(4-Methoxyphenyl)methyl]-4-{4-[(4-methyl-1,3-thiazol-2-yl)carbamoyl]phenoxy}-1H-pyrazolo[3,4-b]pyridin-3-yl}amino)piperidin-1-ium trifluoroacetate (0.8281 g, 0.66 mmol) was dissolved in TFA (18 mL) and stirred at 50° C. for 7 hours then the solvent was evaporated. The crude product was purified by SCX cartridge affording N-(4-methyl-1,3-thiazol-2-yl)-4-[(3-{[(3R)-piperidin-3-yl]amino}-1H-pyrazolo[3,4-b]pyridin-4-yl)oxy]benzamide as a pale yellow solid (186.6 mg, Yield: 74%). LC-MS (ESI): m/z (M+1)+, 450.0.

Compound 139 was prepared following the method described for Ex. 137. LC-MS (ESI): m/z (M+1)+, 587.2. $^1$H NMR (500 MHz, DMSO) δ 12.72 (br. s, 1H), 12.40-12.17 (m, 1H), 8.25-8.16 (m, 3H), 7.47-7.36 (m, 2H), 6.84 (s, 1H), 6.62-6.32 (m, 2H), 6.25-6.15 (m, 1H), 5.16-5.10 (m, 1H), 4.04-3.26 (m, 5H), 3.23-2.91 (m, 2H), 2.32 (s, 3H), 2.09 (s, 3H), 2.04-1.37 (m, 5H), 0.46-0.18 (m, 4H).

Example 140

N-(5-methyl-1,3-thiazol-2-yl)-4-[(3-{[(3R)-piperidin-3-yl]amino}-1H-pyrazolo[3,4-b]pyridin-4-yl)oxy]benzamide (Compound ID 140)

1.25 Preparation of tert-butyl (3R)-3-({1-[(4-methoxyphenyl)methyl]-4-{4-[(5-methy-1,3-thiazol-2-yl)carbamoyl]phenoxy}-1H-pyrazolo[3,4-b]pyridin-3-yl}amino)piperidine-1-carboxylate

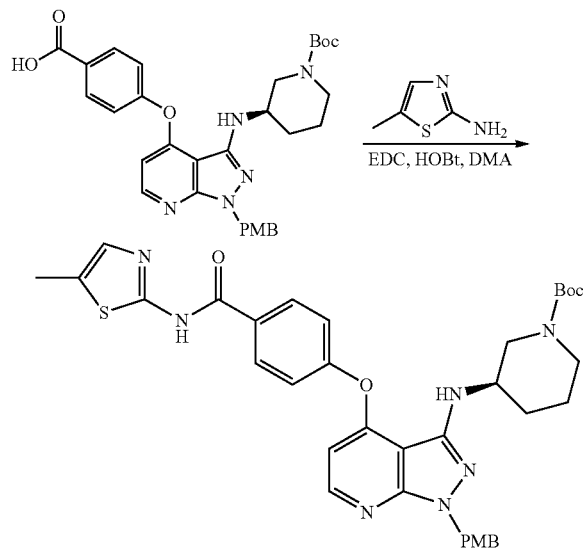

4-[(3-{[(3R)-1-[(tert-Butoxy)carbonyl]piperidin-3-yl]amino}-1-[(4-methoxyphenyl)methyl]-1H-pyrazolo[3,4-b]pyridin-4-yl)oxy]benzoic acid (0.9989 mg, 1.74 mmol) and 5-methylthiophen-2-amine (389.3 mg, 3.44 mmol) were dissolved in DMA, then EDC (661.0 mg, 3.45 mmol) and HOBt (239.7 mg, 1.77 mol) were added, the mixture was stirred and heated at 50° C. for 1.5 hours. The reaction mixture was cooled to room temperature, ethyl acetate and NaHCO$_3$ saturated aqueous solution were added and the two phases separated. The organic phase was washed with brine, dried over Na$_2$SO$_4$, and concentrated to give a crude product that was purified by flash chromatography (silica gel, 100 g, cyclohexane ethyl acetate from 6/4 to 3/7). tert-Butyl (3R)-3-({1-[(4-methoxyphenyl)methyl]-4-{4-[(5-methyl-1,3-thiazol-2-yl)carbamoyl]phenoxy}-1H-pyrazolo[3,4-b]pyridin-3-yl})amino)piperidine-1-carboxylate was obtained as a pale yellow foam (821.5 mg, Yield 70%). LC-MS (ESI): m/z (M+1)+, 670.1.

1.26 Preparation of (3R)-3-({1-[(4-methoxyphenyl)methyl]-4-{4-[(5-methylthiophen-2-yl)carbamoyl]phenoxy}-1H-pyrazolo[3,4-b]pyridin-3-yl}amino)piperidin-1-ium

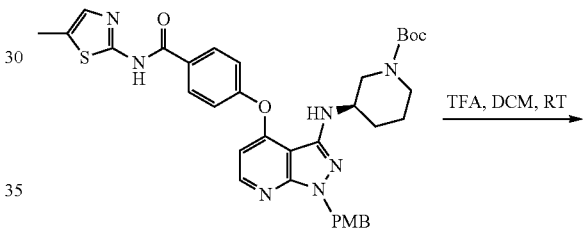

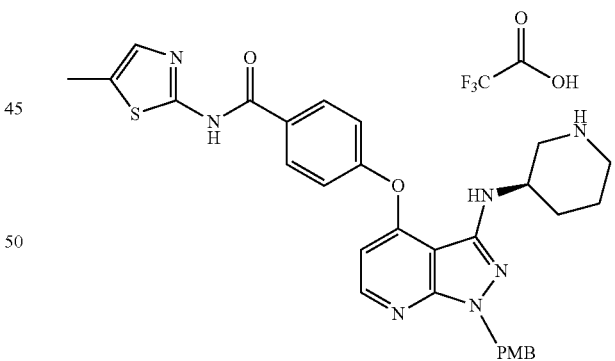

tert-Butyl (3R)-3-({1-[(4-methoxyphenyl)methyl]-4-{4-[(5-methyl-1,3-thiazol-2-yl)carbamoyl]phenoxy}-1H-pyrazolo[3,4-b]pyridin-3-yl})amino)piperidine-1-carboxylate (820.0 mg, 1.22 mmol) was dissolved in DCM (24 mL) and TFA (6 mL) was added. The reaction mixture was stirred at room temperature for 25 min then concentrated to afford (3R)-3-({1-[(4-methoxyphenyl)methyl]-4-{4-[(5-methylthiophen-2-yl)carbamoyl]phenoxy}-1H-pyrazolo[3,4-b]pyridin-3-yl}amino)piperidin-1-ium trifluoroacetate as a yellow oil (2.11 g, Yield: quantitative). LC-MS (ESI): m/z (M+1)+, 570.1.

1.27 Preparation of N-(5-methyl-1,3-thiazol-2-yl)-4-[(3-{[(3R)-piperidin-3-yl]amino}-1H-pyrazolo[3,4-b]pyridin-4-yl)oxy]benzamide

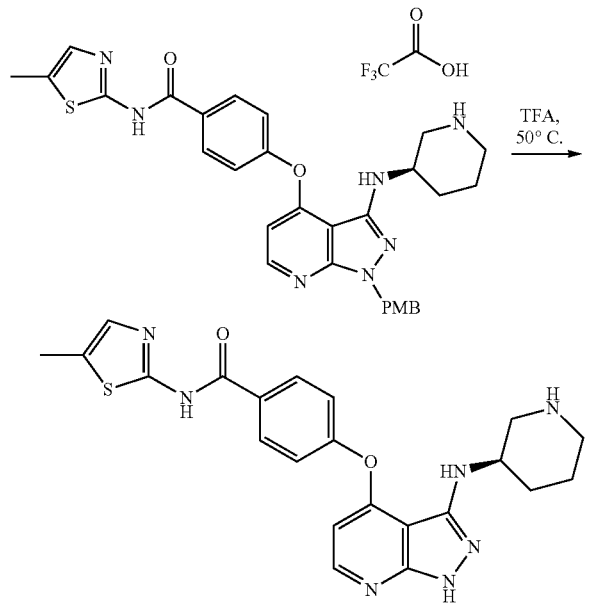

(3R)-3-({1-[(4-methoxyphenyl)methyl]-4-{4-[(5-methyl-thiophen-2-yl)carbamoyl]phenoxy}-1H-pyrazolo[3,4-b]pyridin-3-yl})amino)piperidin-1-ium trifluoroacetate (2.11 g, 1.22 mmol) was dissolved in TFA (30 mL) and stirred at 50° C. for 6.5 hours. NH₃ 1N in MeOH was added and the solvent evaporated. The crude product was purified by SCX cartridge affording N-(5-methyl-1,3-thiazol-2-yl)-4-[(3-{[(3R)-piperidin-3-yl]amino}-1H-pyrazolo[3,4-b]pyridin-4-yl)oxy]benzamide as a pale yellow solid (307.4 mg, Yield: 56%). LC-MS (ESI): m/z (M+1)⁺, 450.0.

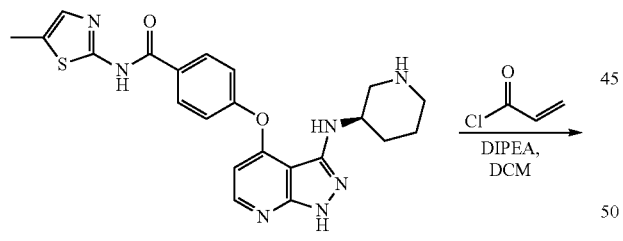

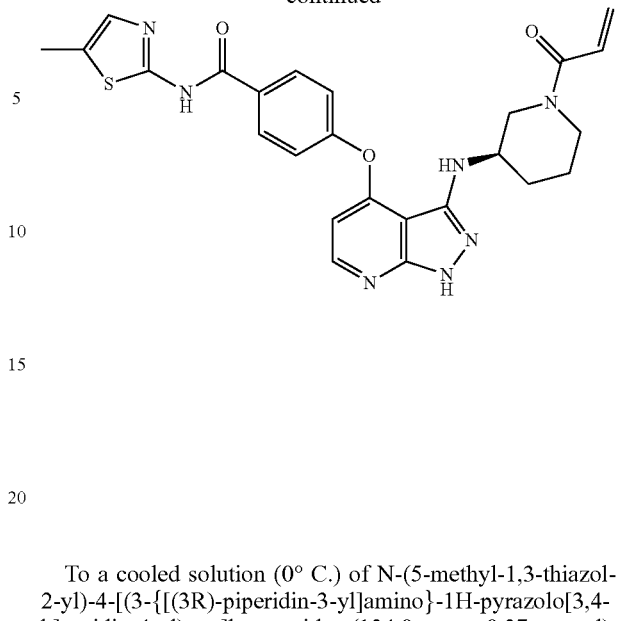

To a cooled solution (0° C.) of N-(5-methyl-1,3-thiazol-2-yl)-4-[(3-{[(3R)-piperidin-3-yl]amino}-1H-pyrazolo[3,4-b]pyridin-4-yl)oxy]benzamide (124.0 mg, 0.27 mmol), DIPEA (290 µL, 1.66 mmol) in DCM (6 ml) a solution of acryloyl chloride (23 µL, 0.27 mmol) in DCM (1.23 mL) was added. The mixture was stirred at 0° C. for 30 min the concentrated to give a yellow solid that was purified by flash chromatography (silica gel NH, 28 g, 4% MeOH in DCM). N-(5-Methyl-1,3-thiazol-2-yl)-4-[(3-{[(3R)-1-(prop-2-enoyl)piperidin-3-yl]amino)}-1H-pyrazolo[3,4-b]pyridin-4-yl)oxy]benzamide was obtained as a white solid (112.6 mg, Yield: 64%). LC-MS (ESI): m/z (M+1)⁺, 504.2. ¹H NMR (500 MHz, DMSO) δ 12.51 (br. s., 1H), 12.35-12.22 (m, 1H), 8.27-8.12 (m, 3H), 7.45-7.36 (m, 2H), 7.23 (s, 1H), 6.85-6.64 (m, 1H), 6.17 (d, J=5.38 Hz, 1H), 6.10-5.51 (m, 2H), 5.30-5.18 (m, 1H), 4.52-3.76 (m, 2H), 3.71-3.59 (m, 1H), 3.29-2.85 (m, 2H), 2.38 (s, 3H), 2.15-1.36 (m, 4H).

Example 141

4-[(3-{[(3R)-1-(but-2-ynoyl)piperidin-3-yl]amino}-1H-pyrazolo[3,4-b]pyridin-4-yl)oxy]-N-(5-methyl-1,3-thiazol-2-yl)benzamide (Compound ID 141)

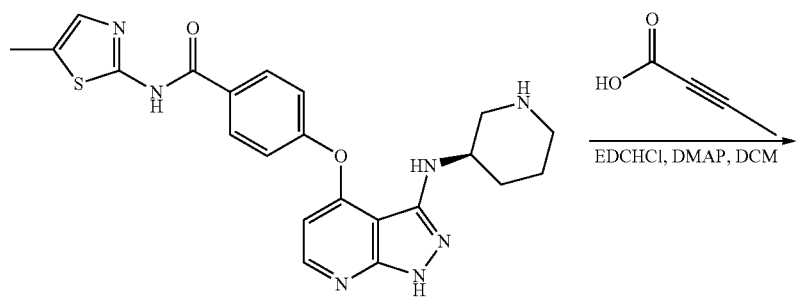

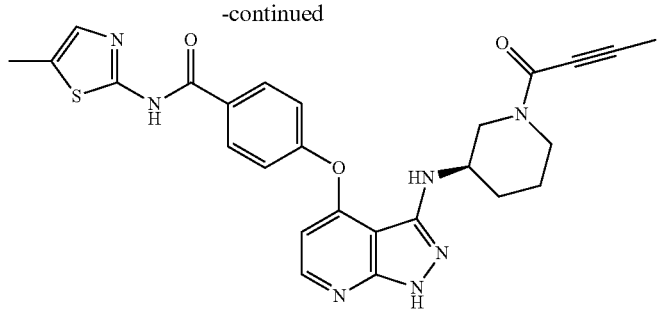

Under nitrogen a solution of N-(5-methyl-1,3-thiazol-2-yl)-4-[(3-{[(3R)-piperidin-3-yl]amino}-1H-pyrazolo[3,4-b]pyridin-4-yl)oxy]benzamide (118 mg, 0.26 mmol), 2-butynoic acid (23.0 mg, 0.27 mmol), EDC.HCl (106.0 mg, 0.54 mmol) and DMAP (3.4 mg, 0.03 mmol) in DCM (4 mL) was stirred at room temperature for 30 min. The mixture was concentrated to give a red crude product that was purified by flash chromatography (silica gel NH, 28 g, 4% MeOH in DCM). 4-[(3-{[(3R)-1-(But-2-ynoyl)piperidin-3-yl]amino}-1H-pyrazolo[3,4-b]pyridin-4-yl)oxy]-N-(5-methyl-1,3-thiazol-2-yl)benzamide was obtained as a white solid (104.7 mg, Yield: 58%). LC-MS (ESI): m/z (M+1)$^+$, 516.2. $^1$H NMR (500 MHz, DMSO) δ 12.50 (br. s., 1H), 12.33 (s, 1H), 8.27-8.17 (m, 3H), 7.44-7.39 (m, 2H), 7.23 (d, J=0.98 Hz, 1H), 6.20-6.14 (m, 1H), 5.20 (d, J=7.34 Hz, 1H), 4.24 (dd, J=12.72, 2.93 Hz, 1H), 3.81-3.65 (m, 2H), 3.46 (dd, J=12.72, 7.83 Hz, 1H), 3.16-3.06 (m, 1H), 2.38 (s, 3H), 2.06-1.97 (m, 1H), 1.79 (s, 3H), 1.77-1.58 (m, 2H), 1.52-1.35 (m, 1H).

Example 142

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3-thiazol-2-yl)benzamide (Compound ID 142)

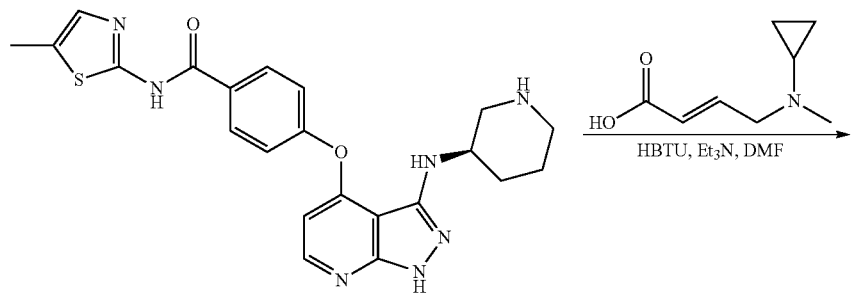

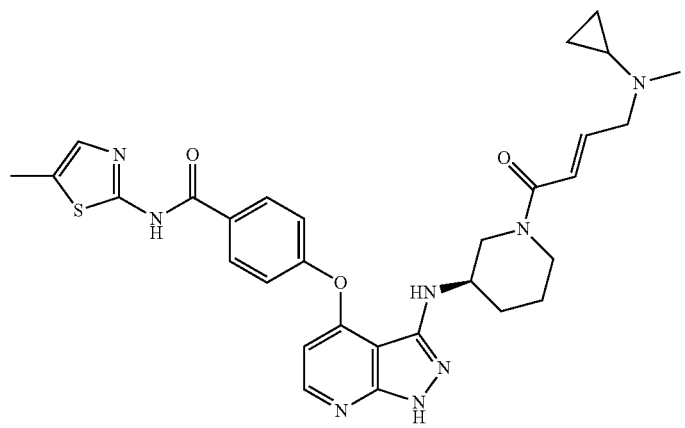

(2E)-4-[Cyclopropyl(methyl)amino]but-2-enoic acid (14.4 mg, 0.092 mmol), was dissolved in DMF (2 mL), HBTU (33.8 mg, 0.089 mmol) was added followed by Et₃N (26 μL, 0.186 mmol). The mixture turned red and was stirred for 20 min. N-(5-methyl-1,3-thiazol-2-yl)-4-[(3-{[(3R)-piperidin-3-yl]amino}-1H-pyrazolo[3,4-b]pyridin-4-yl)oxy] benzamide (40.0 mg, 0.089 mmol) was added and the mixture stirred for 2 hours. The solvent was evaporated and the crude purified first by flash chromatography (RP silica gel, 30 g, H₂O NH₄OH 0.1%/CH₃CN NH₄OH 0.1% from 95/5 to 60/40) then by flash chromatography (silica gel NH, 28 g, MeOH in DCM from 0 to 10%). 4-[(3-{[(3R)-1-[(2E)-4-[Cyclopropyl(methyl)amino]but-2-enoyl]piperidin-3-yl] amino}-1H-pyrazolo[3,4-b]pyridin-4-yl)oxy]-N-(5-methyl-1,3-thiazol-2-yl)benzamide was obtained as a white solid (51.0 mg, Yield: 49%). LC-MS (ESI): m/z (M+1)⁺, 587.2. ¹H NMR (500 MHz, DMSO) δ 12.50 (br. s., 1H), 12.38-12.23 (m, 1H), 8.26-8.17 (m, 3H), 7.45-7.36 (m, 2H), 7.25-7.21 (m, 1H), 6.59-6.46 (m, 2H), 6.21-6.15 (m, 1H), 5.14 (d, J=6.85 Hz, 1H), 3.94 (d, J=12.23 Hz, 1H), 3.85-3.61 (m, 2H), 3.53-3.40 (m, 1H), 3.28-2.92 (m, 3H), 2.38 (s, 3H), 2.09 (s, 3H), 2.02-1.93 (m, 1H), 1.80-1.55 (m, 3H), 1.52-1.37 (m, 1H), 0.44-0.19 (m, 4H).

Example 143

N-(4-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide (Compound ID 143)

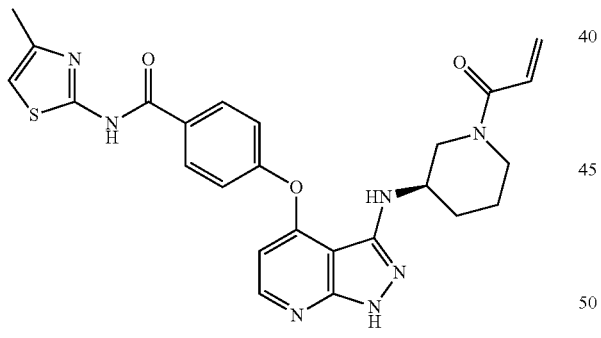

The compound was prepared following the method described for Ex. 140. LC-MS (ESI): m/z (M+1)⁺, 504.1. ¹H NMR (500 MHz, DMSO) δ 12.64 (br. s., 1H), 12.32 (br. s., 1H), 12.32 (br. s., 1H), 8.23 (d, J=8.31 Hz, 2H), 8.19 (d, J=5.38 Hz, 1H), 7.41 (d, J=8.30 Hz, 2H), 6.83 (s, 1H), 6.70 (dd, J=16.40, 10.50 Hz, 1H), 6.17 (d, J=5.38 Hz, 1H), 6.06 (d, J=16.40 Hz, 1H), 5.57 (d, J=10.50 Hz, 1H), 5.23 (d, J=6.85 Hz, 1H), 4.14 (d, J=12.72 Hz, 1H), 4.06-3.93 (m, 1H), 3.64 (br. s., 1H), 3.28-3.21 (m, 1H), 3.06-2.96 (m, 1H), 2.32 (s, 3H), 2.07-1.99 (m, 1H), 1.77-1.63 (m, 2H), 1.51-1.37 (m, 1H).

Example 144

(1r,4r)-N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]cyclohexane-1-carboxamide (Compound 144)

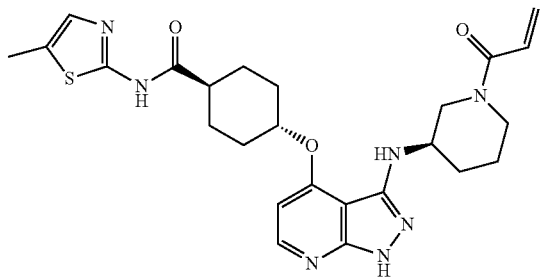 [SMILES: C=CC(=O)N1CCC[C@@H](Nc2n[nH]c3nccc(O[C@H]4CC[C@H](C(=O)Nc5ncc(C)s5)CC4)c23)C1]

1.28 Preparation of methyl (1r,4r)-4-({1-[(4-methoxyphenyl)methyl]-1H-pyrazolo[3,4-b]pyridin-4-yl}oxy)cyclohexane-1-carboxylate

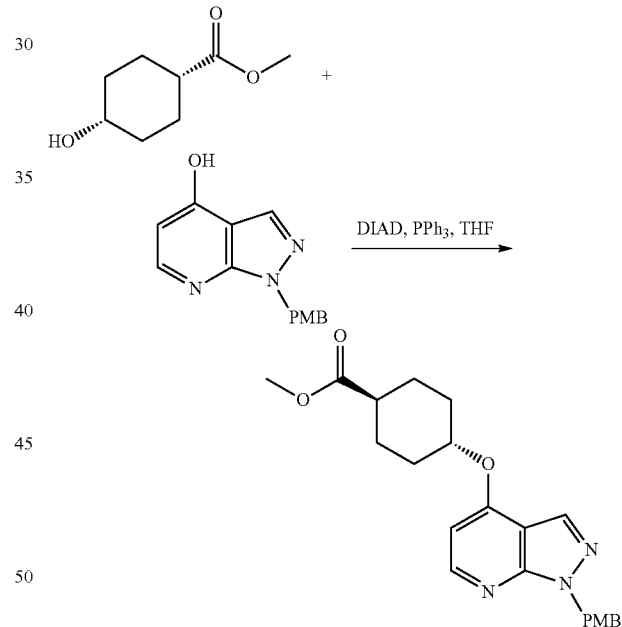

Diisopropyl azodicarboxylate (DIAD) (3.29 mL, 16.75 mmol) was added dropwise at room temperature to a solution of 1-[(4-methoxyphenyl)methyl]-1H-pyrazolo[3,4-b]pyridin-4-ol (2.375 g, 9.306 mmol), triphenylphosphine (PPh₃) (4.393 g, 16.75 mmol) and methyl (1s,4s)-4-hydroxycyclohexane-1-carboxylate (2.65 g, 16.75 mmol) in 85 mL of dry THF. After stirring overnight, more triphenylphosphine (PPh₃) (2.197 g, 8.37 mmol) and more Diisopropyl azodicarboxylate (DIAD) (1.65 mL, 8.37 mmol) were added and the mixture was stirred for further 3 hours. Then again more triphenylphosphine (PPh₃) (2.197 g, 8.37 mmol) and more Diisopropyl azodicarboxylate (DIAD) (1.65 mL, 8.37 mmol) were added and the mixture was stirred for further 3 hours. The solvent was evaporated and the crude product was purified by column chromatography (silica gel, 0% to 33% ethyl acetate in cyclohexane) to give crude methyl (1r,4r)-4-({1-[(4-methoxyphenyl)methyl]-1H-pyrazolo[3,4-b]pyridin-4-yl}oxy)cyclohexane-1-carboxylate (5.0 mmol) as colorless oil. LC-MS (ESI): m/z (M+1) 396.0.

1.29 Preparation of methyl (1r,4r)-4-{1H-pyrazolo[3,4-b]pyridin-4-yloxy}cyclohexane-1-carboxylate

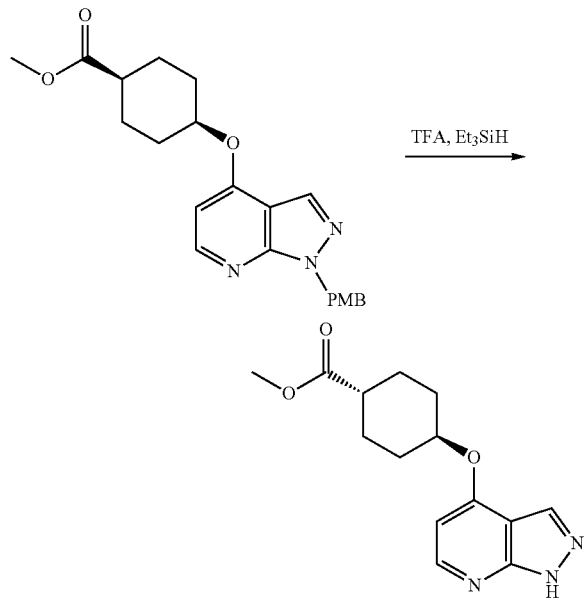

A solution of crude methyl (1r,4r)-4-({1-[(4-methoxyphenyl)methyl]-1H-pyrazolo[3,4-b]pyridin-4-yl})oxy)cyclohexane-1-carboxylate (4.75 mmol) in TFA (70 mL) and Et₃SiH (1.084 mL, 4.75 mmol) was heated to 60° C. for 2 hrs. The reaction mixture was concentrated to give the crude product which was purified by flash chromatography (silica gel, 5% to 40% ethyl acetate in cyclohexane) to afford (1r,4r)-4-{1H-pyrazolo[3,4-b]pyridin-4-yloxy}cyclohexane-1-carboxylate (1.746 g, 5.7 mmol) as a white solid. LC-MS (ESI): m/z (M+1) 276.0.

1.30 Preparation of methyl (1r,4r)-4-({3-iodo-1H-pyrazolo[3,4-b]pyridin-4-yl}oxy)cyclohexane-1-carboxylate

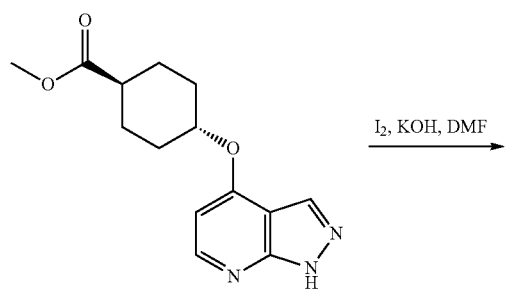

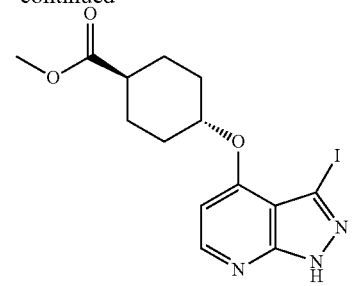

To a solution of methyl (1r,4r)-4-{1H-pyrazolo[3,4-b]pyridin-4-yloxy}cyclohexane-1-carboxylate (1.746 g, 5.7 mmol) in DMF (25 mL) was added KOH (0.960 g, 6.85 mmol) and I₂ (1.738 g, 6.85 mmol). The resulting mixture was heated under N₂ to 50° C. for 2.5 hr. After cooling to r.t., the reaction was quenched with 10% Na₂S₂O₃ solution until the dark color disappeared. The resulting suspension was diluted with water and extracted with ethyl acetate. The combined organic phases were dried over Na₂SO₄, filtered and concentrated to give crude (1r,4r)-4-({3-iodo-1H-pyrazolo[3,4-b]pyridin-4-yl}oxy)cyclohexane-1-carboxylate (5.7 mmol, quantitative yield) as a yellow oil. LC-MS (ESI): m/z (M+1) 401.8.

1.31 Preparation of methyl (1r,4r)-4-({3-iodo-1-[(4-methoxyphenyl)methyl]-1H-pyrazolo[3,4-b]pyridin-4-yl}oxy)cyclohexane-1-carboxylate

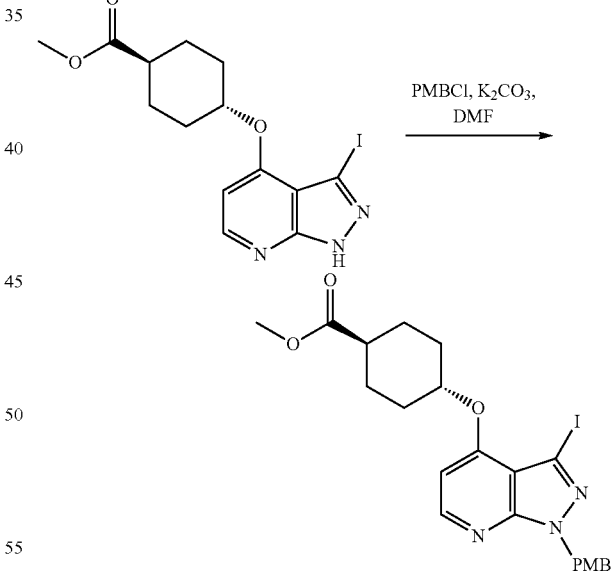

To a solution of crude methyl (1r,4r)-4-({3-iodo-1H-pyrazolo[3,4-b]pyridine-4-yl}oxy)cyclohexane-1-carboxylate (5.7 mmol) in DMF (12 mL) were added K₂CO₃ (1.575 g, 11.4 mmol) and PMBCl (0.927 mL, 6.84 mmol). After stirring at r.t. for 4 hours, more PMBCl (0.231 mL, 1.71 mmol) was added and the mixture was stirred at room temperature for a further 18 hours. The reaction mixture was diluted with water and extracted with EtOAc. The organic phase was dried over Na₂SO₄, filtered and concentrated to give the crude product which was purified by gradient flash chromatography (silica gel, 5% to 40% ethyl acetate in cyclohexane) to afford methyl (1r,4r)-4-({3-iodo-1-[(4-methoxyphenyl)methyl]-1H-pyrazolo[3,4-b]pyridin-4-yl}oxy)cyclohexane-1-carboxylate (1.79 g) as a grey oil. LC-MS (ESI): m/z (M+1) 521.9.

1.32 Preparation of tert-butyl (3R)-3-({1-[(4-methoxyphenyl)methyl]-4-{[(1r,4r)-4-(methoxycarbonyl)cyclohexyl]oxy}-1H-pyrazolo[3,4-b]pyridin-3-yl}amino)piperidine-1-carboxylate

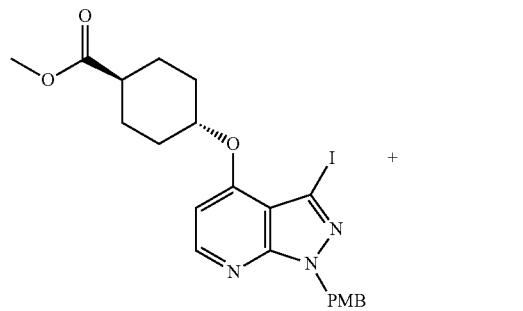

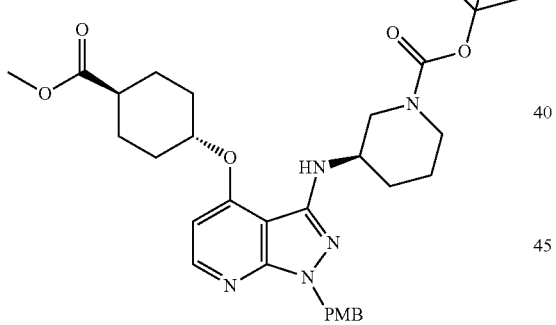

To a mixture of crude methyl (1r,4r)-4-({3-iodo-1-[(4-methoxyphenyl)methyl]-1H-pyrazolo[3,4-b]pyridin-4-yl})oxy)cyclohexane-1-carboxylate (1.79 g, 2.57 mmol), (R)-tert-butyl 3-aminopiperidine-1-carboxylate (0.925 g, 4.62 mmol) and Cs₂CO₃ (2.23 g, 6.86 mmol) in dioxane (18 mL) were added Pd₂(dba)₃ (94 mg, 0.10 mmol) and Xphos (298 mg, 0.515 mmol). The resulting mixture was purged with N₂ (for 10 min.) and then heated at 100° C. for 20 hours under N₂ atmosphere. After cooling to rt, the reaction was diluted with water and products were extracted with ethyl acetate). The organic phase was dried over Na₂SO₄, filtered and concentrated under vacuum. The residue was purified by gradient flash column chromatography (silica gel, 10 to 50% ethyl acetate in cyclohexane) to give tert-butyl (3R)-3-(({1-[(4-methoxyphenyl)methyl]-4-{[(1 r,4r)-4-(methoxycarbonyl)cyclohexyl]oxy}-1H-pyrazolo[3,4-b]pyridin-3-yl}) amino)piperidine-1-carboxylate (152 mg) as grey oil. LC-MS (ESI): m/z (M+1) 594.1.

1.33 Preparation of tert-butyl (3R)-3-({1-[(4-methoxyphenyl)methyl]-4-{[(1r,4r)-4-(methoxycarbonyl)cyclohexyl]oxy}-1H-pyrazolo[3,4-b]pyridin-3-yl}amino)piperidine-1-carboxylate

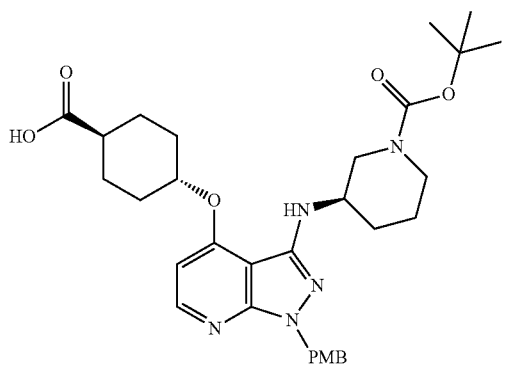

The intermediate was prepared following the method described for Ex. 137. LC-MS (ESI): m/z (M+1)⁺, 580.1.

1.34 Preparation of tert-butyl (3R)-3-({1-[(4-methoxyphenyl)methyl]-4-{[(1r,4r)-4-[(5-methyl-1,3-thiazol-2-yl)carbamoyl]cyclohexyl]oxy}-1H-pyrazolo[3,4-b]pyridin-3-yl}amino)piperidine-1-carboxylate

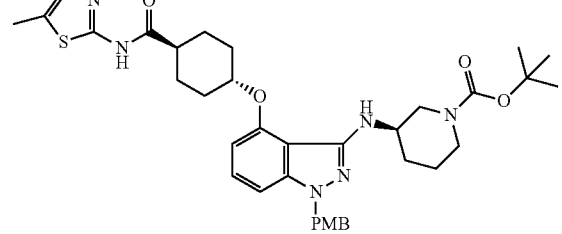

The intermediate was prepared following the method described for Ex. 137. LC-MS (ESI): m/z (M+1)⁺, 676.2.

1.35 Preparation of (1r,4r)-4-({1-[(4-methoxyphenyl)methyl]-3-{[(3R)piperidin-3-yl]amino}-1H-pyrazolo[3,4-b]pyridin-4-yl}oxy)-N-(5-methyl-1,3-thiazol-2 yl)cyclohexane-1-carboxamide; trifluoroacetic acid

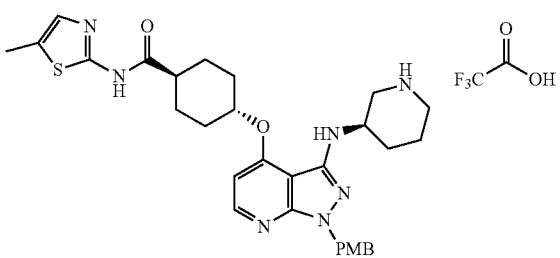

The intermediate was prepared following the method described for Ex. 137. LC-MS (ESI): m/z (M+1)+, 576.5.

1.36 Preparation of (1r,4r)-N-(5-methyl-1,3-thiazol-2-yl)-4-[(3-{[(3R)piperidin-3-yl]amino}-1H-pyrazolo[3,4-b]pyridin-4-yl)oxy]cyclohexane-1-carboxamide

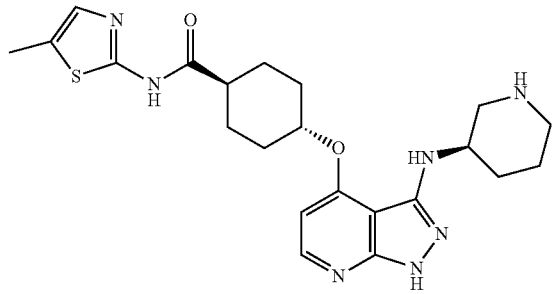 [SMILES: Cc1cnc(NC(=O)[C@H]2CC[C@H](Oc3ccnc4[nH]nc(N[C@@H]5CCCNC5)c34)CC2)s1]

The intermediate was prepared following the method described for Ex. 137. LC-MS (ESI): m/z (M+1)+, 456.1.
Compound 144 was prepared following the method described for Ex. 140. LC-MS (ESI): m/z (M+1)+, 510.2. $^1$H NMR (500 MHz, DMSO) δ 12.09-11.88 (m, 2H), 8.15 (d, J=5.38 Hz, 1H), 7.12 (s, 1H), 6.67-6.53 (m, 2H), 6.06 (d, J=16.63 Hz, 1H), 5.52 (d, J=10.27 Hz, 1H), 4.87-4.72 (m, 1H), 4.65-4.49 (m, 1H), 3.90 (d, J=12.72 Hz, 1H), 3.70 (br. s., 1H), 3.63-3.22 (m, 3H), 2.59-2.45 (m, 1H), 2.33 (s, 3H), 2.24-2.08 (m, 2H), 2.00-1.86 (m, 3H), 1.85-1.72 (m, 1H), 1.72-1.59 (m, 3H), 1.57-1.39 (m, 3H).

Example 145

N-{5-methyl-4H,5H,6H,7H-[1,3]thiazolo[4,5-c]pyridin-2-yl}-4-[(3-{[(3R)-1-(prop-2-enoyl)piperidin-3-yl]amino}-1H-pyrazolo[3,4-b]pyridin-4-yl)oxy]benzamide (Compound 145)

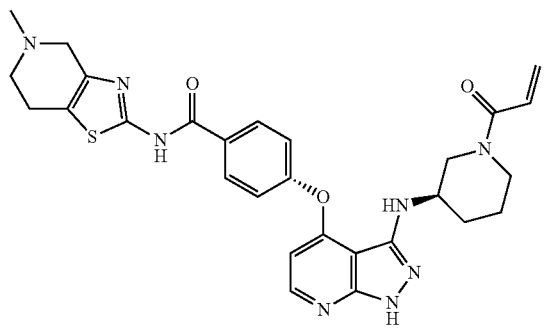

The compound was prepared following the method described for Ex. 140. LC-MS (ESI): m/z (M+1)+, 559.1. $^1$H NMR (500 MHz, DMSO) δ 12.58 (br. s., 1H), 12.32 (br. s., 1H), 8.26-8.16 (m, 3H), 7.41 (d, J=7.83 Hz, 2H), 6.70 (dd, J=16.60, 10.30 Hz, 1H), 6.17 (d, J=5.38 Hz, 1H), 6.06 (d, J=16.60 Hz, 1H), 5.57 (d, J=10.30 Hz, 1H), 5.23 (d, J=6.85 Hz, 1H), 4.14 (d, J=12.72 Hz, 1H), 4.04-3.93 (m, 1H), 3.63 (br. s., 1H), 3.53 (s, 2H), 3.35-3.22 (m, 1H), 3.00 (t, J=10.52 Hz, 1H), 2.76-2.66 (m, 4H), 2.39 (s, 3H), 2.07-1.97 (m, 1H), 1.76-1.60 (m, 2H), 1.50-1.37 (m, 1H).

Example 146

N-(dimethyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide (Compound ID 146)

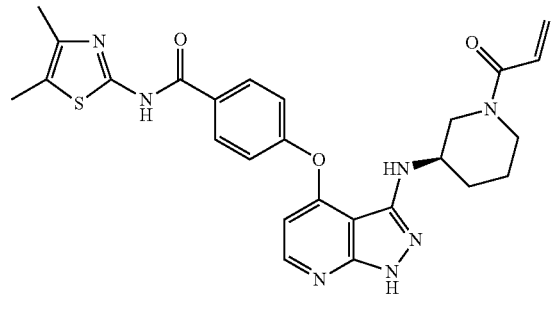 [SMILES: C=CC(=O)N1CCC[C@@H](Nc2n[nH]c3nccc(Oc4ccc(C(=O)Nc5nc(C)c(C)s5)cc4)c23)C1]

1.37 Preparation of tert-butyl (3R)-3-[(4-{4-[(dimethyl-1,3-thiazol-2-yl)carbamoyl]phenoxy}-1-[(4-methoxyphenyl)methyl]-1H-pyrazolo[3,4-b]pyridin-3-yl)amino]piperidine-1-carboxylate

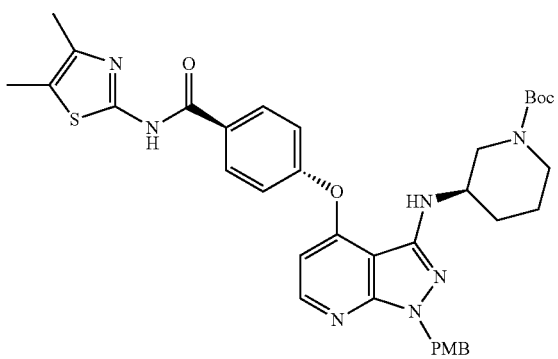

The intermediate was prepared following the method described for Ex. 137. LC-MS (ESI): m/z (M+1)+, 684.7.

1.38 (3R)-3-[(4-{4-[(dimethyl-1,3-thiazol-2-yl)carbamoyl]phenoxy}-1-[(4-methoxyphenyl)methyl]-1H-pyrazolo[3,4-b]pyridin-3-yl)amino]piperidin-1-ium trifluoroacetate

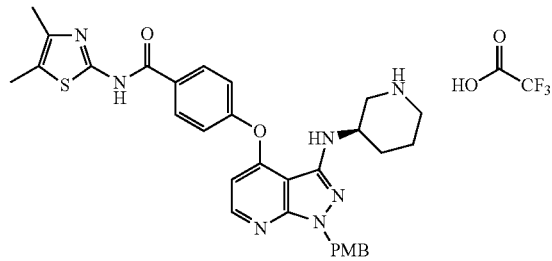

The intermediate was prepared following the method described for Ex. 137. LC-MS (ESI): m/z (M+1)+, 584.2.

1.39 N-(dimethyl-1,3-thiazol-2-yl)-4-[(3-{[(3R)-piperidin-3-yl]amino}-1H-pyrazolo[3,4-b]pyridin-4-yl)oxy]benzamide

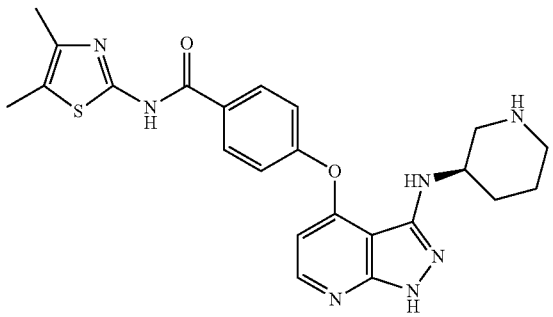 [SMILES: Cc1nc(NC(=O)c2ccc(Oc3ccnc4[nH]nc(N[C@@H]5CCCNC5)c34)cc2)sc1C]

The intermediate was prepared following the method described for Ex. 137. LC-MS (ESI): m/z (M+1)⁺, 464.0.

Compound 146 was prepared following the method described for Ex. 140. LC-MS (ESI): m/z (M+1)⁺, 518.2. ¹H NMR (500 MHz, DMSO) δ 12.49 (br. s, 1H), 12.27 (br. s, 1H), 8.24-8.17 (m, 3H), 7.40 (d, J=7.83 Hz, 2H), 6.86-6.64 (m, 1H), 6.16 (d, J=5.38 Hz, 1H), 6.06 (d, J=16.63 Hz, 1H), 5.69-5.53 (m, 1H), 5.23 (d, J=7.34 Hz, 1H), 4.51-4.09 (m, 1H), 4.07-3.78 (m, 1H), 3.71-3.58 (m, 1H), 3.29-2.85 (m, 2H), 2.27 (s, 3H), 2.21 (s, 3H), 1.99 (s, 4H).

Example 147

1-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-3-(propan-2-yl)urea (Compound ID 147)

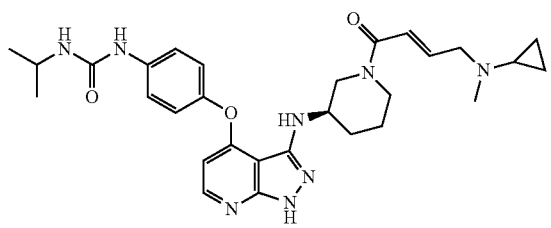 [SMILES: CC(C)NC(=O)Nc1ccc(Oc2ccnc3[nH]nc(N[C@@H]4CCCN(C(=O)/C=C/CN(C)C5CC5)C4)c23)cc1]

1.40 Preparation of tert-butyl (3R)-3-({1-[(4-methoxyphenyl)methyl]-4-(4-{[(propan-2-yl)carbamoyl]amino}phenoxy)-1H-pyrazolo[3,4-b]pyridin-3-yl}amino)piperidine-1-carboxylate

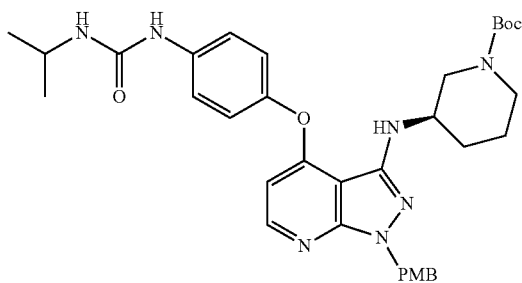

The intermediate was prepared following the method described for Ex. 86. LC-MS (ESI): m/z (M+1)⁺, 630.2

1.41 Preparation of (3R)-3-({1-[(4-methoxyphenyl)methyl]-4-(4-{[(propan-2-yl)carbamoyl]amino}phenoxy)-1H-pyrazolo[3,4-b]pyridin-3-yl}amino)piperidin-1-ium trifluoroacetate

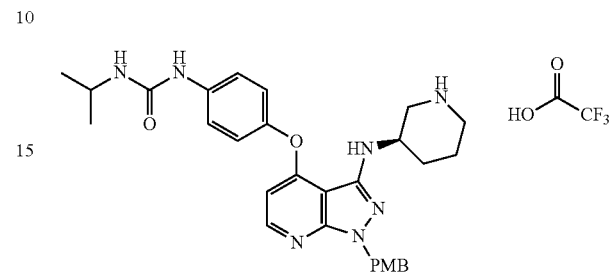

The intermediate was prepared following the method described for Ex. 86. LC-MS (ESI): m/z (M+1)⁺, 530.2.

1.42 Preparation of 1-{4-[(3-{[(3R)-piperidin-3-yl]amino}-1H-pyrazolo[3,4-b]pyridin-4-yl)oxy]phenyl}-3-(propan-2-yl)urea

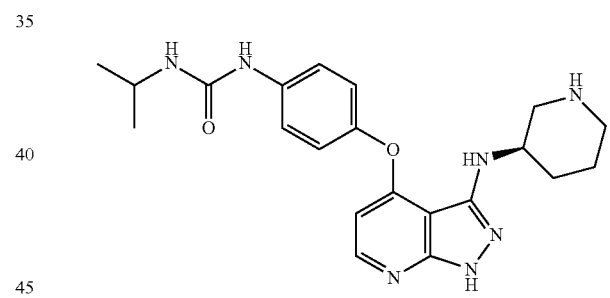

The intermediate was prepared following the method described for Ex. 86. LC-MS (ESI): m/z (M+1)⁺, 410.1.

The target compound was prepared following the method described in example 136 affording 27 mg, 56% yield of 1-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-3-(propan-2-yl)urea as a white solid LC-MS (ESI): m/z (M+1)⁺, 547.3. ¹H NMR (500 MHz, DMSO) δ 12.21 (br. s., 1H), 8.43 (s, 1H), 8.11 (d, J=5.40 Hz, 1H), 7.49 (d, J=8.80 Hz, 2H), 7.12 (d, J=8.80 Hz, 2H), 6.63-6.45 (m, 1H), 6.44-6.32 (m, 1H), 6.02 (d, J=7.34 Hz, 1H), 5.96 (d, J=5.40 Hz, 1H), 5.24-5.04 (m, 1H), 3.97 (d, J=12.23 Hz, 1H), 3.86-3.60 (m, 3H), 3.44 (dd, J=12.23, 7.83 Hz, 1H), 3.28-2.90 (m, 3H), 2.08 (s, 3H), 2.05-1.97 (m, 1H), 1.82-1.54 (m, 3H), 1.51-1.38 (m, 1H), 1.10 (d, J=6.36 Hz, 6H), 0.46-0.17 (m, 4H).

Example 148

1-[(3R)-3-({4-[3-(5-methyl-1,3-thiazol-2-yl)phenoxy]-1H-pyrazolo[3,4-b]pyridin-3-yl}amino)piperidin-1-yl]prop-2-en-1-one (Compound ID 148)

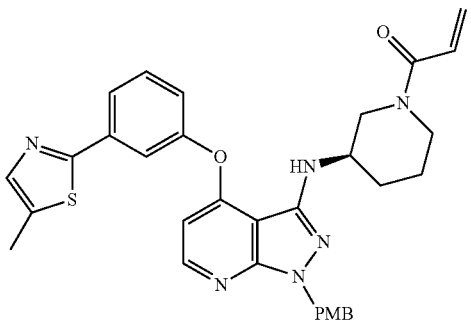

1.43 Preparation of 3-(5-methyl-1,3-thiazol-2-yl)phenol

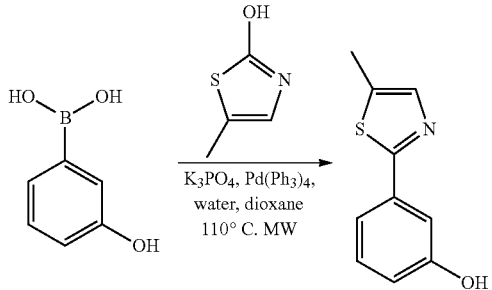

(3-Hydroxyphenyl) boronic acid (170 mg, 1.235 mmol), 2-bromo-5-methyl-1,3-thiazole (200 mg, 1.123 mmol), $K_3PO_4$ (481 mg, 2.246 mmol) and $Pd(Ph_3)_4$ (131 mg, 0.112 mmol) in a mixture 3:1 of dioxane/water (12 mL:4 mL) was heated in MW at 110° C. for 30 min. The mixture was concentrated under vacuum and NaOH aq solution 1 M and DCM were added. The water was extracted several times with more DCM. The layers were separated. To the aqueous phase HCl 1M aqueous solution was added and the phase was extracted again with more DCM. The combined organics were filtered though a phase separator tube and concentrated in vacuo to give the desired product (190 mg, 0.99 mmol, Yield=75%). LC-MS (ESI): m/z (M+1)$^+$, 191.9.

1.44 Preparation of 2-[3-({3-bromo-1-[(4-methoxyphenyl)methyl]-1H-pyrazolo[3,4-b]pyridin-4-yl}oxy)phenyl]-5-methyl-1,3-thiazole

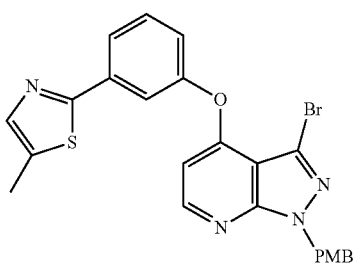

The intermediate was prepared following the method described for Ex. 86. LC-MS (ESI): m/z (M+1)$^+$, 506.9.

1.45 Preparation of tert-butyl (3R)-3-({1-[(4-methoxyphenyl)methyl]-4-[3-(5-methyl-1,3-thiazol-2-yl)phenoxy]-1H-pyrazolo[3,4-b]pyridin-3-yl}amino)piperidine-1-carboxylate

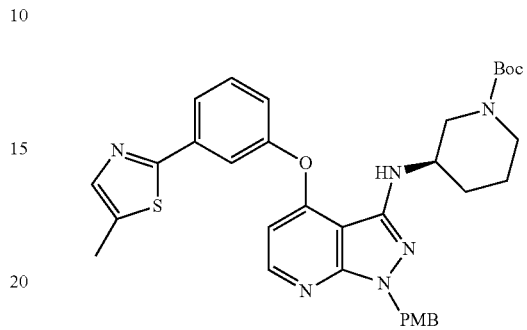

The intermediate was prepared following the method described for Ex. 86. LC-MS (ESI): m/z (M+1)$^+$, 627.1.

1.46 Preparation of 3R)—N-{4-[3-(5-methyl-1,3-thiazol-2-yl)phenoxy]-1H-pyrazolo[3,4-b]pyridine-3-yl}piperidin-3-amine

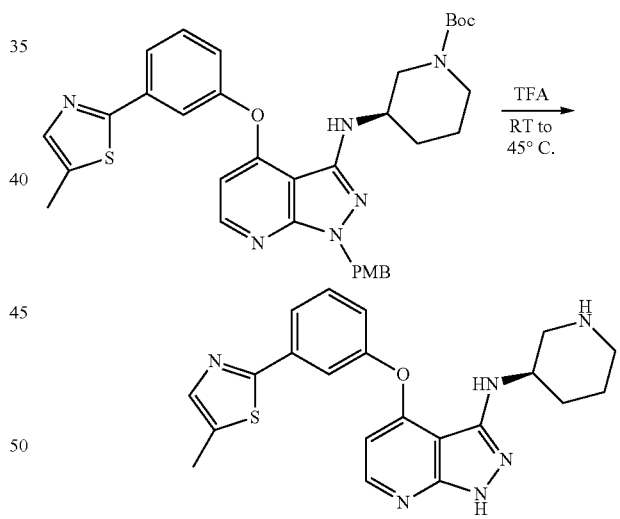

tert-Butyl (3R)-3-({1-[(4-methoxyphenyl)methyl]-4-[3-(5-methyl-1,3-thiazol-2-yl)phenoxy]-1H-pyrazolo[3,4-b]pyridin-3-yl}amino)piperidine-1-carboxylate (530 mg, 0.845 mmol) was dissolved in TFA (10 mL) and the reaction was left stirring at room temperature overnight; then it was heated at 45° C. for 8 hrs. TFA was evaporated and the residue was filtered through an SCX cartridge eluting with $NH_3$ 2 M in MeOH solution. The filtrate was concentrated in vacuo to give the desired product (140 mg). LC-MS (ESI): m/z (M+1)$^+$, 407.01.

Compound 148 was prepared following the method described for Ex. 140. LC-MS (ESI): m/z (M+1)$^+$, 461.0.

Example 149

N-(5-methyl-1,3-thiazol-2-yl)-3-[(3-{[(3R)-1-(prop-2-enoyl)piperidin-3-yl]amino}-1H-pyrazolo[3,4-b]pyridin-4-yl)oxy]benzamide (Compound ID 149)

1.47 Preparation of tert-butyl 3-({1-[(4-methoxyphenyl)methyl]-4-{3-[(5-methyl-1,3-thiazol-2-yl)carbamoyl]phenoxy}-1H-pyrazolo[3,4-b]pyridin-3-yl}amino)piperidine-1-carboxylate

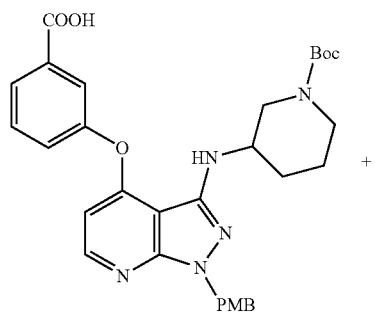

+

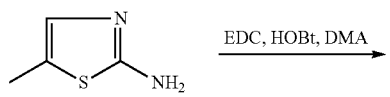

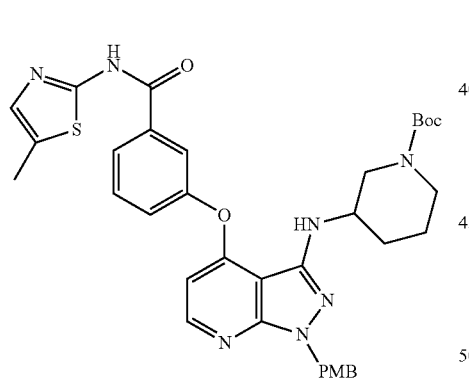

A solution of 3-{[3-({1-[(tert-butoxy)carbonyl]piperidin-3-yl}amino)-1-[(4-methoxyphenyl)methyl]-1H-pyrazolo[3,4-b]pyridin-4-yl]oxy}benzoic acid (503 mg, 0.87 mmol), 5-methyl-1,3-thiazol-2-amine (196 mg, 1.74 mmol), N-(3-dimethylaminopropyl)-N'-ethylcarbodiimide hydrochloride (340 mg, 1.74 mmol) and 1-hydroxybenzotriazole (120 mg, 0.87 mmol) in N,N-Dimethylacetamide (3 mL) was stirred at 50° C. for 2 hours. The solvent was evaporated and the residue was purified by gradient flash-chromatography (silica, 20% to 80% of ethyl acetate in cyclohexane) to afford tert-butyl 3-({1-[(4-methoxyphenyl)methyl]-4-{3-[(5-methyl-1,3-thiazol-2-yl)carbamoyl]phenoxy}-1H-pyrazolo[3,4-b]pyridin-3-yl}amino)piperidine-1-carboxylate (334 mg, 57% yield). LC-MS (ESI): m/z (M+1)$^+$, 670.2

1.48 Preparation of 3-({1-[(4-methoxyphenyl)methyl]-3-[(piperidin-3-yl)amino]-1H-pyrazolo[3,4-b]pyridine-4 yl}oxy)-N-(5-methyl-1,3-thiazol-2 yl)benzamide trifluoroacetate

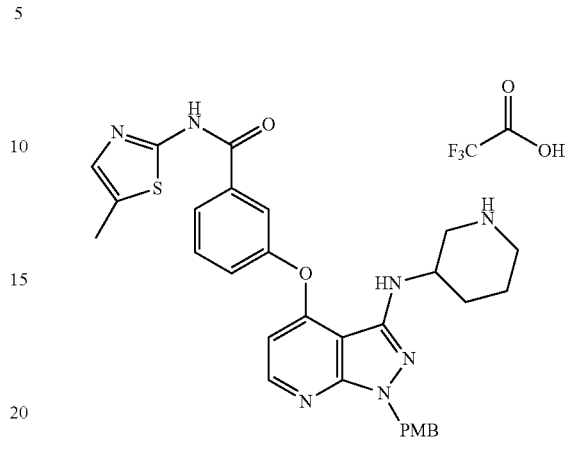

The intermediate was prepared following the method described for Ex. 86. LC-MS (ESI): m/z (M+1)$^+$, 570.1 (free base).

1.49 Preparation of N-(5-methyl-1,3-thiazol-2-yl)-3-[(3-{[(3R)-piperidin-3-yl]amino}-1H-pyrazolo[3,4-b]pyridin-4-yl)oxy]benzamide

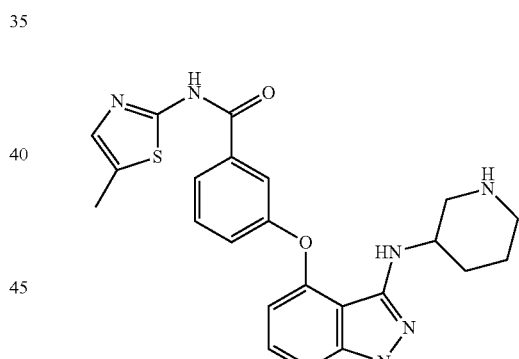

The intermediate was prepared following the method described for Ex. 86. LC-MS (ESI): m/z (M+1)$^+$, 450.1.

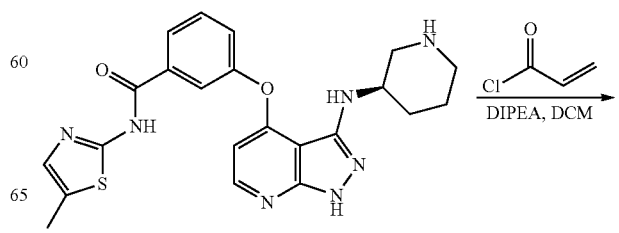

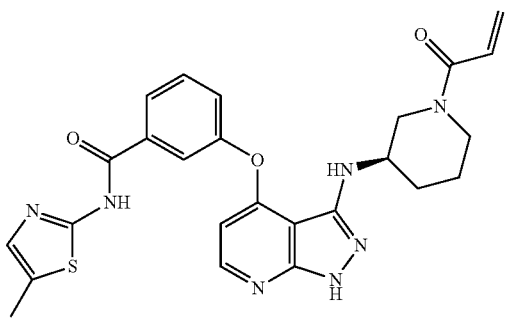

N-(5-methyl-1,3-thiazol-2-yl)-3-[(3-{[(3R)-piperidin-3-yl]amino}-1H-pyrazolo[3,4-b]pyridin-4-yl)oxy]benzamide (70 mg, 0.16 mmol) and N,N-Diisopropylethylamine (139 μL, 0.8 mmol) were dissolved in dichloromethane (3 mL). The reaction was cooled to 0° C. then a solution of acryloyl chloride (13 μL, 0.16 mmol) was added dropwise. The mixture was stirred for 10 minutes then it was concentrated and purified by gradient flash-chromatography (silica-NH, 0% to 10% of methanol in dichloromethane) to afford N-(5-methyl-1,3-thiazol-2-yl)-3-[(3-{[(3R)-1-(prop-2-enoyl)piperidin-3-yl]amino}-1H-pyrazolo[3,4-b]pyridin-4-yl)oxy]benzamide (16.2 mg, 20% yield) as a yellow solid. LC-MS (ESI): m/z (M+1)+, 504.0. $^1$H NMR (500 MHz, DMSO-d6) d ppm 12.55 (br. s., 1H), 12.33-12.20 (m, 1H), 8.17 (d, J=5.38 Hz, 1H), 8.05 (d, J=7.83 Hz, 1H), 8.03-7.98 (m, 1H), 7.68 (t, J=8.07 Hz, 1H), 7.56 (d, J=7.83 Hz, 1H), 7.24-7.20 (m, 1H), 6.85-6.67 (m, 1H), 6.10 (d, J=5.38 Hz, 1H), 6.10-6.00 (m, 1H), 5.67-5.53 (m, 1H), 4.56-4.10 (m, 1H), 4.07-3.77 (m, 1H), 3.73-3.57 (m, 1H), 3.27-2.83 (m, 2H), 2.37 (s, 3H), 2.13-1.33 (m, 4H).

Example 150

(2E)-4-[cyclopropyl(methyl)amino]-1-[(3R)-3-({4-[3-(5-methyl-1,3-thiazol-2-yl)phenoxy]-1H-pyrazolo[3,4-b]pyridin-3-yl}amino)piperidin-1-yl]but-2-en-1-one (Compound ID 150)

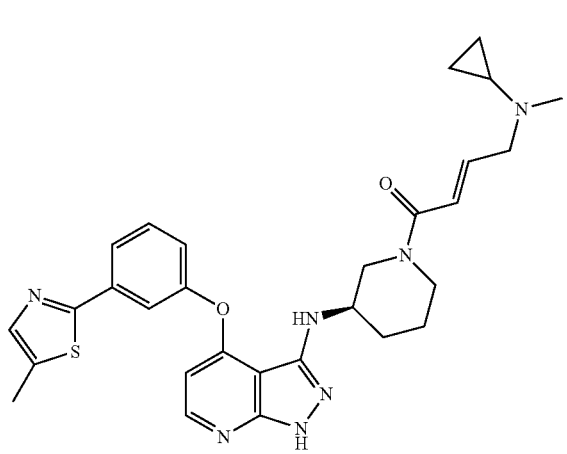 [SMILES: Cc1cnc(-c2cccc(Oc3ccnc4[nH]nc(N[C@@H]5CCCN(C(=O)/C=C/CN(C)C6CC6)C5)c34)c2)s1]

The compound was prepared following the method described for Ex. 142. LC-MS (ESI): m/z (M+1)+, 544.4.

Example 151

(3R)—N-[4-(2-Methyl-4-phenoxyphenoxy)-1H-pyrazolo[3,4-b]pyridin-3-yl]piperidin-3-amine (Compound ID 151)

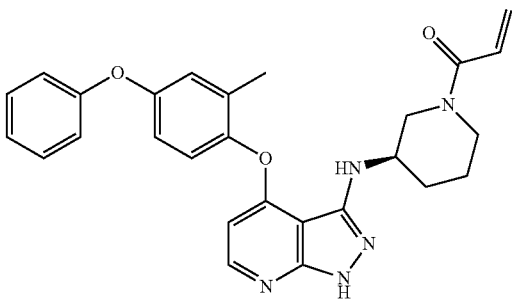 [SMILES: C=CC(=O)N1CCC[C@@H](Nc2n[nH]c3nccc(Oc4ccc(Oc5ccccc5)cc4C)c23)C1]

The compound was prepared following the method described for Ex. 148. LC-MS (ESI): m/z (M+1)+, 515.96. $^1$H NMR (500 MHz, DMSO) δ 12.35-12.02 (m, 1H), 8.12 (d, J=5.38 Hz, 1H), 7.42 (t, J=8.07 Hz, 2H), 7.29-7.22 (m, 1H), 7.16 (t, J=7.34 Hz, 1H), 7.09 (d, J=2.93 Hz, 1H), 7.06 (d, J=7.34 Hz, 2H), 6.96 (dd, J=8.56, 2.69 Hz, 1H), 6.86-6.59 (m, 1H), 6.03 (d, J=16.63 Hz, 1H), 5.93 (d, J=5.38 Hz, 1H), 5.68-5.50 (m, 1H), 5.32-5.20 (m, 1H), 4.45-4.06 (m, 1H), 4.00-3.77 (m, 1H), 3.74-3.61 (m, 1H), 3.32-2.93 (m, 2H), 2.10 (s, 3H), 2.06-1.40 (m, 4H).

Example 152

(1r,4r)-4-[(3-{[(3R)-1-[(2E)-4-[Cyclopropyl(methyl)amino]but-2-enoyl]piperidin-3-yl]amino}-1H-pyrazolo[3,4-b]pyridin-4-yl)oxy]-N-(5-methyl-1,3-thiazol-2-yl)cyclohexane-1-carboxamide (Compound 152)

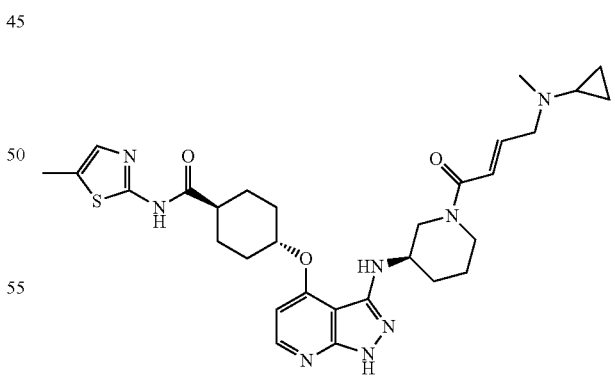

The compound was prepared following the method described for Ex. 142. LC-MS (ESI): m/z (M+1)+, 593.1. $^1$H NMR (500 MHz, DMSO) δ 12.13-11.80 (m, 2H), 8.14 (d, J=5.38 Hz, 1H), 7.15-7.10 (m, 1H), 6.58 (d, J=5.87 Hz, 1H), 6.73-6.15 (m, 2H), 4.85-4.72 (m, 1H), 4.66-4.51 (m, 1H), 3.83-3.58 (m, 4H), 3.57-2.75 (m, 4H), 2.33 (s, 3H), 2.00 (s, 3H), 2.25-1.46 (m, 13H), 0.51-0.11 (m, 4H).

Example 153

1-[(3R)-3-{[4-(3-methyl-4-phenoxyphenoxy)-1H-pyrazolo[3,4-b]pyridin-3-yl]amino}piperidin-1-yl]prop-2-en-1-one (Compound ID 153)

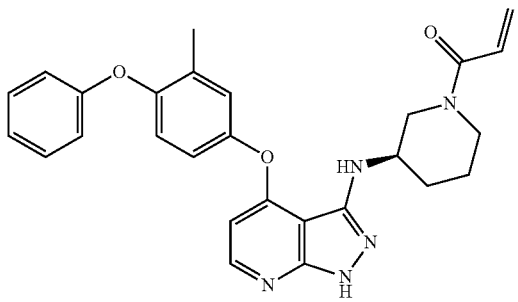 [SMILES: C=CC(=O)N1CCC[C@@H](Nc2n[nH]c3nccc(Oc4ccc(Oc5ccccc5)c(C)c4)c23)C1]

The compound was prepared following the method described for example 148. LC-MS (ESI): m/z (M+1)+, 470.50. $^1$H NMR (500 MHz, DMSO) δ 12.35-12.02 (m, 1H), 8.16 (d, J=5.38 Hz, 1H), 7.41-7.36 (m, 2H), 7.30-7.26 (m, 1H), 7.14 (d, J=8.80 Hz, 1H), 7.10 (t, J=7.34 Hz, 1H), 7.04 (d, J=8.80 Hz, 1H), 6.95 (d, J=7.83 Hz, 2H), 6.87-6.64 (m, 1H), 6.10 (d, J=5.38 Hz, 1H), 6.09-6.01 (m, 1H), 5.67-5.54 (m, 1H), 5.22 (d, J=7.34 Hz, 1H), 4.53-4.10 (m, 1H), 4.06-3.79 (m, 1H), 3.71-3.57 (m, 1H), 3.35-2.83 (m, 2H), 2.20 (s, 3H), 2.12-1.39 (m, 4H).

Example 154

1-[(3R)-3-[(4-{4-[4-(trifluoromethyl)-1H-imidazol-2-yl]phenoxy}-1H-pyrazolo[3,4-b]pyridin-3-yl)amino]piperidin-1-yl]prop-2-en-1-one (Compound ID 154)

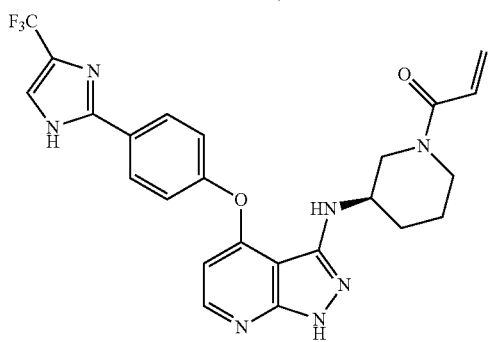 [SMILES: C=CC(=O)N1CCC[C@@H](Nc2n[nH]c3nccc(Oc4ccc(-c5nc(C(F)(F)F)c[nH]5)cc4)c23)C1]

1.50 Preparation of tert-butyl 3-({4-[4-(hydroxymethyl)phenoxy]-1-[(4-methoxyphenyl)methyl]-1H-pyrazolo[3,4-b]pyridin-3-yl}amino)piperidine-1-carboxylate

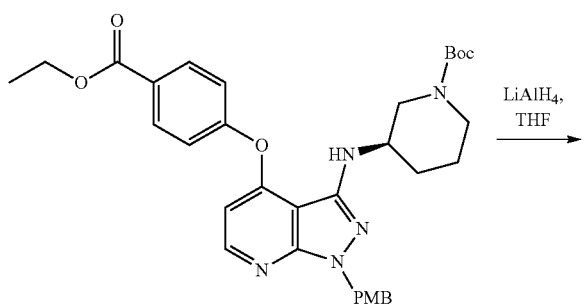

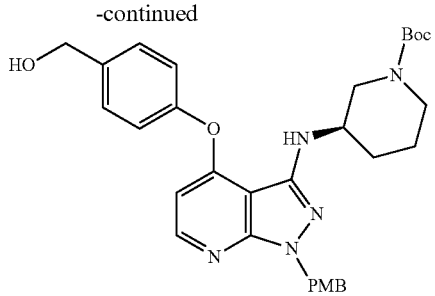

LiAlH$_4$ 2 M solution in THF (0.21 mL) was added dropwise at −10° C. to a solution of tert-butyl 3-({4-[4-(ethoxycarbonyl)phenoxy]-1-[(4-methoxyphenyl)methyl]-1H-pyrazolo[3,4-b]pyridin-3-yl}amino) piperidine-1-carboxylate (267 mg) in 2 mL of THF. After 15 min Na$_2$SO$_4$×10 H$_2$O was added until the freezing ended. The solid was filtered out and washed with DCM and the combined organic layers were concentrated in vacuo to give the desired product (232 mg, 0.3797 mmol, Y=86%). LC-MS (ESI): m/z (M+1)+, 560.1

1.51 Preparation of tert-butyl (3R)-3-{[4-(4-formylphenoxy)-1-[(4-methoxyphenyl)methyl]-1H-pyrazolo[3,4-b]pyridin-3-yl]amino}piperidine-1-carboxylate

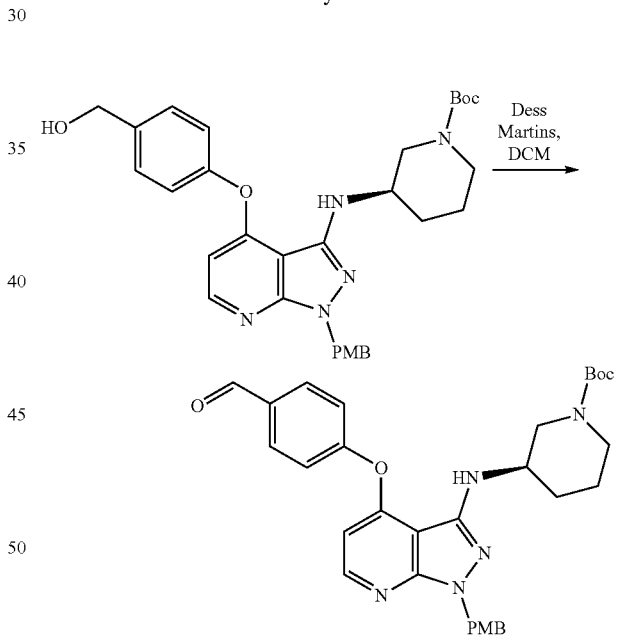

tert-Butyl (3R)-3-({4-[4-(hydroxymethyl)phenoxy]-1-[(4-methoxyphenyl)methyl]-1H-pyrazolo[3,4-b]pyridin-3-yl}amino)piperidine-1-carboxylate (231 mg, 0.412 mmol) was dissolved in DCM (1 mL). Dess Martin Periodinane (270 mg) was added and the reaction was stirred at room temperature for 1 hr. Saturated solutions of NaHCO$_3$/Na$_2$S$_2$O$_3$ 1:1 v/v were added and the reaction was left on stirring for 30 minutes at room temperature. The phases were separated and the organic layer was washed with brine, dried over Na$_2$SO$_4$, filtered and concentrated in vacuo to give the desired aldehyde (270 mg, 0.3 mmol, Y=73%). LC-MS (ESI): m/z (M+1)+, 558.1

1.52 Preparation of tert-butyl (3R)-3-({1-[(4-methoxyphenyl)methyl]-4-{4-[4-(trifluoromethyl)-1H-imidazol-2-yl]phenoxy}-1H-pyrazolo[3,4-b]pyridin-3-yl}amino)piperidine-1-carboxylate

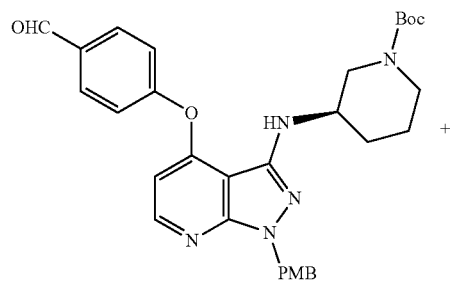

+

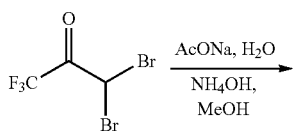

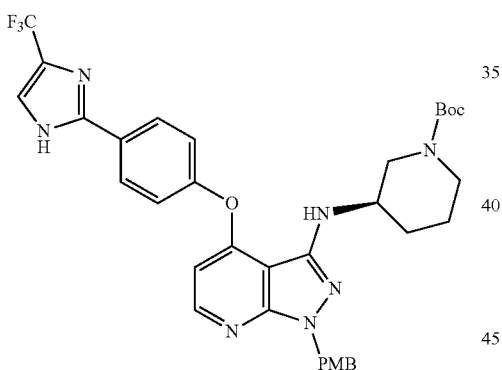

To a solution of AcONa (55 mg, 0.672 mmol) in H₂O (0.3 mL) was added 3,3-dibromo-1,1,1-trifluoropropan-2-one (89 mg, 0.33 mmol) and the mixture was stirred at 100° C. for 30 min. tert-butyl (3R)-3-{[4-(4-formylphenoxy)-1-[(4-methoxyphenyl)methyl]-1H-pyrazolo[3,4-b]pyridin-3-yl]amino}piperidine-1-carboxylate (270 mg, 0.3 mmol) in NH₄OH (0.3 mL) and MeOH (1.8 mL) was added and the mixture was stirred at room temperature overnight. A hot solution of AcONa (60 mg) in 0.3 mL of H₂O and 3,3-dibromo-1,1,1-trifluoropropan-2-one (90 mg) were added to the reaction and the mixture was stirred at room temperature for 72 hr. The reaction was concentrated to give 592 mg of an amorphous solid. Polymer supported trisamina (131 mg) in 2 mL of DCM was added to the solid previously obtained and the mixture was stirred overnight at room temperature. Then it was filtered and the residue purified by silica gel flash chromatography (DCM/MeOH 95/5) to give the desired product (138 mg, 0.064 mmol, Yield: 21%). LC-MS (ESI): m/z (M+1)⁺, 664.2.

1.53 Preparation of (3R)—N-(4-{4-[4-(trifluoromethyl)-1H-imidazol-2-yl]phenoxy}-1H-pyrazolo[3,4-b]pyridin-3-yl)piperidin-3-amine

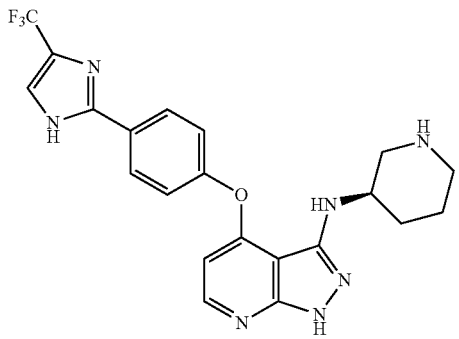 [SMILES: FC(F)(F)c1c[nH]c(-c2ccc(Oc3ccnc4[nH]nc(N[C@@H]5CCCNC5)c34)cc2)n1]

The intermediate was prepared following the method described for Ex. 86. LC-MS (ESI): m/z (M+1)⁺, 444.4.

Compound 154 was prepared following the method described for Ex. 140. LC-MS (ESI): m/z (M+1)⁺, 498.2. ¹H NMR (500 MHz, Acetone) δ 12.39 (br. s., 1H), 11.18-11.62 (m, 1H), 8.06-8.25 (m, 3H), 7.79 (s, 1H), 7.31-7.45 (m, 2H), 6.58-6.87 (m, 1H), 6.06-6.30 (m, 2H), 5.43-5.68 (m, 1H), 4.88-5.28 (m, 1H), 3.14-4.31 (m, 5H), 1.47-2.14 (m, 4H).

Example 155

1-[(3R)-3-[(4-{4-[4-(trifluoromethyl)pyridin-2-yl]phenoxy}-1H-pyrazolo[3,4-b]pyridin-3-yl)amino]piperidin-1-yl]prop-2-en-1-one (Compound ID 155)

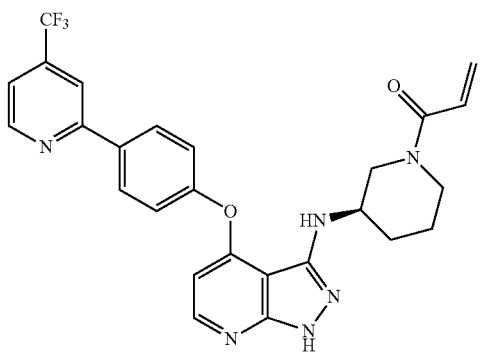 [SMILES: C=CC(=O)N1CCC[C@@H](Nc2n[nH]c3nccc(Oc4ccc(-c5cc(C(F)(F)F)ccn5)cc4)c23)C1]

1.54 Preparation of (trifluoromethyl)pyridin-2-yl]phenol

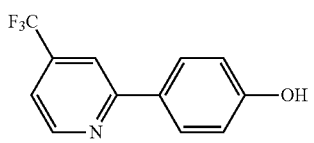

The intermediate was prepared following the method described for Ex. 148. LC-MS (ESI): m/z (M+1)⁺, 239.9.

1.55 Preparation of 2-[4-({3-bromo-1-[(4-methoxyphenyl)methyl]-1H-pyrazolo[3,4-b]pyridin-4-yl}oxy)phenyl]-4-(trifluoromethyl)pyridine

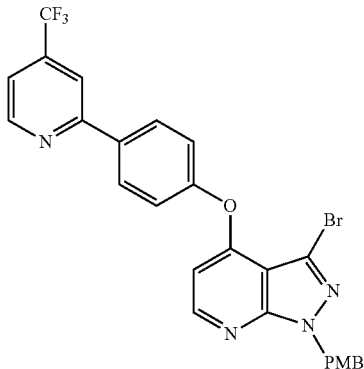

The intermediate was prepared following the method described for Ex. 86. LC-MS (ESI): m/z (M+1)$^+$, 556.9.

1.56 Preparation of tert-butyl (3R)-3-({1-[(4-methoxyphenyl)methyl]-4-{4-[4-(trifluoromethyl)pyridin-2-yl]phenoxy}-1H-pyrazolo[3,4-b]pyridin-3-yl}amino)piperidine-1-carboxylate tert-butyl (3R)-3-aminopiperidine-1-carboxylate

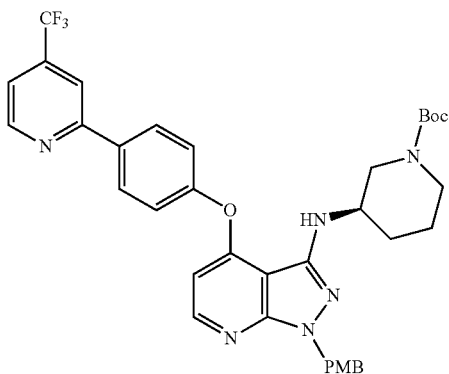

The intermediate was prepared following the method described for Ex. 86. LC-MS (ESI): m/z (M+1)$^+$, 675.1.

1.57 Preparation of 3R)—N-(4-{4-[4-(trifluoromethyl)pyridin-2-yl]phenoxy}-1H-pyrazolo[3,4-b]pyridin-3-yl)piperidin-3-amine

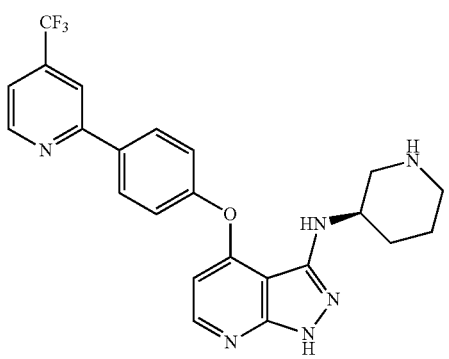 [SMILES: FC(F)(F)c1ccnc(-c2ccc(Oc3ccnc4[nH]nc(N[C@@H]5CCCNC5)c34)cc2)c1]

The intermediate was prepared following the method described for Ex. 148. LC-MS (ESI): m/z (M+1)$^+$, 455.

Compound 155 was prepared following the method described for Ex. 140. LC-MS (ESI): m/z (M+1)$^+$, 509.

Example 156

1-[(3R)-3-{[4-(3-methyl-4-phenoxyphenoxy)-1H-pyrazolo[3,4-b]pyridin-3-yl]amino}piperidin-1-yl]prop-2-en-1-one (Compound ID 156)

1.58 Preparation of (3R)—N-[4-(3-methyl-4-phenoxyphenoxy)-1H-pyrazolo[3,4-b]pyridin-3-yl]piperidin-3-amine

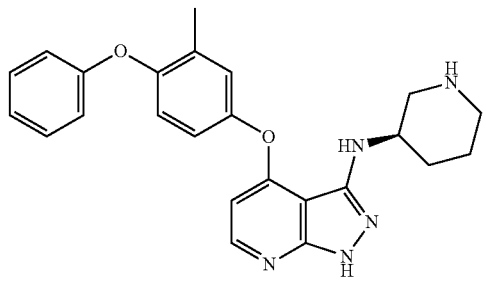 [SMILES: Cc1cc(Oc2ccnc3[nH]nc(N[C@@H]4CCCNC4)c23)ccc1Oc1ccccc1]

The compound was prepared following the method described for Ex. 148. LC-MS (ESI): m/z (M+1)$^+$, 416.4

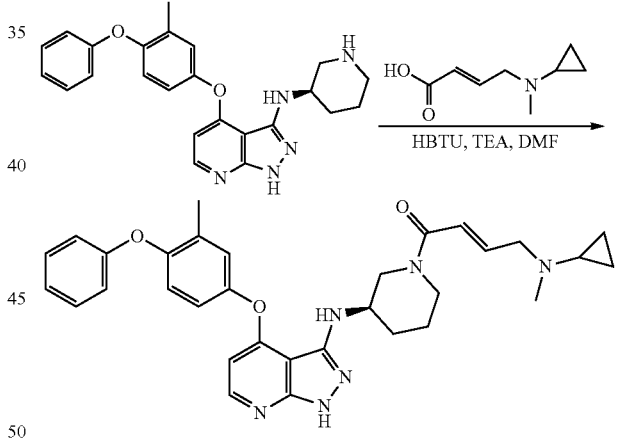

(2E)-4-[cyclopropyl(methyl)amino]-1-[(3R)-3-{[4-(3-methyl-4-phenoxyphenoxy)-1H-pyrazolo[3,4-b]pyridin-3-yl]amino}piperidin-1-yl]but-2-en-1-one (19.9 mg, 97%) was prepared from (3R)—N-[4-(3-methyl-4-phenoxyphenoxy)-1H-pyrazolo[3,4-b]pyridin-3-yl]piperidin-3-amine (93 mg, 0.17 mmol) and (E)-4-(cyclopropyl(methyl)amino)but-2-enoic acid HCl salt (83 mg, 0.26 mmol) following a similar procedure outlined in Ex. 26. LC-MS (ESI): m/z (M+1) 553.5. $^1$H NMR (500 MHz, DMSO-d6) δ ppm 12.48-11.98 (m, 1H), 8.16 (d, J=5.40 Hz, 1H), 7.38 (m, J=16.14 Hz, 2H), 7.30-7.24 (m, 1H), 7.17-7.08 (m, 2H), 7.06-7.01 (m, 1H), 6.95 (d, J=7.83 Hz, 2H), 6.63-6.35 (m, 2H), 6.10 (d, J=5.38 Hz, 1H), 5.27-5.11 (m, 1H), 4.45-3.88 (m, 1H), 3.85-3.59 (m, 2H), 3.51-3.39 (m, 1H), 3.27-2.91 (m, 3H), 2.27-2.06 (m, 6H), 2.06-1.39 (m, 5H), 0.45-0.17 (m, 4H).

Example 157

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(4-methyl-1H-imidazol-2-yl)benzamide (Compound 157)

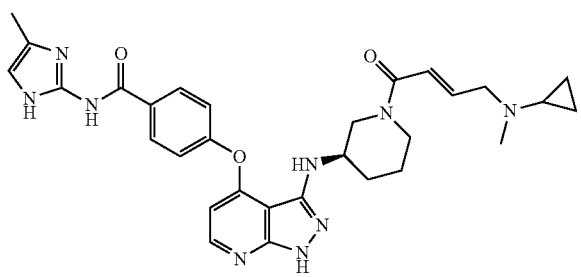 [SMILES: Cc1c[nH]c(NC(=O)c2ccc(Oc3ccnc4[nH]nc(N[C@@H]5CCCN(C(=O)/C=C/CN(C)C6CC6)C5)c34)cc2)n1]

1.59 Preparation of (3R)-3-({1-[(4-methoxyphenyl)methyl]-4-{4-[(4-methyl-1H-imidazol-2-yl)carbamoyl]phenoxy}-1H-pyrazolo[3,4-b]pyridin-3-yl}amino)piperidine-1-carboxylate

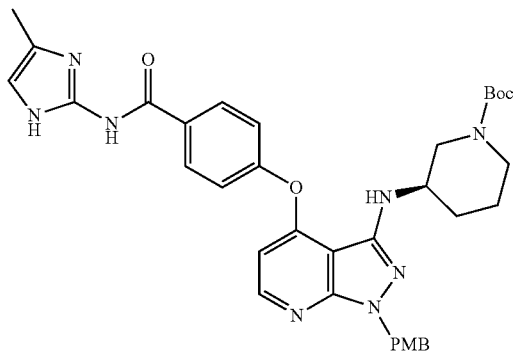

The intermediate was prepared following the method described for the synthesis of Ex. 137. LC-MS (ESI): m/z (M+1)$^+$, 653.2.

1.60 Preparation of (3R)-3-({1-[(4-methoxyphenyl)methyl]-4-{4-[(4-methyl-1H-imidazol-2-yl)carbamoyl]phenoxy}-1H-pyrazolo[3,4-b]pyridin-3-yl}amino)piperidin-1-ium trifluoroacetate

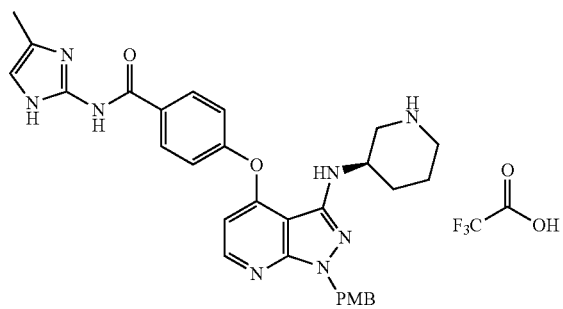

The intermediate was prepared following the method described for Ex. 137. LC-MS (ESI): m/z (M+1)$^+$, 553.1.

1.61 Preparation of N-(4-methyl-1H-imidazol-2-yl)-4-[(3-{[(3R)-piperidin-3-yl]amino}-1H-pyrazolo[3,4-b]pyridin-4-yl)oxy]benzamide

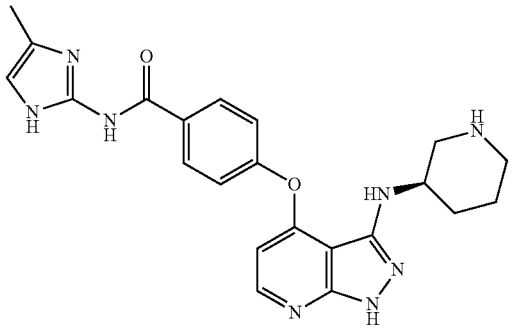 [SMILES: Cc1c[nH]c(NC(=O)c2ccc(Oc3ccnc4[nH]nc(N[C@@H]5CCCNC5)c34)cc2)n1]

The intermediate was prepared following the method described for Ex. 137. LC-MS (ESI): m/z (M+1)$^+$, 433.1.

Compound 157 was prepared following the method described for Ex. 137. LC-MS (ESI): m/z (M+1)$^+$, 570.3. $^1$H NMR (500 MHz, DMSO) δ 12.30 (br. s., 1H), 11.67 (br. s., 2H), 8.27-8.08 (m, 3H), 7.41-7.27 (m, 2H), 6.62-6.48 (m, 2H), 6.44-6.33 (m, 1H), 6.20-6.05 (m, 1H), 5.15 (d, J=6.85 Hz, 1H), 3.96 (d, J=12.72 Hz, 1H), 3.87-3.57 (m, 2H), 3.51-2.91 (m, 4H), 2.12 (s, 3H), 2.08 (br. s., 3H), 2.05-1.96 (m, 1H), 1.79-1.53 (m, 3H), 1.45 (br. s., 1H), 0.18-0.46 (m, 4H).

Example 158

1-[(3R)-3-({4-[4-(5-methyl-1,3-thiazol-2-yl)phenoxy]-1H-pyrazolo[3,4-b]pyridin-3-yl}amino)piperidin-1-yl]prop-2-en-1-one (Compound ID 158)

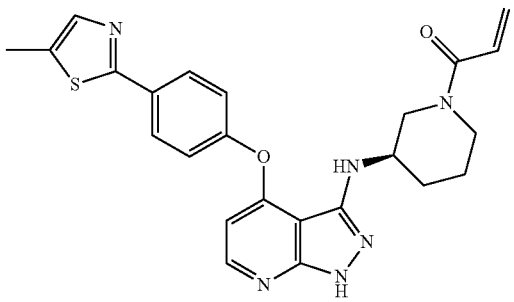 [SMILES: C=CC(=O)N1CCC[C@@H](Nc2n[nH]c3nccc(Oc4ccc(-c5ncc(C)s5)cc4)c23)C1]

1.62 Preparation of 4-(5-methyl-1,3-thiazol-2-yl)phenol

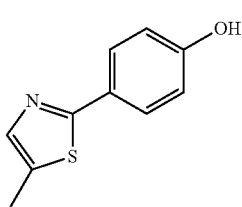

The intermediate was prepared following the method described for Ex. 148. LC-MS (ESI): m/z (M+1)⁺, 191.9.

1.63 Preparation of 2-[4-({3-bromo-1-[(4-methoxyphenyl)methyl]-1H-pyrazolo[3,4-b]pyridin-4-yl}oxy)phenyl]-5-methyl-1,3-thiazole

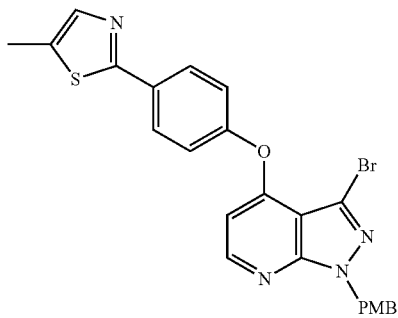

The intermediate was prepared following the method described Ex. 148. LC-MS (ESI): m/z (M+1)⁺, 508.9.

1.64 Preparation of tert-butyl (3R)-3-({1-[(4-methoxyphenyl)methyl]-4-[4-(5-methyl-1,3-thiazol-2-yl)phenoxy]-1H-pyrazolo[3,4-b]pyridin-3-yl}amino)piperidine-1-carboxylate

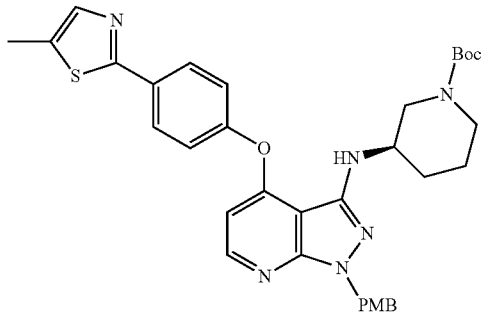

The intermediate was prepared following the method described for Ex. 148. LC-MS (ESI): m/z (M+1)⁺, 627.1.

1.65 Preparation of (3R)—N-{4-[4-(5-methyl-1,3-thiazol-2-yl)phenoxy]-1H-pyrazolo[3,4-b]pyridin-3-yl}piperidin-3-amine

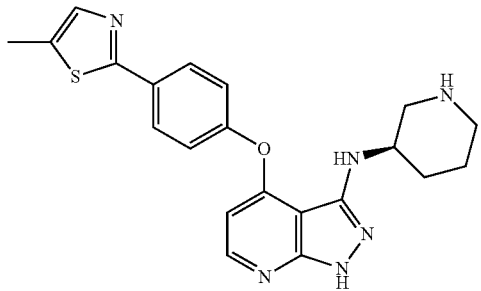 [SMILES: Cc1cnc(-c2ccc(Oc3ccnc4[nH]nc(N[C@@H]5CCCNC5)c34)cc2)s1]

The intermediate was prepared following the method described for Ex. 148. LC-MS (ESI): m/z (M+1)⁺, 407.

Compound 158 was prepared following the method described for Ex. 140. LC-MS (ESI): m/z (M+1)⁺, 461.0. ¹H NMR (500 MHz, DMSO) δ 12.28 (br. s., 1H), 8.16 (d, J=5.87 Hz, 1H), 8.00 (d, J=8.31 Hz, 2H), 7.61-7.64 (m, 1H), 7.38 (d, J=8.31 Hz, 2H), 6.63-6.88 (m, 1H), 6.14 (d, J=5.38 Hz, 1H), 6.05 (d, J=16.63 Hz, 1H), 5.53-5.69 (m, 1H), 5.25 (d, J=7.83 Hz, 1H), 4.09-4.55 (m, 1H), 3.78-4.03 (m, 1H), 3.54-3.70 (m, 1H), 2.88-3.28 (m, 2H), 2.50 (s, 3H), 1.37-2.16 (m, 4H).

Example 159

N-(1,5-dimethyl-1H-pyrazol-3-yl)-4-[(3-{[(3R)-1-(prop-2-enoyl)piperidin-3-yl]amino}-1H-pyrazolo[3,4-b]pyridin-4-yl)oxy]benzamide (Compound ID 159)

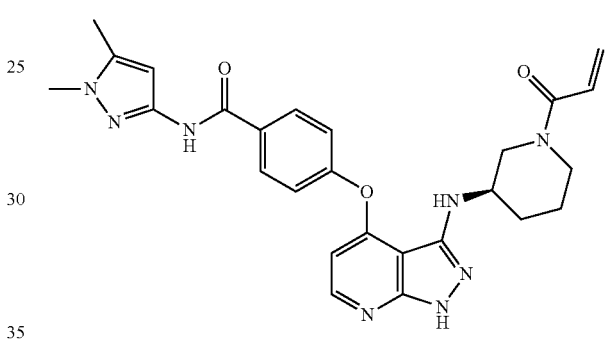

1.66 Preparation of (3R)-3-[(4-{4-[(1,5-dimethyl-1H-pyrazol-3-yl)carbamoyl]phenoxy}-1-[(4-methoxyphenyl)methyl]-1H-pyrazolo[3,4-b]pyridin-3-yl)amino]piperidine-1-carboxylate

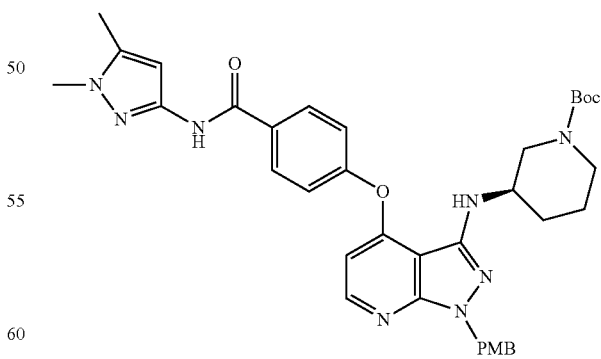

The intermediate was prepared following the method described for Ex. 137. LC-MS (ESI): m/z (M+1)⁺, 667.1.

1.67 Preparation of (3R)-3-[(4-{4-[(1,5-dimethyl-1H-pyrazol-3-yl)carbamoyl]phenoxy}-1-[(4-methoxyphenyl)methyl]-1H-pyrazolo[3,4-b]pyridin-3-yl)amino]piperidin-1-ium trifluoroacetate

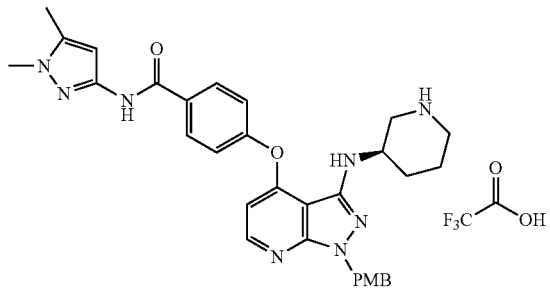

The intermediate was prepared following the method described for Ex. 137. LC-MS (ESI): m/z (M+1)⁺, 567.1.

1.68 Preparation of N-(1,5-dimethyl-1H-pyrazol-3-yl)-4-[(3-{[(3R)-piperidin-3-yl]amino}-1H-pyrazolo[3,4-b]pyridin-4-yl)oxy]benzamide

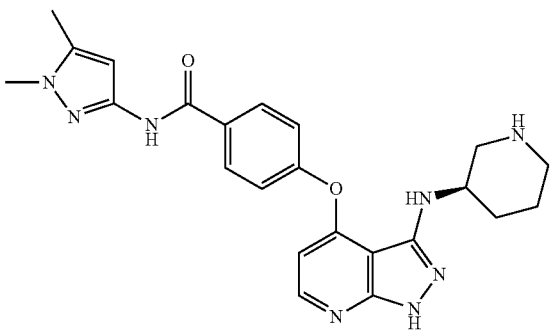 [SMILES: Cc1cc(NC(=O)c2ccc(Oc3ccnc4[nH]nc(N[C@@H]5CCCNC5)c34)cc2)nn1C]

The intermediate was prepared following the method described for Ex. 137. LC-MS (ESI): m/z (M+1)⁺, 447.0.

Compound 159 was prepared following the method described for Ex. 140. LC-MS (ESI): m/z (M+1)⁺, 501.2. ¹H NMR (500 MHz, DMSO) δ 12.47-11.95 (m, 1H), 10.77 (s, 1H), 8.33-8.01 (m, 3H), 7.35 (d, J=7.83 Hz, 2H), 6.93-6.59 (m, 1H), 6.44 (s, 1H), 6.26-5.97 (m, 2H), 5.73-5.47 (m, 1H), 5.22 (d, J=5.38 Hz, 1H), 4.55-3.76 (m, 2H), 3.67 (s, 4H), 3.28-2.88 (m, 2H), 2.26 (s, 3H), 2.03 (d, J=10.27 Hz, 1H), 1.78-1.60 (m, 2H), 1.45 (br. s., 1H).

Example 160

1-[(3R)-3-[(4-{4-[3-(trifluoromethyl)piperidine-1-carbonyl]phenoxy}-1H-pyrazolo[3,4-b]pyridin-3-yl)amino]piperidin-1-yl]prop-2-en-1-one (Compound ID 160)

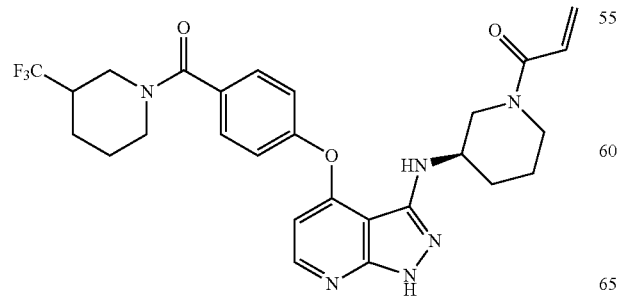

1.69 Preparation of tert-butyl (3R)-3-({1-[(4-methoxyphenyl)methyl]-4-{4-[3-(trifluoromethyl)piperidine-1-carbonyl]phenoxy}-1H-pyrazolo[3,4-b]pyridin-3-yl}amino)piperidine-1-carboxylate

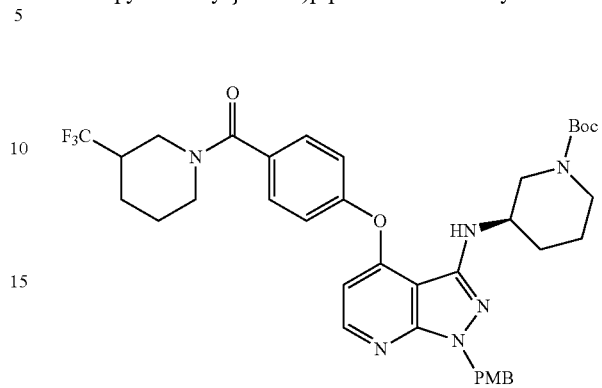

The intermediate was prepared following the method described for Ex. 137. LC-MS (ESI): m/z (M+1)⁺, 709.1.

1.70 Preparation of (3R)-3-({1-[(4-methoxyphenyl)methyl]-4-{4-[3-(trifluoromethyl)piperidine-1-carbonyl]phenoxy}-1H-pyrazolo[3,4-b]pyridin-3-yl}amino)piperidin-1-ium trifluoroacetate

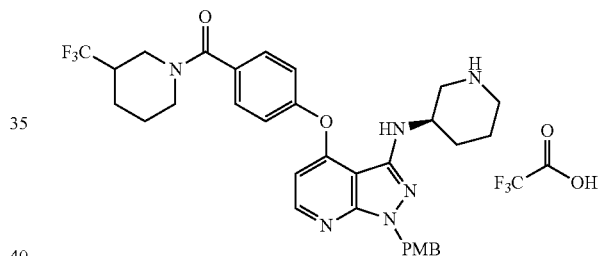

The intermediate was prepared following the method described for Ex. 137. LC-MS (ESI): m/z (M+1)⁺, 609.1.

1.71 Preparation of (3R)—N-(4-{4-[3-(trifluoromethyl)piperidine-1-carbonyl]phenoxy}-1H-pyrazolo[3,4-b]pyridin-3-yl)piperidin-3-amine

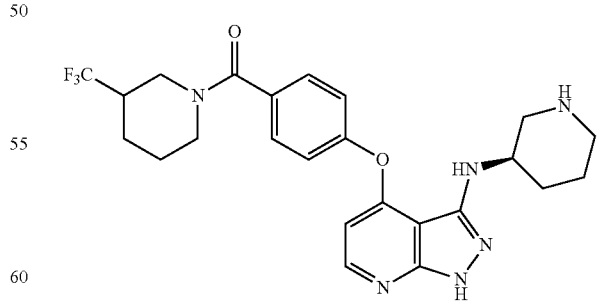

The intermediate was prepared following the method described for Ex. 137. LC-MS (ESI): m/z (M+1)⁺, 489.0.

Compound 160 was prepared following the method described for Ex. 140. LC-MS (ESI): m/z (M+1)⁺, 543.5. ¹H NMR (500 MHz, DMSO) δ 12.38-12.07 (m, 1H), 8.17 (d, J=5.38 Hz, 1H), 7.55 (d, J=6.36 Hz, 2H), 7.36 (d, J=8.31 Hz, 2H), 6.87-6.56 (m, 1H), 6.26-5.94 (m, 2H), 5.77-5.48 (m, 1H), 5.24 (br. s., 1H), 4.69-2.85 (m, 9H), 2.64 (br. s., 1H), 2.09-1.33 (m, 8H).

Example 161

4-[(3-{[(3R)-1-[4-(dimethylamino)butanoyl]piperidin-3-yl]amino}-1H-pyrazolo[3,4-b]pyridin-4-yl)oxy]-N-[4-(trifluoromethyl)pyridin-2-yl]benzamide (Compound ID 161)

1.72 Preparation of tert-butyl 3-({1-[(4-methoxyphenyl)methyl]-4-(4-{[4-(trifluoromethyl)pyridin-2-yl]carbamoyl}phenoxy)-1H-pyrazolo[3,4-b]pyridin-3-yl}amino)piperidine-1-carboxylate

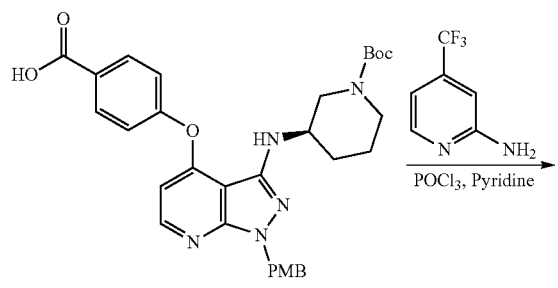

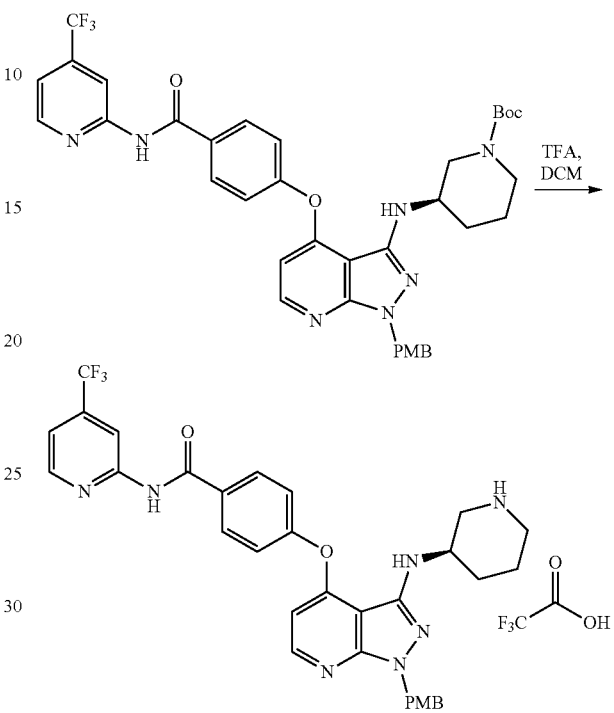

To a solution of 4-[(3-{[(3R)-1-[(tert-butoxy)carbonyl]piperidin-3-yl]amino}-1-[(4-methoxyphenyl)methyl]-1H-pyrazolo[3,4-b]pyridin-4-yl)oxy]benzoic acid (1.47 g, 2.56 mmol) and 4-(trifluoromethyl)pyridin-2-amine (1.25 g, 7.69 mmol) in pyridine (15 mL) was added POCl$_3$ (1.57 g, 10.24 mmol) dropwise at room temperature. After addition, the reaction mixture was stirred at room temperature for 45 min. Ethyl acetate and NaHCO$_3$ saturated aqueous solution were added and the two phases separated. The organic phase was washed twice with water, dried over Na$_2$SO$_4$, filtered and concentrated to give a crude product that was purified by gradient flash chromatography (silica gel, 100 g, from 15 to 65% ethyl acetate in cyclohexane). tert-butyl 3-({1-[(4-methoxyphenyl)methyl]-4-(4-{[4-(trifluoromethyl)pyridin-2-yl]carbamoyl}phenoxy)-1H-pyrazolo[3,4-b]pyridin-3-yl}amino)piperidine-1-carboxylate was obtained as a yellow oil (1.35 g, Yield 54%). LC-MS (ESI): m/z (M+1)$^+$, 718.3.

1.73 Preparation of 4-({1-[(4-methoxyphenyl)methyl]-3-{[(3R)-piperidin-3-yl]amino}-1H-pyrazolo[3,4-b]pyridin-4-yl}oxy)-N-[4-(trifluoromethyl)pyridin-2-yl]benzamide; trifluoroacetic acid To a solution of tert-butyl 3-({1-[(4-methoxyphenyl)methyl]-4-(4-{[4-(trifluoromethyl)pyridin-2-yl]carbamoyl}phenoxy)-1H-pyrazolo[3,4-b]pyridin-3-yl}amino)piperidine-1-carboxylate (1.35 g, 1.37 mmol) in DCM (12 mL) at 0° C. TFA (2.7 mL) was added. The reaction mixture was stirred at this temperature for 30 min then at rt for 45 min then concentrated to afford 4-({1-[(4-methoxyphenyl)methyl]-3-{[(3R)-piperidin-3-yl]amino}-1H-pyrazolo[3,4-b]pyridin-4-yl}oxy)-N-[4-(trifluoromethyl)pyridin-2-yl]benzamide; trifluoroacetic acid as a yellow oil (3.54 g, Yield: quantitative). LC-MS (ESI): m/z (M+1)$^+$, 618.2.

1.74 Preparation of 4-[(3-{[(3R)-piperidin-3-yl]amino}-1H-pyrazolo[3,4-b]pyridin-4-yl)oxy]-N-[4-(trifluoromethyl)pyridin-2-yl]benzamide

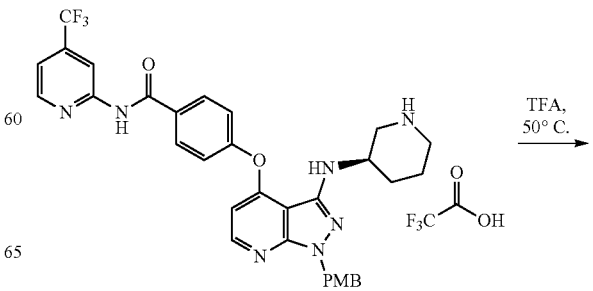

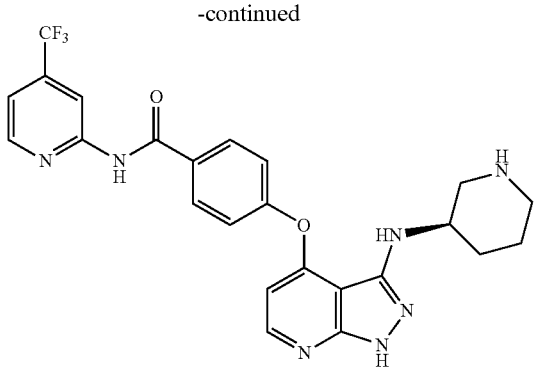

4-({1-[(4-Methoxyphenyl)methyl]-3-{[(3R)-piperidin-3-yl]amino}-1H-pyrazolo[3,4-b]pyridin-4-yl}oxy)-N-[4-(trifluoromethyl)pyridin-2-yl]benzamide; trifluoroacetic acid (3.54 g, 1.37 mmol) was dissolved in TFA (12 mL) and stirred at 50° C. for 2.5 hours then the solvent was evaporated. The crude product was purified by SCX cartridge affording 4-[(3-{[(3R)-piperidin-3-yl]amino}-1H-pyrazolo[3,4-b]pyridin-4-yl)oxy]-N-[4-(trifluoromethyl)pyridin-2-yl]benzamide as a pale yellow solid (948.0 mg, Yield: quantitative). LC-MS (ESI): m/z (M+1)$^+$, 497.96.

1.75 Preparation of 4-[(3-{[(3R)-1-[4-(dimethylamino)butanoyl]piperidin-3-yl]amino}-1H-pyrazolo[3,4-b]pyridin-4-yl)oxy]-N-[4-trifluoromethyl)pyridin-2-yl]benzamide

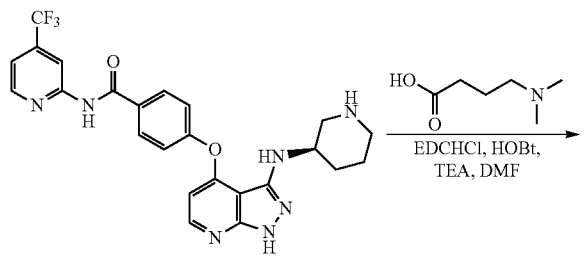

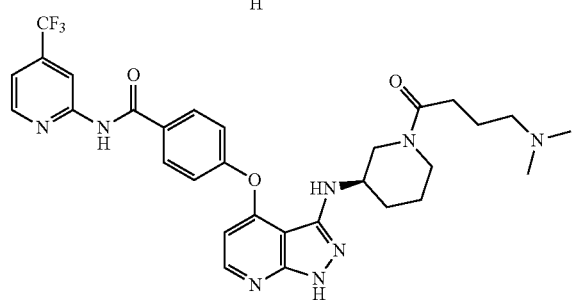

To a solution of 4-[(3-{[(3R)-piperidin-3-yl]amino}-1H-pyrazolo[3,4-b]pyridin-yl)oxy]-N-[4-(trifluoromethyl)pyridin-2-yl]benzamide g, 0.28 mmol) in DMF (6 mL) were added 4-(dimethylamino)butanoic acid hydrochloride (56.3 mg, 0.336 mmol), TEA (78 µL, 0.56 mmol), HOBt (38 mg, 0.28 mmol) and EDC.HCl (64.0 mg, 0.336 mmol) and the mixture was stirred at room temperature for 18 hours. Water was added and the product was extracted three times with AcOEt. The collected organic phases were dried over Na$_2$SO$_4$, filtered and concentrated. The product was purified by preparative HPLC (C18 column, CH$_3$CN in 10 mM ammonium bicarbonate aqueous solution adjusted to pH 10 with ammonia) to give 4-[(3-{[(3R)-1-[4-(dimethylamino)butanoyl]piperidin-3-yl]amino}-1H-pyrazolo[3,4-b]pyridin-4-yl)oxy]-N-[4-(trifluoromethyl)pyridin-2-yl]benzamide as white solid (124.5 mg, Yield: 73%). LC-MS (ESI): m/z (M+1)$^+$, 611.15.

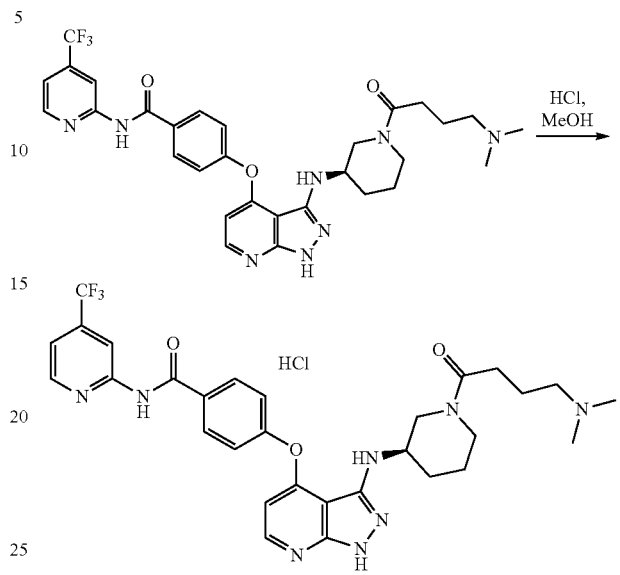

To a solution of 4-[(3-{[(3R)-1-[4-(dimethylamino)butanoyl]piperidin-3-yl]amino}-1H-pyrazolo[3,4-b]pyridin-4-yl)oxy]-N-[4-(trifluoromethyl)pyridin-2-yl]benzamide (124.5 mg, 0.204 mmol) in MeOH (4 ml) was added a solution of HCl (180 µL, 0.224 mmol) 1.25M in MeOH. The mixture was stirred at rt for 1 h, then concentrated to give 4-[(3-{[(3R)-1-[4-(dimethylamino)butanoyl]piperidin-3-yl]amino}-1H-pyrazolo[3,4-b]pyridin-4-yl)oxy]-N-[4-(trifluoromethyl)pyridin-2-yl]benzamide hydrochloride as a yellow solid (113.5 mg, Yield: 86%). LC-MS (ESI): m/z (M+1)$^+$, 611.0. $^1$H NMR (500 MHz, DMSO) δ 12.70-11.93 (m, 1H), 11.37 (s, 1H), 10.65 (br. s., 1H), 8.70 (d, J=4.89 Hz, 1H), 8.56 (s, 1H), 8.25-8.17 (m, 3H), 7.56 (d, J=4.89 Hz, 1H), 7.48-7.35 (m, 2H), 6.28-6.05 (m, 1H), 5.35-5.15 (m, 1H), 4.66-3.52 (m, 3H), 3.49-2.24 (m, 14H), 2.18-1.31 (m, 4H).

Example 162

N-(1,3-benzothiazol-2-yl)-4-[(3-{[(3R)-piperidin-3-yl]amino}-1H-pyrazolo[3,4-b]pyridin-4-yl)oxy]benzamide (Compound ID 162)

1.76 (tert-butyl (3R)-3-[(4-{4-[(1,3-benzothiazol-2-yl)carbamoyl]phenoxy}-1-[(4-methoxyphenyl)methyl]-1H-pyrazolo[3,4-b]pyridin-3-yl)amino]piperidine-1-carboxylate

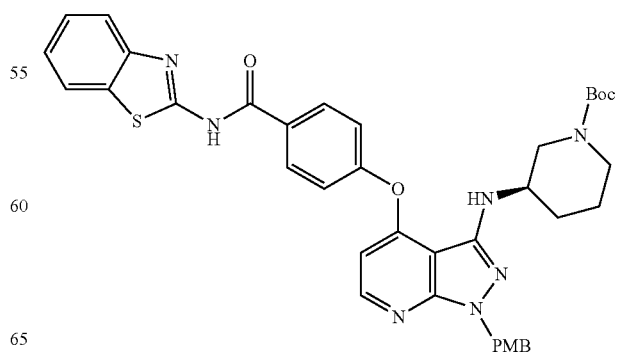

The intermediate was prepared following the method described for Ex. 140. LC-MS (ESI): m/z (M+1)⁺, 706.01.

1.77 Preparation of N-(1,3-benzothiazol-2-yl)-4-({1-[(4-methoxyphenyl)methyl]-3-{[(3R)-piperidin-3-yl]amino}-1H-pyrazolo[3,4-b]pyridin-4-yl}oxy)benzamide trifluoroacetate

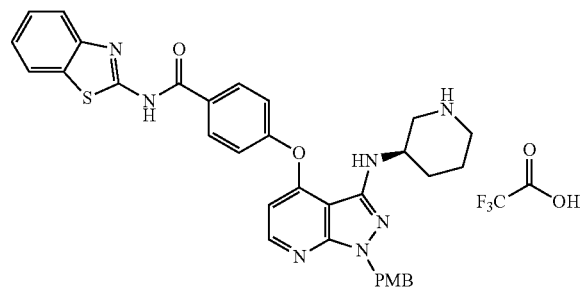

The intermediate was prepared following the method described for Ex. 140. LC-MS (ESI): m/z (M+1)⁺, 606.7.

1.78 Preparation of N-(5-methyl-1,3-thiazol-2-yl)-4-[(3-{[(3R)-piperidin-3-yl]amino}-1H-pyrazolo[3,4-b]pyridin-4-yl)oxy]benzamide

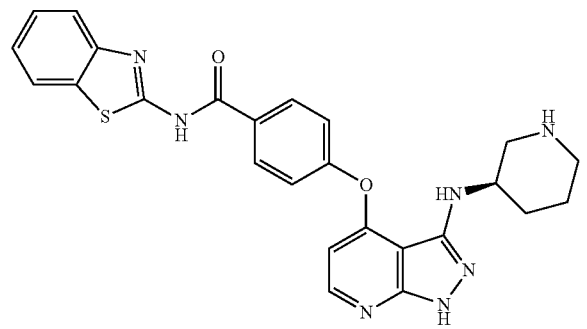 [SMILES: O=C(Nc1nc2ccccc2s1)c1ccc(Oc2ccnc3[nH]nc(N[C@@H]4CCCNC4)c23)cc1]

The intermediate was prepared following the method described for Ex. 140. LC-MS (ESI): m/z (M+1)⁺, 486.0.

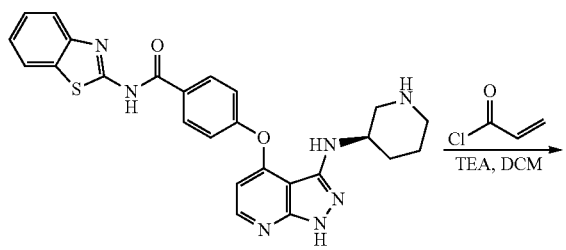

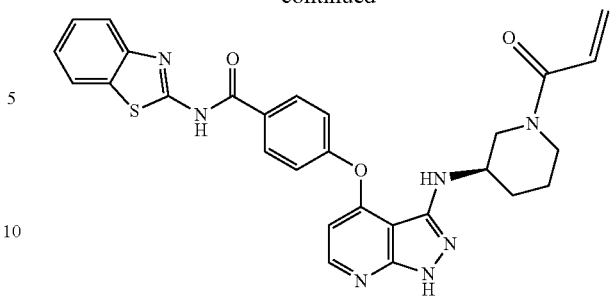

To a cooled solution (0° C.) of N-(5-methyl-1,3-thiazol-2-yl)-4-[(3-{[(3R)-piperidin-3-yl]amino}-1H-pyrazolo[3,4-b]pyridin-4-yl)oxy]benzamide (98.5 mg, 0.27 mmol), TEA (290 μL, 1.66 mmol) in DCM (3 mL) was added a solution of acryloyl chloride (83 μL, 0.27 mmol) in DCM (0.5 mL). The mixture was stirred at 0° C. for 45 min, then concentrated to give a solid that was purified by flash chromatography (silica gel 25 g, ethyl acetate methanol from 98/2 to 95/5). N-(1,3-benzothiazol-2-yl)-4-[(3-{[(3R)-piperidin-3-yl]amino}-1H-pyrazolo[3,4-b]pyridin-4-yl)oxy]benzamide was obtained as a pale yellow solid (26.5 mg, Yield: 24%). LC-MS (ESI): m/z (M+1)⁺, 539.97. ¹H NMR (500 MHz, DMSO) δ 12.96 (br.s., 1H) 12.05-12.49 (m, 1H), 8.29 (d, J=8.80 Hz, 2H), 8.21 (d, J=5.38 Hz, 1H), 8.03 (d, J=7.83 Hz, 1H), 7.79 (d, J=7.83 Hz, 1H), 7.54-7.40 (m, 3H), 7.35 (t, J=7.58 Hz, 1H), 6.89-6.62 (m, 1H), 6.20 (d, J=5.38 Hz, 1H), 6.07 (d, J=16.63 Hz, 1H), 5.67-5.51 (m, 1H), 5.25 (d, J=6.85 Hz, 1H), 4.51-3.77 (m, 2H), 3.64 (br. s., 1H), 3.27-2.89 (m, 2H), 2.03 (d, J=9.78 Hz, 1H), −1.77-1.63 (m, 2H), 1.54-1.39 (m, 1H).

Example 163

1-[(3R)-3-[(4-{4-[3-(trifluoromethyl)piperidine-1-carbonyl]phenoxy}-1H-pyrazolo[3,4-b]pyridin-3-yl)amino]piperidin-1-yl]but-2-yn-1-one (Compound ID 163)

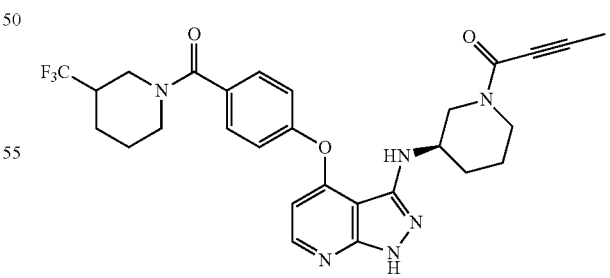

The compound was prepared following the method described for Ex. 141. LC-MS (ESI): m/z (M+1)⁺, 555.5. ¹H NMR (500 MHz, DMSO) δ 12.47-12.01 (m, 1H), 8.17 (t, J=5.87 Hz, 1H), 7.55 (br. s., 2H), 7.36 (d, J=8.80 Hz, 2H), 6.12 (br. s., 1H), 5.21 (br. s., 1H), 4.70-2.77 (m, 9H), 2.64 (s, 1H), 2.12-1.32 (m, 11H).

Example 164

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(dimethyl-1,3-thiazol-2-yl)benzamide (Compound ID 164)

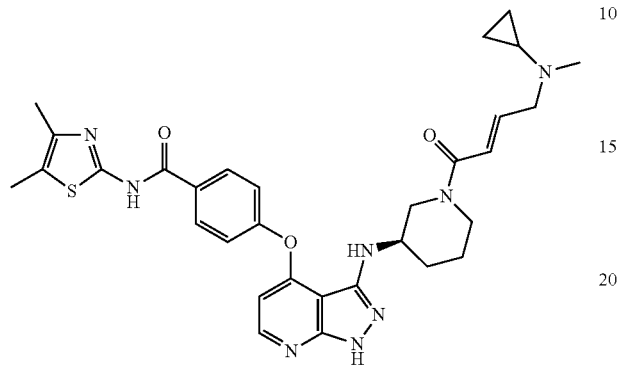

The compound was prepared following the method described for Ex. 137. LC-MS (ESI): m/z (M+1)⁺, 601.3. ¹H NMR (500 MHz, DMSO) δ 12.66-12.10 (m, 2H), 8.22 (d, J=8.80 Hz, 3H), 7.38 (d, J=7.83 Hz, 2H), 6.63-6.29 (m, 2H), 6.17 (br. s., 1H), 5.32-5.00 (m, 1H), 4.41-3.89 (m, 1H), 3.86-3.58 (m, 2H), 3.32 (s, 4H), 2.32-2.05 (m, 9H), 1.99 (br. s., 1H), 1.80-1.33 (m, 4H), 0.50-0.10 (m, 4H).

Example 165

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(1,5-dimethyl-1H-pyrazol-3-yl)benzamide (Compound ID 165)

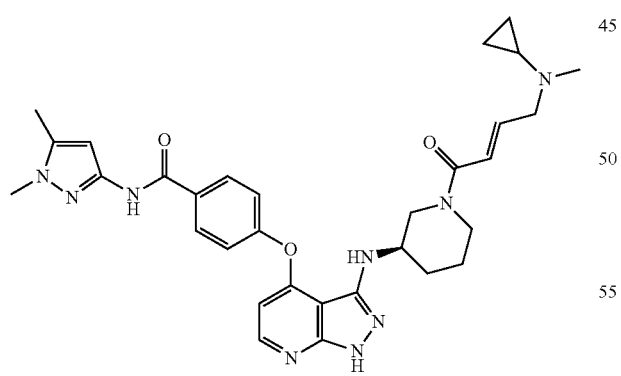

The compound was prepared following the method described for Ex. 137. LC-MS (ESI): m/z (M+1)⁺, 584.3. ¹H NMR (500 MHz, DMSO) δ 12.37-12.17 (m, 1H), 10.77 (s, 1H), 8.18 (br. s., 1H), 8.13 (d, J=8.31 Hz, 2H), 7.33 (d, J=8.31 Hz, 2H), 6.44 (s, 3H), 6.14 (d, J=4.89 Hz, 1H), 5.30-5.06 (m, 1H), 4.46-3.88 (m, 1H), 3.79 (d, J=10.27 Hz, 5H), 3.32 (s, 4H), 2.26 (s, 7H), 1.79-1.36 (m, 4H), 0.50-0.18 (m, 4H).

Example 166

N-(5-cyano-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide (Compound ID 166)

1.79 Preparation of tert-butyl (3R)-3-[(4-{4-[(5-cyano-1,3-thiazol-2-yl)carbamoyl]phenoxy}-1-[(4-methoxyphenyl)methyl]-1H-pyrazolo[3,4-b]pyridin-3-yl)amino]piperidine-1-carboxylate

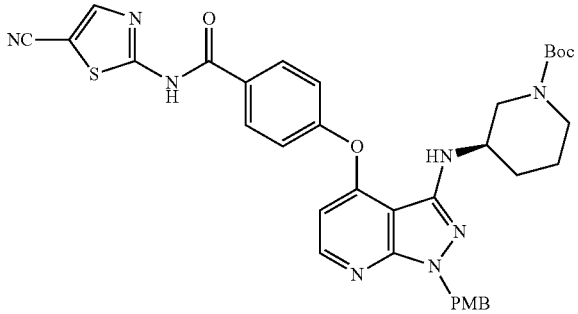

The intermediate was prepared following the method described for Ex. 140. LC-MS (ESI): m/z (M+1)⁺, 681.0.

1.80 Preparation of (3R)-3-[(4-{4-[(5-cyano-1,3-thiazol-2-yl)carbamoyl]phenoxy}-1-[(4-methoxyphenyl)methyl]-1H-pyrazolo[3,4-b]pyridin-3-yl)amino]piperidin-1-ium trifluoroacetate

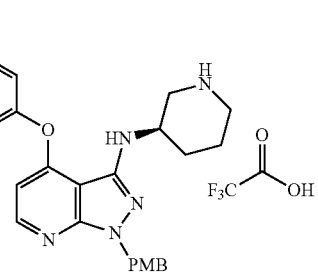

The intermediate was prepared following the method described for Ex. 140. LC-MS (ESI): m/z (M+1)⁺, 681.0.

1.81 Preparation of (3R)-3-[(4-{4-[(5-cyano-1,3-thiazol-2-yl)carbamoyl]phenoxy}-1H-pyrazolo[3,4-b]pyridin-3-yl)amino]piperidin-1-ium

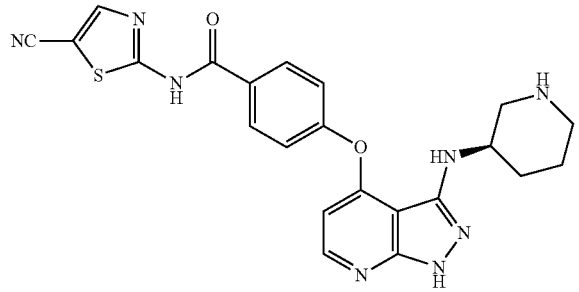 [SMILES: N#Cc1cnc(NC(=O)c2ccc(Oc3ccnc4[nH]nc(N[C@@H]5CCCNC5)c34)cc2)s1]

The intermediate was prepared following the method described for Ex. 140. LC-MS (ESI): m/z (M+1)⁺, 461.3.

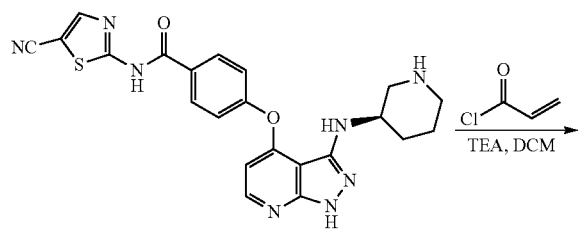

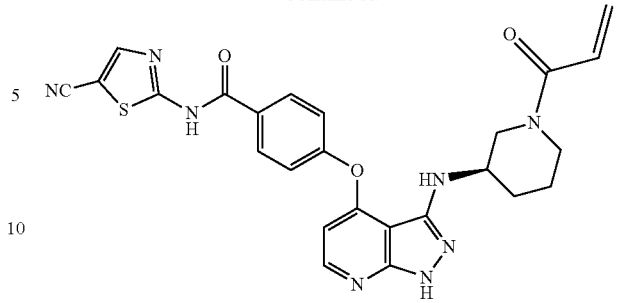

A cooled solution (0° C.) of N-(5-methyl-1,3-thiazol-2-yl)-4-[(3-{[(3R)-piperidin-3-yl]amino}-1H-pyrazolo[3,4-b]pyridin-4-yl)oxy]benzamide (129.3 mg, 0.27 mmol) and TEA (117 μL, 1.66 mmol) in DCM (3.5 mL) was stirred for 1 h. Then a solution of acryloyl chloride (25 μL, 0.27 mmol) in DCM (0.5 ml) was added. The mixture was stirred at 0° C. for 30 min then concentrated to give a solid that was purified by flash chromatography (RP silica gel 30 g, water 0.1% v/v formic acid/ACN from 10:0 to 0:10). N-(1,3-benzothiazol-2-yl)-4-[(3-{[(3R)-piperidin-3-yl]amino}-1H-pyrazolo[3,4-b]pyridin-4-yl)oxy]benzamide was obtained as a pale yellow solid (32 mg, Yield: 22%). LC-MS (ESI): m/z (M+1)⁺, 515.4. ¹H NMR (400 MHz, DMSO-d6) δ ppm 13.67-13.37 (m, 1H), 12.40-12.14 (m, 1H), 8.46 (s, 1H), 8.32-8.23 (m, 2H), 8.23-8.18 (m, 1H), 7.51-7.38 (m, 2H), 6.86-6.62 (m, 1H), 6.20 (d, J=5.48 Hz, 1H), 6.12-5.98 (m, 1H), 5.71-5.50 (m, 1H), 5.30-5.17 (m, 1H), 4.53-3.77 (m, 2H), 3.74-3.55 (m, 1H), 3.31-2.84 (m, 2H), 2.13-1.35 (m, 4H).

Example 167

N-(1,3-benzothiazol-2-yl)-4-[(3-{[(3R)-piperidin-3-yl]amino}-1H-pyrazolo[3,4-b]pyridin-4-yl)oxy]benzamide (Compound ID 167)

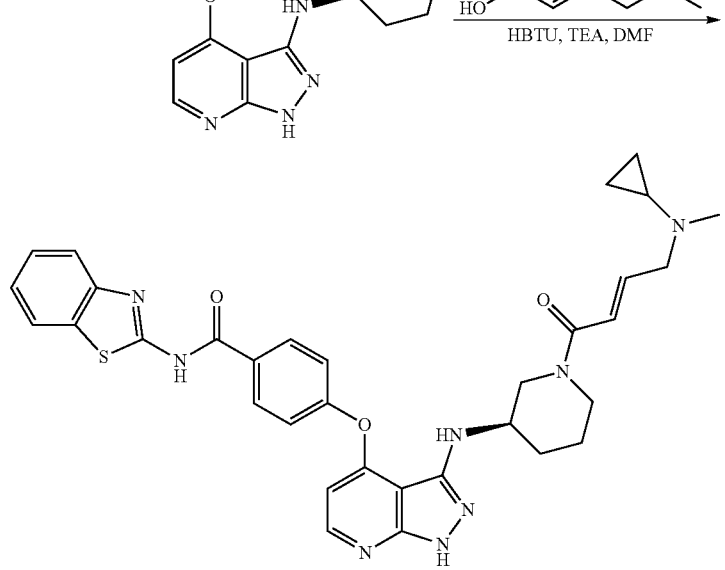

(2E)-4-[Cyclopropyl(methyl)amino]but-2-enoic acid (33.2 mg, 0.21 mmol), was dissolved in DMF (3 mL), HBTU (75.8 mg, 0.20 mmol) was added followed by TEA (55 μL, 0.40 mmol). The mixture was stirred for 25 min at room temperature. N-(1,3-Benzothiazol-2-yl)-4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]benzamide (99.1 mg, 0.20 mmol) was added and the mixture stirred overnight. The solvent was evaporated and the crude purified by flash chromatography (RP silica gel, 30 g, H₂O NH₄OH 0.1%/CH₃CN NH₄OH 0.1% from 10/0 to 20/80). N-(1,3-benzothiazol-2-yl)-4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]benzamide was obtained as a pale yellow solid (69.3 mg, Yield: 53%). LC-MS (ESI): m/z (M+1)⁺, 623.2. ¹H NMR (500 MHz, DMSO-d6) δ ppm 12.92 (br. s., 1H) 12.40-12.20 (m, 1H), 8.29 (d, J=8.80 Hz, 2H), 8.21 (br. s., 1H), 8.01 (d, J=7.83 Hz, 1H), 7.78 (d, J=8.31 Hz, 1H), 7.55-7.24 (m, 4H), 6.64-6.33 (m, 2H), 6.20 (br. s., 1H), 5.32-5.07 (m, 1H), 4.44-3.57 (m, 3H), 3.52-2.92 (m, 4H), 2.28-1.92 (m, 4H), 1.84-1.32 (m, 4H), 0.46-0.07 (m, 4H).

Example 168

4-[(3-{[(3R)-1-(but-2-ynoyl)piperidin-3-yl]amino}-1H-pyrazolo[3,4-b]pyridin-4-yl)oxy]-N-(5-cyano-1,3-thiazol-2-yl)benzamide (Compound ID 168)

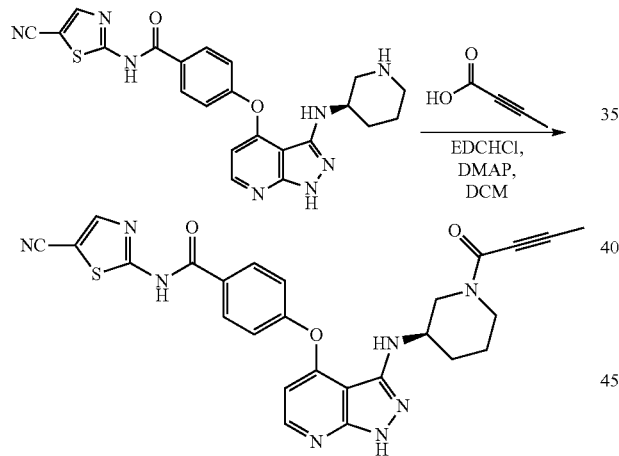

Under nitrogen a solution of N-(5-methyl-1,3-thiazol-2-yl)-4-[(3-{[(3R)-piperidin-3-yl]amino}-1H-pyrazolo[3,4-b]pyridin-4-yl)oxy]benzamide (99.9 mg, mmol), 2-butynoic acid (21.3 mg, mmol), EDC.HCl (82.3 mg, mmol) and DMAP (3.1 mg, 0.03 mmol) in DCM (3 mL) was stirred at room temperature for 30 min. The mixture was concentrated to give a crude product that was purified by flash chromatography (RP silica gel 30 g, water 0.1% v/v formic acid/ACN from 10:0 to 0:10). 4-[(3-{[(3R)-1-(But-2-ynoyl)piperidin-3-yl]amino}-1H-pyrazolo[3,4-b]pyridin-4-yl)oxy]-N-(5-methyl-1,3-thiazol-2-yl)benzamide was obtained as a white solid (49.9 mg, yield: 43%). LC-MS (ESI): m/z (M+1)⁺, 527.0. ¹H NMR (400 MHz, DMSO-d6) δ ppm 13.51 (br. s., 1H), 12.40-12.25 (m, 1H), 8.46 (s, 1H), 8.28 (d, J=9.00 Hz, 2H), 8.23-8.18 (m, 1H), 7.50-7.41 (m, 2H), 6.24-6.16 (m, 1H), 5.27-5.16 (m, 1H), 4.49-4.19 (m, 1H), 4.10-3.54 (m, 2H), 3.52-2.82 (m, 2H), 2.03-1.75 (m, 3H), 2.11-1.31 (m, 4H).

Example 169

(2E)-4-[cyclopropyl(methyl)amino]-1-[(3R)-3-{[4-(2-methyl-4-phenoxyphenoxy)-1H-pyrazolo[3,4-b]pyridin-3-yl]amino}piperidin-1-yl]but-2-en-1-one hydrochloride (Compound ID 169)

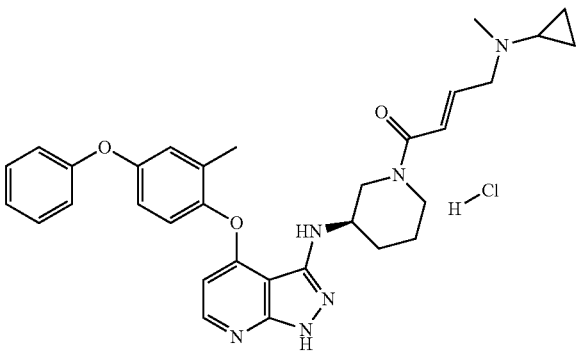

The compound was prepared following the method described for Ex. 156. LC-MS (ESI): m/z (M+1)⁺, 553.30. ¹H NMR (500 MHz, DMSO) δ 12.39-12.20 (m, 1H), 10.36-9.96 (m, 1H), 8.23-8.10 (m, 1H), 7.42 (m, J=0.98 Hz, 2H), 7.31-7.22 (m, 1H), 7.16 (t, J=7.34 Hz, 1H), 7.12-7.09 (m, 1H), 7.06 (d, J=7.83 Hz, 2H), 7.01-6.83 (m, 2H), 6.69-6.53 (m, 1H), 5.96 (d, J=5.38 Hz, 1H), 5.56-5.22 (m, 1H), 4.66-2.87 (m, 7H), 2.85-2.70 (m, 4H), 2.17-1.39 (m, 4H), 2.11 (s, 3H), 1.06-0.69 (m, 4H).

Example 170

1-[(3R)-3-{[4-(4-{[1,3]oxazolo[4,5-b]pyridin-2-yl}phenoxy)-1H-pyrazolo[3,4-b]pyridin-3-yl]amino}piperidin-1-yl]but-2-yn-1-one (Compound ID 170)

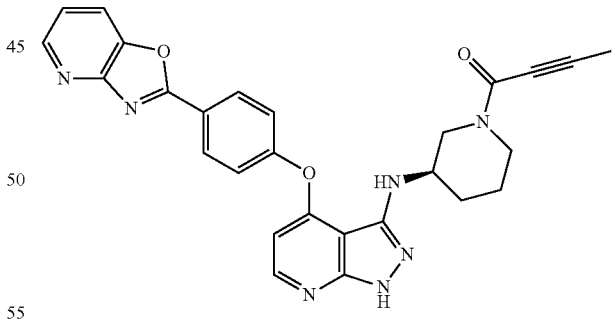

1.82 Preparation of 4-{[1,3]oxazolo[4,5-b]pyridin-2-yl}phenol

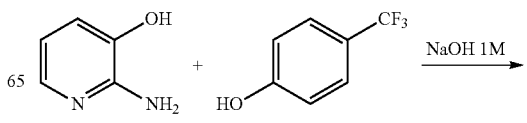

-continued

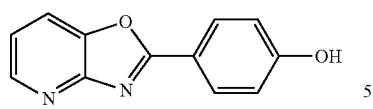

4-(Trifluoromethyl)phenol (199.4 mg) and 2-aminopyridin-3-ol (181.7 mg) in 4.9 mL of 1M NaOH aqueous solution were heated at 80° C. for 2.3 hr and at 90° C. for further 3 hr. The mixture was cooled to rt and then neutralized with 1 M HCl aqueous solution. The obtained slurry was filtered, the filter cake rinsed with more HCl 1N and water, then dried under vacuum overnight to afford the desired compound. (193.2 mg, 0.91 mmol, Yield: 74%). LC-MS (ESI): m/z (M+1)$^+$, 213.1.

1.83 Preparation of 3-bromo-1-[(4-methoxyphenyl)methyl]-4-(4-{[1,3]oxazolo[4,5-b]pyridin-2-yl}phenoxy)-1H-pyrazolo[3,4-b]pyridine

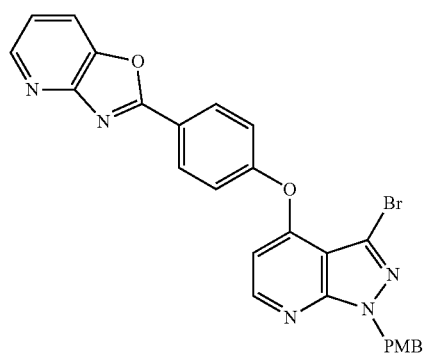

The intermediate was prepared following the method described for Ex. 86. LC-MS (ESI): m/z (M+1)$^+$, 528.0.

1.84 Preparation of tert-butyl (3R)-3-({1-[(4-methoxyphenyl)methyl]-4-(4-{[1,3]oxazolo[4,5-b]pyridin-2-yl}phenoxy)-1H-pyrazolo[3,4-b]pyridin-3-yl}amino)piperidine-1-carboxylate

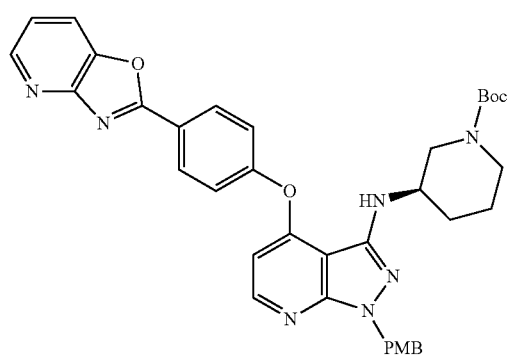

The intermediate was prepared following the method described for Ex. 140. LC-MS (ESI): m/z (M+1)$^+$, 648.4.

1.85 Preparation of 3R)—N-{1-[(4-methoxyphenyl)methyl]-4-(4-{[1,3]oxazolo[4,5-b]pyridin-2-yl}phenoxy)-1H-pyrazolo[3,4-b]pyridin-3-yl}piperidin-3-amine

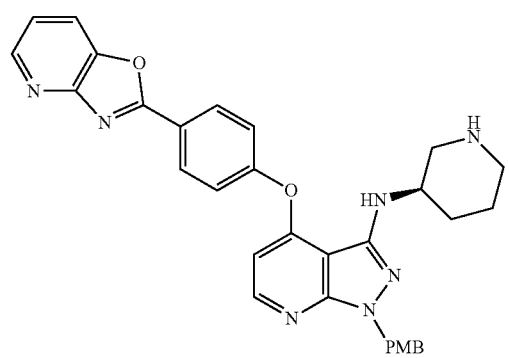

The intermediate was prepared following the method described for Ex. 140. LC-MS (ESI): m/z (M+1)$^+$, 548.3.

1.86 Preparation of (3R)—N-[4-(4-{[1,3]oxazolo[4,5-b]pyridin-2-yl}phenoxy)-1H-pyrazolo[3,4-b]pyridin-3-yl]piperidin-3-amine

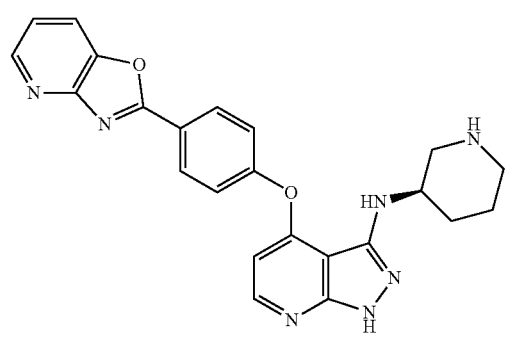 [SMILES: c1cnc2nc(-c3ccc(Oc4ccnc5[nH]nc(N[C@@H]6CCCNC6)c45)cc3)oc2c1]

The intermediate was prepared following the method described for Ex. 140. LC-MS (ESI): m/z (M+1)$^+$, 428.3.

Compound 170 was prepared following the method described for Ex. 141. LC-MS (ESI): m/z (M+1)$^+$, 494.4

Example 171

4-[(3-{[(3R)-1-(prop-2-enoyl)pyrrolidin-3-yl]amino}-1H-pyrazolo[3,4-b]pyridin-4-yl)oxy]-N-[4-(trifluoromethyl)pyridin-2-yl]benzamide (Compound ID 171)

1.87 Preparation of tert-butyl (3R)-3-({4-[4-(ethoxycarbonyl)phenoxy]-1-[(4-methoxyphenyl)methyl]-1H-pyrazolo[3,4-b]pyridin-3-yl}amino)pyrrolidine-1-carboxylate

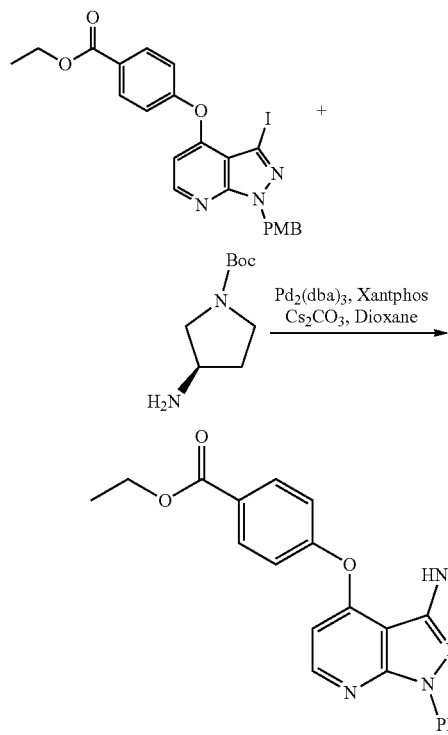

The intermediate was prepared following the method described for Ex. 86. LC-MS (ESI): m/z (M+1)$^+$, 588.0.

1.88 Preparation of 4-[(3-{[(3R)-1-[(tert-butoxy)carbonyl]pyrrolidin-3-yl]amino}-1-[(4-methoxyphenyl)methyl]-1H-pyrazolo[3,4-b]pyridin-4-yl)oxy]benzoic acid

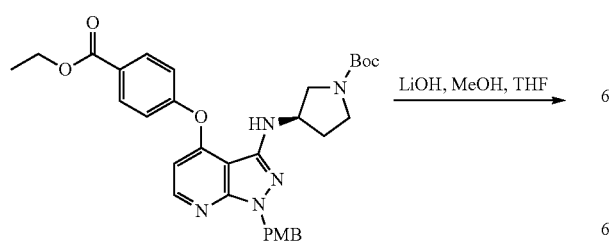

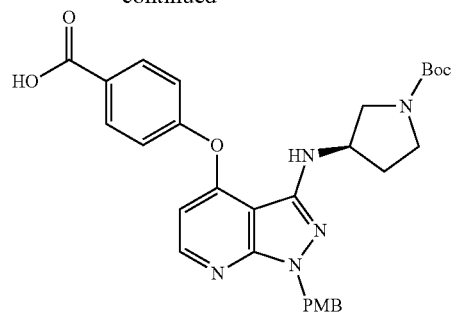

The intermediate was prepared following the method described for Ex. 161. LC-MS (ESI): m/z (M+1)$^+$, 560.0.

1.89 Preparation of tert-butyl (3R)-3-({1-[(4-methoxyphenyl)methyl]-4-(4-{[4-(trifluoromethyl)pyridin-2-yl]carbamoyl}phenoxy)-1H-pyrazolo[3,4-b]pyridin-3-yl}amino)pyrrolidine-1-carboxylate

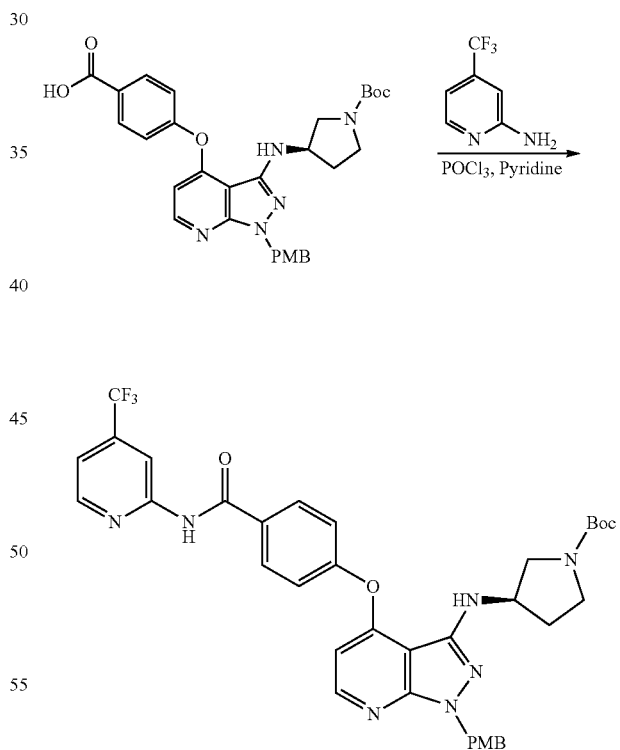

The intermediate was prepared following the method described for Ex. 161. LC-MS (ESI): m/z (M+1)$^+$, 704.0.

1.90 Preparation of 4-({1-[(4-methoxyphenyl)methyl]-3-{[(3R)-pyrrolidin-3-yl]amino}-1H-pyrazolo[3,4-b]pyridin-4-yl}oxy)-N-[4-(trifluoromethyl)pyridin-2-yl]benzamide; trifluoroacetic acid

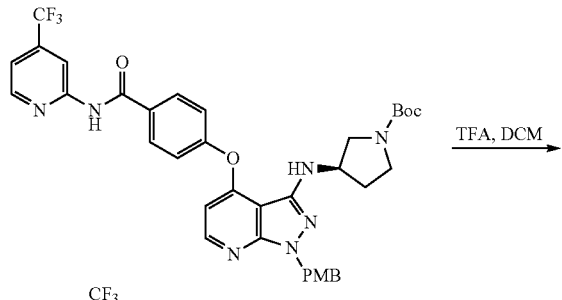

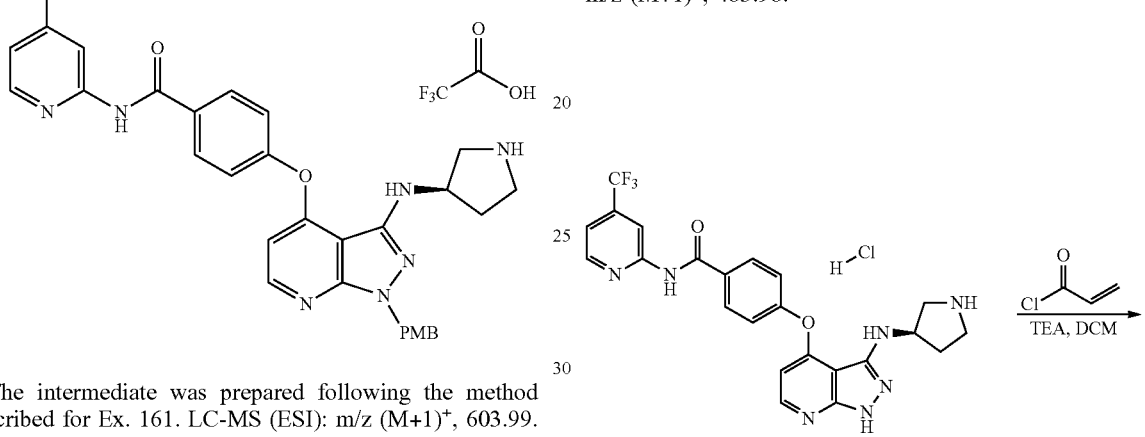

The intermediate was prepared following the method described for Ex. 161. LC-MS (ESI): m/z (M+1)⁺, 603.99.

1.91 Preparation of 4-[(3-{[(3R)-pyrrolidin-3-yl]amino}-1H-pyrazolo[3,4-b]pyridin-4-yl)oxy]-N-[4-(trifluoromethyl)pyridin-2-yl]benzamide hydrochloride 4-({1-[(4-Methoxyphenyl)methyl]-3-{[(3R)-pyrrolidin-3-yl]amino}-1H-pyrazolo[3,4-b]pyridin-4-yl}oxy)-N-[4-(trifluoromethyl)pyridin-2-yl]benzamide trifluoroacetic acid (4.87 g, 3.00 mmol) was dissolved in TFA (20 mL) and stirred at 50° C. for 7 hours then the solvent was evaporated. The crude product was dissolved in a mixture DCM/CH₃CN (8/13) and HCl 1M in EtO₂ was added. The mixture was stirred at r.t. for 1 hr, then it was concentrated. The crude was tritured with Et₂O and filtered to give 4-[(3-{[(3R)-pyrrolidin-3-yl]amino}-1H-pyrazolo[3,4-b]pyridin-4-yl)oxy]-N-[4-(trifluoromethyl)pyridin-2-yl]benzamide hydrochloride as a yellow solid (1.89 g, Yield: quantitative). LC-MS (ESI): m/z (M+1)⁺, 483.98.

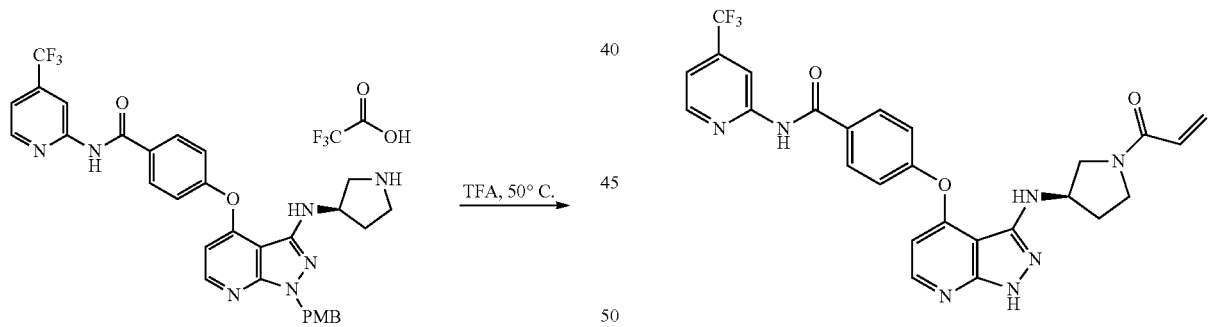

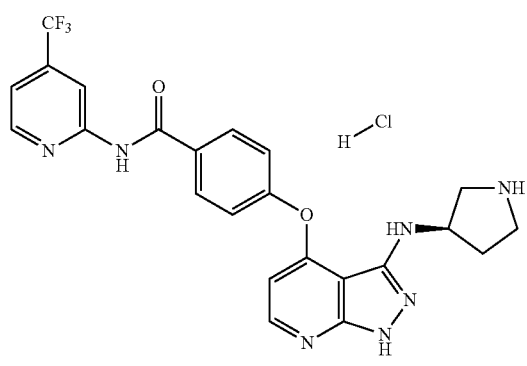

Compound 171 was prepared following the method described for Ex. 162. LC-MS (ESI): m/z (M+1)⁺, 537.95. ¹H NMR (500 MHz, DMSO-d₆) δ ppm 12.37 (br. s., 1H), 11.36 (br. s., 1H), 8.69 (d, J=5.38 Hz, 1H), 8.57-8.54 (m, 1H), 8.25-8.17 (m, 3H) 7.56 (d, J=4.40 Hz, 1H), 7.42 (d, J=7.34 Hz, 2H), 6.650-6.50 (m, 1H), 6.21-6.07 (m, 2H), 5.79-5.53 (m, 2H), 4.39-4.17 (m, 1H), 4.05-3.38 (m, 4H), 2.29-1.93 (m, 2H).

Example 172

N-(1,3-benzothiazol-2-yl)-4-[(3-{[(3R)-1-[4-(dimethylamino)butanoyl]piperidin-3-yl]amino}-1H-pyrazolo[3,4-b]pyridin-4-yl)oxy]benzamide (Compound ID 172)

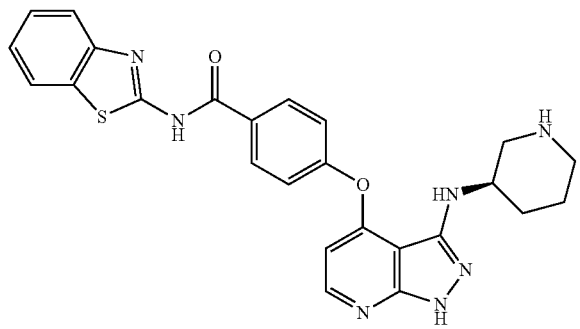

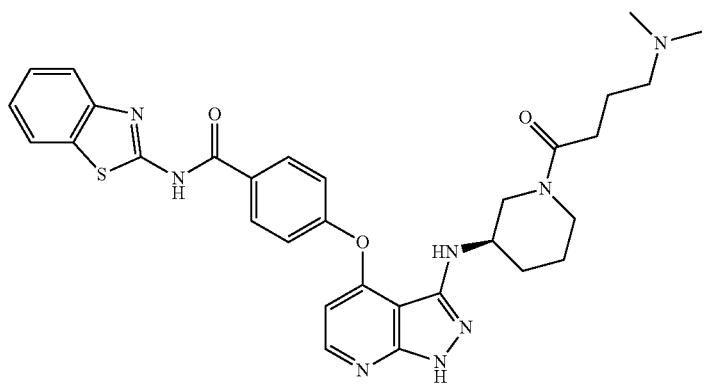

N-(1,3-Benzothiazol-2-yl)-4-[(3-{[(3R)-piperidin-3-yl]amino}-1H-pyrazolo[3,4-b]pyridin-4-yl)oxy]benzamide (200.1 mg, 0.412 mmol) was dissolved in DMF (3 mL). EDC HCl (57.1 mg, 0.494 mmol), HOBt (57.1 mg, 0.412 mmol), TEA (0.115 mL, 0.824 mmol) and 4-(dimethylamino)butanoic acid hydrochloride (83.1 mg, 0.494 mmol) were added and the mixture was stirred overnight at room temperature. EtOAc was added and the mixture was washed with water. The organic layer was collected, dried over $Na_2SO_4$, filtered and concentrated and the crude was purified by gradient flash chromatography (silica gel NH 28 g, DCM methanol from 100/0 to 95/5). N-(1,3-Benzothiazol-2-yl)-4-[(3-{[(3R)-1-[4-(dimethylamino)butanoyl]piperidin-3-yl]amino}-1H-pyrazolo[3,4-b]pyridin-4-yl)oxy]benzamide was obtained as a pale yellow solid (117.5 mg, Yield 48%). LC-MS (ESI): m/z (M+1)$^+$, 599.0. $^1$H NMR (500 MHz, DMSO-d6) δ ppm 12.45-12.19 (m, 2H), 8.30 (d, J=8.80 Hz, 2H), 8.23-8.18 (m, 1H), 8.05-7.71 (m, 2H), 7.52-7.27 (m, 4H), 6.25-6.15 (m, 1H), 5.30-5.11 (m, 1H), 3.73-3.56 (m, 1H), 4.46-2.81 (m, 4H), 2.39-2.16 (m, 4H), 2.19-2.06 (m, 6H), 2.40-1.26 (m, 6H).

Example 173

4-[(3-{[(3R)-1-cyclopropanecarbonylpiperidin-3-yl]amino}-1H-pyrazolo[3,4-b]pyridin-4-yl)oxy]-N-[4-(trifluoromethyl)pyridin-2-yl]benzamide hydrochloride (Compound ID 173)

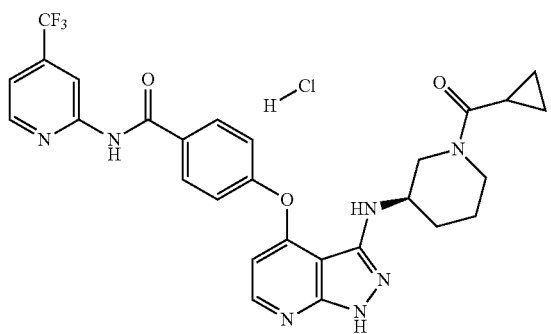

1.92 Preparation of 4-[(3-{[(3R)-1-cyclopropanecarbonylpiperidin-3-yl]amino}-1H-pyrazolo[3,4-b]pyridin-4-yl)oxy]-N-[4-(trifluoromethyl)pyridin-2-yl]benzamide

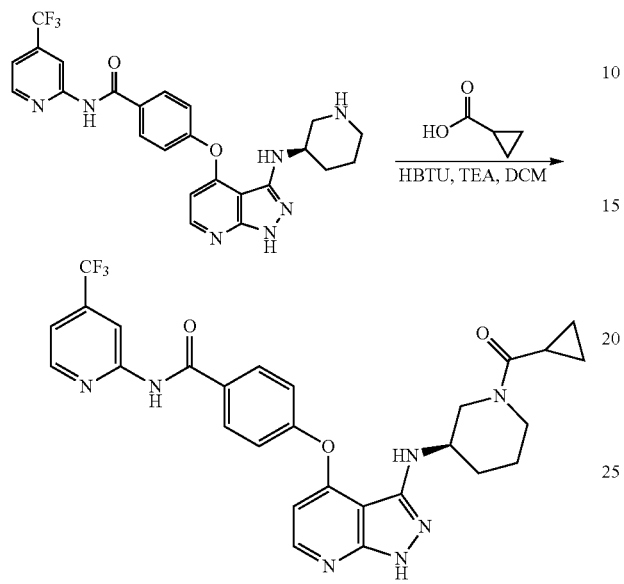

To a solution of 4-[(3-{[(3R)-piperidin-3-yl]amino}-1H-pyrazolo[3,4-b]pyridin-4-yl)oxy]-N-[4-(trifluoromethyl)pyridin-2-yl]benzamide (164.0 mg, 0.28 mmol) in DCM (6 mL) were added cyclopropanecarboxylic acid (29 mg, 0.336 mmol), TEA (117 µL, 0.84 mmol) and HTBU (130.0 mg, 0.342 mmol) and the mixture was stirred at room temperature for 16 hours. Water (10 mL) and aqueous saturated solution of NaHCO₃ (10 mL) were added and the product was extracted twice with AcOEt. The collected organic phases were dried over Na₂SO₄, filtered and concentrated. The product was purified by preparative HPLC (C18 column, CH₃CN in 10 mM ammonium bicarbonate aqueous solution adjusted to pH 10 with ammonia) to give 4-[(3-{[(3R)-1-cyclopropanecarbonylpiperidin-3-yl]amino}-1H-pyrazolo[3,4-b]pyridin-4-yl)oxy]-N-[4-(trifluoromethyl)pyridin-2-yl]benzamide as a yellow solid (90.0 mg, Yield: 57%). LC-MS (ESI): m/z (M+1)⁺, 566.9.

Compound ID 173 was prepared following the method described for Ex. 161. LC-MS (ESI): m/z (M+1)⁺, 566.0. ¹H NMR (500 MHz, DMSO) δ 12.36 (br. s, 1H), 11.39 (br. s, 1H), 8.70 (d, J=5.38 Hz, 1H), 8.56 (s, 1H), 8.33-8.11 (m, 3H), 7.56 (d, J=5.38 Hz, 1H), 7.52-7.34 (m, 2H), 6.18 (br. s., 1H), 5.28 (br. s., 1H), 4.49-2.83 (m, 5H), 2.15-1.30 (m, 5H), 0.85-0.37 (m, 4H).

Example 174

4-[(3-{[(3R)-1-(but-2-ynoyl)pyrrolidin-3-yl]amino}-1H-pyrazolo[3,4-b]pyridin-4-yl)oxy]-N-[4-(trifluoromethyl)pyridin-2-yl]benzamide (Compound ID 174)

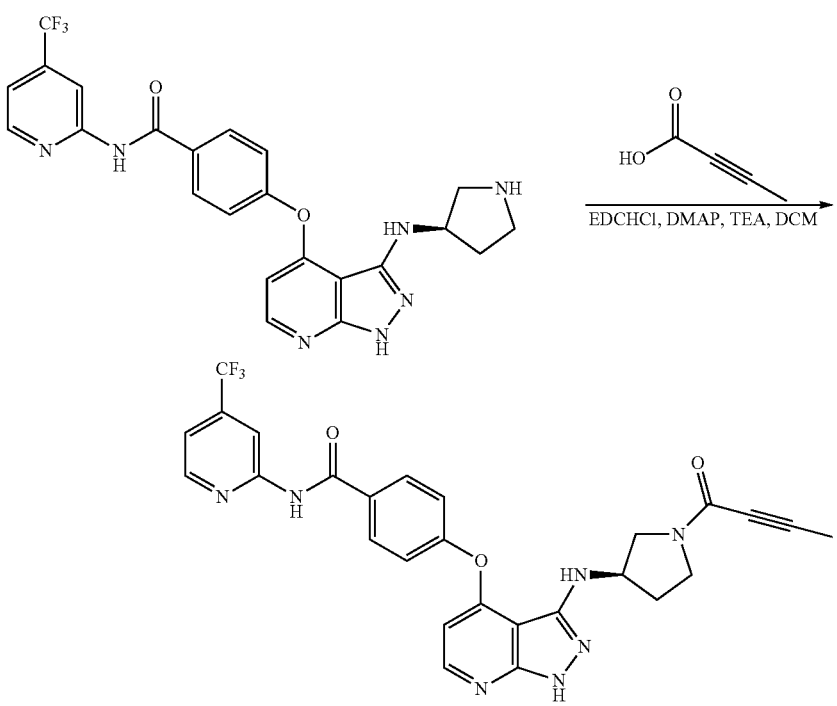

The compound was prepared following the method described for Ex. 141. LC-MS (ESI): m/z (M+1)⁺, 550.0. ¹H NMR (500 MHz, DMSO-d₆) δ ppm 12.34 (br. s, 1H), 11.42-11.33 (m, 1H), 8.69 (d, J=4.89 Hz, 1H), 8.56 (s, 1H), 8.24-8.17 (m, 3H), 7.56 (d, J=4.89 Hz, 1H), 7.46-7.40 (m, 2H), 6.18-6.13 (m, 1H), 5.74-5.64 (m, 1H), 4.35-4.21 (m, 1H), 4.02-3.34 (m, 4H), 2.32-2.01 (m, 2H), 1.99 (s, 3H).

Example 175

4-[(3-{[(3R)-1-(but-2-ynoyl)piperidin-3-yl]amino}-1H-pyrazolo[3,4-b]pyridine-4-yl)oxy]-N-(dimethyl-1,3-thiazol-2-yl)benzamide (Compound ID 175)

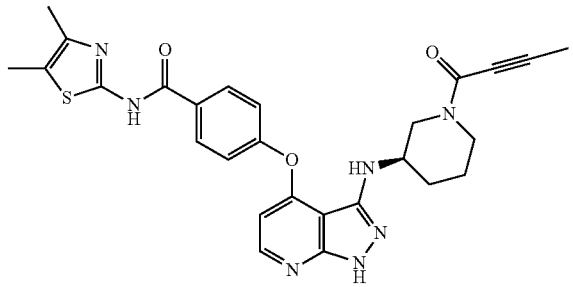 [SMILES: CC#CC(=O)N1CCC[C@@H](Nc2n[nH]c3nccc(Oc4ccc(C(=O)Nc5nc(C)c(C)s5)cc4)c23)C1]

The compound was prepared following the method described for Ex. 141. LC-MS (ESI): m/z (M+1)+, 530.2. 1H NMR (500 MHz, DMSO) δ 12.74-11.92 (m, 2H), 8.33-7.90 (m, 3H), 7.41 (d, J=8.80 Hz, 2H), 6.30-6.05 (m, 1H), 5.21 (dd, J=16.14, 7.83 Hz, 1H), 4.44-3.42 (m, 3H), 3.27-2.84 (m, 2H), 2.28 (s, 3H), 2.21 (s, 3H), 2.08-1.35 (m, 7H).

Example 176

(3R)-3-[(4-{4-[(1,3-benzothiazol-2-yl)carbamoyl]phenoxy}-1H-pyrazolo[3,4-b]pyridin-3-yl)amino]-N-ethylpiperidine-1-carboxamide hydrochloride (Compound ID 176)

To a solution of N-(1,3-benzothiazol-2-yl)-4-[(3-{[(3R)-piperidin-3-yl]amino}-1H-pyrazolo[3,4-b]pyridine-4-yl)oxy]benzamide (200.0 mg, 0.260 mmol) in DCM (1 mL) TEA (0 0.36 mL, 0.286 mmol) and Ethyl isocyanate (0.023 mL, 0.286 mmol) were added at 0 OC. The mixture was stirred at 0° C. for 1 hr then EtOAc was added ant the mixture was washed with water. The collected organic phases were dried over Na2SO4 and concentrated to give a crude that was purified by gradient flash chromatography (silica gel, 25 g, MeOH/DCM from 2/98 to 6/94). (3R)-3-[(4-{4-[(1,3-benzothiazol-2-yl)carbamoyl]phenoxy}-1H-pyrazolo[3,4-b]pyridin-3-yl)amino]-N-ethylpiperidine-1-carboxamide was obtained as a grey solid (187.0 mg, Yield: quantitative).

To (3R)-3-[(4-{4-[(1,3-benzothiazol-2-yl)carbamoyl]phenoxy}-1H-pyrazolo[3,4-b]pyridin-3-yl)amino]-N-ethylpiperidine-1-carboxamide was added MeOH (7 mL) and HCl in MeOH (0.78 mL, 1.25 M). The solution was stirred for 1 hr at room temperature and then the solvent was removed by evaporation. (3R)-3-[(4-{4-[(1,3-benzothiazol-2-yl)carbamoyl]phenoxy}-1H-pyrazolo[3,4-b]pyridin-3-yl)amino]-N-ethylpiperidine-1-carboxamide hydrochloride was obtained as a yellow solid (174.0 mg, Yield: 90%). LC-MS (ESI): m/z (M+1)+, 557.0. 1H NMR (500 MHz, DMSO-d6) δ ppm 13.01 (br.s., 1H) 8.42-8.25 (m, 3H), 8.04 (d, J=7.83 Hz, 1H), 7.80 (d, J=8.31 Hz, 1H), 7.61-7.44 (m, 3H), 7.41-7.27 (m, 1H), 6.66-6.31 (m, 2H), 6.21 (d, J=5.87 Hz, 2H), 3.99 (dd, J=12.72, 3.42 Hz, 1H), 3.72 (d, J=13.21 Hz, 1H), 3.67-3.58 (m, 1H), 3.01 (q, J=6.85 Hz, 2H), 2.91 (dd, J=12.72, 9.29 Hz, 1H), 2.79 (t, J=10.76 Hz, 1H), 2.10-1.93 (m, 1H), 1.72-1.53 (m, 2H), 1.50-1.34 (m, 1H), 0.97 (t, J=7.34 Hz, 3H).

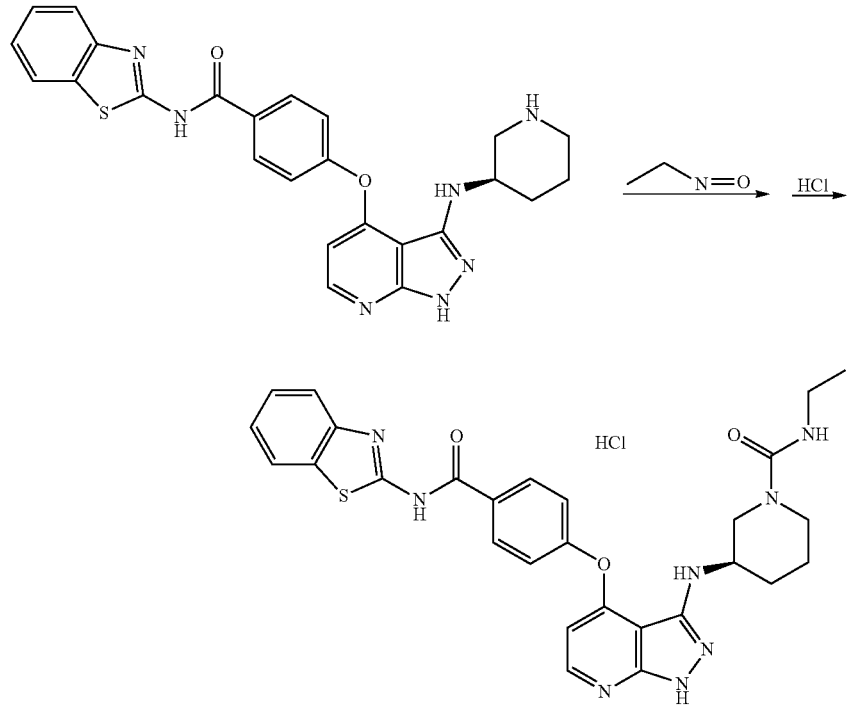

Example 177

4-[(3-{[(3R)-1-(but-2-ynoyl)piperidin-3-yl]amino}-1H-pyrazolo[3,4-b]pyridin-4-yl)oxy]-N-(5-ethyl-1,3-thiazol-2-yl)benzamide (Compound ID 177)

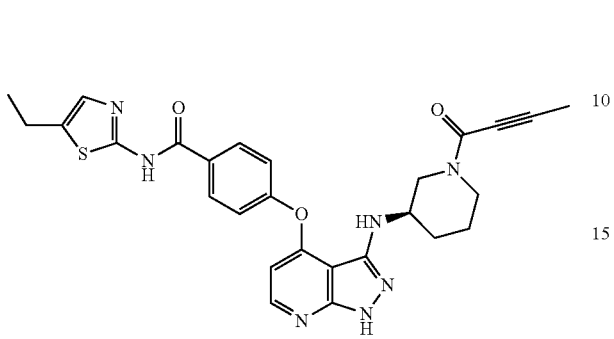

1.93 Preparation of tert-butyl (3R)-3-[(4-{4-[(5-ethyl-1,3-thiazol-2-yl)carbamoyl]phenoxy}-1-[(4-methoxyphenyl)methyl]pyrazolo[3,4-b]pyridin-3-yl)amino]piperidine-1-carboxylate

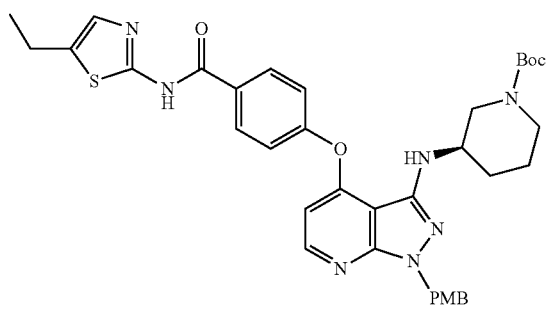

The intermediate was prepared following the method described for Ex. 137. LC-MS (ESI): m/z (M+1)$^+$, 684.0.

1.94 Preparation of (3R)-3-[(4-{4-[(5-ethyl-1,3-thiazol-2-yl)carbamoyl]phenoxy}-1-[(4-methoxyphenyl)methyl]pyrazolo[3,4-b]pyridin-3-yl)amino]piperidin-1-ium trifluoroacetate

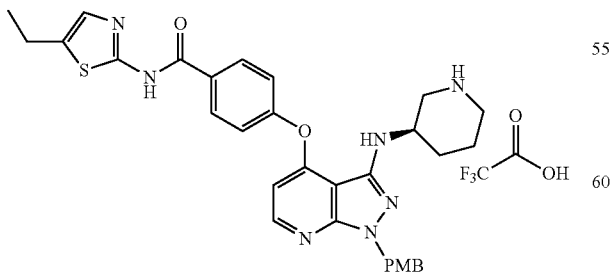

The intermediate was prepared following the method described for Ex. 137. LC-MS (ESI): m/z (M+1)$^+$, 584.0.

1.95 Preparation of N-(5-ethyl-1,3-thiazol-2-yl)-4-({3-[(3R)-piperidin-3-ylamino]-1H-pyrazolo[3,4-b]pyridin-4-yl}oxy)benzamide

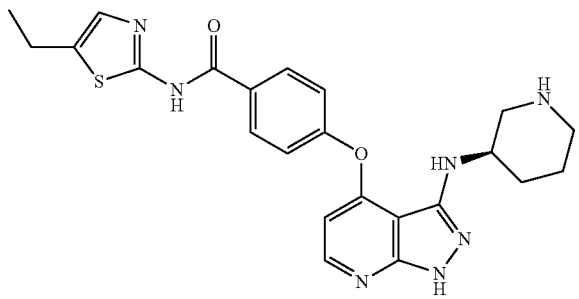 [SMILES: CCc1cnc(NC(=O)c2ccc(Oc3ccnc4[nH]nc(N[C@@H]5CCCNC5)c34)cc2)s1]

The intermediate was prepared following the method described for Ex. 137. LC-MS (ESI): m/z (M+1)$^+$, 464.0.

Compound 177 was prepared following the method described for Ex. 141. LC-MS (ESI): m/z (M+1)$^+$, 530.1. $^1$H NMR (500 MHz, DMSO) δ 12.85-11.92 (m, 2H), 8.27-8.15 (m, 3H), 7.46-7.39 (m, 2H), 7.26 (s, 1H), 6.17 (dd, J=7.34, 5.38 Hz, 1H), 5.21 (dd, J=17.61, 7.83 Hz, 1H), 4.43-3.44 (m, 3H), 3.24-2.85 (m, 2H), 2.78 (q, J=7.34 Hz, 2H), 2.06-1.34 (m, 7H), 1.26 (t, J=7.58 Hz, 3H).

Example 178

N-(5-methyl-1,2-oxazol-3-yl)-4-[(3-{[(3R)-1-(prop-2-enoyl)piperidin-3-yl]amino}-1H-pyrazolo[3,4-b]pyridin-4-yl)oxy]benzamide (Compound ID 178)

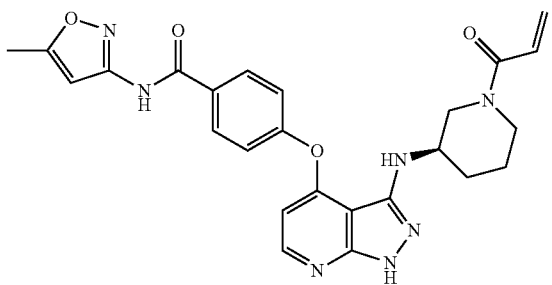 [SMILES: C=CC(=O)N1CCC[C@@H](Nc2n[nH]c3nccc(Oc4ccc(C(=O)Nc5cc(C)on5)cc4)c23)C1]

1.96 Preparation of tert-butyl (3R)-3-({1-[(4-methoxyphenyl)methyl]-4-{4-[(5-methyl-1,2-oxazol-3-yl)carbamoyl]phenoxy}-1H-pyrazolo[3,4-b]pyridin-3-yl}amino)piperidine-1-carboxylate

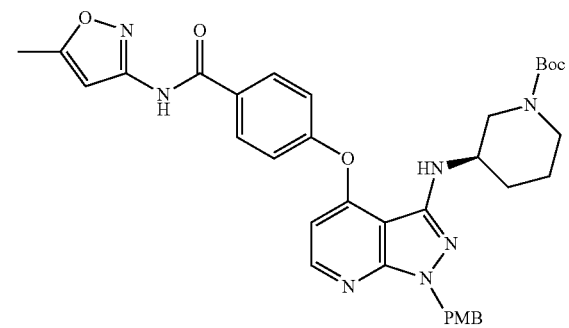

The intermediate was prepared following the method described for Ex. 140. LC-MS (ESI): m/z (M+1)+, 654.1.

1.97 Preparation of 4-({1-[(4-methoxyphenyl)methyl]-3-{[(3R)-piperidin-3-yl]amino}-1H-pyrazolo[3,4-b]pyridin-4-yl}oxy)-N-(5-methyl-1,2-oxazol-3-yl)benzamide trifluoroacetate

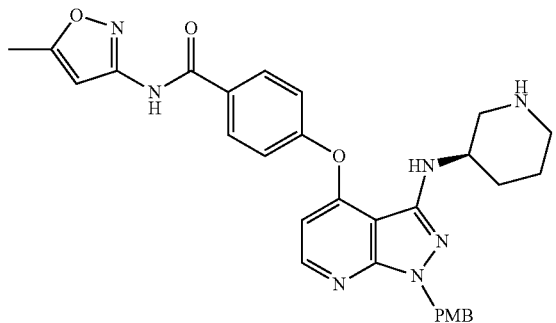

The intermediate was prepared following the method described for Ex. 140. LC-MS (ESI): m/z (M+1)+, 554.1.

1.98 Preparation of N-(5-methyl-1,2-oxazol-3-yl)-4-[(3-{[(3R)-piperidin-3-yl]amino}-1H-pyrazolo[3,4-b]pyridin-4-yl)oxy]benzamide

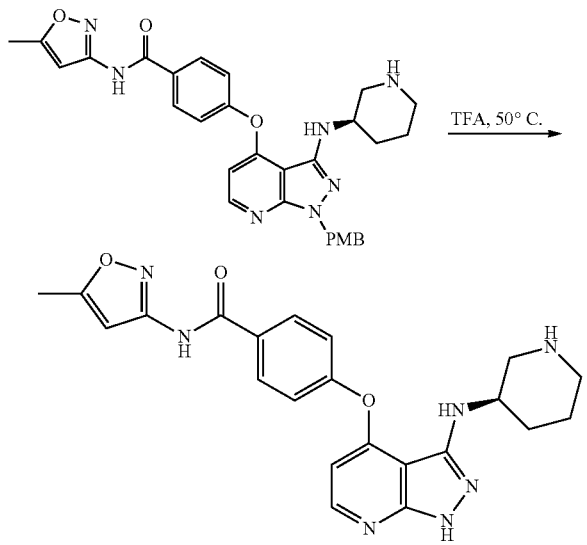

4-({1-[(4-methoxyphenyl)methyl]-3-{[(3R)-piperidin-3-yl]amino}-1H-pyrazolo[3,4-b]pyridin-4-yl})oxy)-N-(5-methyl-1,2-oxazol-3-yl)benzamide trifluoroacetate (0.856 g, 0.52 mmol) was dissolved in TFA (10 mL) and stirred at 50° C. for 6.5 hours. TFA was evaporated and the crude was purified by SCX cartridge affording N-(5-methyl-1,2-oxazol-3-yl)-4-[(3-{[(3R)-piperidin-3-yl]amino}-1H-pyrazolo[3,4-b]pyridin-4-yl)oxy]benzamide as a yellow solid (0.180 mg, Yield: 78%). LC-MS (ESI): m/z (M+1)+, 434.1.

Compound 178 was prepared following the method described for Ex. 140. LC-MS (ESI): m/z (M+1)+, 488.2. 1H NMR (500 MHz, DMSO-d6) δ ppm 12.31 (br. s., 1H), 11.37 (s, 1H), 8.26-8.11 (m, 3H), 7.45-7.36 (m, 2H), 6.77 (s, 1H), 6.87-6.66 (m, 1H), 6.15 (d, J=5.38 Hz, 1H), 6.10-6.01 (m, 1H), 5.68-5.51 (m, 1H), 5.30-5.16 (m, 1H), 4.49-4.08 (m, 1H), 4.06-3.78 (m, 1H), 3.70-3.58 (m, 1H), 3.29-2.80 (m, 2H), 2.43 (s, 3H), 2.10-1.36 (m, 4H).

Example 179

N-(5-ethyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide (Compound ID 179)

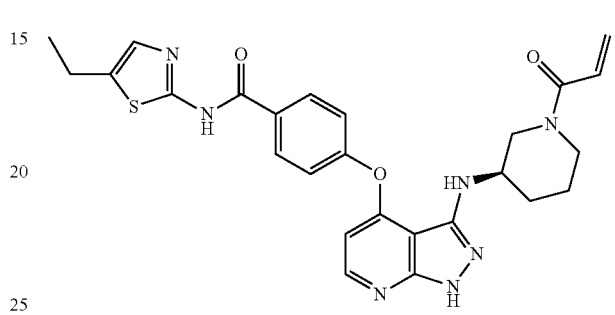

The compound was prepared following the method described for Ex. 140. LC-MS (ESI): m/z (M+1)+, 518.1. 1H NMR (500 MHz, DMSO) δ 12.80-11.77 (m, 2H), 8.28-8.11 (m, 3H), 7.38 (d, J=7.83 Hz, 2H), 7.22 (s, 1H), 6.60-6.90 (m, 1H), 6.14 (d, J=5.38 Hz, 1H), 6.04 (d, J=16.63 Hz, 1H), 5.67-5.49 (m, 1H), 5.21 (d, J=7.34 Hz, 1H), 4.46-3.76 (m, 2H), 3.61 (br. s., 1H), 3.25-2.85 (m, 2H), 2.76 (q, J=7.34 Hz, 2H), 2.00 (d, J=9.78 Hz, 1H), 1.68 (br. s., 2H), 1.43 (br. s., 1H), 1.23 (t, J=7.58 Hz, 3H).

Example 180

4-[(3-{[(3R)-1-(but-2-ynoyl)piperidin-3-yl]amino}-1H-pyrazolo[3,4-b]pyridin-4-yl)oxy]-N-(5-methyl-1,3,4-thiadiazol-2-yl)benzamide (Compound ID 180)

1.99 Preparation of tert-butyl (3R)-3-({1-[(4-methoxyphenyl)methyl]-4-{4-[(5-methyl-1,3,4-thiadiazol-2-yl)carbamoyl]phenoxy}-1H-pyrazolo[3,4-b]pyridin-3-yl}amino)piperidine-1-carboxylate

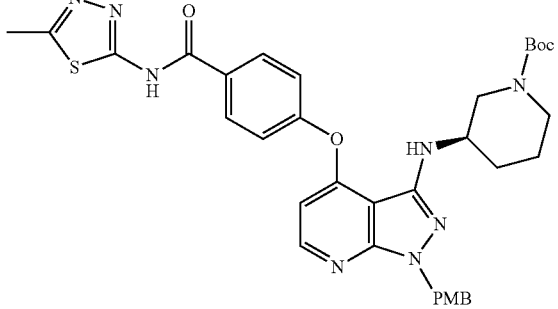

The intermediate was prepared following the method described for Ex. 140. LC-MS (ESI): m/z (M+1)+, 588.1.

1.100 Preparation of 4-({1-[(4-methoxyphenyl)methyl]-3-{[(3R)-piperidin-3-yl]amino}-1H-pyrazolo[3,4-b]pyridin-4-yl}oxy)-N-(5-methyl-1,3,4-thiadiazol-2-yl)benzamide trifluoroacetate

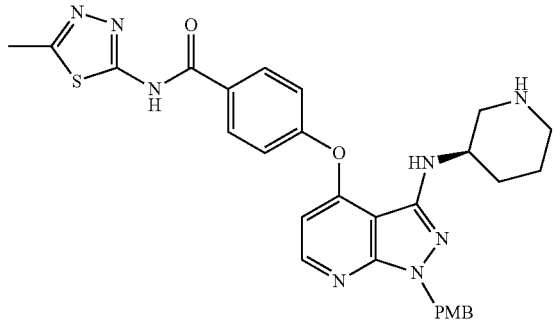

The intermediate was prepared following the method described for Ex. 140. LC-MS (ESI): m/z (M+1)⁺, 571.0.

1.101 Preparation of N-(5-methyl-1,3,4-thiadiazol-2-yl)-4-[(3-{[(3R)-piperidin-3-yl]amino}-1H-pyrazolo[3,4-b]pyridin-4-yl)oxy]benzamide

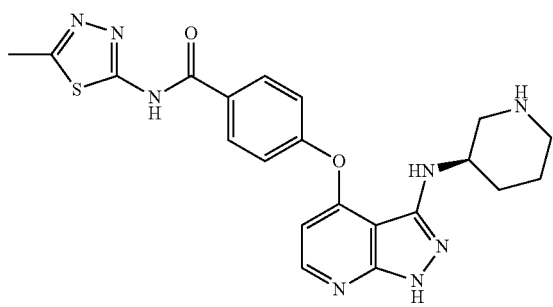 [SMILES: Cc1nnc(NC(=O)c2ccc(Oc3ccnc4[nH]nc(N[C@@H]5CCCNC5)c34)cc2)s1]

The intermediate was prepared following the method described for Ex. 178. LC-MS (ESI): m/z (M+1)⁺, 571.0.

Under nitrogen a solution of N-(5-methyl-1,3,4-thiadiazol-2-yl)-4-[(3-{[(3R)-piperidin-3-yl]amino}-1H-pyrazolo[3,4-b]pyridin-4-yl)oxy]benzamide (121.1 mg, 0.27 mmol), 2-butynoic acid (20.7 mg, 0.27 mmol), EDC·HCl (105.8 mg, 0.54 mmol) and DMAP (3.3 mg, 0.027 mmol) in DCM (4 mL) was stirred at room temperature for 3 hr. The mixture was concentrated to give a crude product that was purified by gradient flash chromatography (RP silica gel, 30 g, water (0.1% v/v formic acid)/acetonitrile from 0/10 to 10/0). 4-[(3-{[(3R)-1-(but-2-ynoyl)piperidin-3-yl]amino}-1H-pyrazolo[3,4-b]pyridin-4-yl)oxy]-N-(5-methyl-1,3,4-thiadiazol-2-yl)benzamide was obtained as a pale red solid (38.3 mg, Yield: 27%). LC-MS (ESI): m/z (M+1)⁺, 517.2. ¹H NMR (500 MHz, DMSO-d6) δ ppm 12.95 (br. s., 1H), 12.39-12.23 (m, 1H), 8.26 (d, J=8.80 Hz, 2H), 8.23-8.18 (m, 1H), 7.50-7.37 (m, 2H), 6.24-6.15 (m, 1H), 5.28-5.17 (m, 1H), 4.24 (d, J=15.65 Hz, 1H), 3.81-3.65 (m, 1H), 3.46 (dd, J=12.72, 7.83 Hz, 1H), 3.11 (t, J=9.54 Hz, 1H), 2.88 (dd, J=12.47, 9.54 Hz, 1H), 2.65 (s, 3H), 2.01 (s, 2H), 1.79 (s, 2H), 1.77-1.68 (m, 1H), 1.68-1.33 (m, 2H).

Example 181

4-[(3-{[(3R)-1-(but-2-ynoyl)pyrrolidin-3-yl]amino}-1H-pyrazolo[3,4-b]pyridin-4-yl)oxy]-N-(5-methyl-1,3-thiazol-2-yl)benzamide (Compound ID 181)

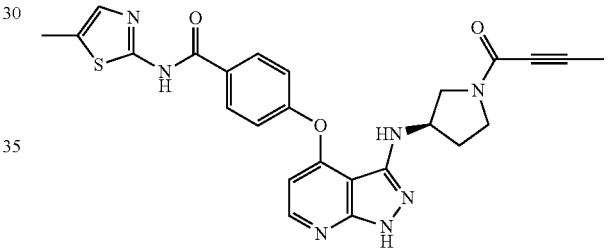

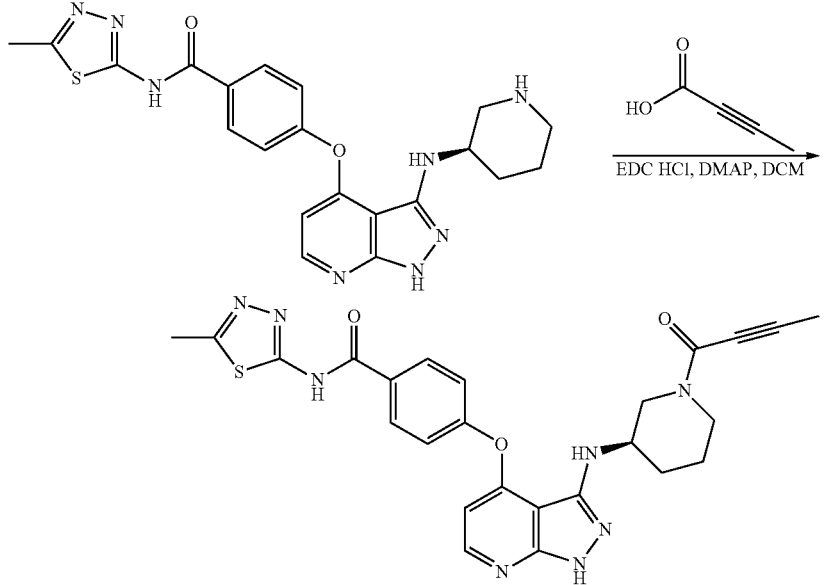

1.102 Preparation of N-(5-methyl-1,3-thiazol-2-yl)-4-[(3-{[(3R)-pyrrolidin-3-yl]amino}-1H-pyrazolo[3,4-b]pyridin-4-yl)oxy]benzamide

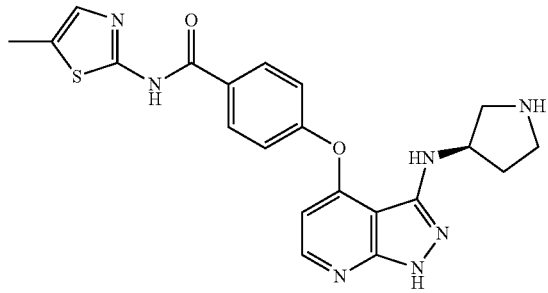 [SMILES: Cc1cnc(NC(=O)c2ccc(Oc3ccnc4[nH]nc(N[C@@H]5CCNC5)c34)cc2)s1]

The intermediate was prepared following the method described for Ex. 140. LC-MS (ESI): m/z (M+1)+, 435.9.

Compound 181 was prepared following the method described for Ex. 141. LC-MS (ESI): m/z (M+1)+, 502.1. $^1$H NMR (500 MHz, DMSO) δ 12.40 (br. s, 2H), 8.27-8.14 (m, 3H), 7.45-7.38 (m, 2H), 7.24-7.20 (m, 1H), 6.19-6.11 (m, 1H), 5.73-5.63 (m, 1H), 4.34-4.21 (m, 1H), 4.01-3.34 (m, 4H), 2.38 (s, 3H), 2.26-2.19 (m, 1H), 2.07-2.01 (m, 1H), 1.98 (s, 3H).

Example 182

(3R)—N-ethyl-3-({4-[4-(7-methyl-1,3-benzoxazol-2-yl)phenoxy]-1H-pyrazolo[3,4-b]pyridin-3-yl}amino)piperidine-1-carboxamide (Compound ID 182)

1.103 Preparation of 4-(7-methyl-1,3-benzoxazol-2-yl)phenol

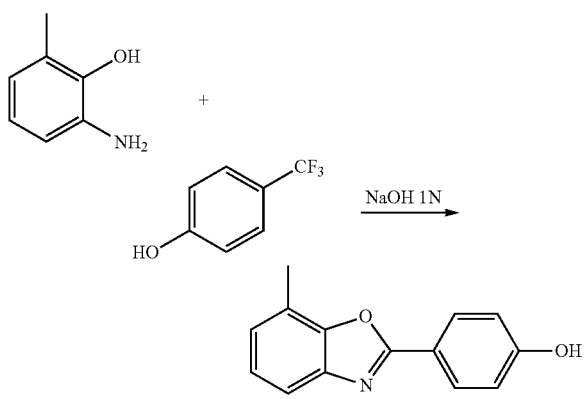

In a sealed tube 4-(trifluoromethyl)phenol (700 mg, 4.318 mmol) and 2-amino-6-methylphenol (745 mg, 6.045 mmol) were weighted and then, aqueous NaOH (17.27 mL, 1 M) was added. The reaction mixture was stirred at 90° C. for 2 h. The reaction was quenched by neutralization with HCl 1N. The obtained solid was filtered and washed with HCl 1N and then with water. The filter cake was dried under vacuum overnight to afford 884.8 mg of violet solid, identified as 4-(7-methyl-1,3-benzoxazol-2-yl)phenol (yield 91%). LC-MS (ESI): m/z (M+1) 226.20.

1.104 Preparation of (3R)—N-{4-[4-(7-methyl-1,3-benzoxazol-2-yl)phenoxy]-1H-pyrazolo[3,4-b]pyridin-3-yl}piperidin-3-amine

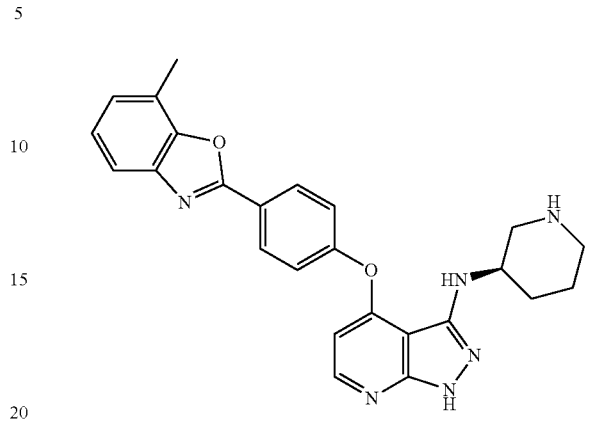

The compound was prepared following the method described for Ex. 148. LC-MS (ESI): m/z (M+1) 441.4.

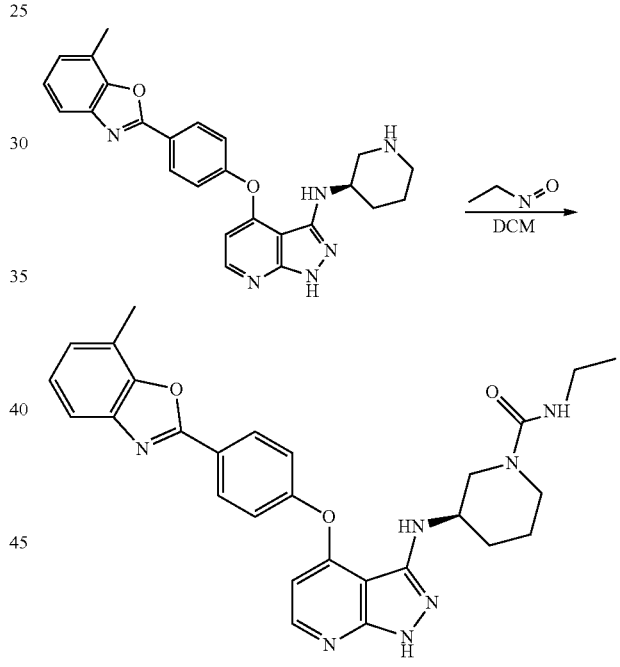

At 0° C., to a solution of (3R)—N-{4-[4-(7-methyl-1,3-benzoxazol-2-yl)phenoxy]-1H-pyrazolo[3,4-b]pyridin-3-yl}piperidin-3-amine, (104.3 mg, 0.236 mmol) in DCM (2 mL) were added TEA (0.066 mL, 0.473 mmol) and ethyl isocyanate (0.02 mL, 0.259 mmol). The resulting mixture was stirred at the same temperature for 90 min. The reaction mixture was, then, poured into a satured solution of NH$_4$Cl (15 mL) and it was extracted with EtOAc. The organic phase was washed with NaHCO$_3$ saturated solution, dried on Na$_2$SO$_4$, filtered and concentrated under vacuum. The crude was purified by gradient flash chromatography on silica gel (10 g) eluting with AcOEt:MeOH from 0 to 20% to provide (3R)—N-ethyl-3-({4-[4-(7-methyl-1,3-benzoxazol-2-yl)phenoxy]-1H-pyrazolo[3,4-b]pyridin-3-yl}amino)piperidine-1-carboxamide as yellow solid (77.8 mg, yield 64%). LC-MS (ESI): m/z (M+1) 512.4.

Example 183

N-(1,3-benzothiazol-2-yl)-4-[(3-{[(3R)-1-(but-2-ynoyl)piperidin-3-yl]amino}-1H-pyrazolo[3,4-b]pyridin-4-yl)oxy]benzamide (Compound ID 183)

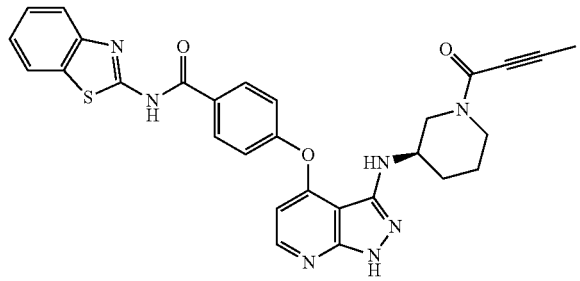 [SMILES: CC#CC(=O)N1CCC[C@@H](Nc2n[nH]c3nccc(Oc4ccc(C(=O)Nc5nc6ccccc6s5)cc4)c23)C1]

The intermediate was prepared following the method described for Ex. 180. LC-MS (ESI): m/z (M+1)$^+$, 552.0. $^1$H NMR (500 MHz, DMSO) δ 13.32-12.58 (m, 1H), 12.41-12.22 (m, 1H), 8.30 (d, J=8.80 Hz, 2H), 8.23-8.18 (m, 1H), 8.05-7.98 (m, 1H), 7.81-7.73 (m, 1H), 7.52-7.42 (m, 3H), 7.37-7.30 (m, 1H), 6.23-6.17 (m, 1H), 5.29-5.17 (m, 1H), 4.51-4.18 (m, 1H), 4.07-3.74 (m, 1H), 3.75-3.52 (m, 1H), 3.50-2.81 (m, 2H), 2.07-1.76 (m, 3H), 2.13-1.33 (m, 4H).

Example 184

(3R)—N-{4-[4-(7-methyl-1,3-benzoxazol-2-yl)phenoxy]-1H-pyrazolo[3,4-b]pyridin-3-yl}-1-(1-methylpiperidine-4-carbonyl)piperidin-3-amine (Compound ID 184)

1.105 Preparation of (3R)—N-{4-[4-(7-methyl-1,3-benzoxazol-2-yl)phenoxy]-1H-pyrazolo[3,4-b]pyridin-3-yl}piperidin-3-amine

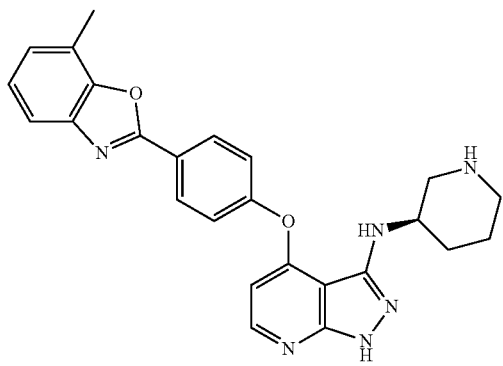 [SMILES: Cc1cccc2nc(-c3ccc(Oc4ccnc5[nH]nc(N[C@@H]6CCCNC6)c45)cc3)oc12]

The compound was prepared following the method described for Ex. 148. LC-MS (ESI): m/z (M+1) 441.4.

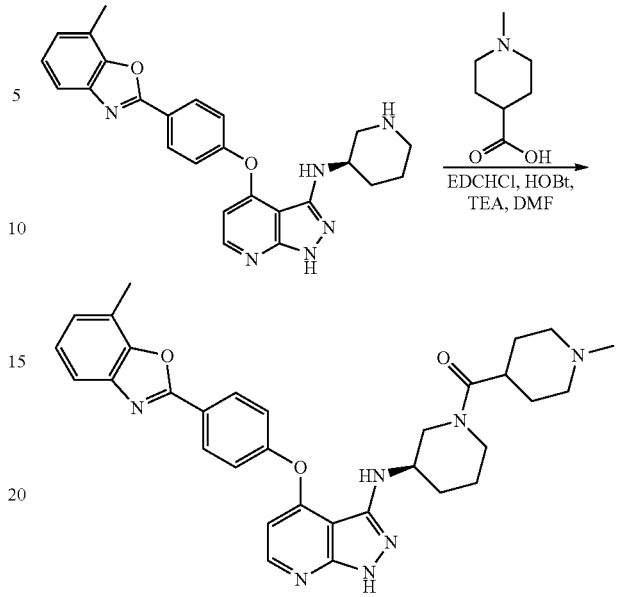

To a solution of (3R)—N-{4-[4-(7-methyl-1,3-benzoxazol-2-yl)phenoxy]-1H-pyrazolo[3,4-b]pyridin-3-yl}piperidin-3-amine (104.3 mg, 0.236 mmol) and TEA (0.07 mL, 0.472 mmol) in DMF (3 mL), 1-methylpiperidine-4-carboxylic acid hydrochloride (50.65 mg, 0.283 mmol), HOBt (31.88 mg, 0.236 mmol), EDC hydrochloride (54.29 mg, 0.283 mmol) were added and the mixture was stirred overnight at RT. The crude was poured into ice and was extracted with EtOAc (20 mL×3), the organic phase was dried over Na2SO4, filtered, and dried under vacuum. The crude was purified by gradient flash chromatography on silica gel (25 g) eluting with AcOEt:MeOH from 0% to 60% to afford 76.2 mg of (3R)—N-{4-[4-(7-methyl-1,3-benzoxazol-2-yl)phenoxy]-1H-pyrazolo[3,4-b]pyridin-3-yl}-1-(1-methylpiperidine-4-carbonyl)piperidin-3-amine (yield 57%). LC-MS (ESI): m/z (M+1) 566.5.

Example 185

4-[(3-{[(3R)-1-(but-2-ynoyl)piperidin-3-yl]amino}-1H-pyrazolo[3,4-b]pyridin-4-yl)oxy]-N-(1,5-dimethyl-1H-pyrazol-3-yl)benzamide (Compound ID 185)

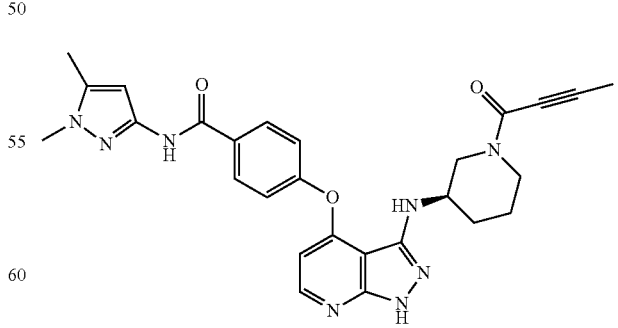

The compound was prepared following the method described for Ex. 141. LC-MS (ESI): m/z (M+1)$^+$, 513.2. $^1$H NMR (500 MHz, DMSO) δ 12.37-12.22 (m, 1H), 10.80-10.74 (m, 1H), 8.21-8.16 (m, 1H), 8.16-8.11 (m, 2H), 7.40-7.34 (m, 2H), 6.47-6.42 (m, 1H), 6.21-6.10 (m, 1H), 5.28-5.16 (m, 1H), 4.49-4.18 (m, 1H), 3.67 (s, 3H), 4.10-3.55 (m, 2H), 3.52-2.84 (m, 2H), 2.26 (s, 3H), 2.10-1.72 (m, 3H), 1.31-2.08 (m, 4H).

Example 186

N-ethyl-3-[4-(4-{[4-(trifluoromethyl)pyridin-2-yl]carbamoyl}phenoxy)-1H-pyrazolo[3,4-b]pyridin-3-yl]piperidine-1-carboxamide (Compound ID 186)

1.106 Preparation of tert-butyl3-{1-[(4-methoxyphenyl)methyl]-4-(4-{[4-(trifluoromethyl)pyridin-2-yl]carbamoyl}phenoxy)-1H-pyrazolo[3,4-b]pyridin-3-yl}piperidine-1-carboxylate

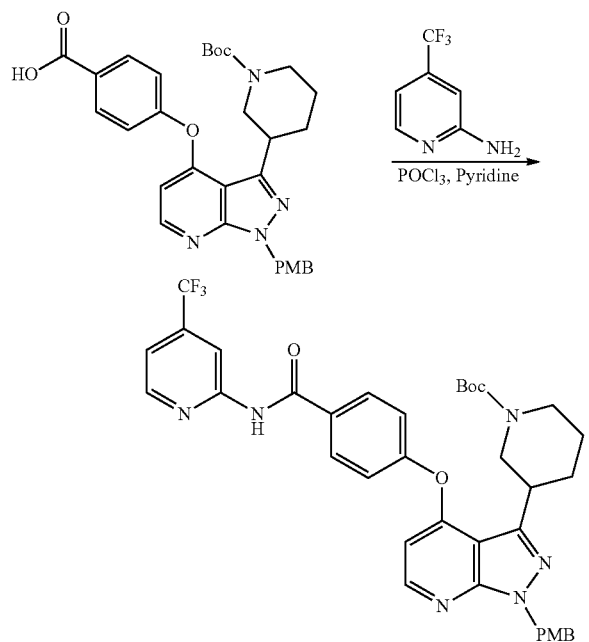

The intermediate was prepared following the method described for Ex. 161. LC-MS (ESI): m/z (M+1)+, 703.0.

1.107 Preparation of 4-({1-[(4-methoxyphenyl)methyl]-3-(piperidin-3-yl)-1H-pyrazolo[3,4-b]pyridin-4-yl}oxy)-N-[4-(trifluoromethyl)pyridin-2-yl]benzamide; trifluoroacetic acid

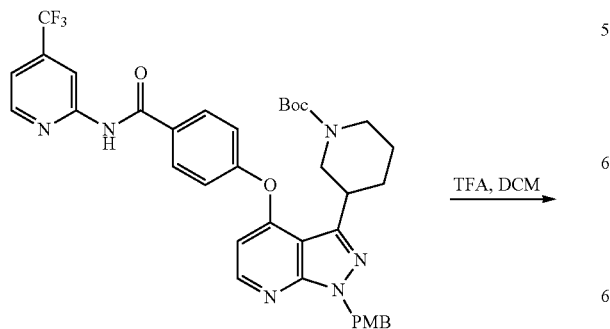

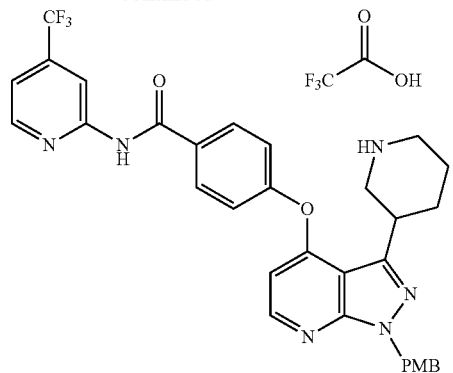

The intermediate was prepared following the method described for Ex. 161. LC-MS (ESI): m/z (M+1)+, 602.98.

1.108 Preparation of 4-{[3-(piperidin-3-yl)-1H-pyrazolo[3,4-b]pyridin-4-yl]oxy}-N-[4-(trifluoromethyl)pyridin-2-yl]benzamide

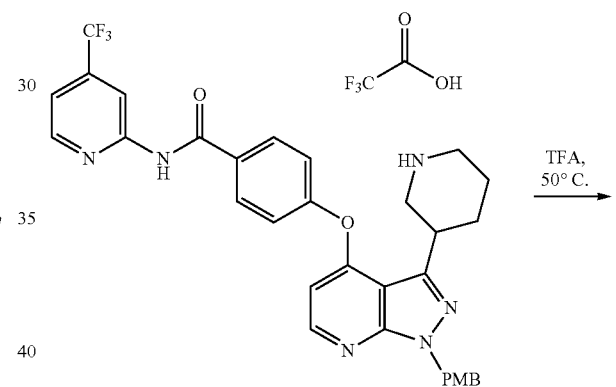

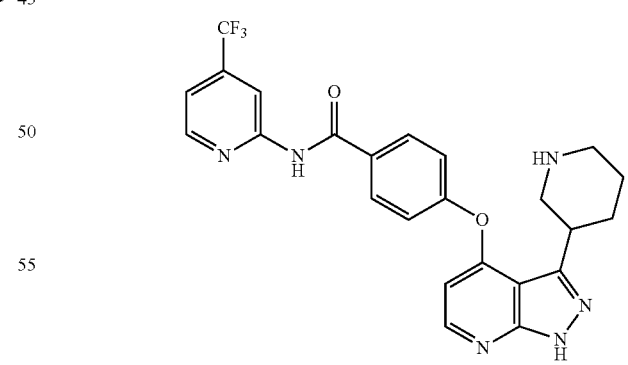

The intermediate was prepared following the method described for x. 161. LC-MS (ESI): m/z (M+1)+, 482.97.

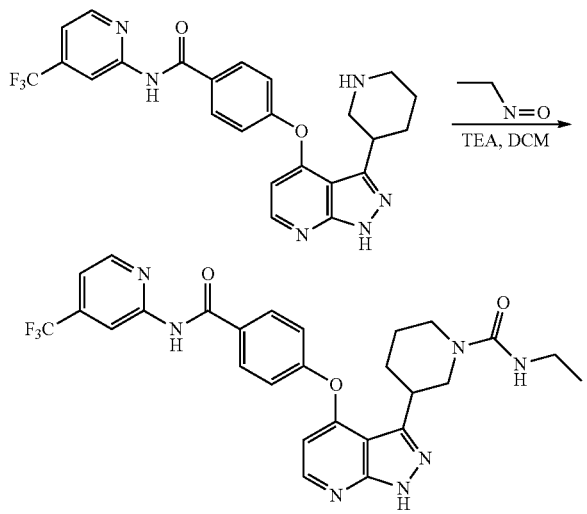

Compound 186 was prepared following the method described for Ex. 189. LC-MS (ESI): m/z (M+1)+, 554.0. ¹H NMR (400 MHz, DMSO-d₆) δ ppm 13.46 (br. s., 1H), 11.36 (br. s, 1H), 8.69 (d, J=5.40 Hz, 1H), 8.56 (s, 1H), 8.34 (d, J=5.38 Hz, 1H), 8.21 (d, J=8.80 Hz, 2H), 7.55 (d, J=5.38 Hz, 1H), 7.47 (d, J=8.80 Hz, 2H), 6.43-6.35 (m, 2H), 4.33 (d, J=13.21 Hz, 1H), 4.02 (d, J=12.72 Hz, 1H), 3.31-3.09 (m, 1H), 3.06-2.87 (m, 3H), 2.69-2.58 (m, 1H), 2.17-2.07 (m, 1H), 1.81 (qd, J=12.63, 3.67 Hz, 1H), 1.74-1.65 (m, 1H), 1.49-1.35 (m, 1H), 0.94 (t, J=7.09 Hz, 3H).

Example 187

N-(5-methyl-1,3,4-thiadiazol-2-yl)-4-[(3-{[(3R)-1-(prop-2-enoyl)piperidin-3-yl]amino}-1H-pyrazolo[3,4-b]pyridin-4-yl)oxy]benzamide (Compound ID 187)

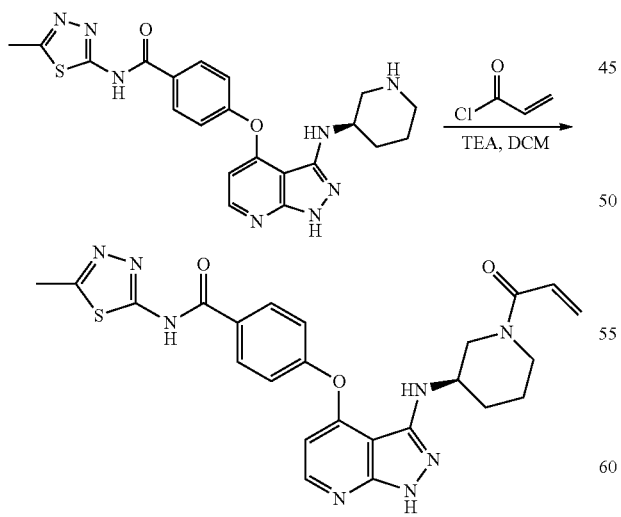

To a cooled solution (0° C.) of N-(5-methyl-1,3,4-thiadiazol-2-yl)-4-[(3-{[(3R)-piperidin-3-yl]amino}-1H-pyrazolo[3,4-b]pyridin-4-yl)oxy]benzamide (0.118 g, 0.27 mmol) and TEA (110 µL, 0.81 mmol) in DCM (3.5 mL) was added a solution of acryloyl chloride (24 µL, 0.3 mmol) in DCM (0.5 mL). The mixture was stirred at 0° C. for 40 min, then concentrated to give a solid that was purified by flash chromatography (silica gel 25 g, ethyl acetate methanol from 95/5 to 85/15). The obtained compound was further purified by flash chromatography (RP water+0.1% v/v of formic acid/acetonitrile from 10/0 to 0/10). N-(1,3-benzothiazol-2-yl)-4-[(3-{[(3R)-piperidin-3-yl]amino)}-1H-pyrazolo[3,4-b]pyridin-4-yl)oxy]benzamide was obtained as a pale yellow solid (21.6 mg, Yield: 16%). LC-MS (ESI): m/z (M+1)+, 505.1. ¹H NMR (500 MHz, DMSO-d6) δ ppm 12.95 (br. s., 1H), 12.30 (br. s, 1H), 8.25 (d, J=8.80 Hz, 2H), 8.20 (d, J=5.38 Hz, 1H), 7.47-7.38 (m, 2H), 6.87-6.63 (m, 1H), 6.18 (d, J=5.38 Hz, 1H), 6.11-6.01 (m, 1H), 5.70-5.54 (m, 1H), 5.24 (d, J=7.34 Hz, 1H), 4.50-4.11 (m, 1H), 4.05-3.77 (m, 1H), 3.70-3.58-(m, 1H), 3.29-2.86 (m, 2H), 2.65 (s, 3H), 2.13-1.37 (m, 4H).

Example 188

(3R)—N-ethyl-3-{[4-(4-{[4-(trifluoromethyl)pyridin-2-yl]carbamoyl}phenoxy)-1H-pyrazolo[3,4-b]pyridin-3-yl]amino}pyrrolidine-1-carboxamide (Compound ID 188)

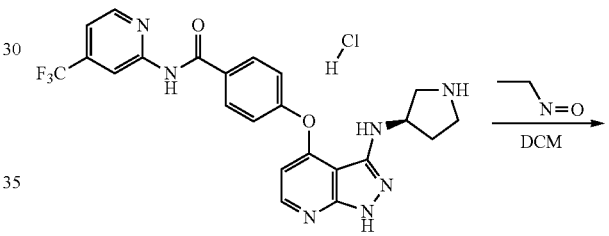

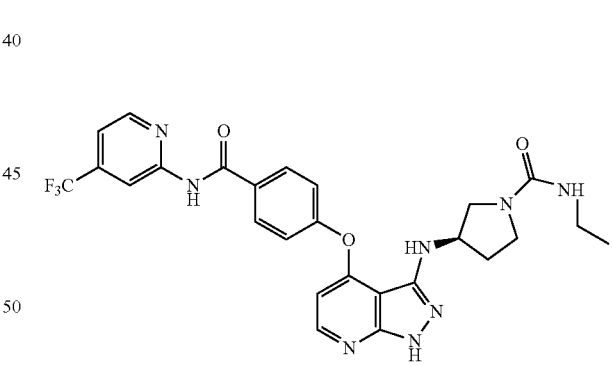

The compound was prepared following the method described for Ex. 189. LC-MS (ESI): m/z (M+1)+, 555.0. ¹H NMR (500 MHz, DMSO-d₆) δ ppm 12.31 (s, 1H), 11.37 (br. s., 1H), 8.67 (d, J=4.40 Hz, 1H), 8.57-8.51 (m, 1H), 8.25-8.15 (m, 3H), 7.52 (br. s., 1H), 7.41 (d, J=8.80 Hz, 2H), 6.14 (d, J=5.38 Hz, 1H), 6.06 (t, J=5.38 Hz, 1H), 5.52 (d, J=6.36 Hz, 4.29-4.15 (m, 1H), 3.62 (dd, J=10.27, 6.85 Hz, 1H), 3.43-3.19 (m, 3H), 3.07-2.96 (m, 2H), 2.23-2.11 (m, 1H), 2.07-1.92 (m, 1H), 0.99 (t, J=7.09 Hz, 3H).

Example 189

(3R)—N-ethyl-3-[(4-{4-[(5-methyl-1,3-thiazol-2-yl)carbamoyl]phenoxy}-1H-pyrazolo[3,4-b]pyridin-3-yl)amino]pyrrolidine-1-carboxamide (Compound ID 189)

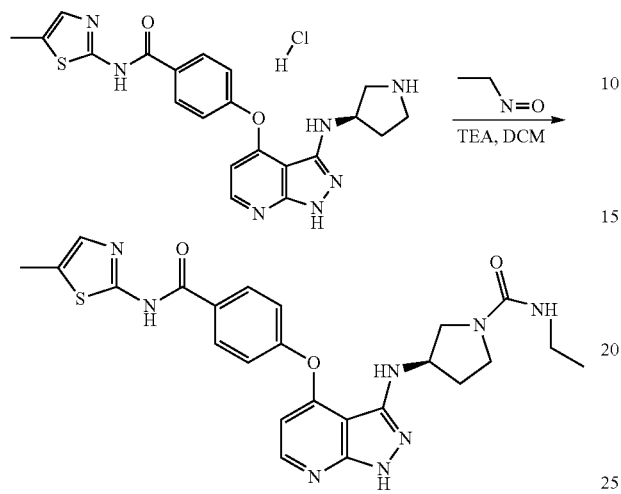

To a suspension of N-(5-methyl-1,3-thiazol-2-yl)-4-((3-[(pyrrolidin-3-yl)amino]-1H-pyrazolo[3,4-b]pyridin-4-yl)oxy)benzamide (120.0 mg, 0.27 mmol) in DCM (2 mL), TEA (80 µL, 0.57 mmol) was added. The mixture was cooled to 0° C. and ethylisocyanate (24 µL, 0.29 mmol) was added. The mixture was stirred at 0° C. for 30 min, some drops of water were added then the solvent was evaporated. The crude product was purified by preparative HPLC (C18 column, CH$_3$CN in H$_2$O 0.1% HCOOH from 10% to 100%). (3R)—N-ethyl-3-[(4-{4-[(5-methyl-1,3-thiazol-2-yl)carbamoyl]phenoxy}-1H-pyrazolo[3,4-b]pyridin-3-yl)amino]pyrrolidine-1-carboxamide was obtained as a white solid (53.8 mg, Yield: 39%). LC-MS (ESI): m/z (M+1)$^+$, 507.1. $^1$H NMR (500 MHz, DMSO) δ 12.51 (br. s., 1H), 12.30 (s, 1H), 8.25-8.15 (m, 3H), 7.41 (d, J=8.31 Hz, 2H), 7.20 (br. s., 1H), 6.14 (d, J=5.38 Hz, 1H), 6.06 (t, J=5.38 Hz, 1H), 5.52 (d, J=6.20 Hz, 1H), 4.22 (sxt, J=6.20 Hz, 1H), 3.62 (dd, J=10.27, 6.20 Hz, 1H), 3.46-3.19 (m, 3H), 3.08-2.96 (m, 2H), 2.42-2.33 (m, 3H), 2.22-2.10 (m, 1H), 2.04-1.93 (m, 1H), 0.99 (t, J=7.09 Hz, 3H).

Example 190

N-(5-methyl-1,3-thiazol-2-yl)-4-[(3-{[(3R)-1-propanoylpyrrolidin-3-yl]amino}-1H-pyrazolo[3,4-b]pyridin-4-yl)oxy]benzamide (Compound ID 190)

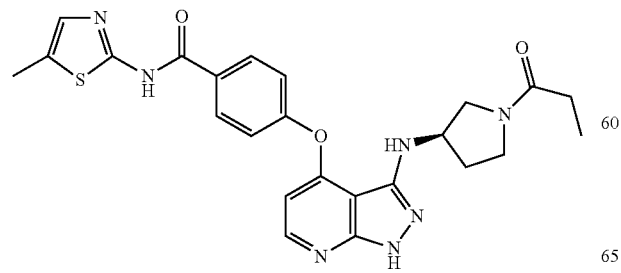

The compound was prepared following the method described for Ex. 86. LC-MS (ESI): m/z (M+1)$^+$, 492.0. $^1$H NMR (500 MHz, DMSO) δ 12.33 (s, 2H), 8.32-8.13 (m, 3H), 7.41 (dd, J=8.61, 6.26 Hz, 2H), 7.23 (s, 1H), 6.17 (dd, J=10.17, 5.48 Hz, 1H), 5.68-5.43 (m, 1H), 4.37-4.13 (m, 1H), 3.89-3.32 (m, 4H), 2.38 (s, 3H), 2.26-1.91 (m, 3H), 0.96 (td, J=7.43, 3.13 Hz, 3H).

Example 191

3-[(3-{[(3R)-1-(prop-2-enoyl)piperidin-3-yl]amino}-1H-pyrazolo[3,4-b]pyridin-4-yl)oxy]-N-[4-(trifluoromethyl)pyridin-2-yl]benzamide (Compound ID 191)

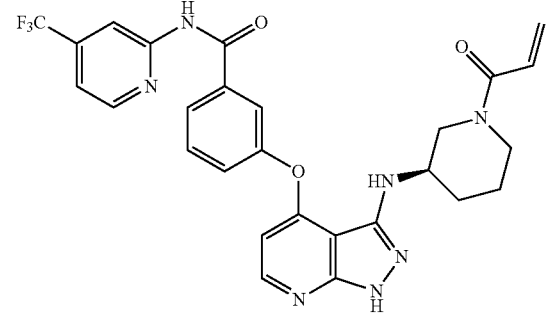 [SMILES: C=CC(=O)N1CCC[C@@H](Nc2n[nH]c3nccc(Oc4cccc(C(=O)Nc5cc(C(F)(F)F)ccn5)c4)c23)C1]

1.109 Preparation of tert-butyl (3R)-3-({1-[(4-methoxyphenyl)methyl]-4-(3-{[4-(trifluoromethyl)pyridin-2-yl]carbamoyl}phenoxy)-1H-pyrazolo[3,4-b]pyridin-3-yl}amino)piperidine-1-carboxylate

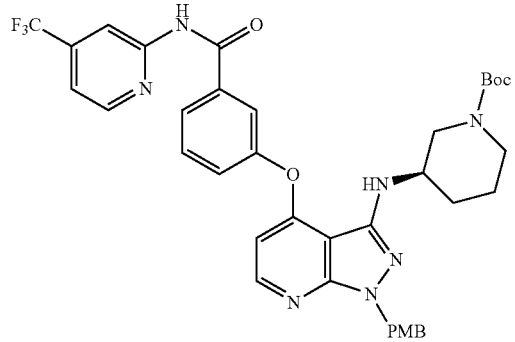

The intermediate was prepared following the method described for Ex. 161. LC-MS (ESI): m/z (M+1)$^+$, 718.1, 736.1

1.110 Preparation of 3-[(3-{[(3R)-piperidin-3-yl]amino}-1H-pyrazolo[3,4-b]pyridin-4-yl)oxy]-N-[4-(trifluoromethyl)pyridin-2-yl]benzamide

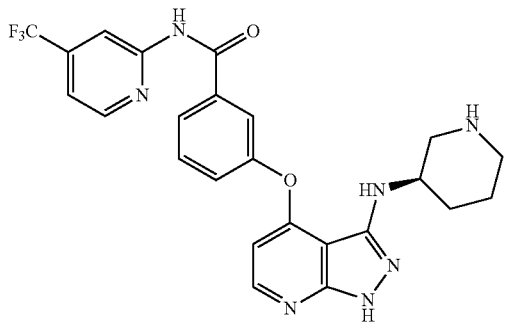 [SMILES: O=C(Nc1cc(C(F)(F)F)ccn1)c1cccc(Oc2ccnc3[nH]nc(N[C@@H]4CCCNC4)c23)c1]

The intermediate was prepared following the method described for Ex. 161. LC-MS (ESI): m/z (M+1)⁺, 498.0

Compound 191 was prepared following the method described for Ex. 149. LC-MS (ESI): m/z (M+1)⁺, 552.0. ¹H NMR (500 MHz, DMSO-d6) d ppm 12.29 (br. s., 1H), 11.43 (br. s, 1H), 8.68 (d, J=5.38 Hz, 1H), 8.53 (s, 1H), 8.21-8.15 (m, 1H), 8.06-7.96 (m, 2H), 7.68 (t, J=8.07 Hz, 1H), 7.60-7.52 (m, 2H), 6.89-6.64 (m, 1H), 6.11 (d, J=5.87 Hz, 1H), 6.10-5.99 (m, 1H), 5.69-5.54 (m, 1H), 5.27 (d, J=7.83 Hz, 1H), 4.54-4.11 (m, 1H), 4.08-3.76 (m, 1H), 3.72-3.59 (m, 1H), 3.29-2.82 (m, 2H), 2.13-1.35 (m, 4H)

Example 192

1-[(3R)-3-({4-[4-(1,3-benzothiazol-2-yl)phenoxy]-1H-pyrazolo[3,4-b]pyridin-3-yl}amino)piperidin-1-yl]prop-2-en-1-one (Compound ID 192)

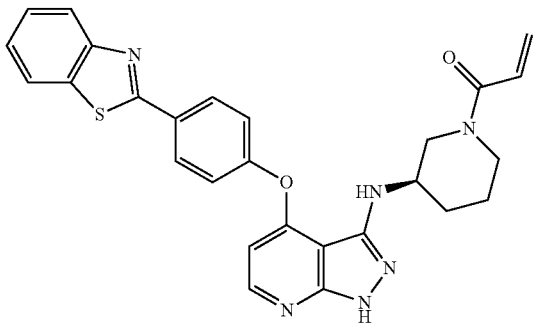 [SMILES: C=CC(=O)N1CCC[C@@H](Nc2n[nH]c3nccc(Oc4ccc(-c5nc6ccccc6s5)cc4)c23)C1]

The compound was prepared following the method described for Ex. 148. LC-MS (ESI): m/z (M+1)⁺, 497.00.

Example 193

4-{[3-(1-cyclopropanecarbonylpiperidin-3-yl)-1H-pyrazolo[3,4-b]pyridin-4-yl]oxy}-N-(5-methyl-1,3-thiazol-2-yl)benzamide (Compound ID 193)

1.111 Preparation of tert-butyl 5-{4-[4-(ethoxycarbonyl)phenoxy]-1-[(4-methoxyphenyl)methyl]-1H-pyrazolo[3,4-b]pyridin-3-yl}-1,2,3,6-tetrahydropyridine-1-carboxylate

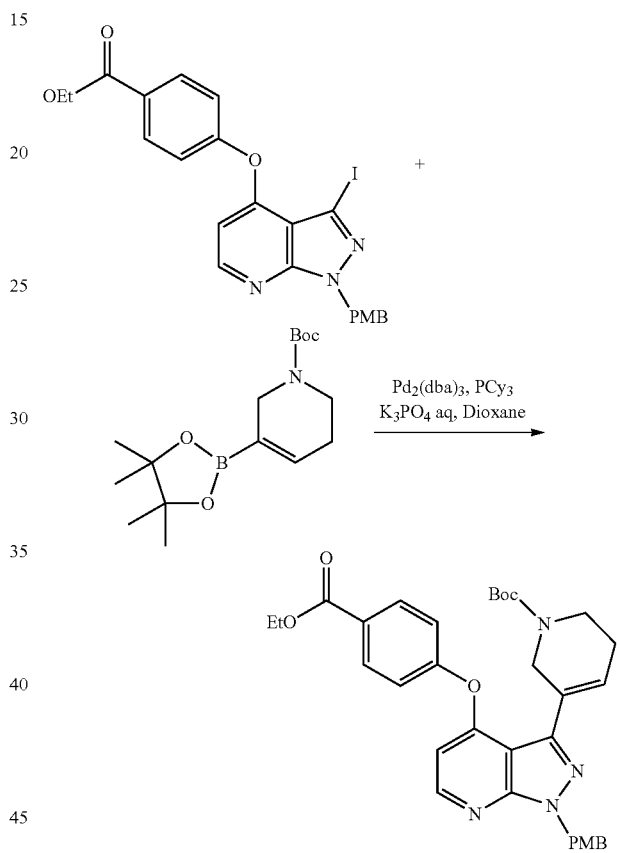

To a mixture of ethyl 4-({3-iodo-1-[(4-methoxyphenyl)methyl]-1H-pyrazolo[3,4-b]pyridin-4-yl}oxy)benzoate (815 mg, 1.54), tert-butyl 5-(tetramethyl-1,3,2-dioxaborolan-2-yl)-1,2,3,6-tetrahydropyridine-1-carboxylate (570.0 mg, 1.84 mmol), K₃PO₄ (990.0 mg, 4.66 mmol), PCy₃ (89 mg, 0.32 mmol) in Toluene (30 mL), was added Pd₂(dba)₃ (143 mg, 0.15 mmol). The mixture was degassed for 10 min, and then heated at 120° C. for 3 hours. EtOH (2 mL), PCy₃ (86 mg, 0.31 mmol) and Pd₂(dba)₃ (145 mg, 0.15 mmol) were added, the mixture degassed for 10 min and then heated at 120° C. for a further 3 hours. Water was added to the mixture (50 mL) and the product was extracted three times with EtOAc. The collected organic phases were dried over Na₂SO₄, concentrated and purified by flash chromatography (silica gel, 100 g, EtOAc in cyclohexane from 0% to 40%) to give tert-butyl 5-{4-[4-(ethoxycarbonyl)phenoxy]-1-[(4-methoxyphenyl)methyl]-1H-pyrazolo[3,4-b]pyridin-3-yl}-1,2,3,6-tetrahydropyridine-1-carboxylate as a colorless oil (1.09 g, Yield: 69%). LC-MS (ESI): m/z (M+1)⁺, 585.1.

1.112 Preparation of tert-butyl 3-{4-[4-(ethoxycarbonyl)phenoxy]-1-[(4-methoxyphenyl)methyl]-1H-pyrazolo[3,4-b]pyridin-3-yl}piperidine-1-carboxylate

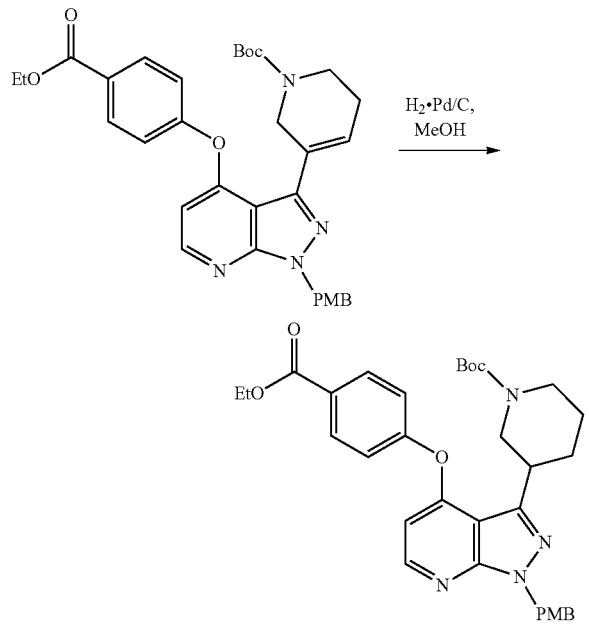

To a solution of tert-butyl 5-{4-[4-(ethoxycarbonyl)phenoxy]-1-[(4-methoxyphenyl)methyl]-1H-pyrazolo[3,4-b]pyridin-3-yl}-1,2,3,6-tetrahydropyridine-1-carboxylate (1.09 g, 1.86 mmol), in MeOH (80 mL) was added Pd/C 10% wet (390 mg, 0.18 mmol) and the mixture was stirred at 20 psi under $H_2$ for 1.5 hours at room temperature. The mixture was then stirred at 50 psi under $H_2$ for 3 hours at 60° C. Pd/C was filtered off, the solvent evaporated to give tert-butyl 3-{4-[4-(ethoxycarbonyl)phenoxy]-1-[(4-methoxyphenyl)methyl]-1H-pyrazolo[3,4-b]pyridin-3-yl}piperidine-1-carboxylate as colorless oil (965.0 mg, Yield: Quant.). LC-MS (ESI): m/z (M+1)$^+$, 587.1.

1.113 Preparation of tert-butyl 3-{4-[4-(ethoxycarbonyl)phenoxy]-1-[(4-methoxyphenyl)methyl]-1H-pyrazolo[3,4-b]pyridin-3-yl}piperidine-1-carboxylate

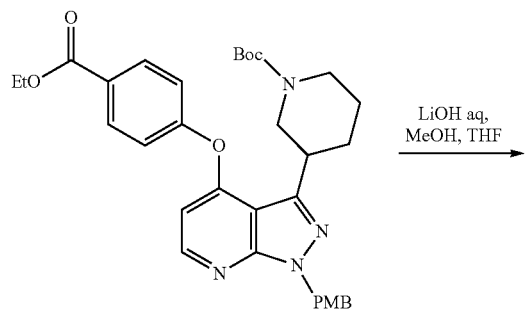

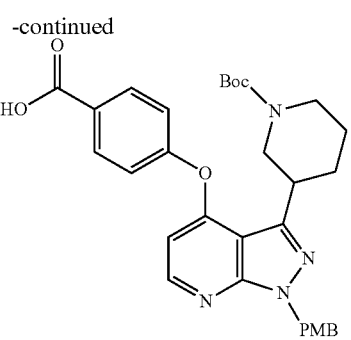

To a solution of tert-butyl 3-{4-[4-(ethoxycarbonyl)phenoxy]-1-[(4-methoxyphenyl)methyl]-1H-pyrazolo[3,4-b]pyridin-3-yl}piperidine-1-carboxylate (965.0 mg, 1.86 mmol) in THF (3 mL), MeOH (3 mL) and $H_2O$ (3 mL) was added LiOH (90.0 mg, 3.72 mmol). The mixture was stirred at room temperature overnight. HCl 1M was added to reach pH=2. The product was then extracted three times with AcOEt. The collected organic phases were dried over $Na_2SO_4$, filtered and evaporated to dryness to give tert-butyl 3-{4-[4-(ethoxycarbonyl)phenoxy]-1-[(4-methoxyphenyl)methyl]-1H-pyrazolo[3,4-b]pyridin-3-yl}piperidine-1-carboxylate as a white solid (917.0 mg, yield: 70%). LC-MS (ESI): m/z (M+1)$^+$, 559.1.

1.114 Preparation of tert-butyl 3-{1-[(4-methoxyphenyl)methyl]-4-{4-[(5-methyl-1,3-thiazol-2-yl)carbamoyl]phenoxy}-1H-pyrazolo[3,4-b]pyridin-3-yl}piperidine-1-carboxylate

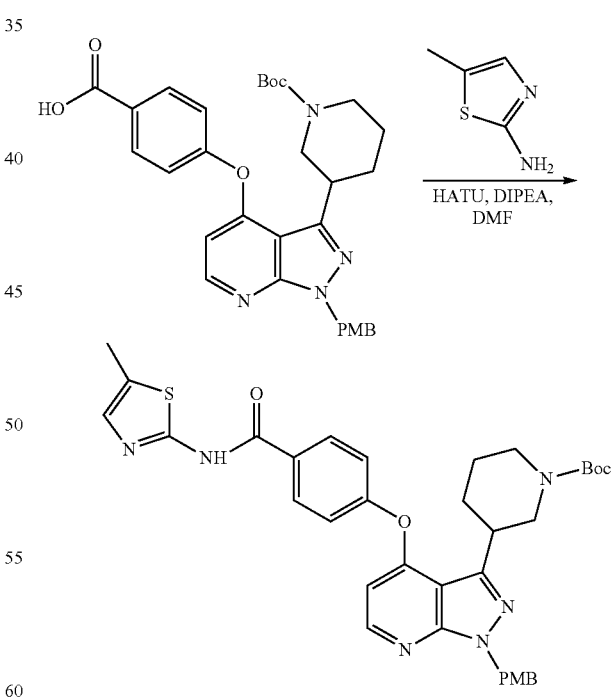

To a solution of 4-[(3-{1-[(tert-butoxy)carbonyl]piperidin-3-yl}-1-[(4-methoxyphenyl)methyl]-1H-pyrazolo[3,4-b]pyridin-4-yl)oxy]benzoic acid (452 mg, 0.65 mmol) in DMF (9 mL) was added 5-methyl-1,3-thiazol-2-amine (105.0 mg, 0.91 mmol), HATU (351, 0.92 mmol) and DIPEA (180 µL, 1.04 mmol). The solution was stirred at room temperature for 5.5 hours, water was added and the mixture extracted three times with AcOEt. The collected organic phases were dried over Na₂SO₄, filtered and evaporated to dryness. The crude product was purified by flash chromatography (silica gel, 50 g, EtOAc in cyclohexane from 10% to 50%) to give tert-butyl 3-{1-[(4-methoxyphenyl)methyl]-4-{4-[(5-methyl-1,3-thiazol-2-yl)carbamoyl]phenoxy}-1H-pyrazolo[3,4-b]pyridin-3-yl}piperidine-1-carboxylate as white solid (438.0 mg, Yield: 78%). LC-MS (ESI): m/z (M+1)⁺, 655.5.

1.115 Preparation of 4-({1-[(4-methoxyphenyl)methyl]-3-(piperidin-3-yl)-1H-pyrazolo[3,4-b]pyridin-4-yl}oxy)-N-(5-methyl-1,3-thiazol-2-yl)benzamide trifluoroacetate

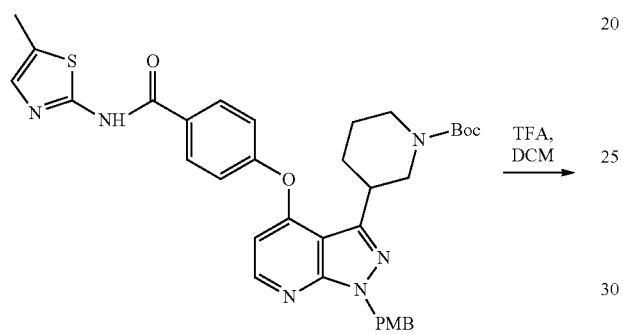

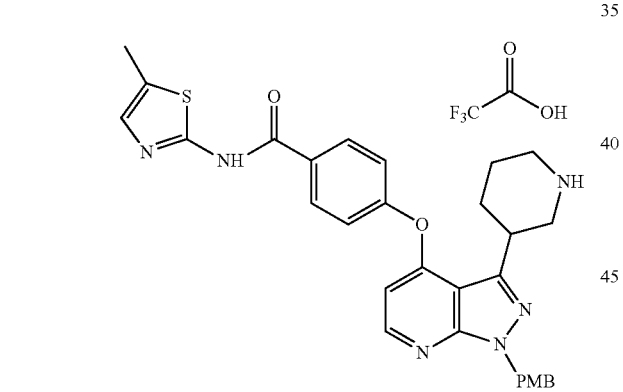

To a solution of tert-butyl 3-{1-[(4-methoxyphenyl)methyl]-4-{4-[(5-methyl-1,3-thiazol-2-yl)carbamoyl]phenoxy}-1H-pyrazolo[3,4-b]pyridin-3-yl}piperidine-1-carboxylate (438.0 mg, 0.51 mmol) in dry DCM (4.5 mL) was added at room temperature TFA (1 mL) dropwise. The solution was stirred at room temperature for 45 min then evaporated to dryness to give 4-({1-[(4-methoxyphenyl)methyl]-3-(piperidin-3-yl)-1H-pyrazolo[3,4-b]pyridin-4-yl}oxy)-N-(5-methyl-1,3-thiazol-2-yl)benzamide trifluoroacetate as a yellow oil (1.196 g, Yield: Quant.). LC-MS (ESI): m/z (M+1)⁺, 555.0.

1.116 Preparation of N-(5-methyl-1,3-thiazol-2-yl)-4-{[3-(piperidin-3-yl)-1H-pyrazolo[3,4-b]pyridin-4-yl]oxy}benzamide

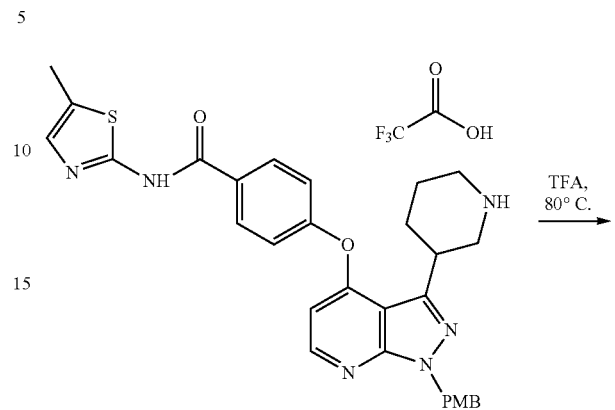

A solution of 4-({1-[(4-methoxyphenyl)methyl]-3-(piperidin-3-yl)-1H-pyrazolo[3,4-b]pyridin-4-yl}oxy)-N-(5-methyl-1,3-thiazol-2-yl)benzamide trifluoroacetate (1.96 mg, 0.51 mmol) in TFA (5 mm) was heated at 55° C. for 4.5 hours, at 60° C. for 3 hours, at 65° C. for 2 hours, at 70° C. for 3 hours then at 80° C. for 5 hours. The solution was concentrated and the residue purified by SCX cartridge to afford N-(5-methyl-1,3-thiazol-2-yl)-4-{[3-(piperidin-3-yl)-1H-pyrazolo[3,4-b]pyridin-4-yl]oxy}benzamide as a white solid (304 mg, Yield: Quant.). LC-MS (ESI): m/z (M+1)⁺, 435.0.

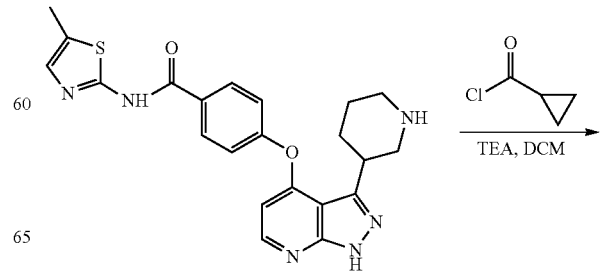

-continued

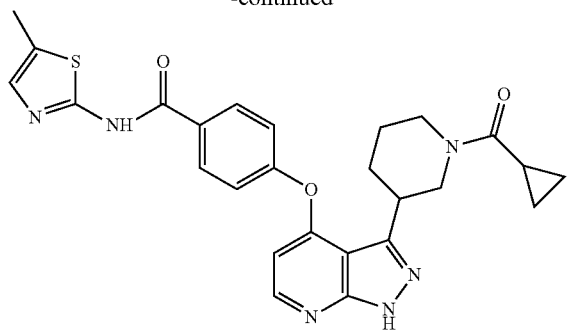

To a solution of N-(5-methyl-1,3-thiazol-2-yl)-4-{[3-(piperidin-3-yl)-1H-pyrazolo[3,4-b]pyridin-4-yl]oxy}benzamide (102.0 mg, 0.17 mmol) in DCM (6 ml) cooled at 0° C. was added dry TEA (47 µL, 0.34 mmol) followed by a solution of cyclopropanecarbonyl chloride (18 µL, 0.196 mmol) in DCM (1 mL). The solution was stirred at room temperature for 16 hours. Aqueous solution of NaHCO$_3$ was added and the product extracted three times with AcOEt. The collected organic phases were dried over Na$_2$SO$_4$, filtered and concentrated. The crude product was purified by flash chromatography (silica gel, 25 g, MeOH in DCM from 1% to 8%) to give 4-{[3-(1-cyclopropanecarbonylpiperidin-3-yl)-1H-pyrazolo[3,4-b]pyridin-4-yl]oxy}-N-(5-methyl-1,3-thiazol-2-yl)benzamide as white solid (22.5 mg, Yield: 26%). LC-MS (ESI): m/z (M+1)$^+$, 502.9.

Example 194

1-[(3R)-3-({4-[4-(1,3-benzoxazol-2-yl)phenoxy]-1H-pyrazolo[3,4-b]pyridin-3-yl}amino)piperidin-1-yl]prop-2-en-1-one (Compound ID 194)

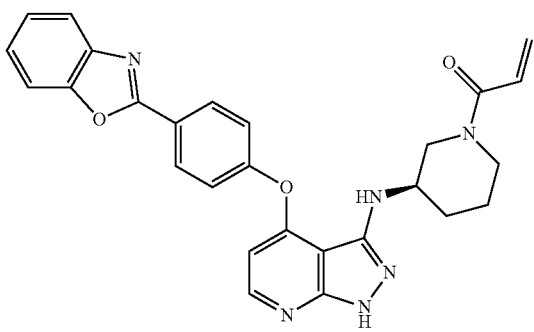 [SMILES: C=CC(=O)N1CCC[C@@H](Nc2n[nH]c3nccc(Oc4ccc(-c5nc6ccccc6o5)cc4)c23)C1]

1.117 Preparation of 4-(1,3-benzoxazol-2-yl)phenol

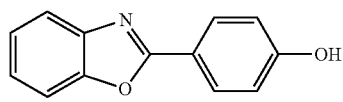 [SMILES: Oc1ccc(-c2nc3ccccc3o2)cc1]

The intermediate was prepared following the method described for Ex. 170. LC-MS (ESI): m/z (M+1)$^+$, 211.9

1.118 Preparation of 2-[4-({3-bromo-1-[(4-methoxyphenyl)methyl]-1H-pyrazolo[3,4-b]pyridin-4-yl}oxy)phenyl]-1,3-benzoxazole

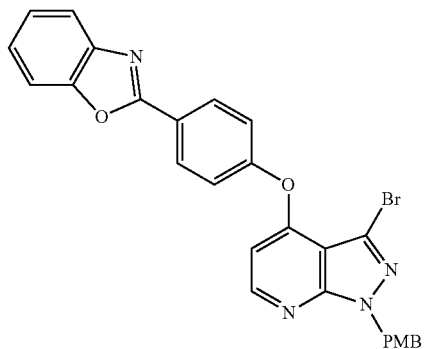

The intermediate was prepared following the method described for the synthesis of the intermediate for Ex. 148. LC-MS (ESI): m/z (M+1)$^+$, 526.89.

1.119 Preparation of tert-butyl (3R)-3-({4-[4-(1,3-benzoxazol-2-yl)phenoxy]-1-[(4-methoxyphenyl)methyl]-1H-pyrazolo[3,4-b]pyridin-3-yl}amino)piperidine-1-carboxylate

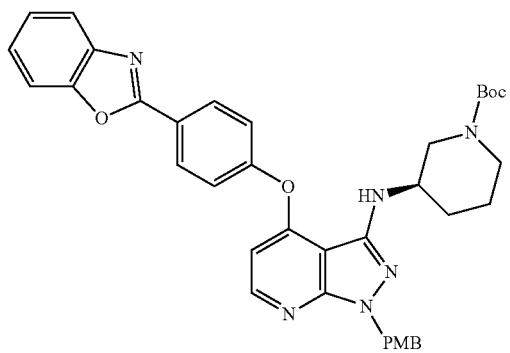

The intermediate was prepared following the method described for the synthesis of the intermediate for Ex. 148. LC-MS (ESI): m/z (M+1)$^+$, 647.1.

1.120 Preparation of (3R)—N-{4-[4-(1,3-benzoxazol-2-yl)phenoxy]-1H-pyrazolo[3,4-b]pyridin-3-yl}piperidin-3-amine

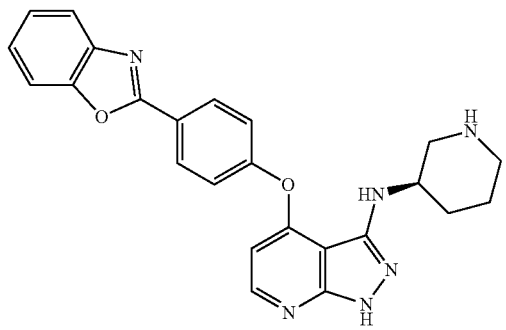 [SMILES: c1ccc2oc(-c3ccc(Oc4ccnc5[nH]nc(N[C@@H]6CCCNC6)c45)cc3)nc2c1]

The intermediate was prepared following the method described for the synthesis of the intermediate for Ex. 148. LC-MS (ESI): m/z (M+1)+, 427.

Compound 194 was prepared following the method described for Ex. 140. LC-MS (ESI): m/z (M+1)+, 481. ¹H NMR (500 MHz, DMSO) δ 12.14-12.42 (m, 1H), 8.33 (d, J=8.80 Hz, 2H), 8.21 (d, J=5.38 Hz, 1H), 7.78-7.89 (m, 2H), 7.52 (d, J=8.80 Hz, 2H), 7.40-7.48 (m, 2H), 6.65-6.85 (m, 1H), 6.23 (d, J=5.38 Hz, 1H), 6.06 (d, J=16.63 Hz, 1H), 5.52-5.70 (m, 1H), 5.28 (d, J=7.34 Hz, 1H), 4.10-4.51 (m, 1H), 3.79-4.07 (m, 1H), 3.64 (br. s., 1H), 3.07-3.28 (m, 1H), 2.86-3.04 (m, 1H), 1.94-2.09 (m, 1H), 1.62-1.80 (m, 2H), 1.35-1.52 (m, 1H).

Example 195

N-ethyl-3-(4-{4-[(5-methyl-1,3-thiazol-2-yl)carbamoyl]phenoxy}-1H-pyrazolo[3,4-b]pyridin-3-yl)piperidine-1-carboxamide (Compound ID 195)

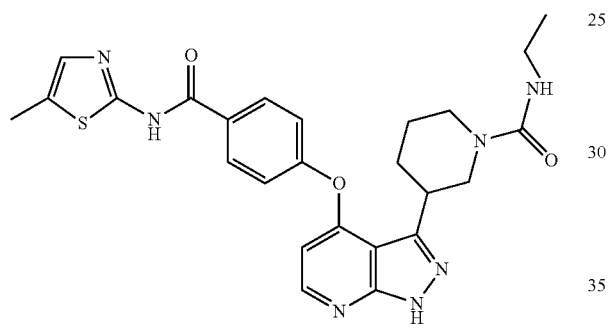

The compound was prepared following the method described for Ex. 189. LC-MS (ESI): m/z (M+1)+, 506.1.

Example 196

1-[(3R)-3-[(4-{4-[5-(trifluoromethyl)pyridin-2-yl]phenoxy}-1H-pyrazolo[3,4-b]pyridin-3-yl)amino]piperidin-1-yl]prop-2-en-1-one (Compound ID 196)

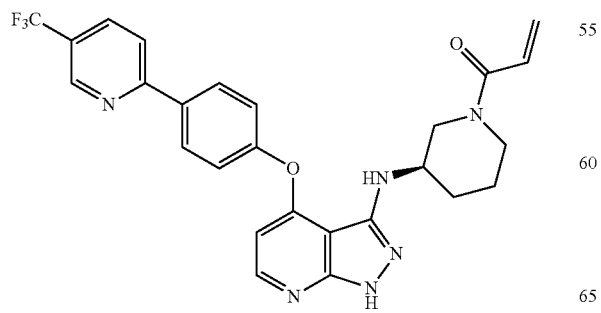

1.121 Preparation of 4-[5-(trifluoromethyl)pyridin-2-yl]phenol

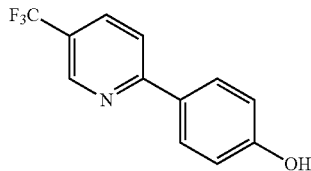 [SMILES: Oc1ccc(-c2ccc(C(F)(F)F)cn2)cc1]

The intermediate was prepared following the method described for Ex. 148. LC-MS (ESI): m/z (M+1)+, 239.9.

1.122 Preparation of 2-[4-({3-bromo-1-[(4-methoxyphenyl)methyl]-1H-pyrazolo[3,4-b]pyridin-4-yl}oxy)phenyl]-5-(trifluoromethyl)pyridine

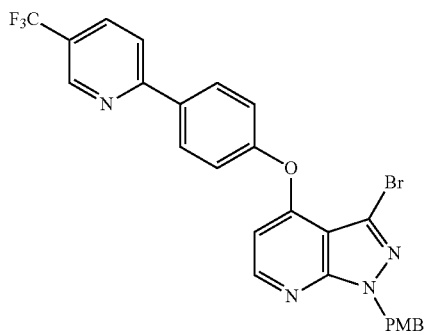

The intermediate was prepared following the method described for Ex. 148. LC-MS (ESI): m/z (M+1)+, 554.88.

1.123 Preparation of tert-butyl (3R)-3-({1-[(4-methoxyphenyl)methyl]-4-{4-[5-(trifluoromethyl)pyridin-2-yl]phenoxy}-1H-pyrazolo[3,4-b]pyridin-3-yl}amino)piperidine-1-carboxylate

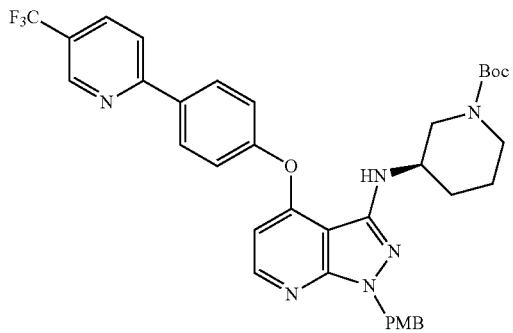

The intermediate was prepared following the method described for Ex. 148. LC-MS (ESI): m/z (M+1)+, 675.1.

1.124 Preparation of (3R)—N-(4-{4-[5-(trifluoromethyl)pyridin-2-yl]phenoxy}-1H-pyrazolo[3,4-b]pyridin-3-yl)piperidin-3-amine

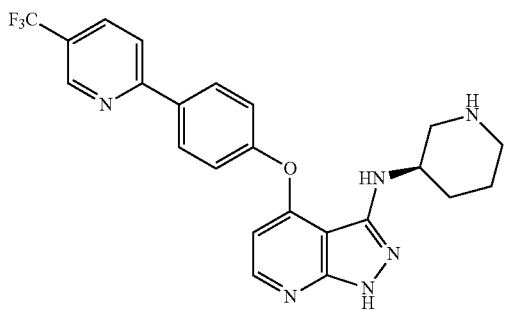 [SMILES: FC(F)(F)c1ccc(-c2ccc(Oc3ccnc4[nH]nc(N[C@@H]5CCCNC5)c34)cc2)nc1]

The intermediate was prepared following the method described for Ex. 148. LC-MS (ESI): m/z (M+1)⁺, 455.
Compound 196 was prepared following the method described for Ex. 140. LC-MS (ESI): m/z (M+1)⁺, 509.

Example 197

(3R)—N-{4-[4-(1,3-benzothiazol-2-yl)phenoxy]-1H-pyrazolo[3,4-b]pyridin-3-yl}-1-(1-methylpiperidine-4-carbonyl)piperidin-3-amine (Compound ID 197)

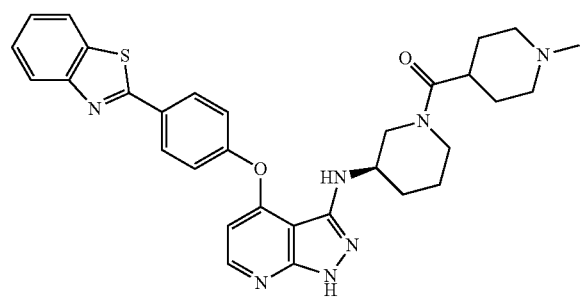 [SMILES: CN1CCC(C(=O)N2CCC[C@@H](Nc3n[nH]c4nccc(Oc5ccc(-c6nc7ccccc7s6)cc5)c34)C2)CC1]

The compound was prepared following the method described for Ex. 184. LC-MS (ESI): m/z (M+1)⁺, 568.40

Example 198

4-[(3-{[(3R)-1-[(2E)-4-(dimethylamino)but-2-enoyl]piperidin-3-yl]amino}-1H-pyrazolo[3,4-b]pyridin-4-yl)oxy]-N-(5-methyl-1,3-thiazol-2-yl)benzamide (Compound ID 198)

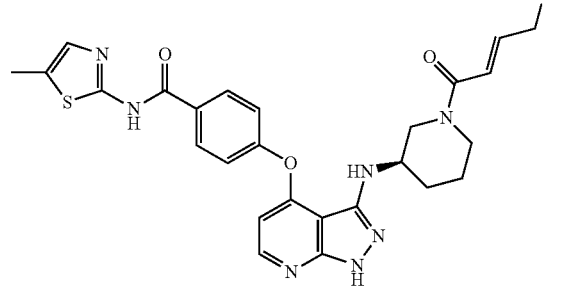

The compound was prepared following the method described for Ex. 141. LC-MS (ESI): m/z (M+1)⁺, 561.0. $^1$H NMR (500 MHz, DMSO) δ 12.77-11.96 (m, 2H), 8.27-8.16 (m, 3H), 7.45-7.34 (m, 2H), 7.26-7.20 (m, 1H), 6.65-6.34 (m, 2H), 6.24-6.12 (m, 1H), 5.29-5.09 (m, 1H), 4.50-3.87 (m, 1H), 3.83-3.59 (m, 2H), 3.46-2.71 (m, 4H), 2.38 (s, 3H), 2.16-1.98 (m, 6H), 2.06-1.37 (m, 4H).

Example 199

4-[(3-{[(3R)-1-(1-methylpiperidine-4-carbonyl)pyrrolidin-3-yl]amino}-1H-pyrazolo[3,4-b]pyridin-4-yl)oxy]-N-[4-(trifluoromethyl)pyridin-2-yl]benzamide (Compound ID 199)

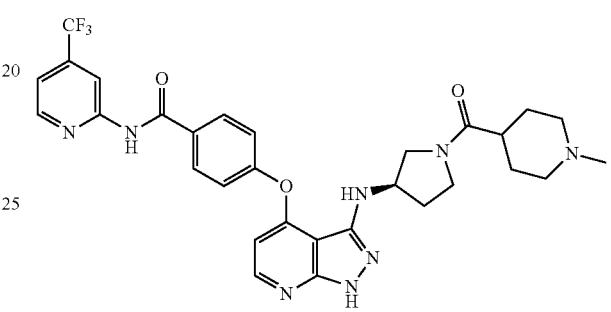

The compound was prepared following the method described for Ex. 86. LC-MS (ESI): m/z (M+1)⁺, 608.98. $^1$H NMR (500 MHz, DMSO) δ 12.42-11.19 (m, 2H), 8.69 (d, J=5.38 Hz, 1H), 8.56 (d, J=3.42 Hz, 1H), 8.24-8.14 (m, 3H), 7.55 (d, J=4.89 Hz, 1H), 7.40 (dd, J=16.63, 8.31 Hz, 2H), 6.26-6.12 (m, 1H), 5.65-5.42 (m, 1H), 4.40-4.10 (m, 1H), 3.92-3.59 (m, 1H), 3.56-3.43 (m, 2H), 3.36 (dd, J=12.23, 4.89 Hz, 1H), 2.80-2.66 (m, 2H), 2.33-2.13 (m, 2H), 2.09 (s, 3H), 1.94 (dd, J=12.47, 7.58 Hz, 1H), 1.80 (td, J=11.98, 3.42 Hz, 2H), 1.64-1.48 (m, 4H).

Example 200

4-[(3-{[(3R)-1-cyclopropanecarbonylpyrrolidin-3-yl]amino}-1H-pyrazolo[3,4-b]pyridin-4-yl)oxy]-N-(5-methyl-1,3-thiazol-2-yl)benzamide (Compound ID 200)

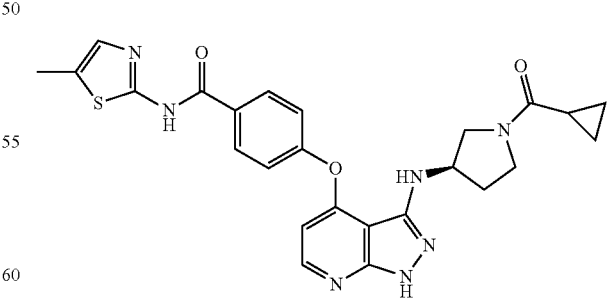

The compound was prepared following the method described for Ex. 86. LC-MS (ESI): m/z (M+1)⁺, 504.3. $^1$H NMR (500 MHz, DMSO) δ 12.33 (s, 2H), 8.27-8.12 (m, 3H), 7.42 (dd, J=8.80, 5.38 Hz, 2H), 7.23 (d, J=0.98 Hz, 1H), 6.16 (t, J=5.38 Hz, 1H), 5.71-5.53 (m, 1H), 4.41-4.13

(m, 1H), 4.09-3.35 (m, 4H), 2.38 (s, 3H), 2.33-1.94 (m, 2H), 1.82-1.64 (m, 1H), 0.75-0.62 (m, 4H).

Example 201

3-{4-[(3-{[(3R)-1-(prop-2-enoyl)piperidin-3-yl]amino}-1H-pyrazolo[3,4-b]pyridin-4-yl)oxy]phenyl}-1-[4-(trifluoromethyl)pyridin-2-yl]urea (Compound ID 201)

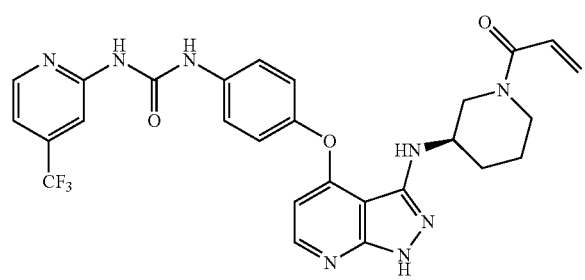 [SMILES: C=CC(=O)N1CCC[C@@H](Nc2n[nH]c3nccc(Oc4ccc(NC(=O)Nc5cc(C(F)(F)F)ccn5)cc4)c23)C1]

1.125 Preparation of tert-butyl (3R)-3-({1-[(4-methoxyphenyl)methyl]-4-[4-({[4-(trifluoromethyl)pyridin-2-yl]carbamoyl}amino)phenoxy]-1H-pyrazolo[3,4-b]pyridin-3-yl}amino)piperidine-1-carboxylate

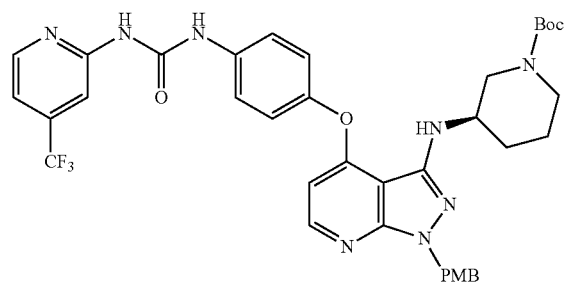

The intermediate was prepared following the method described for Ex. 86. LC-MS (ESI): m/z (M+1)⁺, 733.1.

1.126 Preparation of 3-{4-[(3-{[(3R)-piperidin-3-yl]amino}-1H-pyrazolo[3,4-b]pyridin-4-yl)oxy]phenyl}-1-[4-(trifluoromethyl)pyridin-2-yl]urea

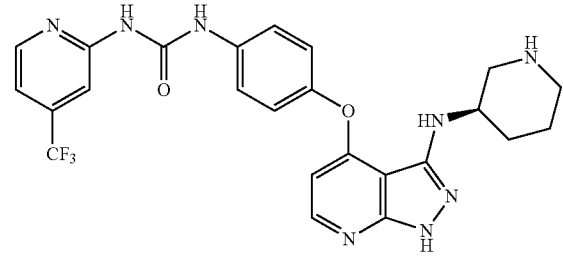 [SMILES: O=C(Nc1ccc(Oc2ccnc3[nH]nc(N[C@@H]4CCCNC4)c23)cc1)Nc1cc(C(F)(F)F)ccn1]

The intermediate was prepared following the method described for Ex. 148. LC-MS (ESI): m/z (M+1)⁺, 513.0.

The target compound was prepared following the method described in example 149 affording 11.1 mg, 19% yield of 3-{4-[(3-{[(3R)-1-(prop-2-enoyl)piperidin-3-yl]amino}-1H-pyrazolo[3,4-b]pyridin-4-yl)oxy]phenyl}-1-[4-(trifluoromethyl)pyridin-2-yl]urea as white solid. LC-MS (ESI): m/z (M+1)⁺, 567.0. ¹H NMR (500 MHz, DMSO-d6) d ppm 12.22 (br. s., 1H), 9.95 (s, 1H), 9.76 (s, 1H), 8.55 (d, J=5.38 Hz, 1H), 8.13 (d, J=5.38 Hz, 1H), 8.08 (s, 1H), 7.65 (d, J=8.30 Hz, 2H), 7.37 (d, J=5.38 Hz, 1H), 7.25 (d, J=8.31 Hz, 2H), 6.91-6.67 (m, 1H), 6.06 (d, J=16.40 Hz, 1H), 6.01 (d, J=5.40 Hz, 1H), 5.71-5.53 (m, 1H), 5.23 (d, J=7.34 Hz, 1H), 4.58-4.12 (m, 1H), 4.06-3.77 (m, 1H), 3.70-3.56 (m, 1H), 3.37-3.22 (m, 1H), 3.05-2.85 (m, 1H), 2.10-2.00 (m, 1H), 1.81-1.61 (m, 2H), 1.51-1.40 (m, 1H).

Example 202

4-[(3-{[(3R)-1-[4-(dimethylamino)butanoyl]pyrrolidin-3-yl]amino}-1H-pyrazolo[3,4-b]pyridin-4-yl)oxy]-N-(5-methyl-1,3-thiazol-2-yl)benzamide (Compound ID 202)

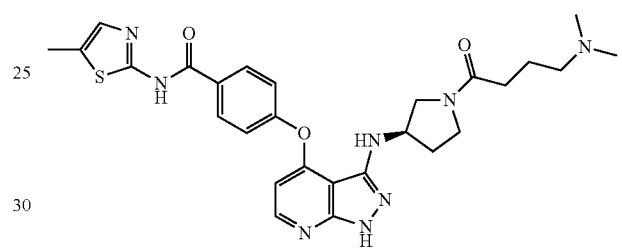

The compound was prepared following the method described for Ex. 86. LC-MS (ESI): m/z (M+1)⁺, 549.0. ¹H NMR (500 MHz, DMSO) δ 12.78-11.98 (m, 2H), 8.26-8.15 (m, 3H), 7.44-7.34 (m, 2H), 7.28-7.20 (m, 1H), 6.21-6.12 (m, 1H), 5.66-5.45 (m, 1H), 4.38-4.10 (m, 1H), 3.91-3.26 (m, 4H), 2.38 (s, 3H), 2.11-2.04 (m, 6H), 2.29-1.94 (m, 6H), 1.65-1.55 (m, 2H).

Example 203

4-[(3-{[(3R)-1-(prop-2-enoyl)piperidin-3-yl]amino}-1H-pyrazolo[3,4-b]pyridin-4-yl)oxy]-N-[4-(trifluoromethyl)pyridin-2-yl]benzamide (Compound ID 203)

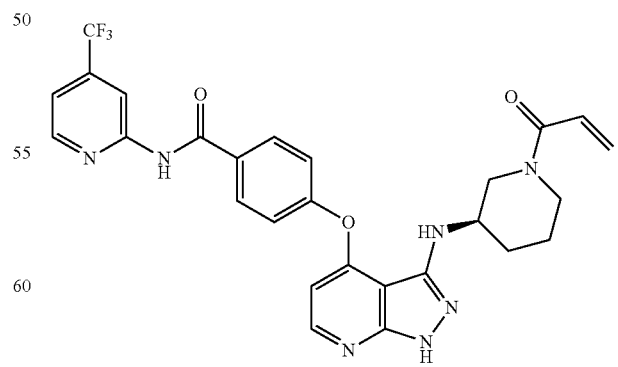

The compound was prepared following the method described for Ex. 140. LC-MS (ESI): m/z (M+1)⁺, 552.0. ¹H NMR (500 MHz, DMSO-d₆) δ ppm 12.32 (br. s., 1H), 11.35-11.32 (m, 1H), 8.69 (d, J=4.89 Hz, 1H), 8.57-8.54 (m, 1H), 8.25-8.15 (m, 3H), 7.56 (d, J=5.38 Hz, 1H), 7.46-7.38 (m, 2H), 6.90-6.61 (m, 1H), 6.23-6.12 (m, 1H), 6.10-6.01 (m, 1H), 5.69-5.51 (m, 1H), 5.29-5.18 (m, 1H), 4.50-4.05 (m, 1H), 4.01-3.58 (m, 2H), 3.50-2.86 (m, 2H), 2.14-1.35 (m, 4H).

Example 204

4-[(3-{[(3R)-1-(1-methylpiperidine-4-carbonyl)piperidin-3-yl]amino}-1H-pyrazolo[3,4-b]pyridin-4-yl)oxy]-N-[4-(trifluoromethyl)pyridin-2-yl]benzamide hydrochloride (Compound ID 204)

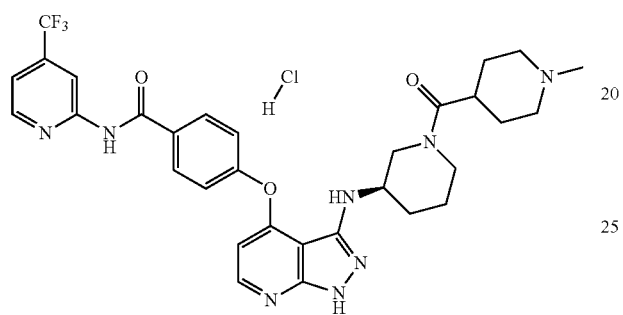

The compound was prepared following the method described for Ex. 161. LC-MS (ESI): m/z (M+1)+, 623.0. 1H NMR (500 MHz, DMSO) δ 12.56-12.07 (m, 1H), 11.38 (s, 1H), 9.56 (br. s., 1H), 8.70 (d, J=5.38 Hz, 1H), 8.56 (s, 1H), 8.25-8.15 (m, 3H), 7.56 (d, J=5.40 Hz, 1H), 7.48-7.33 (m, 2H), 6.20-6.11 (m, 1H), 5.50-5.10 (m, 1H), 4.47-3.67 (m, 2H), 3.58 (br. s., 1H), 3.51-2.29 (m, 10H), 2.24-1.31 (m, 8H).

Example 205

4-[(3-{[(3R)-1-(but-2-ynoyl)piperidin-3-yl]amino}-1H-pyrazolo[3,4-b]pyridin-4-yl)oxy]-N-[4-(trifluoromethyl)pyridin-2-yl]benzamide (Compound ID 205)

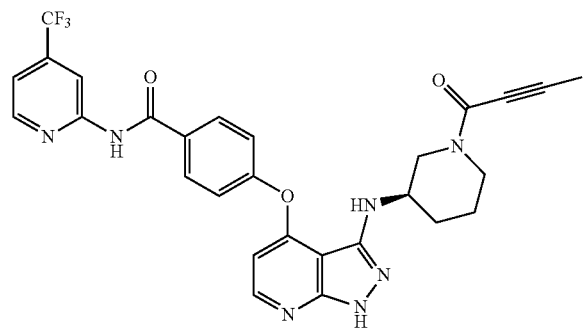 [SMILES: CC#CC(=O)N1CCC[C@@H](Nc2n[nH]c3nccc(Oc4ccc(C(=O)Nc5cc(C(F)(F)F)ccn5)cc4)c23)C1]

The compound was prepared following the method described for Ex. 141. LC-MS (ESI): m/z (M+1)+, 564.0. 1H NMR (500 MHz, DMSO-d6) δ ppm 12.49-12.15 (m, 1H), 11.37 (br. s, 1H), 8.69 (d, J=5.38 Hz, 1H), 8.57-8.54 (m, 1H), 8.24-8.17 (m, 3H), 7.56 (d, J=4.89 Hz, 1H), 7.46-7.38 (m, 2H), 6.22-6.12 (m, 1H), 5.29-5.14 (m, 1H), 4.45-4.17 (m, 1H), 4.10-3.55 (m, 2H), 3.53-2.83 (m, 2H), 2.06-1.74 (m, 3H), 2.10-1.33 (m, 4H).

Example 206

1-[(3R)-3-[(4-{4-[5-(trifluoromethyl)pyridin-2-yl]phenoxy}-1H-pyrazolo[3,4-b]pyridin-3-yl)amino]piperidin-1-yl]but-2-yn-1-one (Compound ID 206)

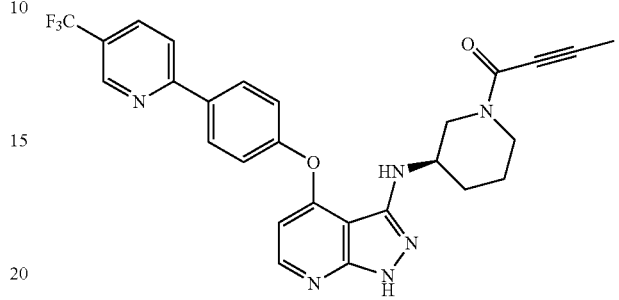

The compound was prepared following the method described for Ex. 141. LC-MS (ESI): m/z (M+1)+, 521.

Example 207

(3R)—N-ethyl-3-{[4-(4-{[4-(trifluoromethyl)pyridin-2-yl]carbamoyl}phenoxy)-1H-pyrazolo[3,4-b]pyridin-3-yl]amino}piperidine-1-carboxamide hydrochloride (Compound ID 207)

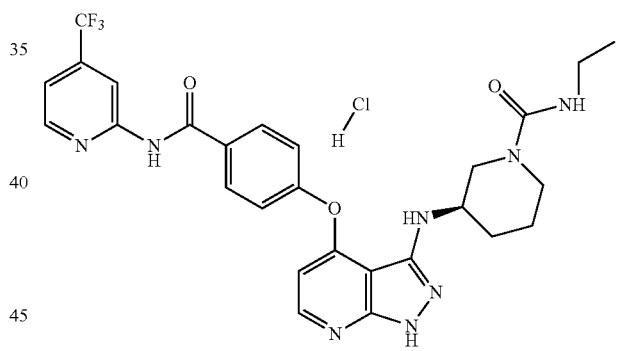

1.128 Preparation of (3R)—N-ethyl-3-{[4-(4-{[4-(trifluoromethyl)pyridin-2-yl]carbamoyl}phenoxy)-1H-pyrazolo[3,4-b]pyridin-3-yl]amino}piperidine-1-carboxamide

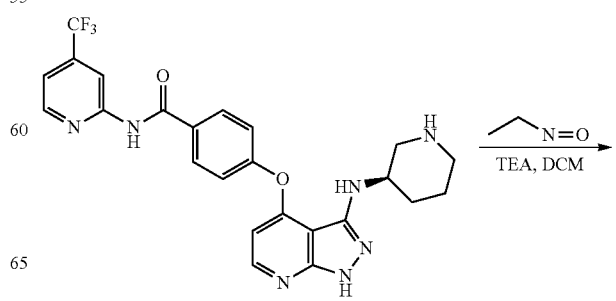

-continued

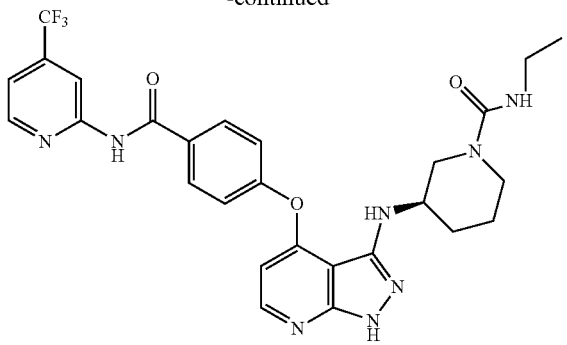

LC-MS (ESI): m/z (M+1)⁺, 568.9. ¹H NMR (500 MHz, DMSO) δ 12.45 (br. s., 1H), 11.40 (s, 1H), 8.70 (d, J=4.89 Hz, 1H), 8.56 (s, 1H), 8.31-8.18 (m, 3H), 7.56 (d, J=4.89 Hz, 1H), 7.47 (d, J=8.31 Hz, 2H), 6.44 (br. s., 1H), 6.17 (d, J=5.38 Hz, 1H), 3.97 (dd, J=12.50, 3.42 Hz, 1H), 3.75-3.57 (m, 2H), 3.01 (q, J=7.34 Hz, 2H), 2.90 (dd, J=12.47, 9.05 Hz, 1H), 2.81 (t, J=10.76 Hz, 1H), 2.06-1.95 (m, 1H), 1.70-1.53 (m, 2H), 1.49-1.33 (m, 1H), 0.97 (t, J=7.34 Hz, 3H).

Example 208

4-[(3-{[(3R)-1-(prop-2-enoyl)piperidin-3-yl]amino}-1H-pyrazolo[3,4-b]pyridin-4-yl)oxy]-N-[5-(trifluoromethyl)-1,3-thiazol-2-yl]benzamide (Compound ID 208)

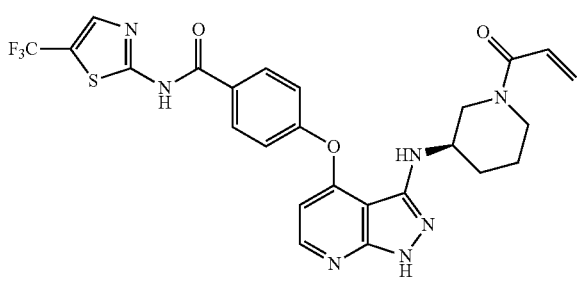 [SMILES: C=CC(=O)N1CCC[C@@H](Nc2n[nH]c3nccc(Oc4ccc(C(=O)Nc5ncc(C(F)(F)F)s5)cc4)c23)C1]

1.129 Preparation of tert-butyl (3R)-3-({1-[(4-methoxyphenyl)methyl]-4-(4-{[5-(trifluoromethyl)-1,3-thiazol-2-yl]carbamoyl}phenoxy)-1H-pyrazolo[3,4-b]pyridin-3-yl}amino)piperidine-1-carboxylate

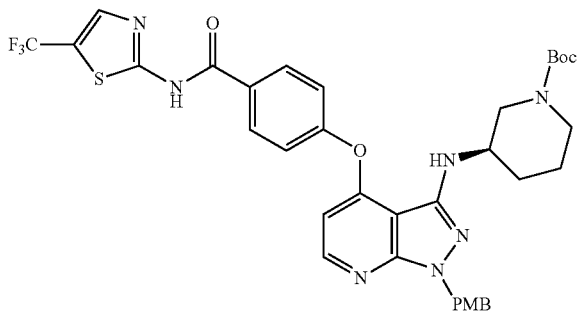

The intermediate was prepared following the method described for Ex. 140. LC-MS (ESI): m/z (M+1)⁺, 724.0.

1.130 Preparation of 4-({1-[(4-methoxyphenyl)methyl]-3-{[(3R)-piperidin-3-yl]amino}-1H-pyrazolo[3,4-b]pyridin-4-yl}oxy)-N-[5-(trifluoromethyl)-1,3-thiazol-2-yl]benzamide trifluoroacetate The intermediate was prepared following the method described for Ex. 140. LC-MS (ESI): m/z (M+1)⁺, 624.0.

1.131 Preparation of 4-[(3-{[(3R)-piperidin-3-yl]amino}-1H-pyrazolo[3,4-b]pyridin-4-yl)oxy]-N-[5-(trifluoromethyl)-1,3-thiazol-2-yl]benzamide The intermediate was prepared following the method described for Ex. 140. LC-MS (ESI): m/z (M+1)⁺, 504.0

Compound 208 was prepared following the method described for Ex. 116. LC-MS (ESI): m/z (M+1)⁺, 557.9. ¹H NMR (500 MHz, DMSO-d6) δ ppm 13.31 (br. s., 1H), 12.30 (br. s, 1H), 8.36-8.16 (m, 4H), 7.51-7.38 (m, 2H), 6.88-6.65 (m, 1H), 6.19 (d, J=5.38 Hz, 1H), 6.11-6.01 (m, 1H), 5.69-5.53 (m, 1H), 5.29-5.20 (m, 1H), 4.54-4.07 (m, 1H), 4.02-3.78 (m, 1H), 3.71-3.57 (m, 1H), 3.28-2.82 (m, 2H), 2.20-1.36 (m, 4H).

Example 209

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3,4-thiadiazol-2-yl)benzamide (Compound ID 209)

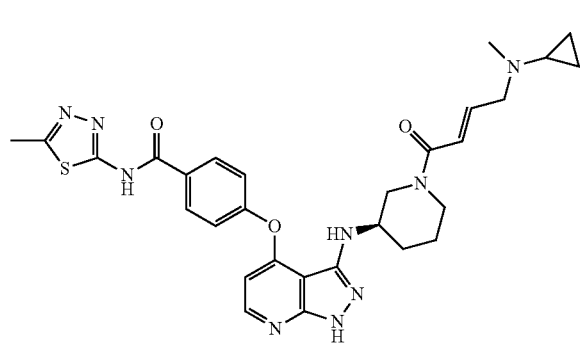 [SMILES: Cc1nnc(NC(=O)c2ccc(Oc3ccnc4[nH]nc(N[C@@H]5CCCN(C(=O)/C=C/CN(C)C6CC6)C5)c34)cc2)s1]

The intermediate was prepared following the method described for Ex. 167. LC-MS (ESI): m/z (M+1)⁺, 588.1 ¹H NMR (500 MHz, DMSO-d6) δ ppm 12.96 (br. s, 1H), 12.30 (br. s, 1H), 8.25 (d, J=8.80 Hz, 3H), 7.51-7.33 (m, 2H), 6.64-6.31 (m, 2H), 6.23-6.13 (m, 1H), 5.29-5.09 (m, 1H), 4.39-3.87 (m, 1H), 3.84-3.51 (m, 2H), 3.49-2.93 (m, 4H), 2.65 (s, 3H), 2.26-2.04 (m, 3H), 2.03-1.29 (m, 5H), 0.52-0.15 (m, 4H).

Example 210

4-[(3-{[(3R)-1-(but-2-ynoyl)piperidin-3-yl]amino}-1H-pyrazolo[3,4-b]pyridin-4-yl)oxy]-N-methyl-N-(5-methyl-1,3-thiazol-2-yl)benzamide (Compound ID 210)

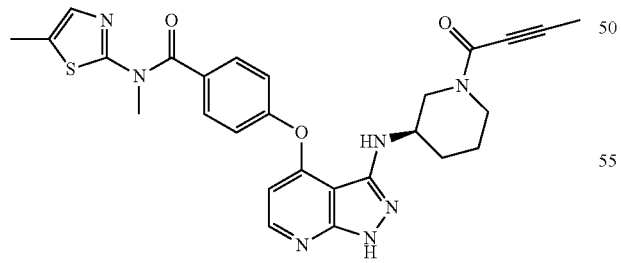

The compound was prepared following the method described for Ex. 141. LC-MS (ESI): m/z (M+1)⁺, 530.1.

Example 211

N-methyl-N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide (Compound ID 211)

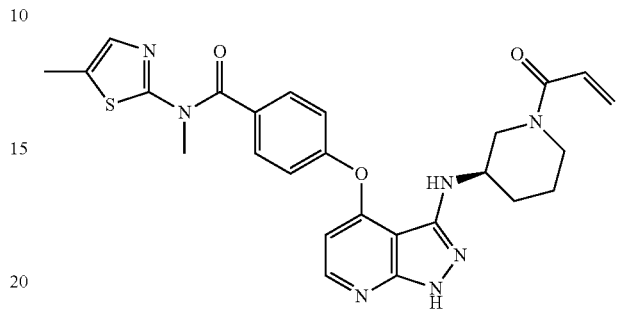

The compound was prepared following the method described for Ex. 140. LC-MS (ESI): m/z (M+1)⁺, 518.1. ¹H NMR (500 MHz, DMSO) δ 12.37-12.17 (m, 1H), 8.19 (d, J=5.38 Hz, 1H), 7.78 (d, J=8.31 Hz, 2H), 7.42 (d, J=8.30 Hz, 2H), 7.32-7.28 (m, 1H), 6.88-6.65 (m, 1H), 6.17 (d, J=5.38 Hz, 1H), 6.06 (d, J=16.63 Hz, 1H), 5.70-5.51 (m, 1H), 5.25 (d, J=7.34 Hz, 1H), 4.49-4.11 (m, 1H), 4.05-3.81 (m, 1H), 3.64 (br. s., 1H), 3.56 (s, 3H), 3.43-2.89 (m, 2H), 2.40 (s, 3H), 2.10-1.97 (m, 1H), 1.80-1.61 (m, 2H), 1.54-1.34 (m, 1H).

Example 212

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-[4-(trifluoromethyl)pyridin-2-yl]benzamide (Compound ID 212)

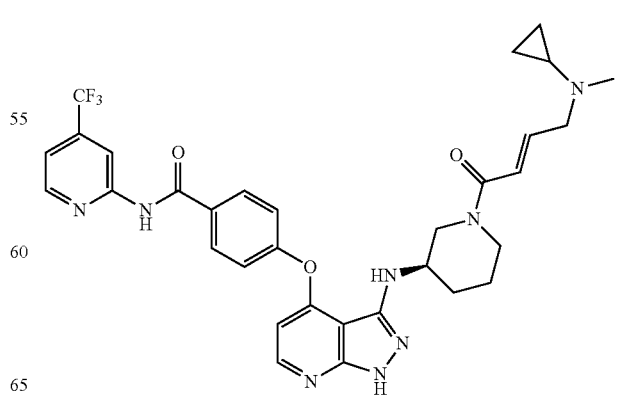

1.19 Preparation of tert-butyl 3-({1-[(4-methoxyphenyl)methyl]-4-(4-{[4-(trifluoromethyl)pyridin-2-yl]carbamoyl}phenoxy)-1H-pyrazolo[3,4-b]pyridin-3-yl}amino)piperidine-1-carboxylate

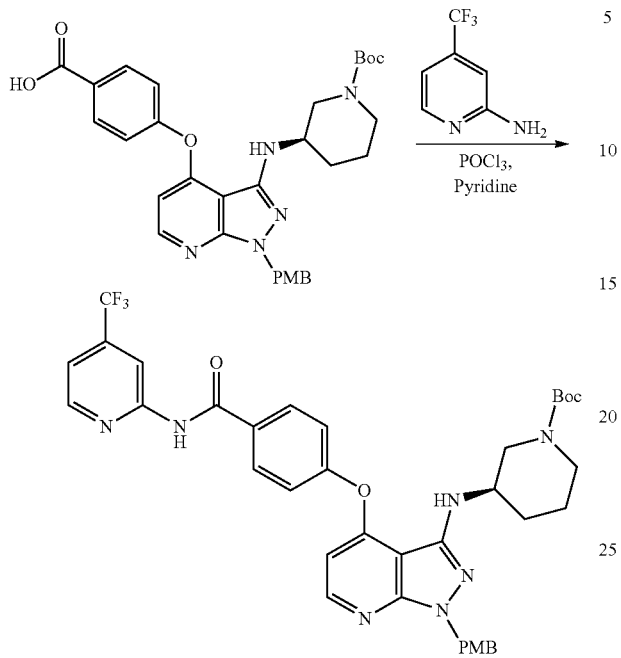

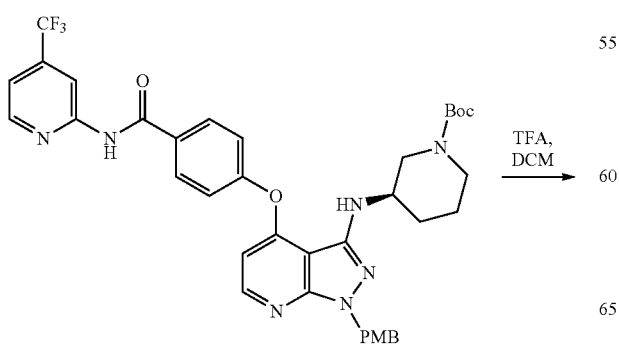

To a solution of 4-[(3-{[(3R)-1-[(tert-butoxy)carbonyl]piperidin-3-yl]amino}-1-[(4-methoxyphenyl)methyl]-1H-pyrazolo[3,4-b]pyridin-4-yl)oxy]benzoic acid (1.47 g, 2.56 mmol) and 4-(trifluoromethyl)pyridin-2-amine (1.25 g, 7.69 mmol) in pyridine (15 mL) was added POCl₃ (1.57 g, 10.24 mmol) dropwise at room temperature. After the addition, the reaction mixture was stirred at room temperature for 45 min. Ethyl acetate and NaHCO₃ saturated aqueous solution were added and the two phases separated. The organic phase was washed twice with water, dried over Na₂SO₄, filtered and concentrated to give a crude product that was purified by flash chromatography (silica gel, 100 g, from 15 to 65% ethyl acetate in cyclohexane). tert-Butyl 3-({1-[(4-methoxyphenyl)methyl]-4-(4-{[4-(trifluoromethyl)pyridin-2-yl]carbamoyl}phenoxy)-1H-pyrazolo[3,4-b]pyridin-3-yl}amino)piperidine-1-carboxylate was obtained as a yellow oil (1.35 g, Yield 54%). LC-MS (ESI): m/z (M+1)⁺, 718.3.

1.20 Preparation of 4-({1-[(4-methoxyphenyl)methyl]-3-{[(3R)-piperidin-3-yl]amino}-1H-pyrazolo[3,4-b]pyridin-4-yl}oxy)-N-[4-(trifluoromethyl)pyridin-2-yl]benzamide; trifluoroacetic acid

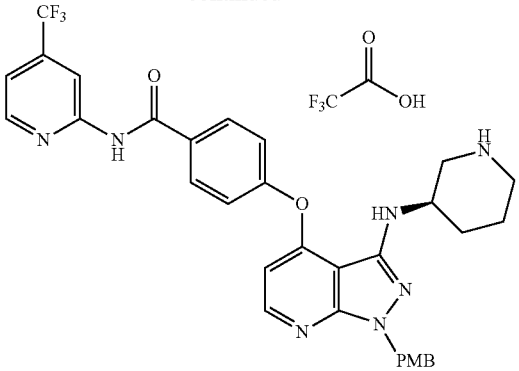

To a solution of tert-butyl 3-({1-[(4-methoxyphenyl)methyl]-4-(4-{[4-(trifluoromethyl)pyridin-2-yl]carbamoyl}phenoxy)-1H-pyrazolo[3,4-b]pyridin-3-yl}amino)piperidine-1-carboxylate (1.35 g, 1.37 mmol) in DCM (12 ml) at 0° C. TFA (2.7 mL) was added. The reaction mixture was stirred at this temperature for 30 min then at rt for 45 min then concentrated to afford 4-({1-[(4-methoxyphenyl)methyl]-3-{[(3R)-piperidin-3-yl]amino}-1H-pyrazolo[3,4-b]pyridin-4-yl}oxy)-N-[4-(trifluoromethyl)pyridin-2-yl]benzamide; trifluoroacetic acid as a yellow oil (3.54 g, Yield: quantitative). LC-MS (ESI): m/z (M+1)⁺, 618.2.

1.21 Preparation of 4-[(3-{[(3R)-piperidin-3-yl]amino}-1H-pyrazolo[3,4-b]pyridin-4-yl)oxy]-N-[4-(trifluoromethyl)pyridin-2-yl]benzamide

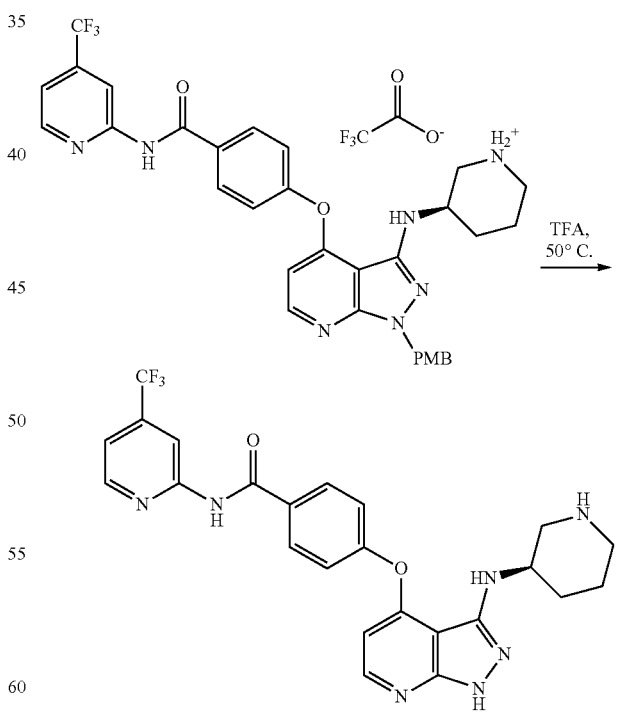

4-({1-[(4-Methoxyphenyl)methyl]-3-{[(3R)-piperidin-3-yl]amino}-1H-pyrazolo[3,4-b]pyridin-4-yl}oxy)-N-[4-(trifluoromethyl)pyridin-2-yl]benzamide; trifluoroacetic acid (3.54 g, 1.37 mmol) was dissolved in TFA (12 mL) and stirred at 50° C. for 2.5 hours then the solvent was evaporated. The crude product was purified by SCX cartridge affording 4-[(3-{[(3R)-piperidin-3-yl]amino}-1H-pyrazolo[3,4-b]pyridin-4-yl)oxy]-N-[4-(trifluoromethyl)pyridin-2-yl]benzamide as a pale yellow solid (948.0 mg, Yield: quantitative). LC-MS (ESI): m/z (M+1)+, 497.96.

Compound 212 was prepared following the method described for Ex. 142. LC-MS (ESI): m/z (M+1)+, 635.2. 1H NMR (500 MHz, DMSO) δ 12.35 (br. s., 1H), 11.37 (s, 1H), 8.69 (d, J=4.89 Hz, 1H), 8.56 (s, 1H), 8.25-8.15 (m, 3H), 7.56 (d, J=4.89 Hz, 1H), 7.47-7.32 (m, 2H), 6.65-6.32 (m, 2H), 6.25-6.11 (m, 1H), 5.32-5.02 (m, 1H), 4.40-3.86 (m, 1H), 3.83-3.58 (m, 2H), 3.54-2.88 (m, 4H), 2.24-2.03 (m, 3H), 2.02-1.35 (m, 5H), 0.50-0.14 (m, 4H).

Example 213

1-[(3R)-3-{[4-(4-{[1,3]oxazolo[4,5-b]pyridin-2-yl}phenoxy)-1H-pyrazolo[3,4-b]pyridin-3-yl]amino}piperidin-1-yl]prop-2-en-1-one (Compound ID 213)

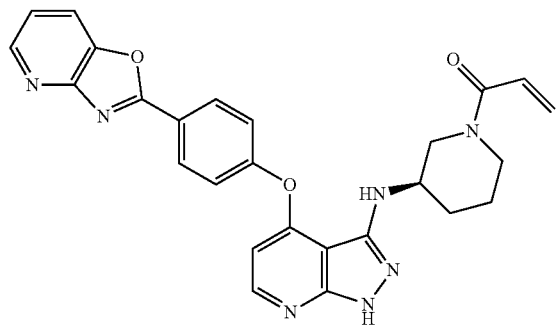 [SMILES: C=CC(=O)N1CCC[C@@H](Nc2n[nH]c3nccc(Oc4ccc(-c5nc6ncccc6o5)cc4)c23)C1]

The compound was prepared following the method described for Ex. 140. LC-MS (ESI): m/z (M+1)+, 482.4.

Example 214

3-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-1-[4-(trifluoromethyl)pyridin-2-yl]urea (Compound ID 214)

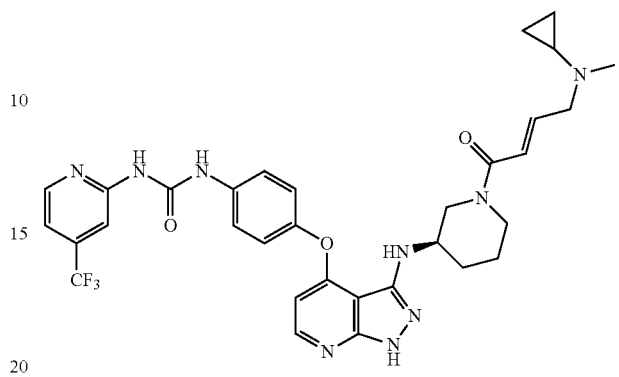

The compound was prepared following the method described for Ex. 136. LC-MS (ESI): m/z (M+1)+, 650.1. 1H NMR (500 MHz, DMSO-d6) d ppm 12.31-12.12 (m, 1H), 9.94 (br. s., 1H), 9.79 (br. s., 1H), 9.79 (br. s., 1H), 8.55 (d, J=5.38 Hz, 1H), 8.16-8.10 (m, 1H), 8.07 (s, 1H), 7.65 (d, J=8.80 Hz, 2H), 7.37 (d, J=5.40 Hz, 1H), 7.30-7.20 (m, 2H), 6.61-6.32 (m, 2H), 6.01 (d, J=5.38 Hz, 1H), 5.27-5.12 (m, 1H), 4.42-3.92 (m, 1H), 3.85-3.61 (m, 2H), 3.54-2.90 (m, 4H), 2.25-1.95 (m, 4H), 1.84-1.37 (m, 4H), 0.48-0.17 (m, 4H).

Example 215

4-[(3-{[(3R)-1-cyclopropanecarbonylpyrrolidin-3-yl]amino}-1H-pyrazolo[3,4-b]pyridin-4-yl)oxy]-N-[4-(trifluoromethyl)pyridin-2-yl]benzamide (Compound ID 215)

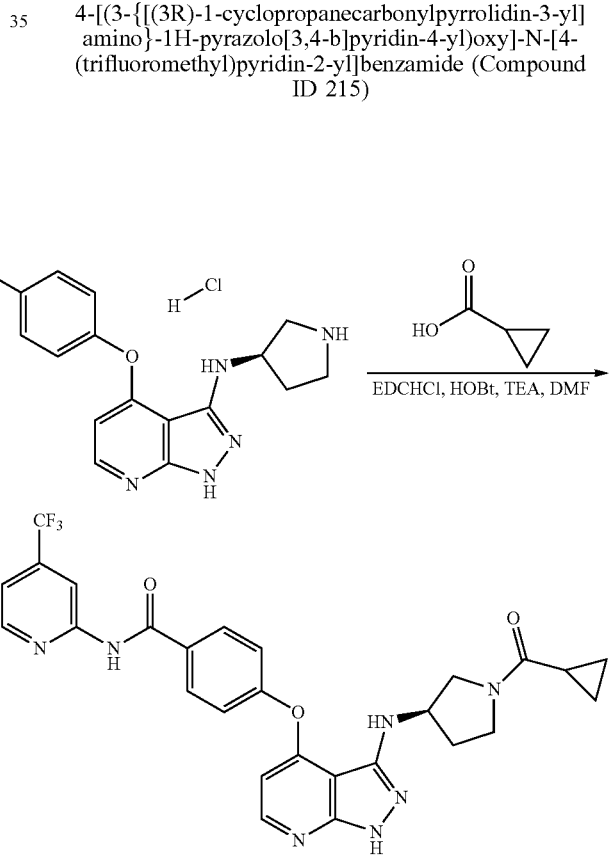

The compound was prepared following the method described for Ex. 161. LC-MS (ESI): m/z (M+1)⁺, 551.98. ¹H NMR (400 MHz, DMSO-d₆) δ ppm 12.37 (br. s., 1H), 11.37 (s, 1H), 8.69 (d, J=5.09 Hz, 2H), 8.55 (s, 1H), 8.27-8.14 (m, 3H), 7.56 (d, J=5.09 Hz, 1H), 7.44 (d, J=8.22 Hz, 2H), 6.17 (d, J=5.48 Hz, 1H), 5.87-5.35 (m, 1H), 4.43-4.12 (m, 1H), 4.11-3.25 (m, 4H), 2.32-1.90 (m, 2H), 1.83-1.62 (m, 1H), 0.84-0.62 (m, 4H).

Example 216

(3R)-3-({4-[4-(1,3-benzothiazol-2-yl)phenoxy]-1H-pyrazolo[3,4-b]pyridin-3-yl}amino)-N-ethylpiperidine-1-carboxamide (Compound ID 216)

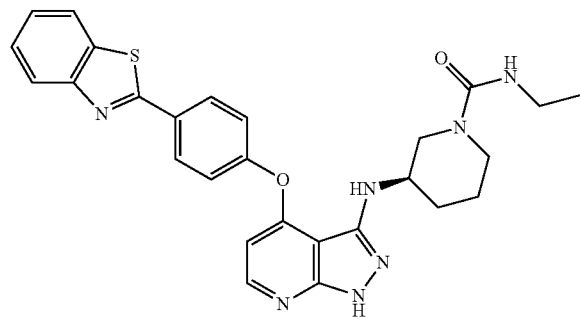 [SMILES: CCNC(=O)N1CCC[C@@H](Nc2n[nH]c3nccc(Oc4ccc(-c5nc6ccccc6s5)cc4)c23)C1]

The compound was prepared following the method described for Ex. 182. LC-MS (ESI): m/z (M+1)⁺, 514.40.

Example 217

N-(5-methyl-1,3-thiazol-2-yl)-4-({3-[1-(1-methylpiperidine-4-carbonyl)piperidin-3-yl]-1H-pyrazolo[3,4-b]pyridin-4-yl}oxy)benzamide (Compound ID 217)

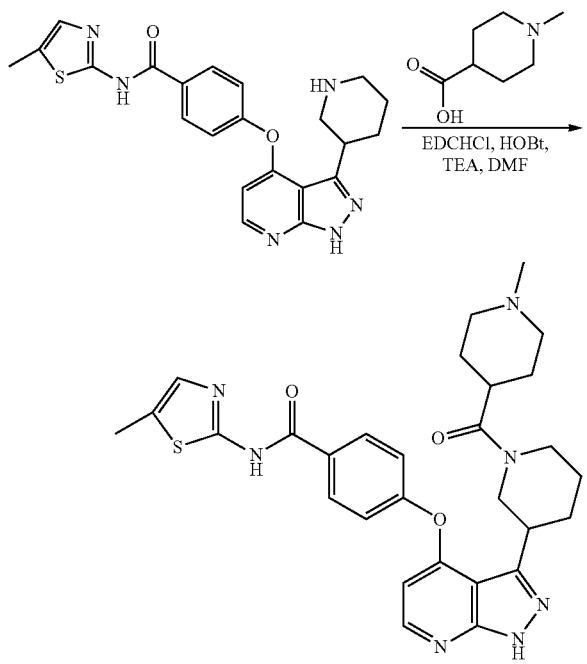

To a solution of N-(5-methyl-1,3-thiazol-2-yl)-4-{[3-(piperidin-3-yl)-1H-pyrazolo[3,4-b]pyridin-4-yl]oxy}benzamide (102.0 mg, 0.17 mmol) in DMF (3 ml) were added 1-methylpiperidine-4-carboxylic acid (39.0 mg, 0.20 mmol), TEA (47 μL, 0.34 mmol), HOBt (21 mg, 0.16 mmol) and EDC.HCl (42.0 mg, 0.22 mmol) and the mixture was stirred at room temperature for 18 hours. An aqueous solution of NaHCO₃ was added and the product was extracted three times with ethyl acetate. The collected organic phases were dried over Na₂SO₄, filtered and concentrated. The product was purified by preparative HPLC (C18 column, CH₃CN in H₂O 0.1% HCOOH from 10% to 100%) and by flash chromatography (silica gel NH, 25 g, MeOH in DCM from 1% to 5%) to give N-(5-methyl-1,3-thiazol-2-yl)-4-({3-[1-(1-methylpiperidine-4-carbonyl)piperidin-3-yl]-1H-pyrazolo[3,4-b]pyridin-4-yl}oxy)benzamide as white solid (28.0 mg, Yield: 29%). LC-MS (ESI): m/z (M+1)⁺, 560.0.

Example 218

4-{[3-(1-cyclopropanecarbonylpiperidin-3-yl)-1H-pyrazolo[3,4-b]pyridin-4-yl]oxy}-N-[4-(trifluoromethyl)pyridin-2-yl]benzamide (Compound ID 218)

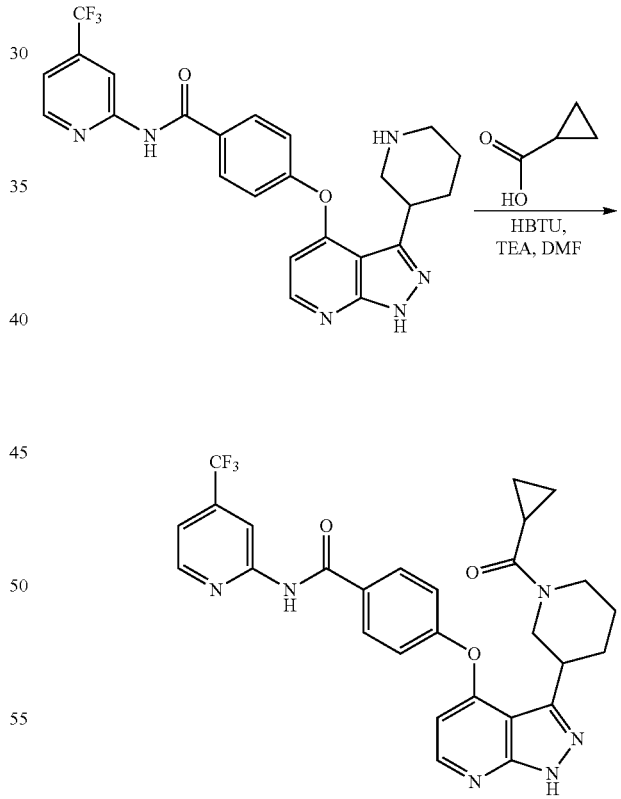

The compound was prepared following the method described for Ex. 161. LC-MS (ESI): m/z (M+1)⁺, 550.97. ¹H NMR (400 MHz, DMSO-d₆) δ ppm 13.50 (br. s., 1H), 11.38 (br. s, 1H), 8.69 (d, J=4.89 Hz, 1H), 8.55 (s, 1H), 8.34 (d, J=4.89 Hz, 1H), 8.20 (d, J=8.80 Hz, 2H), 7.55 (d, J=4.89 Hz, 1H), 7.50-7.36 (m, 2H), 6.50-6.28 (m, 1H), 4.82-4.58 (m, 1H), 4.44-4.19 (m, 1H), 3.44-2.59 (m, 3H), 2.27-1.74 (m, 4H), 1.60-1.33 (m, 1H), 0.79-0.11 (m, 4H).

Example 219

1-[(3R)-3-({4-[4-(7-methyl-1,3-benzoxazol-2-yl)phenoxy]-1H-pyrazolo[3,4-b]pyridin-3-yl}amino)piperidin-1-yl]propan-1-one (Compound ID 219)

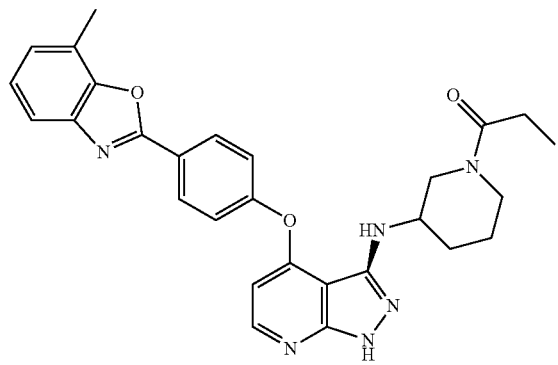

1.132 Preparation of 4-(7-methyl-1,3-benzoxazol-2-yl)phenol

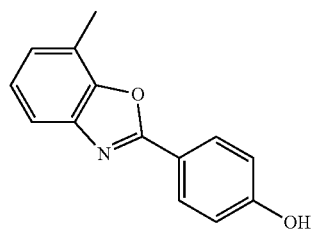 [SMILES: Cc1cccc2nc(-c3ccc(O)cc3)oc12]

The intermediate was prepared following the method described for the synthesis of the intermediate for Ex. 170. LC-MS (ESI): m/z (M+1)$^+$, 226.2.

1.133 Preparation of 2-[4-({3-bromo-1-[(4-methoxyphenyl)methyl]-1H-pyrazolo[3,4-b]pyridin-4-yl}oxy)phenyl]-7-methyl-1,3-benzoxazole

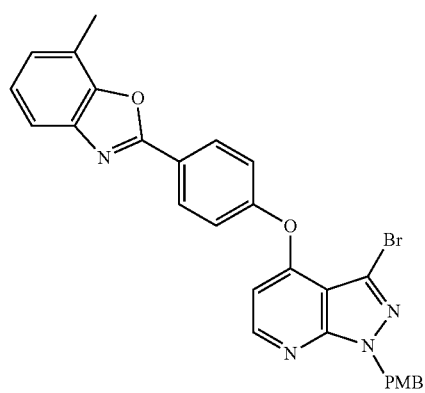

The intermediate was prepared following the method described for Ex. 148. LC-MS (ESI): m/z (M+1)$^+$, 541.3.

1.134 Preparation of tert-butyl (3R)-3-({1-[(4-methoxyphenyl)methyl]-4-[4-(7-methyl-1,3-benzoxazol-2-yl)phenoxy]-1H-pyrazolo[3,4-b]pyridin-3-yl}amino)piperidine-1-carboxylate

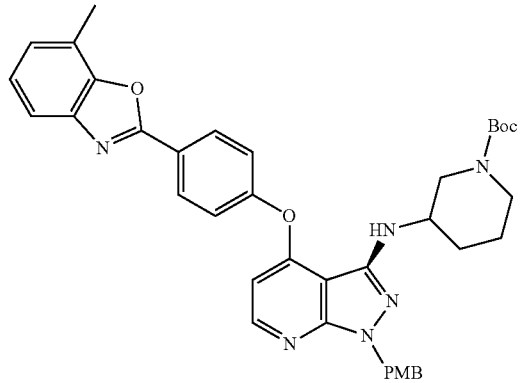

The intermediate was prepared following the method described for Ex. 148. LC-MS (ESI): m/z (M+1)$^+$, 661.6.

1.135 Preparation of 3R)—N-{1-[(4-methoxyphenyl)methyl]-4-[4-(7-methyl-1,3-benzoxazol-2-yl)phenoxy]-1H-pyrazolo[3,4-b]pyridin-3-yl}piperidin-3-amine

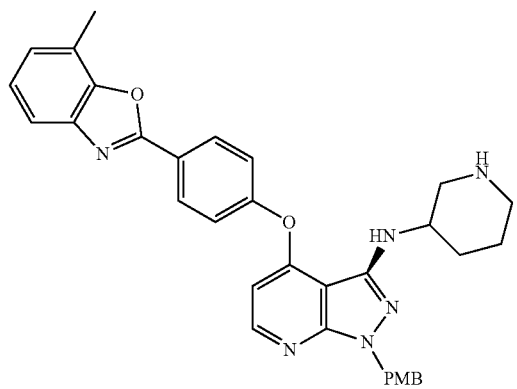

The intermediate was prepared following the method described for Ex. 148. LC-MS (ESI): m/z (M+1)$^+$, 561.5.

1.136 Preparation of (3R)—N-{4-[4-(7-methyl-1,3-benzoxazol-2-yl)phenoxy]-1H-pyrazolo[3,4-b]pyridin-3-yl}piperidin-3-amine

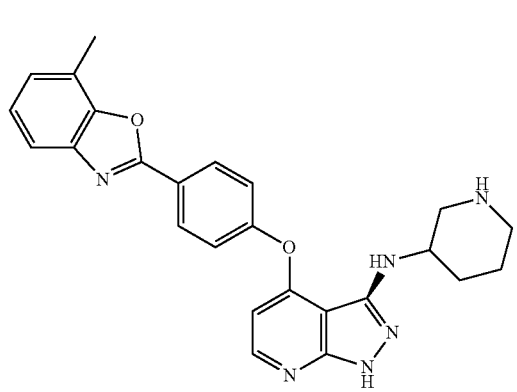

The intermediate was prepared following the method describe or Ex. 148. LC-MS (ESI): m/z (M+1)$^+$, 441.4.

Compound ID 219 was prepared following the method described for Ex. 86. LC-MS (ESI): m/z (M+1)+, 497.4.

Example 220

(3R)-1-cyclopropanecarbonyl-N-{4-[4-(7-methyl-1,3-benzoxazol-2-yl)phenoxy]-1H-pyrazolo[3,4-b]pyridin-3-yl}piperidin-3-amine (Compound ID 220)

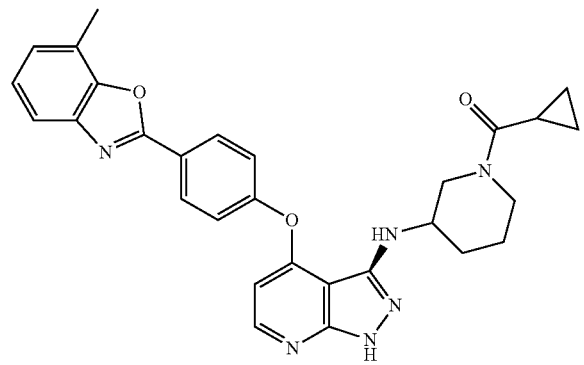

The compound was prepared following the method described for Ex. 86. LC-MS (ESI): m/z (M+1)+, 509.4.

Example 221

N-(5-methyl-1,3-thiazol-2-yl)-4-[(3-{[(3R)-1-(1-methylpiperidine-4-carbonyl)pyrrolidin-3-yl]amino}-1H-pyrazolo[3,4-b]pyridin-4-yl)oxy]benzamide (Compound ID 221)

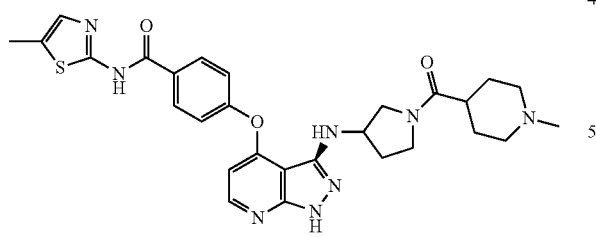

The compound was prepared following the method described for Ex. 86. LC-MS (ESI): m/z (M+1)+, 561.0. $^1$H NMR (500 MHz, DMSO) δ 12.69-12.18 (m, 2H), 8.24-8.18 (m, 3H), 7.44-7.35 (m, 2H), 7.26-7.19 (m, 1H), 6.25-6.12 (m, 1H), 5.63-5.44 (m, 1H), 4.36-4.13 (m, 1H), 3.96-3.38 (m, 4H), 2.80-2.66 (m, 2H), 2.38 (s, 3H), 2.13-2.07 (m, 3H), 1.99 (s, 3H), 1.87-1.75 (m, 2H), 1.62-1.46 (m, 4H).

Example 222

1-[(3R)-3-({4-[4-(1,3-benzothiazol-2-yl)phenoxy]-1H-pyrazolo[3,4-b]pyridin-3-yl}amino)piperidin-1-yl]propan-1-one (Compound ID 222)

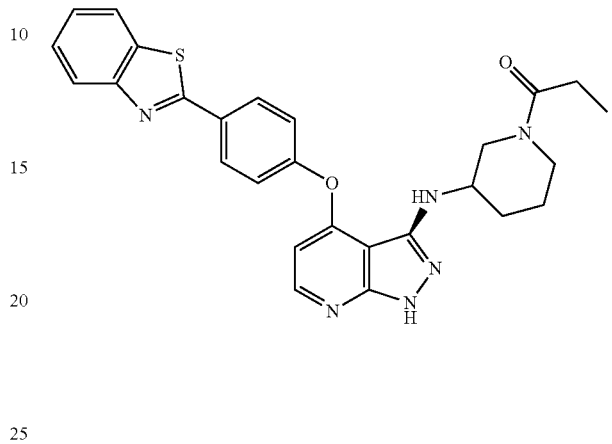

The compound was prepared following the method described for Ex. 184. LC-MS (ESI): m/z (M+1)+, 499.30.

Example 223

N-(1,3-benzothiazol-2-yl)-4-[(3-{[(3R)-1-(1-methyl-piperidine-4-carbonyl)piperidin-3-yl]amino}-1H-pyrazolo[3,4-b]pyridin-4-yl)oxy]benzamide (Compound ID 223)

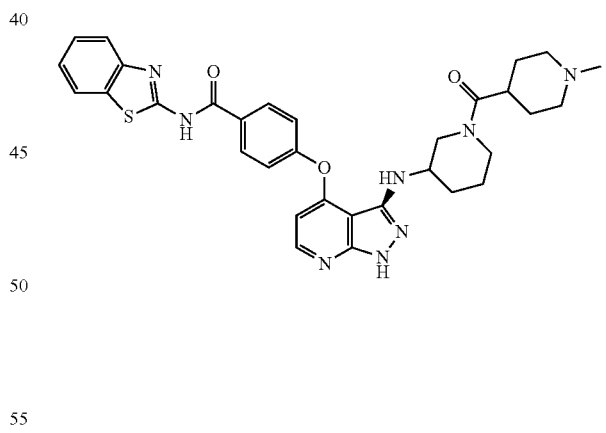

N-(1,3-Benzothiazol-2-yl)-4-[(3-{[(3R)-1-(1-methylpiperidine-4-carbonyl)piperidin-3-yl]amino}-1H-pyrazolo[3,4-b]pyridin-4-yl)oxy]benzamide was prepared following the method described for compound 172. LC-MS (ESI): m/z (M+1)+, 611.0. $^1$H NMR (400 MHz, DMSO-d6) δ ppm 13.63-11.41 (m, 2H), 8.30 (d, J=8.78 Hz, 2H), 8.25-8.17 (m, 1H), 8.01 (d, J=7.53 Hz, 1H), 7.77 (d, J=7.50 Hz, 1H), 7.51-7.39 (m, 3H), 7.37-7.29 (m, 1H), 6.19 (d, J=5.27 Hz, 1H), 5.32-5.08 (m, 1H), 4.37-3.97 (m, 1H), 3.96-3.54 (m, 2H), 3.28-2.89 (m, 2H), 2.87-2.59 (m, 2H), 2.57-2.35 (m, 1H), 2.15 (s, 3H), 2.07-1.30 (m, 10H).

Example 224

(3R)-3-({4-[4-(1H-1,3-benzodiazol-2-yl)phenoxy]-1H-pyrazolo[3,4-b]pyridin-3-yl}amino)-N-ethylpiperidine-1-carboxamide (Compound ID 224)

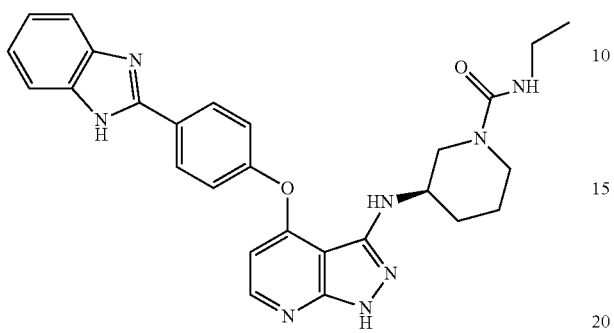

1.137 Preparation of 2-[4-({3-bromo-1-[(4-methoxyphenyl)methyl]-1H-pyrazolo[3,4-b]pyridin-4-yl}oxy)phenyl]-1H-1,3-benzodiazole

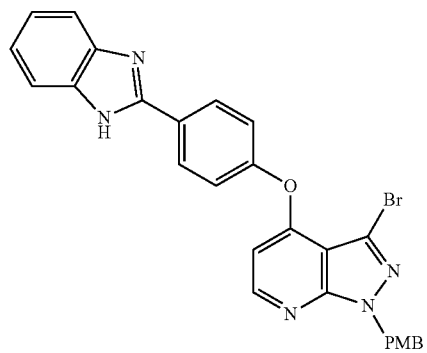

The intermediate was prepared following the method described for Ex. 86. LC-MS (ESI): m/z (M+1)$^+$, 525.87.

1.138 Preparation of 2-[4-({3-bromo-1-[(4-methoxyphenyl)methyl]-1H-pyrazolo[3,4-b]pyridin-4-yl}oxy)phenyl]-1-[(4-methoxyphenyl)methyl]-1H-1,3-benzodiazole

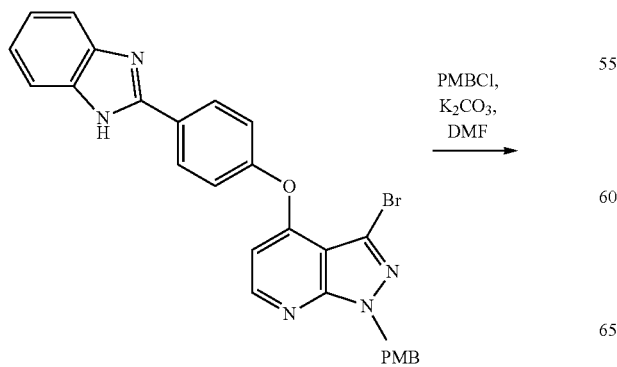

A solution of 2-[4-((3-bromo-1-[(4-methoxyphenyl)methyl]-1H-pyrazolo[3,4-b]pyridin-4-yl)oxy)phenyl]-1H-1,3-benzodiazole (521 mg, 0.99 mmol) in 16 ml of DMF and K$_2$CO$_3$ (273 mg, 1.98 mmol) was cooled to 0° C. 1-(chloromethyl)-4-methoxybenzene (0.2 ml, 1.485 mmol) was added and the mixture was stirred at room temperature. Water was added and extracted with EtOAc. The organic phase was washed with brine, dried over Na$_2$SO$_4$, filtered and concentrated to give a crude that was desired product (194 mg, 0.225 mmol, Yield: 23%). LC-MS (ESI): m/z (M+1)$^+$, 645.94.

1.139 Preparation of tert-butyl (3R)-3-({1-[(4-methoxyphenyl)methyl]-4-(4-{1-[(4-methoxyphenyl)methyl]-1H-1,3-benzodiazol-2-yl}phenoxy)-1H-pyrazolo[3,4-b]pyridin-3-yl}amino)piperidine-1-carboxylate

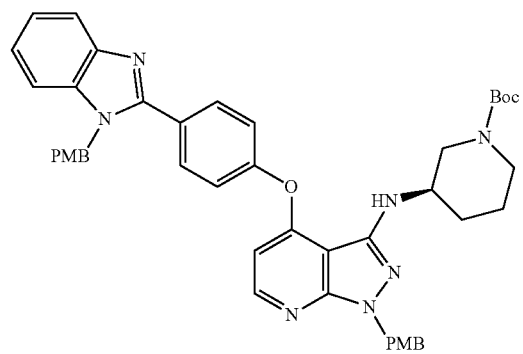

The intermediate was prepared following the method described for Ex. 86. LC-MS (ESI): m/z (M+1)$^+$, 766.1.

1.140 Preparation of (3R)—N-[4-(4-{1-[(4-methoxyphenyl)methyl]-1H-1,3-benzodiazol-2-yl}phenoxy)-1H-pyrazolo[3,4-b]pyridin-3-yl]piperidin-3-amine

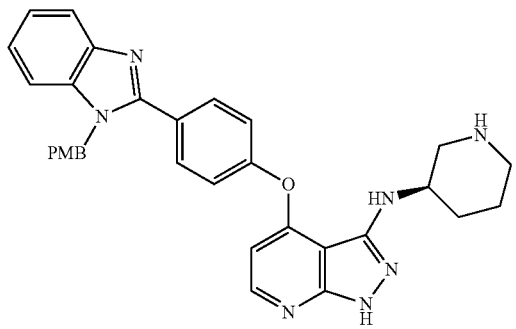

The intermediate was prepared following the method described for Ex. 86. LC-MS (ESI): m/z (M+1)+, 426.0.

1.141 Preparation of (3R)—N-{1-[(4-methoxyphenyl)methyl]-4-[4-(7-methyl-1,3-benzoxazol-2-yl)phenoxy]-1H-pyrazolo[3,4-b]pyridin-3-yl}piperidin-3-amine trifluoroacetic acid

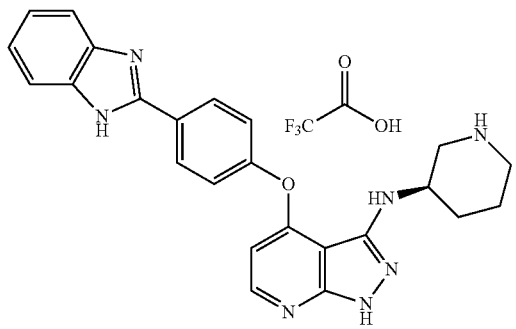

(3R)—N-[4-(4-{1-[(4-Methoxyphenyl)methyl]-1H-1,3-benzodiazol-2-yl}phenoxy)-1H-pyrazolo[3,4-b]pyridin-3-yl]piperidin-3-amine (139.6 mg, 0.255 mmol) in TFA (1.5 mL) was stirred at 70° C. for 16 h. The mixture was concentrated in vacuo obtaining the desired product (273 mg, 0.506 mmol, quantitative yield). LC-MS (ESI): m/z (M+1)+, 425.99.

The title compound was prepared following the method described for Ex. 189. LC-MS (ESI): m/z (M+1)+, 497.0.

Example 225

4-[(3-{[(3R)-1-propanoylpiperidin-3-yl]amino}-1H-pyrazolo[3,4-b]pyridin-4-yl)oxy]-N-[4-(trifluoromethyl)pyridin-2-yl]benzamide (Compound ID 225)

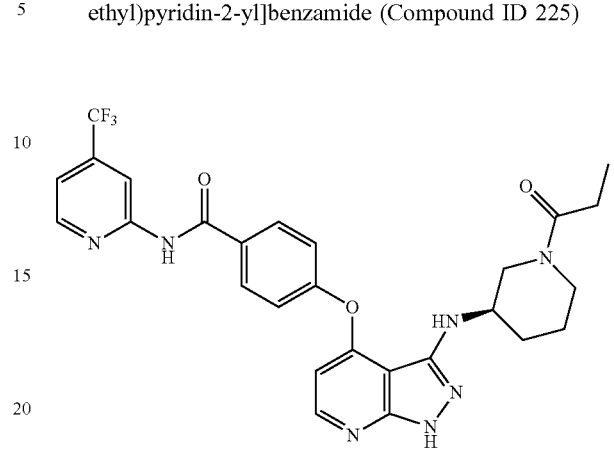

The compound was prepared following the method described for Ex. 173. LC-MS (ESI): m/z (M+1)+, 554.0. $^1$H NMR (500 MHz, DMSO) δ 12.51-12.16 (m, 1H), 11.37 (s, 1H), 8.69 (d, J=5.21 Hz, 1H), 8.56 (s, 1H), 8.28-8.14 (m, 3H), 7.56 (dd, J=5.21, 0.82 Hz, 1H), 7.48-7.37 (m, 2H), 6.24-6.09 (m, 1H), 5.29-5.14 (m, 1H), 4.44-3.55 (m, 3H), 3.16-2.78 (m, 2H), 2.41-2.17 (m, 2H), 2.07-1.91 (m, 1H), 1.79-1.56 (m, 2H), 1.38 (dd, J=10.29, 3.16 Hz, 1H), 0.97 (q, J=7.78 Hz, 3H).

Example 226

N-(1,3-benzothiazol-2-yl)-4-[(3-{[(3R)-1-(3-methyloxetane-3-carbonyl)piperidin-3-yl]amino}-1H-pyrazolo[3,4-b]pyridin-4-yl)oxy]benzamide (Compound ID 226)

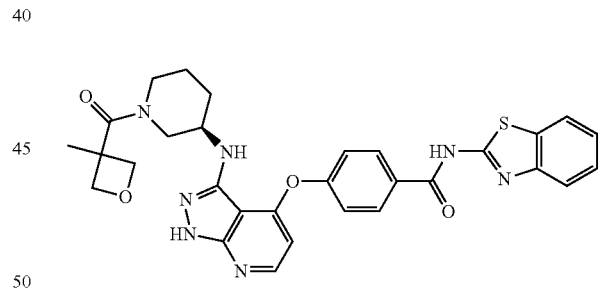

To a solution of N-(1,3-benzothiazol-2-yl)-4-[(3-{[(3R)-piperidin-3-yl]amino}-1H-pyrazolo[3,4-b]pyridin-4-yl)oxy]benzamide (150.0 mg, 0.21 mmol) in DCM (7 mL) and isopropanol (0.5 mL) 3-methyloxetane-3-carboxylic acid (31.0 mg, 0.23 mmol) and TEA (0.067 mL, 0.42 mmol) were added. The solution was cooled to 0° C. and T$_3$P (0.165 mL, 0.28 mmol) was added. The solution was stirred for 40 min at room temperature, and then the mixture was diluted with DCM and washed by water and saturated solution of NaHCO$_3$. The organic phase was concentrated and the crude obtained was purified by gradient flash chromatography (25 g silica gel, MeOH/DCM from 2/98 to 7/93). N-(1,3-Benzothiazol-2-yl)-4-[(3-{[(3R)-1-(3-methyloxetane-3-carbonyl)piperidin-3-yl]amino}-1H-pyrazolo[3,4-b]pyridin-4-yl)oxy]benzamide was obtained as a white solid (70.0 mg, yield: 57%). LC-MS (ESI): m/z (M+1)+, 583.95. $^1$H NMR 1H NMR (500 MHz, DMSO) δ 12.98 (br. s., 1H), 12.40-12.24 (m, 1H), 8.30 (d, J=8.51 Hz, 2H), 8.21 (d, J=5.49 Hz, 1H), 8.03 (d, J=7.68 Hz, 1H), 7.79 (d, J=7.41 Hz, 1H), 7.52-7.42 (m, 3H), 7.35 (t, J=7.55 Hz, 1H), 6.19 (d, J=5.49 Hz, 1H), 5.39-5.18 (m, 1H), 4.99-4.69 (m, 2H), 4.46-2.57 (m, 7H), 2.07-1.95 (m, 1H), 1.82-1.33 (m, 6H).

Example 227

(R)—N-ethyl-3-(4-(4-(4-methylpyridin-2-ylcarbamoyl)phenoxy)-1H-pyrazolo[3,4-b]pyridin-3-ylamino)piperidine-1-carboxamide (Compound ID 227)

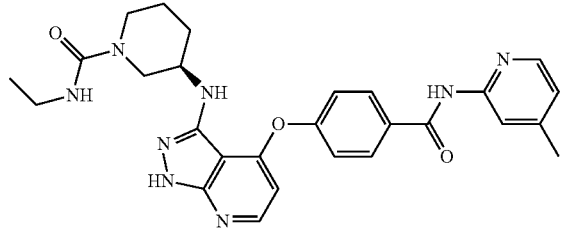 [SMILES: CCNC(=O)N1CCC[C@@H](Nc2n[nH]c3nccc(Oc4ccc(C(=O)Nc5cc(C)ccn5)cc4)c23)C1]

The compound was prepared following methods described herein.

Example 228

4-({3-[(3R)-3-[(ethylcarbamoyl)amino]piperidin-1-yl]-1H-pyrazolo[3,4-b]pyridin-4-yl}oxy)-N-[4-(trifluoromethyl)pyridin-2-yl]benzamide (Compound ID 228)

1.145 Preparation of ethyl 4-({3-[(3R)-3-{[(tert-butoxy)carbonyl]amino}piperidin-1-yl]-1-[(4-methoxyphenyl)methyl]-1H-pyrazolo[3,4-b]pyridin-4-yl}oxy)benzoate

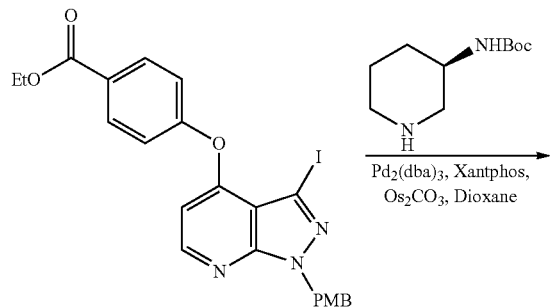

The intermediate was prepared following the method described for Ex. 86. LC-MS (ESI): m/z (M+1)+, 602.0.

1.146 Preparation of ({3-[(3R)-3-{[(tert-butoxy)carbonyl]amino}piperidin-1-yl]-1-[(4-methoxyphenyl)methyl]-1H-pyrazolo[3,4-b]pyridin-4-yl}oxy)benzoic acid

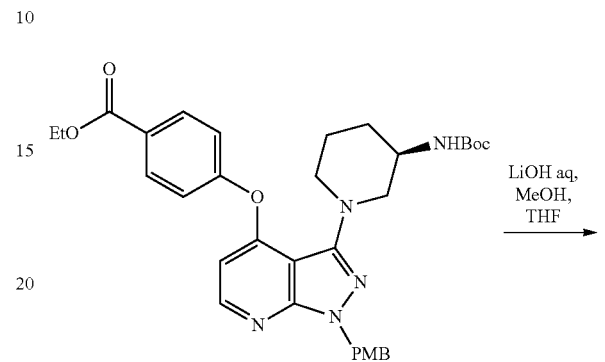

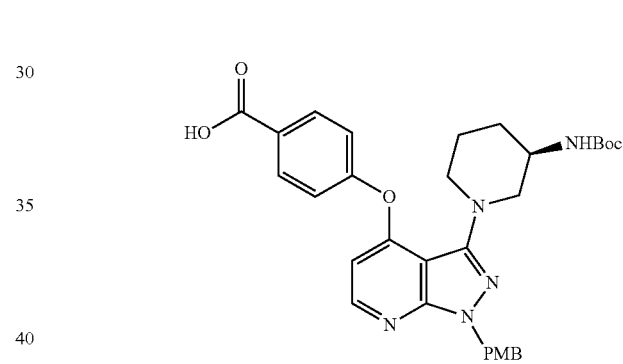

The intermediate was prepared following the method described for Ex. 161. LC-MS (ESI): m/z (M+1)+, 574.0.

1.147 Preparation of tert-butyl N-[(3R)-1-{1-[(4-methoxyphenyl)methyl]-4-(4-{[4-(trifluoromethyl)pyridin-2yl]carbamoyl}phenoxy)-1H-pyrazolo[3,4-b]pyridin-3-yl}piperidin-3-yl]carbamate

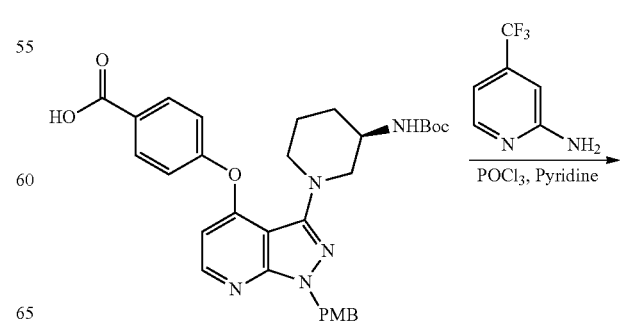

-continued

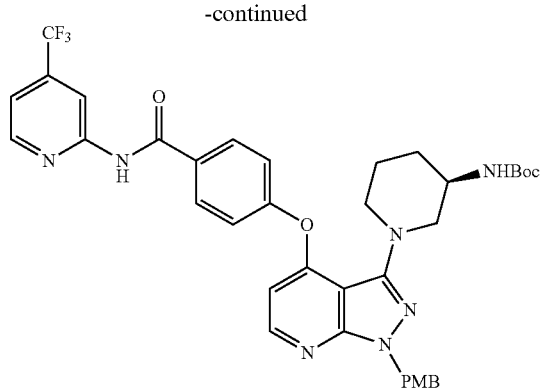

The intermediate was prepared following the method described for Ex. 161. LC-MS (ESI): m/z (M+1)+, 718.0.

1.148 Preparation of 4-({3-[(3R)-3-aminopiperidin-1-yl]-1-[(4-methoxyphenyl)methyl]-1H-pyrazolo[3,4-b]pyridin-4-yl}oxy)-N-[4-(trifluoromethyl)pyridin-2-yl]benzamide; trifluoroacetic acid

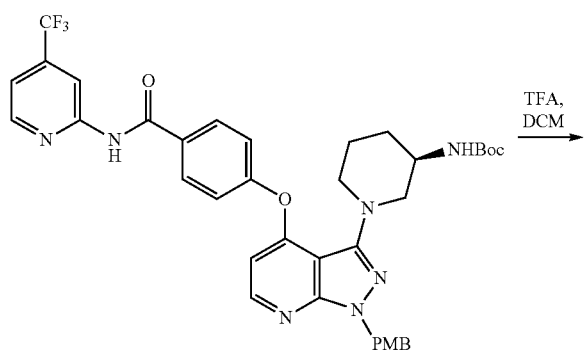

The intermediate was prepared following the method described for Ex. 161. LC-MS (ESI): m/z (M+1)+, 618.0.

1.149 Preparation of 4-({3-[(3R)-3-aminopiperidin-1-yl]-1-[(4-methoxyphenyl)methyl]-1H-pyrazolo[3,4-b]pyridin-4-yl}oxy)-N-[4-(trifluoromethyl)pyridin-2-yl]benzamide

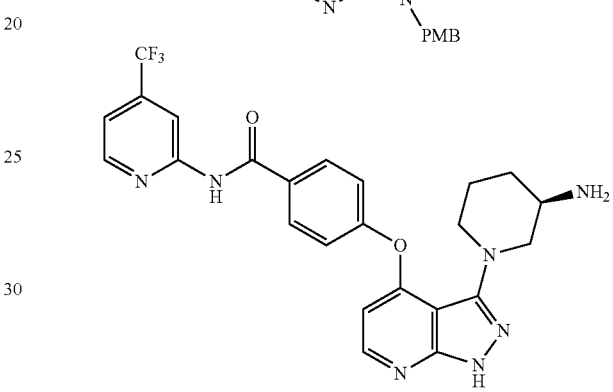

The intermediate was prepared following the method described for Ex. 161. LC-MS (ESI): m/z (M+1)+, 497.9.

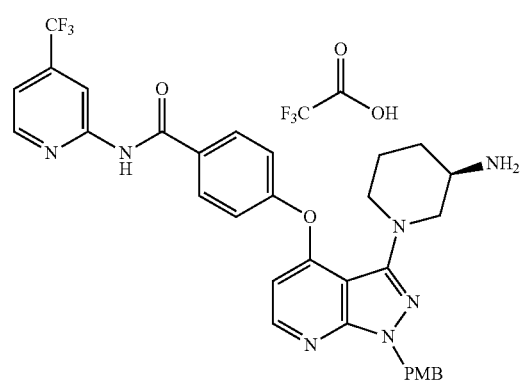

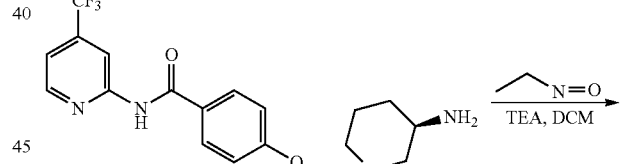

The compound was prepared following the method described for Ex. 16189. LC-MS (ESI): m/z (M+1)+, 568.9. 1H NMR (500 MHz, DMSO) 12.71 (br. s., 1H), 11.33 ((br.

s, 1H), 8.69 (d, J=4.94 Hz, 1H), 8.55 (s, 1H), 8.27 (dd, J=5.21, 1.37 Hz, 1H), 8.18 (d, J=7.41 Hz, 2H), 7.55 (d, J=4.94 Hz, 1H), 7.41 (d, J=7.14 Hz, 2H), 6.32 (dd, J=5.35, 1.24 Hz, 1H), 5.82 (d, J=7.68 Hz, 1H), 5.75 (t, J=5.21 Hz, 1H), 3.74-3.43 (m, 3H), 3.03-2.87 (m, 3H), 2.81 (t, J=9.47 Hz, 1H), 1.81-1.67 (m, 2H), 1.60 (d, J=9.61 Hz, 1H), 1.32 (q, J=8.97 Hz, 1H), 0.93 (td, J=7.14, 1.10 Hz, 3H).

Example 229

(3R)—N-ethyl-3-[(4-{4-[(pyridin-2-yl)carbamoyl]phenoxy}-1H-pyrazolo[3,4-b]pyridin-3-yl)amino]piperidine-1-carboxamide (Compound ID 229)

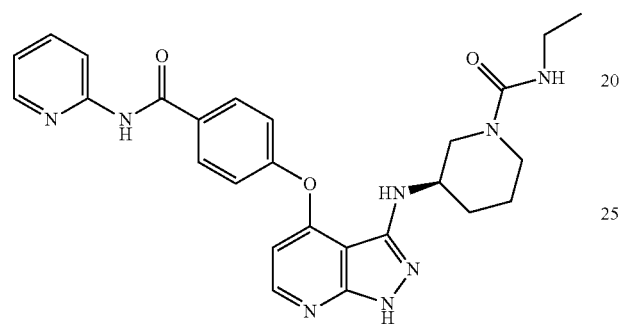

1.150 Preparation of tert-butyl (3R)-3-({1-[(4-methoxyphenyl)methyl]-4-{4-[(pyridin-2-yl)carbamoyl]phenoxy}-1H-pyrazolo[3,4-b]pyridin-3 yl}amino)piperidine-1-carboxylate

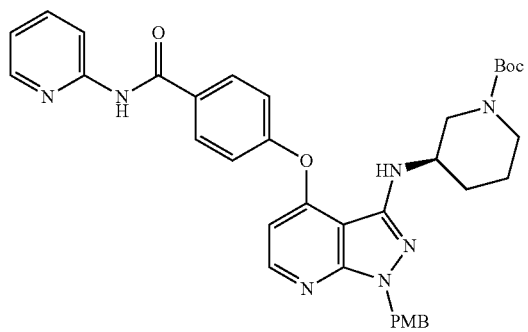

The intermediate was prepared following the method described for the synthesis of Ex. 137. LC-MS (ESI): m/z (M+1)⁺, 650.1.

1.151 Preparation of 4-({1-[(4-methoxyphenyl)methyl]-3-{[(3R)-piperidin-3-yl]amino}-1H-pyrazolo[3,4-b]pyridin-4-yl}oxy)-N-(pyridin-2-yl)benzamide; trifluoroacetic acid

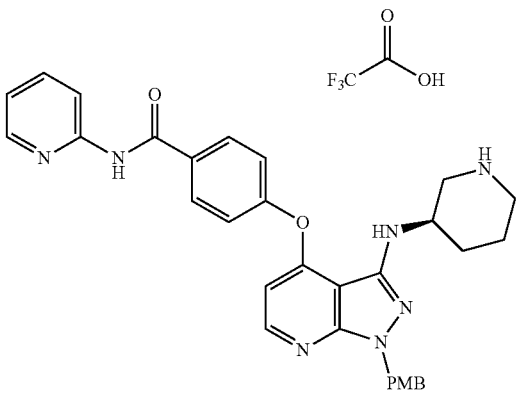

The intermediate was prepared following the method described for Ex. 137. LC-MS (ESI): m/z (M+1)⁺, 550.0.

1.152 Preparation of 4-[(3-{[(3R)-piperidin-3-yl]amino}-1H-pyrazolo[3,4-b]pyridin-4-yl)oxy]-N-(pyridin-2-yl)benzamide

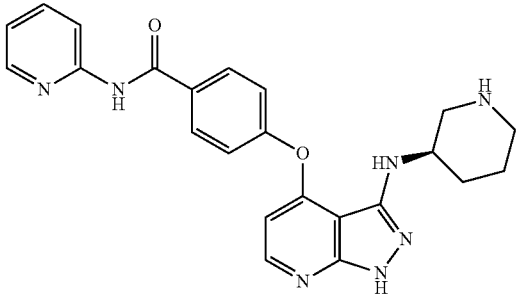 [SMILES: O=C(Nc1ccccn1)c1ccc(Oc2ccnc3[nH]nc(N[C@@H]4CCCNC4)c23)cc1]

The intermediate was prepared following the method described for Ex. 137. LC-MS (ESI): m/z (M+1)⁺, 430.0.

Compound 229 was prepared following the method described for Ex. 189. LC-MS (ESI): m/z (M+1)⁺, 501.0. ¹H NMR (500 MHz, DMSO) δ 12.22 (br. s., 1H), 10.84 (br. s., 1H), 8.43-8.34 (m, 1H), 8.21-8.12 (m, 4H), 7.88-7.79 (m, 1H), 7.37 (d, J=8.77 Hz, 2H), 7.20-7.12 (m, 1H), 6.36 (t, J=5.37 Hz, 1H), 6.13 (d, J=5.26 Hz, 1H), 5.18 (d, J=7.89 Hz, 1H), 4.03-3.85 (m, 1H), 3.71-3.51 (m, 2H), 3.05-2.92 (m, 2H), 2.89-2.76 (m, 2H), 2.04-1.87 (m, 1H), 1.68-1.47 (m, 2H), 1.45-1.27 (m, 1H), 0.94 (t, J=7.13 Hz, 3H).

Example 230

4-({3-[(3R)-3-[4-(dimethylamino)butanamido]piperidin-1-yl]-1H-pyrazolo[3,4-b]pyridin-4-yl}oxy)-N-[4-(trifluoromethyl)pyridin-2-yl]benzamide (Compound 230)

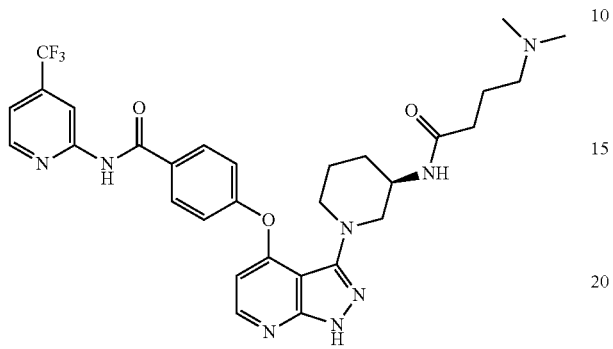

The compound was prepared following the method described for Ex. 217. LC-MS (ESI): m/z (M+1)⁺, 611.3. ¹H NMR (500 MHz, DMSO) δ 10.03 (br. s., 1H), 9.44 (br. s., 1H), 8.70 (s, 1H), 8.52 (d, J=5.04 Hz, 1H), 8.28 (d, J=5.48 Hz, 1H), 8.05 (d, J=8.55 Hz, 2H), 7.34 (m, J=8.55 Hz, 3H), 7.04-6.98 (m, 1H), 6.29 (d, J=5.48 Hz, 1H), 4.24-4.10 (m, 1H), 3.61-3.47 (m, 2H), 3.41-3.31 (m, 1H), 3.29-3.18 (m, 1H), 2.27 (br. s., 6H), 2.37-1.36 (m, 10H).

Example 231

1-[(3R)-3-({4-[4-(1H-1,3-benzodiazol-2-yl)phenoxy]-1H-pyrazolo[3,4-b]pyridin-3-yl}amino)piperidin-1-yl]propan-1-one (Compound ID 231)

1.153 Preparation of 2-[4-({3-bromo-1-[(4-methoxyphenyl)methyl]-1H-pyrazolo[3,4-b]pyridin-4-yl}oxy)phenyl]-1H-1,3-benzodiazole

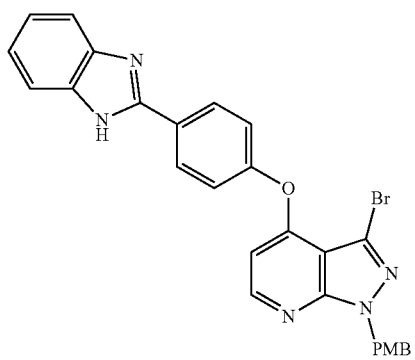

The intermediate was prepared following the method described for Ex. 86. LC-MS (ESI): m/z (M+1)⁺, 525.87.

1.154 Preparation of 2-[4-({3-bromo-1-[(4-methoxyphenyl)methyl]-1H-pyrazolo[3,4-b]pyridin-4-yl}oxy)phenyl]-1-[(4-methoxyphenyl)methyl]-1H-1,3-benzodiazole

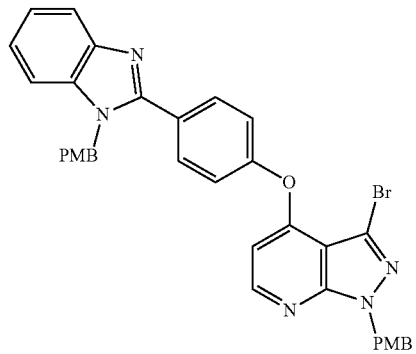

The intermediate was prepared following the method described for Ex. 224 LC-MS (ESI): m/z (M+1)⁺, 645.94.

1.155 Preparation of tert-butyl (3R)-3-({1-[(4-methoxyphenyl)methyl]-4-(4-{1-[(4-methoxyphenyl)methyl]-1H-1,3-benzodiazol-2-yl}phenoxy)-1H-pyrazolo[3,4-b]pyridin-3-yl}amino)piperidine-1-carboxylate

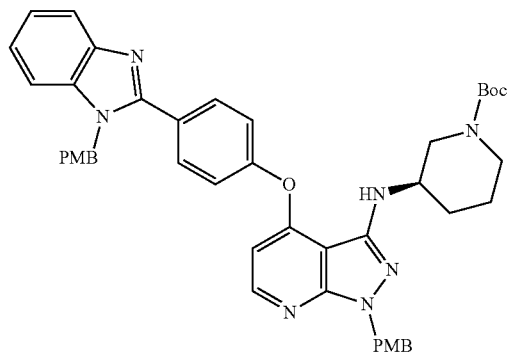

The intermediate was prepared following the method described for Ex. 86. LC-MS (ESI): m/z (M+1)⁺, 766.1.

1.156 Preparation of (3R)—N-[4-(4-{1-[(4-methoxyphenyl)methyl]-1H-1,3-benzodiazol-2-yl}phenoxy)-1H-pyrazolo[3,4-b]pyridin-3-yl]piperidin-3-amine

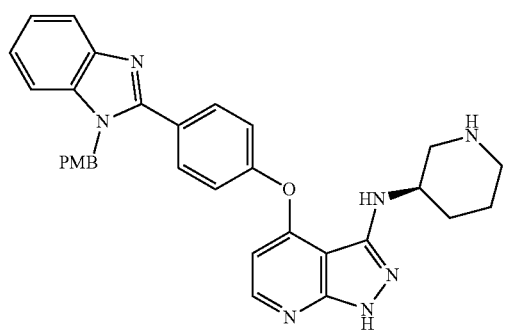

The intermediate was prepared following the method described or Ex. 86. LC-MS (ESI): m/z (M+1)⁺, 426.0.

1.157 Preparation of (3R)—N-{1-[(4-methoxyphenyl)methyl]-4-[4-(7-methyl-1,3-benzoxazol-2-yl)phenoxy]-1H-pyrazolo[3,4-b]pyridin-3-yl}piperidin-3-amine trifluoroacetic acid

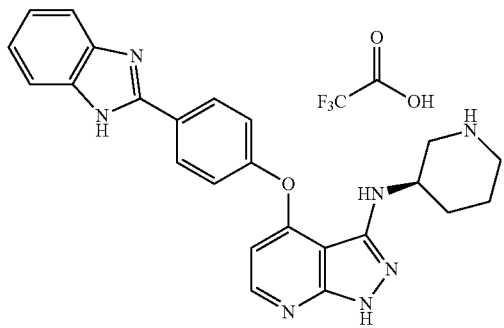

The intermediate was prepared following the method described for Ex. 224. LC-MS (ESI): m/z (M+1)⁺, 425.99.

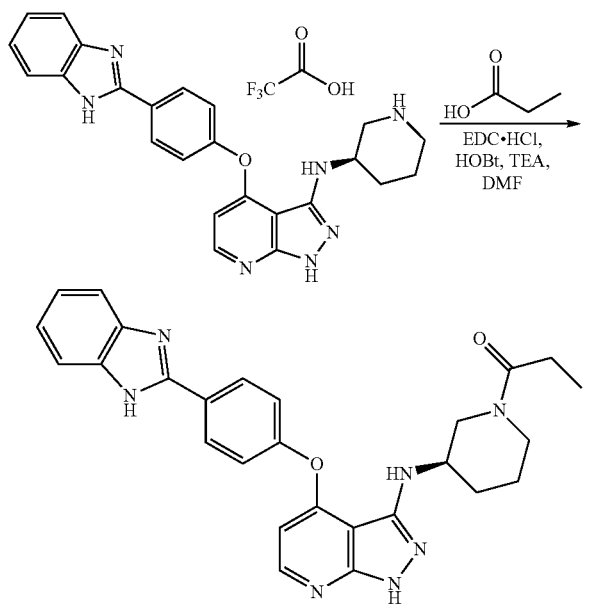

(3R)—N-{1-[(4-Methoxyphenyl)methyl]-4-[4-(7-methyl-1,3-benzoxazol-2-yl)phenoxy]-1H-pyrazolo[3,4-b]pyridin-3-yl}piperidin-3-amine trifluoroacetic acid (136.0 mg, 0.252 mmol) was dissolved in DMF (3 mL). EDC HCl (74.8 mg, 0.390 mmol), HOBt (45.0 mg, 0.333 mmol), TEA (0.090 mL, 0.824 mmol) and propanoic acid (0.028 mL, 0.383 mmol) were added and the mixture was stirred overnight at room temperature. EtOAc was added and the mixture was washed by water. The organic layer was collected, dried over Na₂SO₄, filtered and concentrated and the crude was purified by flash chromatography (silica gel 25 g, DCM methanol from 100/0 to 95/5). The crude obtained was further purified by LC-PREP (water+0.1% HCOOH/Acetonitrile from 97/3 to 0/100). 1-[(3R)-3-({4-[4-(1H-1,3-benzodiazol-2-yl)phenoxy]-1H-pyrazolo[3,4-b]pyridin-3-yl}amino)piperidin-1-yl]propan-1-one was obtained as a white solid (7.3 mg, Yield: 6%). LC-MS (ESI): m/z (M+1)⁺, 482.1. ¹H NMR (500 MHz, DMSO) δ 12.97 (br. s., 1H), 12.31-12.19 (m, 1H), 8.34-8.25 (m, 2H), 8.22-8.14 (m, 1H), 7.67 (d, J=7.41 Hz, 1H), 7.54 (d, J=7.68 Hz, 1H), 7.49-7.43 (m, 2H), 7.28-7.15 (m, 2H), 6.21-6.13 (m, 1H), 5.31-5.16 (m, 1H), 4.43-4.33 (m, 1H), 4.12-3.99 (m, 1H), 3.70-3.57 (m, 1H), 3.11-3.00 (m, 1H), 2.89-2.74 (m, 1H), 2.34-2.23 (m, 2H), 2.06-1.98 (m, 1H), 1.77-1.33 (m, 3H), 1.01-0.92 (m, 3H).

Example 232

4-[(3-{[(3R)-1-cyclopropanecarbonylpiperidin-3-yl]amino}-1H-pyrazolo[3,4-b]pyridin-4-yl)oxy]-N-(pyridin-2-yl)benzamide (Compound ID 232)

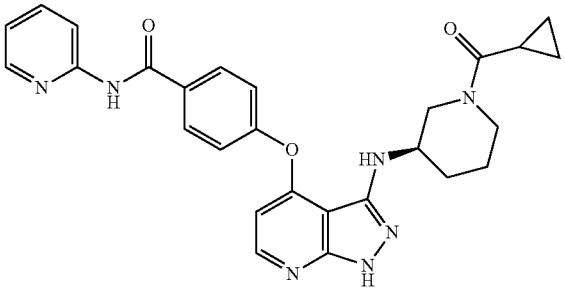 [SMILES: O=C(Nc1ccccn1)c1ccc(Oc2ccnc3[nH]nc(N[C@@H]4CCCN(C(=O)C5CC5)C4)c23)cc1]

The compound was prepared following the method described for Ex. 173. LC-MS (ESI): m/z (M+1)⁺, 498.1. ¹H NMR (500 MHz, DMSO) δ 12.35-12.14 (m, 1H), 10.87 (s, 1H), 8.41 (ddd, J=4.89, 1.96, 0.98 Hz, 1H), 8.25-8.12 (m, 4H), 7.86 (ddd, J=8.44, 7.46, 1.96 Hz, 1H), 7.40 (d, J=8.80 Hz, 2H), 7.18 (ddd, J=7.34, 4.89, 0.98 Hz, 1H), 6.15 (br. s., 1H), 5.21 (br. s., 1H), 4.42-4.16 (m, 1H), 4.04-3.37 (m, 3H), 3.10-2.84 (m, 1H), 2.07-1.30 (m, 5H), 0.81-0.39 (m, 4H).

Example 233

(3R)—N,N-dimethyl-3-[(4-{4-[(pyridin-2-yl)carbamoyl]phenoxy}-1H-pyrazolo[3,4-b]pyridin-3-yl)amino]piperidine-1-carboxamide (Compound ID 233)

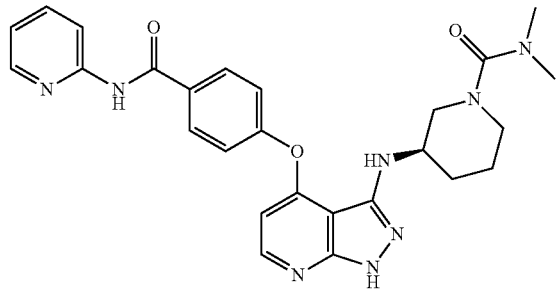 [SMILES: CN(C)C(=O)N1CCC[C@@H](Nc2n[nH]c3nccc(Oc4ccc(C(=O)Nc5ccccn5)cc4)c23)C1]

N,N-Dimethylcarbamoyl chloride (0.031 mL, 0.338 mmol) was added dropwise at room temperature to a solution of 4-[(3-{[(3R)-piperidin-3-yl]amino}-1H-pyrazolo[3,4-b]pyridin-4-yl)oxy]-N-(pyridin-2-yl)benzamide (132 mg, 0.307 mmol) and N,N-diisopropylethylamine (0.107 mL, 0.614 mmol) in 3.5 mL of dry DMF. The mixture was stirred at room temperature for 3 hours. The solvent was evaporated and the crude product was purified by chromatography (silica gel, eluet=from 2% to 7% of MeOH in DCM) to give (3R)—N,N-dimethyl-3-[(4-{4-[(pyridin-2-yl)carbamoyl]phenoxy}-1H-pyrazolo[3,4-b]pyridin-3-yl)amino]piperidine-1-carboxamide (74.5 mg, 0.149 mmol, Yield=48%) as pale yellow solid. LC-MS (ESI): m/z (M+1)$^+$, 501.3. $^1$H NMR (500 MHz, DMSO) δ 12.22 (s, 1H), 10.88 (s, 1H), 8.42-8.39 (m, 1H), 8.23-8.16 (m, 4H), 7.88-7.83 (m, 1H), 7.41 (d, J=8.78 Hz, 2H), 7.21-7.16 (m, 1H), 6.15 (d, J=5.49 Hz, 1H), 5.30 (d, J=7.96 Hz, 1H), 3.77-3.69 (m, 1H), 3.68-3.62 (m, 1H), 3.32-3.26 (m, 1H), 2.88-2.77 (m, 2H), 2.69 (s, 6H), 1.99-1.88 (m, 1H), 1.73-1.58 (m, 2H), 1.54-1.43 (m, 1H).

Example 234

4-({3-[(3S)-3-[(ethylcarbamoyl)amino]piperidin-1-yl]-1H-pyrazolo[3,4-b]pyridin-4-yl}oxy)-N-[4-(trifluoromethyl)pyridin-2-yl]benzamide (Compound ID 234)

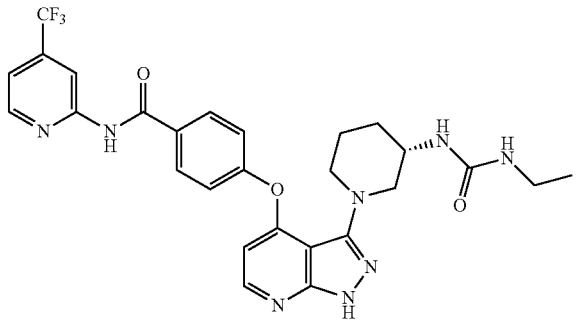 [SMILES: CCNC(=O)N[C@H]1CCCN(c2n[nH]c3nccc(Oc4ccc(C(=O)Nc5cc(C(F)(F)F)ccn5)cc4)c23)C1]

The compound was prepared following the method described for Ex. 189. LC-MS (ESI): m/z (M+1)$^+$, 569.4. $^1$H NMR (500 MHz, DMSO) δ 12.71 (br. s., 1H), 11.33 (br. s., 1H), 8.68 (d, J=5.21 Hz, 1H), 8.55 (s, 1H), 8.27 (d, J=5.21 Hz, 1H), 8.15-8.20 (m, 2H), 7.54 (dd, J=5.08, 0.96 Hz, 1H), 7.38-7.43 (m, 2H), 6.32 (d, J=5.21 Hz, 1H), 5.82 (d, J=7.96 Hz, 1H), 5.75 (t, J=5.49 Hz, 1H), 3.45-3.71 (m, 3H), 2.88-3.01 (m, 3H), 2.76-2.85 (m, 1H), 1.66-1.80 (m, 2H), 1.53-1.64 (m, 1H), 1.26-1.37 (m, 1H), 0.93 (t, J=7.27 Hz, 3H).

Example 235

(3R)—N-ethyl-3-{[4-(2-methyl-4-phenoxyphenoxy)-1H-pyrazolo[3,4-b]pyridin-3-yl]amino}piperidine-1-carboxamide (Compound ID 235)

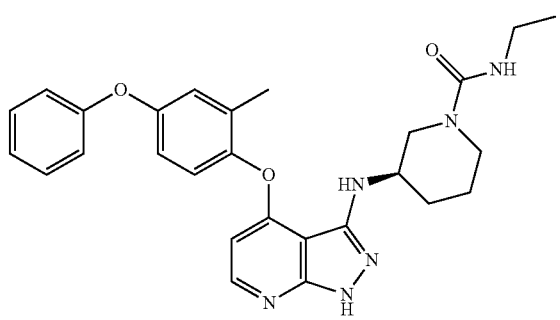 [SMILES: CCNC(=O)N1CCC[C@@H](Nc2n[nH]c3nccc(Oc4ccc(Oc5ccccc5)cc4C)c23)C1]

The compound was prepared following the method described for Ex. 189. LC-MS (ESI): m/z (M+1)$^+$, 487.2. $^1$H NMR (500 MHz, DMSO) δ 12.26-12.06 (m, 1H), 8.12 (d, J=5.21 Hz, 1H), 7.41 (dd, J=8.51, 7.41 Hz, 2H), 7.25 (d, J=8.78 Hz, 1H), 7.18-7.13 (m, 1H), 7.09 (d, J=3.02 Hz, 1H), 7.07-7.03 (m, 2H), 6.96 (dd, J=8.78, 3.02 Hz, 1H), 6.40 (t, J=5.35 Hz, 1H), 5.93 (d, J=5.49 Hz, 1H), 5.25 (d, J=8.23 Hz, 1H), 3.92 (dd, J=12.76, 3.71 Hz, 1H), 3.70-3.59 (m, 2H), 3.02-2.94 (m, 3H), 2.93-2.86 (m, 1H), 2.11 (s, 3H), 2.03-1.91 (m, 1H), 1.71-1.58 (m, 2H), 1.45-1.33 (m, 1H), 0.94 (t, J=7.14 Hz, 3H).

Example 236

4-({3-[(2-methoxyethyl)amino]-1H-pyrazolo[3,4-b]pyridin-4-yl}oxy)-N-[4-(trifluoromethyl)pyridin-2-yl]benzamide (Compound ID 236)

1.158 Preparation of 4-({3-[(2-methoxyethyl)amino]-1-[(4-methoxyphenyl)methyl]-1H-pyrazolo[3,4-b]pyridin-4-yl}oxy)-N-[4-(trifluoromethyl)pyridin-2-yl]benzamide

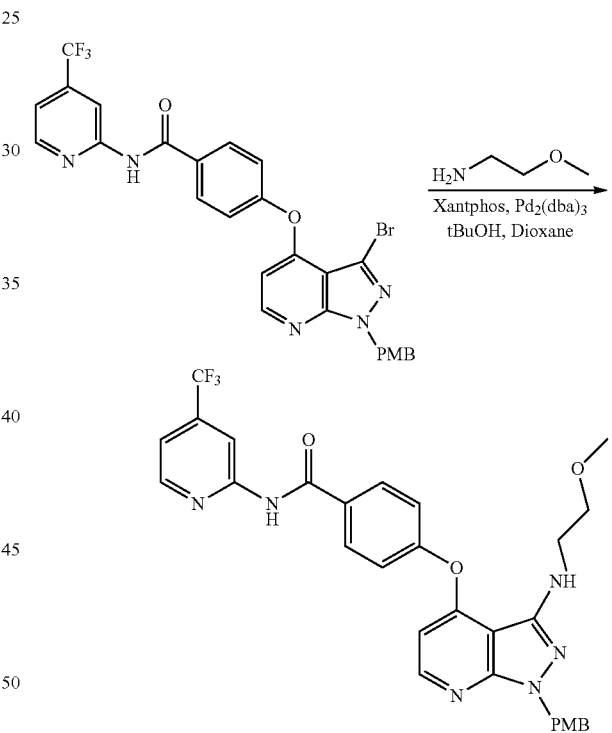

To a solution of 4-({3-bromo-1-[(4-methoxyphenyl)methyl]-1H-pyrazolo[3,4-b]pyridin-4-yl}oxy)-N-[4-(trifluoromethyl)pyridin-2-yl]benzamide (200 mg, 0.334 mmol) and 2-methoxyethylamine (0.145 mL, 1.671 mmol) in dioxane (6 mL) was added xantphos (58.2 mg, 0.100 mmol), Pd$_2$(dba)$_3$ (31 mg, 0.34 mmol), tBuOK (113 mg, 1.0 mmol) and the mixture was degassed by a stream of N$_2$ for 5 min followed by stirring at 120° C. for 16 hrs. After cooling to room temperature, the reaction mixture was diluted with ethyl acetate and washed with water. The organic layer was dried over Na$_2$SO$_4$. Evaporation of the solvent followed by flash chromatography on silica gel (10-100% ethyl acetate in cyclohexane) afforded the title compound (63 mg, Yield: 32%) as yellow oil. LC-MS (ESI): m/z (M+1)$^+$, 593.4.

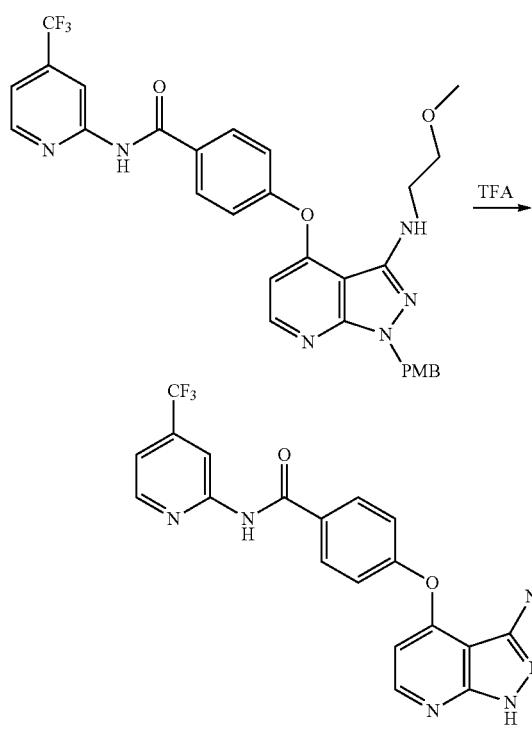

4-({3-[(2-methoxyethyl)amino]-1H-pyrazolo[3,4-b]pyridin-4-yl}oxy)-N-[4-(trifluoromethyl)pyridin-2-yl]benzamide (236) (58 mg, quant.) was obtained as a white powder from 4-({3-[(2-methoxyethyl)amino]-1-[(4-methoxyphenyl)methyl]-1H-pyrazolo[3,4-b]pyridin-4-yl}oxy)-N-[4-(trifluoromethyl)pyridin-2-yl]benzamide (63 mg, 0.106 mmol), following a similar procedure outlined in the preparation of (R)-1-(3-(4-(4-chlorophenoxy)-1H-pyrazolo[3,4-b]pyridin-3-ylamino)pyrrolidin-1-yl)prop-2-en-1-one. LC-MS (ESI): m/z (M+1)+, 473.3. $^1$H NMR (500 MHz, DMSO) δ 12.23 (br. s., 1H), 11.37 (s, 1H), 8.69 (d, J=5.04 Hz, 1H), 8.55 (s, 1H), 8.27-8.14 (m, 3H), 7.56 (d, J=5.04 Hz, 1H), 7.44 (d, J=8.44 Hz, 2H), 6.15 (d, J=5.48 Hz, 1H), 3.60-3.51 (m, 2H), 3.48-3.39 (m, 2H), 3.27 (s, 3H).

Example 238

Preparation of Compound ID 238

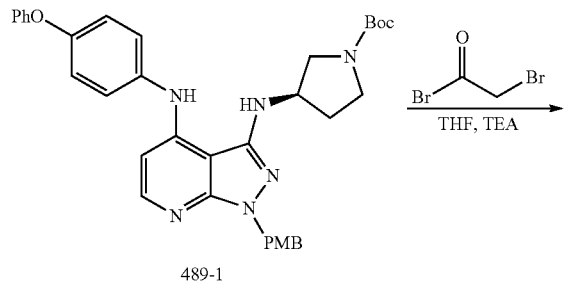

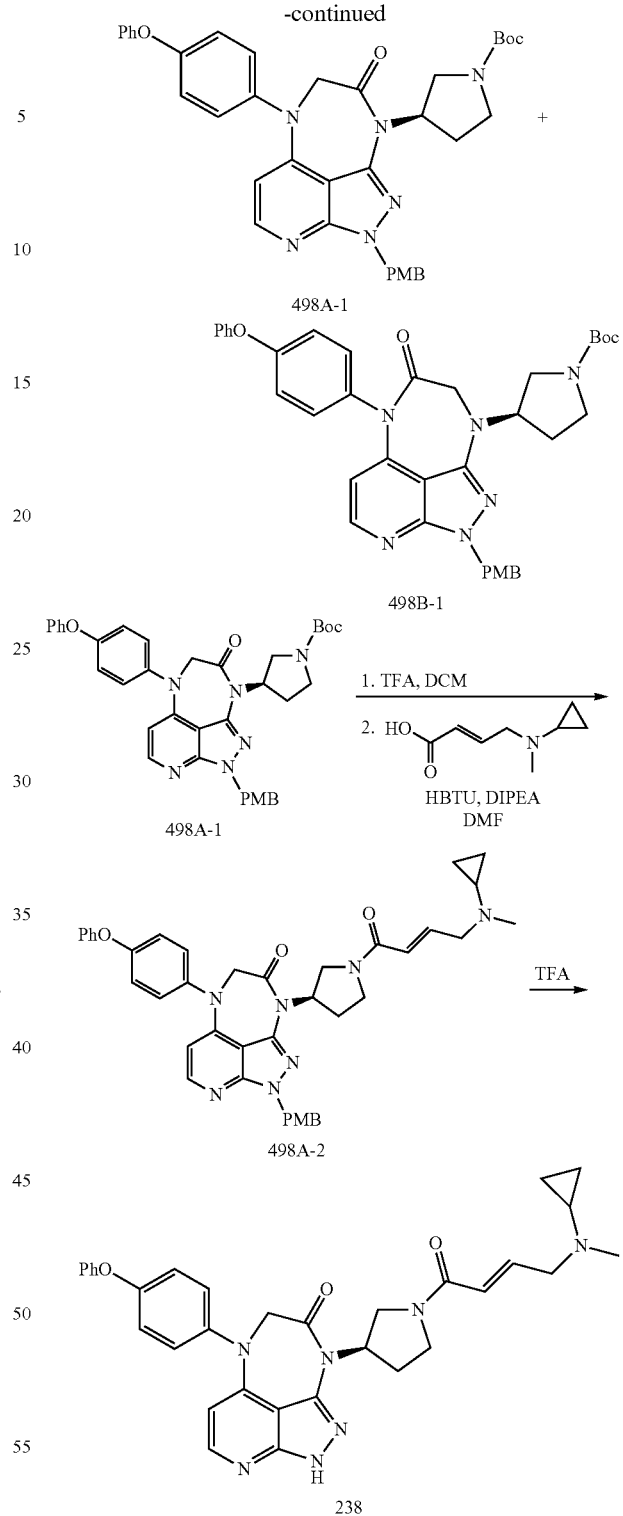

At 0° C., to a solution of (R)-tert-butyl 3-(1-(4-methoxybenzyl)-4-(4-phenoxyphenyl amino)-1H-pyrazolo[3,4-b]pyridin-3-ylamino)pyrrolidine-1-carboxylate (489-1) (100 mg, 0.17 mmol) in anhydrous THF (2 mL) was added 2-bromoacetyl bromide (0.15 mL, 1.65 mmol) and TEA (0.35 mL, 2.51 mmol) dropwise under N$_2$ atmosphere. After being stirred at 60° C. overnight, the reaction mixture was quenched with H$_2$O (20 mL) and extracted with EA (25 mL×2). The combined organic phase was washed with brine, dried over Na$_2$SO$_4$, filtered and concentrated to give the crude product which was purified by flash chromatography (silica gel, 0 to 50% EA in PE) to afford 498A-1 (56 mg, 52% yield) as a colorless oil and 498A-1 (46 mg, 42% yield) as a colorless oil. LC-MS (ESI): m/z (M+1) 647.1.

To a solution of 498A-1 (56 mg) in DCM (4 mL) was added TFA (1 mL). The resulting mixture was stirred at room temperature for 30 min and then concentrated under reduced pressure to afford the de-Boc product. The intermediate was reacted with acrylic acid (20 mg, 0.28 mmol) under typical HBTU condensation condition and purified by flash chromatography (silica gel, 0 to 100% ethyl acetated in petroleum ether) to afford the corresponding amide which was then heated up to 60° C. in TFA (4 mL) under N$_2$ atmosphere for 4 hr. The reaction mixture was then concentrated under reduced pressure to give the crude product which was purified by preparative HPLC (RP, C18, 10 to 95% acetonitrile in water (0.2% NH$_3$.H$_2$O)) to afford desired compound Compound 238 (18 mg) as a white solid. LC-MS (ESI): m/z (M+1) 684.1. LC-MS (ESI): m/z (M+1) 564.2. $^1$H NMR (400 MHz, DMSO): δ 8.03 (d, J=5.4 Hz, 1H), 7.49-7.37 (m, 4H), 7.18 (t, J=7.6 Hz, 1H), 7.15-7.04 (m, 4H), 6.70-6.60 (m, 1H), 6.35 (dd, J=35.7, 14.1 Hz, 1H), 6.06-5.91 (m, 1H), 5.68-5.43 (m, 1H), 4.59 (d, J=3.1 Hz, 2H), 4.09-3.43 (m, 5H), 3.22 (d, J=6.4 Hz, 2H), 2.78-2.58 (m, 1H), 2.22 (d, J=15.6 Hz, 3H), 2.12-1.98 (m, 1H), 1.79-1.63 (m, 1H), 0.53-0.37 (m, 2H), 0.30 (m, 2H).

Example 239

Preparation of Compound ID 239

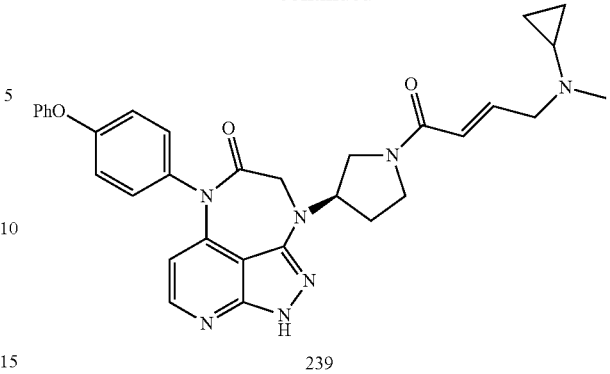

239

Compound ID 239 (14 mg) was obtained as a white powder from 498B-1 (46 mg, 0.07 mmol) and (E)-4-(cyclopropyl(methyl)amino)but-2-enoic acid (45 mg, 0.14 mmol), following a similar procedure outlined in the preparation of Compound 238. LC-MS (ESI): m/z (M+1) 684.1 for Compound 239. LC-MS (ESI): m/z (M+1) 564.2. $^1$H NMR (400 MHz, DMSO) δ 12.67 (s, 1H), 8.17 (d, J=5.4 Hz, 1H), 7.46 (t, J=7.8 Hz, 2H), 7.38-7.26 (m, 2H), 7.22 (t, J=7.0 Hz, 1H), 7.18-7.06 (m, 4H), 6.73-6.60 (m, 1H), 6.36 (dd, J=15.3, 10.1 Hz, 1H), 5.82 (d, J=5.3 Hz, 1H), 4.71-4.47 (m, 1H), 4.16 (d, J=9.8 Hz, 2H), 4.05-3.52 (m, 4H), 3.29-3.23 (m, 2H), 2.38-2.27 (m, 1H), 2.23 (d, J=7.0 Hz, 3H), 2.19-2.04 (m, 1H), 1.78-1.60 (m, 1H), 0.48-0.36 (m, 2H), 0.36-0.21 (m, 2H).

Example 240

(R)—N-(4-methylpyridin-2-yl)-4-(3-(1-(oxazole-2-carbonyl)piperidin-3-ylamino)-1H-pyrazolo[3,4-b]pyridin-4-yloxy)benzamide (Compound ID 240)

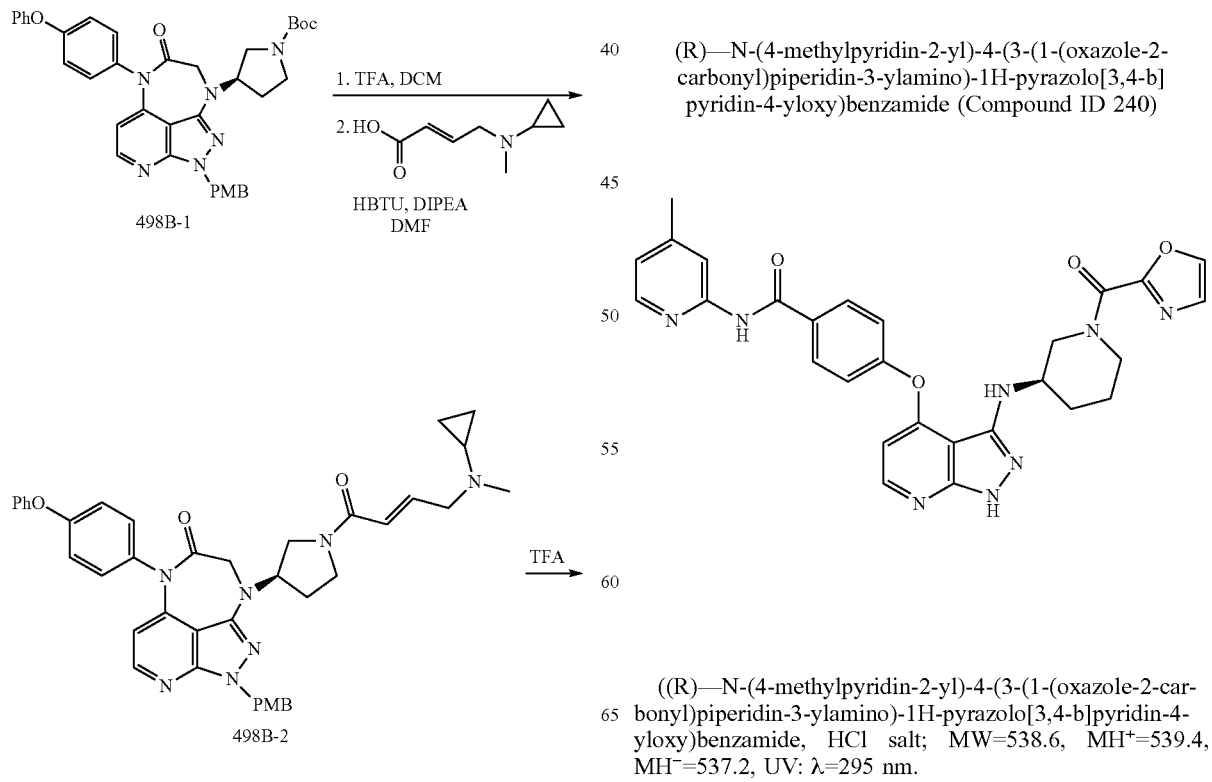

((R)—N-(4-methylpyridin-2-yl)-4-(3-(1-(oxazole-2-carbonyl)piperidin-3-ylamino)-1H-pyrazolo[3,4-b]pyridin-4-yloxy)benzamide, HCl salt; MW=538.6, MH$^+$=539.4, MH$^-$=537.2, UV: λ=295 nm.

Example 241

(R)—N-(4-methylpyridin-2-yl)-4-(3-(1-(thiazole-2-carbonyl)piperidin-3-ylamino)-1H-pyrazolo[3,4-b]pyridin-4-yloxy)benzamide (Compound ID 241)

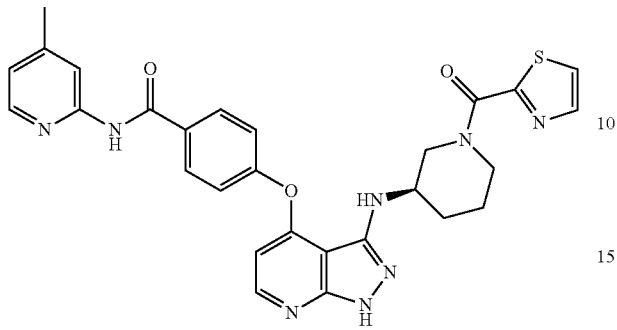

(R)—N-(4-methylpyridin-2-yl)-4-(3-(1-(thiazole-2-carbonyl)piperidin-3-ylamino)-1H-pyrazolo[3,4-b]pyridin-4-yloxy)benzamide, HCl salt; MW=554.6, MH⁺=555.4, MH⁻=553.2, UV: λ=293 nm.

Example 242

(R)-4-(3-(1-(1H-imidazole-2-carbonyl)piperidin-3-ylamino)-1H-pyrazolo[3,4-b]pyridin-4-yloxy)-N-(4-methylpyridin-2-yl)benzamide (Compound ID 242)

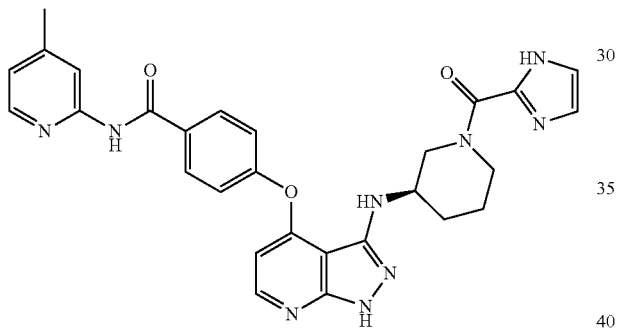

(R)-4-(3-(1-(1H-imidazole-2-carbonyl)piperidin-3-ylamino)-1H-pyrazolo[3,4-b]pyridin-4-yloxy)-N-(4-methylpyridin-2-yl)benzamide, HCl salt; MW=537.6, MH⁺=538.3, MH⁻=536.2, UV: λ=294 nm.

Example 243

(R)-4-(3-(1-(4-fluorobenzoyl)piperidin-3-ylamino)-1H-pyrazolo[3,4-b]pyridin-4-yloxy)-N-(4-methylpyridin-2-yl)benzamide (Compound ID 243)

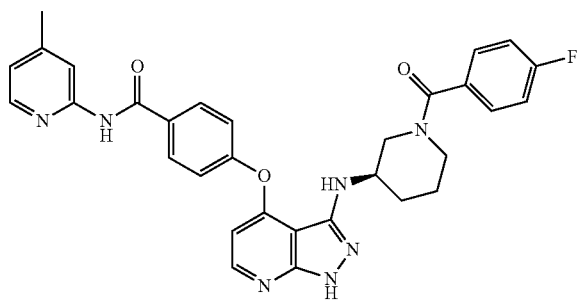 [SMILES: Cc1ccnc(NC(=O)c2ccc(Oc3ccnc4[nH]nc(N[C@@H]5CCCN(C(=O)c6ccc(F)cc6)C5)c34)cc2)c1]

(R)-4-(3-(1-(4-fluorobenzoyl)piperidin-3-ylamino)-1H-pyrazolo[3,4-b]pyridin-4-yloxy)-N-(4-methylpyridin-2-yl)benzamide, HCl salt; MW=565.6, MH⁺=566.4, MH⁻=564.2, UV: λ=295 nm.

Example 244

(R)-4-(3-(1-(4-chlorobenzoyl)piperidin-3-ylamino)-1H-pyrazolo[3,4-b]pyridin-4-yloxy)-N-(4-methylpyridin-2-yl)benzamide (Compound ID 244)

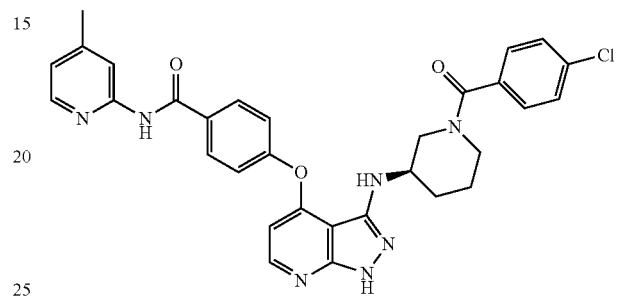

(R)-4-(3-(1-(4-chlorobenzoyl)piperidin-3-ylamino)-1H-pyrazolo[3,4-b]pyridin-4-yloxy)-N-(4-methylpyridin-2-yl)benzamide, HCl salt; MW=582.0, MH⁺=582.2/583.4/584.5, MH⁻=580.2/582.1, UV: λ=295 nm.

Example 245

(R)-4-(3-(1-(4-methylbenzoyl)piperidin-3-ylamino)-1H-pyrazolo[3,4-b]pyridin-4-yloxy)-N-(4-methylpyridin-2-yl)benzamide (Compound ID 245)

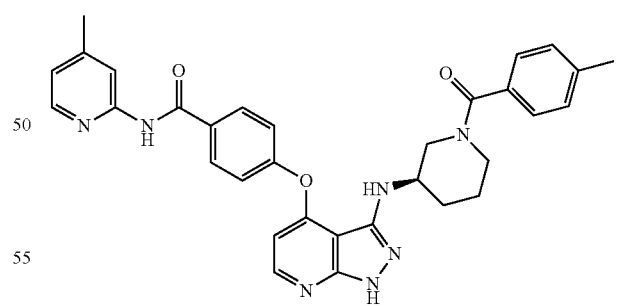

(R)-4-(3-(1-(4-methylbenzoyl)piperidin-3-ylamino)-1H-pyrazolo[3,4-b]pyridin-4-yloxy)-N-(4-methylpyridin-2-yl)benzamide, HCl salt; MW=561.6, MH⁺=562.5, MH⁻=560.2, UV: λ=295 nm.

Example 246

(R)-4-(3-(1-(4-methoxybenzoyl)piperidin-3-ylamino)-1H-pyrazolo[3,4-b]pyridin-4-yloxy)-N-(4-methylpyridin-2-yl)benzamide (Compound ID 246)

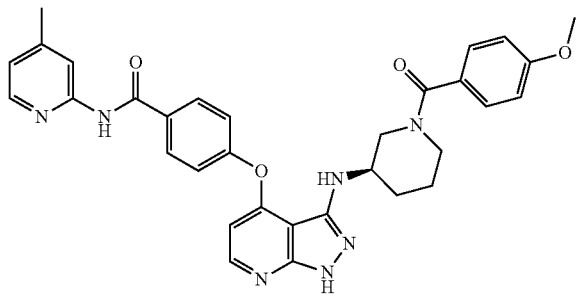 [SMILES: COc1ccc(C(=O)N2CCC[C@@H](Nc3n[nH]c4nccc(Oc5ccc(C(=O)Nc6cc(C)ccn6)cc5)c34)C2)cc1]

(R)-4-(3-(1-(4-methoxybenzoyl)piperidin-3-ylamino)-1H-pyrazolo[3,4-b]pyridin-4-yloxy)-N-(4-methylpyridin-2-yl)benzamide, HCl salt; MW=577.6, MH$^+$=578.5, MH$^-$=576.2, UV: λ=295 nm.

Example 247

(R)-4-(3-(1-(3-fluorobenzoyl)piperidin-3-ylamino)-1H-pyrazolo[3,4-b]pyridin-4-yloxy)-N-(4-methylpyridin-2-yl)benzamide (Compound ID 247)

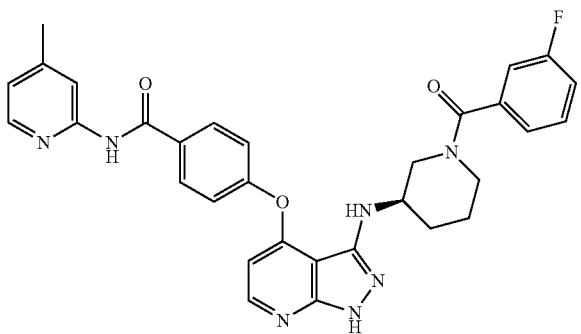 [SMILES: Cc1ccnc(NC(=O)c2ccc(Oc3ccnc4[nH]nc(N[C@@H]5CCCN(C(=O)c6cccc(F)c6)C5)c34)cc2)c1]

(R)-4-(3-(1-(3-fluorobenzoyl)piperidin-3-ylamino)-1H-pyrazolo[3,4-b]pyridin-4-yloxy)-N-(4-methylpyridin-2-yl)benzamide, HCl salt; MW=565.6, MH$^+$=566.5, MH$^-$=564.3, UV: λ=295 nm.

Example 248

(R)-4-(3-(1-(2-fluorobenzoyl)piperidin-3-ylamino)-1H-pyrazolo[3,4-b]pyridin-4-yloxy)-N-(4-methylpyridin-2-yl)benzamide (Compound ID 248)

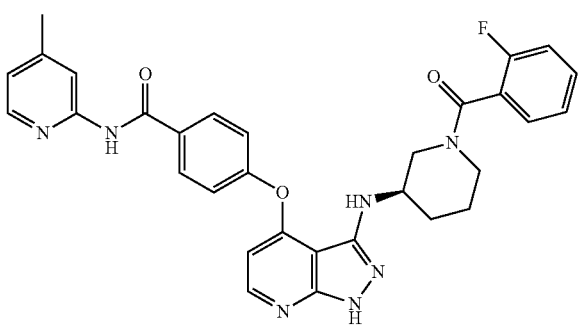 [SMILES: Cc1ccnc(NC(=O)c2ccc(Oc3ccnc4[nH]nc(N[C@@H]5CCCN(C(=O)c6ccccc6F)C5)c34)cc2)c1]

(R)-4-(3-(1-(2-fluorobenzoyl)piperidin-3-ylamino)-1H-pyrazolo[3,4-b]pyridin-4-yloxy)-N-(4-methylpyridin-2-yl)benzamide, HCl salt; MW=565.6, MH$^+$=566.5, MH$^-$=564.3, UV: λ=295 nm.

Example 249

(R)—N-(4-isopropyl-3-methylphenyl)-3-(3-(pyrrolidin-3-ylamino)-1H-pyrazolo[3,4-b]pyridin-4-yloxy)benzamide (Compound ID 249)

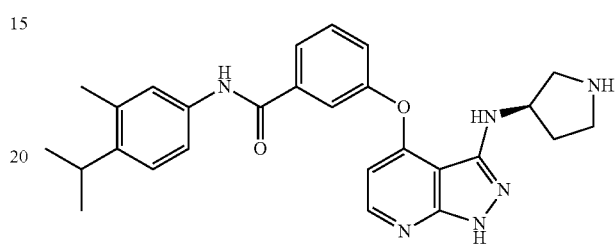

(R)—N-(4-isopropyl-3-methylphenyl)-3-(3-(pyrrolidin-3-ylamino)-1H-pyrazolo[3,4-b]pyridin-4-yloxy)benzamide, HCl salt was made using similar procedures as Example 122; MW=470.6, MH$^+$=471.3, MH$^-$=469.2, UV: λ=slope-like (280 nm).

Example 250

(R)-3-(3-(1-acryloylpiperidin-3-ylamino)-1H-pyrazolo[3,4-b]pyridin-4-yloxy)-N-(4-isopropyl-3-methylphenyl)benzamide (Compound ID 250)

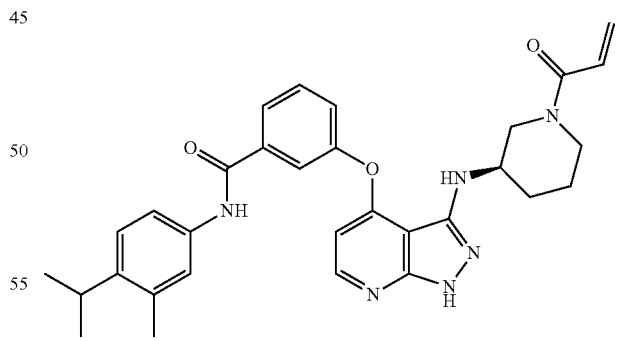

(R)-3-(3-(1-acryloylpiperidin-3-ylamino)-1H-pyrazolo[3,4-b]pyridin-4-yloxy)-N-(4-isopropyl-3-methylphenyl)benzamide, HCl salt was made using similar procedures as Example 1. (25.1 mg, 31%); MW=538.6, MH$^+$=539.6, MH$^-$=537.2, UV: λ=slope-like (280 nm).

Example 251

(R)-3-(3-(1-(4-hydroxybut-2-ynoyl)piperidin-3-ylamino)-1H-pyrazolo[3,4-b]pyridin-4-yloxy)-N-(4-isopropyl-3-methylphenyl)benzamide (Compound ID 251)

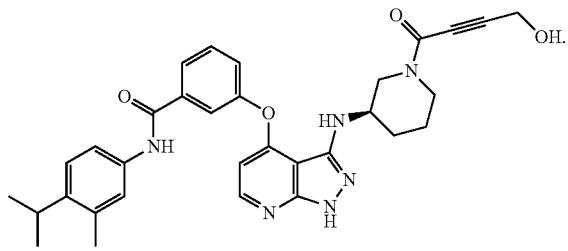 [SMILES: Cc1cc(NC(=O)c2cccc(Oc3ccnc4[nH]nc(N[C@@H]5CCCN(C(=O)C#CCO)C5)c34)c2)ccc1C(C)C]

(R)-3-(3-(1-(4-hydroxybut-2-ynoyl)piperidin-3-ylamino)-1H-pyrazolo[3,4-b]pyridin-4-yloxy)-N-(4-isopropyl-3-methylphenyl)benzamide, HCl salt (21.3 mg, 25%) was made using similar procedures as Example 122 and the piperidine N-substituent was installed via peptide coupling as described in Example 1. MW=566.6, MH$^+$=567.7, MH$^-$=565.3, UV: λ=280 nm.

Example 252

(R)-3-(3-(1-but-2-ynoylpiperidin-3-ylamino)-1H-pyrazolo[3,4-b]pyridin-4-ylamino)-N-(4-isopropyl-3-methylphenyl)benzamide (Compound ID 252)

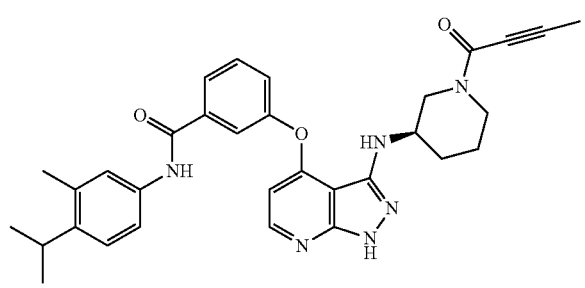 [SMILES: CC#CC(=O)N1CCC[C@@H](Nc2n[nH]c3nccc(Oc4cccc(C(=O)Nc5ccc(C(C)C)c(C)c5)c4)c23)C1]

Compound 252 was made using procedures in Example 127, a yellow solid, formic acid salt (5.7 mg, 24%); MW=549.7, MH$^+$=550.5, MH$^-$=548.2, UV: λ=291 nm.

Example 253

(R)—N-(4-isopropyl-3-methylphenyl)-3-(3-(piperidin-3-ylamino)-1H-pyrazolo[3,4-b]pyridin-4-ylamino)benzamide (Compound ID 253)

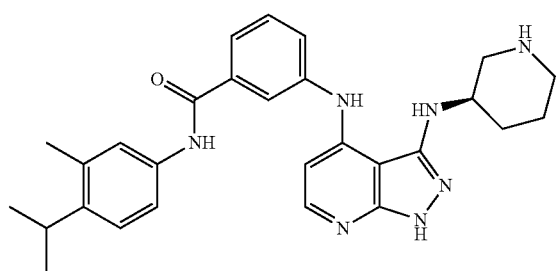 [SMILES: Cc1cc(NC(=O)c2cccc(Nc3ccnc4[nH]nc(N[C@@H]5CCCNC5)c34)c2)ccc1C(C)C]

(R)—N-(4-isopropyl-3-methylphenyl)-3-(3-(piperidin-3-ylamino)-1H-pyrazolo[3,4-b]pyridin-4-ylamino)benzamide was made using procedures in Example 127: a yellow solid, HCl salt (6.6 mg, 12%); MW=483.6, MH$^+$=484.3, MH$^-$=482.3, UV: λ=290 nm.

Example 254

(R)—N-cyclohexyl-3-(3-(piperidin-3-ylamino)-1H-pyrazolo[3,4-b]pyridin-4-yloxy)benzamide (Compound ID 254)

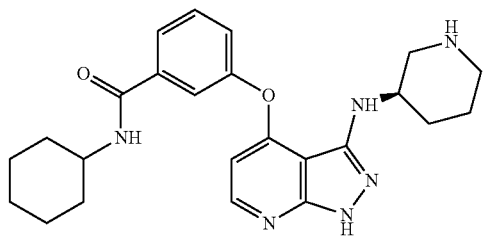 [SMILES: O=C(NC1CCCCC1)c1cccc(Oc2ccnc3[nH]nc(N[C@@H]4CCCNC4)c23)c1]

(R)—N-cyclohexyl-3-(3-(piperidin-3-ylamino)-1H-pyrazolo[3,4-b]pyridin-4-yloxy)benzamide, HCl salt, a yellow solid, was made using similar procedures as Example 122 (6.3 mg); MW=434.5, MH$^+$=435.2, MH$^-$=433.2, UV: λ=323 nm.

Example 255

(R)-piperidin-1-yl(3-(3-(piperidin-3-ylamino)-1H-pyrazolo[3,4-b]pyridin-4-yloxy)phenyl)methanone (Compound ID 255)

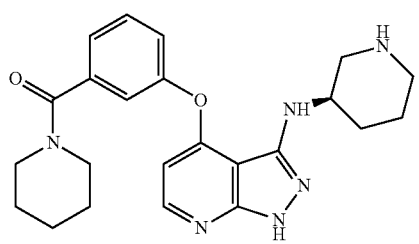 [SMILES: O=C(c1cccc(Oc2ccnc3[nH]nc(N[C@@H]4CCCNC4)c23)c1)N1CCCCC1]

(R)-piperidin-1-yl(3-(3-(piperidin-3-ylamino)-1H-pyrazolo[3,4-b]pyridin-4-yloxy)phenyl)methanone, HCl salt (7.1 mg) was made using similar procedures as Example 122. MW=420.5, MH$^+$=421.2, MH$^-$=419.1, UV: λ=325 nm.

Example 256

(R)-morpholino(3-(3-(piperidin-3-ylamino)-1H-pyrazolo[3,4-b]pyridin-4-yloxy)phenyl)methanone (Compound ID 256)

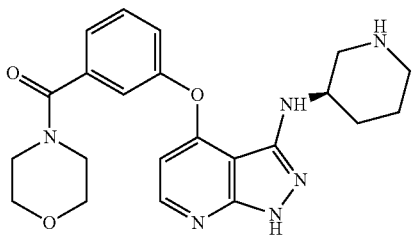 [SMILES: O=C(c1cccc(Oc2ccnc3[nH]nc(N[C@@H]4CCCNC4)c23)c1)N1CCOCC1]

(R)-morpholino(3-(3-(piperidin-3-ylamino)-1H-pyrazolo[3,4-b]pyridin-4-yloxy)phenyl)methanone, HCl salt (8.7 mg) was made using similar procedures as Example 122. MW=422.5, MH$^+$=423.3, MH$^-$=421.1, UV: λ=325 nm.

Example 257

(R)-1-(4-(3-(3-(piperidin-3-ylamino)-1H-pyrazolo[3,4-b]pyridin-4-yloxy)benzoyl)piperazin-1-yl)ethanone (Compound ID 257)

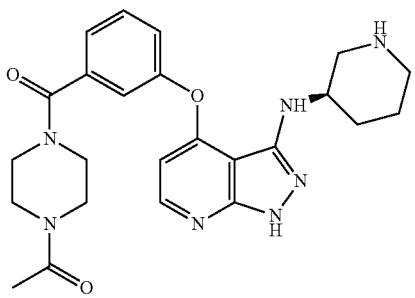 [SMILES: CC(=O)N1CCN(C(=O)c2cccc(Oc3ccnc4[nH]nc(N[C@@H]5CCCNC5)c34)c2)CC1]

(R)-1-(4-(3-(3-(piperidin-3-ylamino)-1H-pyrazolo[3,4-b]pyridin-4-yloxy)benzoyl)piperazin-1-yl)ethanone, HCl salt (140 mg, 70%) was made using similar procedures as Example 122. MW=463.5, MH$^+$=464.3, MH$^-$=462.2, UV: λ=325 nm.

Example 258

(R)—N-(4-isopropyl-3-methylphenyl)-3-(3-(piperidin-3-ylamino)-1H-pyrazolo[3,4-b]pyridin-4-yloxy)benzamide (Compound ID 258)

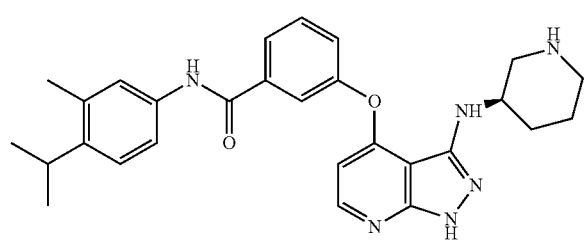 [SMILES: Cc1cc(NC(=O)c2cccc(Oc3ccnc4[nH]nc(N[C@@H]5CCCNC5)c34)c2)ccc1C(C)C]

(R)—N-(4-isopropyl-3-methylphenyl)-3-(3-(piperidin-3-ylamino)-1H-pyrazolo[3,4-b]pyridin-4-yloxy)benzamide, HCl salt (650 mg) was made using similar procedures as Example 122. MW=484.6, MH$^+$=485.6, MH$^-$=483.2, UV: λ=slope-like (280 nm).

Example 259

(R)—N-(4-isopropyl-3-methylphenyl)-3-(3-(piperidin-3-yloxy)-1H-pyrazolo[3,4-b]pyridin-4-ylamino)benzamide (Compound ID 259)

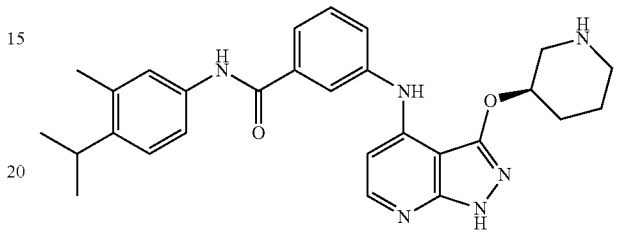

The title compound was made using similar procedures as Example 132: as HCl salt (4.4 mg); MW=484.6, MH$^+$=485.3, MH$^-$=483.2, UV: λ=279 nm.

Example 260

(S)—N-(4-isopropyl-3-methylphenyl)-3-(3-(pyrrolidin-3-ylamino)-1H-pyrazolo[3,4-b]pyridin-4-yloxy)benzamide (Compound ID 260)

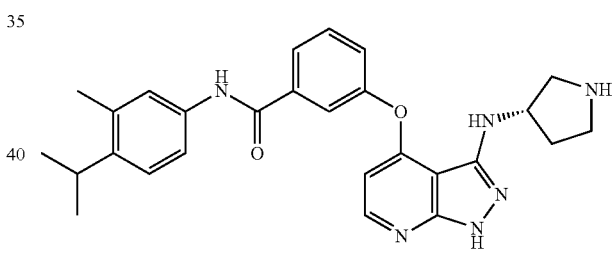

The title compound was made using similar procedures similar to that described in Example 124, HCl salt (7.8 mg); MW=470.6, MH$^+$=471.3, MH$^-$=469.2, UV: λ=slope-like (280 nm).

Example 261

(4-(4-phenoxyphenoxy)-N-(piperidin-4-yl)-1H-pyrazolo[3,4-b]pyridin-3-amine (Compound ID 261)

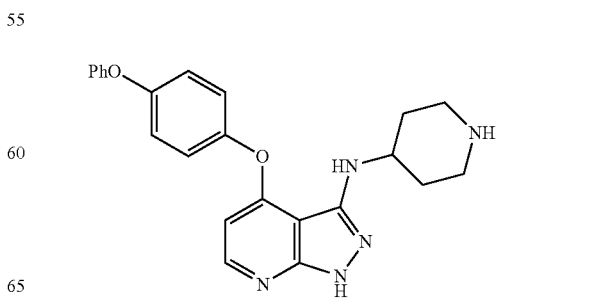

Using similar procedures as described in Example 122, the title compound was made: a yellow solid, HCl salt (250 mg, 99%); MW=401.5, MH$^+$=402.2, MH$^-$=400.2, UV: λ=232, 324 nm.

Example 262

4-(4-phenoxyphenoxy)-N-(piperidin-4-ylmethyl)-1H-pyrazolo[3,4-b]pyridin-3-amine (Compound ID 262)

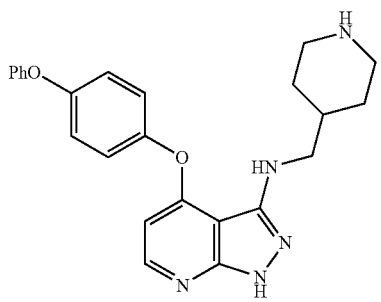 [SMILES: c1ccc(Oc2ccc(Oc3ccnc4[nH]nc(NCC5CCNCC5)c34)cc2)cc1]

Using similar procedures as described in Example 122, the title compound was made: a yellow solid, HCl salt (341 mg, 99%); MW=415.5, MH$^+$=416.1, MH$^-$=414.1, UV: λ=233, 327 nm.

Example 263

(R)-4-(4-phenoxyphenoxy)-N-(piperidin-3-ylmethyl)-1H-pyrazolo[3,4-b]pyridin-3-amine (Compound ID 263)

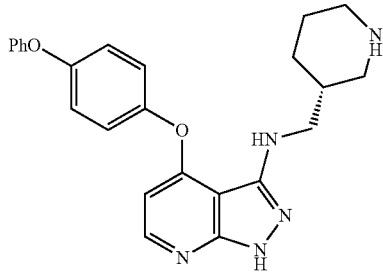 [SMILES: c1ccc(Oc2ccc(Oc3ccnc4[nH]nc(NC[C@@H]5CCCNC5)c34)cc2)cc1]

Using similar procedures as described in Example 122, the title compound was made: a yellow solid, HCl salt (385 mg, 99%); MW=415.5, MH$^+$=416.3, MH$^-$=414.1, UV: λ=233, 327 nm.

Example 264

(S)-4-(4-phenoxyphenoxy)-N-(pyrrolidin-3-ylmethyl)-1H-pyrazolo[3,4-b]pyridin-3-amine (Compound ID 264)

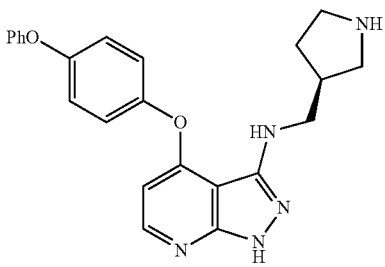 [SMILES: c1ccc(Oc2ccc(Oc3ccnc4[nH]nc(NC[C@H]5CCNC5)c34)cc2)cc1]

Using similar procedures as described in Example 122, the title compound was made: a yellow solid, HCl salt (344 mg, 99%); MW=401.5, MH$^+$=402.2, MH$^-$=400.2, UV: λ=230, 324 nm.

Example 265

1-(4-(4-(4-phenoxyphenoxy)-1H-pyrazolo[3,4-b]pyridin-3-ylamino)piperidin-1-yl)prop-2-en-1-one (Compound ID 265)

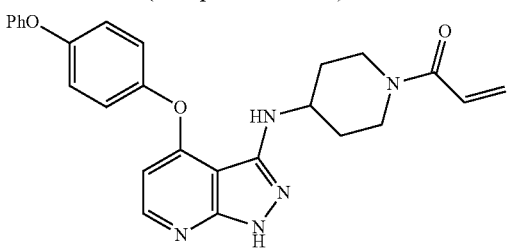

Using similar procedures as described in Example 122, the title compound was made: a yellow solid, formic acid salt (20.1 mg, 34%); MW=455.5, MH$^+$=456.4, MH$^-$=454.1, UV: λ=231, 325 nm.

Example 266

1-(4-((4-(4-phenoxyphenoxy)-1H-pyrazolo[3,4-b]pyridin-3-ylamino)methyl)piperidin-1-yl)prop-2-en-1-one (Compound ID 266)

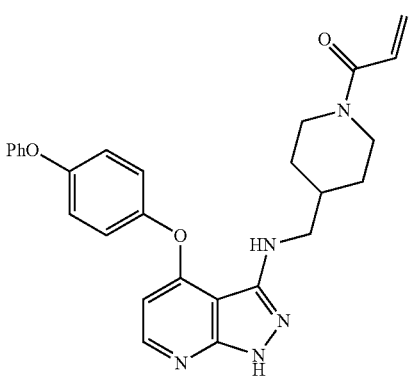 [SMILES: C=CC(=O)N1CCC(CNc2n[nH]c3nccc(Oc4ccc(Oc5ccccc5)cc4)c23)CC1]

Using similar procedures as described in Example 122, the title compound was made: a yellow solid, formic acid salt (24.5 mg, 29%); MW=469.5, MH⁺=470.4, MH⁻=468.2, UV: λ=233, 304, 327 nm.

Example 267

(S)-1-(3-((4-(4-phenoxyphenoxy)-1H-pyrazolo[3,4-b]pyridin-3-ylamino)methyl)piperidin-1-yl)prop-2-en-1-one (Compound ID 267)

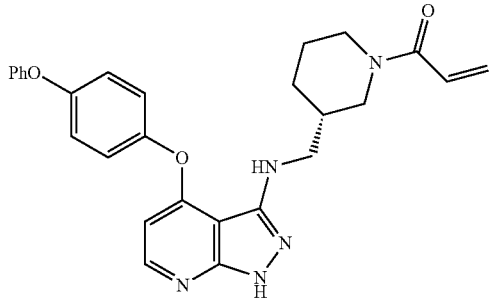 [SMILES: C=CC(=O)N1CCC[C@@H](CNc2n[nH]c3nccc(Oc4ccc(Oc5ccccc5)cc4)c23)C1]

Using similar procedures as described in Example 122, the title compound was made: a yellow solid, formic acid salt (14.9 mg, 25%); MW=469.5, MH⁺=470.4, MH⁻=468.1, UV: λ=230, 305, 361 nm.

Example 268

(R)-1-(3-((4-(4-phenoxyphenoxy)-1H-pyrazolo[3,4-b]pyridin-3-ylamino)methyl)pyrrolidin-1-yl)prop-2-en-1-one (Compound ID 268)

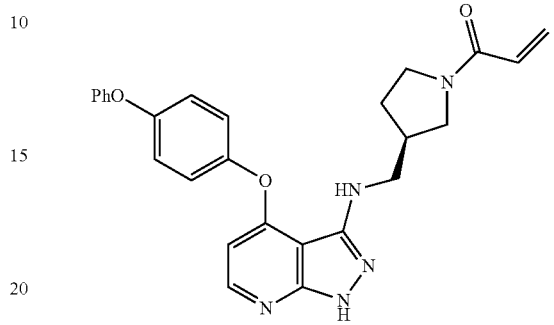

Using similar procedures as described in Example 122, the title compound was made: a yellow solid, formic acid salt (3.4 mg, 6%); MW=455.5, MH⁺=456.3, MH⁻=N/A, UV: λ=224, 364 nm.

Exemplary Compounds of the Invention

TABLE 1

Exemplary Compounds of the Invention

| Compd ID | NAME OR STRUCTURE |
|---|---|
| 1 | 1-[(3R)-3-{[4-(4-chlorophenoxy)-1H-pyrazolo[3,4-b]pyridin-3-yl]amino}pyrrolidin-1-yl]prop-2-en-1-one |
| 2 | 1-[(3R)-3-{[4-(4-chlorophenoxy)-1H-pyrazolo[3,4-b]pyridin-3-yl](methyl)amino}pyrrolidin-1-yl]prop-2-en-1-one |
| 3 | (2E)-1-[(3R)-{[4-(4-chlorophenoxy)-1H-pyrazolo[3,4-b]pyridin-3-yl]amino}pyrrolidin-1-yl]-4-(dimethylamino)but-2-en-1-one |
| 4 | 1-[(3R)-3-{[4-(4-phenoxyphenoxy)-1H-pyrazolo[3,4-b]pyridin-3-yl]amino}pyrrolidin-1-yl]prop-2-en-1-one |
| 5 | (2E)-4-(dimethylamino)-1-[(3R)-3-{[4-(4-phenoxyphenoxy)-1H-pyrazolo[3,4-b]pyridin-3-yl]amino}pyrrolidin-1-yl]but-2-en-1-one |
| 6 | 1-[(3R)-3-{[4-(4-phenoxyphenoxy)-1H-pyrazolo[3,4-b]pyridin-3-yl]amino}piperidin-1-yl]prop-2-en-1-one |
| 7 | 1-[(3R)-3-{[4-(4-chlorophenoxy)-1H-pyrrolo[2,3-b]pyridin-3-yl]amino}pyrrolidin-1-yl]prop-2-en-1-one |
| 8 | (2E)-4-[cyclopropyl(methyl)amino]-1-[(3R)-3-{[4-(4-phenoxyphenoxy)-1H-pyrazolo[3,4-b]pyridin-3-yl]amino}piperidin-1-yl]but-2-en-1-one |
| 9 | (2E)-4-[(2-methoxyethyl)(methyl)amino]-1-[(3R)-3-{[4-(4-phenoxyphenoxy)-1H-pyrazolo[3,4-b]pyridin-3-yl]amino}pyrrolidin-1-yl]but-2-en-1-one |
| 10 | (2E)-4-[cyclopropyl(methyl)amino]-1-[(3R)-3-{[4-(4-phenoxyphenoxy)-1H-pyrazolo[3,4-b]pyridin-3-yl]amino}pyrrolidin-1-yl]but-2-en-1-one |
| 11 | (2E)-4-[cyclopropyl(methyl)amino]-1-[(3R)-3-{[4-(3-phenoxyphenoxy)-1H-pyrazolo[3,4-b]pyridin-3-yl]amino}pyrrolidin-1-yl]but-2-en-1-one |
| 12 | (2E)-4-(dimethylamino)-1-[(3R)-3-{[4-(3-phenoxyphenoxy)-1H-pyrazolo[3,4-b]pyridin-3-yl]amino}pyrrolidin-1-yl]but-2-en-1-one |
| 13 | (2E)-4-(dimethylamino)-1-[(3R)-3-{[4-(3-phenoxyphenoxy)-1H-pyrazolo[3,4-b]pyridin-3-yl]amino}piperidin-1-yl]but-2-en-1-one |
| 14 | (2E)-4-(dimethylamino)-1-[(3R)-3-({4-[(4-phenoxyphenyl)amino]-1H-pyrazolo[3,4-b]pyridin-3-yl}oxy)pyrrolidin-1-yl]but-2-en-1-one |
| 15 | 1-benzyl-4-[(3-{[(3R)-1-[(2E)-4-(dimethylamino)but-2-enoyl]pyrrolidin-3-yl]amino}-1H-pyrazolo[3,4-b]pyridin-4-yl)oxy]-1,2-dihydropyridin-2-one |
| 16 | (2E)-1-[(3R)-3-({4-[3-chloro-4-(1,3-oxazol-2-yl)phenoxy]-1H-pyrazolo[3,4-b]pyridin-3-yl}amino)pyrrolidin-1-yl]-4-(dimethylamino)but-2-en-1-one |
| 17 | (2E)-4-(dimethylamino)-1-[(3R)-3-({4-[(3-phenoxyphenyl)amino]-1H-pyrazolo[3,4-b]pyridin-3-yl}oxy)pyrrolidin-1-yl]but-2-en-1-one |
| 18 | (2E)-3-cyclopropyl-2-[(E)-(3R)-{[4-(4-phenoxyphenoxy)-1H-pyrazolo[3,4-b]pyridin-3-yl]amino}pyrrolidine-1-carbonyl]prop-2-enenitrile |
| 19 | (2E)-2-[(E)-(3R)-3-{[4-(4-phenoxyphenoxy)-1H-pyrazolo[3,4-b]pyridin-3-yl]amino}pyrrolidine-1-carbonyl]-3-phenylprop-2-enenitrile |

TABLE 1-continued

Exemplary Compounds of the Invention

| Compd ID | NAME OR STRUCTURE |
|---|---|
| 20 | (2E)-4-(dimethylamino)-1-[(3R)-3-[(4-{3-[(pyrimidin-4-yl)amino]phenoxy}-1H-pyrazolo[3,4-b]pyridin-3-yl)amino]pyrrolidin-1-yl]but-2-en-1-one |
| 21 | (2E)-4-(dimethylamino)-N-methyl-N-[(1s,4s)-4-{[4-(3-phenoxyphenoxy)-1H-pyrazolo[3,4-b]pyridin-3-yl]amino}cyclohexyl]but-2-enamide |
| 22 | (2E)-4-[cyclopropyl(methyl)amino]-1-[(3R)-3-{[4-(4-phenoxyphenoxy)-1H-pyrazolo[3,4-b]pyridin-3-yl]oxy}pyrrolidin-1-yl]but-2-en-1-one |
| 23 | (2E)-4-[cyclopropyl(methyl)amino]-1-[(3R)-3-({4-[(4-phenoxyphenyl)amino]-1H-pyrazolo[3,4-b]pyridin-3-yl}amino)pyrrolidin-1-yl]but-2-en-1-one |
| 24 | (2E)-4-(dimethylamino)-1-[(3R)-3-[(4-{[(3S)-1-phenylpyrrolidin-3-yl]oxy}-1H-pyrazolo[3,4-b]pyridin-3-yl)amino]pyrrolidin-1-yl]but-2-en-1-one |
| 25 | 2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzene-1-sulfonamide |
| 26 | (2E)-2-[(E)-(3R)-3-{[4-(4-phenoxyphenoxy)-1H-pyrazolo[3,4-b]pyridin-3-yl]amino}pyrrolidine-1-carbonyl]-3-(pyridin-2-yl)prop-2-enenitrile |
| 27 | (2E)-3-cyclobutyl-2-[(E)-(3R)-3-{[4-(4-phenoxyphenoxy)-1H-pyrazolo[3,4-b]pyridin-3-yl]amino}pyrrolidine-1-carbonyl]prop-2-enenitrile |
| 28 | (2E)-3-(1H-imidazol-2-yl)-2-[(E)-(3R)-3-{[4-(4-phenoxyphenoxy)-1H-pyrazolo[3,4-b]pyridin-3-yl]amino}pyrrolidine-1-carbonyl]prop-2-enentrile |
| 29 | (2Z)-2-cyano-N-methyl-3-(3-{[4-(4-phenoxyphenoxy)-1H-pyrazolo[3,4-b]pyridin-3-yl]amino}phenyl)prop-2-enamide |
| 30 | 4-{[4-(4-phenoxyphenoxy)-1H-pyrazolo[3,4-b]pyridin-3-yl]amino}pyridine-2-carbonitrile |
| 31 | (2Z)-2-fluoro-N-methyl-3-(3-{[4-(4-phenoxyphenoxy)-1H-pyrazolo[3,4-b]pyridin-3-yl]amino}phenyl)prop-2-enamide |
| 32 | (2E)-4-(dimethylamino)-1-{3-[4-(4-phenoxyphenoxy)-1H-pyrazolo[3,4-b]pyridin-3-yl]piperidin-1-yl}but-2-en-1-one |
| 33 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(trifluoromethyl)pyridin-2-yl]benzamide |
| 34 | 2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzonitrile |
| 35 | 2-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-5-phenoxybenzonitrile |
| 36 | (2E)-4-[cyclopropyl(methyl)amino]-1-[(2S)-2-({[4-(4-phenoxyphenoxy)-1H-pyrazolo[3,4-b]pyridin-3-yl]amino}methyl)pyrrolidin-1-yl]but-2-en-1-one |
| 37 | (2E)-4-[cyclopropyl(methyl)amino]-1-[(2S)-2-({[4-(4-phenoxyphenoxy)-1H-pyrazolo[3,4-b]pyridin-3-yl]amino}methyl)piperidin-1-yl]but-2-en-1-one |
| 38 | (2E)-4-[cyclopropyl(methyl)amino]-N-methyl-N-(3-{[4-(4-phenoxyphenoxy)-1H-pyrazolo[3,4-b]pyridin-3-yl]amino}phenyl)but-2-enamide |
| 39 | (2E)-4-(dimethylamino)-1-[(3R)-3-{[4-(4-phenoxyphenoxy)-1H-pyrazolo[3,4-d]pyrimidin-3-yl]amino}pyrrolidin-1-yl]but-2-en-1-one |
| 40 | (2E)-4-[cyclopropyl(methyl)amino]-1-[(3R)-3-({4-[4-(1H-1,2,3-triazol-5-ylmethoxy)phenoxy]-1H-pyrazolo[3,4-b]pyridin-3-yl}amino)pyrrolidin-1-yl]but-2-en-1-one |
| 41 | 2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzamide |
| 44 | 3-oxo-3-[(3R)-3-{[4-(4-phenoxyphenoxy)-1H-pyrazolo[3,4-b]pyridin-3-yl]amino}pyrrolidin-1-yl]propanenitrile |
| 45 | (3R)-1-methyl-N-[4-(4-phenoxyphenoxy)-1H-pyrazolo[3,4-b]pyridin-3-yl]pyrrolidin-3-amine |
| 46 | 1-[(3R)-3-{[4-(4-phenoxyphenoxy)-1H-pyrazolo[3,4-b]pyridin-3-yl]amino}pyrrolidin-1-yl]ethan-1-one |
| 47 | N-(oxan-4-yl)-4-(4-phenoxyphenoxy)-1H-pyrazolo[3,4-b]pyridin-3-amine |
| 48 | (2E)-4-[cyclopropyl(methyl)amino]-1-[(3R)-3-{[4-(4-phenoxyphenoxy)-1H-pyrazolo[3,4-d]pyrimidin-3-yl]amino}pyrrolidin-1-yl]but-2-en-1-one |
| 49 | (2E)-4-[cyclopropyl(methyl)amino]-N-[(3R)-1-[(2E)-4-[cyclopropyl(methyl)amino]but-2-enoyl]pyrrolidin-3-yl]-N-[4-(4-phenoxyphenoxy)-1H-pyrazolo[3,4-d]pyrimidin-3-yl]but-2-enamide |
| 50 | (3R)-N-[4-(4-phenoxyphenoxy)-1H-pyrazolo[3,4-d]pyrimidin-3-yl]piperidin-3-amine |
| 51 | 1-[(3R)-3-{[4-(4-phenoxyphenoxy)-1H-pyrazolo[3,4-d]pyrimidin-3-yl]amino}piperidin-1-yl]propan-1-one |
| 52 | N-[4-(4-phenoxyphenoxy)-1H-pyrazolo[3,4-d]pyrimidin-3-yl]-N-[(3R)-1-propanoylpiperidin-3-yl]propanamide |
| 53 | (2E)-4-(dimethylamino)-1-[(3R)-3-{[4-(4-phenoxyphenoxy)-1H-pyrazolo[3,4-d]pyrimidin-3-yl]amino}piperidin-1-yl]but-2-en-1-one |
| 54 | (2E)-4-(dimethylamino)-1-[(3R)-3-{[4-(2-hydroxy-3-phenoxyphenoxy)-1H-pyrazolo[3,4-b]pyridin-3-yl]amino}pyrrolidin-1-yl]but-2-en-1-one |
| 55 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyridin-2-yl)benzamide |
| 56 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-propylpyridin-2-yl)benzamide |
| 57 | (2E)-4-[cyclopropyl(methyl)amino]-N-(2-{[4-(4-phenoxyphenoxy)-1H-pyrazolo[3,4-b]pyridin-3-yl]amino}phenyl)but-2-enamide |
| 58 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-methoxypyridin-2-yl)benzamide |

TABLE 1-continued

Exemplary Compounds of the Invention

| Compd ID | NAME OR STRUCTURE |
|---|---|
| 59 | 4-{[4-(4-phenoxyphenoxy)-1H-pyrazolo[3,4-b]pyridin-3-yl]amino}pyridine-2-carboxamide |
| 60 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-cyclopropylpyridin-2-yl)benzamide |
| 61 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(propan-2-yl)pyridin-2-yl]benzamide |
| 62 | N-(4-cyanopyridin-2-yl)-4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]benzamide |
| 63 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyrimidin-2-yl)benzamide |
| 64 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyrimidin-4-yl)benzamide |
| 65 | N-(cyanomethyl)-4-{[4-(4-phenoxyphenoxy)-1H-pyrazolo[3,4-b]pyridin-3-yl]amino}pyridine-2-carboxamide |
| 66 | 4-[(3-{[(3R)-1-propanoylpyrrolidin-3-yl]amino}-1H-pyrazolo[3,4-b]pyridin-4-yl)oxy]-N-[4-(trifluoromethyl)pyridin-2-yl]benzamide |
| 67 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(1H-imidazol-2-yl)benzamide |
| 68 | 4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(dimethylamino)pyridin-2-yl]benzamide |
| 69 | N-(1H-1,3-benzodiazol-2-yl)-4-[(3-{[(3R)-1-propanoylpyrrolidin-3-yl]amino}-1H-pyrazolo[3,4-b]pyridin-4-yl)oxy]benzamide |
| 70 | 4-[(3-{[(3R)-1-propanoylpyrrolidin-3-yl]amino}-1H-pyrazolo[3,4-b]pyridin-4-yl)amino]-N-[4-(trifluoromethyl)pyridin-2-yl]benzamide |
| 71 | 4-[(3-{[(3R)-1-propanoylpyrrolidin-3-yl]oxy}-1H-pyrazolo[3,4-b]pyridin-4-yl)amino]-N-[4-(trifluoromethyl)pyridin-2-yl]benzamide |
| 72 | N-(5-methyl-1,3-thiazol-2-yl)-4-[(3-{[(3R)-1-propanoylpyrrolidin-3-yl]amino}-1H-pyrazolo[3,4-b]pyridin-4-yl)oxy]benzamide |
| 73 | N-(1-methyl-1H-imidazol-2-yl)-4-[(3-{[(3R)-1-propanoylpyrrolidin-3-yl]amino}-1H-pyrazolo[3,4-b]pyridin-4-yl)oxy]benzamide |
| 74 | N-(6-oxo-1,6-dihydropyrimidin-2-yl)-4-[(3-{[(3R)-1-propanoylpyrrolidin-3-yl]amino}-1H-pyrazolo[3,4-b]pyridin-4-yl)oxy]benzamide |
| 75 | N-(5-methyl-4H-1,2,4-triazol-3-yl)-4-[(3-{[(3R)-1-propanoylpyrrolidin-3-yl]amino}-1H-pyrazolo[3,4-b]pyridin-4-yl)oxy]benzamide |
| 76 | (R,E)-N-(4-cyclopropoxypyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide; |
| 77 | N-(4-cyanopyridin-2-yl)-4-({3-[(oxan-4-yl)amino]-1H-pyrazolo[3,4-b]pyridin-4-yl}oxy)benzamide |
| 78 | ethyl (3R)-3-[(4-{4-[(4-cyanopyridin-2-yl)carbamoyl]phenoxy}-1H-pyrazolo[3,4-b]pyridin-3-yl)amino]piperidine-1-carboxylate |
| 79 | (3R)-3-[(4-{4-[(4-cyanopyridin-2-yl)carbamoyl]phenoxy}-1H-pyrazolo[3,4-b]pyridin-3-yl)amino]-N-ethylpiperidine-1-carboxamide |
| 80 | N-(4-cyanopyridin-2-yl)-4-[(3-{[(3R)-1-(3-methoxypropanoyl)piperidin-3-yl]amino}-1H-pyrazolo[3,4-b]pyridin-4-yl)oxy]benzamide |
| 81 | N-(4-cyanopyridin-2-yl)-4-[(3-{[(3R)-1-cyclopropanecarbonylpiperidin-3-yl]amino}-1H-pyrazolo[3,4-b]pyridin-4-yl)oxy]benzamide |
| 82 | N-(4-cyanopyridin-2-yl)-4-[(3-{[(R,4R)-4-hydroxycyclohexyl]amino}-1H-pyrazolo[3,4-b]pyridin-4-yl)oxy]benzamide |
| 83 | N-(4-cyanopyridin-2-yl)-4-[(3-{[(3R)-1-(3-methyloxetane-3-carbonyl)piperidin-3-yl]amino}-1H-pyrazolo[3,4-b]pyridin-4-yl)oxy]benzamide |
| 84 | 4-[(3-{[(3R)-1-(3-methyloxetane-3-carbonyl)piperidin-3-yl]amino}-1H-pyrazolo[3,4-b]pyridin-4-yl)oxy]-N-[4-(trifluoromethyl)pyridin-2-yl]benzamide |
| 85 | N-(4-cyanopyridin-2-yl)-4-[(3-{[(1S,4S)-4-methoxycyclohexyl]amino}-1H-pyrazolo[3,4-b]pyridin-4-yl)oxy]benzamide |
| 86 | 4-[(3-{[(3R)-1-(3-methyloxetane-3-carbonyl)piperidin-3-yl]amino}-1H-pyrazolo[3,4-b]pyridin-4-yl)oxy]-N-(4-methylpyridin-2-yl)benzamide |
| 87 | 4-[(3-{[(3R)-1-(4-methyloxane-4-carbonyl)piperidin-3-yl]amino}-1H-pyrazolo[3,4-b]pyridin-4-yl)oxy]-N-(4-methylpyridin-2-yl)benzamide |
| 88 | 4-[(3-{[(3R)-1-(1-methylcyclobutanecarbonyl)piperidin-3-yl]amino}-1H-pyrazolo[3,4-b]pyridin-4-yl)oxy]-N-(4-methylpyridin-2-yl)benzamide |
| 89 | 4-[(3-{[(3R)-1-(3-methyloxolane-3-carbonyl)piperidin-3-yl]amino}-1H-pyrazolo[3,4-b]pyridin-4-yl)oxy]-N-(4-methylpyridin-2-yl)benzamide |
| 90 | N-(4-methylpyridin-2-yl)-4-[(3-{[(3R)-1-(oxetan-3-carbonyl)piperidin-3-yl]amino}-1H-pyrazolo[3,4-b]pyridin-4-yl)oxy]benzamide |
| 91 | N-(4-methylpyridin-2-yl)-4-[(3-{[(3R)-1-(morpholine-4-carbonyl)piperidin-3-yl]amino}-1H-pyrazolo[3,4-b]pyridin-4-yl)oxy]benzamide |
| 92 | 4-[(3-{[(3R)-1-(1-methylpiperidine-4-carbonyl)piperidin-3-yl]amino}-1H-pyrazolo[3,4-b]pyridin-4-yl)oxy]-N-(4-methylpyridin-2-yl)benzamide |
| 93 | phenyl (3R)-3-[(4-{4-[(4-methylpyridin-2-yl)carbamoyl]phenoxy}-1H-pyrazolo[3,4-b]pyridin-3-yl)amino]piperidine-1-carboxylate |
| 94 | N-(4-methylpyridin-2-yl)-4-[(3-{[(3R)-1-[(2S)-oxolane-2-carbonyl]piperidin-3-yl]amino}-1H-pyrazolo[3,4-b]pyridin-4-yl)oxy]benzamide |

TABLE 1-continued

Exemplary Compounds of the Invention

| Compd ID | NAME OR STRUCTURE |
|---|---|
| 95 | 4-[(3-{[(3R)-1-[5-(dimethylamino)pentanoyl]piperidin-3-yl]amino}-1H-pyrazolo[3,4-b]pyridin-4-yl)oxy]-N-(4-methylpyridin-2-yl)benzamide |
| 96 | N-(4-methylpyridin-2-yl)-4-[(3-{[(3R)-1-(piperidin-4-carbonyl)piperidin-3-yl]amino}-1H-pyrazolo[3,4-b]pyridin-4-yl)oxy]benzamide |
| 97 | 4-[(3-{[(3R)-1-[(methylcarbamoyl)carbonyl]piperidin-3-yl]amino}-1H-pyrazolo[3,4-b]pyridin-4-yl)oxy]-N-(4-methylpyridin-2-yl)benzamide |
| 98 | 4-[(3-{[(3R)-1-[(dimethylcarbamoyl)carbonyl]piperidin-3-yl]amino}-1H-pyrazolo[3,4-b]pyridin-4-yl)oxy]-N-(4-methylpyridin-2-yl)benzamide |
| 99 | 4-[(3-{[(3R)-1-[1-(methoxymethyl)cyclobutanecarbonyl]piperidin-3-yl]amino}-1H-pyrazolo[3,4-b]pyridin-4-yl)oxy]-N-(4-methylpyridin-2-yl)benzamide |
| 100 | 4-[(3-{[(3R)-1-cyclopropanecarbonylpiperidin-3-yl]amino}-1H-pyrazolo[3,4-b]pyridin-4-yl)oxy]-N-(4-methylpyridin-2-yl)benzamide |
| 101 | 4-[(3-{[(3R)-1-(1-cyanocyclopropanecarbonyl)piperidin-3-yl]amino}-1H-pyrazolo[3,4-b]pyridin-4-yl)oxy]-N-(4-methylpyridin-2-yl)benzamide |
| 102 | 4-[(3-{[(3R)-1-(2-cyano-2,2-dimethylacetyl)piperidin-3-yl]amino}-1H-pyrazolo[3,4-b]pyridin-4-yl)oxy]-N-(4-methylpyridin-2-yl)benzamide |
| 103 | tert-butyl 4-methyl-4-[(3R)-3-[(4-{4-[(4-methylpyridin-2-yl)carbamoyl]phenoxy}-1H-pyrazolo[3,4-b]pyridin-3-yl)amino]piperidine-1-carbonyl]piperidine-1-carboxylate |
| 104 | 4-[(3-{[(3R)-1-(4-methylpiperidine-4-carbonyl)piperidin-3-yl]amino}-1H-pyrazolo[3,4-b]pyridin-4-yl)oxy]-N-(4-methylpyridin-2-yl)benzamide |
| 105 | N-(4-methylpyridin-2-yl)-4-[(3-{[(3R)-1-(oxane-4-carbonyl)piperidin-3-yl]amino}-1H-pyrazolo[3,4-b]pyridin-4-yl)oxy]benzamide |
| 106 | (3R)-N,N-dimethyl-3-[(4-{4-[(4-methylpyridin-2-yl)carbamoyl]phenoxy}-1H-pyrazolo[3,4-b]pyridin-3-yl)amino]piperidine-1-carboxamide |
| 107 | 4-[(3-{[(3R)-1-cyclopentanecarbonylpiperidin-3-yl]amino}-1H-pyrazolo[3,4-b]pyridin-4-yl)oxy]-N-(4-methylpyridin-2-yl)benzamide |
| 108 | ethyl (3R)-3-[(4-{4-[(4-methylpyridin-2-yl)carbamoyl]phenoxy}-1H-pyrazolo[3,4-b]pyridin-3-yl)amino]piperidine-1-carboxalate |
| 109 | 4-[(3-{[(3R)-1-benzoylpiperidin-3-yl]amino}-1H-pyrazolo[3,4-b]pyridin-4-yl)oxy]-N-(4-methylpyridin-2-yl)benzamide |
| 110 | N-(4-methylpyridin-2-yl)-4-[(3-{[(3R)-1-(pyridine-2-carbonyl)piperidin-3-yl]amino}-1H-pyrazolo[3,4-b]pyridin-4-yl)oxy]benzamide |
| 111 | 4-[(3-{[(3R)-1-(3-methyloxetane-3-carbonyl)piperidin-3-yl]amino}-1H-pyrazolo[3,4-b]pyridin-4-yl)oxy]-N-(pyridin-2-yl)benzamide |
| 112 | 4-[(3-{[(3R)-1-(4-methyloxane-4-carbonyl)piperidin-3-yl]amino}-1H-pyrazolo[3,4-b]pyridin-4-yl)oxy]N-(pyridin-2-yl)benzamide |
| 113 | 4-[(3-{[(3R)-1-(3-methyloxetane-3-carbonyl)piperidin-3-yl]amino}-1H-pyrazolo[3,4-b]pyridin-4-yl)oxy]-N-(6-methylpyridin-2-yl)benzamide |
| 114 | 4-[(3-{[(3R)-1-(4-methyloxane-4-carbonyl)piperidin-3-yl]amino}-1H-pyrazolo[3,4-b]pyridin-4-yl)oxy]-N-(6-methylpyridin-2-yl)benzamide |
| 115 | N-(4-methylpyridin-2-yl)-4-[(3-{[(3R)-1-[(3R)-oxolane-3-carbonyl]piperidin-3-yl]amino}-1H-pyrazolo[3,4-b]pyridin-4-yl)oxy]benzamide |
| 116 | N-(4-methylpyridin-2-yl)-4-[(3-{[(3R)-1-[(3S)-oxolane-3-carbonyl]piperidin-3-yl]amino}-1H-pyrazolo[3,4-b]pyridin-4-yl)oxy]benzamide |
| 117 | N-(4-methylpyridin-2-yl)-4-[(3-{[(3R)-1-[(2S)-oxolane-2-carbonyl]piperidin-3-yl]amino}-1H-pyrazolo[3,4-b]pyridin-4-yl)oxy]benzamide |
| 118 | 4-[(3-{[(3R)-1-[3-(dimethylamino)propanoyl]piperidin-3-yl]amino}-1H-pyrazolo[3,4-b]pyridin-4-yl)oxy]-N-(4-methylpyridin-2-yl)benzamide |
| 119 | 4-[(3-{[(3R)-1-(3-methoxypropanoyl)piperidin-3-yl]amino}-1H-pyrazolo[3,4-b]pyridin-4-yl)oxy]-N-(4-methylpyridin-2-yl)benzamide |
| 120 | 4-[(3-{[(3R)-1-(1-methylcyclopropanecarbonyl)piperidin-3-yl]amino}-1H-pyrazolo[3,4-b]pyridin-4-yl)oxy]-N-(4-methylpyridin-2-yl)benzamide |
| 121 | 3-(4-phenoxyphenyl)-1H-pyrazolo[3,4-b]pyrimidin-4-amine |
| 122 | N-[3-methyl-4-(propan-2-yl)phenyl]-3-[(3-{[(3R)-1-(prop-2-enoyl)pyrrolidin-3-yl]amino}-1H-pyrazolo[3,4-b]pyridin-4-yl)oxy]benzamide |
| 123 | 3-[(3-{[(3R)-1-acetylpyrrolidin-3-yl]amino}-1H-pyrazolo[3,4-b]pyridin-4-yl)oxy]-N-[3-methyl-4-(propan-2-yl)phenyl]benzamide |
| 124 | 3-[(3-{[(3S)-1-acetylpyrrolidin-3-yl]amino}-1H-pyrazolo[3,4-b]pyridin-4-yl)oxy]-N-[3-methyl-4-(propan-2-yl)phenyl]benzamide |
| 125 | 3-[(3-{[(3S)-1-cyclopropanecarbonylpyrrolidin-3-yl]amino}-1H-pyrazolo[3,4-b]pyridin-4-yl)oxy]-N-[3-methyl-4-(propan-2-yl)phenyl]benzamide |
| 126 | N-[3-methyl-4-(propan-2-yl)phenyl]-3-[(3-{[(3S)-1-(prop-2-enoyl)pyrrolidin-3-yl]amino}-1H-pyrazolo[3,4-b]pyridin-4-yl)oxy]benzamide |
| 127 | 3-[(3-{[(3R)-1-cyclopropanecarbonylpiperidin-3-yl]amino}-1H-pyrazolo[3,4-b]pyridin-4-yl)amino]-N-[3-methyl-4-(propan-2-yl)phenyl]benzamide |
| 128 | 3-[(3-{[(3S)-1-(4-fluorobenzoyl)pyrrolidin-3-yl]amino}-1H-pyrazolo[3,4-b]pyridin-4-yl)oxy]-N-[3-methyl-4-(propan-2-yl)phenyl]benzamide |
| 129 | N-[3-methyl-4-(propan-2-yl)phenyl]-3-[(3-{[(3R)-1-(prop-2-enoyl)piperidin-3-yl]amino}-1H-pyrazolo[3,4-b]pyridin-4-yl)amino]benzamide |
| 130 | 3-[(3-{[(3R)-1-(4-fluorobenzoyl)piperidin-3-yl]amino}-1H-pyrazolo[3,4-b]pyridin-4-yl)amino]-N-[3-methyl-4-(propan-2-yl)phenyl]benzamide |
| 131 | 3-[(3-{[(3R)-1-acetylpiperidin-3-yl]amino}-1H-pyrazolo[3,4-b]pyridin-4-yl)amino]-N-[3-methyl-4-(propan-2-yl)phenyl]benzamide |
| 132 | N-[3-methyl-4-(propan-2-yl)phenyl]-3-[(3-{[(3R)-1-(prop-2-enoyl)piperidin-3-yl]oxy}-1H-pyrazolo[3,4-b]pyridin-4-yl)amino]benzamide |

TABLE 1-continued

Exemplary Compounds of the Invention

| Compd ID | NAME OR STRUCTURE |
|---|---|
| 133 | N-[3-methyl-4-(propan-2-yl)phenyl]-3-[(3-{[(3R)-1-(morpholine-4-carbonyl)piperidin-3-yl]amino}-1H-pyrazolo[3,4-b]pyridin-4-yl)amino]benzamide |
| 134 | 3-[(3-{[(3R)-1-cyclopropanecarbonylpiperidin-3-yl]oxy}-1H-pyrazolo[3,4-b]pyridin-4-yl)amino]-N-[3-methyl-4-(propan-2-yl)phenyl]benzamide |
| 135 | 3-[(3-{[(3R)-1-acetylpiperidin-3-yl]oxy}-1H-pyrazolo[3,4-b]pyridin-4-yl)amino]-N-[3-methyl-4-(propan-2-yl)phenyl]benzamide |
| 136 | 1-{4-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-3-ethylurea |
| 137 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-{5-methyl-4H,5H,6H,7H-[1,3]thiazolo[4,5-c]pyridin-2-yl}benzamide |
| 138 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-[3-(trifluoromethyl)phenyl]benzamide |
| 139 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(4-methyl-1,3-thiazol-2-yl)benzamide |
| 140 | N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide |
| 141 | 4-[(3-{[(3R)-1-(but-2-ynoyl)piperidin-3-yl]amino}-1H-pyrazolo[3,4-b]pyridin-4-yl)oxy]-N-(5-methyl-1,3-thiazol-2-yl)benzamide |
| 142 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3-thiazol-2-yl)benzamide |
| 143 | N-(4-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide |
| 144 | (1r,4r)-N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]cyclohexane-1-carboxamide |
| 145 | N-{5-methyl-4H,5H,6H,7H-[1,3]thiazolo[4,5-c]pyridin-2-yl}-4-[(3-{[(3R)-1-(prop-2-enoyl)piperidin-3-yl]amino}-1H-pyrazolo[3,4-b]pyridin-4-yl)oxy]benzamide |
| 146 | N-(dimethyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide |
| 147 | 1-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-3-(propan-2-yl)urea |
| 148 | 1-[(3R)-3-({4-[3-(5-methyl-1,3-thiazol-2-yl)phenoxy]-1H-pyrazolo[3,4-b]pyridin-3-yl}amino)piperidin-1-yl]prop-2-en-1-one |
| 149 | N-(5-methyl-1,3-thiazol-2-yl)-3-[(3-{[(3R)-1-(prop-2-enoyl)piperidin-3-yl]amino}-1H-pyrazolo[3,4-b]pyridin-4-yl)oxy]benzamide |
| 150 | (2E)-4-[cyclopropyl(methyl)amino]-1-[(3R)-3-({4-[3-(5-methyl-1,3-thiazol-2-yl)phenoxy]-1H-pyrazolo[3,4-b]pyridin-3-yl}amino)piperidin-1-yl]but-2-en-1-one |
| 151 | 1-[(3R)-3-{[4-(2-methyl-4-phenoxyphenoxy)-1H-pyrazolo[3,4-b]pyridin-3-yl]amino}piperidin-1-yl]prop-2-en-1-one |
| 152 | (1r,4r)-4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3-thiazol-2-yl)cyclohexane-1-carboxamide |
| 153 | 1-[(3R)-3-{[4-(3-methyl-4-phenoxyphenoxy)-1H-pyrazolo[3,4-b]pyridin-3-yl]amino}piperidin-1-yl]prop-2-en-1-one |
| 154 | 1-[(3R)-3-[(4-{4-[4-(trifluormethyl)-1H-imidazol-2-yl]phenoxy}-1H-pyrazolo[3,4-b]pyridin-3-yl)amino]piperidin-1-yl]prop-2-en-1-one |
| 155 | 1-[(3S)-3-[(4-{4-[4-(trifluoromethyl)pyridin-2-yl]phenoxy}-1H-pyrazolo[3,4-b]pyridin-3-yl)amino]piperidin-1-yl]prop-2-en-1-one |
| 156 | (2E)-4-[cyclopropyl(methyl)amino]-1-[(3R)-3-{[4-(3-methyl-4-phenoxyphenoxy)-1H-pyrazolo[3,4-b]pyridin-3-yl]amino}piperidin-1-yl]but-2-en-1-one |
| 157 | 4-[(3-{[(3R)-1-[(2E)-4-[cyclpropyl(methyl)amino]but-2-enoyl]piperidin-3-yl]amino}-1H-pyrazolo[3,4-b]pyridin-4-yl)oxy]-N-(4-methyl-1H-imidazol-2-yl)benzamide |
| 158 | 1-[(3R)-3-({4-[4-(5-methyl-1,3-thiazol-2-yl)phenoxy]-1H-pyrazolo[3,4-b]pyridin-3-yl}amino)piperidin-1-yl]prop-2-en-1-one |
| 159 | N-(1,5-dimethyl-1H-pyrazol-3-yl)-4-[(3-{[(3R)-1-(prop-2-enoyl)piperidin-3-yl]amino}-1H-pyrazolo[3,4-b]pyridin-4-yl)oxy]benzamide |
| 160 | 1-[(3R)-3-[(4-{4-[3-(trifluoromethyl)piperidin-1-carbonyl]phenoxy}-1H-pyrazolo[3,4-b]pyridin-3-yl)amino]piperidin-1-yl]prop-2-en-1-one |
| 161 | 4-[(3-{[(3R)-1-[4-(dimethylamino)butanoyl]piperidin-3-yl]amino}-1H-pyrazolo[3,4-b]pyridin-4-yl)oxy]-N-[4-(trifluoromethyl)pyridin-2-yl]benzamide |
| 162 | N-(1,3-benzothiazol-2-yl)-4-[(3-{[(3S)-1-(prop-2-enoyl)piperidin-3-yl]amino}-1H-pyrazolo[3,4-b]pyridin-4-yl)oxy]benzamide |
| 163 | 1-[(3R)-3-[(4-{4-[3-(trifluoromethyl)piperidine-1-carbonyl]phenoxy}-1H-pyrazolo[3,4-b]pyridin-3-yl)amino]piperidin-1-yl]but-2-yn-1-one |
| 164 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(dimethyl-1,3-thiazol-2-yl)benzamide |
| 165 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(1,5-dimethyl-1H-pyrazol-3-yl)benzamide |
| 166 | N-(5-cyano-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide |

TABLE 1-continued

Exemplary Compounds of the Invention

Compd ID NAME OR STRUCTURE

167 N-(1,3-benzothiazol-2-yl)-4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]benzamide
168 4-[(3-{[(3R)-1-(but-2-ynoyl)piperidin-3-yl]amino}-1H-pyrazolo[3,4-b]pyridin-4-yl)oxy]-N-(5-cyano-1,3-thiazol-2-yl)benzamide
169 (2E)-4-[cyclopropyl(methyl)amino]-1-[(3R)-3-{[4-(2-methyl-4-phenoxyphenoxy)-1H-pyrazolo[3,4-b]pyridin-3-yl]amino}piperidin-1-yl]but-2-en-1-one
170 1-[(3R)-3-{[4-(4-{[1,3]oxazolo[4,5-b]pyridin-2-yl}phenoxy)-1H-pyrazolo[3,4-b]pyridin-3-yl]amino}piperidin-1-yl]but-2-yn-1-one
171 4-[(3-{[(3R)-1-(prop-2-enoyl)pyrrolidin-3-yl]amino}-1H-pyrazolo[3,4-b]pyridin-4-yl)oxy]-N-[4-(trifluoromethyl)pyridin-2-yl]benzamide
172 N-(1,3-benzothiazol-2-yl)-4-[(3-{[(3R)-1-[4-(dimethylamino)butanoyl]piperidin-3-yl]amino}-1H-pyrazolo[3,4-b]pyridin-4-yl)oxy]benzamide
173 4-[(3-{[(3R)-1-cyclopropanecarbonylpiperidin-3-yl]amino}-1H-pyrazolo[3,4-b]pyridin-4-yl)oxy]-N-[4-(trifluoromethyl)pyridin-2-yl]benzamide
174 4-[(3-{[(3R)-1-(but-2-ynoyl)pyrrolidin-3-yl]amino}-1H-pyrazolo[3,4-b]pyridin-4-yl)oxy]-N-[4-(trifluoromethyl)pyridin-2-yl]benzamide
175 4-[(3-{[(3R)-1-(but-2-ynoyl)piperidin-3-yl]amino}-1H-pyrazolo[3,4-b]pyridin-4-yl)oxy]-N-(dimethyl-1,3-thiazol-2-yl)benzamide
176 (3R)-3-[(4-{4-[(1,3-benzothiazol-2-yl)carbamoyl]phenoxy}-1H-pyrazolo[3,4-b]pyridin-3-yl)amino]-N-ethylpiperidine-1-carboxamide
177 4-[(3-{[(3R)-1-(but-2-ynoyl)piperidin-3-yl]amino}-1H-pyrazolo[3,4-b]pyridin-4-yl)oxy]-N-(5-ethyl-1,3-thiazol-2-yl)benzamide
178 N-(5-methyl-1,2-oxazol-3-yl)-4-[(3-{[(3R)-1-(prop-2-enoyl)piperidin-3-yl]amino}-1H-pyrazolo[3,4-b]pyridin-4-yl)oxy]benzamide
179 N-(5-ethyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide
180 4-[(3-{[(3R)-1-(but-2-ynoyl)piperidin-3-yl]amino}-1H-pyrazolo[3,4-b]pyridin-4-yl)oxy]-N-(5-methyl-1,3,4-thiadiazol-2-yl)benzamide
181 4-[(3-{[(3R)-1-(but-2-ynoyl)pyrrolidin-3-yl]amino}-1H-pyrazolo[3,4-b]pyridin-4-yl)oxy]-N-(5-methyl-1,3-thiazol-2-yl)benzamide
182 (3R)-N-ethyl-3-({4-[4-(7-methyl-1,3-benzoxazol-2-yl)phenoxy]-1H-pyrazolo[3,4-b]pyridin-3-yl}amino)piperidine-1-carboxamide
183 N-(1,3-benzothiazol-2-yl)-4-[(3-{[(3R)-1-(but-2-ynoyl)piperidin-3-yl]amino}-1H-pyrazolo[3,4-b]pyridin-4-yl)oxy]benzamide
184 (3R)-N-{4-[4-(7-methyl-1,3-benzothiazol-2-yl)phenoxy]-1H-pyrazolo[3,4-b]pyridin-3-yl}-1-(1-methylpiperidine-4-carbonyl)piperidin-3-amine
185 4-[(3-{[(3R)-1-(but-2-ynoyl)piperidin-3-yl]amino}-1H-pyrazolo[3,4-b]pyridin-4-yl)oxy]-N-(1,5-dimethyl-1H-pyrazol-3-yl)benzamide
186 N-ethyl-3-[4-(4-{[4-(trifluoromethyl)pyridin-2-yl]carbamoyl}phenoxy)-1H-pyrazolo[3,4-b]pyridin-3-yl]piperidine-1-carboxamide
187 N-(5-methyl-1,3,4-thiadiazol-2-yl)-4-[(3-{[(3R)-1-(prop-2-enoyl)piperidin-3-yl]amino}-1H-pyrazolo[3,4-b]pyridin-4-yl)oxy]benzamide
188 (3R)-N-ethyl-3-{[4-(4-{[4-(trifluormethyl)pyridin-2-yl]carbamoyl}phenoxy)-1H-pyrazolo[3,4-b]pyridin-3-yl]amino}pyrrolidine-1-carboxamide
189 N-ethyl-3-[(4-{4-[(5-methyl-1,3-thiazol-2-yl)carbamoyl]phenoxy}-1H-pyrazolo[3,4-b]pyridin-3-yl)amino]pyrrolidine-1-carboxamide
190 N-(5-methyl-1,3-thiazol-2-yl)-4-({3-[(1-propanoylpyrrolidin-3-yl)amino]-1H-pyrazolo[3,4-b]pyridin-4-yl}oxy)benzamide
191 3-[(3-{[(3R)-1-(prop-2-enoyl)piperidin-3-yl]amino}-1H-pyrazolo[3,4-b]pyridin-4-yl)oxy]-N-[4-(trifluoromethyl)pyridin-2-yl]benzamide
192 1-[(3R)-3-({4-[4-(1,3-benzothiazol-2-yl)phenoxy]-1H-pyrazolo[3,4-b]pyridin-3-yl}amino)piperidin-1-yl]prop-2-en-1-one
193 4-{[3-(1-cyclopropanecarbonylpiperidin-3-yl)-1H-pyrazolo[3,4-b]pyridin-4-yl]oxy}-N-(5-methyl-1,3-thiazol-2-yl)benzamide
194 1-[(3R)-3-({4-[4-(1,3-benzoxazol-2-yl)phenoxy]-1H-pyrazolo[3,4-b]pyridin-3-yl}amino)piperidin-1-yl]prop-2-en-1-one
195 N-ethyl-3-(4-{4-[(5-methyl-1,3-thiazol-2-yl)carbamoyl]phenoxy}-1H-pyrazolo[3,4-b]pyridin-3-yl)piperidine-1-carboxamide
196 1-[(3S)-3-[(4-{4-[5-(trifluoromethyl)pyridin-2-yl]phenoxy}-1H-pyrazolo[3,4-b]pyridin-3-yl)amino]piperidin-1-yl]prop-2-en-1-one
197 (3R)-N-{4-[4-(1,3-benzothiazol-2-yl)phenoxy]-1H-pyrazolo[3,4-b]pyridin-3-yl}-1-(1-methylpiperidine-4-carbonyl)piperidin-3-amine
198 4-[(3-{[(3R)-1-[(2E)-4-(dimethylamino)but-2-enoyl]piperidin-3-yl]amino}-1H-pyrazolo[3,4-b]pyridin-4-yl)oxy]-N-(5-methyl-1,3-thiazol-2-yl)benzamide
199 4-[(3-{[1-(1-methylpiperidin-4-carbonyl)pyrrolidin-3-yl]amino}-1H-pyrazolo[3,4-b]pyridin-4-yl)oxy]-N-[4-(trifluoromethyl)pyridin-2-yl]benzamide
200 4-[(3-{[(3R)-1-cyclopropanecarbonylpyrrolidin-3-yl]amino}-1H-pyrazolo[3,4-b]pyridin-4-yl)oxy]-N-(5-methyl-1,3-thiazol-2-yl)benzamide
201 1-{4-[(3-{[(3R)-1-(prop-2-enoyl)piperidin-3-yl]amino}-1H-pyrazolo[3,4-b]pyridin-4-yl)oxy]phenyl}-3-[4-(trifluoromethyl)pyridin-2-yl]urea
202 4-[(3-{[(3R)-1-[4-(dimethylamino)butanoyl]pyrrolidin-3-yl]amino}-1H-pyrazolo[3,4-b]pyridin-4-yl)oxy]-N-(5-methyl-1,3-thiazol-2-yl)benzamide
203 4-[(3-{[(3R)-1-(prop-2-enoyl)piperidin-3-yl]amino}-1H-pyrazoo[3,4-b]pyridin-4-yl)oxy]-N-[4-(trifluoromethyl)pyridin-2-yl]benzamide
204 4-[(3-{[(3R)-1-(1-methylpiperidine-4-carbonyl)piperidin-3-yl]amino}-1H-pyrazolo[3,4-b]pyridin-4-yl)oxy]-N-[4-(trifluoromethyl)pyridin-2-yl]benzamide

TABLE 1-continued

Exemplary Compounds of the Invention

| Compd ID | NAME OR STRUCTURE |
|---|---|
| 205 | 4-[(3-{[(3R)-1-(but-2-ynoyl)piperidin-3-yl]amino}-1H-pyrazolo[3,4-b]pyridin-4-yl)oxy]-N-[4-(trifluoromethyl)pyridin-2-yl]benzamide |
| 206 | 1-[(3R)-3-[(4-{4-[5-(trifluoromethyl)pyridin-2-yl]phenoxy}-1H-pyrazolo[3,4-b]pyridin-3-yl)amino]piperidin-1-yl]but-2-yn-1-one |
| 207 | (3R)-N-ethyl-3-{[4-(4-{[4-(trifluoromethyl)pyridin-2-yl]carbamoyl}phenoxy)-1H-pyrazolo[3,4-b]pyridin-3-yl]amino}piperidine-1-carboxamide |
| 208 | 4-[(3-{[(3R)-1-(prop-2-enoyl)piperidin-3-yl]amino}-1H-pyrazolo[3,4-b]pyridin-4-yl)oxy]-N-[5-(trifluoromethyl)-1,3-thiazol-2-yl]benzamide |
| 209 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3,4-thiadiazol-2-yl)benzamide |
| 210 | 4-[(3-{[(3R)-1-(but-2-ynoyl)piperidin-3-yl]amino}-1H-pyrazolo[3,4-b]pyridin-4-yl)oxy]-N-methyl-N-(5-methyl-1,3-thiazol-2-yl)benzamide |
| 211 | N-methyl-N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide |
| 212 | 4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-[4-(trifluoromethyl)pyridin-2-yl]benzamide |
| 213 | 1-[(3R)-3-{[4-(4-{[1,3]oxazolo[4,5-b]pyridin-2-yl}phenoxy)-1H-pyrazolo[3,4-b]pyridin-3-yl]amino}piperidin-1-yl]prop-2-en-1-one |
| 214 | 3-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-1-[4-(trifluoromethyl)pyridin-2-yl]urea |
| 215 | 4-[(3-{[(3R)-1-cyclopropanecarbonylpyrrolidin-3-yl]amino}-1H-pyrazolo[3,4-b]pyridin-4-yl)oxy]-N-[4-(trifluoromethyl)pyridin-2-yl]benzamide |
| 216 | (3R)-3-({4-[4-(1,3-benzothiazol-2-yl)phenoxy]-1H-pyrazolo[3,4-b]pyridin-3-yl}amino)-N-ethylpiperidine-1-carboxamide |
| 217 | N-(5-methyl-1,3-thiazol-2-yl)-4-({3-[1-(1-methylpiperidine-4-carbonyl)piperidin-3-yl]-1H-pyrazolo[3,4-b]pyridin-4-yl}oxy)benzamide |
| 218 | 4-{[3-(1-cyclopropanecarbonylpiperidin-3-yl)-1H-pyrazolo[3,4-b]pyridin-4-yl]oxy}-N-[4-(trifluoromethyl)pyridin-2-yl]benzamide |
| 219 | 1-[(3R)-3-({4-[4-(7-methyl-1,3-benzoxazol-2-yl)phenoxy]-1H-pyrazolo[3,4-b]pyridin-3-yl}amino)piperidin-1-yl]propan-1-one |
| 220 | (3R)-1-cyclopropanecarbonyl-N-{4-[4-(7-methyl-1,3-benzoxazol-2-yl)phenoxy]-1H-pyrazolo[3,4-b]pyridin-3-yl}piperidin-3-amine |
| 221 | N-(5-methyl-1,3-thiazol-2-yl)-4-[(3-{[(3R)-1-(1-methylpiperidine-4-carbonyl)pyrrolidin-3-yl]amino}-1H-pyrazolo[3,4-b]pyridin-4-yl)oxy]benzamide |
| 222 | 1-[(3R)-3-({4-[4-(1,3-benzothiazol-2-yl)phenoxy]-1H-pyrazolo[3,4-b]pyridin-3-yl}amino)piperidin-1-yl]propan-1-one |
| 223 | N-(1,3-benzothiazol-2-yl)-4-[(3-{[(3R)-1-(1-methylpiperidine-4-carbonyl)piperidin-3-yl]amino}-1H-pyrazolo[3,4-b]pyridin-4-yl)oxy]benzamide |
| 224 | (3R)-3-({4-[4-(1H-1,3-benzodiazol-2-yl)phenoxy]-1H-pyrazolo[3,4-b]pyridin-3-yl}amino)-N-ethylpiperidine-1-carboxamide |
| 225 | 4-[(3-{[(3R)-1-propanoylpiperidin-3-yl]amino}-1H-pyrazolo[3,4-b]pyridin-4-yl)oxy]-N-[4-(trifluoromethyl)pyridin-2-yl]benzamide |
| 226 | N-(1,3-benzothiazol-2-yl)-4-[(3-{[(3R)-1-(3-methyloxetane-3-carbonyl)piperidin-3-yl]amino}-1H-pyrazolo[3,4-b]pyridin-4-yl)oxy]benzamide |
| 227 | (R)-N-ethyl-3-(4-(4-(4-methylpyridin-2-ylcarbamoyl)phenoxy)-1H-pyrazolo[3,4-b]pyridin-3-ylamino)piperidine-1-carboxamide |
| 228 | 4-({3-[(3R)-3-[(ethylcarbamoyl)amino]piperidin-1-yl]-1H-pyrazolo[3,4-b]pyridin-4-yl}oxy)-N-[4-(trifluoromethyl)pyridin-2-yl]benzamide |
| 229 | (3R)-N-ethyl-3-[(4-{4-[(pyridin-2-yl)carbamoyl]phenoxy}-1H-pyrazolo[3,4-b]pyridin-3-yl)amino]piperidine-1-carboxamide |
| 230 | 4-({3-[(3R)-3-[4-(dimethylamino)butanamido]piperidin-1-yl]-1H-pyrazolo[3,4-b]pyridin-4-yl}oxy)-N-[4-(trifluoromethyl)pyridin-2-yl]benzamide |
| 231 | 1-[(3R)-3-({4-[4-(1H-1,3-benzodiazol-2-yl)phenoxy]-1H-pyrazolo[3,4-b]pyridin-3-yl}amino)piperidin-1-yl]propan-1-one |
| 232 | 4-[(3-{[(3R)-1-cyclopropanecarbonylpiperidin-3-yl]amino}-1H-pyrazolo[3,4-b]pyridin-4-yl)oxy]-N-(pyridin-2-yl)benzamide |
| 233 | (3R)-N,N-dimethyl-3-[(4-{4-[(pyridin-2-yl)carbamoyl]phenoxy}-1H-pyrazolo[3,4-b]pyridin-3-yl)amino]piperidine-1-carboxamide |
| 234 | 4-({3-[(3S)-3-[(ethylcarbamoyl)amino]piperidin-1-yl]-1H-pyrazolo[3,4-b]pyridin-4-yl}oxy)-N-[4-(trifluoromethyl)pyridin-2-yl]benzamide |
| 235 | (3R)-N-ethyl-3-{[4-(2-methyl-4-phenoxyphenoxy)-1H-pyrazolo[3,4-b]pyridin-3-yl]amino}piperidine-1-carboxamide |
| 236 | 4-({3-[(2-methoxyethyl)amino]-1H-pyrazolo[3,4-b]pyridin-4-yl}oxy)-N-[4-(trifluoromethyl)pyridin-2-yl]benzamide |

TABLE 1-continued

Exemplary Compounds of the Invention

| Compd ID | NAME OR STRUCTURE |
|---|---|
| 238 | 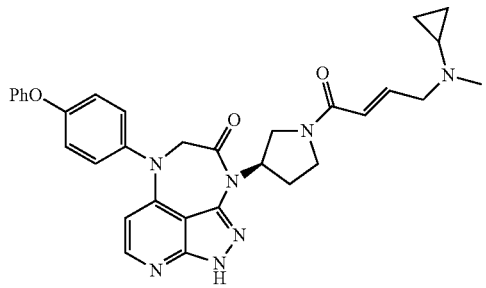 [SMILES: CN(C/C=C/C(=O)N1CC[C@@H](N2C(=O)CN(c3ccc(Oc4ccccc4)cc3)c3ccnc4[nH]nc2c34)C1)C1CC1] |
| 239 | 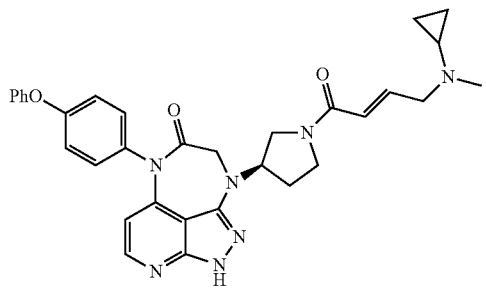 [SMILES: CN(C/C=C/C(=O)N1CC[C@@H](N2CC(=O)N(c3ccc(Oc4ccccc4)cc3)c3ccnc4[nH]nc2c34)C1)C1CC1] |

The following compounds have been or can be prepared according to the synthetic methods, or some variations thereof, described herein. The compounds can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

TABLE 2

Additional Exemplifying Compounds:

| Compd ID | Structure | Name |
|---|---|---|
| 269 | 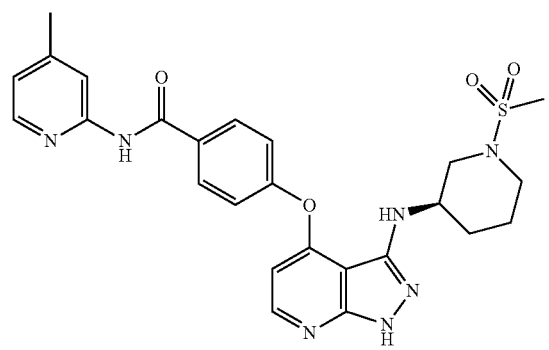 [SMILES: Cc1ccnc(NC(=O)c2ccc(Oc3ccnc4[nH]nc(N[C@@H]5CCCN(S(C)(=O)=O)C5)c34)cc2)c1] | (R)-N-(4-methylpyridin-2-yl)-4-(3-(1-(methylsulfonyl)piperidin-3-ylamino)-1H-pyrazolo[3,4-b]pyridin-4-yloxy)benzamide |

TABLE 2-continued

Additional Exemplifying Compounds:

| Compd ID | Structure | Name |
|---|---|---|
| 270 | 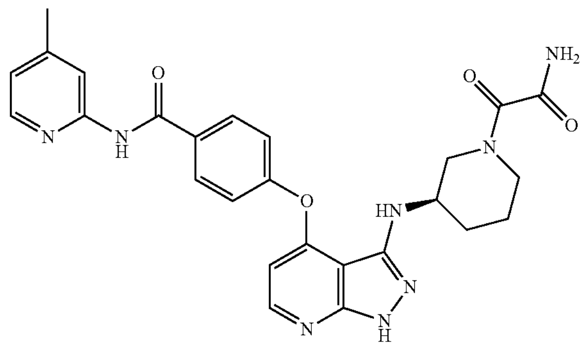 [SMILES: Cc1ccnc(NC(=O)c2ccc(Oc3ccnc4[nH]nc(N[C@@H]5CCCN(C(=O)C(N)=O)C5)c34)cc2)c1] | (R)-4-(3-(1-(2-amino-2-oxoacetyl)piperidin-3-ylamino)-1H-pyrazolo[3,4-b]pyridin-4-yloxy)-N-(4-methylpyridin-2-yl)benzamide |
| 271 | 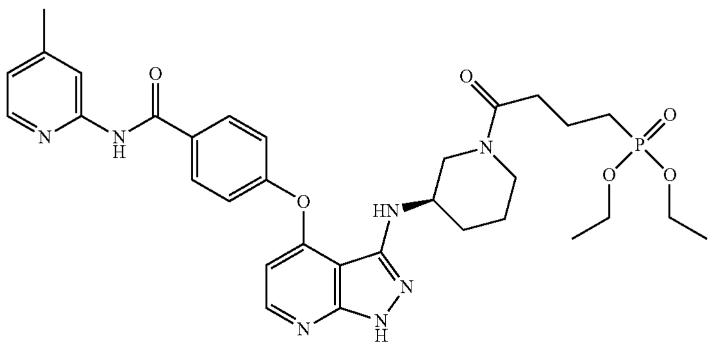 [SMILES: CCOP(=O)(CCCC(=O)N1CCC[C@@H](Nc2n[nH]c3nccc(Oc4ccc(C(=O)Nc5cc(C)ccn5)cc4)c23)C1)OCC] | (R)-diethyl 4-(3-(4-(4-(4-methylpyridin-2-ylcarbamoyl)phenoxy)-1H-pyrazolo[3,4-b]pyridin-3-ylamino)piperidin-1-yl)-4-oxobutylphosphonate |
| 272 | 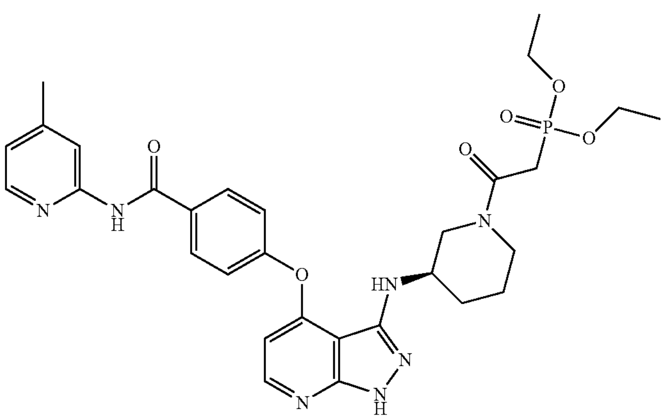 [SMILES: CCOP(=O)(CC(=O)N1CCC[C@@H](Nc2n[nH]c3nccc(Oc4ccc(C(=O)Nc5cc(C)ccn5)cc4)c23)C1)OCC] | (R)-diethyl 2-(3-(4-(4-(4-methylpyridin-2-ylcarbamoyl)phenoxy)-1H-pyrazolo[3,4-b]pyridin-3-ylamino)piperidin-1-yl)-2-oxoethylphosphonate |
| 273 | 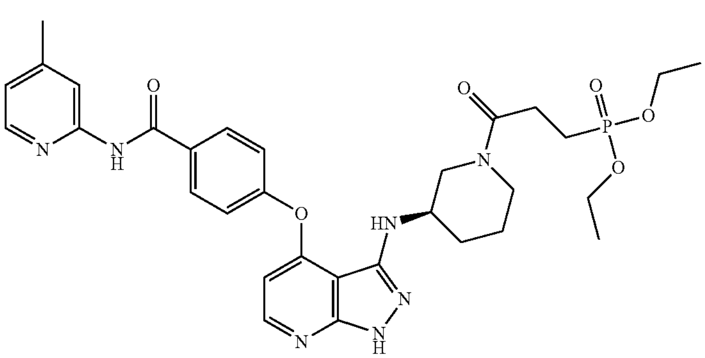 [SMILES: CCOP(=O)(CCC(=O)N1CCC[C@@H](Nc2n[nH]c3nccc(Oc4ccc(C(=O)Nc5cc(C)ccn5)cc4)c23)C1)OCC] | (R)-diethyl 3-(3-(4-(4-(4-methylpyridin-2-ylcarbamoyl)phenoxy)-1H-pyrazolo[3,4-b]pyridin-3-ylamino)piperidin-1-yl)-3-oxopropylphosphonate |

TABLE 2-continued

Additional Exemplifying Compounds:

| Compd ID | Structure | Name |
|---|---|---|
| 274 | 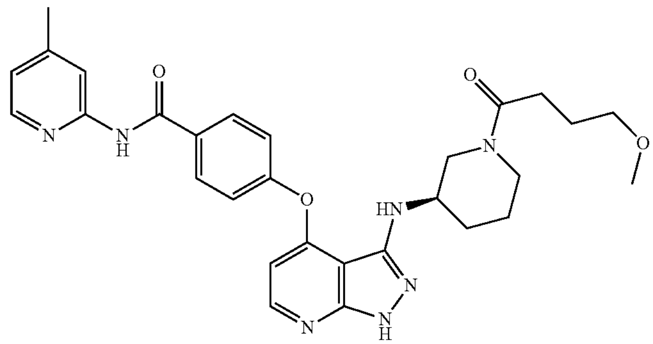 [SMILES: COCCCC(=O)N1CCC[C@@H](Nc2n[nH]c3nccc(Oc4ccc(C(=O)Nc5cc(C)ccn5)cc4)c23)C1] | (R)-4-(3-(1-(4-methoxybutanoyl)piperidin-3-ylamino)-1H-pyrazolo[3,4-b]pyridin-4-yloxy)-N-(4-methylpyridin-2-yl)benzamide |
| 275 | 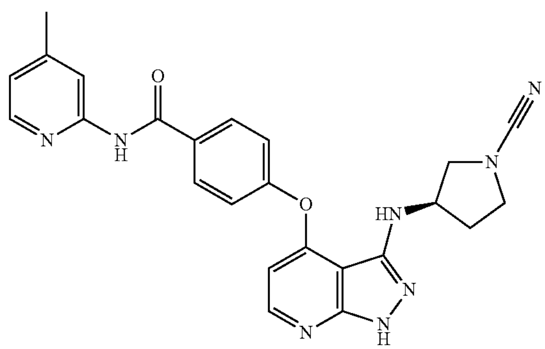 [SMILES: Cc1ccnc(NC(=O)c2ccc(Oc3ccnc4[nH]nc(N[C@@H]5CCN(C#N)C5)c34)cc2)c1] | (R)-4-(3-(1-cyanopyrrolidin-3-ylamino)-1H-pyrazolo[3,4-b]pyridin-4-yloxy)-N-(4-methylpyridin-2-yl)benzamide |
| 276 | 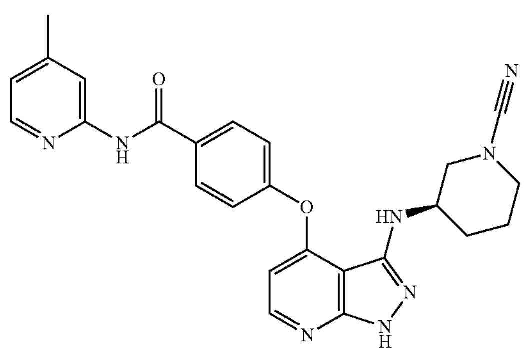 [SMILES: Cc1ccnc(NC(=O)c2ccc(Oc3ccnc4[nH]nc(N[C@@H]5CCCN(C#N)C5)c34)cc2)c1] | (R)-4-(3-(1-cyanopiperidin-3-ylamino)-1H-pyrazolo[3,4-b]pyridin-4-yloxy)-N-(4-methylpyridin-2-yl)benzamide |
| 277 | 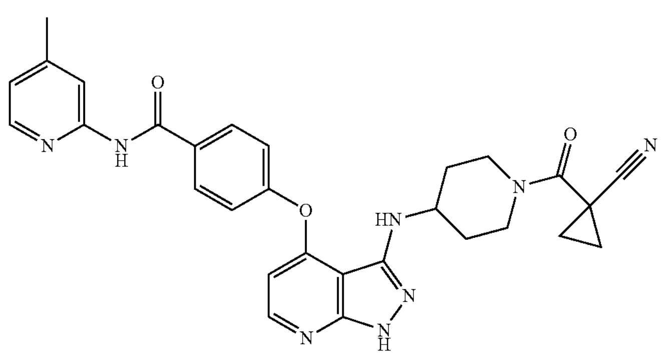 [SMILES: Cc1ccnc(NC(=O)c2ccc(Oc3ccnc4[nH]nc(NC5CCN(C(=O)C6(C#N)CC6)CC5)c34)cc2)c1] | 4-(3-(1-(1-cyanocyclopropanecarbonyl)piperidin-4-ylamino)-1H-pyrazolo[3,4-b]pyridin-4-yloxy)-N-(4-methylpyridin-2-yl)benzamide |

TABLE 2-continued

Additional Exemplifying Compounds:

| Compd ID | Structure | Name |
|---|---|---|
| 278 | 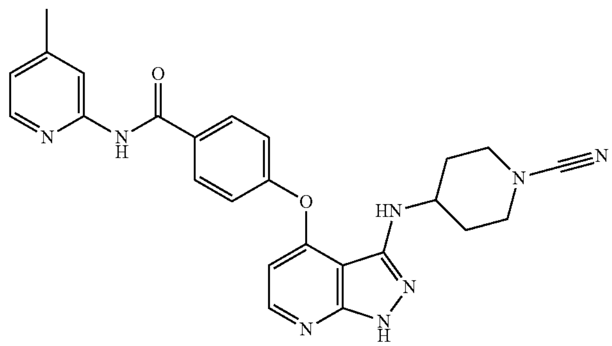 [SMILES: Cc1ccnc(NC(=O)c2ccc(Oc3ccnc4[nH]nc(NC5CCN(C#N)CC5)c34)cc2)c1] | 4-(3-(1-cyanopiperidin-4-ylamino)-1H-pyrazolo[3,4-b]pyridin-4-yloxy)-N-(4-methylpyridin-2-yl)benzamide |
| 279 | 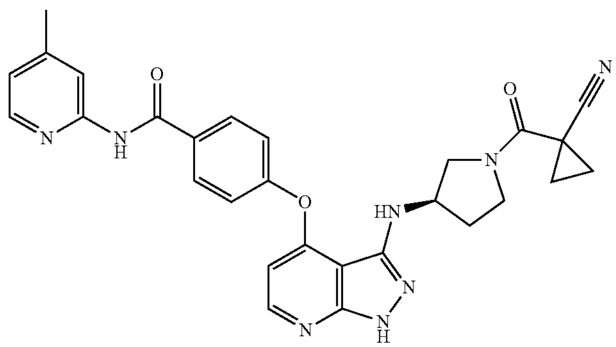 [SMILES: Cc1ccnc(NC(=O)c2ccc(Oc3ccnc4[nH]nc(N[C@@H]5CCN(C(=O)C6(C#N)CC6)C5)c34)cc2)c1] | (R)-4-(3-(1-(1-cyanocyclopropane-carbonyl)pyrrolidin-3-ylamino)-1H-pyrazolo[3,4-b]pyridin-4-yloxy)-N-(4-methylpyridin-2-yl)benzamide |
| 280 | 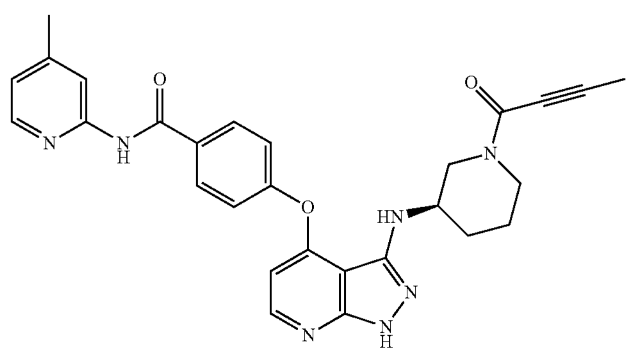 [SMILES: CC#CC(=O)N1CCC[C@@H](Nc2n[nH]c3nccc(Oc4ccc(C(=O)Nc5cc(C)ccn5)cc4)c23)C1] | (R)-4-(3-(1-but-2-ynoylpiperidin-3-ylamino)-1H-pyrazolo[3,4-b]pyridin-4-yloxy)-N-(4-methylpyridin-2-yl)benzamide |
| 281 | 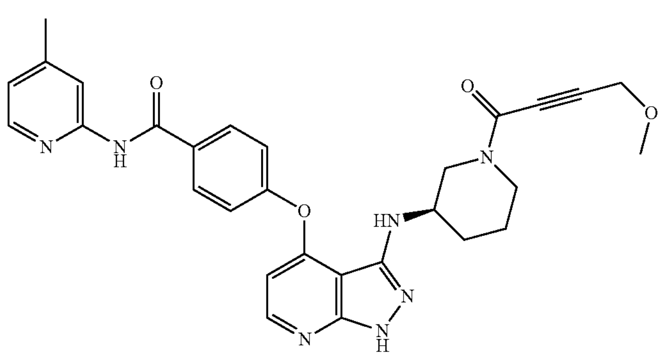 [SMILES: COCC#CC(=O)N1CCC[C@@H](Nc2n[nH]c3nccc(Oc4ccc(C(=O)Nc5cc(C)ccn5)cc4)c23)C1] | (R)-4-(3-(1-(4-methoxybut-2-ynoyl)piperidin-3-ylamino)-1H-pyrazolo[3,4-b]pyridin-4-yloxy)-N-(4-methylpyridin-2-yl)benzamide |

TABLE 2-continued

Additional Exemplifying Compounds:

| Compd ID | Structure | Name |
|---|---|---|
| 282 | 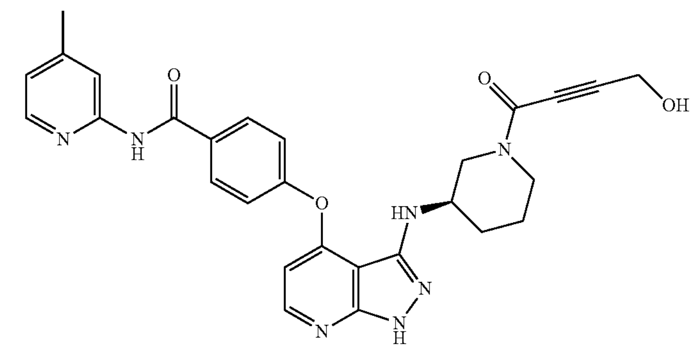 [SMILES: Cc1ccnc(NC(=O)c2ccc(Oc3ccnc4[nH]nc(N[C@@H]5CCCN(C(=O)C#CCO)C5)c34)cc2)c1] | (R)-4-(3-(1-(4-hydroxybut-2-ynoyl)piperidin-3-ylamino)-1H-pyrazolo[3,4-b]pyridin-4-yloxy)-N-(4-methylpyridin-2-yl)benzamide |
| 283 | 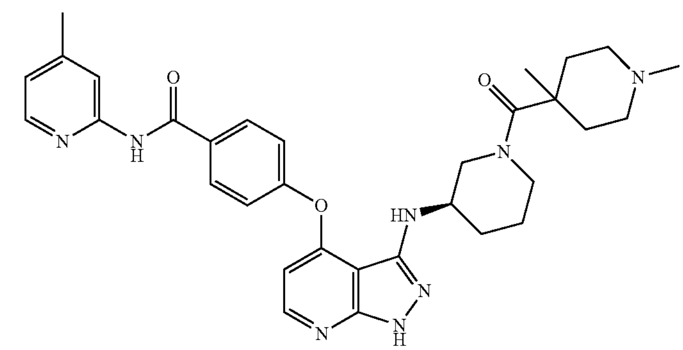 [SMILES: Cc1ccnc(NC(=O)c2ccc(Oc3ccnc4[nH]nc(N[C@@H]5CCCN(C(=O)C6(C)CCN(C)CC6)C5)c34)cc2)c1] | (R)-4-(3-(1-(1,4-dimethylpiperidine-4-carbonyl)piperidin-3-ylamino)-1H-pyrazolo[3,4-b]pyridin-4-yloxy)-N-(4-methylpyridin-2-yl)benzamide |
| 284 | 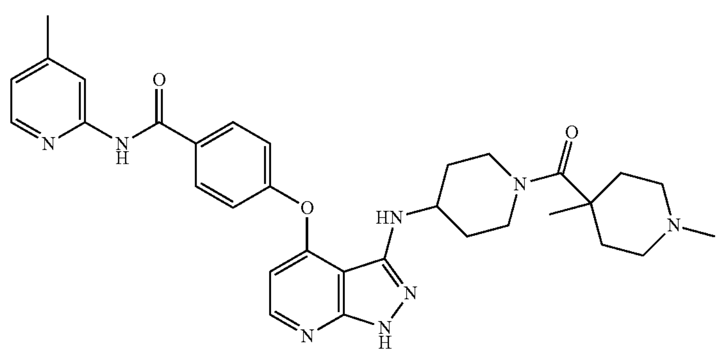 [SMILES: Cc1ccnc(NC(=O)c2ccc(Oc3ccnc4[nH]nc(NC5CCN(C(=O)C6(C)CCN(C)CC6)CC5)c34)cc2)c1] | 4-(3-(1-(1,4-dimethylpiperidine-4-carbonyl)piperidin-4-ylamino)-1H-pyrazolo[3,4-b]pyridin-4-yloxy)-N-(4-methylpyridin-2-yl)benzamide |
| 285 | 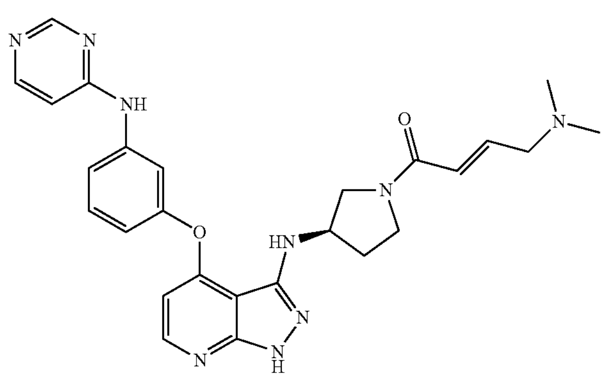 [SMILES: CN(C)C/C=C/C(=O)N1CC[C@@H](Nc2n[nH]c3nccc(Oc4cccc(Nc5ccncn5)c4)c23)C1] | (R,E)-4-(dimethylamino)-1-(3-(4-(3-(pyrimidin-4-ylamino)phenoxy)-1H-pyrazolo[3,4-b]pyridin-3-ylamino)pyrrolidin-1-yl)but-2-en-1-one |

TABLE 2-continued

Additional Exemplifying Compounds:

| Compd ID | Structure | Name |
|---|---|---|
| 286 | 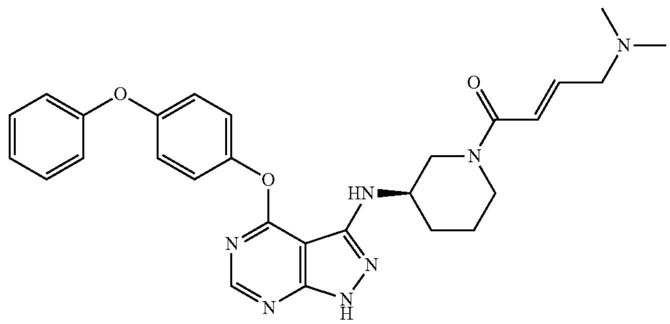 [SMILES: CN(C)C/C=C/C(=O)N1CCC[C@@H](Nc2n[nH]c3ncnc(Oc4ccc(Oc5ccccc5)cc4)c23)C1] | (R,E)-4-(dimethylamino)-1-(3-(4-(4-phenoxyphenoxy)-1H-pyrazolo[3,4-b]pyrimidin-3-ylamino)piperidin-1-yl)but-2-en-1-one |

Example 269

Btk In Vitro Inhibitory Activity

The Btk $IC_{50}$s of compounds disclosed herein is determined in both a cellular kinase assay and in a cellular functional assay of BCR-induced calcium flux as described below.

Btk kinase activity is determined using a time-resolved fluorescence resonance energy transfer (TR-FRET) methodology. Measurements are performed in a reaction volume of 50 μL using 96-well assay plates. Kinase enzyme, inhibitor, ATP (at the $K_m$ for the kinase), and 1 M peptide substrate (Biotin-AVLESEEELYSSARQ-$NH_2$) are incubated in a reaction buffer composed of 20 mM Tris, 50 mM NaCl, $MgCl_2$ (5-25 mM depending on the kinase), $MnCl_2$ (0-10 mM), 1 mM DTT, 0.1 mM EDTA, 0.01% bovine serum albumin, 0.005% Tween-20, and 10% DMSO at pH 7.4 for one hour. The reaction is quenched by the addition of 1.2 equivalents of EDTA (relative to divalent cation) in 25 μL of 1× Lance buffer (Perkin-Elmer). Streptavidin-APC (Perkin-Elmer) and Eu-labeled p-Tyr100 antibody (Perkin-Elmer) in 1× Lance buffer are added in a 25 μL volume to give final concentrations of 100 nM and 2.5 nM, respectively, and the mixture is allowed to incubate for one hour. The TR-FRET signal is measured on a multimode plate reader with an excitation wavelength ($\lambda_{Ex}$) of 330 nm and detection wavelengths ($\lambda_{Em}$) of 615 and 665 nm. Activity is determined by the ratio of the fluorescence at 665 nm to that at 615 nm. For each compound, enzyme activity is measured at various concentrations of compound. Negative control reactions are performed in the absence of inhibitor in replicates of six, and two no-enzyme controls are used to determine baseline fluorescence levels. Inhibition constants, $K_i$(app), ware obtained using the program BatchK$_i$ (Kuzmic et al. (2000), *Anal. Biochem.* 286:45-50). $IC_{50}$s are obtained according to the equation:

$$IC_{50} = \{Ki(\text{app})/(1+[ATP]/K_m^{ATP})\} + [E]_{total}/2;$$

For all kinases, $[ATP] = K_m^{ATP}$, $[Btk]_{total} = 0.5$ nM and $[Lck]_{total} = 6$ nM.

Example 270

Inhibition of a Panel of Kinases

The degree of inhibition of a panel of kinases is determined using the in vitro HotSpot kinase assay (purified enzymes, $^{33}$P-ATP, an appropriate substrate and 1 uM ATP).

TABLE 3

$IC_{50}$ Values for Exemplary Compounds of the Invention

| Compd ID | Btk ($IC_{50}$) | EGFR ($IC_{50}$) | LCK ($IC_{50}$) | JAK3 ($IC_{50}$) |
|---|---|---|---|---|
| 1 | A | B | C | C |
| 2 | A | — | — | — |
| 3 | A | B | D | — |
| 4 | A | A | A | B |
| 5 | A | A | A | D |
| 6 | A | A | A | B |
| 7 | A | C | C | — |
| 8 | A | B | A | D |
| 9 | A | A | A | D |
| 10 | A | B | A | — |
| 11 | A | C | C | — |
| 12 | A | C | C | — |
| 13 | A | B | B | — |
| 14 | A | A | A | — |
| 15 | B | D | D | — |
| 16 | B | C | C | — |
| 17 | A | A | B | — |
| 18 | A | A | B | — |
| 19 | A | B | B | — |
| 20 | D | C | D | — |
| 21 | A | B | B | B |
| 22 | A | A | A | — |
| 23 | A | B | A | — |
| 24 | B | D | C | — |
| 25 | B | B | B | — |
| 26 | A | B | B | — |
| 27 | A | B | B | — |
| 28 | A | A | B | — |
| 29 | A | A | B | — |
| 30 | C | B | B | — |
| 31 | B | B | B | — |
| 32 | A | B | A | — |
| 33 | A | C | B | — |
| 34 | A | C | B | — |
| 35 | B | D | C | — |
| 36 | A | C | A | — |
| 37 | A | C | B | — |
| 38 | A | B | B | — |
| 39 | A | A | B | — |
| 40 | A | A | B | — |
| 41 | B | — | — | — |
| 44 | A | B | A | — |
| 45 | A | B | A | — |
| 46 | A | B | A | — |
| 47 | A | A | A | — |
| 48 | B | B | C | — |
| 49 | B | — | — | — |
| 50 | D | D | — | — |
| 51 | B | A | B | — |
| 52 | B | — | — | — |

TABLE 3-continued

IC$_{50}$ Values for Exemplary Compounds of the Invention

| Compd ID | Btk (IC$_{50}$) | EGFR (IC$_{50}$) | LCK (IC$_{50}$) | JAK3 (IC$_{50}$) |
| --- | --- | --- | --- | --- |
| 53 | — | — | — | — |
| 54 | C | C | D | — |
| 55 | A | D | C | — |
| 56 | A | C | B | — |
| 57 | D | D | D | — |
| 58 | A | D | C | — |
| 59 | B | B | A | — |
| 60 | A | C | B | — |
| 61 | A | C | B | — |
| 62 | A | C | C | — |
| 63 | B | D | D | — |
| 64 | B | D | D | — |
| 65 | B | B | A | — |
| 66 | A | C | B | — |
| 67 | B | D | D | — |
| 68 | A | D | C | — |
| 69 | B | D | B | — |
| 70 | A | C | B | — |
| 71 | A | C | B | — |
| 72 | A | C | C | C |
| 73 | D | D | D | — |
| 74 | D | D | D | — |
| 75 | D | D | D | — |
| 76 | A | B | B | — |
| 77 | A | C | B | — |
| 78 | A | C | B | — |
| 79 | A | A | B | — |
| 80 | A | A | B | — |
| 81 | A | C | B | — |
| 82 | A | — | B | — |
| 83 | A | — | B | — |
| 84 | A | — | B | — |
| 85 | A | B | B | — |
| 86 | A | — | — | D |
| 87 | A | D | C | — |
| 88 | A | D | C | — |
| 89 | A | D | C | — |
| 90 | A | C | B | — |
| 91 | A | D | C | — |
| 92 | A | C | B | — |
| 93 | B | D | C | D |
| 94 | A | C | B | D |
| 95 | A | C | A | D |
| 96 | A | C | B | D |
| 97 | A | C | B | D |
| 98 | A | D | B | D |
| 99 | A | D | B | D |
| 100 | A | C | B | D |
| 101 | A | D | B | D |
| 102 | A | D | B | D |
| 103 | A | D | C | D |
| 104 | A | C | B | D |
| 105 | A | D | C | D |
| 106 | A | C | B | D |
| 107 | A | D | C | D |
| 108 | A | C | B | D |
| 109 | A | D | C | D |
| 110 | A | D | C | D |
| 111 | A | D | C | D |
| 112 | A | D | C | D |
| 113 | B | D | C | D |
| 114 | B | D | C | D |
| 115 | A | D | B | D |
| 116 | A | C | B | D |
| 117 | A | D | D | C |
| 118 | A | C | A | D |
| 119 | A | C | B | D |
| 120 | A | D | B | D |
| 121 | A | — | — | — |
| 122 | A | B | A | A |
| 123 | B | C | A | C |
| 124 | >B | C | A | C |
| 125 | >B | D | A | C |
| 126 | B | C | A | B |
| 127 | >B | — | C | D |
| 128 | >B | D | A | D |
| 129 | A | — | C | A |
| 130 | >B | — | D | D |
| 131 | >B | — | C | D |
| 132 | A | A | C | A |
| 133 | >B | D | C | D |
| 134 | >B | D | C | D |
| 135 | >B | C | C | D |
| 136 | D | — | — | — |
| 137 | B | D | D | D |
| 138 | B | — | — | — |
| 139 | B | C | D | C |
| 140 | A | B | B | A |
| 141 | A | D | C | C |
| 142 | A | C | C | C |
| 143 | A | C | C | A |
| 144 | B | C | D | B |
| 145 | A | D | D | A |
| 146 | A | B | B | A |
| 147 | D | — | — | — |
| 148 | B | B | D | C |
| 149 | A | A | C | A |
| 150 | C | — | — | — |
| 151 | A | A | A | B |
| 152 | D | — | — | — |
| 153 | A | A | B | B |
| 154 | A | C | D | C |
| 155 | B | — | — | — |
| 156 | A | B | B | D |
| 157 | C | — | — | — |
| 158 | A | B | C | C |
| 159 | A | C | D | B |
| 160 | A | — | — | — |
| 161 | A | B | A | D |
| 162 | A | A | B | A |
| 163 | B | — | — | — |
| 164 | A | C | C | C |
| 165 | B | D | D | D |
| 166 | A | — | — | — |
| 167 | A | C | B | C |
| 168 | A | — | — | — |
| 169 | A | B | A | C |
| 170 | B | — | — | — |
| 171 | A | — | — | — |
| 172 | A | B | A | A |
| 173 | A | C | B | D |
| 174 | A | — | — | — |
| 175 | A | D | B | D |
| 176 | A | D | B | B |
| 177 | A | C | B | C |
| 178 | A | C | D | B |
| 179 | A | A | B | A |
| 180 | C | — | — | — |
| 181 | A | C | C | D |
| 182 | B | D | D | — |
| 183 | A | D | B | B |
| 184 | C | D | D | — |
| 185 | B | D | D | D |
| 186 | B | C | B | — |
| 187 | B | B | D | A |
| 188 | A | C | B | D |
| 189 | A | D | C | — |
| 190 | A | C | C | — |
| 191 | A | A | B | A |
| 192 | A | B | B | B |
| 193 | B | C | D | — |
| 194 | A | C | C | B |
| 195 | B | C | C | — |
| 196 | B | C | D | B |
| 197 | B | D | B | — |
| 198 | A | C | B | D |
| 199 | A | B | B | D |
| 200 | A | C | C | D |
| 201 | A | A | A | A |
| 202 | A | D | C | D |
| 203 | A | A | B | B |
| 204 | A | C | A | D |

TABLE 3-continued

IC$_{50}$ Values for Exemplary Compounds of the Invention

| Compd ID | Btk (IC$_{50}$) | EGFR (IC$_{50}$) | LCK (IC$_{50}$) | JAK3 (IC$_{50}$) |
|---|---|---|---|---|
| 205 | A | C | B | D |
| 206 | D | — | — | — |
| 207 | A | C | B | D |
| 208 | A | — | — | — |
| 209 | D | — | — | — |
| 210 | B | — | — | — |
| 211 | A | — | — | — |
| 212 | A | — | — | — |
| 213 | B | — | — | — |
| 214 | B | — | — | — |
| 215 | A | D | C | D |
| 216 | B | D | C | D |
| 217 | B | C | C | D |
| 218 | B | C | C | D |
| 219 | D | D | D | D |
| 220 | C | D | D | D |
| 221 | A | C | B | D |
| 222 | B | D | B | D |
| 224 | C | D | C | D |
| 225 | A | B | B | D |
| 226 | A | D | B | C |
| 227 | A | D | C | D |
| 228 | A | C | B | D |
| 229 | A | C | D | D |
| 230 | B | D | D | D |
| 231 | D | D | D | D |
| 232 | A | C | D | D |
| 233 | A | D | D | D |
| 234 | B | D | D | D |
| 235 | A | C | — | D |
| 236 | B | C | — | D |
| 238 | B | — | — | — |
| 239 | A | — | — | — |
| 240 | A | — | B | D |
| 241 | A | — | B | D |
| 242 | A | — | B | D |
| 243 | A | — | C | D |
| 244 | A | — | C | D |
| 245 | A | — | C | D |
| 246 | A | — | C | D |
| 247 | A | — | C | D |
| 248 | A | — | C | D |
| 249 | >B | — | — | — |
| 250 | A | A | A | A |
| 251 | A | A | B | A |
| 252 | B | >B | >B | >B |
| 253 | >B | — | — | — |
| 254 | >B | — | — | — |
| 255 | >B | — | — | — |
| 256 | >B | — | — | — |
| 257 | >B | — | — | — |
| 258 | >B | — | — | — |
| 259 | >B | — | — | — |
| 260 | >B | — | — | — |
| 261 | A | — | — | — |
| 262 | B | — | — | — |
| 263 | B | — | — | — |
| 264 | >B | — | — | — |
| 265 | A | — | — | — |
| 266 | A | — | — | — |
| 267 | A | — | — | — |
| 268 | A | — | — | — |
| 269 | A | C | B | D |
| 270 | A | B | B | D |
| 271 | A | D | B | D |
| 272 | A | D | B | D |
| 273 | A | D | C | D |
| 274 | A | D | B | D |
| 275 | A | C | B | D |
| 276 | A | C | B | D |
| 277 | B | C | C | D |
| 278 | A | C | B | D |
| 279 | A | D | C | D |
| 280 | A | D | B | D |
| 281 | A | C | C | B |
| 282 | A | B | B | B |
| 283 | A | D | B | D |
| 284 | B | D | B | D |

IC$_{50}$: A < 100 nM;
100 nM ≤ B ≤ 1 µM;
1 µM < C ≤ 10 µM;
D > 10 µM;
— = no data Example 271

Pharmaceutical Compositions

The compositions described below are presented with a compound of Formula (A)-(C), (IA), (I), (IIa)-(IIb), (IIIa)-(IIId), (IVa)-(IVh), (Va)-(Vh), (VIa)-(VIf), (VIIa)-(VIIi), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) for illustrative purposes.

Example 271a

Parenteral Composition

To prepare a parenteral pharmaceutical composition suitable for administration by injection, 100 mg of a water-soluble salt of a compound of Formula (A)-(C), (IA), (I), (IIa)-(IIb), (IIIa)-(IIId), (IVa)-(IVh), (Va)-(Vh), (VIa)-(VIf), (VIIa)-(VIIi), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) is dissolved in DMSO and then mixed with 10 mL of 0.9% sterile saline. The mixture is incorporated into a dosage unit form suitable for administration by injection.

Example 271b

Oral Composition

To prepare a pharmaceutical composition for oral delivery, 100 mg of a compound of Formula (A)-(C), (IA), (I), (IIa)-(IIb), (IIIa)-(IIId), (IVa)-(IVh), (Va)-(Vh), (VIa)-(VIf), (VIIa)-(VIIi), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) is mixed with 750 mg of starch. The mixture is incorporated into an oral dosage unit for, such as a hard gelatin capsule, which is suitable for oral administration.

Example 271c

Sublingual (Hard Lozenge) Composition

To prepare a pharmaceutical composition for buccal delivery, such as a hard lozenge, mix 100 mg of a compound of Formula (A)-(C), (IA), (I), (IIa)-(IIb), (IIIa)-(IIId), (IVa)-(IVh), (Va)-(Vh), (VIa)-(VIf), (VIIa)-(VIIi), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 271d

Inhalation Composition

To prepare a pharmaceutical composition for inhalation delivery, 20 mg of a compound of Formula (A)-(C), (IA), (I), (IIa)-(IIb), (IIIa)-(IIId), (IVa)-(IVh), (Va)-(Vh), (VIa)-(VIf), (VIIa)-(VIIi), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) is mixed with 50 mg of anhydrous citric acid and 100 mL of 0.9% sodium chloride solution. The mixture is incorporated into an inhalation delivery unit, such as a nebulizer, which is suitable for inhalation administration.

Example 271e

Rectal Gel Composition

To prepare a pharmaceutical composition for rectal delivery, 100 mg of a compound of Formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 271f

Topical Gel Composition

To prepare a pharmaceutical topical gel composition, 100 mg of a compound of Formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 271 g

Ophthalmic Solution Composition

To prepare a pharmaceutical ophthalmic solution composition, 100 mg of a compound of Formula (A)-(C), (IA), (I), (IIa)-(IIb), (IIIa)-(IIId), (IVa)-(IVh), (Va)-(Vh), (VIa)-(VIf), (VIIa)-(VIIl), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 272

Clinical Trial of a Compound Described Herein and Combination Chemotherapy in Treating Older Patients with Previously Untreated B-Cell Lymphoma The purpose of this study is to determine how well giving a compound of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIIl), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) together with combination chemotherapy works in treating older patients with previously untreated B cell lymphoma.
Criteria
Disease Characteristics:
  Histological diagnosis of aggressive B-cell lymphoma
  Previously untreated disease
  Stage I-IV disease
  CD20-positive disease
  Any International Prognostic Index (IPI) score
  No secondary lymphoma after prior chemotherapy or radiotherapy
  No primary CNS lymphoma
  No primary gastrointestinal (MALT) lymphoma
Patient Characteristics:
  ECOG performance status 0-2
  Life expectancy≥3 months
  AST and ALT≤3 times normal unless related to lymphoma
  Bilirubin≤2 mg/dL unless related to lymphoma
  Creatinine≤2 times normal unless related to lymphoma
  Fertile patients must use effective contraception
  No known allergic reactions against foreign proteins
  No active infections requiring systemically administered antibiotics or antiviral medications
  No noncompensated heart failure
  No dilatative cardiomyopathy
  No coronary heart disease with ST-segment depression in ECG
  No myocardial infarction during the past 6 months
  No chronic lung disease with hypoxemia
  No severe noncompensated hypertension
  No severe noncompensated diabetes mellitus
  No clinical signs of cerebral dysfunction
  No severe psychiatric disease
  No known HIV infection
  No active chronic hepatitis B or C infection
  No other concurrent diseases that exclude the administration of therapy as outlined by the study protocol
  More than 12 weeks since prior clinical trial participation
  No prior participation in this study
  No prior therapy, including murine antibody, for this cancer
  No prior organ transplantation
  No concurrent response-adapted radiotherapy ("iceberg radiotherapy")
  No other concurrent anticancer chemotherapy or other study medication
Study Design
Ages Eligible for Study: 61 Years to 80 Years
Genders Eligible for Study: Both
Accepts Healthy Volunteers: No
All patients undergo the following treatment
  Prephase treatment: Patients receive vincristine subcutaneously on day −6 and oral prednisone on days −6 to 0.

Immunochemotherapy and radiotherapy: Patients receive CHOP chemotherapy comprising cyclophosphamide IV over 15 minutes, doxorubicin hydrochloride IV, and vincristine IV on day 1 and oral prednisone once daily on days 1-5. Patients also receive pegfilgrastim subcutaneously on days 4, 18, and 32. Treatment with CHOP chemotherapy repeats every 14 days for up to 6 courses in the absence of disease progression or unacceptable toxicity. Patients who show no response after course 4 of CHOP chemotherapy proceed to salvage chemotherapy off study.

Patients are evaluated 2-4 weeks after completion of CHOP. Patients with initial bulky disease (i.e., diameter≥7.5 cm) or extranodal involvement AND achieving complete remission (CR), unconfirmed CR (CRu), or partial remission undergo radiotherapy 5 days a week for 4 weeks. Patients who do not achieve CR or CRu 2 months after completion of radiotherapy proceed to salvage chemotherapy off study. Patients are then stratified according to center, International Prognostic Index (1-2 vs 3-5), disease involvement (bulky vs extranodal vs bulky and/or extranodal), age (61-70 years old vs 71-80 years old), and gender. Patients are randomized to 1 of 2 treatment arms.

Arm I: Patients receive compound of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) at 500 mg once daily for 105 days.

Arm II (pharmacokinetic-based dose of compound of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId) or (XVIIa)-(XVIId)) at 500 mg once daily for 35 days. Some patients undergo blood sample collection periodically during and after treatment for pharmacokinetic studies.

After completion of study treatment, patients are followed every 3 months for 2 years, every 6 months for 3 years, and then once a year thereafter.

Primary Outcome Measures

Pharmacokinetics (in first 20 patients of each cohort with a distinct variation of the compound of Formula (A)-(C), (IA), (I), (IIa)-(IIb), (IIIa)-(IIId), (IVa)-(IVh), (Va)-(Vh), (VIa)-(VIf), (VIIa)-(VIII), (VIIIa)-(VIIII), (IXa)-(IXl), (Xa)-(Xd), (XIa)-(XId), (XIIa)-(XIId), (XIIIa)-(XIIId), (XIVa)-(XIVd), (XVa)-(XVd), (XVIa)-(XVId), or (XVIIa)-(XVIId) schedule)

Safety and treatment related deaths at 3 months after study completion

Toxicity assessed by NCI criteria, adverse events, serious adverse events, protocol adherence, and treatment-related deaths at 3 months after study completion Secondary Outcome Measures Time to treatment failure assessed at 2 years within the study and periodically thereafter Complete response rate assessed at 2 years within the study and periodically thereafter Progression rate Survival time Progression-free survival It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A compound according to Formula (B) having the structure:

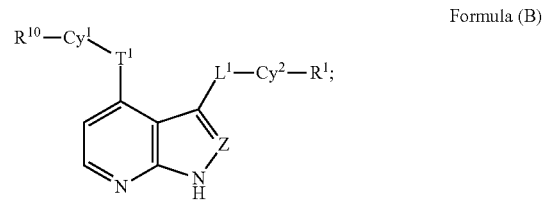

Formula (B)

or a solvate, pharmaceutically acceptable salt thereof; or a stereoisomer or an isotopic variant thereof;

wherein:

Z is =N—;

$L^1$ is —N($R^5$)—;

$T^1$ is —O—;

$Cy^1$ is substituted or unsubstituted aryl, substituted or unsubstituted heteroaryl or substituted or unsubstituted cycloalkyl;

$Cy^2$ is substituted or unsubstituted cycloalkyl, substituted or unsubstituted heterocycloalkyl, substituted or unsubstituted aryl, or substituted or unsubstituted heteroaryl;

$R^1$ is H, halo, alkyl, OH, alkoxyalkyl, hydroxyalkyl, haloalkyl, cyano, —O—$R^{1a}$, —C(O)—$R^{1a}$, —C(S)—$R^{1a}$, —C(O)—O—$R^{1b}$, —C(O)—C(O)—N($R^{1c}$)$R^{1d}$, —N($R^{1c}$)—C(O)$R^{1d}$, —C(O)—N($R^{1c}$)$R^{1d}$, —S(O)$_p$—$R^{1a}$, or —S(O)$_p$—N($R^{1c}$)$R^{1d}$;

$R^{10}$ is halo, cyano, nitro, oxo, thioxo, —$R^{10b}$—$R^{10c}$ alkoxyalkyl, hydroxyalkyl, haloalkyl, —$R^{10b}$—OR$^{10a}$, —$R^{10b}$—OC(O)$R^{10a}$, —$R^{10b}$—SR$^{10a}$, —$R^{10b}$—C(O) R$^{10a}$, —$R^{10b}$—C(S)R$^{10a}$, —$R^{10b}$—C(O)OR$^{10a}$, —$R^{10b}$—C(O)N(R$^{10a}$)R$^{10a}$, —$R^{10b}$—O—$R^{10e}$—C(O) N(R$^{10a}$)$_2$, —$R^{10b}$—OCH$_2$R$^{10a}$, —$R^{10b}$—SCH$_2$R$^{10a}$, —$R^{10b}$—N(R$^{10d}$)C(O)R$^{10c}$, —$R^{10b}$—N(R$^{10d}$)C(O) OR$^{10c}$, —$R^{10b}$—N(R$^{10d}$)C(O)N(R$^{10a}$)R$^{10a}$, —$R^{10b}$—N(R$^{10a}$)R$^{10a}$, —$R^{10b}$—N(R$^{10d}$)S(O)$_p$R$^{10a}$, —S(O)$_p$R$^{10a}$, —$R^{10b}$—S(O)$_p$OR$^{10a}$, or —$R^{10b}$—S(O)$_p$N(R$^{10a}$)R$^{10a}$;

p is 1 or 2;

each of $R^{1a}$, $R^{1b}$, $R^{1c}$, $R^{1d}$, and $R^{10a}$ is independently H, cyano, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

$R^{10b}$ is a single bond or a straight or branched alkylene or alkenylene chain;

$R^{10c}$ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

$R^{10d}$ is H, substituted or unsubstituted $C_1$-$C_6$alkyl, or substituted or unsubstituted $C_3$-$C_8$cycloalkyl;

$R^{10e}$ is a straight or branched alkylene or alkenylene chain;

$R^5$ is independently H, —C(O)—$R^{5a}$, $C_1$-$C_6$ alkyl, or $C_1$-$C_6$ heteroalkyl;

$R^{5a}$ is substituted or unsubstituted $C_1$-$C_4$alkyl, substituted or unsubstituted $C_2$-$C_4$alkenyl, or substituted or unsubstituted $C_2$-$C_4$alkynyl;

provided that $Cy^1$-$R^{10}$ together is other than substituted or unsubstituted 2-F-phenyl.

2. A compound of Formula (I) having the structure:

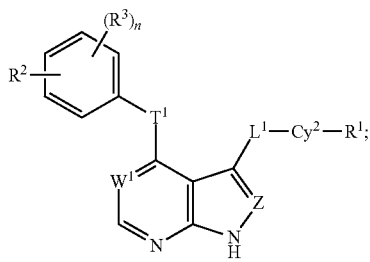

Formula (I)

or a solvate, pharmaceutically acceptable salt thereof; or a stereoisomer or an isotopic variant thereof;

wherein:

$W^1$ is =C(H);

Z is =N—;

$L^1$ is —N($R^5$)—;

$T^1$ is —O—;

$Cy^2$ is substituted or unsubstituted cycloalkyl, substituted or unsubstituted heterocycloalkyl, substituted or unsubstituted aryl, or substituted or unsubstituted heteroaryl;

$R^1$ is cyano, —C(O)—$R^{1a}$, —C(S)—$R^{1a}$, —C(O)—O—$R^{1b}$, —C(O)—N($R^{1c}$)$R^{1d}$, —S(O)$_p$—$R^{1a}$, or —S(O)$_p$—N($R^{1c}$)$R^{1d}$;

p is 1 or 2;

each of $R^{1a}$, $R^{1b}$, $R^{1c}$ and $R^{1d}$ is independently H, cyano, substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl;

$R^2$ is halogen, —CN, —NO$_2$, —OH, —OR$^{20}$, —OCF$_3$, —OCH$_2$F, —OCF$_2$H, —CF$_3$, —SR$^{21}$, —N(R$^{21}$)C(=O)R$^{23}$, —N(R$^{21}$)S(=O)$_2$R$^{23}$, —S(=O)$_2$N(R$^{21}$)(R$^{22}$), —S(=O)R$^{23}$, —S(O)$_2$R$^{23}$, —C(O)R$^{23}$, —OC(=O)R$^{23}$, —CO$_2$R$^{21}$, —N(R$^{21}$)(R$^{22}$), substituted or unsubstituted alkyl, substituted or unsubstituted heteroalkyl, substituted or unsubstituted heterocycloalkyl, substituted or unsubstituted cycloalkyl, or -L$^2$-Cy$^3$;

$L^2$ is a single bond, —CH$_2$—, —CH(OH)—, —C(O)—, —CH$_2$O—, —OCH$_2$—, —SCH$_2$, —CH$_2$S—, —C(O)N(R$^{21}$)—, —N(R$^{21}$)C(O)—, —N(R$^{21}$)—, —O—, —S—, —S(O)—, —S(O)$_2$—, —N(R$^{21}$)S(O)$_2$—, —N(R$^{21}$)S(O)—, or —S(O)$_2$N(R$^{21}$)—;

Cy$^3$ is a substituted or unsubstituted cycloalkyl, unsubstituted heterocycloalkyl, substituted or unsubstituted aryl, or a substituted or unsubstituted heteroaryl;

each $R^3$ is independently halogen, —CN, —NO$_2$, —OH, —OCF$_3$, —OCH$_2$F, —OCF$_2$H, —CF$_3$, —SR$^{21}$, —N(R$^{21}$)S(=O)$_2$R$^{23}$, —S(=O)$_2$N(R$^{21}$)(R$^{22}$), —S(O)R$^{23}$, —S(O)$_2$R$^{23}$, —C(O)R$^{23}$, —OC(=O)R$^{23}$, —CO$_2$R$^{21}$, —N(R$^{21}$)(R$^{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

each of $R^5$ is independently H, $C_1$-$C_6$ alkyl, or $C_1$-$C_6$ heteroalkyl;

$R^{20}$ is substituted or unsubstituted $C_1$-$C_6$alkyl, substituted or unsubstituted $C_1$-$C_8$heteroalkyl, substituted or unsubstituted heteroaryl, or substituted or unsubstituted aryl;

$R^{21}$ and $R^{22}$ are each independently H, substituted or unsubstituted $C_1$-$C_6$alkyl, or substituted or unsubstituted $C_3$-$C_8$cycloalkyl;

$R^{23}$ is each independently substituted or unsubstituted $C_1$-$C_6$alkyl, or substituted or unsubstituted $C_3$-$C_8$cycloalkyl; and n is 0-4.

3. The compound according to claim 1, wherein $R^5$ is $C_1$-$C_6$ alkyl.

4. The compound according to claim 1, wherein $L^1$ is —NH—.

5. The compound according to claim 1, wherein the compound is according to Formula (IIa):

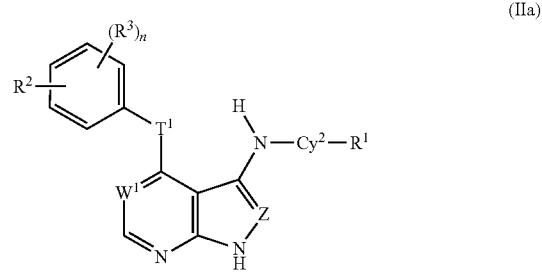

(IIa)

or a solvate, pharmaceutically acceptable salt thereof; or a stereoisomer or an isotopic variant thereof;

wherein:

$W^1$ is —C(H)—;

$R^2$ is halogen, —CN, —NO$_2$, —OH, —OR$^{20}$, —OCF$_3$, —OCH$_2$F, —OCF$_2$H, —CF$_3$, —SR$^{21}$, —N(R$^{21}$)C(=O)R$^{23}$, —N(R$^{21}$)S(=O)$_2$R$^{23}$, —S(=O)$_2$N(R$^{21}$)(R$^{22}$), —S(=O)R$^{23}$, —S(=O)$_2$R$^{23}$, —C(=O)R$^{23}$, —OC(=O)R$^{23}$, —CO$_2$R$^{21}$, —N(R$^{21}$)(R$^{22}$), substituted or unsubstituted alkyl, substituted or unsubstituted heteroalkyl, substituted or unsubstituted heterocycloalkyl, substituted or unsubstituted cycloalkyl, or -L$^2$-Cy$^3$;

$L^2$ is a single bond, —CH$_2$—, —CH(OH)—, —C(O)—, —CH$_2$O—, —OCH$_2$—, —SCH$_2$—, —CH$_2$S—, —C(O)N(R$^{21}$)—, —N(R$^{21}$)C(O)—, —N(R$^{21}$)—, —O—, —S—, —S(O)—, —S(O)$_2$—, —N(R$^{21}$)S(O)$_2$—, —N(R$^{21}$)S(O)—, or —S(O)$_2$N(R$^{21}$)—;

Cy$^3$ is a substituted or unsubstituted cycloalkyl, unsubstituted heterocycloalkyl, substituted or unsubstituted aryl, or a substituted or unsubstituted heteroaryl;

n is 0-4; and each $R^3$ is independently halogen, —CN, —NO$_2$, —OH, —OCF$_3$, —OCH$_2$F, —OCF$_2$H, —CF$_3$, —SR$^{21}$, —N(R$^{21}$)S(=O)$_2$R$^{23}$, —S(=O)$_2$N(R$^{21}$)(R$^{22}$), —S(=O)R$^{23}$, —S(=O)$_2$R$^{23}$, —C(=O)R$^{23}$, —OC(=O)R$^{23}$, —CO$_2$R$^{21}$, —N(R$^{21}$)(R$^{22}$), substituted or unsubstituted alkyl, substituted or unsubstituted alkoxy, substituted or unsubstituted heteroalkyl, substituted or unsubstituted heterocycloalkyl, or substituted or unsubstituted cycloalkyl;

$R^{20}$ is substituted or unsubstituted $C_1$-$C_6$alkyl, substituted or unsubstituted $C_1$-$C_8$heteroalkyl, substituted or unsubstituted heteroaryl, or substituted or unsubstituted aryl;

$R^{21}$ and $R^{22}$ are, each independently, H, substituted or unsubstituted $C_1$-$C_6$alkyl, or substituted or unsubstituted $C_3$-$C_8$cycloalkyl; and $R^{23}$ is, each independently, substituted or unsubstituted $C_1$-$C_6$alkyl, or substituted or unsubstituted $C_3$-$C_8$cycloalkyl.

6. The compound according to claim 5, wherein the compound is according to Formula (IVb):

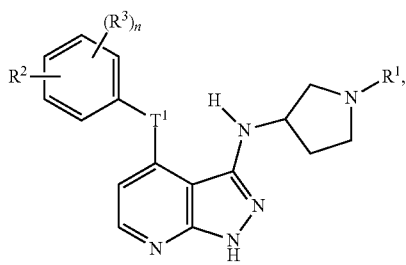

IVb or a solvate, pharmaceutically acceptable salt thereof; or a stereoisomer or an isotopic variant thereof.

7. The compound according to claim 5, wherein the compound is according to Formula (Vb):

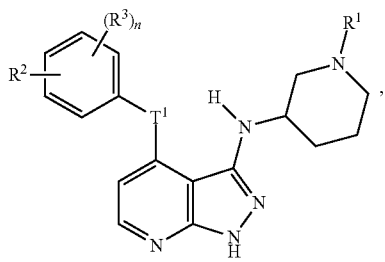

Vb or a solvate, pharmaceutically acceptable salt, thereof; or a stereoisomer or an isotopic variant thereof.

8. The compound according to claim 5, wherein the compound is according to Formula (VIa), or (VIb):

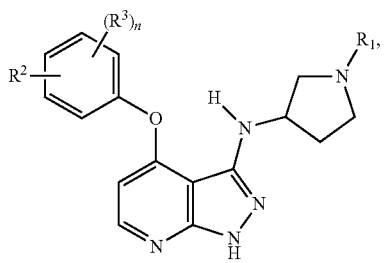

VIa

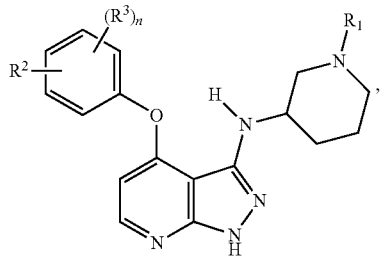

VIb or a solvate, pharmaceutically acceptable salt thereof; or a stereoisomer or an isotopic variant thereof.

9. The compound according to claim 5, wherein the compound is according to Formula (VIIa), (VIIb), (VIIc), or (VIId):

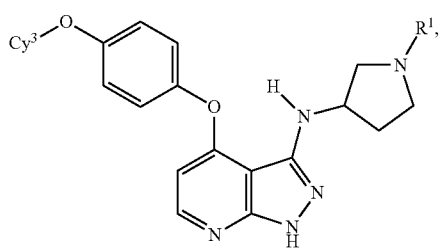

VIIa

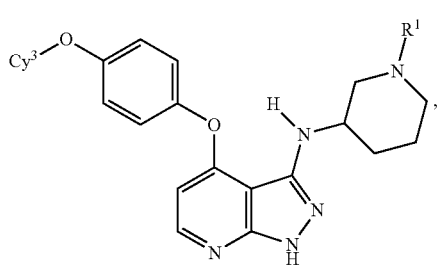

VIIb

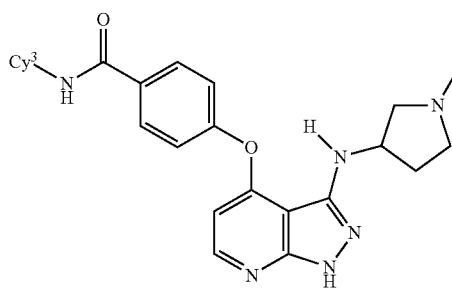

VIIc or

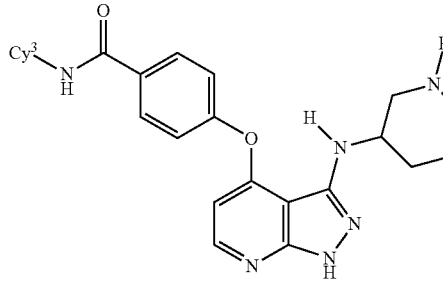

VIId or a solvate, pharmaceutically acceptable salt thereof; or a stereoisomer or an isotopic variant thereof.

10. The compound according to claim 9, wherein Cy³ is phenyl or pyridyl and is unsubstituted or substituted with halo, CN, alkyl, haloalkyl, cycloalkyl, hydroxyl, or alkoxy.

11. The compound according to claim 5, wherein the compound is according to Formula (IXa), (IXb), (IXc), or (IXd):

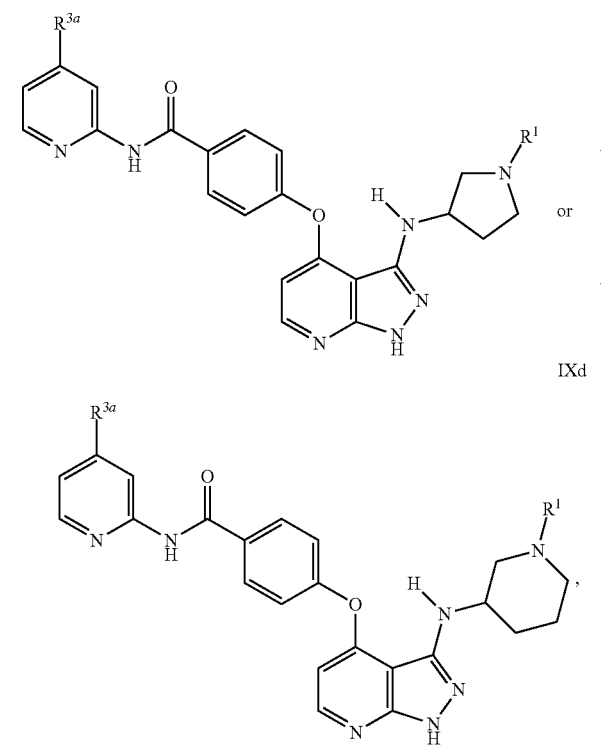

or a solvate, pharmaceutically acceptable salt thereof; or a stereoisomer or an isotopic variant thereof;

wherein $R^{3a}$ is alkyl, haloalkyl, cycloalkyl, CN, or OH.

12. The compound according to claim 1, wherein $R^{1a}$ is CN,

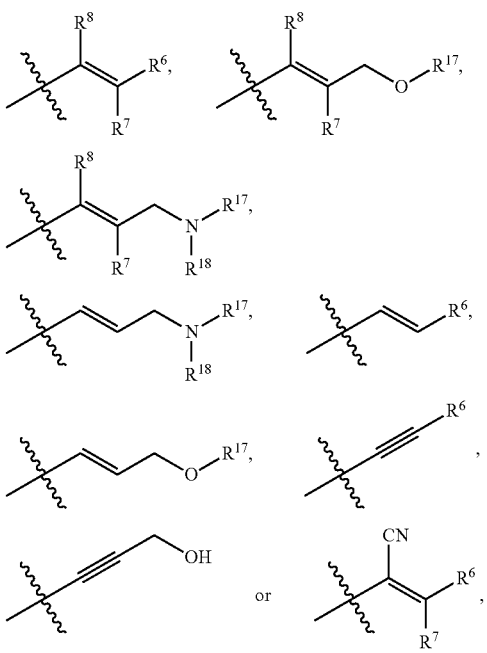

wherein $R^6$, $R^7$ and $R^8$ are each independently H, CN, halo, substituted or unsubstituted $C_1$-$C_4$alkyl, substituted or unsubstituted $C_3$-$C_8$cycloalkyl, substituted or unsubstituted 3- to 8-membered heterocycloalkyl, substituted or unsubstituted $C_6$-$C_{12}$aryl, or substituted or unsubstituted 5- to 8-membered heteroaryl; or $R^7$ and $R^8$ together form a bond;

and $R^{17}$ and $R^{18}$ are independently H, substituted or unsubstituted $C_1$-$C_3$alkyl, substituted or unsubstituted $C_3$-$C_6$cycloalkyl, substituted or unsubstituted 3- to 8-membered heterocycloalkyl, substituted or unsubstituted $C_6$-$C_{12}$aryl, or substituted or unsubstituted 3- to 8-membered heteroaryl.

13. The compound according to claim 1, wherein the compound is according to Formula (Xa), (Xb), (Xc) or (Xd):

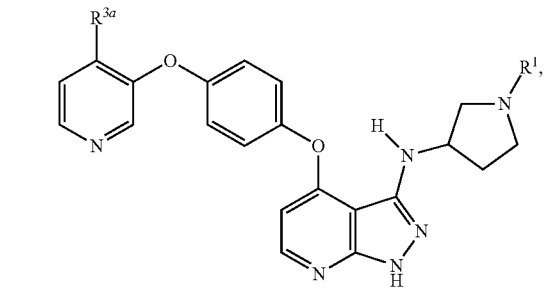

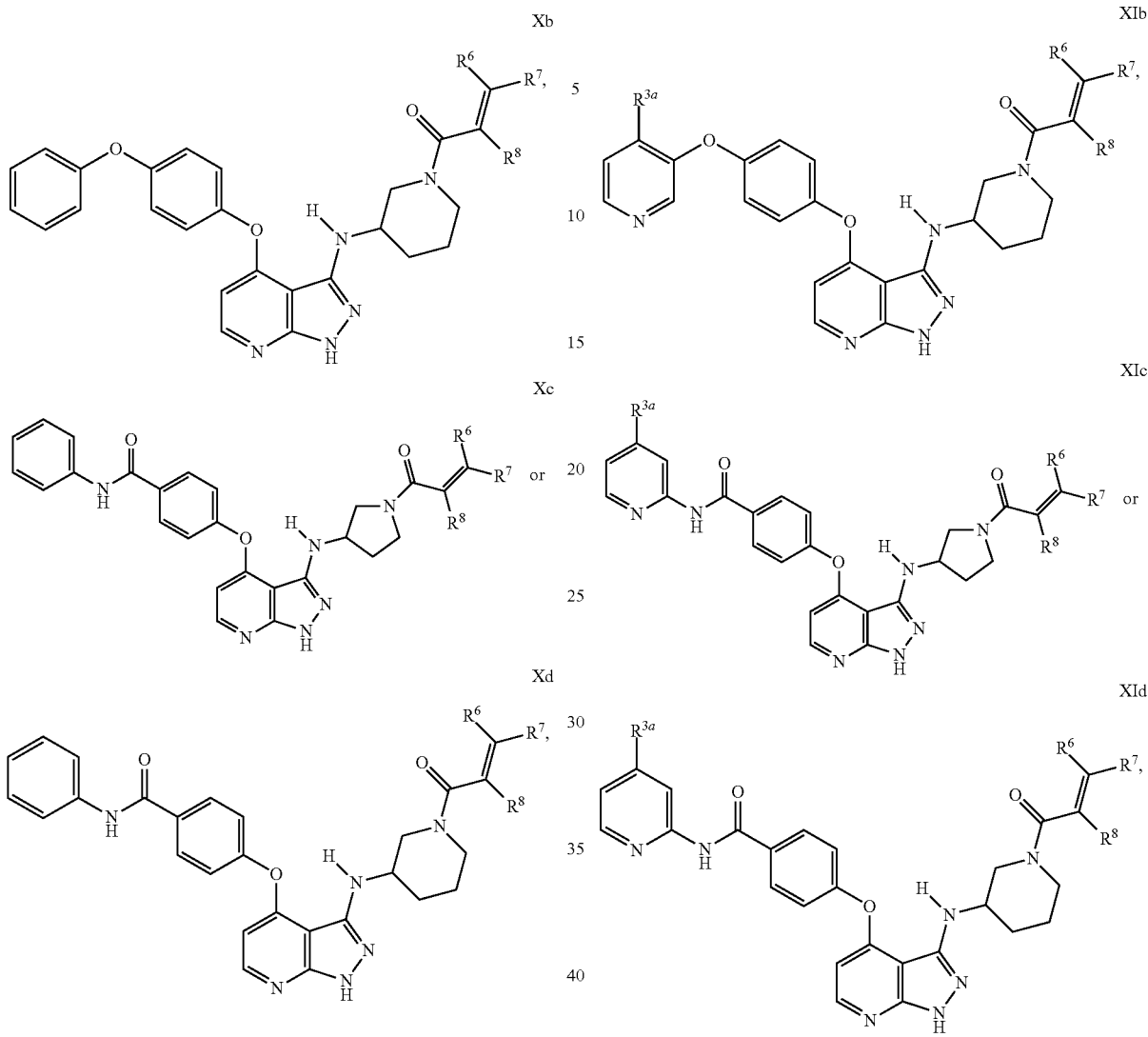

or a solvate, pharmaceutically acceptable salt thereof; or a stereoisomer or an isotopic variant thereof;

and wherein $R^6$ is H or alkyl, $R^7$ is H or substituted or unsubstituted alkyl, $R^8$ is H, CN, alkyl, or cycloalkyl; or $R^7$ and $R^8$ are joined to form a bond.

14. The compound according to claim 1, wherein the compound is according to Formula (XIa), (XIb), (XIc) or (XId):

or a solvate, pharmaceutically acceptable salt thereof; or a stereoisomer or an isotopic variant thereof;

and wherein $R^{3a}$ is alkyl, haloalkyl, cycloalkyl, CN, or OH; $R^6$ is H or alkyl, $R^7$ is H or substituted or unsubstituted alkyl, $R^8$ is H, CN, alkyl, or cycloalkyl; or $R^7$ and $R^8$ are joined to form a bond.

15. The compound according to claim 1, wherein the compound is according to Formula (XIIa), (XIIb), (XIIc) or (XIId):

-continued

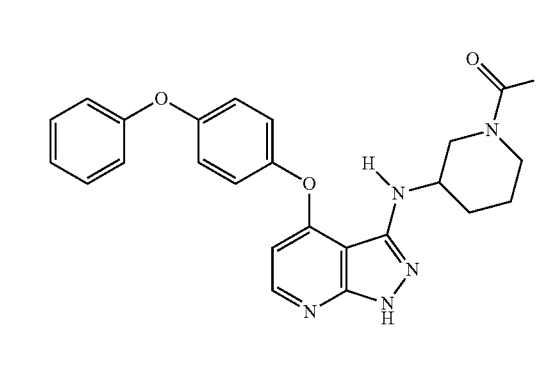
XIIb

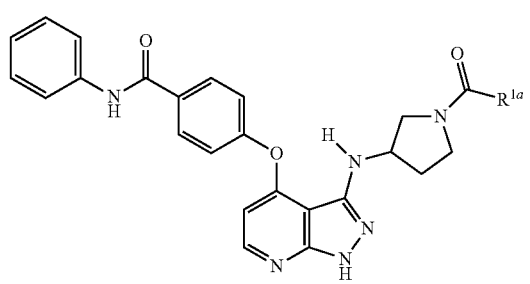
XIIc

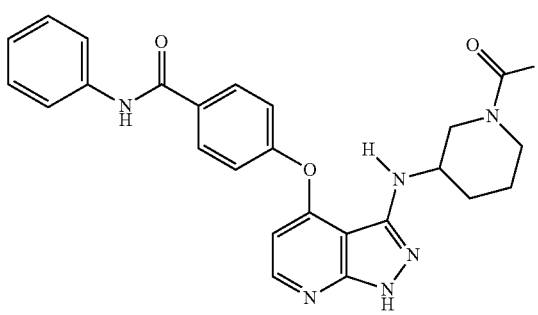
or

XIId

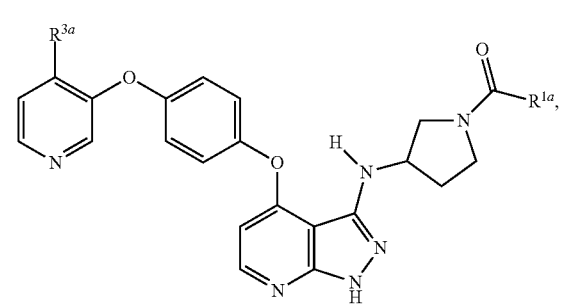

or a solvate, pharmaceutically acceptable salt thereof; or a stereoisomer or an isotopic variant thereof.

16. The compound according to claim 1, wherein the compound is according to Formula (XIIIa), (XIIIb), (XIIIc) or (XIIId):

XIIIa

-continued

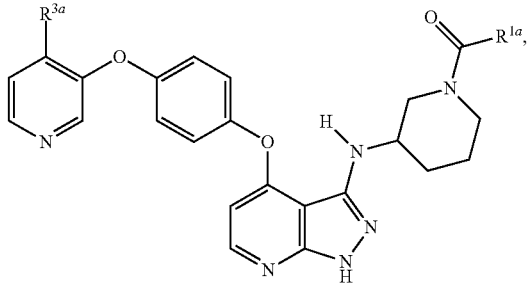
XIIIb

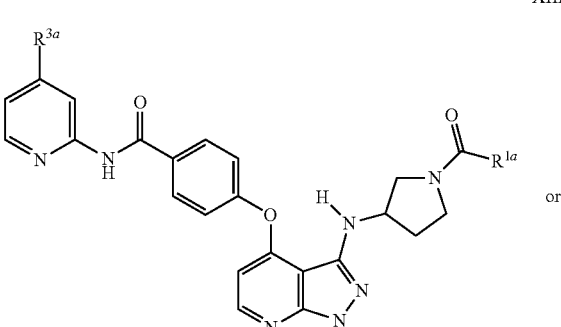
XIIIc

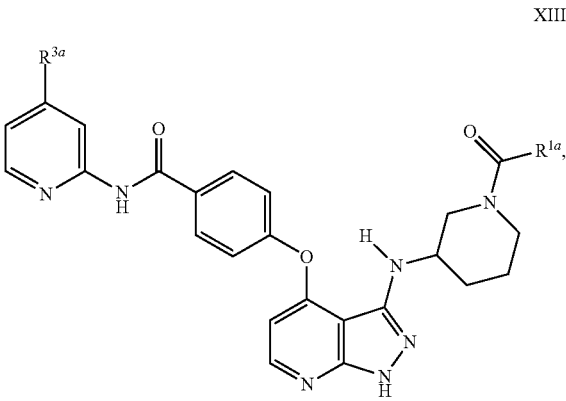
or

XIIId or a solvate, pharmaceutically acceptable salt thereof; or a stereoisomer or an isotopic variant thereof;
and wherein $R^{3a}$ is alkyl, haloalkyl, cycloalkyl, CN, or OH.

17. A compound selected from:
1-[(3R)-3-{[4-(4-chlorophenoxy)-1H-pyrazolo[3,4-b]pyridin-3-yl]amino}pyrrolidin-1-yl]prop-2-en-1-one;
1-[(3R)-3-{[4-(4-chlorophenoxy)-1H-pyrazolo[3,4-b]pyridin-3-yl](methyl)amino}pyrrolidin-1-yl]prop-2-en-1-one;
(2E)-1-[(3R)-3-{[4-(4-chlorophenoxy)-1H-pyrazolo[3,4-b]pyridin-3-yl]amino}pyrrolidin-1-yl]-4-(dimethylamino)but-2-en-1-one;
1-[(3R)-3-{[4-(4-phenoxyphenoxy)-1H-pyrazolo[3,4-b]pyridin-3-yl]amino}pyrrolidin-1-yl]prop-2-en-1-one;
(2E)-4-(dimethylamino)-1-[(3R)-3-{[4-(4-phenoxyphenoxy)-1H-pyrazolo[3,4-b]pyridin-3-yl]amino}pyrrolidin-1-yl]but-2-en-1-one;
1-[(3R)-3-{[4-(4-phenoxyphenoxy)-1H-pyrazolo[3,4-b]pyridin-3-yl]amino}piperidin-1-yl]prop-2-en-1-one;
(2E)-4-[cyclopropyl(methyl)amino]-1-[(3R)-3-{[4-(4-phenoxyphenoxy)-1H-pyrazolo[3,4-b]pyridin-3-yl]amino}piperidin-1-yl]but-2-en-1-one;

(2E)-4-[(2-methoxyethyl)(methyl)amino]-1-[(3R)-3-{[4-(4-phenoxyphenoxy)-1H-pyrazolo[3,4-b]pyridin-3-yl]amino}pyrrolidin-1-yl]but-2-en-1-one;
(2E)-4-[cyclopropyl(methyl)amino]-1-[(3R)-3-{[4-(4-phenoxyphenoxy)-1H-pyrazolo[3,4-b]pyridin-3-yl]amino}pyrrolidin-1-yl]but-2-en-1-one;
(2E)-4-[cyclopropyl(methyl)amino]-1-[(3R)-3-{[4-(3-phenoxyphenoxy)-1H-pyrazolo[3,4-b]pyridin-3-yl]amino}pyrrolidin-1-yl]but-2-en-1-one;
(2E)-4-(dimethylamino)-1-[(3R)-3-{[4-(3-phenoxyphenoxy)-1H-pyrazolo[3,4-b]pyridin-3-yl]amino}pyrrolidin-1-yl]but-2-en-1-one;
(2E)-4-(dimethylamino)-1-[(3R)-3-{[4-(3-phenoxyphenoxy)-1H-pyrazolo[3,4-b]pyridin-3-yl]amino}piperidin-1-yl]but-2-en-1-one;
1-benzyl-4-[(3-{[(3R)-1-[(2E)-4-(dimethylamino)but-2-enoyl]pyrrolidin-3-yl]amino}-1H-pyrazolo[3,4-b]pyridin-4-yl)oxy]-1,2-dihydropyridin-2-one;
(2E)-1-[(3R)-3-({4-[3-chloro-4-(1,3-oxazol-2-yl)phenoxy]-1H-pyrazolo[3,4-b]pyridin-3-yl}amino)pyrrolidin-1-yl]-4-(dimethylamino)but-2-en-1-one;
(2E)-3-cyclopropyl-2-[(E)-(3R)-3-{[4-(4-phenoxyphenoxy)-1H-pyrazolo[3,4-b]pyridin-3-yl]amino}pyrrolidine-1-carbonyl]prop-2-enenitrile;
(2E)-2-[(E)-(3R)-3-{[4-(4-phenoxyphenoxy)-1H-pyrazolo[3,4-b]pyridin-3-yl]amino}pyrrolidine-1-carbonyl]-3-phenylprop-2-enenitrile;
(2E)-4-(dimethylamino)-1-[(3R)-3-[(4-{3-[(pyrimidin-4-yl)amino]phenoxy}-1H-pyrazolo[3,4-b]pyridin-3-yl)amino]pyrrolidin-1-yl]but-2-en-1-one;
(2E)-4-(dimethylamino)-N-methyl-N-[(1s,4s)-4-{[4-(3-phenoxyphenoxy)-1H-pyrazolo[3,4-b]pyridin-3-yl]amino}cyclohexyl]but-2-enamide;
(2E)-4-[cyclopropyl(methyl)amino]-1-[(3R)-3-{[4-(4-phenoxyphenoxy)-1H-pyrazolo[3,4-b]pyridin-3-yl]oxy}pyrrolidin-1-yl]but-2-en-1-one;
(2E)-2-[(E)-(3R)-3-{[4-(4-phenoxyphenoxy)-1H-pyrazolo[3,4-b]pyridin-3-yl]amino}pyrrolidine-1-carbonyl]-3-(pyridin-2-yl)prop-2-enenitrile;
(2E)-3-cyclobutyl-2-[(E)-(3R)-3-{[4-(4-phenoxyphenoxy)-1H-pyrazolo[3,4-b]pyridin-3-yl]amino}pyrrolidine-1-carbonyl]prop-2-enenitrile;
(2E)-3-(1H-imidazol-2-yl)-2-[(E)-(3R)-3-{[4-(4-phenoxyphenoxy)-1H-pyrazolo[3,4-b]pyridin-3-yl]amino}pyrrolidine-1-carbonyl]prop-2-enenitrile;
4-{[4-(4-phenoxyphenoxy)-1H-pyrazolo[3,4-b]pyridin-3-yl]amino}pyridine-2-carbonitrile;
(2E)-4-(dimethylamino)-1-{3-[4-(4-phenoxyphenoxy)-1H-pyrazolo[3,4-b]pyridin-3-yl]piperidin-1-yl}but-2-en-1-one;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(trifluoromethyl)pyridin-2-yl]benzamide;
2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzonitrile;
2-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-5-phenoxybenzonitrile;
(2E)-4-[cyclopropyl(methyl)amino]-N-methyl-N-(3-{[4-(4-phenoxyphenoxy)-1H-pyrazolo[3,4-b]pyridin-3-yl]amino}phenyl)but-2-enamide;
(2E)-4-[cyclopropyl(methyl)amino]-1-[(3R)-3-({4-[4-(1H-1,2,3-triazol-5-ylmethoxy)phenoxy]-1H-pyrazolo[3,4-b]pyridin-3-yl}amino)pyrrolidin-1-yl]but-2-en-1-one;
2-[(3-{[(3R)-1-[(2E)-4-(dimethylamino)but-2-enoyl]pyrrolidin-3-yl]amino}-1H-pyrazolo[3,4-b]pyridin-4-yl)oxy]-5-phenoxybenzamide;
3-oxo-3-[(3R)-3-{[4-(4-phenoxyphenoxy)-1H-pyrazolo[3,4-b]pyridin-3-yl]amino}pyrrolidin-1-yl]propanenitrile;
(3R)-1-methyl-N-[4-(4-phenoxyphenoxy)-1H-pyrazolo[3,4-b]pyridin-3-yl]pyrrolidin-3-amine;
1-[(3R)-3-{[4-(4-phenoxyphenoxy)-1H-pyrazolo[3,4-b]pyridin-3-yl]amino}pyrrolidin-1-yl]ethan-1-one;
N-(oxan-4-yl)-4-(4-phenoxyphenoxy)-1H-pyrazolo[3,4-b]pyridin-3-amine;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyridin-2-yl)benzamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-propylpyridin-2-yl)benzamide;
(2E)-4-[cyclopropyl(methyl)amino]-N-(2-{[4-(4-phenoxyphenoxy)-1H-pyrazolo[3,4-b]pyridin-3-yl]amino}phenyl)but-2-enamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-methoxypyridin-2-yl)benzamide;
4-{[4-(4-phenoxyphenoxy)-1H-pyrazolo[3,4-b]pyridin-3-yl]amino}pyridine-2-carboxamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(4-cyclopropylpyridin-2-yl)benzamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(propan-2-yl)pyridin-2-yl]benzamide;
N-(4-cyanopyridin-2-yl)-4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]benzamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyrimidin-2-yl)benzamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(pyrimidin-4-yl)benzamide;
N-(cyanomethyl)-4-{[4-(4-phenoxyphenoxy)-1H-pyrazolo[3,4-b]pyridin-3-yl]amino}pyridine-2-carboxamide;
4-[(3-{[(3R)-1-propanoylpyrrolidin-3-yl]amino}-1H-pyrazolo[3,4-b]pyridin-4-yl)oxy]-N-[4-(trifluoromethyl)pyridin-2-yl]benzamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-(1H-imidazol-2-yl)benzamide;
4-[(3-{[(3R)-1-[(2E)-4-[cyclopropyl(methyl)amino]but-2-enoyl]pyrrolidin-3-yl]amino}-1H-pyrazolo[3,4-b]pyridin-4-yl)oxy]-N-[4-(dimethylamino)pyridin-2-yl]benzamide;
N-(1H-1,3-benzodiazol-2-yl)-4-[(3-{[(3R)-1-propanoylpyrrolidin-3-yl]amino}-1H-pyrazolo[3,4-b]pyridin-4-yl)oxy]benzamide;
N-(5-methyl-1,3-thiazol-2-yl)-4-[(3-{[(3R)-1-propanoylpyrrolidin-3-yl]amino}-1H-pyrazolo[3,4-b]pyridin-4-yl)oxy]benzamide;
N-(1-methyl-1H-imidazol-2-yl)-4-[(3-{[(3R)-1-propanoylpyrrolidin-3-yl]amino}-1H-pyrazolo[3,4-b]pyridin-4-yl)oxy]benzamide;

N-(6-oxo-1,6-dihydropyrimidin-2-yl)-4-[(3-{[(3R)-1-propanoylpyrrolidin-3-yl]amino}-1H-pyrazolo[3,4-b]pyridin-4-yl)oxy]benzamide;

N-(5-methyl-4H-1,2,4-triazol-3-yl)-4-[(3-{[(3R)-1-propanoylpyrrolidin-3-yl]amino}-1H-pyrazolo[3,4-b]pyridin-4-yl)oxy]benzamide;

(R,E)-N-(4-cyclopropoxypyridin-2-yl)-4-(3-(1-(4-(cyclopropyl(methyl)amino)but-2-enoyl)pyrrolidin-3-ylamino)-1H-pyrazolo[3,4-b]pyridin-4-yloxy)benzamide;

N-(4-cyanopyridin-2-yl)-4-({3-[(oxan-4-yl)amino]-1H-pyrazolo[3,4-b]pyridin-4-yl}oxy)benzamide;

ethyl (3R)-3-[(4-{4-[(4-cyanopyridin-2-yl)carbamoyl]phenoxy}-1H-pyrazolo[3,4-b]pyridin-3-yl)amino]piperidine-1-carboxylate;

(3R)-3-[(4-{4-[(4-cyanopyridin-2-yl)carbamoyl]phenoxy}-1H-pyrazolo[3,4-b]pyridin-3-yl)amino]-N-ethylpiperidine-1-carboxamide;

N-(4-cyanopyridin-2-yl)-4-[(3-{[(3R)-1-(3-methoxypropanoyl)piperidin-3-yl]amino}-1H-pyrazolo[3,4-b]pyridin-4-yl)oxy]benzamide;

N-(4-cyanopyridin-2-yl)-4-[(3-{[(3R)-1-cyclopropanecarbonylpiperidin-3-yl]amino}-1H-pyrazolo[3,4-b]pyridin-4-yl)oxy]benzamide;

N-(4-cyanopyridin-2-yl)-4-[(3-{[(1R,4R)-4-hydroxycyclohexyl]amino}-1H-pyrazolo[3,4-b]pyridin-4-yl)oxy]benzamide;

N-(4-cyanopyridin-2-yl)-4-[(3-{[(3R)-1-(3-methyloxetane-3-carbonyl)piperidin-3-yl]amino}-1H-pyrazolo[3,4-b]pyridin-4-yl)oxy]benzamide;

4-[(3-{[(3R)-1-(3-methyloxetane-3-carbonyl)piperidin-3-yl]amino}-1H-pyrazolo[3,4-b]pyridin-4-yl)oxy]-N-[4-(trifluoromethyl)pyridin-2-yl]benzamide;

N-(4-cyanopyridin-2-yl)-4-[(3-{[(1S,4S)-4-methoxycyclohexyl]amino}-1H-pyrazolo[3,4-b]pyridin-4-yl)oxy]benzamide;

4-[(3-{[(3R)-1-(3-methyloxetane-3-carbonyl)piperidin-3-yl]amino}-1H-pyrazolo[3,4-b]pyridin-4-yl)oxy]-N-(4-methylpyridin-2-yl)benzamide;

4-[(3-{[(3R)-1-(4-methyloxane-4-carbonyl)piperidin-3-yl]amino}-1H-pyrazolo[3,4-b]pyridin-4-yl)oxy]-N-(4-methylpyridin-2-yl)benzamide;

4-[(3-{[(3R)-1-(1-methylcyclobutanecarbonyl)piperidin-3-yl]amino}-1H-pyrazolo[3,4-b]pyridin-4-yl)oxy]-N-(4-methylpyridin-2-yl)benzamide;

4-[(3-{[(3R)-1-(3-methyloxolane-3-carbonyl)piperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(oxetane-3-carbonyl)piperidin-3-yl]amino}-1H-pyrazolo[3,4-b]pyridin-4-yl)oxy]benzamide;

N-(4-methylpyridin-2-yl)-4-[(3-{[(3R)-1-(morpholine-4-carbonyl)piperidin-3-yl]amino}-1H-pyrazolo[3,4-b]pyridin-4-yl)oxy]benzamide;

4-[(3-{[(3R)-1-(1-methylpiperidine-4-carbonyl)piperidin-3-yl]amino}-1H-pyrazolo[3,4-b]pyridin-4-yl)oxy]-N-(4-methylpyridin-2-yl)benzamide;

phenyl (3R)-3-[(4-{4-[(4-methylpyridin-2-yl)carbamoyl]phenoxy}-1H-pyrazolo[3,4-b]pyridin-3-yl)amino]piperidine-1-carboxylate;

N-(4-methylpyridin-2-yl)-4-[(3-{[(3R)-1-[(2S)-oxolane-2-carbonyl]piperidin-3-yl]amino}-1H-pyrazolo[3,4-b]pyridin-4-yl)oxy]benzamide;

4-[(3-{[(3R)-1-[5-(dimethylamino)pentanoyl]piperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(piperidine-4-carbonyl)piperidin-3-yl]amino}-1H-pyrazolo[3,4-b]pyridin-4-yl)oxy]benzamide;

4-[(3-{[(3R)-1-[(methylcarbamoyl)carbonyl]piperidin-3-yl]amino}-1H-pyrazolo[3,4-b]pyridin-4-yl)oxy]-N-(4-methylpyridin-2-yl)benzamide;

4-[(3-{[(3R)-1-[(dimethylcarbamoyl)carbonyl]piperidin-3-yl]amino}-1H-pyrazolo[3,4-b]pyridin-4-yl)oxy]-N-(4-methylpyridin-2-yl)benzamide;

4-[(3-{[(3R)-1-[1-(methoxymethyl)cyclobutanecarbonyl]piperidin-3-yl]amino}-1H-pyrazolo[3,4-b]pyridin-4-yl)oxy]-N-(4-methylpyridin-2-yl)benzamide;

4-[(3-{[(3R)-1-cyclopropanecarbonylpiperidin-3-yl]amino}-1H-pyrazolo[3,4-b]pyridin-4-yl)oxy]-N-(4-methylpyridin-2-yl)benzamide;

4-[(3-{[(3R)-1-(1-cyanocyclopropanecarbonyl)piperidin-3-yl]amino}-1H-pyrazolo[3,4-b]pyridin-4-yl)oxy]-N-(4-methylpyridin-2-yl)benzamide;

4-[(3-{[(3R)-1-(2-cyano-2,2-dimethylacetyl)piperidin-3-yl]amino}-1H-pyrazolo[3,4-b]pyridin-4-yl)oxy]-N-(4-methylpyridin-2-yl)benzamide;

tert-butyl 4-methyl-4-[(3R)-3-[(4-{4-[(4-methylpyridin-2-yl)carbamoyl]phenoxy}-1H-pyrazolo[3,4-b]pyridin-3-yl)amino]piperidine-1-carbonyl]piperidine-1-carboxylate;

4-[(3-{[(3R)-1-(4-methylpiperidine-4-carbonyl)piperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(oxane-4-carbonyl)piperidin-3-yl]amino}-1H-pyrazolo[3,4-b]pyridin-4-yl)oxy]benzamide;

(3R)—N,N-dimethyl-3-[(4-{4-[(4-methylpyridin-2-yl)carbamoyl]phenoxy}-1H-pyrazolo[3,4-b]pyridin-3-yl)amino]piperidine-1-carboxamide;

4-[(3-{[(3R)-1-cyclopentanecarbonylpiperidin-3-yl]amino}-1H-pyrazolo[3,4-b]pyridin-4-yl)oxy]-N-(4-methylpyridin-2-yl)benzamide;

ethyl (3R)-3-[(4-{4-[(4-methylpyridin-2-yl)carbamoyl]phenoxy}-1H-pyrazolo[3,4-b]pyridin-3-yl)amino]piperidine-1-carboxylate;

4-[(3-{[(3R)-1-benzoylpiperidin-3-yl]amino}-1H-pyrazolo[3,4-b]pyridin-4-yl)oxy]-N-(4-methylpyridin-2-yl)benzamide;

N-(4-methylpyridin-2-yl)-4-[(3-{[(3R)-1-(pyridine-2-carbonyl)piperidin-3-yl]amino}-1H-pyrazolo[3,4-b]pyridin-4-yl)oxy]benzamide;

4-[(3-{[(3R)-1-(3-methyloxetane-3-carbonyl)piperidin-3-yl]amino}-1H-pyrazolo[3,4-b]pyridin-4-yl)oxy]-N-(pyridin-2-yl)benzamide;

4-[(3-{[(3R)-1-(4-methyloxane-4-carbonyl)piperidin-3-yl]amino}-1H-pyrazolo[3,4-b]pyridin-4-yl)oxy]-N-(pyridin-2-yl)benzamide;

4-[(3-{[(3R)-1-(3-methyloxetane-3-carbonyl)piperidin-3-yl]amino}-1H-pyrazolo[3,4-b]pyridin-4-yl)oxy]-N-(6-methylpyridin-2-yl)benzamide;

4-[(3-{[(3R)-1-(4-methyloxane-4-carbonyl)piperidin-3-yl]amino}-1H-pyrazolo[3,4-b]pyridin-4-yl)oxy]-N-(6-methylpyridin-2-yl)benzamide;

N-(4-methylpyridin-2-yl)-4-[(3-{[(3R)-1-[(3R)-oxolane-3-carbonyl]piperidin-3-yl]amino}-1H-pyrazolo[3,4-b]pyridin-4-yl)oxy]benzamide;

N-(4-methylpyridin-2-yl)-4-[(3-{[(3R)-1-[(3S)-oxolane-3-carbonyl]piperidin-3-yl]amino}-1H-pyrazolo[3,4-b]pyridin-4-yl)oxy]benzamide;

N-(4-methylpyridin-2-yl)-4-[(3-{[(3R)-1-[(2S)-oxolane-2-carbonyl]piperidin-3-yl]amino}-1H-pyrazolo[3,4-b]pyridin-4-yl)oxy]benzamide;

4-[(3-{[(3R)-1-[3-(dimethylamino)propanoyl]piperidin-3-yl]amino}-1H-pyrazolo[3,4-b]pyridin-4-yl)oxy]-N-(4-methylpyridin-2-yl)benzamide;

4-[(3-{[(3R)-1-(3-methoxypropanoyl)piperidin-3-yl]amino}-1H-pyrazolo[3,4-b]pyridin-4-yl)oxy]-N-(4-methylpyridin-2-yl)benzamide;

4-[(3-{[(3R)-1-(1-methylcyclopropanecarbonyl)piperidin-3-yl]amino}-1H-pyrazolo[3,4-b]pyridin-4-yl)oxy]-N-(4-methylpyridin-2-yl)benzamide;

N-[3-methyl-4-(propan-2-yl)phenyl]-3-[(3-{[(3R)-1-(prop-2-enoyl)pyrrolidin-3-yl]amino}-1H-pyrazolo[3,4-b]pyridin-4-yl)oxy]benzamide;

3-[(3-{[(3R)-1-acetylpyrrolidin-3-yl]amino}-1H-pyrazolo[3,4-b]pyridin-4-yl)oxy]-N-[3-methyl-4-(propan-2-yl)phenyl]benzamide;

3-[(3-{[(3S)-1-acetylpyrrolidin-3-yl]amino}-1H-pyrazolo[3,4-b]pyridin-4-yl)oxy]-N-[3-methyl-4-(propan-2-yl)phenyl]benzamide;

3-[(3-{[(3S)-1-cyclopropanecarbonylpyrrolidin-3-yl]amino}-1H-pyrazolo[3,4-b]pyridin-4-yl)oxy]-N-[3-methyl-4-(propan-2-yl)phenyl]benzamide;

N-[3-methyl-4-(propan-2-yl)phenyl]-3-[(3-{[(3S)-1-(prop-2-enoyl)pyrrolidin-3-yl]amino}-1H-pyrazolo[3,4-b]pyridin-4-yl)oxy]benzamide;

3-[(3-{[(3S)-1-(4-fluorobenzoyl)pyrrolidin-3-yl]amino}-1H-pyrazolo[3,4-b]pyridin-4-yl)oxy]-N-[3-methyl-4-(propan-2-yl)phenyl]benzamide;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-{5-methyl-4H,5H,6H,7H-[1,3]thiazolo[4,5-c]pyridin-2-yl}benzamide;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-[3-(trifluoromethyl)phenyl]benzamide;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(4-methyl-1,3-thiazol-2-yl)benzamide;

N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide;

4-[(3-{[(3R)-1-(but-2-ynoyl)piperidin-3-yl]amino}-1H-pyrazolo[3,4-b]pyridin-4-yl)oxy]-N-(5-methyl-1,3-thiazol-2-yl)benzamide;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3-thiazol-2-yl)benzamide;

N-(4-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide;

(1r,4r)-N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]cyclohexane-1-carboxamide;

N-{5-methyl-4H,5H,6H,7H-[1,3]thiazolo[4,5-c]pyridin-2-yl}-4-[(3-{[(3R)-1-(prop-2-enoyl)piperidin-3-yl]amino}-1H-pyrazolo[3,4-b]pyridin-4-yl)oxy]benzamide;

N-(dimethyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide;

1-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-3-(propan-2-yl)urea;

1-[(3R)-3-({4-[3-(5-methyl-1,3-thiazol-2-yl)phenoxy]-1H-pyrazolo[3,4-b]pyridin-3-yl}amino)piperidin-1-yl]prop-2-en-1-one;

N-(5-methyl-1,3-thiazol-2-yl)-3-[(3-{[(3R)-1-(prop-2-enoyl)piperidin-3-yl]amino}-1H-pyrazolo[3,4-b]pyridin-4-yl)oxy]benzamide;

(2E)-4-[cyclopropyl(methyl)amino]-1-[(3R)-3-({4-[3-(5-methyl-1,3-thiazol-2-yl)phenoxy]-1H-pyrazolo[3,4-b]pyridin-3-yl}amino)piperidin-1-yl]but-2-en-1-one;

1-[(3R)-3-{[4-(2-methyl-4-phenoxyphenoxy)-1H-pyrazolo[3,4-b]pyridin-3-yl]amino}piperidin-1-yl]prop-2-en-1-one;

(1r,4r)-4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3-thiazol-2-yl)cyclohexane-1-carboxamide;

1-[(3R)-3-{[4-(3-methyl-4-phenoxyphenoxy)-1H-pyrazolo[3,4-b]pyridin-3-yl]amino}piperidin-1-yl]prop-2-en-1-one;

1-[(3R)-3-[(4-{4-[4-(trifluoromethyl)-1H-imidazol-2-yl]phenoxy}-1H-pyrazolo[3,4-b]pyridin-3-yl)amino]piperidin-1-yl]prop-2-en-1-one;

1-[(3S)-3-[(4-{4-[4-(trifluoromethyl)pyridin-2-yl]phenoxy}-1H-pyrazolo[3,4-b]pyridin-3-yl)amino]piperidin-1-yl]prop-2-en-1-one;

(2E)-4-[cyclopropyl(methyl)amino]-1-[(3R)-3-{[4-(3-methyl-4-phenoxyphenoxy)-1H-pyrazolo[3,4-b]pyridin-3-yl]amino}piperidin-1-yl]but-2-en-1-one;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(4-methyl-1H-imidazol-2-yl)benzamide;

1-[(3R)-3-({4-[4-(5-methyl-1,3-thiazol-2-yl)phenoxy]-1H-pyrazolo[3,4-b]pyridin-3-yl}amino)piperidin-1-yl]prop-2-en-1-one;

N-(1,5-dimethyl-1H-pyrazol-3-yl)-4-[(3-{[(3R)-1-(prop-2-enoyl)piperidin-3-yl]amino}-1H-pyrazolo[3,4-b]pyridin-4-yl)oxy]benzamide;

1-[(3R)-3-[(4-{4-[3-(trifluoromethyl)piperidine-1-carbonyl]phenoxy}-1H-pyrazolo[3,4-b]pyridin-3-yl)amino]piperidin-1-yl]prop-2-en-1-one;

4-[(3-{[(3R)-1-[4-(dimethylamino)butanoyl]piperidin-3-yl]amino}-1H-pyrazolo[3,4-b]pyridin-4-yl)oxy]-N-[4-(trifluoromethyl)pyridin-2-yl]benzamide;

N-(1,3-benzothiazol-2-yl)-4-[(3-{[(3S)-1-(prop-2-enoyl)piperidin-3-yl]amino}-1H-pyrazolo[3,4-b]pyridin-4-yl)oxy]benzamide;

1-[(3R)-3-[(4-{4-[3-(trifluoromethyl)piperidine-1-carbonyl]phenoxy}-1H-pyrazolo[3,4-b]pyridin-3-yl)amino]piperidin-1-yl]but-2-yn-1-one;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(dimethyl-1,3-thiazol-2-yl)benzamide;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(1,5-dimethyl-1H-pyrazol-3-yl)benzamide;

N-(5-cyano-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide;

N-(1,3-benzothiazol-2-yl)-4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]benzamide;

4-[(3-{[(3R)-1-(but-2-ynoyl)piperidin-3-yl]amino}-1H-pyrazolo[3,4-b]pyridin-4-yl)oxy]-N-(5-cyano-1,3-thiazol-2-yl)benzamide;

(2E)-4-[cyclopropyl(methyl)amino]-1-[(3R)-3-{[4-(2-methyl-4-phenoxyphenoxy)-1H-pyrazolo[3,4-b]pyridin-3-yl]amino}piperidin-1-yl]but-2-en-1-one;

1-[(3R)-3-{[4-(4-{[1,3]oxazolo[4,5-b]pyridin-2-yl}phenoxy)-1H-pyrazolo[3,4-b]pyridin-3-yl]amino}piperidin-1-yl]but-2-yn-1-one;

4-[(3-{[(3R)-1-(prop-2-enoyl)pyrrolidin-3-yl]amino}-1H-pyrazolo[3,4-b]pyridin-4-yl)oxy]-N-[4-(trifluoromethyl)pyridin-2-yl]benzamide;

N-(1,3-benzothiazol-2-yl)-4-[(3-{[(3R)-1-[4-(dimethylamino)butanoyl]piperidin-3-yl]amino}-1H-pyrazolo[3,4-b]pyridin-4-yl)oxy]benzamide;

4-[(3-{[(3R)-1-cyclopropanecarbonylpiperidin-3-yl]amino}-1H-pyrazolo[3,4-b]pyridin-4-yl)oxy]-N-[4-(trifluoromethyl)pyridin-2-yl]benzamide;

4-[(3-{[(3R)-1-(but-2-ynoyl)pyrrolidin-3-yl]amino}-1H-pyrazolo[3,4-b]pyridin-4-yl)oxy]-N-[4-(trifluoromethyl)pyridin-2-yl]benzamide;

4-[(3-{[(3R)-1-(but-2-ynoyl)piperidin-3-yl]amino}-1H-pyrazolo[3,4-b]pyridin-4-yl)oxy]-N-(dimethyl-1,3-thiazol-2-yl)benzamide;

(3R)-3-[(4-{4-[(1,3-benzothiazol-2-yl)carbamoyl]phenoxy}-1H-pyrazolo[3,4-b]pyridin-3-yl)amino]-N-ethylpiperidine-1-carboxamide;

4-[(3-{[(3R)-1-(but-2-ynoyl)piperidin-3-yl]amino}-1H-pyrazolo[3,4-b]pyridin-4-yl)oxy]-N-(5-ethyl-1,3-thiazol-2-yl)benzamide;

N-(5-methyl-1,2-oxazol-3-yl)-4-[(3-{[(3R)-1-(prop-2-enoyl)piperidin-3-yl]amino}-1H-pyrazolo[3,4-b]pyridin-4-yl)oxy]benzamide;

N-(5-ethyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide;

4-[(3-{[(3R)-1-(but-2-ynoyl)piperidin-3-yl]amino}-1H-pyrazolo[3,4-b]pyridin-4-yl)oxy]-N-(5-methyl-1,3,4-thiadiazol-2-yl)benzamide;

4-[(3-{[(3R)-1-(but-2-ynoyl)pyrrolidin-3-yl]amino}-1H-pyrazolo[3,4-b]pyridin-4-yl)oxy]-N-(5-methyl-1,3-thiazol-2-yl)benzamide;

(3R)—N-ethyl-3-({4-[4-(7-methyl-1,3-benzoxazol-2-yl)phenoxy]-1H-pyrazolo[3,4-b]pyridin-3-yl}amino)piperidine-1-carboxamide;

N-(1,3-benzothiazol-2-yl)-4-[(3-{[(3R)-1-(but-2-ynoyl)piperidin-3-yl]amino}-1H-pyrazolo[3,4-b]pyridin-4-yl)oxy]benzamide;

(3R)—N-{4-[4-(7-methyl-1,3-benzoxazol-2-yl)phenoxy]-1H-pyrazolo[3,4-b]pyridin-3-yl}-1-(1-methylpiperidine-4-carbonyl)piperidin-3-amine;

4-[(3-{[(3R)-1-(but-2-ynoyl)piperidin-3-yl]amino}-1H-pyrazolo[3,4-b]pyridin-4-yl)oxy]-N-(1,5-dimethyl-1H-pyrazol-3-yl)benzamide;

N-(5-methyl-1,3,4-thiadiazol-2-yl)-4-[(3-{[(3R)-1-(prop-2-enoyl)piperidin-3-yl]amino}-1H-pyrazolo[3,4-b]pyridin-4-yl)oxy]benzamide;

(3R)—N-ethyl-3-{[4-(4-{[4-(trifluoromethyl)pyridin-2-yl]carbamoyl}phenoxy)-1H-pyrazolo[3,4-b]pyridin-3-yl]amino}pyrrolidine-1-carboxamide;

N-ethyl-3-[(4-{4-[(5-methyl-1,3-thiazol-2-yl)carbamoyl]phenoxy}-1H-pyrazolo[3,4-b]pyridin-3-yl)amino]pyrrolidine-1-carboxamide;

N-(5-methyl-1,3-thiazol-2-yl)-4-({3-[(1-propanoylpyrrolidin-3-yl)amino]-1H-pyrazolo[3,4-b]pyridin-4-yl}oxy)benzamide;

3-[(3-{[(3R)-1-(prop-2-enoyl)piperidin-3-yl]amino}-1H-pyrazolo[3,4-b]pyridin-4-yl)oxy]-N-[4-(trifluoromethyl)pyridin-2-yl]benzamide;

1-[(3R)-3-({4-[4-(1,3-benzothiazol-2-yl)phenoxy]-1H-pyrazolo[3,4-b]pyridin-3-yl}amino)piperidin-1-yl]prop-2-en-1-one;

1-[(3R)-3-({4-[4-(1,3-benzoxazol-2-yl)phenoxy]-1H-pyrazolo[3,4-b]pyridin-3-yl}amino)piperidin-1-yl]prop-2-en-1-one;

1-[(3S)-3-[(4-{4-[5-(trifluoromethyl)pyridin-2-yl]phenoxy}-1H-pyrazolo[3,4-b]pyridin-3-yl)amino]piperidin-1-yl]prop-2-en-1-one;

4-[(3-{[(3R)-1-[(2E)-4-(dimethylamino)but-2-enoyl]piperidin-3-yl]amino}-1H-pyrazolo[3,4-b]pyridin-4-yl)oxy]-N-(5-methyl-1,3-thiazol-2-yl)benzamide;

4-[(3{[1-(1-methylpiperidine-4-carbonyl)pyrrolidin-3-yl]amino}-1H-pyrazolo[3,4-b]pyridin-4-yl)oxy]-N-[4-(trifluoromethyl)pyridin-2-yl]benzamide;

4-[(3-{[(3R)-1-cyclopropanecarbonylpyrrolidin-3-yl]amino}-1H-pyrazolo[3,4-b]pyridin-4-yl)oxy]-N-(5-methyl-1,3-thiazol-2-yl)benzamide;

1-{4-[(3-{[(3R)-1-(prop-2-enoyl)piperidin-3-yl]amino}-1H-pyrazolo[3,4-b]pyridin-4-yl)oxy]phenyl}-3-[4-(trifluoromethyl)pyridin-2-yl]urea;

4-[(3-{[(3R)-1-[4-(dimethylamino)butanoyl]pyrrolidin-3-yl]amino}-1H-pyrazolo[3,4-b]pyridin-4-yl)oxy]-N-(5-methyl-1,3-thiazol-2-yl)benzamide;

4-[(3-{[(3R)-1-(prop-2-enoyl)piperidin-3-yl]amino}-1H-pyrazolo[3,4-b]pyridin-4-yl)oxy]-N-[4-(trifluoromethyl)pyridin-2-yl]benzamide;

4-[(3-{[(3R)-1-(1-methylpiperidine-4-carbonyl)piperidin-3-yl]amino}-1H-pyrazolo[3,4-b]pyridin-4-yl)oxy]-N-[4-(trifluoromethyl)pyridin-2-yl]benzamide;

4-[(3-{[(3R)-1-(but-2-ynoyl)piperidin-3-yl]amino}-1H-pyrazolo[3,4-b]pyridin-4-yl)oxy]-N-[4-(trifluoromethyl)pyridin-2-yl]benzamide;

1-[(3R)-3-[(4-{4-[5-(trifluoromethyl)pyridin-2-yl]phenoxy}-1H-pyrazolo[3,4-b]pyridin-3-yl)amino]piperidin-1-yl]but-2-yn-1-one;

(3R)—N-ethyl-3-{[4-(4-{[4-(trifluoromethyl)pyridin-2-yl]carbamoyl}phenoxy)-1H-pyrazolo[3,4-b]pyridin-3-yl]amino}piperidine-1-carboxamide;

4-[(3-{[(3R)-1-(prop-2-enoyl)piperidin-3-yl]amino}-1H-pyrazolo[3,4-b]pyridin-4-yl)oxy]-N-[5-(trifluoromethyl)-1,3-thiazol-2-yl]benzamide;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-(5-methyl-1,3,4-thiadiazol-2-yl)benzamide;

4-[(3-{[(3R)-1-(but-2-ynoyl)piperidin-3-yl]amino}-1H-pyrazolo[3,4-b]pyridin-4-yl)oxy]-N-methyl-N-(5-methyl-1,3-thiazol-2-yl)benzamide;

N-methyl-N-(5-methyl-1,3-thiazol-2-yl)-4-[(3-{[(3R)-1-(prop-2-enoyl)piperidin-3-yl]amino}-1H-pyrazolo[3,4-b]pyridin-4-yl)oxy]benzamide;

4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]-N-[4-(trifluoromethyl)pyridin-2-yl]benzamide;

1-[(3R)-3-{[4-(4-{[1,3]oxazolo[4,5-b]pyridin-2-yl}phenoxy)-1H-pyrazolo[3,4-b]pyridin-3-yl]amino}piperidin-1-yl]prop-2-en-1-one;

3-{4-[(3-{[(3R)-1-[(2E)-4-[cyclopropyl(methyl)amino]but-2-enoyl]piperidin-3-yl]amino}-1H-pyrazolo[3,4-b]pyridin-4-yl)oxy]phenyl}-1-[4-(trifluoromethyl)pyridin-2-yl]urea;

4-[(3-{[(3R)-1-cyclopropanecarbonylpyrrolidin-3-yl] amino}-1H-pyrazolo[3,4-b]pyridin-4-yl)oxy]-N-[4-(trifluoromethyl)pyridin-2-yl]benzamide;

(3R)-3-({4-[4-(1,3-benzothiazol-2-yl)phenoxy]-1H-pyrazolo[3,4-b]pyridin-3-yl}amino)-N-ethylpiperidine-1-carboxamide;

1-[(3R)-3-({4-[4-(7-methyl-1,3-benzoxazol-2-yl)phenoxy]-1H-pyrazolo[3,4-b]pyridin-3-yl}amino)piperidin-1-yl]propan-1-one;

(3R)-1-cyclopropanecarbonyl-N-{4-[4-(7-methyl-1,3-benzoxazol-2-yl)phenoxy]-1H-pyrazolo[3,4-b]pyridin-3-yl}piperidin-3-amine;

N-(5-methyl-1,3-thiazol-2-yl)-4-[(3-{[(3R)-1-(1-methylpiperidine-4-carbonyl)pyrrolidin-3-yl]amino}-1H-pyrazolo[3,4-b]pyridin-4-yl)oxy]benzamide;

1-[(3R)-3-({4-[4-(1,3-benzothiazol-2-yl)phenoxy]-1H-pyrazolo[3,4-b]pyridin-3-yl}amino)piperidin-1-yl]propan-1-one;

N-(1,3-benzothiazol-2-yl)-4-[(3-{[(3R)-1-(1-methylpiperidine-4-carbonyl)piperidin-3-yl]amino}-1H-pyrazolo[3,4-b]pyridin-4-yl)oxy]benzamide;

(3R)-3-({4-[4-(1H-1,3-benzodiazol-2-yl)phenoxy]-1H-pyrazolo[3,4-b]pyridin-3-yl}amino)-N-ethylpiperidine-1-carboxamide;

4-[(3-{[(3R)-1-propanoylpiperidin-3-yl]amino}-1H-pyrazolo[3,4-b]pyridin-4-yl)oxy]-N-[4-(trifluoromethyl)pyridin-2-yl]benzamide;

N-(1,3-benzothiazol-2-yl)-4-[(3-{[(3R)-1-(3-methyloxetane-3-carbonyl)piperidin-3-yl]amino}-1H-pyrazolo[3,4-b]pyridin-4-yl)oxy]benzamide;

(R)—N-ethyl-3-(4-(4-(4-methylpyridin-2-ylcarbamoyl)phenoxy)-1H-pyrazolo[3,4-b]pyridin-3-ylamino)piperidine-1-carboxamide;

(3R)—N-ethyl-3-[(4-{4-[(pyridin-2-yl)carbamoyl]phenoxy}-1H-pyrazolo[3,4-b]pyridin-3-yl)amino]piperidine-1-carboxamide;

1-[(3R)-3-({4-[4-(1H-1,3-benzodiazol-2-yl)phenoxy]-1H-pyrazolo[3,4-b]pyridin-3-yl}amino)piperidin-1-yl]propan-1-one;

4-[(3-{[(3R)-1-cyclopropanecarbonylpiperidin-3-yl] amino}-1H-pyrazolo[3,4-b]pyridin-4-yl)oxy]-N-(pyridin-2-yl)benzamide;

(3R)—N,N-dimethyl-3-[(4-{4-[(pyridin-2-yl)carbamoyl]phenoxy}-1H-pyrazolo[3,4-b]pyridin-3-yl)amino]piperidine-1-carboxamide;

(3R)—N-ethyl-3-{[4-(2-methyl-4-phenoxyphenoxy)-1H-pyrazolo[3,4-b]pyridin-3-yl]amino}piperidine-1-carboxamide;

(R)—N-(4-methylpyridin-2-yl)-4-(3-(1-(methylsulfonyl)piperidin-3-ylamino)-1H-pyrazolo[3,4-b]pyridin-4-yloxy)benzamide;

(R)-4-(3-(1-(2-amino-2-oxoacetyl)piperidin-3-ylamino)-1H-pyrazolo[3,4-b]pyridin-4-yloxy)-N-(4-methylpyridin-2-yl)benzamide;

(R)-diethyl 4-(3-(4-(4-(4-methylpyridin-2-ylcarbamoyl)phenoxy)-1H-pyrazolo[3,4-b]pyridin-3-ylamino)piperidin-1-yl)-4-oxobutylphosphonate;

(R)-diethyl 2-(3-(4-(4-(4-methylpyridin-2-ylcarbamoyl)phenoxy)-1H-pyrazolo[3,4-b]pyridin-3-ylamino)piperidin-1-yl)-2-oxoethylphosphonate;

(R)-diethyl 3-(3-(4-(4-(4-methylpyridin-2-ylcarbamoyl)phenoxy)-1H-pyrazolo[3,4-b]pyridin-3-ylamino)piperidin-1-yl)-3-oxopropylphosphonate;

(R)-4-(3-(1-(4-methoxybutanoyl)piperidin-3-ylamino)-1H-pyrazolo[3,4-b]pyridin-4-yloxy)-N-(4-methylpyridin-2-yl)benzamide;

(R)-4-(3-(1-cyanopyrrolidin-3-ylamino)-1H-pyrazolo[3,4-b]pyridin-4-yloxy)-N-(4-methylpyridin-2-yl)benzamide;

(R)-4-(3-(1-cyanopiperidin-3-ylamino)-1H-pyrazolo[3,4-b]pyridin-4-yloxy)-N-(4-methylpyridin-2-yl)benzamide;

4-(3-(1-(1-cyanocyclopropanecarbonyl)piperidin-4-ylamino)-1H-pyrazolo[3,4-b]pyridin-4-yloxy)-N-(4-methylpyridin-2-yl)benzamide;

4-(3-(1-cyanopiperidin-4-ylamino)-1H-pyrazolo[3,4-b]pyridin-4-yloxy)-N-(4-methylpyridin-2-yl)benzamide;

(R)-4-(3-(1-(1-cyanocyclopropanecarbonyl)pyrrolidin-3-ylamino)-1H-pyrazolo[3,4-b]pyridin-4-yloxy)-N-(4-methylpyridin-2-yl)benzamide;

(R)-4-(3-(1-but-2-ynoylpiperidin-3-ylamino)-1H-pyrazolo[3,4-b]pyridin-4-yloxy)-N-(4-methylpyridin-2-yl)benzamide;

(R)-4-(3-(1-(4-methoxybut-2-ynoyl)piperidin-3-ylamino)-1H-pyrazolo[3,4-b]pyridin-4-yloxy)-N-(4-methylpyridin-2-yl)benzamide;

(R)-4-(3-(1-(4-hydroxybut-2-ynoyl)piperidin-3-ylamino)-1H-pyrazolo[3,4-b]pyridin-4-yloxy)-N-(4-methylpyridin-2-yl)benzamide;

(R)-4-(3-(1-(1,4-dimethylpiperidine-4-carbonyl)piperidin-3-ylamino)-1H-pyrazolo[3,4-b]pyridin-4-yloxy)-N-(4-methylpyridin-2-yl)benzamide;

4-(3-(1-(1,4-dimethylpiperidine-4-carbonyl)piperidin-4-ylamino)-1H-pyrazolo[3,4-b]pyridin-4-yloxy)-N-(4-methylpyridin-2-yl)benzamide; and (R,E)-4-(dimethylamino)-1-(3-(4-(3-(pyrimidin-4-ylamino)phenoxy)-1H-pyrazolo[3,4-b]pyridin-3-ylamino)pyrrolidin-1-yl)but-2-en-1-one;

or a stereoisomer or an isotopic variant thereof, or a pharmaceutically acceptable salt or solvate of the compound or stereoisomer or an isotopic variant.

18. A pharmaceutical composition comprising a pharmaceutically acceptable carrier and a pharmaceutically effective amount of a compound of claim 1.

* * * * *